(12) United States Patent
Fan et al.

(10) Patent No.: US 11,535,677 B2
(45) Date of Patent: Dec. 27, 2022

(54) CHIMERIC ANTIGEN RECEPTORS TARGETING BCMA AND METHODS OF USE THEREOF

(71) Applicant: Legend Biotech USA Inc., New Castle, DE (US)

(72) Inventors: Xiaohu Fan, Edmonton (CA); Qiuchuan Zhuang, Jiangsu (CN); Pingyan Wang, Anhui (CN); Lin Wang, Jiangsu (CN); Lei Yang, Anhui (CN); Jiaying Hao, Jiangsu (CN); Dan Zhao, Jiangsu (CN); Xian He, Jiangsu (CN)

(73) Assignee: LEGEND BIOTECH USA INC., Wilmington, DE (US)

( * ) Notice: Subject to any disclaimer, the term of this patent is extended or adjusted under 35 U.S.C. 154(b) by 272 days.

(21) Appl. No.: 16/303,587

(22) PCT Filed: Aug. 10, 2017

(86) PCT No.: PCT/CN2017/096938
§ 371 (c)(1),
(2) Date: Nov. 20, 2018

(87) PCT Pub. No.: WO2018/028647
PCT Pub. Date: Feb. 15, 2018

(65) Prior Publication Data
US 2020/0078399 A1 Mar. 12, 2020

(30) Foreign Application Priority Data

Aug. 10, 2016 (WO) ................ PCT/CN2016/094408

(51) Int. Cl.
| | |
|---|---|
| C07K 16/28 | (2006.01) |
| C07K 14/725 | (2006.01) |
| C07K 14/705 | (2006.01) |
| C07K 16/30 | (2006.01) |
| A61K 35/17 | (2015.01) |
| C12N 5/0783 | (2010.01) |
| C07K 19/00 | (2006.01) |
| C12N 5/10 | (2006.01) |
| C12N 15/62 | (2006.01) |
| C12N 15/63 | (2006.01) |

(52) U.S. Cl.
CPC .......... *C07K 16/2878* (2013.01); *A61K 35/17* (2013.01); *C07K 14/7051* (2013.01); *C07K 14/70517* (2013.01); *C07K 14/70521* (2013.01); *C07K 14/70575* (2013.01); *C07K 14/70578* (2013.01); *C07K 14/70596* (2013.01); *C07K 16/2803* (2013.01); *C07K 16/2887* (2013.01); *C07K 16/2896* (2013.01); *C07K 16/30* (2013.01); *C07K 16/3061* (2013.01); *C07K 19/00* (2013.01); *C12N 5/0636* (2013.01); *C12N 5/10* (2013.01); *C12N 15/62* (2013.01); *C12N 15/63* (2013.01); *C07K 2317/22* (2013.01); *C07K 2317/31* (2013.01); *C07K 2317/35* (2013.01); *C07K 2317/569* (2013.01); *C07K 2317/622* (2013.01); *C07K 2319/02* (2013.01); *C07K 2319/03* (2013.01); *C07K 2319/21* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | |
|---|---|---|
| 10,934,363 B2 | 3/2021 | Fan et al. |
| 11,186,647 B2 | 11/2021 | Fan et al. |
| 2010/0136018 A1 | 6/2010 | Dolk et al. |
| 2012/0034160 A1 | 2/2012 | Ghayur et al. |
| 2013/0156769 A1 | 6/2013 | Kufer et al. |
| 2014/0099340 A1 | 4/2014 | June et al. |
| 2014/0161828 A1 | 6/2014 | Armitage et al. |
| 2015/0038684 A1 | 2/2015 | Jensen |
| 2016/0046724 A1 | 2/2016 | Brogdon et al. |
| 2018/0230225 A1 | 8/2018 | Fan et al. |
| 2021/0163615 A1 | 6/2021 | Fan et al. |
| 2021/0261675 A1 | 8/2021 | Fan et al. |
| 2022/0127371 A1 | 4/2022 | Fan et al. |

FOREIGN PATENT DOCUMENTS

| | | |
|---|---|---|
| AU | 2016305075 B2 | 10/2019 |
| AU | 2017311089 B2 | 3/2021 |
| CA | 2994579 A1 | 2/2017 |
| CN | 103483453 A | 1/2014 |
| CN | 104136458 A | 11/2014 |
| CN | 104379179 A | 2/2015 |

(Continued)

OTHER PUBLICATIONS

Muyldermans (ARB, 82:17.1-17.23, 2013).*

(Continued)

*Primary Examiner* — Brad Duffy
(74) *Attorney, Agent, or Firm* — Jones Day

(57) ABSTRACT

Provided herein are single-domain antibodies targeting BCMA, and chimeric antigen receptors (such as monovalent CAR, and multivalent CAR including bi-epitope CAR) having one or more anti-BCMA single-domain antibodies. Further provided are engineered immune effector cells (such as T cells) having the chimeric antigen receptors. Pharmaceutical compositions, kits and methods of treating cancer are also provided.

26 Claims, 25 Drawing Sheets

Specification includes a Sequence Listing.

(56) References Cited

FOREIGN PATENT DOCUMENTS

| CN | 104583230 A | 4/2015 | | |
|---|---|---|---|---|
| CN | 105143263 A | 12/2015 | | |
| CN | 105384825 A | 3/2016 | | |
| CN | 105658671 A | 6/2016 | | |
| CN | 105777911 A | 7/2016 | | |
| CN | 108395481 A | 8/2018 | | |
| CN | 109306014 A | 2/2019 | | |
| CN | 109153731 B | 4/2021 | | |
| EP | 3029067 A1 | 6/2016 | | |
| JP | 2015-504306 A | 2/2015 | | |
| JP | 2015-513394 A | 5/2015 | | |
| JP | 2018526984 A | 9/2018 | | |
| WO | 199824893 A2 | 6/1998 | | |
| WO | WO 2008074867 A2 | 6/2008 | | |
| WO | WO 2008074867 A3 | 6/2008 | | |
| WO | WO 2011154453 A1 | 12/2011 | | |
| WO | 2013123061 A1 | 8/2013 | | |
| WO | WO 2013126729 A1 | 8/2013 | | |
| WO | WO-2013154760 A1 * | 10/2013 | ....... | C07K 14/70517 |
| WO | WO 2014011988 A2 | 1/2014 | | |
| WO | WO 2014011988 A3 | 1/2014 | | |
| WO | WO 2014089335 A2 | 6/2014 | | |
| WO | WO 2014089335 A3 | 6/2014 | | |
| WO | WO 2014122143 A1 | 8/2014 | | |
| WO | WO 2014153270 A1 | 9/2014 | | |
| WO | WO 2014165707 A2 | 10/2014 | | |
| WO | WO 2014165707 A3 | 10/2014 | | |
| WO | WO 2015052538 A1 | 4/2015 | | |
| WO | 2015120187 A1 | 8/2015 | | |
| WO | WO 2015142675 A2 | 9/2015 | | |
| WO | WO 2015142675 A3 | 9/2015 | | |
| WO | 2016014789 A2 | 1/2016 | | |
| WO | WO 2016014565 A2 | 1/2016 | | |
| WO | WO 2016014565 A3 | 1/2016 | | |
| WO | 2016094304 A2 | 6/2016 | | |
| WO | WO 2017015246 A1 | 1/2017 | | |
| WO | 2017025038 A1 | 2/2017 | | |
| WO | 2018028647 A1 | 2/2018 | | |
| WO | WO 2018193394 A1 | 10/2018 | | |
| WO | WO 2019001474 A1 | 1/2019 | | |
| WO | WO 2019133969 A2 | 7/2019 | | |
| WO | WO 2019133969 A3 | 7/2019 | | |
| WO | WO 2019157496 A1 | 8/2019 | | |
| WO | WO 2021037221 A1 | 3/2021 | | |
| WO | WO 2021037222 A1 | 3/2021 | | |
| WO | WO 2021121228 A1 | 6/2021 | | |

OTHER PUBLICATIONS

International Preliminary Report on Patentability dated Nov. 18, 2016 in International Application No. PCT/CN2016/094408.
International Preliminary Report on Patentability dated Feb. 13, 2018 in International Application No. PCT/CN2016/094408.
Agaugue, et al; "Development of Safer & Optimized CAR-T Cells Using Lentiviral Vectors.", Cancer-Immunotherapy, Cancer Vaccines I, Molecular Therapy, vol. 23, pp. 88 (May 2015).
Chang, et al; "Chimeric antigen receptor-modified T cells against several target antigens in multiple myeloma.", ACCR 106th Annual Meeting, (Apr. 2015).
Jamnani, et al., "T cells expressing VHH-directed oligoclonal chimeric HER2 antigen receptors: Towards tumor-directed oligoclonal T cell therapy", Biochimica et Biophysica Acta, vol. 1840, pp. 378-386, (2013).
Ramadoss, et al., "An Anti?B Cell Maturation Antigen Bispecific Antibody for Multiple Myeloma", Journal of the American Chemical Society, vol. 213, pp. 5288-5291, (2015).
Grada, et al., "TanCAR:A Novel Bispecific Chimeric Antigen Receptor for Cancer Immunotherapy", Molecular Therapy—Nucleic Acids, vol. 2, e105, pp. 1-11, (2013).
DeAglio et al., "CD38/CD19: a lipid raft-dependent signaling complex in human B cells," Blood, vol. 109, No. e105, pp. 5390-5398 (2007).

Kalled et al., "The role of BAFF in immune function and implications for autoimmunity," Immunological Review, vol. 204, pp. 43-54 (2015).
Konopleva et al., "Ligation of Cell Surface CD38 Protein with Agonistic Monoclonal Antibody Induces a Cell Growth Signal in Myeloid Leukemia Cells," The Journal of Immunology, vol. 161, pp. 4702-4708 (1998).
Lin et al., "Flow Cytometric Immunophenotypic Analysis of 306 Cases of Multiple Myeloma," Am. J. Clin. Pathol., vol. 121, pp. 482-488 (2004).
Lokhorst et al., "Targeting CD38 with Daratumumab Monotherapy in Multiple Myeloma," The New England Journal of Medicine, vol. 373, pp. 1-13 (2015) Downloaded from nejm.org on Aug. 26, 2015.
Mackay et al., "BAFF and APRIL: A Tutorial on B Cell Survival," Annu. Rev. Immunol., vol. 21, pp. 231-264 (2003).
Neri et al., "Neutralizing B-Cell-Activating Factor Antibody Improves Survival and Inhibits Osteoclastogenesis in a Severe Combined Immunodeficient Human Multiple Myeloma Model," Clin. Cancer Res., vol. 13, No. 19, pp. 5903-5909 (2007).
Novak et al., "Expression of BCMA, TACI, and BAFF-R in multiple myeloma: a mechanism for growth and survival," Blood, vol. 103, No. 2, pp. 689-694 (2004).
Oden et al., "Potent anti-tumor response by targeting B cell maturation antigen (BCMA) in a mouse model of multiple myeloma," Molecular Oncology, vol. 9, pp. 1348-1358 (2015).
Thompson et al., "BAFF Binds to the Tumor Necrosis Factor Receptor-like Molecule B Cell Maturation Antigen and is Important for Maintaining the Peripheral B Cell Population," J. Exp. Med., vol. 192, No. 1, pp. 129-135 (Jul. 2, 2000).
International Preliminary Report on Patentability dated Feb. 22, 2018 in International Application No. PCT/CN2016/094408.
International Search Report dated Nov. 18, 2016 in International Application No. PCT/CN2016/094408.
Written Opinion dated Nov. 18, 2016 in International Application No. PCT/CN2016/094408.
Hoffmann et al., "Serial Killing of tumor cells by cytotoxic T Cells redirected with a CD19-/CD3-bispecific single-chain antibody construct" Int. J. Cancer, 115, pp. 98-104, 2005.
Hegde et al., "Tandem CAR T cells targeting HER2 and IL 13Ra2 mitigate tumor antigen escape", Journal of Clinical Investigation, 126(8), pp. 3036-3052, 2016.
Int'l Search Report dated Nov. 8, 2017 in Int'l Application No. PCT/CN2017/096938.
Int'l Written Opinion of the Int'l Searching Authority dated Nov. 8, 2017 in Int'l Application No. PCT/CN2017/096938.
Int'l Preliminary Report on Patentability dated Feb. 12, 2019 in Int'l Application No. PCT/CN2017/096938.
Brentjens et al., 2013, "CD19-targeted T cells rapidly induce molecular remissions in adults with chemotherapy-refractory acute lymphoblastic leukemia", Sci Transl Med., 5(177):177ra38 (11 pages).
De Munter et al., 2018, "Nanobody Based Dual Specific CARs", Int J Mol Sci., 19(2):403 (11 pages).
Grupp et al., 2013, "Chimeric antigen receptor-modified T cells for acute lymphoid leukemia", N Engl J Med., 368(16):1509-1518.
Kalos et al., 2011, "T cells with chimeric antigen receptors have potent antitumor effects and can establish memory in patients with advanced leukemia", Sci Transl Med., 3(95):95ra73 (13 pages).
Khanka et al., 2015, "Nanobody-based cancer therapy of solid tumors", Nanomedicine (Lond), 10(1):161-174.
Liu et al., 2014, "Thermal stability and refolding capability of shark derived single domain antibodies", Mol Immunol., 59(2):194-199.
Revets et al., 2005, "Nanobodies as novel agents for cancer therapy," Expert Opin. Biol. Ther., 5(1):111-124.
Schmitz et al., 2013, "Structural evaluation of EGFR inhibition mechanisms for nanobodies/VHH domains," Structure, 21(7):1214-1224.
Wang et al., 2013, "Construction and selection of camelized human sdAbs library against TNF-α", Military Medical Sciences, 37(5):339-344, English abstract only.
Yan et al., 2015, "Characterization and applications of Nanobodies against human procalcitonin selected from a novel naïve Nanobody phage display library", J Nanobiotechnology, 13:33 (11 pages).

(56) References Cited

OTHER PUBLICATIONS

Ajina et al., 2018, "Strategies to Address Chimeric Antigen Receptor Tonic Signaling," Mol. Cancer Ther., 17(9):1795-1815.

Bluhm et al., 2018, "CAR T Cells with Enhanced Sensitivity to B Cell Maturation Antigen for the Targeting of B Cell Non-Hodgkin's Lymphoma and Multiple Myeloma," Mol. Ther., 26(8):1906-1920.

Fan et al., 2019, "FP-182: Preclinical assessment of LCAR-B38M, a novel BCMA-targeting chimeric antigen receptor (CAR)-T cell therapy in relapsed/refractory multiple myeloma," 17th International Myeloma Workshop, Sep. 12-15, 2019, Clinical Lymphoma, Myeloma & Leukemia, 19(10):e160.

GenBank Reference NP_054373.1, nef protein [Simian immunodeficiency virus], Aug. 13, 2018 (2 pages).

International Search Report and Written Opinion for International Patent Application No. PCT/CN2020/112181 (Pub No. WO 2021037221) dated Oct. 28, 2020 (12 pages).

International Search Report and Written Opinion for International Patent Application No. PCT/CN2020/112182 (Pub No. WO 2021037222) dated Dec. 3, 2020 (11 pages).

International Search Report and Written Opinion for International Patent Application No. PCT/CN2020/136570 (Pub No. WO 2021121228) dated Mar. 11, 2021 (15 pages).

Lee et al., 1998, "Identification of an immunoreceptor tyrosine-based activation motif of K1 transforming protein of Kaposi's sarcoma-associated herpesvirus," Mol. Cell Biol., 18(9):5219-5228.

Loskog et al., 2006, "Addition of the CD28 signaling domain to chimeric T-cell receptors enhances chimeric T-cell resistance to T regulatory cells," Leukemia, 20(10):1819-1828.

Manrique et al., 2017, "Endocytic sorting motif interactions involved in Nef-mediated downmodulation of CD4 and CD3," Nat. Commun., 8(1):442 (14 pages).

Nomura et al., 2014, "Identification of SIV Nef CD8(+) T cell epitopes restricted by a MHC class I haplotype associated with lower viral loads in a macaque AIDS model," Biochem. Biophys. Res. Commun., 450(2):942-947.

Schaefer et al., 2002, "The conserved process of TCR/CD3 complex down-modulation by SIV Nef is mediated by the central core, not endocytic motifs," Virology, 302(1):106-122.

Wei et al., 2015, "Advances in immunotherapy of multiple myeloma by using chimeric antigen receptor-modified lymphocytes," Acad. J. Chin. PLA Med. Sch., 36(11):1156-1159, in Chinese with English abstract.

Yu et al., 2019, "Next generation chimeric antigen receptor T cells: safety strategies to overcome toxicity," Mol. Cancer, 18(1):125 (13 pages).

\* cited by examiner

|  |  | 1 | 11 | 21 | 31 | 41 | 51 |
|---|---|---|---|---|---|---|---|
| (SEQ ID NO: 396) | | MLQMAGQCSQ | NEYFDSLLHA | CIPCQLRCSS | NTPPLTCQRY | CNASVTNSVK | GTNA |

Disulfide bonds

| Code | Position | | | | | | |
|---|---|---|---|---|---|---|---|
| 269EP001 | 1-10 | MLQMAGQCSQ | (SEQ ID NO: 389) | | | | |
| 269EP002 | 8-21 | CSQ | NEYFDSLLHA | C | (SEQ ID NO: 390) | | |
| 269EP003 | 11-23 | | NEYFDSLLHA | CIP | (SEQ ID NO: 391) | | |
| 269EP004 | 20-30 | | A | CIPCQLRCSS | (SEQ ID NO: 392) | | |
| 269EP005 | 24-42 | | | CQLRCSS | NTPPLTCQRY | CN | (SEQ ID NO: 393) |
| 269EP006 | 36-43 | | | | TCQRY | CNA | (SEQ ID NO: 394) |
| 269EP007 | 43-54 | | | | | ASVTNSVK | GTNA (SEQ ID NO: 395) |

FIG. 8B

SEQUENCE LISTING

```
<160> NUMBER OF SEQ ID NOS: 399

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

Asp Tyr Tyr Ala Ile Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Thr Tyr Gly Met Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Thr Phe Thr Met Gly
1               5
```

```
<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Ile Asn Ala Met Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Ser Ile Val Met Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Arg Ala Val Ile Val
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Ser Asp Val Met Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asn Asp His Met Ala
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Lys Asn Thr Val Ala
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: Synthetic Construct

<400> SEQUENCE: 10

Ser His Val Met Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Thr Tyr Phe Met Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Ile Asn Val Met Ala
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Thr Phe Thr Met Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Ile Asn Ala Met Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Lys Asn Thr Val Ala
1               5

<210> SEQ ID NO 16
```

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Ser Ile Val Met Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Thr Phe Thr Met Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

Lys Asn Thr Val Ala
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Ile Asn Thr Met Asp
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Construct

<400> SEQUENCE: 20

Lys Asn Thr Val Ala
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Construct

<400> SEQUENCE: 21

Asp Tyr Trp Met His
1               5

<210> SEQ ID NO 22
<211> LENGTH: 5
```

```
<212> TYPE: PRT
<213> ORGANISM: Artificial Sequence
<220> FEATURE:
<223> OTHER INFORMATION: Synthetic Construct

<400> SEQUENCE: 22

Ser Asn Thr Met Ala
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct

<400> SEQUENCE: 23

Thr Phe Thr Met Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Construct

<400> SEQUENCE: 24

Val Ala Ala Ile Ser Leu
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Lys Asn Thr Val Ala
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Thr Phe Thr Met Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Thr Phe Thr Met Gly
1               5

<210> SEQ ID NO 28
<211> LENGTH: 5
<212> TYPE: PRT
```

<213> ORGANISM: Artificial Sequence
<220> FEATURE:
<223> OTHER INFORMATION: Synthetic Construct

<400> SEQUENCE: 28

Ser Ile Val Met Gly
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Thr Phe Thr Met Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct

<400> SEQUENCE: 30

Thr Phe Thr Met Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct

<400> SEQUENCE: 31

Thr Phe Thr Met Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Construct

<400> SEQUENCE: 32

Thr Phe Thr Met Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Thr Phe Thr Met Gly
1               5

<210> SEQ ID NO 34
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 34

Asn His Val Met Gly
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Asn Tyr Ile Leu Ala
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Thr Phe Thr Met Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic Construct

<400> SEQUENCE: 37

Thr Phe Thr Met Gly
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Construct

<400> SEQUENCE: 38

Asn Asn Phe Val Met Gly
1               5

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct

<400> SEQUENCE: 39

Cys Ile Ser Arg Ser Asp Gly Ser Thr Tyr Tyr Ala Asp Ser Val Lys
1               5                   10                  15

Gly

<210> SEQ ID NO 40
<211> LENGTH: 19
<212> TYPE: PRT
```

```
<213> ORGANISM: Artificial Sequence
<220> FEATURE:
<223> OTHER INFORMATION: Synthetic Construct

<400> SEQUENCE: 40

Ser Lys Ala Ser Met Asn Tyr Ser Gly Arg Thr Tyr Tyr Ala Asp Ser
1               5                   10                  15

Val Lys Gly

<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Ala Ile Ser Leu Ser Pro Thr Leu Ala Tyr Tyr Ala Glu Ser Val Lys
1               5                   10                  15

Gly

<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

Ser Ile Arg Gly Leu Gly Arg Thr Asn Tyr Asp Asp Ser Val Lys Gly
1               5                   10                  15

<210> SEQ ID NO 43
<211> LENGTH: 17
<212> TYPE: PRT
<213> ORGANISM: Artificial Sequence
<220> FEATURE:
<223> OTHER INFORMATION: Synthetic Construct

<400> SEQUENCE: 43

Ala Ile Met Trp Asn Asp Gly Ile Thr Tyr Leu Gln Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Phe Ile Lys Pro Ser Asp Gly Thr Ile Tyr Tyr Ile Asp Ser Leu Lys
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: Synthetic Construct

<400> SEQUENCE: 45
```

Ala Ile Met Trp Asn Asp Gly Ile Thr Tyr Leu Gln Asp Ser Val Lys
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Ala Ile Asp Trp Ser Gly Arg Thr Thr Asn Tyr Ala Asp Pro Val Glu
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic Construct

<400> SEQUENCE: 47

Ser Ile Thr Trp Asp Gly Arg Thr Thr Tyr Tyr Ala Asp Ser Val Lys
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: Synthetic Construct

<400> SEQUENCE: 48

Val Ile Gly Trp Arg Asp Ile Ser Thr Ser Tyr Ala Asp Ser Val Lys
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: Synthetic Construct

<400> SEQUENCE: 49

Gly Ile Ala Trp Ser Gly Gly Ser Thr Ala Tyr Ala Asp Ser Val Lys
1               5                   10                  15

Gly

<210> SEQ ID NO 50
<211> LENGTH: 16
<212> TYPE: PRT
<213> ORGANISM: Artificial Sequence
<220> FEATURE:
<223> OTHER INFORMATION: Synthetic Construct

<400> SEQUENCE: 50

Ala Val Thr Arg Asp Gly Arg Lys Ser Cys Gly Asp Ser Val Lys Gly
1               5                   10                  15

```
<210> SEQ ID NO 51
<211> LENGTH: 17
<212> TYPE: PRT
<213> ORGANISM: Artificial Sequence
<220> FEATURE:
<223> OTHER INFORMATION: Synthetic Construct

<400> SEQUENCE: 51

Ser Ile Thr Trp Asp Gly Arg Ser Ala Tyr Tyr Ala Glu Ser Val Lys
1               5                   10                  15
Gly

<210> SEQ ID NO 52
<211> LENGTH: 16
<212> TYPE: PRT
<213> ORGANISM: Artificial Sequence
<220> FEATURE:
<223> OTHER INFORMATION: Synthetic Construct

<400> SEQUENCE: 52

Thr Ile Thr Arg Gly Gly Ser Thr Asn Tyr Gly Pro Ser Val Lys Gly
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Ser Ile Thr Cys Asp Gly Arg Thr Thr Tyr Tyr Ala Asn Ser Val Asn
1               5                   10                  15
Gly

<210> SEQ ID NO 54
<211> LENGTH: 17
<212> TYPE: PRT
<213> ORGANISM: Artificial Sequence
<220> FEATURE:
<223> OTHER INFORMATION: Synthetic Construct

<400> SEQUENCE: 54

Ala Ile Met Trp Asn Asp Gly Leu Thr Tyr Leu Gln Gly Ser Val Lys
1               5                   10                  15
Gly

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct

<400> SEQUENCE: 55

Ala Ile Ser Leu Ser Pro Thr Leu Ala Tyr Tyr Ala Glu Ser Val Lys
1               5                   10                  15
Gly

<210> SEQ ID NO 56
<211> LENGTH: 17
<212> TYPE: PRT
<213> ORGANISM: Artificial Sequence
<220> FEATURE:
<223> OTHER INFORMATION: Synthetic Construct
```

<400> SEQUENCE: 56

Ser Ile Thr Trp Asp Gly Arg Thr Thr Tyr Tyr Ala Asp Ser Val Lys
1               5                   10                  15
Gly

<210> SEQ ID NO 57
<211> LENGTH: 17
<212> TYPE: PRT
<213> ORGANISM: Artificial Sequence
<220> FEATURE:
<223> OTHER INFORMATION: Synthetic Construct

<400> SEQUENCE: 57

Ala Ile Ser Leu Ser Pro Thr Leu Ala Tyr Tyr Ala Glu Ser Val Lys
1               5                   10                  15
Gly

<210> SEQ ID NO 58
<211> LENGTH: 17
<212> TYPE: PRT
<213> ORGANISM: Artificial Sequence
<220> FEATURE:
<223> OTHER INFORMATION: Synthetic Construct

<400> SEQUENCE: 58

Ser Ile Thr Cys Asp Gly Arg Thr Thr Tyr Tyr Ala Asn Ser Val Lys
1               5                   10                  15
Gly

<210> SEQ ID NO 59
<211> LENGTH: 17
<212> TYPE: PRT
<213> ORGANISM: Artificial Sequence
<220> FEATURE:
<223> OTHER INFORMATION: Synthetic Construct

<400> SEQUENCE: 59

Ser Ile Asp Thr Ser Gly Gln Thr Thr Tyr Tyr Ala Asp Ser Leu Lys
1               5                   10                  15
Gly

<210> SEQ ID NO 60
<211> LENGTH: 17
<212> TYPE: PRT
<213> ORGANISM: Artificial Sequence
<220> FEATURE:
<223> OTHER INFORMATION: Synthetic Construct

<400> SEQUENCE: 60

Ser Thr Thr Trp Asn Gly Arg Ser Thr Tyr Tyr Ala Asp Ser Val Lys
1               5                   10                  15
Gly

<210> SEQ ID NO 61
<211> LENGTH: 15
<212> TYPE: PRT
<213> ORGANISM: Artificial Sequence
<220> FEATURE:
<223> OTHER INFORMATION: Synthetic Construct

<400> SEQUENCE: 61

Asp Ile Ser Gly Gly Arg Thr Asn Tyr Ala Asp Ser Val Lys Gly

-continued

```
<210> SEQ ID NO 62
<211> LENGTH: 21
<212> TYPE: PRT
<213> ORGANISM: Artificial Sequence
<220> FEATURE:
<223> OTHER INFORMATION: Synthetic Construct

<400> SEQUENCE: 62

Phe Thr Ile Ser Arg Asp Asn Ala Lys Asn Thr Val Val Leu Gln Met
1               5                   10                  15

Asn Ser Leu Lys Pro
            20

<210> SEQ ID NO 63
<211> LENGTH: 17
<212> TYPE: PRT
<213> ORGANISM: Artificial Sequence
<220> FEATURE:
<223> OTHER INFORMATION: Synthetic Construct

<400> SEQUENCE: 63

Ser Ile Thr Trp Asp Gly Arg Thr Thr Tyr Tyr Ala Asp Ser Val Lys
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Synthetic Construct

<400> SEQUENCE: 64

Ala Ile Ser Leu Ser Pro Thr Leu Ala Tyr Tyr Ala Glu Ser Val Lys
1               5                   10                  15

Gly

<210> SEQ ID NO 65
<211> LENGTH: 19
<212> TYPE: PRT
<213> ORGANISM: Artificial Sequence
<220> FEATURE:
<223> OTHER INFORMATION: Synthetic Construct

<400> SEQUENCE: 65

Ala Ile Ser Leu Ser Pro Thr Leu Ala Tyr Tyr Ala Glu Ser Val Lys
1               5                   10                  15

Gly Lys Gly

<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

Ala Ile Met Trp Asn Asp Gly Ile Thr Tyr Leu Gln Asp Ser Val Lys
1               5                   10                  15

Gly
```

```
<210> SEQ ID NO 67
<211> LENGTH: 17
<212> TYPE: PRT
<213> ORGANISM: Artificial Sequence
<220> FEATURE:
<223> OTHER INFORMATION: Synthetic Construct

<400> SEQUENCE: 67

Ala Ile Asn Leu Ser Pro Thr Leu Thr Tyr Tyr Ala Glu Ser Val Lys
1               5                   10                  15
Gly

<210> SEQ ID NO 68
<211> LENGTH: 17
<212> TYPE: PRT
<213> ORGANISM: Artificial Sequence
<220> FEATURE:
<223> OTHER INFORMATION: Synthetic Construct

<400> SEQUENCE: 68

Ser Ile Thr Leu Ile Pro Thr Phe Pro Tyr Tyr Ala Tyr Ser Val Lys
1               5                   10                  15
Gly

<210> SEQ ID NO 69
<211> LENGTH: 17
<212> TYPE: PRT
<213> ORGANISM: Artificial Sequence
<220> FEATURE:
<223> OTHER INFORMATION: Synthetic Construct

<400> SEQUENCE: 69

Ala Ile Ser Leu Ser Pro Thr Leu Ala Tyr Tyr Ala Glu Ser Val Lys
1               5                   10                  15
Gly

<210> SEQ ID NO 70
<211> LENGTH: 17
<212> TYPE: PRT
<213> ORGANISM: Artificial Sequence
<220> FEATURE:
<223> OTHER INFORMATION: Synthetic Construct

<400> SEQUENCE: 70

Ala Ile Ser Leu Ser Pro Thr Leu Ala Tyr Tyr Ala Glu Ser Val Lys
1               5                   10                  15
Gly

<210> SEQ ID NO 71
<211> LENGTH: 17
<212> TYPE: PRT
<213> ORGANISM: Artificial Sequence
<220> FEATURE:
<223> OTHER INFORMATION: Synthetic Construct

<400> SEQUENCE: 71

Val Ile Gly Trp Arg Asp Ile Asn Ala Ser Tyr Ala Asp Ser Val Lys
1               5                   10                  15
Gly

<210> SEQ ID NO 72
<211> LENGTH: 17
<212> TYPE: PRT
<213> ORGANISM: Artificial Sequence
```

```
<220> FEATURE:
<223> OTHER INFORMATION: Synthetic Construct

<400> SEQUENCE: 72

Val Ile Gly Trp Arg Asp Ile Ser Thr Ser Tyr Ala Asp Ser Val Lys
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Synthetic Construct

<400> SEQUENCE: 73

His Ile Ser Arg Ser Gly Gly Lys Ser Gly Tyr Gly Asp Ser Val Lys
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Synthetic Construct

<400> SEQUENCE: 74

Ala Ile Ser Leu Ser Pro Thr Leu Ala Tyr Tyr Ala Glu Ser Val Lys
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: Synthetic Construct

<400> SEQUENCE: 75

Ala Ile Ser Leu Ser Pro Thr Leu Ala Tyr Tyr Ala Glu Pro Val Lys
1               5                   10                  15

Gly

<210> SEQ ID NO 76
<211> LENGTH: 17
<212> TYPE: PRT
<213> ORGANISM: Artificial Sequence
<220> FEATURE:
<223> OTHER INFORMATION: Synthetic Construct

<400> SEQUENCE: 76

Ala Ile Ser Leu Ser Pro Thr Leu Ala Tyr Tyr Val Glu Ser Val Lys
1               5                   10                  15

Gly

<210> SEQ ID NO 77
<211> LENGTH: 14
<212> TYPE: PRT
<213> ORGANISM: Artificial Sequence
<220> FEATURE:
<223> OTHER INFORMATION: Synthetic Construct

<400> SEQUENCE: 77
```

```
Ala Gly Ala Asp Cys Ser Gly Tyr Leu Arg Asp Tyr Glu Phe
1               5                   10
```

<210> SEQ ID NO 78
<211> LENGTH: 18
<212> TYPE: PRT
<213> ORGANISM: Artificial Sequence
<220> FEATURE:
<223> OTHER INFORMATION: Synthetic Construct

<400> SEQUENCE: 78

```
Ala Gly Thr Gly Cys Ser Thr Tyr Gly Cys Phe Asp Ala Gln Ile Ile
1               5                   10                  15

Asp Tyr
```

<210> SEQ ID NO 79
<211> LENGTH: 13
<212> TYPE: PRT
<213> ORGANISM: Artificial Sequence
<220> FEATURE:
<223> OTHER INFORMATION: Synthetic Construct

<400> SEQUENCE: 79

```
Ala Asp Arg Lys Ser Val Met Ser Ile Arg Pro Asp Tyr
1               5                   10
```

<210> SEQ ID NO 80
<211> LENGTH: 13
<212> TYPE: PRT
<213> ORGANISM: Artificial Sequence
<220> FEATURE:
<223> OTHER INFORMATION: Synthetic Construct

<400> SEQUENCE: 80

```
Val Tyr Val Thr Leu Leu Gly Gly Val Asn Arg Asp Tyr
1               5                   10
```

<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

```
Ala Ser Lys Gly Arg Tyr Ser Glu Tyr Glu Tyr
1               5                   10
```

<210> SEQ ID NO 82
<211> LENGTH: 17
<212> TYPE: PRT
<213> ORGANISM: Artificial Sequence
<220> FEATURE:
<223> OTHER INFORMATION: Synthetic Construct

<400> SEQUENCE: 82

```
Ala Ser Pro Glu Asp Trp Tyr Thr Asp Trp Ile Asp Trp Ser Ile Tyr
1               5                   10                  15

Arg
```

<210> SEQ ID NO 83
<211> LENGTH: 11
<212> TYPE: PRT
<213> ORGANISM: Artificial Sequence
<220> FEATURE:

<223> OTHER INFORMATION: Synthetic Construct

<400> SEQUENCE: 83

Ala Ser Lys Gly Arg Tyr Ser Glu Tyr Glu Tyr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic Construct

<400> SEQUENCE: 84

Val Leu Arg Ala Trp Ile Ser Tyr Asp Asn Asp Tyr
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic Construct

<400> SEQUENCE: 85

Asp Leu Gly Lys Trp Pro Ala Gly Pro Ala Asp Tyr
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Construct

<400> SEQUENCE: 86

Ala Arg Arg Ile Asp Ala Ala Asp Phe Asp Ser
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic Construct

<400> SEQUENCE: 87

Ser Arg Gly Ile Glu Val Glu Glu Phe Gly Ala
1               5                   10

<210> SEQ ID NO 88
<211> LENGTH: 16
<212> TYPE: PRT
<213> ORGANISM: Artificial Sequence
<220> FEATURE:
<223> OTHER INFORMATION: Synthetic Construct

<400> SEQUENCE: 88

Asp Gly Trp Gly Ala Thr Thr Leu Asp Tyr Thr Tyr Gly Met Asp Tyr
1               5                   10                  15

<210> SEQ ID NO 89
<211> LENGTH: 12
<212> TYPE: PRT
<213> ORGANISM: Artificial Sequence
<220> FEATURE:
<223> OTHER INFORMATION: Synthetic Construct

```
<400> SEQUENCE: 89

Asp Arg Lys Ser Val Met Ser Ile Arg Pro Asp Tyr
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetic Construct

<400> SEQUENCE: 90

Glu Arg Leu Asp Gly Ser Gly Tyr Gly Tyr Glu Tyr Asp Tyr
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic Construct

<400> SEQUENCE: 91

Tyr Arg Lys Ser Ile Met Ser Ile Gln Pro Asp Tyr
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic Construct

<400> SEQUENCE: 92

Asp Arg Lys Ser Val Met Ser Ile Arg Pro Asp Tyr
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic Construct

<400> SEQUENCE: 93

Arg Arg Ile Asp Ala Ala Asp Phe Asp Ser
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic Construct

<400> SEQUENCE: 94

Leu Gly Lys Trp Pro Ala Gly Pro Ala Asp Tyr
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic Construct
```

```
<400> SEQUENCE: 95

Asp Arg Lys Ser Val Met Ser Ile Arg Pro Asp Tyr
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic Construct

<400> SEQUENCE: 96

Leu Gly Lys Trp Pro Ala Gly Ser Ala Asp Tyr
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic Construct

<400> SEQUENCE: 97

Arg Tyr Arg Gly Gly Thr Trp Tyr Gly Met Ala Asn
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic Construct

<400> SEQUENCE: 98

Leu Gly Lys Trp Pro Ala Gly Pro Ala Asp Tyr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthetic Construct

<400> SEQUENCE: 99

Asp Arg Lys Ser Val Met Ser Ile Arg Pro Asp Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic Construct

<400> SEQUENCE: 100

Asp Arg Lys Ser Val Met Ser Ile Arg Pro Asp Tyr
1               5                   10

<210> SEQ ID NO 101
<211> LENGTH: 16
<212> TYPE: PRT
<213> ORGANISM: Artificial Sequence
<220> FEATURE:
<223> OTHER INFORMATION: Synthetic Construct

<400> SEQUENCE: 101
```

```
Thr Ala Ser Cys His Leu Phe Gly Leu Gly Ser Gly Ala Phe Val Ser
1               5                   10                  15

<210> SEQ ID NO 102
<211> LENGTH: 10
<212> TYPE: PRT
<213> ORGANISM: Artificial Sequence
<220> FEATURE:
<223> OTHER INFORMATION: Synthetic Construct

<400> SEQUENCE: 102

Ser Lys Asp Arg Tyr Ser Glu Tyr Glu Tyr
1               5                   10

<210> SEQ ID NO 103
<211> LENGTH: 8
<212> TYPE: PRT
<213> ORGANISM: Artificial Sequence
<220> FEATURE:
<223> OTHER INFORMATION: Synthetic Construct

<400> SEQUENCE: 103

Lys Asn Gly Gly Pro Val Asp Tyr
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic Construct

<400> SEQUENCE: 104

Ser Lys Gly Arg Tyr Ser Glu Tyr Glu Tyr
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic Construct

<400> SEQUENCE: 105

Glu Arg Lys Ser Val Met Ala Ile Pro Pro Asp Tyr
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic Construct

<400> SEQUENCE: 106

Tyr Arg Lys Tyr Leu Met Ser Ile Leu Pro Asp Tyr
1               5                   10

<210> SEQ ID NO 107
<211> LENGTH: 18
<212> TYPE: PRT
<213> ORGANISM: Artificial Sequence
<220> FEATURE:
<223> OTHER INFORMATION: Synthetic Construct

<400> SEQUENCE: 107
```

Asn Arg Asn Ser Gln Arg Val Ile Ala Ala Leu Ser Trp Ile Gly Met
1               5                   10                  15

Asn Tyr

<210> SEQ ID NO 108
<211> LENGTH: 10
<212> TYPE: PRT
<213> ORGANISM: Artificial Sequence
<220> FEATURE:
<223> OTHER INFORMATION: Synthetic Construct

<400> SEQUENCE: 108

Arg Arg Ile Asp Ala Ala Asp Phe Asp Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic Construct

<400> SEQUENCE: 109

Arg Arg Ile Asp Ala Thr Asp Phe Asp Ser
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Arg Arg Ile Asp Ala Ala Asp Phe Asp Ser
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic Construct

<400> SEQUENCE: 111

Pro Leu Trp Tyr Gly Ser Pro Thr Leu Ile Asp Tyr
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic Construct

<400> SEQUENCE: 112

Asp Arg Lys Ser Val Met Ser Ile Arg Pro Asp Tyr
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic Construct

<400> SEQUENCE: 113

Asp Arg Lys Ser Val Met Ser Ile Arg Pro Asp Tyr
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic Construct

<400> SEQUENCE: 114

Asp Arg Lys Ser Val Met Ser Ile Arg Pro Asp Tyr
1               5                   10

<210> SEQ ID NO 115
<211> LENGTH: 122
<212> TYPE: PRT
<213> ORGANISM: Artificial Sequence
<220> FEATURE:
<223> OTHER INFORMATION: Synthetic Construct

<400> SEQUENCE: 115

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ile Cys Ile Ser Arg Ser Asp Gly Ser Thr Tyr Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
            100                 105                 110

Gly Gln Gly Thr Gln Val Thr Val Ser Ser
        115                 120

<210> SEQ ID NO 116
<211> LENGTH: 128
<212> TYPE: PRT
<213> ORGANISM: Artificial Sequence
<220> FEATURE:
<223> OTHER INFORMATION: Synthetic Construct

<400> SEQUENCE: 116

Gln Val Lys Leu Glu Glu Ser Gly Gly Arg Leu Val Gln Pro Arg Gly
1               5                   10                  15

Ser Leu Arg Leu Ser Cys Ala Gly Ser Gly Arg Thr Phe Ser Thr Tyr
            20                  25                  30

Gly Met Ala Trp Phe Arg Gln Ala Pro Gly Lys Glu Arg Glu Phe Val
        35                  40                  45

Ala Ser Lys Ala Ser Met Asn Tyr Ser Gly Arg Thr Tyr Tyr Ala Asp
    50                  55                  60

Ser Val Lys Gly Arg Phe Thr Ile Ala Arg Asp Asn Ala Lys Asn Met
65                  70                  75                  80

Val Phe Leu Gln Met Asn Asn Leu Lys Pro Glu Asp Thr Ala Val Tyr
                85                  90                  95

Tyr Cys Ala Ala Gly Thr Gly Cys Ser Thr Tyr Gly Cys Phe Asp Ala
            100                 105                 110

Gln Ile Ile Asp Tyr Trp Gly Lys Gly Thr Leu Val Thr Val Ser Ser
    115                 120                 125

<210> SEQ ID NO 117
<211> LENGTH: 118
<212> TYPE: PRT
<213> ORGANISM: Artificial Sequence
<220> FEATURE:
<223> OTHER INFORMATION: Synthetic Construct

<400> SEQUENCE: 117

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115

<210> SEQ ID NO 118
<211> LENGTH: 120
<212> TYPE: PRT
<213> ORGANISM: Artificial Sequence
<220> FEATURE:
<223> OTHER INFORMATION: Synthetic Construct

<400> SEQUENCE: 118

Ala Val Gln Leu Val Asp Ser Gly Gly Gly Leu Val Gln Pro Gly Gly
1               5                   10                  15

Ser Leu Arg Leu Ser Cys Val Ala Ser Gly Gly Ile Phe Val Ile Asn
            20                  25                  30

Ala Met Gly Trp Tyr Arg Gln Ala Pro Gly Lys Gln Arg Glu Leu Val
        35                  40                  45

Ala Ser Ile Arg Gly Leu Gly Arg Thr Asn Tyr Asp Asp Ser Val Lys
    50                  55                  60

Gly Arg Phe Thr Ile Ser Arg Asp Asn Ala Asn Thr Val Tyr Leu
65                  70                  75                  80

Gln Met Asn Ser Leu Glu Pro Glu Asp Thr Ala Val Tyr Tyr Cys Thr
                85                  90                  95

Val Tyr Val Thr Leu Leu Gly Val Asn Arg Asp Tyr Trp Gly Gln
            100                 105                 110

Gly Thr Gln Val Thr Val Ser Ser
        115                 120

<210> SEQ ID NO 119
<211> LENGTH: 119
<212> TYPE: PRT
<213> ORGANISM: Artificial Sequence

```
<220> FEATURE:
<223> OTHER INFORMATION: Synthetic Construct

<400> SEQUENCE: 119

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Glu Tyr Glu Tyr Trp Gly Gln Gly
            100                 105                 110

Thr Gln Val Thr Val Ser Ser
        115

<210> SEQ ID NO 120
<211> LENGTH: 128
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Glu Ser Gly Gly Gly Val Val Gln Ala Gly Gly
1               5                   10                  15

Ser Leu Thr Val Ser Cys Thr Ala Ser Gly Phe Thr Phe Asp Arg Ala
            20                  25                  30

Val Ile Val Trp Phe Arg Gln Ala Pro Gly Lys Gly Arg Glu Gly Val
        35                  40                  45

Ser Phe Ile Lys Pro Ser Asp Gly Thr Ile Tyr Tyr Ile Asp Ser Leu
    50                  55                  60

Lys Gly Arg Phe Thr Ile Ser Ser Asp Ile Ala Lys Asn Thr Val Tyr
65                  70                  75                  80

Leu Gln Met Lys Ser Leu Glu Ser Glu Asp Ser Ala Val Tyr Tyr Cys
                85                  90                  95

Ala Ala Ser Pro Glu Asp Trp Tyr Thr Asp Trp Ile Asp Trp Ser Ile
            100                 105                 110

Tyr Arg Trp Gln His Trp Gly Gln Gly Thr Gln Val Thr Val Ser Ser
        115                 120                 125

<210> SEQ ID NO 121
<211> LENGTH: 119
<212> TYPE: PRT
<213> ORGANISM: Artificial Sequence
<220> FEATURE:
<223> OTHER INFORMATION: Synthetic Construct

<400> SEQUENCE: 121

Glu Val Gln Leu Val Glu Ser Gly Gly Gly Met Val Gln Ala Gly Asp
1               5                   10                  15

Ser Leu Arg Leu Ser Cys Val Gln Ser Thr Tyr Thr Val Asn Ser Asp
            20                  25                  30
```

```
Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
 50                  55                  60

Lys Gly Arg Phe Thr Ile Phe Arg Asp Asn Ala Lys Asn Thr Val Tyr
 65                  70                  75                  80

Leu Gln Met Asn Ser Leu Lys Leu Glu Asp Thr Ala Val Tyr Tyr Cys
                 85                  90                  95

Ala Ala Ser Lys Gly Arg Tyr Ser Glu Tyr Glu Tyr Trp Gly Gln Gly
                100                 105                 110

Thr Gln Val Thr Val Ser Ser
        115
```

<210> SEQ ID NO 122
<211> LENGTH: 120
<212> TYPE: PRT
<213> ORGANISM: Artificial Sequence
<220> FEATURE:
<223> OTHER INFORMATION: Synthetic Construct

<400> SEQUENCE: 122

```
Ala Val Gln Leu Val Glu Ser Gly Gly Gly Leu Val Gln Ala Gly Asp
 1               5                  10                  15

Ser Leu Arg Leu Ser Cys Thr Ala Ser Gly Ala Thr Leu Thr Asn Asp
                 20                  25                  30

His Met Ala Trp Phe Arg Gln Ala Pro Gly Lys Gly Arg Glu Phe Val
                 35                  40                  45

Ala Ala Ile Asp Trp Ser Gly Arg Thr Thr Asn Tyr Ala Asp Pro Val
 50                  55                  60

Glu Gly Arg Phe Thr Ile Ser Arg Asn Asn Ala Lys Asn Thr Val Tyr
 65                  70                  75                  80

Leu Glu Met Asn Ser Leu Lys Leu Glu Asp Thr Ala Val Tyr Tyr Cys
                 85                  90                  95

Ala Val Leu Arg Ala Trp Ile Ser Tyr Asp Asn Asp Tyr Trp Gly Gln
                100                 105                 110

Gly Thr Gln Val Thr Val Ser Ser
        115                 120
```

<210> SEQ ID NO 123
<211> LENGTH: 120
<212> TYPE: PRT
<213> ORGANISM: Artificial Sequence
<220> FEATURE:
<223> OTHER INFORMATION: Synthetic Construct

<400> SEQUENCE: 123

```
Gln Val Gln Leu Val Glu Ser Gly Gly Gly Leu Val Gln Ala Gly Gly
 1               5                  10                  15

Ser Leu Arg Leu Ser Cys Ala Ala Ser Gly Gly Thr Leu Ser Lys Asn
                 20                  25                  30

Thr Val Ala Trp Phe Arg Gln Ala Pro Gly Lys Glu Arg Gly Phe Val
                 35                  40                  45

Ala Ser Ile Thr Trp Asp Gly Arg Thr Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Val Cys
                 85                  90                  95
```

```
Ala Asp Leu Gly Lys Trp Pro Ala Gly Pro Ala Asp Tyr Trp Gly Gln
            100                 105                 110

Gly Thr Gln Val Thr Val Ser Ser
        115                 120

<210> SEQ ID NO 124
<211> LENGTH: 119
<212> TYPE: PRT
<213> ORGANISM: Artificial Sequence
<220> FEATURE:
<223> OTHER INFORMATION: Synthetic Construct

<400> SEQUENCE: 124

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser
        115

<210> SEQ ID NO 125
<211> LENGTH: 119
<212> TYPE: PRT
<213> ORGANISM: Artificial Sequence
<220> FEATURE:
<223> OTHER INFORMATION: Synthetic Construct

<400> SEQUENCE: 125

Ala Val Gln Leu Val Glu Ser Gly Gly Gly Leu Val Gln Ala Gly Asp
1               5                   10                  15

Ser Leu Arg Leu Thr Cys Thr Ala Ser Gly Arg Ala Phe Ser Thr Tyr
            20                  25                  30

Phe Met Ala Trp Phe Arg Gln Ala Pro Gly Lys Glu Arg Glu Phe Val
        35                  40                  45

Ala Gly Ile Ala Trp Ser Gly Gly Ser Thr Ala Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ser Arg Gly Ile Glu Val Glu Glu Phe Gly Ala Trp Gly Gln Gly
            100                 105                 110

Thr Gln Val Thr Val Ser Ser
        115

<210> SEQ ID NO 126
<211> LENGTH: 124
<212> TYPE: PRT
```

<213> ORGANISM: Artificial Sequence
<220> FEATURE:
<223> OTHER INFORMATION: Synthetic Construct

<400> SEQUENCE: 126

```
Glu Val Gln Leu Val Glu Ser Gly Gly Gly Leu Val Pro Pro Gly Gly
1               5                   10                  15

Ser Leu Arg Leu Ser Cys Thr Ala Ser Gly Ser Thr Val Ser Ile Asn
            20                  25                  30

Val Met Ala Trp Tyr Arg Gln Val Ser Gly Lys Gln Arg Glu Leu Val
        35                  40                  45

Ala Ala Val Thr Arg Asp Gly Arg Lys Ser Cys Gly Asp Ser Val Lys
    50                  55                  60

Gly Arg Phe Thr Ile Ser Arg Asp Gly Ala Lys Asn Ala Val Tyr Leu
65                  70                  75                  80

Gln Met Asn Ser Leu Lys Pro Glu Asp Thr Ala Val Tyr Leu Cys Gly
                85                  90                  95

Ala Asp Gly Trp Gly Ala Thr Thr Leu Asp Tyr Thr Tyr Gly Met Asp
            100                 105                 110

Tyr Trp Gly Lys Gly Thr Gln Val Thr Val Ser Ser
        115                 120
```

<210> SEQ ID NO 127
<211> LENGTH: 118
<212> TYPE: PRT
<213> ORGANISM: Artificial Sequence
<220> FEATURE:
<223> OTHER INFORMATION: Synthetic Construct

<400> SEQUENCE: 127

```
Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Gly Phe Val Ala Ser Ile
        35                  40                  45

Thr Trp Asp Gly Arg Ser Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115
```

<210> SEQ ID NO 128
<211> LENGTH: 122
<212> TYPE: PRT
<213> ORGANISM: Artificial Sequence
<220> FEATURE:
<223> OTHER INFORMATION: Synthetic Construct

<400> SEQUENCE: 128

```
Gln Val Gln Leu Val Glu Ser Gly Gly Gly Leu Val Gln Pro Gly Gly
1               5                   10                  15

Ser Leu Arg Leu Ala Cys Glu Ala Pro Gly Ser Gly Asn Ser Ile Asn
            20                  25                  30
```

```
Ala Met Gly Trp Tyr Arg Gln Thr Pro Gly Lys Arg Glu Leu Val
        35                  40                  45

Ala Thr Ile Thr Arg Gly Gly Ser Thr Asn Tyr Gly Pro Ser Val Lys
    50                  55                  60

Gly Arg Phe Thr Ile Thr Arg Asp Asn Val Lys Asn Thr Val His Leu
 65                  70                  75                  80

Gln Met Asn Ser Leu Lys Pro Asp Asp Thr Ala Val Tyr Tyr Cys Asn
                 85                  90                  95

Ala Glu Arg Leu Asp Gly Ser Gly Tyr Gly Tyr Glu Tyr Asp Tyr Trp
            100                 105                 110

Gly Gln Gly Thr Gln Val Thr Val Ser Ser
            115                 120
```

<210> SEQ ID NO 129
<211> LENGTH: 121
<212> TYPE: PRT
<213> ORGANISM: Artificial Sequence
<220> FEATURE:
<223> OTHER INFORMATION: Synthetic Construct

<400> SEQUENCE: 129

```
Gln Val Lys Leu Glu Glu Ser Gly Gly Gly Leu Val Gln Ala Gly Gly
 1               5                  10                  15

Ser Leu Arg Leu Ser Cys Ala Ala Ser Gly Gly Thr Leu Ser Lys Asn
            20                  25                  30

Thr Val Ala Trp Val Arg Gln Ala Pro Gly Lys Glu Arg Gly Phe Val
        35                  40                  45

Thr Ser Ile Thr Cys Asp Gly Arg Thr Thr Tyr Tyr Ala Asn Ser Val
    50                  55                  60

Asn Gly Arg Phe Pro Ile Asn Arg Asn Asn Ala Glu Asn Leu Val Val
 65                  70                  75                  80

Leu Gln Met Asn Ser Leu Lys Pro Asp Asp Thr Ala Leu Tyr Tyr Cys
                 85                  90                  95

Ala Ala Tyr Arg Lys Ser Ile Met Ser Ile Gln Pro Asp Tyr Trp Gly
            100                 105                 110

Gln Gly Thr Gln Val Thr Val Ser Ser
            115                 120
```

<210> SEQ ID NO 130
<211> LENGTH: 121
<212> TYPE: PRT
<213> ORGANISM: Artificial Sequence
<220> FEATURE:
<223> OTHER INFORMATION: Synthetic Construct

<400> SEQUENCE: 130

```
Asp Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45

Gly Ala Ile Met Trp Asn Asp Gly Leu Thr Tyr Leu Gln Gly Ser Val
    50                  55                  60

Lys Gly Arg Phe Thr Ile Ser Arg Asp Asn Ala Lys Asn Thr Val Val
 65                  70                  75                  80

Leu Gln Met Asn Ser Leu Lys Pro Glu Asp Thr Ala Leu Tyr Tyr Cys
```

```
                    85                  90                  95
Ala Ala Asp Arg Lys Ser Val Met Ser Ile Arg Pro Asp Tyr Trp Gly
                100                 105                 110

Gln Gly Thr Gln Val Thr Val Ser Ser
            115                 120

<210> SEQ ID NO 131
<211> LENGTH: 116
<212> TYPE: PRT
<213> ORGANISM: Artificial Sequence
<220> FEATURE:
<223> OTHER INFORMATION: Synthetic Construct

<400> SEQUENCE: 131

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Val Tyr Tyr Cys Ala Ala Arg
                85                  90                  95

Arg Ile Asp Ala Ala Asp Phe Asp Ser Trp Gly Gln Gly Thr Gln Val
                100                 105                 110

Thr Val Ser Ser
        115

<210> SEQ ID NO 132
<211> LENGTH: 120
<212> TYPE: PRT
<213> ORGANISM: Artificial Sequence
<220> FEATURE:
<223> OTHER INFORMATION: Synthetic Construct

<400> SEQUENCE: 132

Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Phe Arg Gln Ala Pro Gly Lys Glu Arg Gly Phe Val
        35                  40                  45

Ala Ser Ile Thr Trp Asp Gly Arg Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Val Cys
                85                  90                  95

Ala Asp Leu Gly Lys Trp Pro Ala Gly Pro Ala Asp Tyr Trp Gly Gln
                100                 105                 110

Gly Thr Gln Val Thr Val Ser Ser
            115                 120

<210> SEQ ID NO 133
<211> LENGTH: 121
```

<212> TYPE: PRT
<213> ORGANISM: Artificial Sequence
<220> FEATURE:
<223> OTHER INFORMATION: Synthetic Construct

<400> SEQUENCE: 133

Gln Val Gln Leu Val Glu Ser Gly Gly Gly Leu Val Gln Pro Gly Gly
1               5                   10                  15

Ser Leu Thr Leu Ser Cys Ala Ala Ser Gly Ser Ile Asp Ser Ile Asn
            20                  25                  30

Thr Met Asp Trp Phe Arg Gln Ala Pro Gly Lys Glu Arg Glu Phe Val
        35                  40                  45

Ala Ala Ile Ser Leu Ser Pro Thr Leu Ala Tyr Tyr Ala Glu Ser Val
    50                  55                  60

Lys Gly Arg Phe Thr Ile Ser Arg Asp Asn Ala Lys Asn Thr Val Val
65                  70                  75                  80

Leu Gln Met Asn Ser Leu Lys Pro Glu Asp Thr Ala Leu Tyr Tyr Cys
                85                  90                  95

Ala Ala Asp Arg Lys Ser Val Met Ser Ile Arg Pro Asp Tyr Trp Gly
            100                 105                 110

Gln Gly Thr Gln Val Thr Val Ser Ser
        115                 120

<210> SEQ ID NO 134
<211> LENGTH: 120
<212> TYPE: PRT
<213> ORGANISM: Artificial Sequence
<220> FEATURE:
<223> OTHER INFORMATION: Synthetic Construct

<400> SEQUENCE: 134

Asp Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Val Arg Gln Ala Pro Gly Lys Glu Arg Gly Phe Val
        35                  40                  45

Thr Ser Ile Thr Cys Asp Gly Arg Thr Thr Tyr Tyr Ala Asn Ser Val
    50                  55                  60

Lys Gly Arg Phe Pro Ile Ser Arg Asp Asn Ala Glu Asn Thr Val Tyr
65                  70                  75                  80

Leu Gln Met Asn Ser Leu Lys Pro Glu Asp Thr Ala Gly Tyr Val Cys
                85                  90                  95

Ala Asp Leu Gly Lys Trp Pro Ala Gly Ser Ala Asp Tyr Trp Gly Gln
            100                 105                 110

Gly Thr His Val Thr Val Ser Ser
        115                 120

<210> SEQ ID NO 135
<211> LENGTH: 121
<212> TYPE: PRT
<213> ORGANISM: Artificial Sequence
<220> FEATURE:
<223> OTHER INFORMATION: Synthetic Construct

<400> SEQUENCE: 135

Gln Val Lys Leu Glu Glu Ser Gly Gly Gly Leu Val Gln Pro Gly Gly
1               5                   10                  15

Ser Leu Arg Leu Ser Cys Thr Ala Ser Glu Phe Thr Phe Ser Asp Tyr

```
            20                  25                  30
Trp Met His Trp Val Arg Gln Ala Pro Gly Lys Gly Leu Glu Trp Val
        35                  40                  45

Ala Ser Ile Asp Thr Ser Gly Gln Thr Thr Tyr Tyr Ala Asp Ser Leu
 50                  55                  60

Lys Gly Arg Phe Thr Ile Ser Arg Asp Asn Ala Lys Ser Thr Leu Tyr
65                  70                  75                  80

Leu Gln Met Asn Ser Leu Lys Ser Glu Asp Thr Gly Val Tyr Phe Cys
                85                  90                  95

Ala Lys Arg Tyr Arg Gly Gly Thr Trp Tyr Gly Met Ala Asn Trp Gly
            100                 105                 110

Lys Gly Thr Gln Val Thr Val Ser Ser
            115                 120
```

<210> SEQ ID NO 136
<211> LENGTH: 120
<212> TYPE: PRT
<213> ORGANISM: Artificial Sequence
<220> FEATURE:
<223> OTHER INFORMATION: Synthetic Construct

<400> SEQUENCE: 136

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Ser Asn
            20                  25                  30

Thr Met Ala Trp Phe Arg Gln Ala Pro Gly Lys Glu Arg Glu Phe Val
        35                  40                  45

Ala Ser Thr Thr Trp Asn Gly Arg Ser Thr Tyr Tyr Ala Asp Ser Val
 50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Val Cys
                85                  90                  95

Ala Asp Leu Gly Lys Trp Pro Ala Gly Pro Ala Asp Tyr Trp Gly Gln
            100                 105                 110

Gly Thr Gln Val Thr Val Ser Ser
            115                 120
```

<210> SEQ ID NO 137
<211> LENGTH: 116
<212> TYPE: PRT
<213> ORGANISM: Artificial Sequence
<220> FEATURE:
<223> OTHER INFORMATION: Synthetic Construct

<400> SEQUENCE: 137

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Gln Arg Glu Leu Val Ala Asp Ile
        35                  40                  45

Ser Gly Gly Arg Thr Asn Tyr Ala Asp Ser Val Lys Gly Arg Phe Thr
 50                  55                  60

Ile Ser Arg Asp Asn Ala Lys Asn Thr Val Tyr Leu Gln Met Asn Ser
65                  70                  75                  80
```

```
Leu Lys Pro Glu Asp Thr Ala Val Tyr Tyr Cys Ala Ala Asp Arg Lys
                85                  90                  95

Ser Val Met Ser Ile Arg Pro Asp Tyr Trp Gly Gln Gly Thr Gln Val
            100                 105                 110

Thr Val Ser Ser
        115

<210> SEQ ID NO 138
<211> LENGTH: 104
<212> TYPE: PRT
<213> ORGANISM: Artificial Sequence
<220> FEATURE:
<223> OTHER INFORMATION: Synthetic Construct

<400> SEQUENCE: 138

Gln Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Thr Val Ala
            20                  25                  30

Ala Ile Ser Leu Ser Pro Thr Leu Ala Tyr Tyr Ala Glu Ser Val Lys
            35                  40                  45

Gly Arg Phe Thr Ile Ser Arg Asp Asn Ala Lys Asn Thr Val Val Leu
    50                  55                  60

Gln Met Asn Ser Leu Lys Pro Glu Asp Thr Ala Leu Tyr Tyr Cys Ala
65                  70                  75                  80

Ala Asp Arg Lys Ser Val Met Ser Ile Arg Pro Asp Tyr Trp Gly Gln
                85                  90                  95

Gly Thr Gln Val Thr Val Ser Ser
            100

<210> SEQ ID NO 139
<211> LENGTH: 125
<212> TYPE: PRT
<213> ORGANISM: Artificial Sequence
<220> FEATURE:
<223> OTHER INFORMATION: Synthetic Construct

<400> SEQUENCE: 139

Asp Val Gln Leu Val Glu Ser Gly Gly Gly Leu Glu Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Phe Arg Gln Ala Pro Gly Lys Glu Arg Gly Phe Val
            35                  40                  45

Ala Ser Ile Thr Trp Asp Gly Arg Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ser Thr Ala Ser Cys His Leu Phe Gly Leu Gly Ser Gly Ala Phe
            100                 105                 110

Val Ser Trp Gly Arg Gly Thr Gln Val Thr Val Ser Ser
            115                 120                 125

<210> SEQ ID NO 140
<211> LENGTH: 116
<212> TYPE: PRT
<213> ORGANISM: Artificial Sequence
```

<220> FEATURE:
<223> OTHER INFORMATION: Synthetic Construct

<400> SEQUENCE: 140

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe His Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Ser
                85                  90                  95

Lys Asp Arg Tyr Ser Glu Tyr Glu Tyr Trp Gly Gln Gly Thr Gln Val
            100                 105                 110

Thr Val Ser Ser
            115

<210> SEQ ID NO 141
<211> LENGTH: 114
<212> TYPE: PRT
<213> ORGANISM: Artificial Sequence
<220> FEATURE:
<223> OTHER INFORMATION: Synthetic Construct

<400> SEQUENCE: 141

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Lys Lys
                85                  90                  95

Asn Gly Gly Pro Val Asp Tyr Trp Gly Lys Gly Thr Gln Val Thr Val
            100                 105                 110

Ser Ser

<210> SEQ ID NO 142
<211> LENGTH: 119
<212> TYPE: PRT
<213> ORGANISM: Artificial Sequence
<220> FEATURE:
<223> OTHER INFORMATION: Synthetic Construct

<400> SEQUENCE: 142

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val

```
            35                  40                  45
Gly Ala Ile Met Trp Asn Asp Gly Ile Thr Tyr Leu Gln Asp Ser Val
     50                  55                  60

Lys Gly Arg Phe Thr Ile Phe Arg Asp Asn Ala Lys Asn Thr Val Tyr
 65                  70                  75                  80

Leu Gln Met Asn Ser Leu Lys Leu Glu Asp Thr Ala Val Tyr Tyr Cys
                 85                  90                  95

Ala Ala Ser Lys Gly Arg Tyr Ser Glu Tyr Glu Tyr Trp Gly Gln Gly
                100                 105                 110

Thr Gln Val Thr Val Ser Ser
            115

<210> SEQ ID NO 143
<211> LENGTH: 118
<212> TYPE: PRT
<213> ORGANISM: Artificial Sequence
<220> FEATURE:
<223> OTHER INFORMATION: Synthetic Construct

<400> SEQUENCE: 143

Gln Val Lys Leu Glu Glu Ser Gly Gly Arg Leu Val Gln Ala Gly Gly
  1               5                  10                  15

Ser Leu Lys Leu Ser Trp Ala Ala Ser Gly Arg Thr Phe Thr Met Gly
                 20                  25                  30

Trp Phe Arg Gln Ala Pro Gly Lys Glu Arg Glu Phe Val Thr Ala Ile
             35                  40                  45

Asn Leu Ser Pro Thr Leu Thr Tyr Tyr Ala Glu Ser Val Lys Gly Arg
 50                  55                  60

Phe Pro Ile Ser Arg Asn Asn Ala Gln Asn Thr Val Val Leu Gln Met
 65                  70                  75                  80

Asn Ser Leu Lys Pro Glu Asp Thr Ala Leu Tyr Tyr Cys Ala Ala Glu
                 85                  90                  95

Arg Lys Ser Val Met Ala Ile Pro Pro Asp Tyr Trp Gly Gln Gly Thr
                100                 105                 110

Gln Val Thr Val Ser Ser
            115

<210> SEQ ID NO 144
<211> LENGTH: 118
<212> TYPE: PRT
<213> ORGANISM: Artificial Sequence
<220> FEATURE:
<223> OTHER INFORMATION: Synthetic Construct

<400> SEQUENCE: 144

Glu Val Gln Leu Val Glu Ser Gly Gly Gly Leu Val Gln Ala Gly Gly
  1               5                  10                  15

Ser Leu Arg Leu Ser Cys Ala Ala Ser Gly Arg Thr Phe Thr Met Gly
                 20                  25                  30

Gly Phe Arg Arg Val Pro Arg Asp Glu Arg Glu Phe Val Ala Ser Ile
             35                  40                  45

Thr Leu Ile Pro Thr Phe Pro Tyr Tyr Ala Tyr Ser Val Lys Gly Arg
 50                  55                  60

Phe Ala Leu Phe Arg Asp Asn Pro Asn Thr Val Ile Leu Leu Met
 65                  70                  75                  80

Ile Ser Leu Lys Pro Glu Asp Pro Asp Leu Tyr Tyr Cys Ala Ser Tyr
                 85                  90                  95
```

Arg Lys Tyr Leu Met Ser Ile Leu Pro Asp Tyr Trp Gly Gln Gly Thr
            100                 105                 110

Gln Gly Thr Val Ser Ser
        115

<210> SEQ ID NO 145
<211> LENGTH: 124
<212> TYPE: PRT
<213> ORGANISM: Artificial Sequence
<220> FEATURE:
<223> OTHER INFORMATION: Synthetic Construct

<400> SEQUENCE: 145

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Asp Leu Gln Met
65                  70                  75                  80

Asn Ser Leu Lys Pro Glu Asp Thr Ala Val Tyr Phe Cys Ala Ala Asn
                85                  90                  95

Arg Asn Ser Gln Arg Val Ile Ala Ala Leu Ser Trp Ile Gly Met Asn
            100                 105                 110

Tyr Trp Gly Glu Trp Thr Gln Val Thr Val Ser Ser
        115                 120

<210> SEQ ID NO 146
<211> LENGTH: 116
<212> TYPE: PRT
<213> ORGANISM: Artificial Sequence
<220> FEATURE:
<223> OTHER INFORMATION: Synthetic Construct

<400> SEQUENCE: 146

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Lys Thr Leu Tyr Leu Arg Met
65                  70                  75                  80

Asn Ser Leu Lys Pro Glu Asp Thr Ala Val Tyr Tyr Cys Ala Ala Arg
                85                  90                  95

Arg Ile Asp Ala Ala Asp Phe Asp Ser Trp Gly Gln Gly Thr Gln Val
            100                 105                 110

Thr Val Ser Ser
        115

<210> SEQ ID NO 147
<211> LENGTH: 116
<212> TYPE: PRT
<213> ORGANISM: Artificial Sequence

```
<220> FEATURE:
<223> OTHER INFORMATION: Synthetic Construct

<400> SEQUENCE: 147

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Arg Ala Pro Gly Lys Glu Arg Glu Ser Val Ala Val Ile
        35                  40                  45

Gly Trp Arg Asp Ile Asn Ala Ser Tyr Ala Asp Ser Val Lys Gly Arg
    50                  55                  60

Phe Ala Ile Ser Arg Asp Asn Ala Lys Lys Thr Leu Tyr Leu Gln Met
65                  70                  75                  80

Asn Ser Leu Lys Pro Glu Asp Thr Ala Val Tyr Tyr Cys Ala Ala Arg
                85                  90                  95

Arg Ile Asp Ala Thr Asp Phe Asp Ser Trp Gly Gln Gly Thr Gln Val
            100                 105                 110

Thr Val Ser Ser
        115

<210> SEQ ID NO 148
<211> LENGTH: 119
<212> TYPE: PRT
<213> ORGANISM: Artificial Sequence
<220> FEATURE:
<223> OTHER INFORMATION: Synthetic Construct

<400> SEQUENCE: 148

Gln Val Lys Leu Glu Glu Ser Gly Gly Gly Leu Val Gln Thr Gly Gly
1               5                   10                  15

Ser Leu Arg Leu Ser Cys Ala Ala Ser Glu His Thr Phe Ser Asn His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Arg Gly Gln Gly
            100                 105                 110

Thr Gln Val Thr Val Ser Ser
        115

<210> SEQ ID NO 149
<211> LENGTH: 123
<212> TYPE: PRT
<213> ORGANISM: Artificial Sequence
<220> FEATURE:
<223> OTHER INFORMATION: Synthetic Construct

<400> SEQUENCE: 149

Ala Val Gln Leu Val Asp Ser Gly Gly Gly Leu Val Gln Ala Gly Gly
1               5                   10                  15

Ser Leu Arg Ile Ser Cys Ala Val Ser Gly Arg Thr Ser Ser Asn Tyr
            20                  25                  30
```

Ile Leu Ala Trp Phe Arg Gln Ala Pro Gly Lys Glu Arg Asp Phe Val
            35                  40                  45

Ala His Ile Ser Arg Ser Gly Gly Lys Ser Gly Tyr Gly Asp Ser Val
 50                  55                  60

Lys Gly Arg Phe Thr Ile Ser Arg Asp Asn Ala Glu Asn Thr Val Arg
 65                  70                  75                  80

Val Tyr Leu Gln Met Asn Ser Leu Lys Pro Gly Asp Thr Ala Val Tyr
                 85                  90                  95

Tyr Cys Asn Arg Pro Leu Trp Tyr Gly Ser Pro Thr Leu Ile Asp Tyr
                 100                 105                 110

Trp Gly Gln Gly Thr Gln Val Thr Val Ser Ser
            115                 120

<210> SEQ ID NO 150
<211> LENGTH: 118
<212> TYPE: PRT
<213> ORGANISM: Artificial Sequence
<220> FEATURE:
<223> OTHER INFORMATION: Synthetic Construct

<400> SEQUENCE: 150

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
            35                  40                  45

Ser Leu Ser Pro Thr Leu Ala Tyr Tyr Ala Glu Ser Val Lys Gly Arg
 50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
                100                 105                 110

Gln Val Thr Val Ser Ser
            115

<210> SEQ ID NO 151
<211> LENGTH: 118
<212> TYPE: PRT
<213> ORGANISM: Artificial Sequence
<220> FEATURE:
<223> OTHER INFORMATION: Synthetic Construct

<400> SEQUENCE: 151

Ala Val Gln Leu Val Asp Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
            35                  40                  45

Ser Leu Ser Pro Thr Leu Ala Tyr Tyr Ala Glu Pro Val Lys Gly Arg
 50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115

<210> SEQ ID NO 152
<211> LENGTH: 121
<212> TYPE: PRT
<213> ORGANISM: Artificial Sequence
<220> FEATURE:
<223> OTHER INFORMATION: Synthetic Construct

<400> SEQUENCE: 152

Asp Val Gln Leu Val Glu Ser Gly Gly Gly Val Gln Thr Gly Gly
1               5                   10                  15

Ser Leu Arg Leu Ser Cys Thr Ala Ser Gly Arg Thr Leu Asn Asn Phe
            20                  25                  30

Val Met Gly Trp Phe Arg Gln Ala Pro Gly Lys Glu Arg Glu Phe Val
        35                  40                  45

Ala Ala Ile Ser Leu Ser Pro Thr Leu Ala Tyr Tyr Val Glu Ser Val
    50                  55                  60

Lys Gly Arg Phe Thr Ile Ser Arg Asp Asn Ala Lys Asn Thr Val Val
65                  70                  75                  80

Leu Gln Met Asn Ser Leu Lys Pro Glu Asp Thr Ala Leu Tyr Tyr Cys
                85                  90                  95

Ala Ala Asp Arg Lys Ser Val Met Ser Ile Arg Pro Asp Tyr Trp Gly
            100                 105                 110

Gln Gly Thr Gln Val Thr Val Ser Ser
        115                 120

<210> SEQ ID NO 153
<211> LENGTH: 366
<212> TYPE: DNA
<213> ORGANISM: Artificial Sequence
<220> FEATURE:
<223> OTHER INFORMATION: Synthetic Construct

<400> SEQUENCE: 153
caggtgcagc tggtggagtc tgggggaggc ttggtgcagc ctggggggtc tctgaggctc      60
tcctgtgaag cctctggatt cactttggat tattatgcca taggctggtt ccgccaggcc     120
ccagggaagg agcgcgaggg ggtcatatgt attagtagaa gtgatggtag cacatactat     180
gcagactccg tgaagggccg attcaccatc tccagagaca cgccaagaa acggtgtat       240 ctgcaaatga tcagcctgaa acctgaggac acggccgctt attactgtgc agcaggggcc     300
gattgttcgg ggtacctacg agattatgag ttcggggc agggacccca ggtcaccgtc       360
tcctca                                                                 366

<210> SEQ ID NO 154
<211> LENGTH: 384
<212> TYPE: DNA
<213> ORGANISM: Artificial Sequence
<220> FEATURE:
<223> OTHER INFORMATION: Synthetic Construct

<400> SEQUENCE: 154
caggtaaagc tggaggagtc tgggggacga ttggtgcagc caaggggctc tctgagactc      60
tcctgtgcag gctctggacg cactttcagt acctatggta tggcctggtt ccgccaggct     120

| | |
|---|---|
| ccagggaagg agcgtgagtt cgtagcgtct aaagcatcga tgaattacag cggtagaaca | 180 |
| tactatgcag actccgtgaa gggccgattc accatcgcca gagacaacgc caagaacatg | 240 |
| gtgtttctgc aaatgaacaa cctgaagcct gaggacacgg ccgtttatta ctgtgcagcg | 300 |
| ggcactggat gctcaacata tggtgttttt gacgcccaga taatagacta ctggggcaaa | 360 |
| gggaccctgg tcaccgtctc ctca | 384 |

<210> SEQ ID NO 155
<211> LENGTH: 354
<212> TYPE: DNA
<213> ORGANISM: Artificial Sequence
<220> FEATURE:
<223> OTHER INFORMATION: Synthetic Construct

<400> SEQUENCE: 155

| | |
|---|---|
| gaggtgcagc tggtggagtc tgggggaggc ttggtgcagg ctggggggtc tctgagactc | 60 |
| tcctgtgcag cctctggacg caccttcacc atggggtggt tccgtcaggc tccagggaag | 120 |
| gagcgtgagt ttgtagcagc tattagtttg agtcctactt tagcatatta tgcagagtcc | 180 |
| gtgaagggcc gattcaccat cagccgagac aacgccaaga acacggtggt tttgcaaatg | 240 |
| aacagcctga aacctgagga cacggccctt tattactgtg cagcagaccg gaaatcagta | 300 |
| atgtctattc ggcccgacta ctggggccag gggacccagg tcaccgtctc ctca | 354 |

<210> SEQ ID NO 156
<211> LENGTH: 360
<212> TYPE: DNA
<213> ORGANISM: Artificial Sequence
<220> FEATURE:
<223> OTHER INFORMATION: Synthetic Construct

<400> SEQUENCE: 156

| | |
|---|---|
| gccgtgcagc tggtggattc tgggggaggc ttggtgcagc ctggggggtc tctgagactc | 60 |
| tcctgtgtag cctctggagg tatcttcgtc atcaatgcca tgggctggta ccgccaggct | 120 |
| ccaggaaagc agcgcgagtt ggtcgcatct attcgtggac taggcagaac aaactatgac | 180 |
| gactccgtga agggccgatt caccatctcc agagacaacg ccaacaacac ggtgtatctg | 240 |
| cagatgaaca gcctggaacc tgaggacacg gccgtctact actgtacagt ctacgttaca | 300 |
| ctacttggtg gggttaatag ggactactgg ggccagggga cccaggtcac cgtctcctca | 360 |

<210> SEQ ID NO 157
<211> LENGTH: 357
<212> TYPE: DNA
<213> ORGANISM: Artificial Sequence
<220> FEATURE:
<223> OTHER INFORMATION: Synthetic Construct

<400> SEQUENCE: 157

| | |
|---|---|
| gaggtgcagc tggtggagtc tgggggagga ttggtgcagg ctggggggctc tctgagactc | 60 |
| tcctgtgcag cctctggacg gaccttcagt agcattgtca tgggctggtt ccgccaggct | 120 |
| ccagggaagg agcgtgagtt tgtaggagcg attatgtgga atgatggtat tacatacttg | 180 |
| caagactccg tgaagggccg atttaccatc ttcagagaca tgccaagaa cacggtgtat | 240 |
| ctgcaaatga acagcctgaa acttgaggat acggccgttt attactgtgc agcatccaag | 300 |
| ggtagatact cggaatatga gtactgggc caggggaccc aggtcaccgt ctcctca | 357 |

<210> SEQ ID NO 158
<211> LENGTH: 384

```
<212> TYPE: DNA
<213> ORGANISM: Artificial Sequence
<220> FEATURE:
<223> OTHER INFORMATION: Synthetic Construct

<400> SEQUENCE: 158
gaggtgcagc tggtggagtc tgggggaggc gtggtgcagg ctgggggtc tctgacagtc        60 tcctgtacag cctctggatt cactttcgac cgtgctgtca tagtctggtt ccgccaggcc      120
cccgggaagg gccgtgaggg ggtctcattt attaaaccta gtgatggcac catatactac      180
attgactccc tgaagggccg attcacgatc tccagtgaca tcgccaagaa tacggtatat      240
ctgcaaatga aaagtctgga atcggaggac tcggccgttt attactgtgc ggcctcgcct      300
gaggactggt acacggattg gatcgactgg agtatatatc ggtggcagca ctggggccag      360
gggacccagg tcactgtctc ctca                                             384

<210> SEQ ID NO 159
<211> LENGTH: 357
<212> TYPE: DNA
<213> ORGANISM: Artificial Sequence
<220> FEATURE:
<223> OTHER INFORMATION: Synthetic Construct

<400> SEQUENCE: 159
gaggtgcagc tggtggagtc tgggggagga atggtgcagg ctggggactc tctgagacta       60
tcctgtgtgc agtctactta caccgtcaat agcgatgtca tgggctggtt ccgccaggct      120
ccagggaagg agcgtgagtt tgtaggagcg attatgtgga atgatggtat tacatacttg      180
caagactccg tgaagggccg atttaccatc ttcagagaca cgccaagaa cacggtgtat       240 ctgcaaatga acagcctgaa acttgaggat acggccgttt attactgtgc agcatccaag      300
ggtagatact cggaatatga gtactgggcc caggggaccc aggtcaccgt ctcctca        357

<210> SEQ ID NO 160
<211> LENGTH: 360
<212> TYPE: DNA
<213> ORGANISM: Artificial Sequence
<220> FEATURE:
<223> OTHER INFORMATION: Synthetic Construct

<400> SEQUENCE: 160
gcggtgcagc tggtggagtc tgggggagga ttggtgcagg ctggggactc tctgagactc       60
tcctgtacag cctctggtgc aaccttgact aacgatcaca tggcatggtt ccgccaggct      120
ccagggaagg ggcgtgaatt tgtagcagct attgactgga gtggtcgtac cacaaattac      180
gcagaccccg tagagggccg attcaccatc tccagaaaca cgccaagaa cacggtgtat       240 ctggaaatga acagcctgaa acttgaggac acggccgttt attactgtgc ggtcctccgc      300
gcttggatct catatgacaa tgactactgg ggccagggga cccaggtcac cgtctcctca      360

<210> SEQ ID NO 161
<211> LENGTH: 360
<212> TYPE: DNA
<213> ORGANISM: Artificial Sequence
<220> FEATURE:
<223> OTHER INFORMATION: Synthetic Construct

<400> SEQUENCE: 161
caggtgcagc tggtggagtc tgggggagga ttggtgcagg ctgggggctc tctgagactc       60
tcctgtgcag cctctggagg caccttaagt aaaaataccg tggcttggtt ccgccaggct      120
```

```
ccagggaagg agcgtgggtt tgtagcgtct attacctggg atggtcgtac gacatactat      180
gcagactccg tgaagggccg attcaccatc tccagagaca acgccaagaa cacagtgtat      240
ctgcaaatga acagcctgaa acctgaggat acggccgttt atgtctgtgc agacttaggg      300
aaatggcctg cgggcccggc ggactactgg ggccagggga cccaggtcac cgtctcctca      360
```

<210> SEQ ID NO 162
<211> LENGTH: 357
<212> TYPE: DNA
<213> ORGANISM: Artificial Sequence
<220> FEATURE:
<223> OTHER INFORMATION: Synthetic Construct

<400> SEQUENCE: 162

```
caggtaaagc tggaggagtc tgggggaggc ttggtgcagg ctgggcggtc tctgagactc       60
tcctgtgcag cctctgaaca caccttcagt agccatgtca tgggctggtt ccgccaggct      120
ccagggaagg agcgtgagtc tgttgcagtt attggctgga gagatattag cacaagctat      180
gcagactccg tgaagggccg attcaccatc tccagagaca acgccaagaa gacgctgtat      240
ctgcaaatga atagcctgaa acctgaggac acggccgttt actactgtgc agcacgtcgg      300
atcgacgcag ctgactttga ttcctggggg caggggaccc aggtcaccgt ctcctcg        357
```

<210> SEQ ID NO 163
<211> LENGTH: 357
<212> TYPE: DNA
<213> ORGANISM: Artificial Sequence
<220> FEATURE:
<223> OTHER INFORMATION: Synthetic Construct

<400> SEQUENCE: 163

```
gcggtgcagc tggtggagtc tgggggagga ttggtgcagg ctggggactc tctgagactc       60
acctgtacag cctctggacg cgccttcagt acctatttca tggcctggtt ccgccaggct      120
ccagggaagg agcgtgagtt tgtagcagga attgcatgga gtggtggtag cacggcgtat      180
gcagactccg tgaagggccg attcaccatc tccagagaca acgccaagaa cacggtgtat      240
ctgcaaatga acagcctgaa atctgaggac acggccgttt attactgtgc cagcagggga      300
attgaggtcg aagagtttgg tgcctggggc caggggaccc aggtcaccgt ctcgtcg        357
```

<210> SEQ ID NO 164
<211> LENGTH: 372
<212> TYPE: DNA
<213> ORGANISM: Artificial Sequence
<220> FEATURE:
<223> OTHER INFORMATION: Synthetic Construct

<400> SEQUENCE: 164

```
gaggtgcagc tggtggagtc tgggggaggc ttggtgccgc ctgggggtc tctgagactc        60 tcctgtacag cctctggaag cacagtcagc atcaatgtca tggcctggta ccgccaggtt      120
tcagggaagc agcgcgagtt ggtcgcggcc gttactaggg atggtaggaa aagttgtgga      180
gactccgtga agggccgatt caccatttcc agagacggcg ccaagaatgc ggtatatttg      240
caaatgaaca gtctgaaacc tgaggacaca gcgtctatt tatgtggagc cgatggttgg      300
ggtgctacta ccttagatta tacctacggc atggactatt ggggcaaagg gacccaggtc      360
accgtctcct ca                                                          372
```

<210> SEQ ID NO 165
<211> LENGTH: 354

```
<212> TYPE: DNA
<213> ORGANISM: Artificial Sequence
<220> FEATURE:
<223> OTHER INFORMATION: Synthetic Construct

<400> SEQUENCE: 165
gcggtgcagc tggtggagtc tggggagga ttggtgcagg ctgggggctc tctgagactc      60
tcctgtgcag cctctggacg caccttcacc atgggtggt tccgtcaggc tccagggaag     120
gagcgtgggt ttgtagcgtc tattacctgg gatggtcgtt cggcatacta tgcagagtcc    180
gtgaagggcc gattcaccat cagccgagac aacgccaaga acacggtggt tttgcaaatg    240
aacagcctga aacctgagga cacggccctt tattactgtg cagcagaccg gaaatcagta    300
atgtctattc ggcccgacta ctggggccag ggacccagg tcaccgtctc ctca           354

<210> SEQ ID NO 166
<211> LENGTH: 366
<212> TYPE: DNA
<213> ORGANISM: Artificial Sequence
<220> FEATURE:
<223> OTHER INFORMATION: Synthetic Construct

<400> SEQUENCE: 166
caggtacagc tggtggagtc tggggagga ttggtgcagc ctgggggtc tctaagactc       60 gcatgtgaag cgcctggaag cggcaatagt atcaatgcca tggctggta ccggcagact     120 ccggggaagc ggcgcgagtt ggtcgcaact attactcggg gtggtagcac gaactatgga    180
ccctccgtga agggccgatt cacgatcacc agagacaatg tcaagaatac ggtgcatctg    240
cagatgaaca gcctgaaacc tgacgacacg gccgtctatt attgcaatgc ggagaggctg    300
gacggctcgg ggtacggata tgagtatgat tactggggcc aggggaccca ggtcaccgtc    360
tcctca                                                               366

<210> SEQ ID NO 167
<211> LENGTH: 363
<212> TYPE: DNA
<213> ORGANISM: Artificial Sequence
<220> FEATURE:
<223> OTHER INFORMATION: Synthetic Construct

<400> SEQUENCE: 167
caggtaaagc tggaggagtc tggggagga ttggtgcagg ctgggggctc tctgagactc      60
tcctgtgcag cctctggagg caccttaagt aagaataccg tggcttgggt ccgccaggct    120
ccagggaagg agcgtgggtt tgtaacgtct attacctgtg atggtcgtac gacatactat    180
gcgaactccg taaacggccg attccccatc aaccgaaaca cgccgagaa tttggtggtt    240 ttgcaaatga acagcctgaa acctgacgac acggcccttt attactgtgc agcataccgg    300
aagtcaataa tgtctattca gcccgactac tggggccagg gacccaggt caccgtctcc    360 tca                                                                  363

<210> SEQ ID NO 168
<211> LENGTH: 363
<212> TYPE: DNA
<213> ORGANISM: Artificial Sequence
<220> FEATURE:
<223> OTHER INFORMATION: Synthetic Construct

<400> SEQUENCE: 168
gatgtgcagc tggtggagtc tggggagga ttggtgcagg ctgggggctc tctgagactc      60
```

```
tcctgtgcag cctctggacg gaccttcagt agcattgtca tgggctggtt ccgccaggct    120
ccagggaagg agcgtgagtt tgtaggagcg attatgtgga atgatggtct gacatacttg    180
caagggtccg tgaagggccg attcaccatt tccagagaca cgccaagaa cacggtggtt     240 ttgcaaatga acagcctgaa acctgaggac acggcccttt attactgtgc agcagaccgg    300
aaatcagtaa tgtctattcg gcccgactac tggggccagg ggacccaggt caccgtctcc    360
tca                                                                  363
```

<210> SEQ ID NO 169
<211> LENGTH: 348
<212> TYPE: DNA
<213> ORGANISM: Artificial Sequence
<220> FEATURE:
<223> OTHER INFORMATION: Synthetic Construct

<400> SEQUENCE: 169

```
caggtacagc tggtggagtc tgggggagga ttggtgcagg ctggggctc tctgagactc      60 tcctgtgcag cctctggacg caccttcacc atggggtggt ccgtcaggc tccagggaag    120 gagcgtgagt ttgtagcagc tattagtttg agtcctactt tagcatatta tgcagagtcc    180
gtgaagggcc gattcaccat cagccgagac aacgccaaga cacggtggt tttgcaaatg    240 aacagcctga aacctgagga cacggccgtt tactactgtg cagcacgtcg gatcgacgca    300
gctgactttg attcctgggg gcagggggacc caggtcaccg tctcctca               348
```

<210> SEQ ID NO 170
<211> LENGTH: 360
<212> TYPE: DNA
<213> ORGANISM: Artificial Sequence
<220> FEATURE:
<223> OTHER INFORMATION: Synthetic Construct

<400> SEQUENCE: 170

```
caggtacagc tggtggagtc tgggggagga ttggtgcagg ctggggctc tctgagactc      60 tcctgtgcag cctctggagg caccttaagt aaaaataccg tggcttggtt ccgccaggct    120
ccagggaagg agcgtgggtt tgtagcgtct attacctggg atggtcgtac gacatactat    180
gcagactccg tgaagggccg attcaccatc tccagagaca cgccaagaa cacagtgtat    240 ctgcaaatga acagcctgaa acctgaggat acggccgttt atgtctgtgc agacttaggg    300
aaatggcctg cgggcccggc ggactactgg ggccagggga cccaggtcac cgtctcctca    360
```

<210> SEQ ID NO 171
<211> LENGTH: 363
<212> TYPE: DNA
<213> ORGANISM: Artificial Sequence
<220> FEATURE:
<223> OTHER INFORMATION: Synthetic Construct

<400> SEQUENCE: 171

```
caggtgcagc tggtggagtc tgggggaggc ttggtgcagc ctgggggggtc tctgacactc      60 tcctgtgcag cctctggaag catcgacagt atcaatacca tggactggtt ccgtcaggct    120
ccagggaagg agcgtgagtt tgtagcagct attagtttga gtcccacttt agcatattat    180
gcagagtccg tgaagggccg attcaccatc agccgagaca cgccaagaa cacggtggtt    240 ttgcaaatga acagcctgaa acctgaggac acggcccttt attactgtgc agcagaccgg    300
aaatcagtaa tgtctattcg gcccgactac tggggccagg ggacccaggt caccgtctcc    360
tca                                                                  363
```

<210> SEQ ID NO 172
<211> LENGTH: 360
<212> TYPE: DNA
<213> ORGANISM: Artificial Sequence
<220> FEATURE:
<223> OTHER INFORMATION: Synthetic Construct

<400> SEQUENCE: 172

```
gatgtgcagc tggtggagtc tgggggagga ttggtgcagg ctgggggctc tctgagactc      60
tcctgtgcag cctctggagg caccttaagt aagaataccg tggcttgggt ccgccaggct     120
ccagggaagg agcgtgggtt tgtaacgtct attacctgtg atggtcgtac gacatactat     180
gcgaactccg tgaagggccg attccccatc tccagagaca acgccgagaa cacagtgtat     240
ctgcaaatga acagcctgaa acctgaggat acggccggtt atgtctgtgc agacttaggg     300
aagtggcctg cgggttcggc ggactactgg ggccagggga cccacgtcac cgtctcctcc     360
```

<210> SEQ ID NO 173
<211> LENGTH: 363
<212> TYPE: DNA
<213> ORGANISM: Artificial Sequence
<220> FEATURE:
<223> OTHER INFORMATION: Synthetic Construct

<400> SEQUENCE: 173

```
caggtaaagc tggaggagtc tgggggaggc ttggtgcagc ctgggggtc tctgagactc       60
tcctgtacag cctcggaatt cacattcagt gactactgga tgcattgggt ccgtcaggct     120
ccggggaagg ggctcgagtg ggtcgcatct atagatacta gtggacagac cacatactat     180
gcagactccc tgaagggccg attcaccatc tccagagaca acgccaagag cacgttgtat     240
ctgcaaatga acagtctgaa atctgaagac acggcgtgt atttctgtgc aaaacgatat      300
aggggtggta cctggtatgg catggccaac tggggcaaag gacccaggt caccgtctcc      360
tca                                                                    363
```

<210> SEQ ID NO 174
<211> LENGTH: 360
<212> TYPE: DNA
<213> ORGANISM: Artificial Sequence
<220> FEATURE:
<223> OTHER INFORMATION: Synthetic Construct

<400> SEQUENCE: 174

```
caggtgcagc tggtggagtc tgggggagga ttggtgcagg ctgggggctc tctgagactc      60
tcctgtgcag cctctggacg caccttaagt agtaatacca tggcttggtt ccgccaggct     120
ccagggaagg agcgtgagtt tgtagcgtct actacctgga atggtcgtag cacatactat     180
gcagactccg tgaagggccg attcaccatc tccagagaca acgccaagaa cacgatgtat     240
ctgcaaatga acagcctgaa acctgaggat acggccgttt atgtctgtgc agacttaggg     300
aaatggcctg cgggcccggc ggactactgg ggccagggga cccaggtcac cgtctcctca     360
```

<210> SEQ ID NO 175
<211> LENGTH: 348
<212> TYPE: DNA
<213> ORGANISM: Artificial Sequence
<220> FEATURE:
<223> OTHER INFORMATION: Synthetic Construct

<400> SEQUENCE: 175

| | |
|---|---|
| caggtgcagc tggtggagtc tggggagga ttggtgcagg ctgggggctc tctgagactc | 60 |
| tcctgtgcag cctctggacg caccttcacc atggggtggt tccgtcaggc tccaggaag | 120 |
| cagcgcgaat tggtcgcaga tattagtggt ggtcgcacaa actatgcaga ttccgtgaag | 180 |
| ggacgattca ccatctccag agacaacgcc aagaacacgg tatatctgca aatgaacagc | 240 |
| ctgaaacctg aggacacggc cgtttattac tgtgcagcag accggaaatc agtaatgtct | 300 |
| attcggcccg actactgggg ccaggggacc caggtcaccg tctcctca | 348 |

<210> SEQ ID NO 176
<211> LENGTH: 312
<212> TYPE: DNA
<213> ORGANISM: Artificial Sequence
<220> FEATURE:
<223> OTHER INFORMATION: Synthetic Construct

<400> SEQUENCE: 176

| | |
|---|---|
| caggtgcagc tggtggagtc tgggggaggc ttggtgcagg ctgggggcctc tctgagactc | 60 |
| tcctgtgcag cctctggacg caccttcacc gtggcagcta ttagtttgag tcctactttta | 120 |
| gcatattatg cagagtccgt gaagggccga ttcaccatca gccgagacaa cgccaagaac | 180 |
| acggtggttt tgcaaatgaa cagcctgaaa cctgaggaca cggcccttta ttactgtgca | 240 |
| gcagaccgga aatcagtaat gtctattcgg cccgactact ggggccaggg gacccaggtc | 300 |
| accgtctcct ca | 312 |

<210> SEQ ID NO 177
<211> LENGTH: 375
<212> TYPE: DNA
<213> ORGANISM: Artificial Sequence
<220> FEATURE:
<223> OTHER INFORMATION: Synthetic Construct

<400> SEQUENCE: 177

| | |
|---|---|
| gatgtgcagc tggtggagtc tgggggagga ttggagcagg ctgggggctc tctgagactc | 60 |
| tcctgtgcag cctctggagg caccttaagt aaaaatacccg tggcttggtt ccgccaggct | 120 |
| ccagggaagg agcgtgggtt tgtagcgtct attacctggg atggtcgtac gacatactat | 180 |
| gcagactccg tgaagggccg attcaccatc tccagagaca cgccaagaa cacagtgtat | 240 |
| ctgcaaatga acagcctgaa acctgaggat acgccgtttt attactgtgc gtcgacggca | 300 |
| tcgtgccacc tcttcggatt ggggtccggg gcctttgtgt cctggggccg ggggacccag | 360 |
| gtcaccgtct cctca | 375 |

<210> SEQ ID NO 178
<211> LENGTH: 348
<212> TYPE: DNA
<213> ORGANISM: Artificial Sequence
<220> FEATURE:
<223> OTHER INFORMATION: Synthetic Construct

<400> SEQUENCE: 178

| | |
|---|---|
| gcggtgcagc tggtggagtc tgggggagga ttggtgcagg ctgggggctc tctgagactc | 60 |
| tcctgtgcag cctctggacg caccttcacc atggggtggt tccatcaggc tccaggaag | 120 |
| gagcgtgagt ttgtagcagc tattagtttg agtcctactt tagcatatta tgcagagtcc | 180 |
| gtgaagggcc gattcaccat cagccgagac aacgccaaga acacggtggt tttgcaaatg | 240 |
| aacagcctga aacctgagga cacgccctt tattactgtg cagcatccaa ggatagatat | 300 |
| tcggaatatg agtactgggg ccaggggacc caggtcaccg tctcctca | 348 |

<210> SEQ ID NO 179
<211> LENGTH: 342
<212> TYPE: DNA
<213> ORGANISM: Artificial Sequence
<220> FEATURE:
<223> OTHER INFORMATION: Synthetic Construct

<400> SEQUENCE: 179

```
caggtaaagc tggaggagtc tggggaggga ttggtgcagg ctgggggctc tctgagactc      60
tcctgtgcag cctctggacg caccttcacc atggggtggt tccgtcaggc tccagggaag     120
gagcgtgagt ttgtagcagc tattagtttg agtcctactt tagcatatta tgcagagtcc     180
gtgaagggcc gattcaccat cagccgagac aacgccaaga acacggtggt tttgcaaatg     240
aacagcctga aacctgagga cacggccctt tattactgtg caaaaaaaaa cgggggggcct     300
gtggactact ggggcaaagg gacccaggtc accgtctcct ca                        342
```

<210> SEQ ID NO 180
<211> LENGTH: 357
<212> TYPE: DNA
<213> ORGANISM: Artificial Sequence
<220> FEATURE:
<223> OTHER INFORMATION: Synthetic Construct

<400> SEQUENCE: 180

```
gatgtgcagc tggtggagtc tggggaggc ttggtgcagc ctgggggtc tctgagactc       60
tcctgtgcag cctctggacg gaccttcagt agcattgtca tgggctggtt ccgccaggct    120
ccagggaagg agcgtgagtt tgtaggagcg attatgtgga atgatggtat tacatacttg    180
caagactccg tgaagggccg atttaccatc ttcagagaca acgccaagaa cacggtgtat    240
ctgcaaatga acagcctgaa acttgaggat acggccgttt attactgtgc agcatccaag    300
ggtagatact cggaatatga gtactggggc caggggaccc aggtcaccgt ctcctca      357
```

<210> SEQ ID NO 181
<211> LENGTH: 354
<212> TYPE: DNA
<213> ORGANISM: Artificial Sequence
<220> FEATURE:
<223> OTHER INFORMATION: Synthetic Construct

<400> SEQUENCE: 181

```
caggtaaagc tggaggaatc tggggaagga ttggtgcagg ctgggggctc tctgaaactc      60
tcctgggcag cctctggacg caccttcacc atggggtggt tccgtcaggc tccagggaag    120
gaacgtgagt ttgtaacagc tattaatttg agtcctactt taacatatta tgcagaatcc    180
gtgaagggcc gattcccat cagccgaaac aacgcccaga acacggtggt tttgcaaatg     240
aacagcctga aacctgagga cacggccctt tattactgtg cagcagaacg gaaatcagta    300
atggctattc cgcccgacta ctggggccag gggacccagg tcaccgtctc ctca           354
```

<210> SEQ ID NO 182
<211> LENGTH: 354
<212> TYPE: DNA
<213> ORGANISM: Artificial Sequence
<220> FEATURE:
<223> OTHER INFORMATION: Synthetic Construct

<400> SEQUENCE: 182

```
gaggtgcagc tggtggagtc tggggaggga ttggtgcagg ctgggggctc tctgagactc      60
```

| | |
|---|---|
| tcctgtgcag cctctggacg caccttcacc atgggggggt tccgtcgggt tcctcgggat | 120 |
| gagcgggagt ttgtagcatc tattactttg attcctactt ttccttatta tgcatattcc | 180 |
| gtgaagggcc gattcgccct cttccgagac aaccccaaca acaccgtgat tttgctgatg | 240 |
| atcagcctga aacctgagga cccggacctt tattactgtg cttcataccg gaaataccta | 300 |
| atgtctattc tgcccgacta ctggggccag gggacccagg gcaccgtctc ctcc | 354 |

```
<210> SEQ ID NO 183
<211> LENGTH: 372
<212> TYPE: DNA
<213> ORGANISM: Artificial Sequence
<220> FEATURE:
<223> OTHER INFORMATION: Synthetic Construct

<400> SEQUENCE: 183
```

| | |
|---|---|
| caggtaaagc tggaggagtc tgggggagga ttggtgcagg ctgggggctc tctgagactc | 60 |
| tcctgtgcag cctctggacg caccttcacc atggggtggt tccgtcaggc tccagggaag | 120 |
| gagcgtgagt ttgtagcagc tattagtttg agtcctactt tagcatatta tgcagagtcc | 180 |
| gtgaagggcc gattcaccat cagccgagac aacgccaaga acacggtgga tctgcaaatg | 240 |
| aacagcctga aacctgagga cacggccgtc tatttctgtg cagcaaatcg gaactcccaa | 300 |
| cgggtaattg cggcactgtc ctggattggc atgaactact ggggcgaatg gacccaggtc | 360 |
| accgtctcct cc | 372 |

```
<210> SEQ ID NO 184
<211> LENGTH: 348
<212> TYPE: DNA
<213> ORGANISM: Artificial Sequence
<220> FEATURE:
<223> OTHER INFORMATION: Synthetic Construct

<400> SEQUENCE: 184
```

| | |
|---|---|
| caggtgcagc tggtggagtc tgggggagga ttggtgcagg ctgggggctc tctgagactc | 60 |
| tcctgtgcag cctctggacg caccttcacc atggggtggt tccgtcaggc tccagggaag | 120 |
| gagcgtgagt ttgtagcagc tattagtttg agtcctactt tagcatatta tgcagagtcc | 180 |
| gtgaagggcc gattcaccat ctccagagac aacgccaaga agacgctgta tctgcgaatg | 240 |
| aatagcctga aacctgagga cacggccgtt tactactgtg cagcacgtcg gatcgacgca | 300 |
| gctgactttg attcctgggg gcaggggacc caggtcaccg tctcctca | 348 |

```
<210> SEQ ID NO 185
<211> LENGTH: 348
<212> TYPE: DNA
<213> ORGANISM: Artificial Sequence
<220> FEATURE:
<223> OTHER INFORMATION: Synthetic Construct

<400> SEQUENCE: 185
```

| | |
|---|---|
| caggtaaagc tggaggagtc tgggggagga ttggtgcagg ctgggggctc tctgagactc | 60 |
| tcctgtgcag cctctggacg caccttcacc atgggtggt tccgtcgggc tccagggaag | 120 |
| gagcgtgagt ctgttgcagt tattggctgg agagatatta acgcaagcta tgcagactcc | 180 |
| gtgaagggcc gattcgccat ctccagagac aacgccaaga agacgctgta tctgcagatg | 240 |
| aatagcctga aacctgagga cacggccgtt tactactgtg cagcacgtcg gatcgacgca | 300 |
| actgactttg attcctgggg gcaggggacc caggtcaccg tctcctca | 348 |

```
<210> SEQ ID NO 186
<211> LENGTH: 357
<212> TYPE: DNA
<213> ORGANISM: Artificial Sequence
<220> FEATURE:
<223> OTHER INFORMATION: Synthetic Construct

<400> SEQUENCE: 186
caggtaaagc tggaggagtc tgggggagga ttggtgcaga ctgggggctc tctgagactc      60
tcctgtgcag cctctgaaca caccttcagt aaccatgtca tggctggtt ccgccaggct      120 ccagggaagg agcgtgagtc tgttgcagtt attggctgga gagatattag cacaagctat    180
gcagactccg tgaagggccg attcaccatc tccagagaca cgccaagaa gacgctgtat     240 ctgcaaatga atagcctgaa acctgaggac acggccgttt actactgtgc agcacgtcgg    300
atcgacgcag ctgactttga ttcccggggg cagggaccc aggtcaccgt ctcctca       357

<210> SEQ ID NO 187
<211> LENGTH: 369
<212> TYPE: DNA
<213> ORGANISM: Artificial Sequence
<220> FEATURE:
<223> OTHER INFORMATION: Synthetic Construct

<400> SEQUENCE: 187
gccgtgcagc tggtggattc tgggggagga ttggtgcagg ctgggggctc tctgagaatt      60
tcctgtgcag tctctggacg cacctccagt aactatatat tggcctggtt ccgtcaggct     120
ccaggaaaag agcgtgactt tgtagcacat attagccgga gtggtggtaa gtccggctat    180
ggagactccg tgaagggccg attcaccatc tccagagaca cgccgagaa cacggtcagg     240 gtgtatctgc aaatgaacag tctgaaacct ggggacacgg ccgtctatta ctgtaatcgc    300
cccctctggt acggaagtcc cacgttgatt gactactggg gccaggggac ccaggtcacc   360
gtctcctca                                                            369

<210> SEQ ID NO 188
<211> LENGTH: 354
<212> TYPE: DNA
<213> ORGANISM: Artificial Sequence
<220> FEATURE:
<223> OTHER INFORMATION: Synthetic Construct

<400> SEQUENCE: 188
gcggtgcagc tggtggagtc tgggggaggc ttggtgcagc ctgggggtc tctgagactc      60 tcctgtgcag cctctggacg caccttcacc atggggtggt ccgtcaggc tccagggaag    120 gagcgtgagt ttgtagcagc tattagtttg agtcctactt tagcatatta tgcagagtcc    180
gtgaagggcc gattcaccat cagccgagac aacgccaaga acacggtggt tttgcaaatg   240
aacagcctga aacctgagga cacggccctt tattactgtg cagcagaccg gaaatcagta   300
atgtctattc ggcccgacta ctggggccag gggacccagg tcaccgtctc ctca         354

<210> SEQ ID NO 189
<211> LENGTH: 354
<212> TYPE: DNA
<213> ORGANISM: Artificial Sequence
<220> FEATURE:
<223> OTHER INFORMATION: Synthetic Construct

<400> SEQUENCE: 189
gcggtgcagc tggtggagtc tgggggagga ttggtgcagg ctgggggctc tctgagactc      60
```

```
tcctgtgcag cctctggacg caccttcacc atggggtggt tccgtcaggc tccagggaag    120
gagcgtgagt ttgtagcagc tattagtttg agtcctactt tagcatatta tgcagagtcc    180
gtgaagggcc gattcaccat cagccgagac aacgccaaga acacggtggt tttgcaaatg    240
aacagcctga aacctgagga cacggcccct tattactgtg cagcagaccg gaaatcagta    300
atgtctattc ggcccgacta ctggggccag gggacccagg tcaccgtctc ctca          354
```

<210> SEQ ID NO 190
<211> LENGTH: 363
<212> TYPE: DNA
<213> ORGANISM: Artificial Sequence
<220> FEATURE:
<223> OTHER INFORMATION: Synthetic Construct

<400> SEQUENCE: 190

```
gatgtgcagc tggtggagtc tgggggagga tcggtgcaga ctggggggctc tctgagactc    60 tcctgtacag cctctggacg caccctcaat aactttgtca tgggctggtt ccgtcaggct   120
ccagggaagg agcgtgagtt tgtagcagct attagtttga gtcctacttt agcatattat   180
gtagagtccg tgaagggccg attcaccatc agccgagaca acgccaagaa cacggtggtt   240
ttgcaaatga acagcctgaa acctgaggac acggcccttt attactgtgc agcagaccgg   300
aaatcagtaa tgtctattcg gcccgactac tggggccagg gacccaggt caccgtctcc    360 tca                                                                  363
```

<210> SEQ ID NO 191
<211> LENGTH: 21
<212> TYPE: PRT
<213> ORGANISM: Artificial Sequence
<220> FEATURE:
<223> OTHER INFORMATION: Synthetic Construct

<400> SEQUENCE: 191

Met Ala Leu Pro Val Thr Ala Leu Leu Leu Pro Leu Ala Leu Leu Leu
1               5                   10                  15

His Ala Ala Arg Pro
            20

<210> SEQ ID NO 192
<211> LENGTH: 45
<212> TYPE: PRT
<213> ORGANISM: Artificial Sequence
<220> FEATURE:
<223> OTHER INFORMATION: Synthetic Construct

<400> SEQUENCE: 192

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 193
<211> LENGTH: 24
<212> TYPE: PRT
<213> ORGANISM: Artificial Sequence
<220> FEATURE:
<223> OTHER INFORMATION: Synthetic Construct

<400> SEQUENCE: 193

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 194
<211> LENGTH: 27
<212> TYPE: PRT
<213> ORGANISM: Artificial Sequence
<220> FEATURE:
<223> OTHER INFORMATION: Synthetic Construct

<400> SEQUENCE: 194

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 195
<211> LENGTH: 41
<212> TYPE: PRT
<213> ORGANISM: Artificial Sequence
<220> FEATURE:
<223> OTHER INFORMATION: Synthetic Construct

<400> SEQUENCE: 195

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40
```

<210> SEQ ID NO 196
<211> LENGTH: 42
<212> TYPE: PRT
<213> ORGANISM: Artificial Sequence
<220> FEATURE:
<223> OTHER INFORMATION: Synthetic Construct

<400> SEQUENCE: 196

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40
```

<210> SEQ ID NO 197
<211> LENGTH: 113
<212> TYPE: PRT
<213> ORGANISM: Artificial Sequence
<220> FEATURE:
<223> OTHER INFORMATION: Synthetic Construct

<400> SEQUENCE: 197

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45
```

```
Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Ala Leu Pro Pro
                100                 105                 110

Arg
```

<210> SEQ ID NO 198
<211> LENGTH: 113
<212> TYPE: PRT
<213> ORGANISM: Artificial Sequence
<220> FEATURE:
<223> OTHER INFORMATION: Synthetic Construct

<400> SEQUENCE: 198

```
Arg Val Lys Phe Ser Arg Ser Ala Asp Ala Pro Ala Tyr Lys Gln Gly
 1               5                  10                  15

Gln Asn Gln Leu Tyr Asn Glu Leu Asn Leu Gly Arg Arg Glu Glu Tyr
                 20                  25                  30

Asp Val Leu Asp Lys Arg Arg Gly Arg Asp Pro Glu Met Gly Gly Lys
                 35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Ala Leu Pro Pro
                100                 105                 110

Arg
```

<210> SEQ ID NO 199
<211> LENGTH: 63
<212> TYPE: DNA
<213> ORGANISM: Artificial Sequence
<220> FEATURE:
<223> OTHER INFORMATION: Synthetic Construct

<400> SEQUENCE: 199
atggccttac cagtgaccgc cttgctcctg ccgctggcct tgctgctcca cgccgccagg    60
ccg                                                                 63

<210> SEQ ID NO 200
<211> LENGTH: 63
<212> TYPE: DNA
<213> ORGANISM: Artificial Sequence
<220> FEATURE:
<223> OTHER INFORMATION: Synthetic Construct

<400> SEQUENCE: 200
atggctctgc ccgtcactgc tctgctgctg cccctggctc tgctgctgca cgccgcaaga    60
ccc                                                                 63

<210> SEQ ID NO 201
<211> LENGTH: 135
<212> TYPE: DNA

<213> ORGANISM: Artificial Sequence
<220> FEATURE:
<223> OTHER INFORMATION: Synthetic Construct

<400> SEQUENCE: 201

```
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135
```

<210> SEQ ID NO 202
<211> LENGTH: 72
<212> TYPE: DNA
<213> ORGANISM: Artificial Sequence
<220> FEATURE:
<223> OTHER INFORMATION: Synthetic Construct

<400> SEQUENCE: 202

```
atctacatct gggcgccctt ggccgggact tgtggggtcc ttctcctgtc actggttatc    60
accctttact gc                                                       72
```

<210> SEQ ID NO 203
<211> LENGTH: 81
<212> TYPE: DNA
<213> ORGANISM: Artificial Sequence
<220> FEATURE:
<223> OTHER INFORMATION: Synthetic Construct

<400> SEQUENCE: 203

```
ttttgggtgc tggtggtggt tggtggagtc ctggcttgct atagcttgct agtaacagtg    60
gcctttatta ttttctgggt g                                             81
```

<210> SEQ ID NO 204
<211> LENGTH: 123
<212> TYPE: DNA
<213> ORGANISM: Artificial Sequence
<220> FEATURE:
<223> OTHER INFORMATION: Synthetic Construct

<400> SEQUENCE: 204

```
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123
```

<210> SEQ ID NO 205
<211> LENGTH: 126
<212> TYPE: DNA
<213> ORGANISM: Artificial Sequence
<220> FEATURE:
<223> OTHER INFORMATION: Synthetic Construct

<400> SEQUENCE: 205

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 206
<211> LENGTH: 336
<212> TYPE: DNA
<213> ORGANISM: Artificial Sequence
<220> FEATURE:
<223> OTHER INFORMATION: Synthetic Construct
```

<400> SEQUENCE: 206

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc    240
cggagggggca agggcacga tggcctttac cagggtctca gtacagccac caaggacacc    300
tacgacgccc ttcacatgca ggccctgccc cctcgc                              336
```

<210> SEQ ID NO 207
<211> LENGTH: 336
<212> TYPE: DNA
<213> ORGANISM: Artificial Sequence
<220> FEATURE:
<223> OTHER INFORMATION: Synthetic Construct

<400> SEQUENCE: 207

```
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc    240
cggagggggca agggcacga tggcctttac cagggtctca gtacagccac caaggacacc    300
tacgacgccc ttcacatgca ggccctgccc cctcgc                              336
```

<210> SEQ ID NO 208
<211> LENGTH: 5
<212> TYPE: PRT
<213> ORGANISM: Artificial Sequence
<220> FEATURE:
<223> OTHER INFORMATION: Synthetic Construct

<400> SEQUENCE: 208

Gly Gly Gly Gly Ser
1               5

<210> SEQ ID NO 209
<211> LENGTH: 10
<212> TYPE: PRT
<213> ORGANISM: Artificial Sequence
<220> FEATURE:
<223> OTHER INFORMATION: Synthetic Construct

<400> SEQUENCE: 209

Gly Gly Gly Gly Ser Gly Gly Gly Gly Ser
1               5                   10

<210> SEQ ID NO 210
<211> LENGTH: 16
<212> TYPE: PRT
<213> ORGANISM: Artificial Sequence
<220> FEATURE:
<223> OTHER INFORMATION: Synthetic Construct

<400> SEQUENCE: 210

Gly Gly Gly Ser Gly Gly Gly Ser Gly Gly Gly Ser Gly Gly Gly Ser
1               5                   10                  15

<210> SEQ ID NO 211
<211> LENGTH: 24

<212> TYPE: PRT
<213> ORGANISM: Artificial Sequence
<220> FEATURE:
<223> OTHER INFORMATION: Synthetic Construct

<400> SEQUENCE: 211

Gly Gly Gly Gly Ser Gly Gly Gly Ser Gly Gly Gly Gly Gly
1               5                   10                  15

Ser Gly Ser Gly Gly Gly Gly Ser
            20

<210> SEQ ID NO 212
<211> LENGTH: 34
<212> TYPE: PRT
<213> ORGANISM: Artificial Sequence
<220> FEATURE:
<223> OTHER INFORMATION: Synthetic Construct

<400> SEQUENCE: 212

Gly Gly Gly Gly Ser Gly Gly Gly Ser Gly Gly Gly Gly Gly
1               5                   10                  15

Ser Gly Ser Gly Gly Gly Gly Ser Gly Gly Gly Gly Ser Gly Gly
            20                  25                  30

Gly Ser

<210> SEQ ID NO 213
<211> LENGTH: 15
<212> TYPE: PRT
<213> ORGANISM: Artificial Sequence
<220> FEATURE:
<223> OTHER INFORMATION: Synthetic Construct

<400> SEQUENCE: 213

Gly Gly Gly Gly Ser Gly Gly Gly Ser Gly Gly Gly Gly Ser
1               5                   10                  15

<210> SEQ ID NO 214
<211> LENGTH: 20
<212> TYPE: PRT
<213> ORGANISM: Artificial Sequence
<220> FEATURE:
<223> OTHER INFORMATION: Synthetic Construct

<400> SEQUENCE: 214

Gly Gly Gly Gly Ser Gly Gly Gly Ser Gly Gly Gly Gly Ser Gly
1               5                   10                  15

Gly Gly Gly Ser
            20

<210> SEQ ID NO 215
<211> LENGTH: 25
<212> TYPE: PRT
<213> ORGANISM: Artificial Sequence
<220> FEATURE:
<223> OTHER INFORMATION: Synthetic Construct

<400> SEQUENCE: 215

Gly Gly Gly Gly Ser Gly Gly Gly Ser Gly Gly Gly Gly Ser Gly
1               5                   10                  15

Gly Gly Ser Gly Gly Gly Gly Ser
            20                  25

<210> SEQ ID NO 216
<211> LENGTH: 420

```
<212> TYPE: PRT
<213> ORGANISM: Artificial Sequence
<220> FEATURE:
<223> OTHER INFORMATION: Synthetic Construct

<400> SEQUENCE: 216

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Gln
                20                  25                  30

Leu Val Glu Ser Gly Gly Leu Val Gln Pro Gly Gly Ser Leu Arg
        35                  40                  45

Leu Ser Cys Glu Ala Ser Gly Phe Thr Leu Asp Tyr Tyr Ala Ile Gly
    50                  55                  60

Trp Phe Arg Gln Ala Pro Gly Lys Glu Arg Glu Gly Val Ile Cys Ile
65                  70                  75                  80

Ser Arg Ser Asp Gly Ser Thr Tyr Tyr Ala Asp Ser Val Lys Gly Arg
                85                  90                  95

Phe Thr Ile Ser Arg Asp Asn Ala Lys Lys Thr Val Tyr Leu Gln Met
            100                 105                 110

Ile Ser Leu Lys Pro Glu Asp Thr Ala Ala Tyr Tyr Cys Ala Ala Gly
        115                 120                 125

Ala Asp Cys Ser Gly Tyr Leu Arg Asp Tyr Glu Phe Arg Gly Gln Gly
    130                 135                 140

Thr Gln Val Thr Val Ser Ser Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Phe Trp Val Leu Val Val Val Gly Gly Val
        195                 200                 205

Leu Ala Cys Tyr Ser Leu Leu Val Thr Val Ala Phe Ile Ile Phe Trp
    210                 215                 220

Val Arg Ser Lys Arg Ser Arg Leu Leu His Ser Asp Tyr Met Asn Met
225                 230                 235                 240

Thr Pro Arg Arg Pro Gly Pro Thr Arg Lys His Tyr Gln Pro Tyr Ala
                245                 250                 255

Pro Pro Arg Asp Phe Ala Ala Tyr Arg Ser Lys Arg Gly Arg Lys Lys
            260                 265                 270

Leu Leu Tyr Ile Phe Lys Gln Pro Phe Met Arg Pro Val Gln Thr Thr
        275                 280                 285

Gln Glu Glu Asp Gly Cys Ser Cys Arg Phe Pro Glu Glu Glu Glu Gly
    290                 295                 300

Gly Cys Glu Leu Arg Val Lys Phe Ser Arg Ser Ala Asp Ala Pro Ala
305                 310                 315                 320

Tyr Lys Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
            340                 345                 350

Met Gly Gly Lys Pro Arg Arg Lys Asn Pro Gln Glu Gly Leu Tyr Asn
        355                 360                 365

Glu Leu Gln Lys Asp Lys Met Ala Glu Ala Tyr Ser Glu Ile Gly Met
    370                 375                 380
```

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
            405                 410                 415

Leu Pro Pro Arg
            420

<210> SEQ ID NO 217
<211> LENGTH: 426
<212> TYPE: PRT
<213> ORGANISM: Artificial Sequence
<220> FEATURE:
<223> OTHER INFORMATION: Synthetic Construct

<400> SEQUENCE: 217

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Lys
            20                  25                  30

Leu Glu Glu Ser Gly Gly Arg Leu Val Gln Pro Arg Gly Ser Leu Arg
        35                  40                  45

Leu Ser Cys Ala Gly Ser Gly Arg Thr Phe Ser Thr Tyr Gly Met Ala
50                  55                  60

Trp Phe Arg Gln Ala Pro Gly Lys Glu Arg Glu Phe Val Ala Ser Lys
65                  70                  75                  80

Ala Ser Met Asn Tyr Ser Gly Arg Thr Tyr Tyr Ala Asp Ser Val Lys
            85                  90                  95

Gly Arg Phe Thr Ile Ala Arg Asp Asn Ala Lys Asn Met Val Phe Leu
        100                 105                 110

Gln Met Asn Asn Leu Lys Pro Glu Asp Thr Ala Val Tyr Tyr Cys Ala
    115                 120                 125

Ala Gly Thr Gly Cys Ser Thr Tyr Gly Cys Phe Asp Ala Gln Ile Ile
130                 135                 140

Asp Tyr Trp Gly Lys Gly Thr Leu Val Thr Val Ser Ser Thr Ser Thr
145                 150                 155                 160

Thr Thr Pro Ala Pro Arg Pro Pro Thr Pro Ala Pro Thr Ile Ala Ser
            165                 170                 175

Gln Pro Leu Ser Leu Arg Pro Glu Ala Cys Arg Pro Ala Ala Gly Gly
        180                 185                 190

Ala Val His Thr Arg Gly Leu Asp Phe Ala Cys Asp Phe Trp Val Leu
    195                 200                 205

Val Val Val Gly Gly Val Leu Ala Cys Tyr Ser Leu Leu Val Thr Val
210                 215                 220

Ala Phe Ile Ile Phe Trp Val Arg Ser Lys Arg Ser Arg Leu Leu His
225                 230                 235                 240

Ser Asp Tyr Met Asn Met Thr Pro Arg Arg Pro Gly Pro Thr Arg Lys
            245                 250                 255

His Tyr Gln Pro Tyr Ala Pro Pro Arg Asp Phe Ala Ala Tyr Arg Ser
        260                 265                 270

Lys Arg Gly Arg Lys Lys Leu Leu Tyr Ile Phe Lys Gln Pro Phe Met
    275                 280                 285

Arg Pro Val Gln Thr Thr Gln Glu Glu Asp Gly Cys Ser Cys Arg Phe
290                 295                 300

Pro Glu Glu Glu Glu Gly Gly Cys Glu Leu Arg Val Lys Phe Ser Arg
305                 310                 315                 320

```
Ser Ala Asp Ala Pro Ala Tyr Lys Gln Gly Gln Asn Gln Leu Tyr Asn
                325                 330                 335

Glu Leu Asn Leu Gly Arg Arg Glu Glu Tyr Asp Val Leu Asp Lys Arg
            340                 345                 350

Arg Gly Arg Asp Pro Glu Met Gly Gly Lys Pro Arg Arg Lys Asn Pro
        355                 360                 365

Gln Glu Gly Leu Tyr Asn Glu Leu Gln Lys Asp Lys Met Ala Glu Ala
    370                 375                 380

Tyr Ser Glu Ile Gly Met Lys Gly Glu Arg Arg Arg Gly Lys Gly His
385                 390                 395                 400

Asp Gly Leu Tyr Gln Gly Leu Ser Thr Ala Thr Lys Asp Thr Tyr Asp
                405                 410                 415

Ala Leu His Met Gln Ala Leu Pro Pro Arg
                420                 425

<210> SEQ ID NO 218
<211> LENGTH: 416
<212> TYPE: PRT
<213> ORGANISM: Artificial Sequence
<220> FEATURE:
<223> OTHER INFORMATION: Synthetic Construct

<400> SEQUENCE: 218

Met Ala Leu Pro Val Thr Ala Leu Leu Pro Leu Ala Leu Leu Leu
1               5                   10                  15

His Ala Ala Arg Pro Val Asn Arg Thr Arg Arg Met His Glu Val Gln
                20                  25                  30

Leu Val Glu Ser Gly Gly Gly Val Gln Ala Gly Ser Leu Arg
            35                  40                  45

Leu Ser Cys Ala Ala Ser Gly Arg Thr Phe Thr Met Gly Trp Phe Arg
    50                  55                  60

Gln Ala Pro Gly Lys Glu Arg Glu Phe Val Ala Ala Ile Ser Leu Ser
65                  70                  75                  80

Pro Thr Leu Ala Tyr Tyr Ala Glu Ser Val Lys Gly Arg Phe Thr Ile
                85                  90                  95

Ser Arg Asp Asn Ala Lys Asn Thr Val Val Leu Gln Met Asn Ser Leu
                100                 105                 110

Lys Pro Glu Asp Thr Ala Leu Tyr Tyr Cys Ala Ala Asp Arg Lys Ser
            115                 120                 125

Val Met Ser Ile Arg Pro Asp Tyr Trp Gly Gln Gly Thr Gln Val Thr
    130                 135                 140

Val Ser Ser Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Phe Trp Val Leu Val Val Gly Gly Val Leu Ala Cys Tyr
    195                 200                 205

Ser Leu Leu Val Thr Val Ala Phe Ile Ile Phe Trp Val Arg Ser Lys
    210                 215                 220

Arg Ser Arg Leu Leu His Ser Asp Tyr Met Asn Met Thr Pro Arg Arg
225                 230                 235                 240

Pro Gly Pro Thr Arg Lys His Tyr Gln Pro Tyr Ala Pro Pro Arg Asp
                245                 250                 255
```

```
Phe Ala Ala Tyr Arg Ser Lys Arg Gly Arg Lys Lys Leu Leu Tyr Ile
            260                 265                 270

Phe Lys Gln Pro Phe Met Arg Pro Val Gln Thr Thr Gln Glu Glu Asp
        275                 280                 285

Gly Cys Ser Cys Arg Phe Pro Glu Glu Glu Gly Gly Cys Glu Leu
    290                 295                 300

Arg Val Lys Phe Ser Arg Ser Ala Asp Ala Pro Ala Tyr Lys Gln Gly
305                 310                 315                 320

Gln Asn Gln Leu Tyr Asn Glu Leu Asn Gly Arg Arg Glu Glu Tyr
            325                 330                 335

Asp Val Leu Asp Lys Arg Arg Gly Arg Asp Pro Glu Met Gly Gly Lys
            340                 345                 350

Pro Arg Arg Lys Asn Pro Gln Glu Gly Leu Tyr Asn Glu Leu Gln Lys
            355                 360                 365

Asp Lys Met Ala Glu Ala Tyr Ser Glu Ile Gly Met Lys Gly Glu Arg
            370                 375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                405                 410                 415

<210> SEQ ID NO 219
<211> LENGTH: 418
<212> TYPE: PRT
<213> ORGANISM: Artificial Sequence
<220> FEATURE:
<223> OTHER INFORMATION: Synthetic Construct

<400> SEQUENCE: 219

Met Ala Leu Pro Val Thr Ala Leu Leu Leu Pro Leu Ala Leu Leu Leu
1               5                   10                  15

His Ala Ala Arg Pro Val Asn Arg Thr Arg Met His Ala Val Gln
            20                  25                  30

Leu Val Asp Ser Gly Gly Gly Leu Val Gln Pro Gly Gly Ser Leu Arg
        35                  40                  45

Leu Ser Cys Val Ala Ser Gly Gly Ile Phe Val Ile Asn Ala Met Gly
    50                  55                  60

Trp Tyr Arg Gln Ala Pro Gly Lys Gln Arg Glu Leu Val Ala Ser Ile
65              70                  75                  80

Arg Gly Leu Gly Arg Thr Asn Tyr Asp Asp Ser Val Lys Gly Arg Phe
            85                  90                  95

Thr Ile Ser Arg Asp Asn Ala Asn Asn Thr Val Tyr Leu Gln Met Asn
            100                 105                 110

Ser Leu Glu Pro Glu Asp Thr Ala Val Tyr Tyr Cys Thr Val Tyr Val
            115                 120                 125

Thr Leu Leu Gly Gly Val Asn Arg Asp Tyr Trp Gly Gln Gly Thr Gln
130                 135                 140

Val Thr Val Ser Ser Thr Ser Thr Thr Pro Ala Pro Arg Pro Pro
145                 150                 155             160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
            180                 185                 190

Phe Ala Cys Asp Phe Trp Val Leu Val Val Val Gly Gly Val Leu Ala
        195                 200                 205
```

```
Cys Tyr Ser Leu Leu Val Thr Val Ala Phe Ile Ile Phe Trp Val Arg
    210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
                260                 265                 270

Tyr Ile Phe Lys Gln Pro Phe Met Arg Pro Val Gln Thr Thr Gln Glu
                275                 280                 285

Glu Asp Gly Cys Ser Cys Arg Phe Pro Glu Glu Glu Gly Gly Cys
290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
                340                 345                 350

Gly Lys Pro Arg Arg Lys Asn Pro Gln Glu Gly Leu Tyr Asn Glu Leu
                355                 360                 365

Gln Lys Asp Lys Met Ala Glu Ala Tyr Ser Glu Ile Gly Met Lys Gly
                370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                405                 410                 415

Pro Arg

<210> SEQ ID NO 220
<211> LENGTH: 417
<212> TYPE: PRT
<213> ORGANISM: Artificial Sequence
<220> FEATURE:
<223> OTHER INFORMATION: Synthetic Construct

<400> SEQUENCE: 220

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Glu Val Gln
                20                  25                  30

Leu Val Glu Ser Gly Gly Gly Leu Val Gln Ala Gly Gly Ser Leu Arg
            35                  40                  45

Leu Ser Cys Ala Ala Ser Gly Arg Thr Phe Ser Ser Ile Val Met Gly
        50                  55                  60

Trp Phe Arg Gln Ala Pro Gly Lys Glu Arg Glu Phe Val Gly Ala Ile
65              70                  75                  80

Met Trp Asn Asp Gly Ile Thr Tyr Leu Gln Asp Ser Val Lys Gly Arg
                85                  90                  95

Phe Thr Ile Phe Arg Asp Asn Ala Lys Asn Thr Val Tyr Leu Gln Met
                100                 105                 110

Asn Ser Leu Lys Leu Glu Asp Thr Ala Val Tyr Tyr Cys Ala Ala Ser
            115                 120                 125

Lys Gly Arg Tyr Ser Glu Tyr Glu Tyr Trp Gly Gln Gly Thr Gln Val
        130                 135                 140

Thr Val Ser Ser Thr Ser Thr Thr Thr Pro Ala Pro Arg Pro Pro Thr
```

```
            145                 150                 155                 160
        Pro Ala Pro Thr Ile Ala Ser Gln Pro Leu Ser Leu Arg Pro Glu Ala
                        165                 170                 175

Cys Arg Pro Ala Ala Gly Gly Ala Val His Thr Arg Gly Leu Asp Phe
                        180                 185                 190

Ala Cys Asp Phe Trp Val Leu Val Val Gly Gly Val Leu Ala Cys
                        195                 200                 205

Tyr Ser Leu Leu Val Thr Val Ala Phe Ile Ile Phe Val Arg Ser
                        210                 215                 220

Lys Arg Ser Arg Leu Leu His Ser Asp Tyr Met Asn Met Thr Pro Arg
        225                 230                 235                 240

Arg Pro Gly Pro Thr Arg Lys His Tyr Gln Pro Tyr Ala Pro Pro Arg
                        245                 250                 255

Asp Phe Ala Ala Tyr Arg Ser Lys Arg Gly Arg Lys Lys Leu Leu Tyr
                        260                 265                 270

Ile Phe Lys Gln Pro Phe Met Arg Pro Val Gln Thr Thr Gln Glu Glu
                        275                 280                 285

Asp Gly Cys Ser Cys Arg Phe Pro Glu Glu Glu Glu Gly Gly Cys Glu
                        290                 295                 300

Leu Arg Val Lys Phe Ser Arg Ser Ala Asp Ala Pro Ala Tyr Lys Gln
        305                 310                 315                 320

Gly Gln Asn Gln Leu Tyr Asn Glu Leu Asn Leu Gly Arg Arg Glu Glu
                        325                 330                 335

Tyr Asp Val Leu Asp Lys Arg Arg Gly Arg Asp Pro Glu Met Gly Gly
                        340                 345                 350

Lys Pro Arg Arg Lys Asn Pro Gln Glu Gly Leu Tyr Asn Glu Leu Gln
                        355                 360                 365

Lys Asp Lys Met Ala Glu Ala Tyr Ser Glu Ile Gly Met Lys Gly Glu
                        370                 375                 380

Arg Arg Arg Gly Lys Gly His Asp Gly Leu Tyr Gln Gly Leu Ser Thr
        385                 390                 395                 400

Ala Thr Lys Asp Thr Tyr Asp Ala Leu His Met Gln Ala Leu Pro Pro
                        405                 410                 415

Arg

<210> SEQ ID NO 221
<211> LENGTH: 426
<212> TYPE: PRT
<213> ORGANISM: Artificial Sequence
<220> FEATURE:
<223> OTHER INFORMATION: Synthetic Construct

<400> SEQUENCE: 221

Met Ala Leu Pro Val Thr Ala Leu Leu Leu Pro Leu Ala Leu Leu Leu
        1               5                   10                  15

His Ala Ala Arg Pro Val Asn Arg Thr Arg Arg Met His Glu Val Gln
                        20                  25                  30

Leu Val Glu Ser Gly Gly Gly Val Gln Ala Gly Gly Ser Leu Thr
                        35                  40                  45

Val Ser Cys Thr Ala Ser Gly Phe Thr Phe Asp Arg Ala Val Ile Val
                        50                  55                  60

Trp Phe Arg Gln Ala Pro Gly Lys Gly Arg Glu Gly Val Ser Phe Ile
        65                  70                  75                  80

Lys Pro Ser Asp Gly Thr Ile Tyr Tyr Ile Asp Ser Leu Lys Gly Arg
                        85                  90                  95
```

```
Phe Thr Ile Ser Ser Asp Ile Ala Lys Asn Thr Val Tyr Leu Gln Met
            100                 105                 110

Lys Ser Leu Glu Ser Glu Asp Ser Ala Val Tyr Tyr Cys Ala Ala Ser
        115                 120                 125

Pro Glu Asp Trp Tyr Thr Asp Trp Ile Asp Trp Ser Ile Tyr Arg Trp
130                 135                 140

Gln His Trp Gly Gln Gly Thr Gln Val Thr Val Ser Ser Thr Ser Thr
145                 150                 155                 160

Thr Thr Pro Ala Pro Arg Pro Pro Thr Pro Ala Pro Thr Ile Ala Ser
            165                 170                 175

Gln Pro Leu Ser Leu Arg Pro Glu Ala Cys Arg Pro Ala Ala Gly Gly
            180                 185                 190

Ala Val His Thr Arg Gly Leu Asp Phe Ala Cys Asp Phe Trp Val Leu
            195                 200                 205

Val Val Val Gly Gly Val Leu Ala Cys Tyr Ser Leu Leu Val Thr Val
        210                 215                 220

Ala Phe Ile Ile Phe Trp Val Arg Ser Lys Arg Ser Arg Leu Leu His
225                 230                 235                 240

Ser Asp Tyr Met Asn Met Thr Pro Arg Arg Pro Gly Pro Thr Arg Lys
            245                 250                 255

His Tyr Gln Pro Tyr Ala Pro Pro Arg Asp Phe Ala Ala Tyr Arg Ser
            260                 265                 270

Lys Arg Gly Arg Lys Lys Leu Leu Tyr Ile Phe Lys Gln Pro Phe Met
        275                 280                 285

Arg Pro Val Gln Thr Thr Gln Glu Glu Asp Gly Cys Ser Cys Arg Phe
            290                 295                 300

Pro Glu Glu Glu Glu Gly Gly Cys Glu Leu Arg Val Lys Phe Ser Arg
305                 310                 315                 320

Ser Ala Asp Ala Pro Ala Tyr Lys Gln Gly Gln Asn Gln Leu Tyr Asn
            325                 330                 335

Glu Leu Asn Leu Gly Arg Arg Glu Glu Tyr Asp Val Leu Asp Lys Arg
            340                 345                 350

Arg Gly Arg Asp Pro Glu Met Gly Gly Lys Pro Arg Arg Lys Asn Pro
        355                 360                 365

Gln Glu Gly Leu Tyr Asn Glu Leu Gln Lys Asp Lys Met Ala Glu Ala
370                 375                 380

Tyr Ser Glu Ile Gly Met Lys Gly Glu Arg Arg Arg Gly Lys Gly His
385                 390                 395                 400

Asp Gly Leu Tyr Gln Gly Leu Ser Thr Ala Thr Lys Asp Thr Tyr Asp
            405                 410                 415

Ala Leu His Met Gln Ala Leu Pro Pro Arg
            420                 425

<210> SEQ ID NO 222
<211> LENGTH: 417
<212> TYPE: PRT
<213> ORGANISM: Artificial Sequence
<220> FEATURE:
<223> OTHER INFORMATION: Synthetic Construct

<400> SEQUENCE: 222

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Glu Val Gln
            20                  25                  30
```

Leu Val Glu Ser Gly Gly Gly Met Val Gln Ala Gly Asp Ser Leu Arg
 35                  40                  45

Leu Ser Cys Val Gln Ser Thr Tyr Thr Val Asn Ser Asp Val Met Gly
 50                  55                  60

Trp Phe Arg Gln Ala Pro Gly Lys Glu Arg Glu Phe Val Gly Ala Ile
 65                  70                  75                  80

Met Trp Asn Asp Gly Ile Thr Tyr Leu Gln Asp Ser Val Lys Gly Arg
                 85                  90                  95

Phe Thr Ile Phe Arg Asp Asn Ala Lys Asn Thr Val Tyr Leu Gln Met
                100                 105                 110

Asn Ser Leu Lys Leu Glu Asp Thr Ala Val Tyr Tyr Cys Ala Ala Ser
                115                 120                 125

Lys Gly Arg Tyr Ser Glu Tyr Glu Tyr Trp Gly Gln Gly Thr Gln Val
                130                 135                 140

Thr Val Ser Ser Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
                180                 185                 190

Ala Cys Asp Phe Trp Val Leu Val Val Gly Gly Val Leu Ala Cys
                195                 200                 205

Tyr Ser Leu Leu Val Thr Val Ala Phe Ile Ile Phe Trp Val Arg Ser
                210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
                260                 265                 270

Ile Phe Lys Gln Pro Phe Met Arg Pro Val Gln Thr Thr Gln Glu Glu
                275                 280                 285

Asp Gly Cys Ser Cys Arg Phe Pro Glu Glu Glu Glu Gly Gly Cys Glu
                290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
                340                 345                 350

Lys Pro Arg Arg Lys Asn Pro Gln Glu Gly Leu Tyr Asn Glu Leu Gln
                355                 360                 365

Lys Asp Lys Met Ala Glu Ala Tyr Ser Glu Ile Gly Met Lys Gly Glu
                370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 223
<211> LENGTH: 418
<212> TYPE: PRT

<213> ORGANISM: Artificial Sequence
<220> FEATURE:
<223> OTHER INFORMATION: Synthetic Construct

<400> SEQUENCE: 223

```
Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Ala Val Gln
            20                  25                  30

Leu Val Glu Ser Gly Gly Gly Leu Val Gln Ala Gly Asp Ser Leu Arg
        35                  40                  45

Leu Ser Cys Thr Ala Ser Gly Ala Thr Leu Thr Asn Asp His Met Ala
50                  55                  60

Trp Phe Arg Gln Ala Pro Gly Lys Gly Arg Glu Phe Val Ala Ala Ile
65                  70                  75                  80

Asp Trp Ser Gly Arg Thr Thr Asn Tyr Ala Asp Pro Val Glu Gly Arg
                85                  90                  95

Phe Thr Ile Ser Arg Asn Asn Ala Lys Asn Thr Val Tyr Leu Glu Met
            100                 105                 110

Asn Ser Leu Lys Leu Glu Asp Thr Ala Val Tyr Tyr Cys Ala Val Leu
        115                 120                 125

Arg Ala Trp Ile Ser Tyr Asp Asn Asp Tyr Trp Gly Gln Gly Thr Gln
130                 135                 140

Val Thr Val Ser Ser Thr Ser Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
            180                 185                 190

Phe Ala Cys Asp Phe Trp Val Leu Val Val Val Gly Gly Val Leu Ala
        195                 200                 205

Cys Tyr Ser Leu Leu Val Thr Val Ala Phe Ile Ile Phe Trp Val Arg
210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
            260                 265                 270

Tyr Ile Phe Lys Gln Pro Phe Met Arg Pro Val Gln Thr Thr Gln Glu
        275                 280                 285

Glu Asp Gly Cys Ser Cys Arg Phe Pro Glu Glu Glu Glu Gly Gly Cys
290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
            340                 345                 350

Gly Lys Pro Arg Arg Lys Asn Pro Gln Glu Gly Leu Tyr Asn Glu Leu
        355                 360                 365

Gln Lys Asp Lys Met Ala Glu Ala Tyr Ser Glu Ile Gly Met Lys Gly
370                 375                 380

Glu Arg Arg Arg Gly Lys Gly His Asp Gly Leu Tyr Gln Gly Leu Ser
```

```
                385                 390                 395                 400
Thr Ala Thr Lys Asp Thr Tyr Asp Ala Leu His Met Gln Ala Leu Pro
                    405                 410                 415
Pro Arg

<210> SEQ ID NO 224
<211> LENGTH: 418
<212> TYPE: PRT
<213> ORGANISM: Artificial Sequence
<220> FEATURE:
<223> OTHER INFORMATION: Synthetic Construct

<400> SEQUENCE: 224

Met Ala Leu Pro Val Thr Ala Leu Leu Leu Pro Leu Ala Leu Leu Leu
1               5                   10                  15

His Ala Ala Arg Pro Val Asn Arg Thr Arg Met His Gln Val Gln
                20                  25                  30

Leu Val Glu Ser Gly Gly Gly Leu Val Gln Ala Gly Gly Ser Leu Arg
            35                  40                  45

Leu Ser Cys Ala Ala Ser Gly Gly Thr Leu Ser Lys Asn Thr Val Ala
        50                  55                  60

Trp Phe Arg Gln Ala Pro Gly Lys Glu Arg Gly Phe Val Ala Ser Ile
65                  70                  75                  80

Thr Trp Asp Gly Arg Thr Thr Tyr Tyr Ala Asp Ser Val Lys Gly Arg
                85                  90                  95

Phe Thr Ile Ser Arg Asp Asn Ala Lys Asn Thr Val Tyr Leu Gln Met
            100                 105                 110

Asn Ser Leu Lys Pro Glu Asp Thr Ala Val Tyr Val Cys Ala Asp Leu
        115                 120                 125

Gly Lys Trp Pro Ala Gly Pro Ala Asp Tyr Trp Gly Gln Gly Thr Gln
130                 135                 140

Val Thr Val Ser Ser Thr Ser Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
            180                 185                 190

Phe Ala Cys Asp Phe Trp Val Leu Val Val Gly Gly Val Leu Ala
        195                 200                 205

Cys Tyr Ser Leu Leu Val Thr Val Ala Phe Ile Ile Phe Trp Val Arg
210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
            260                 265                 270

Tyr Ile Phe Lys Gln Pro Phe Met Arg Pro Val Gln Thr Thr Gln Glu
        275                 280                 285

Glu Asp Gly Cys Ser Cys Arg Phe Pro Glu Glu Glu Gly Gly Cys
290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335
```

```
Glu Tyr Asp Val Leu Asp Lys Arg Arg Gly Arg Asp Pro Glu Met Gly
            340                 345                 350

Gly Lys Pro Arg Arg Lys Asn Pro Gln Glu Gly Leu Tyr Asn Glu Leu
            355                 360                 365

Gln Lys Asp Lys Met Ala Glu Ala Tyr Ser Glu Ile Gly Met Lys Gly
            370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
            405                 410                 415

Pro Arg

<210> SEQ ID NO 225
<211> LENGTH: 417
<212> TYPE: PRT
<213> ORGANISM: Artificial Sequence
<220> FEATURE:
<223> OTHER INFORMATION: Synthetic Construct

<400> SEQUENCE: 225

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Lys
            20                  25                  30

Leu Glu Glu Ser Gly Gly Gly Leu Val Gln Ala Gly Arg Ser Leu Arg
            35                  40                  45

Leu Ser Cys Ala Ala Ser Glu His Thr Phe Ser Ser His Val Met Gly
        50                  55                  60

Trp Phe Arg Gln Ala Pro Gly Lys Glu Arg Glu Ser Val Ala Val Ile
65                  70                  75                  80

Gly Trp Arg Asp Ile Ser Thr Ser Tyr Ala Asp Ser Val Lys Gly Arg
                85                  90                  95

Phe Thr Ile Ser Arg Asp Asn Ala Lys Lys Thr Leu Tyr Leu Gln Met
            100                 105                 110

Asn Ser Leu Lys Pro Glu Asp Thr Ala Val Tyr Tyr Cys Ala Ala Arg
            115                 120                 125

Arg Ile Asp Ala Ala Asp Phe Asp Ser Trp Gly Gln Gly Thr Gln Val
130                 135                 140

Thr Val Ser Ser Thr Ser Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Gly Gly Val Leu Ala Cys
            195                 200                 205

Tyr Ser Leu Leu Val Thr Val Ala Phe Ile Ile Phe Trp Val Arg Ser
            210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270
```

```
Ile Phe Lys Gln Pro Phe Met Arg Pro Val Gln Thr Thr Gln Glu Glu
            275                 280                 285

Asp Gly Cys Ser Cys Arg Phe Pro Glu Glu Glu Gly Gly Cys Glu
    290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
            340                 345                 350

Lys Pro Arg Arg Lys Asn Pro Gln Glu Gly Leu Tyr Asn Glu Leu Gln
            355                 360                 365

Lys Asp Lys Met Ala Glu Ala Tyr Ser Glu Ile Gly Met Lys Gly Glu
370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 226
<211> LENGTH: 417
<212> TYPE: PRT
<213> ORGANISM: Artificial Sequence
<220> FEATURE:
<223> OTHER INFORMATION: Synthetic Construct

<400> SEQUENCE: 226

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Ala Val Gln
            20                  25                  30

Leu Val Glu Ser Gly Gly Gly Leu Val Gln Ala Gly Asp Ser Leu Arg
        35                  40                  45

Leu Thr Cys Thr Ala Ser Gly Arg Ala Phe Ser Thr Tyr Phe Met Ala
50                  55                  60

Trp Phe Arg Gln Ala Pro Gly Lys Glu Arg Glu Phe Val Ala Gly Ile
65                  70                  75                  80

Ala Trp Ser Gly Gly Ser Thr Ala Tyr Ala Asp Ser Val Lys Gly Arg
                85                  90                  95

Phe Thr Ile Ser Arg Asp Asn Ala Lys Asn Thr Val Tyr Leu Gln Met
            100                 105                 110

Asn Ser Leu Lys Ser Glu Asp Thr Ala Val Tyr Tyr Cys Ala Ser Arg
        115                 120                 125

Gly Ile Glu Val Glu Glu Phe Gly Ala Trp Gly Gln Gly Thr Gln Val
130                 135                 140

Thr Val Ser Ser Thr Ser Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Gly Gly Val Leu Ala Cys
        195                 200                 205

Tyr Ser Leu Leu Val Thr Val Ala Phe Ile Ile Phe Trp Val Arg Ser
```

```
                210                 215                 220
Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
                260                 265                 270

Ile Phe Lys Gln Pro Phe Met Arg Pro Val Gln Thr Thr Gln Glu Glu
            275                 280                 285

Asp Gly Cys Ser Cys Arg Phe Pro Glu Glu Glu Glu Gly Cys Glu
290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
                340                 345                 350

Lys Pro Arg Arg Lys Asn Pro Gln Glu Gly Leu Tyr Asn Glu Leu Gln
                355                 360                 365

Lys Asp Lys Met Ala Glu Ala Tyr Ser Glu Ile Gly Met Lys Gly Glu
                370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 227
<211> LENGTH: 376
<212> TYPE: PRT
<213> ORGANISM: Artificial Sequence
<220> FEATURE:
<223> OTHER INFORMATION: Synthetic Construct

<400> SEQUENCE: 227

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Gln
                20                  25                  30

Leu Val Glu Ser Gly Gly Gly Leu Val Gln Pro Gly Gly Ser Leu Arg
            35                  40                  45

Leu Ser Cys Glu Ala Ser Gly Phe Thr Leu Asp Tyr Tyr Ala Ile Gly
        50                  55                  60

Trp Phe Arg Gln Ala Pro Gly Lys Glu Arg Gly Val Ile Cys Ile
65                  70                  75                  80

Ser Arg Ser Asp Gly Ser Thr Tyr Tyr Ala Asp Ser Val Lys Gly Arg
                85                  90                  95

Phe Thr Ile Ser Arg Asp Asn Ala Lys Lys Thr Val Tyr Leu Gln Met
                100                 105                 110

Ile Ser Leu Lys Pro Glu Asp Thr Ala Ala Tyr Tyr Cys Ala Ala Gly
            115                 120                 125

Ala Asp Cys Ser Gly Tyr Leu Arg Asp Tyr Glu Phe Arg Gly Gln Gly
        130                 135                 140

Thr Gln Val Thr Val Ser Ser Thr Ser Thr Thr Thr Pro Ala Pro Arg
145                 150                 155                 160
```

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Ile Tyr Ile Trp Ala Pro Leu Ala Gly Thr
        195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
            260                 265                 270

Asp Ala Pro Ala Tyr Gln Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg
    370                 375

<210> SEQ ID NO 228
<211> LENGTH: 373
<212> TYPE: PRT
<213> ORGANISM: Artificial Sequence
<220> FEATURE:
<223> OTHER INFORMATION: Synthetic Construct

<400> SEQUENCE: 228

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Lys
            20                  25                  30

Leu Glu Glu Ser Gly Gly Gly Leu Val Gln Ala Gly Arg Ser Leu Arg
        35                  40                  45

Leu Ser Cys Ala Ala Ser Glu His Thr Phe Ser Ser His Val Met Gly
    50                  55                  60

Trp Phe Arg Gln Ala Pro Gly Lys Glu Arg Glu Ser Val Ala Val Ile
65                  70                  75                  80

Gly Trp Arg Asp Ile Ser Thr Ser Tyr Ala Asp Ser Val Lys Gly Arg
                85                  90                  95

Phe Thr Ile Ser Arg Asp Asn Ala Lys Lys Thr Leu Tyr Leu Gln Met
            100                 105                 110

Asn Ser Leu Lys Pro Glu Asp Thr Ala Val Tyr Tyr Cys Ala Ala Arg
        115                 120                 125

Arg Ile Asp Ala Ala Asp Phe Asp Ser Trp Gly Gln Gly Thr Gln Val
    130                 135                 140

```
Thr Val Ser Ser Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
            165                 170                 175

Cys Arg Pro Ala Ala Gly Gly Ala Val His Thr Arg Gly Leu Asp Phe
        180                 185                 190

Ala Cys Asp Ile Tyr Ile Trp Ala Pro Leu Ala Gly Thr Cys Gly Val
    195                 200                 205

Leu Leu Leu Ser Leu Val Ile Thr Leu Tyr Cys Lys Arg Gly Arg Lys
210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255

Gly Gly Cys Glu Leu Arg Val Lys Phe Ser Arg Ser Ala Asp Ala Pro
            260                 265                 270

Ala Tyr Gln Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370

<210> SEQ ID NO 229
<211> LENGTH: 372
<212> TYPE: PRT
<213> ORGANISM: Artificial Sequence
<220> FEATURE:
<223> OTHER INFORMATION: Synthetic Construct

<400> SEQUENCE: 229

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Glu Val Gln
            20                  25                  30

Leu Val Glu Ser Gly Gly Gly Leu Val Gln Ala Gly Gly Ser Leu Arg
        35                  40                  45

Leu Ser Cys Ala Ala Ser Gly Arg Thr Phe Thr Met Gly Trp Phe Arg
    50                  55                  60

Gln Ala Pro Gly Lys Glu Arg Glu Phe Val Ala Ala Ile Ser Leu Ser
65                  70                  75                  80

Pro Thr Leu Ala Tyr Tyr Ala Glu Ser Val Lys Gly Arg Phe Thr Ile
                85                  90                  95

Ser Arg Asp Asn Ala Lys Asn Thr Val Val Leu Gln Met Asn Ser Leu
            100                 105                 110

Lys Pro Glu Asp Thr Ala Leu Tyr Tyr Cys Ala Ala Asp Arg Lys Ser
        115                 120                 125
```

```
Val Met Ser Ile Arg Pro Asp Tyr Trp Gly Gln Gly Thr Gln Val Thr
    130                 135                 140

Val Ser Ser Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Ile Tyr Ile Trp Ala Pro Leu Ala Gly Thr Cys Gly Val Leu
        195                 200                 205

Leu Leu Ser Leu Val Ile Thr Leu Tyr Cys Lys Arg Gly Arg Lys Lys
    210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
            260                 265                 270

Tyr Gln Gln Gly Gln Asn Gln Leu Tyr Asn Glu Leu Asn Leu Gly Arg
        275                 280                 285

Arg Glu Glu Tyr Asp Val Leu Asp Lys Arg Arg Gly Arg Asp Pro Glu
    290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
            340                 345                 350

Leu Ser Thr Ala Thr Lys Asp Thr Tyr Asp Ala Leu His Met Gln Ala
        355                 360                 365

Leu Pro Pro Arg
    370

<210> SEQ ID NO 230
<211> LENGTH: 372
<212> TYPE: PRT
<213> ORGANISM: Artificial Sequence
<220> FEATURE:
<223> OTHER INFORMATION: Synthetic Construct

<400> SEQUENCE: 230

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Pro Pro Gly Gly Ser Leu Arg Leu Ser Cys Thr Ala Ser Gly Ser
        35                  40                  45

Thr Val Ser Ile Asn Val Met Ala Trp Tyr Arg Gln Val Ser Gly Lys
    50                  55                  60

Gln Arg Glu Leu Val Ala Ala Val Thr Arg Asp Gly Arg Lys Ser Cys
65                  70                  75                  80

Gly Asp Ser Val Lys Gly Arg Phe Thr Ile Ser Arg Asp Gly Ala Lys
                85                  90                  95

Asn Ala Val Tyr Leu Gln Met Asn Ser Leu Lys Pro Glu Asp Thr Ala
            100                 105                 110
```

Val Tyr Leu Cys Gly Ala Asp Gly Trp Gly Ala Thr Thr Leu Asp Tyr
            115                 120                 125

Thr Tyr Gly Met Asp Tyr Trp Gly Lys Gly Thr Gln Val Thr Val Ser
130                 135                 140

Ser Ala Ala Thr Ser Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Ile Tyr Ile Trp Ala Pro Leu Ala Gly Thr Cys Gly Val Leu
            195                 200                 205

Leu Leu Ser Leu Val Ile Thr Leu Tyr Cys Lys Arg Gly Arg Lys Lys
            210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
            260                 265                 270

Tyr Gln Gln Gly Gln Asn Gln Leu Tyr Asn Glu Leu Asn Leu Gly Arg
            275                 280                 285

Arg Glu Glu Tyr Asp Val Leu Asp Lys Arg Arg Gly Arg Asp Pro Glu
            290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
            340                 345                 350

Leu Ser Thr Ala Thr Lys Asp Thr Tyr Asp Ala Leu His Met Gln Ala
            355                 360                 365

Leu Pro Pro Arg
    370

<210> SEQ ID NO 231
<211> LENGTH: 364
<212> TYPE: PRT
<213> ORGANISM: Artificial Sequence
<220> FEATURE:
<223> OTHER INFORMATION: Synthetic Construct

<400> SEQUENCE: 231

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Gly
    50                  55                  60

Phe Val Ala Ser Ile Thr Trp Asp Gly Arg Ser Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Thr Ser Thr Thr Thr
130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
            165                 170                 175

His Thr Arg Gly Leu Asp Phe Ala Cys Asp Ile Tyr Ile Trp Ala Pro
        180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
        210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
            245                 250                 255

Ser Arg Ser Ala Asp Ala Pro Ala Tyr Gln Gln Gly Gln Asn Gln Leu
        260                 265                 270

Tyr Asn Glu Leu Asn Leu Gly Arg Arg Glu Glu Tyr Asp Val Leu Asp
    275                 280                 285

Lys Arg Arg Gly Arg Asp Pro Glu Met Gly Gly Lys Pro Arg Arg Lys
290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
            325                 330                 335

Gly His Asp Gly Leu Tyr Gln Gly Leu Ser Thr Ala Thr Lys Asp Thr
        340                 345                 350

Tyr Asp Ala Leu His Met Gln Ala Leu Pro Pro Arg
        355                 360

<210> SEQ ID NO 232
<211> LENGTH: 368
<212> TYPE: PRT
<213> ORGANISM: Artificial Sequence
<220> FEATURE:
<223> OTHER INFORMATION: Synthetic Construct

<400> SEQUENCE: 232

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ala Cys Glu Ala Pro Gly Ser
        35                  40                  45

Gly Asn Ser Ile Asn Ala Met Gly Trp Tyr Arg Gln Thr Pro Gly Lys
    50                  55                  60

Arg Arg Glu Leu Val Ala Thr Ile Thr Arg Gly Gly Ser Thr Asn Tyr
65                  70                  75                  80

Gly Pro Ser Val Lys Gly Arg Phe Thr Ile Thr Arg Asp Asn Val Lys
            85                  90                  95

Asn Thr Val His Leu Gln Met Asn Ser Leu Lys Pro Asp Asp Thr Ala
                100                 105                 110

Val Tyr Tyr Cys Asn Ala Glu Arg Leu Asp Gly Ser Gly Tyr Gly Tyr
            115                 120                 125

Glu Tyr Asp Tyr Trp Gly Gln Gly Thr Gln Val Thr Val Ser Ser Thr
        130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Ile Tyr
            180                 185                 190

Ile Trp Ala Pro Leu Ala Gly Thr Cys Gly Val Leu Leu Leu Ser Leu
        195                 200                 205

Val Ile Thr Leu Tyr Cys Lys Arg Gly Arg Lys Lys Leu Leu Tyr Ile
    210                 215                 220

Phe Lys Gln Pro Phe Met Arg Pro Val Gln Thr Thr Gln Glu Glu Asp
225                 230                 235                 240

Gly Cys Ser Cys Arg Phe Pro Glu Glu Glu Glu Gly Gly Cys Glu Leu
                245                 250                 255

Arg Val Lys Phe Ser Arg Ser Ala Asp Ala Pro Ala Tyr Gln Gln Gly
            260                 265                 270

Gln Asn Gln Leu Tyr Asn Glu Leu Asn Leu Gly Arg Arg Glu Glu Tyr
        275                 280                 285

Asp Val Leu Asp Lys Arg Arg Gly Arg Asp Pro Glu Met Gly Gly Lys
    290                 295                 300

Pro Arg Arg Lys Asn Pro Gln Glu Gly Leu Tyr Asn Glu Leu Gln Lys
305                 310                 315                 320

Asp Lys Met Ala Glu Ala Tyr Ser Glu Ile Gly Met Lys Gly Glu Arg
                325                 330                 335

Arg Arg Gly Lys Gly His Asp Gly Leu Tyr Gln Gly Leu Ser Thr Ala
            340                 345                 350

Thr Lys Asp Thr Tyr Asp Ala Leu His Met Gln Ala Leu Pro Pro Arg
        355                 360                 365

<210> SEQ ID NO 233
<211> LENGTH: 367
<212> TYPE: PRT
<213> ORGANISM: Artificial Sequence
<220> FEATURE:
<223> OTHER INFORMATION: Synthetic Construct

<400> SEQUENCE: 233

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

```
Glu Asn Leu Val Val Leu Gln Met Asn Ser Leu Lys Pro Asp Asp Thr
                100                 105                 110

Ala Leu Tyr Tyr Cys Ala Ala Tyr Arg Lys Ser Ile Met Ser Ile Gln
            115                 120                 125

Pro Asp Tyr Trp Gly Gln Gly Thr Gln Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 234
<211> LENGTH: 367
<212> TYPE: PRT
<213> ORGANISM: Artificial Sequence
<220> FEATURE:
<223> OTHER INFORMATION: Synthetic Construct

<400> SEQUENCE: 234

Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Ser Ser Ile Val Met Gly Trp Phe Arg Gln Ala Pro Gly Lys
    50                  55                  60

Glu Arg Glu Phe Val Gly Ala Ile Met Trp Asn Asp Gly Leu Thr Tyr
65                  70                  75                  80

Leu Gln Gly Ser Val Lys Gly Arg Phe Thr Ile Ser Arg Asp Asn Ala
                85                  90                  95
```

Lys Asn Thr Val Val Leu Gln Met Asn Ser Leu Lys Pro Glu Asp Thr
            100                 105                 110

Ala Leu Tyr Tyr Cys Ala Ala Asp Arg Lys Ser Val Met Ser Ile Arg
            115                 120                 125

Pro Asp Tyr Trp Gly Gln Gly Thr Gln Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
                195                 200                 205

Ile Thr Leu Tyr Cys Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
                    245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
        290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
            355                 360                 365

<210> SEQ ID NO 235
<211> LENGTH: 362
<212> TYPE: PRT
<213> ORGANISM: Artificial Sequence
<220> FEATURE:
<223> OTHER INFORMATION: Synthetic Construct

<400> SEQUENCE: 235

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Val Tyr
            100                 105                 110

Tyr Cys Ala Ala Arg Arg Ile Asp Ala Ala Asp Phe Asp Ser Trp Gly
            115                 120                 125

Gln Gly Thr Gln Val Thr Val Ser Ser Thr Ser Thr Thr Thr Pro Ala
            130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
            165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
            195                 200                 205

Lys Arg Gly Arg Lys Lys Leu Leu Tyr Ile Phe Lys Gln Pro Phe Met
            210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
            245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
            275                 280                 285

Arg Gly Arg Asp Pro Glu Met Gly Gly Lys Pro Arg Arg Lys Asn Pro
            290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
            325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
            355                 360

<210> SEQ ID NO 236
<211> LENGTH: 366
<212> TYPE: PRT
<213> ORGANISM: Artificial Sequence
<220> FEATURE:
<223> OTHER INFORMATION: Synthetic Construct

<400> SEQUENCE: 236

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Phe Arg Gln Ala Pro Gly Lys
            50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
            85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Thr Ser Thr
130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp Ile Tyr Ile Trp
            180                 185                 190

Ala Pro Leu Ala Gly Thr Cys Gly Val Leu Leu Leu Ser Leu Val Ile
        195                 200                 205

Thr Leu Tyr Cys Lys Arg Gly Arg Lys Lys Leu Leu Tyr Ile Phe Lys
210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu Arg Val
                245                 250                 255

Lys Phe Ser Arg Ser Ala Asp Ala Pro Ala Tyr Gln Gln Gly Gln Asn
            260                 265                 270

Gln Leu Tyr Asn Glu Leu Asn Leu Gly Arg Arg Glu Glu Tyr Asp Val
        275                 280                 285

Leu Asp Lys Arg Arg Gly Arg Asp Pro Glu Met Gly Gly Lys Pro Arg
290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                325                 330                 335

Gly Lys Gly His Asp Gly Leu Tyr Gln Gly Leu Ser Thr Ala Thr Lys
            340                 345                 350

Asp Thr Tyr Asp Ala Leu His Met Gln Ala Leu Pro Pro Arg
        355                 360                 365

<210> SEQ ID NO 237
<211> LENGTH: 367
<212> TYPE: PRT
<213> ORGANISM: Artificial Sequence
<220> FEATURE:
<223> OTHER INFORMATION: Synthetic Construct

<400> SEQUENCE: 237

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Thr Leu Ser Cys Ala Ala Ser Gly Ser
        35                  40                  45

Ile Asp Ser Ile Asn Thr Met Asp Trp Phe Arg Gln Ala Pro Gly Lys
    50                  55                  60

Glu Arg Glu Phe Val Ala Ala Ile Ser Leu Ser Pro Thr Leu Ala Tyr
65                  70                  75                  80

Tyr Ala Glu Ser Val Lys Gly Arg Phe Thr Ile Ser Arg Asp Asn Ala
                85                  90                  95

Lys Asn Thr Val Val Leu Gln Met Asn Ser Leu Lys Pro Glu Asp Thr
            100                 105                 110

Ala Leu Tyr Tyr Cys Ala Ala Asp Arg Lys Ser Val Met Ser Ile Arg
        115                 120                 125

Pro Asp Tyr Trp Gly Gln Gly Thr Gln Val Thr Val Ser Ser Thr Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
    290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 238
<211> LENGTH: 366
<212> TYPE: PRT
<213> ORGANISM: Artificial Sequence
<220> FEATURE:
<223> OTHER INFORMATION: Synthetic Construct

<400> SEQUENCE: 238

Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Lys Gly Arg Phe Pro Ile Ser Arg Asp Asn Ala
                85                  90                  95

Glu Asn Thr Val Tyr Leu Gln Met Asn Ser Leu Lys Pro Glu Asp Thr
            100                 105                 110

Ala Gly Tyr Val Cys Ala Asp Leu Gly Lys Trp Pro Ala Gly Ser Ala
            115                 120                 125

Asp Tyr Trp Gly Gln Gly Thr His Val Thr Val Ser Ser Thr Ser Thr
        130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp Ile Tyr Ile Trp
            180                 185                 190

Ala Pro Leu Ala Gly Thr Cys Gly Val Leu Leu Leu Ser Leu Val Ile
        195                 200                 205

Thr Leu Tyr Cys Lys Arg Gly Arg Lys Lys Leu Leu Tyr Ile Phe Lys
    210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu Arg Val
                245                 250                 255

Lys Phe Ser Arg Ser Ala Asp Ala Pro Ala Tyr Gln Gln Gly Gln Asn
            260                 265                 270

Gln Leu Tyr Asn Glu Leu Asn Leu Gly Arg Arg Glu Glu Tyr Asp Val
        275                 280                 285

Leu Asp Lys Arg Arg Gly Arg Asp Pro Glu Met Gly Gly Lys Pro Arg
    290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                325                 330                 335

Gly Lys Gly His Asp Gly Leu Tyr Gln Gly Leu Ser Thr Ala Thr Lys
            340                 345                 350

Asp Thr Tyr Asp Ala Leu His Met Gln Ala Leu Pro Pro Arg
        355                 360                 365

<210> SEQ ID NO 239
<211> LENGTH: 367
<212> TYPE: PRT
<213> ORGANISM: Artificial Sequence
<220> FEATURE:
<223> OTHER INFORMATION: Synthetic Construct

<400> SEQUENCE: 239

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Pro Gly Gly Ser Leu Arg Leu Ser Cys Thr Ala Ser Glu Phe
        35                  40                  45

Thr Phe Ser Asp Tyr Trp Met His Trp Val Arg Gln Ala Pro Gly Lys
    50                  55                  60

Gly Leu Glu Trp Val Ala Ser Ile Asp Thr Ser Gly Gln Thr Thr Tyr
65                  70                  75                  80

Tyr Ala Asp Ser Leu Lys Gly Arg Phe Thr Ile Ser Arg Asp Asn Ala
                85                  90                  95

```
Lys Ser Thr Leu Tyr Leu Gln Met Asn Ser Leu Lys Ser Glu Asp Thr
            100                 105                 110

Gly Val Tyr Phe Cys Ala Lys Arg Tyr Arg Gly Thr Trp Tyr Gly
            115                 120                 125

Met Ala Asn Trp Gly Lys Gly Thr Gln Val Thr Val Ser Ser Thr Ser
130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
            195                 200                 205

Ile Thr Leu Tyr Cys Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
            290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
            355                 360                 365
```

<210> SEQ ID NO 240
<211> LENGTH: 366
<212> TYPE: PRT
<213> ORGANISM: Artificial Sequence
<220> FEATURE:
<223> OTHER INFORMATION: Synthetic Construct

<400> SEQUENCE: 240

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Leu Ser Ser Asn Thr Met Ala Trp Phe Arg Gln Ala Pro Gly Lys
    50                  55                  60

Glu Arg Glu Phe Val Ala Ser Thr Thr Trp Asn Gly Arg Ser Thr Tyr
65                  70                  75                  80

Tyr Ala Asp Ser Val Lys Gly Arg Phe Thr Ile Ser Arg Asp Asn Ala
                85                  90                  95
```

```
Lys Asn Thr Met Tyr Leu Gln Met Asn Ser Leu Lys Pro Glu Asp Thr
                100                 105                 110

Ala Val Tyr Val Cys Ala Asp Leu Gly Lys Trp Pro Ala Gly Pro Ala
            115                 120                 125

Asp Tyr Trp Gly Gln Gly Thr Gln Val Thr Val Ser Ser Thr Ser Thr
        130                 135                 140

Thr Thr Pro Ala Pro Arg Pro Pro Thr Pro Ala Pro Thr Ile Ala Ser
145                 150                 155                 160

Gln Pro Leu Ser Leu Arg Pro Glu Ala Cys Arg Pro Ala Ala Gly Gly
                165                 170                 175

Ala Val His Thr Arg Gly Leu Asp Phe Ala Cys Asp Ile Tyr Ile Trp
            180                 185                 190

Ala Pro Leu Ala Gly Thr Cys Gly Val Leu Leu Leu Ser Leu Val Ile
        195                 200                 205

Thr Leu Tyr Cys Lys Arg Gly Arg Lys Lys Leu Leu Tyr Ile Phe Lys
210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Gly Gly Cys Glu Leu Arg Val
                245                 250                 255

Lys Phe Ser Arg Ser Ala Asp Ala Pro Ala Tyr Gln Gln Gly Gln Asn
                260                 265                 270

Gln Leu Tyr Asn Glu Leu Asn Leu Gly Arg Arg Glu Glu Tyr Asp Val
                275                 280                 285

Leu Asp Lys Arg Arg Gly Arg Asp Pro Glu Met Gly Gly Lys Pro Arg
            290                 295                 300

Arg Lys Asn Pro Gln Glu Gly Leu Tyr Asn Glu Leu Gln Lys Asp Lys
305                 310                 315                 320

Met Ala Glu Ala Tyr Ser Glu Ile Gly Met Lys Gly Glu Arg Arg Arg
                325                 330                 335

Gly Lys Gly His Asp Gly Leu Tyr Gln Gly Leu Ser Thr Ala Thr Lys
            340                 345                 350

Asp Thr Tyr Asp Ala Leu His Met Gln Ala Leu Pro Pro Arg
        355                 360                 365

<210> SEQ ID NO 241
<211> LENGTH: 362
<212> TYPE: PRT
<213> ORGANISM: Artificial Sequence
<220> FEATURE:
<223> OTHER INFORMATION: Synthetic Construct

<400> SEQUENCE: 241

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Gln Arg Glu
        50                  55                  60

Leu Val Ala Asp Ile Ser Gly Arg Thr Asn Tyr Ala Asp Ser Val
65                  70                  75                  80

Lys Gly Arg Phe Thr Ile Ser Arg Asp Asn Ala Lys Asn Thr Val Tyr
                85                  90                  95
```

```
Leu Gln Met Asn Ser Leu Lys Pro Glu Asp Thr Ala Val Tyr Tyr Cys
                100                 105                 110

Ala Ala Asp Arg Lys Ser Val Met Ser Ile Arg Pro Asp Tyr Trp Gly
            115                 120                 125

Gln Gly Thr Gln Val Thr Val Ser Ser Thr Ser Thr Thr Thr Pro Ala
    130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
    195                 200                 205

Lys Arg Gly Arg Lys Lys Leu Leu Tyr Ile Phe Lys Gln Pro Phe Met
210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
    275                 280                 285

Arg Gly Arg Asp Pro Glu Met Gly Gly Lys Pro Arg Arg Lys Asn Pro
290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
    355                 360

<210> SEQ ID NO 242
<211> LENGTH: 350
<212> TYPE: PRT
<213> ORGANISM: Artificial Sequence
<220> FEATURE:
<223> OTHER INFORMATION: Synthetic Construct

<400> SEQUENCE: 242

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Ala Ser Leu Arg Leu Ser Cys Ala Ala Ser Gly Arg
        35                  40                  45

Thr Phe Thr Val Ala Ala Ile Ser Leu Ser Pro Thr Leu Ala Tyr Tyr
    50                  55                  60

Ala Glu Ser Val Lys Gly Arg Phe Thr Ile Ser Arg Asp Asn Ala Lys
65                  70                  75                  80

Asn Thr Val Val Leu Gln Met Asn Ser Leu Lys Pro Glu Asp Thr Ala
                85                  90                  95
```

Leu Tyr Tyr Cys Ala Ala Asp Arg Lys Ser Val Met Ser Ile Arg Pro
                100                 105                 110

Asp Tyr Trp Gly Gln Gly Thr Gln Val Thr Val Ser Ser Thr Ser Thr
            115                 120                 125

Thr Thr Pro Ala Pro Arg Pro Pro Thr Pro Ala Pro Thr Ile Ala Ser
    130                 135                 140

Gln Pro Leu Ser Leu Arg Pro Glu Ala Cys Arg Pro Ala Ala Gly Gly
145                 150                 155                 160

Ala Val His Thr Arg Gly Leu Asp Phe Ala Cys Asp Ile Tyr Ile Trp
                165                 170                 175

Ala Pro Leu Ala Gly Thr Cys Gly Val Leu Leu Leu Ser Leu Val Ile
            180                 185                 190

Thr Leu Tyr Cys Lys Arg Gly Arg Lys Lys Leu Leu Tyr Ile Phe Lys
    195                 200                 205

Gln Pro Phe Met Arg Pro Val Gln Thr Thr Gln Glu Glu Asp Gly Cys
210                 215                 220

Ser Cys Arg Phe Pro Glu Glu Glu Gly Gly Cys Glu Leu Arg Val
225                 230                 235                 240

Lys Phe Ser Arg Ser Ala Asp Ala Pro Ala Tyr Gln Gln Gly Gln Asn
                245                 250                 255

Gln Leu Tyr Asn Glu Leu Asn Leu Gly Arg Arg Glu Glu Tyr Asp Val
            260                 265                 270

Leu Asp Lys Arg Arg Gly Arg Asp Pro Glu Met Gly Gly Lys Pro Arg
    275                 280                 285

Arg Lys Asn Pro Gln Glu Gly Leu Tyr Asn Glu Leu Gln Lys Asp Lys
290                 295                 300

Met Ala Glu Ala Tyr Ser Glu Ile Gly Met Lys Gly Glu Arg Arg Arg
305                 310                 315                 320

Gly Lys Gly His Asp Gly Leu Tyr Gln Gly Leu Ser Thr Ala Thr Lys
                325                 330                 335

Asp Thr Tyr Asp Ala Leu His Met Gln Ala Leu Pro Pro Arg
            340                 345                 350

<210> SEQ ID NO 243
<211> LENGTH: 371
<212> TYPE: PRT
<213> ORGANISM: Artificial Sequence
<220> FEATURE:
<223> OTHER INFORMATION: Synthetic Construct

<400> SEQUENCE: 243

Met Ala Leu Pro Val Thr Ala Leu Leu Leu Pro Leu Ala Leu Leu Leu
1               5                   10                  15

His Ala Ala Arg Pro Asp Val Gln Val Glu Ser Gly Gly Gly Leu
                20                  25                  30

Glu Gln Ala Gly Gly Ser Leu Arg Leu Ser Cys Ala Ala Ser Gly Gly
            35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

```
Ala Val Tyr Tyr Cys Ala Ser Thr Ala Ser Cys His Leu Phe Gly Leu
        115                 120                 125

Gly Ser Gly Ala Phe Val Ser Trp Gly Arg Gly Thr Gln Val Thr Val
        130                 135                 140

Ser Ser Thr Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
        165                 170                 175

Pro Ala Ala Gly Gly Ala Val His Thr Arg Gly Leu Asp Phe Ala Cys
        180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
        210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
        245                 250                 255

Cys Glu Leu Arg Val Lys Phe Ser Arg Ser Ala Asp Ala Pro Ala Tyr
        260                 265                 270

Gln Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
        290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
        325                 330                 335

Gly Glu Arg Arg Arg Gly Lys Gly His Asp Gly Leu Tyr Gln Gly Leu
        340                 345                 350

Ser Thr Ala Thr Lys Asp Thr Tyr Asp Ala Leu His Met Gln Ala Leu
        355                 360                 365

Pro Pro Arg
    370

<210> SEQ ID NO 244
<211> LENGTH: 362
<212> TYPE: PRT
<213> ORGANISM: Artificial Sequence
<220> FEATURE:
<223> OTHER INFORMATION: Synthetic Construct

<400> SEQUENCE: 244

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe His Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
            85                  90                  95
```

Val Val Leu Gln Met Asn Ser Leu Lys Pro Glu Asp Thr Ala Leu Tyr
            100                 105                 110

Tyr Cys Ala Ala Ser Lys Asp Arg Tyr Ser Glu Tyr Glu Tyr Trp Gly
            115                 120                 125

Gln Gly Thr Gln Val Thr Val Ser Ser Thr Ser Thr Thr Thr Pro Ala
            130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
            165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
            195                 200                 205

Lys Arg Gly Arg Lys Lys Leu Leu Tyr Ile Phe Lys Gln Pro Phe Met
            210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
            245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
            275                 280                 285

Arg Gly Arg Asp Pro Glu Met Gly Gly Lys Pro Arg Arg Lys Asn Pro
            290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
            325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
            355                 360

<210> SEQ ID NO 245
<211> LENGTH: 360
<212> TYPE: PRT
<213> ORGANISM: Artificial Sequence
<220> FEATURE:
<223> OTHER INFORMATION: Synthetic Construct

<400> SEQUENCE: 245

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Glu Arg Glu
            50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
            85                  90                  95

Val Val Leu Gln Met Asn Ser Leu Lys Pro Glu Asp Thr Ala Leu Tyr
            100                 105                 110

Tyr Cys Ala Lys Lys Asn Gly Gly Pro Val Asp Tyr Trp Gly Lys Gly
            115                 120                 125

Thr Gln Val Thr Val Ser Ser Thr Ser Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Lys Arg
            195                 200                 205

Gly Arg Lys Lys Leu Leu Tyr Ile Phe Lys Gln Pro Phe Met Arg Pro
        210                 215                 220

Val Gln Thr Thr Gln Glu Glu Asp Gly Cys Ser Cys Arg Phe Pro Glu
225                 230                 235                 240

Glu Glu Glu Gly Gly Cys Glu Leu Arg Val Lys Phe Ser Arg Ser Ala
                245                 250                 255

Asp Ala Pro Ala Tyr Gln Gln Gly Gln Asn Gln Leu Tyr Asn Glu Leu
            260                 265                 270

Asn Leu Gly Arg Arg Glu Glu Tyr Asp Val Leu Asp Lys Arg Arg Gly
        275                 280                 285

Arg Asp Pro Glu Met Gly Gly Lys Pro Arg Arg Lys Asn Pro Gln Glu
290                 295                 300

Gly Leu Tyr Asn Glu Leu Gln Lys Asp Lys Met Ala Glu Ala Tyr Ser
305                 310                 315                 320

Glu Ile Gly Met Lys Gly Glu Arg Arg Arg Gly Lys Gly His Asp Gly
                325                 330                 335

Leu Tyr Gln Gly Leu Ser Thr Ala Thr Lys Asp Thr Tyr Asp Ala Leu
            340                 345                 350

His Met Gln Ala Leu Pro Pro Arg
            355                 360

<210> SEQ ID NO 246
<211> LENGTH: 365
<212> TYPE: PRT
<213> ORGANISM: Artificial Sequence
<220> FEATURE:
<223> OTHER INFORMATION: Synthetic Construct

<400> SEQUENCE: 246

Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Leu
            20                  25                  30

Val Gln Pro Gly Gly Ser Leu Arg Leu Ser Cys Ala Ala Ser Gly Arg
        35                  40                  45

Thr Phe Ser Ser Ile Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

```
Lys Asn Thr Val Tyr Leu Gln Met Asn Ser Leu Lys Leu Glu Asp Thr
                100                 105                 110

Ala Val Tyr Tyr Cys Ala Ala Ser Lys Gly Arg Tyr Ser Glu Tyr Glu
            115                 120                 125

Tyr Trp Gly Gln Gly Thr Gln Val Thr Val Ser Ser Thr Ser Thr Thr
        130                 135                 140

Thr Pro Ala Pro Arg Pro Pro Thr Pro Ala Pro Thr Ile Ala Ser Gln
145                 150                 155                 160

Pro Leu Ser Leu Arg Pro Glu Ala Cys Arg Pro Ala Ala Gly Gly Ala
                165                 170                 175

Val His Thr Arg Gly Leu Asp Phe Ala Cys Asp Ile Tyr Ile Trp Ala
            180                 185                 190

Pro Leu Ala Gly Thr Cys Gly Val Leu Leu Leu Ser Leu Val Ile Thr
        195                 200                 205

Leu Tyr Cys Lys Arg Gly Arg Lys Lys Leu Leu Tyr Ile Phe Lys Gln
    210                 215                 220

Pro Phe Met Arg Pro Val Gln Thr Thr Gln Glu Glu Asp Gly Cys Ser
225                 230                 235                 240

Cys Arg Phe Pro Glu Glu Glu Glu Gly Gly Cys Glu Leu Arg Val Lys
                245                 250                 255

Phe Ser Arg Ser Ala Asp Ala Pro Ala Tyr Gln Gln Gly Gln Asn Gln
            260                 265                 270

Leu Tyr Asn Glu Leu Asn Leu Gly Arg Arg Glu Glu Tyr Asp Val Leu
        275                 280                 285

Asp Lys Arg Arg Gly Arg Asp Pro Glu Met Gly Gly Lys Pro Arg Arg
    290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
            340                 345                 350

Thr Tyr Asp Ala Leu His Met Gln Ala Leu Pro Pro Arg
        355                 360                 365

<210> SEQ ID NO 247
<211> LENGTH: 364
<212> TYPE: PRT
<213> ORGANISM: Artificial Sequence
<220> FEATURE:
<223> OTHER INFORMATION: Synthetic Construct

<400> SEQUENCE: 247

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Ala Gly Gly Ser Leu Lys Leu Ser Trp Ala Ala Ser Gly Arg
        35                  40                  45

Thr Phe Thr Met Gly Trp Phe Arg Gln Ala Pro Gly Lys Glu Arg Glu
    50                  55                  60

Phe Val Thr Ala Ile Asn Leu Ser Pro Thr Leu Thr Tyr Tyr Ala Glu
65                  70                  75                  80

Ser Val Lys Gly Arg Phe Pro Ile Ser Arg Asn Asn Ala Gln Asn Thr
                85                  90                  95
```

Val Val Leu Gln Met Asn Ser Leu Lys Pro Glu Asp Thr Ala Leu Tyr
            100                 105                 110

Tyr Cys Ala Ala Glu Arg Lys Ser Val Met Ala Ile Pro Asp Tyr
            115                 120                 125

Trp Gly Gln Gly Thr Gln Val Thr Val Ser Ser Thr Ser Thr Thr Thr
130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
            165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
            210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
            245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
            275                 280                 285

Lys Arg Arg Gly Arg Asp Pro Glu Met Gly Gly Lys Pro Arg Arg Lys
            290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
            325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
            355                 360

<210> SEQ ID NO 248
<211> LENGTH: 364
<212> TYPE: PRT
<213> ORGANISM: Artificial Sequence
<220> FEATURE:
<223> OTHER INFORMATION: Synthetic Construct

<400> SEQUENCE: 248

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
            35                  40                  45

Thr Phe Thr Met Gly Gly Phe Arg Val Pro Arg Asp Glu Arg Glu
        50                  55                  60

Phe Val Ala Ser Ile Thr Leu Ile Pro Thr Phe Pro Tyr Tyr Ala Tyr
65                  70                  75                  80

Ser Val Lys Gly Arg Phe Ala Leu Phe Arg Asp Asn Pro Asn Asn Thr
            85                  90                  95

Val Ile Leu Leu Met Ile Ser Leu Lys Pro Glu Asp Pro Asp Leu Tyr
            100                 105                 110

Tyr Cys Ala Ser Tyr Arg Lys Tyr Leu Met Ser Ile Leu Pro Asp Tyr
            115                 120                 125

Trp Gly Gln Gly Thr Gln Gly Thr Val Ser Ser Thr Ser Thr Thr Thr
130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
            165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
            210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
            245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
            275                 280                 285

Lys Arg Arg Gly Arg Asp Pro Glu Met Gly Gly Lys Pro Arg Arg Lys
            290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
            325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
            355                 360

<210> SEQ ID NO 249
<211> LENGTH: 370
<212> TYPE: PRT
<213> ORGANISM: Artificial Sequence
<220> FEATURE:
<223> OTHER INFORMATION: Synthetic Construct

<400> SEQUENCE: 249

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Glu Arg Glu
            50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
            85                  90                  95

Val Asp Leu Gln Met Asn Ser Leu Lys Pro Glu Asp Thr Ala Val Tyr
            100                 105                 110

Phe Cys Ala Ala Asn Arg Asn Ser Gln Arg Val Ile Ala Ala Leu Ser
            115                 120                 125

Trp Ile Gly Met Asn Tyr Trp Gly Glu Trp Thr Gln Val Thr Val Ser
            130                 135                 140

Ser Thr Ser Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
            195                 200                 205

Ser Leu Val Ile Thr Leu Tyr Cys Lys Arg Gly Arg Lys Lys Leu Leu
            210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Gln
            260                 265                 270

Gln Gly Gln Asn Gln Leu Tyr Asn Glu Leu Asn Leu Gly Arg Arg Glu
            275                 280                 285

Glu Tyr Asp Val Leu Asp Lys Arg Arg Gly Arg Asp Pro Glu Met Gly
            290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
            355                 360                 365

Pro Arg
    370

<210> SEQ ID NO 250
<211> LENGTH: 362
<212> TYPE: PRT
<213> ORGANISM: Artificial Sequence
<220> FEATURE:
<223> OTHER INFORMATION: Synthetic Construct

<400> SEQUENCE: 250

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Glu Arg Glu
        50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Thr
                85                  90                  95

Leu Tyr Leu Arg Met Asn Ser Leu Lys Pro Glu Asp Thr Ala Val Tyr
            100                 105                 110

Tyr Cys Ala Ala Arg Arg Ile Asp Ala Ala Asp Phe Asp Ser Trp Gly
        115                 120                 125

Gln Gly Thr Gln Val Thr Val Ser Ser Thr Thr Thr Thr Pro Ala
130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
        195                 200                 205

Lys Arg Gly Arg Lys Lys Leu Leu Tyr Ile Phe Lys Gln Pro Phe Met
210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Gln Gln Gly Gln Asn Gln Leu Tyr Asn
            260                 265                 270

Glu Leu Asn Leu Gly Arg Arg Glu Glu Tyr Asp Val Leu Asp Lys Arg
        275                 280                 285

Arg Gly Arg Asp Pro Glu Met Gly Gly Lys Pro Arg Arg Lys Asn Pro
290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
        355                 360

<210> SEQ ID NO 251
<211> LENGTH: 362
<212> TYPE: PRT
<213> ORGANISM: Artificial Sequence
<220> FEATURE:
<223> OTHER INFORMATION: Synthetic Construct

<400> SEQUENCE: 251

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Thr Met Gly Trp Phe Arg Ala Pro Gly Lys Glu Arg Glu
        50                  55                  60

Ser Val Ala Val Ile Gly Trp Arg Asp Ile Asn Ala Ser Tyr Ala Asp
65                  70                  75                  80

```
Ser Val Lys Gly Arg Phe Ala Ile Ser Arg Asp Asn Ala Lys Lys Thr
             85                  90                  95
Leu Tyr Leu Gln Met Asn Ser Leu Lys Pro Glu Asp Thr Ala Val Tyr
            100                 105                 110
Tyr Cys Ala Ala Arg Arg Ile Asp Ala Thr Asp Phe Asp Ser Trp Gly
            115                 120                 125
Gln Gly Thr Gln Val Thr Val Ser Ser Thr Thr Thr Thr Pro Ala
        130                 135                 140
Pro Arg Pro Pro Thr Pro Ala Pro Thr Ile Ala Ser Gln Pro Leu Ser
145                 150                 155                 160
Leu Arg Pro Glu Ala Cys Arg Pro Ala Ala Gly Gly Ala Val His Thr
                165                 170                 175
Arg Gly Leu Asp Phe Ala Cys Asp Ile Tyr Ile Trp Ala Pro Leu Ala
            180                 185                 190
Gly Thr Cys Gly Val Leu Leu Leu Ser Leu Val Ile Thr Leu Tyr Cys
            195                 200                 205
Lys Arg Gly Arg Lys Lys Leu Leu Tyr Ile Phe Lys Gln Pro Phe Met
            210                 215                 220
Arg Pro Val Gln Thr Thr Gln Glu Glu Asp Gly Cys Ser Cys Arg Phe
225                 230                 235                 240
Pro Glu Glu Glu Glu Gly Gly Cys Glu Leu Arg Val Lys Phe Ser Arg
                245                 250                 255
Ser Ala Asp Ala Pro Ala Tyr Gln Gln Gly Gln Asn Gln Leu Tyr Asn
            260                 265                 270
Glu Leu Asn Leu Gly Arg Arg Glu Glu Tyr Asp Val Leu Asp Lys Arg
            275                 280                 285
Arg Gly Arg Asp Pro Glu Met Gly Gly Lys Pro Arg Arg Lys Asn Pro
            290                 295                 300
Gln Glu Gly Leu Tyr Asn Glu Leu Gln Lys Asp Lys Met Ala Glu Ala
305                 310                 315                 320
Tyr Ser Glu Ile Gly Met Lys Gly Glu Arg Arg Arg Gly Lys Gly His
                325                 330                 335
Asp Gly Leu Tyr Gln Gly Leu Ser Thr Ala Thr Lys Asp Thr Tyr Asp
            340                 345                 350
Ala Leu His Met Gln Ala Leu Pro Pro Arg
            355                 360

<210> SEQ ID NO 252
<211> LENGTH: 365
<212> TYPE: PRT
<213> ORGANISM: Artificial Sequence
<220> FEATURE:
<223> OTHER INFORMATION: Synthetic Construct

<400> SEQUENCE: 252

Met Ala Leu Pro Val Thr Ala Leu Leu Leu Pro Leu Ala Leu Leu Leu
1               5                   10                  15
His Ala Ala Arg Pro Gln Val Lys Leu Glu Glu Ser Gly Gly Gly Leu
                20                  25                  30
Val Gln Thr Gly Gly Ser Leu Arg Leu Ser Cys Ala Ala Ser Glu His
            35                  40                  45
Thr Phe Ser Asn His Val Met Gly Trp Phe Arg Gln Ala Pro Gly Lys
            50                  55                  60
Glu Arg Glu Ser Val Ala Val Ile Gly Trp Arg Asp Ile Ser Thr Ser
65                  70                  75                  80
```

```
Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Arg Gly Gln Gly Thr Gln Val Thr Val Ser Ser Thr Ser Thr Thr
    130                 135                 140

Thr Pro Ala Pro Arg Pro Pro Thr Pro Ala Pro Thr Ile Ala Ser Gln
145                 150                 155                 160

Pro Leu Ser Leu Arg Pro Glu Ala Cys Arg Pro Ala Ala Gly Gly Ala
                165                 170                 175

Val His Thr Arg Gly Leu Asp Phe Ala Cys Asp Ile Tyr Ile Trp Ala
                180                 185                 190

Pro Leu Ala Gly Thr Cys Gly Val Leu Leu Leu Ser Leu Val Ile Thr
                195                 200                 205

Leu Tyr Cys Lys Arg Gly Arg Lys Lys Leu Leu Tyr Ile Phe Lys Gln
    210                 215                 220

Pro Phe Met Arg Pro Val Gln Thr Thr Gln Glu Glu Asp Gly Cys Ser
225                 230                 235                 240

Cys Arg Phe Pro Glu Glu Glu Glu Gly Gly Cys Glu Leu Arg Val Lys
                245                 250                 255

Phe Ser Arg Ser Ala Asp Ala Pro Ala Tyr Gln Gln Gly Gln Asn Gln
                260                 265                 270

Leu Tyr Asn Glu Leu Asn Leu Gly Arg Arg Glu Glu Tyr Asp Val Leu
    275                 280                 285

Asp Lys Arg Arg Gly Arg Asp Pro Glu Met Gly Gly Lys Pro Arg Arg
290                 295                 300

Lys Asn Pro Gln Glu Gly Leu Tyr Asn Glu Leu Gln Lys Asp Lys Met
305                 310                 315                 320

Ala Glu Ala Tyr Ser Glu Ile Gly Met Lys Gly Glu Arg Arg Arg Gly
                325                 330                 335

Lys Gly His Asp Gly Leu Tyr Gln Gly Leu Ser Thr Ala Thr Lys Asp
                340                 345                 350

Thr Tyr Asp Ala Leu His Met Gln Ala Leu Pro Pro Arg
    355                 360                 365

<210> SEQ ID NO 253
<211> LENGTH: 369
<212> TYPE: PRT
<213> ORGANISM: Artificial Sequence
<220> FEATURE:
<223> OTHER INFORMATION: Synthetic Construct

<400> SEQUENCE: 253

Met Ala Leu Pro Val Thr Ala Leu Leu Leu Pro Leu Ala Leu Leu Leu
1               5                   10                  15

His Ala Ala Arg Pro Ala Val Gln Leu Val Asp Ser Gly Gly Gly Leu
            20                  25                  30

Val Gln Ala Gly Gly Ser Leu Arg Ile Ser Cys Ala Val Ser Gly Arg
        35                  40                  45

Thr Ser Ser Asn Tyr Ile Leu Ala Trp Phe Arg Gln Ala Pro Gly Lys
    50                  55                  60

Glu Arg Asp Phe Val Ala His Ile Ser Arg Ser Gly Gly Lys Ser Gly
65                  70                  75                  80
```

Tyr Gly Asp Ser Val Lys Gly Arg Phe Thr Ile Ser Arg Asp Asn Ala
                85                  90                  95

Glu Asn Thr Val Arg Val Tyr Leu Gln Met Asn Ser Leu Lys Pro Gly
            100                 105                 110

Asp Thr Ala Val Tyr Tyr Cys Asn Arg Pro Leu Trp Tyr Gly Ser Pro
        115                 120                 125

Thr Leu Ile Asp Tyr Trp Gly Gln Gly Thr Gln Val Thr Val Ser Ser
    130                 135                 140

Thr Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Gln Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 254
<211> LENGTH: 364
<212> TYPE: PRT
<213> ORGANISM: Artificial Sequence
<220> FEATURE:
<223> OTHER INFORMATION: Synthetic Construct

<400> SEQUENCE: 254

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Thr Ser Thr Thr Thr
    130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
                180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
                260                 265                 270

Tyr Asn Glu Leu Asn Leu Gly Arg Arg Glu Glu Tyr Asp Val Leu Asp
            275                 280                 285

Lys Arg Arg Gly Arg Asp Pro Glu Met Gly Gly Lys Pro Arg Arg Lys
        290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
        355                 360

<210> SEQ ID NO 255
<211> LENGTH: 364
<212> TYPE: PRT
<213> ORGANISM: Artificial Sequence
<220> FEATURE:
<223> OTHER INFORMATION: Synthetic Construct

<400> SEQUENCE: 255

Met Ala Leu Pro Val Thr Ala Leu Leu Leu Pro Leu Ala Leu Leu Leu
1               5                   10                  15

His Ala Ala Arg Pro Ala Val Gln Leu Val Asp Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Pro Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Thr Ser Thr Thr Thr
    130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Ser Leu Val Ile Thr Leu
        195                 200                 205

Tyr Cys Lys Arg Gly Arg Lys Lys Leu Leu Tyr Ile Phe Lys Gln Pro
210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
        275                 280                 285

Lys Arg Arg Gly Arg Asp Pro Glu Met Gly Gly Lys Pro Arg Arg Lys
    290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
        355                 360

<210> SEQ ID NO 256
<211> LENGTH: 367
<212> TYPE: PRT
<213> ORGANISM: Artificial Sequence
<220> FEATURE:
<223> OTHER INFORMATION: Synthetic Construct

<400> SEQUENCE: 256

Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Ser
            20                  25                  30

Val Gln Thr Gly Gly Ser Leu Arg Leu Ser Cys Thr Ala Ser Gly Arg
        35                  40                  45

Thr Leu Asn Asn Phe Val Met Gly Trp Phe Arg Gln Ala Pro Gly Lys
    50                  55                  60

Glu Arg Glu Phe Val Ala Ala Ile Ser Leu Ser Pro Thr Leu Ala Tyr
65                  70                  75                  80

Tyr Val Glu Ser Val Lys Gly Arg Phe Thr Ile Ser Arg Asp Asn Ala
                85                  90                  95

Lys Asn Thr Val Val Leu Gln Met Asn Ser Leu Lys Pro Glu Asp Thr
            100                 105                 110

Ala Leu Tyr Tyr Cys Ala Ala Asp Arg Lys Ser Val Met Ser Ile Arg
            115                 120                 125

Pro Asp Tyr Trp Gly Gln Gly Thr Gln Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
        275                 280                 285

Val Leu Asp Lys Arg Arg Gly Arg Asp Pro Glu Met Gly Gly Lys Pro
290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 257
<211> LENGTH: 1263
<212> TYPE: DNA
<213> ORGANISM: Artificial Sequence
<220> FEATURE:
<223> OTHER INFORMATION: Synthetic Construct

<400> SEQUENCE: 257
atggccttac cagtgaccgc cttgctcctg ccgctggcct tgctgctcca cgccgccagg        60
ccggttaacc gcacgcgtcg catgcatcag gtgcagctgg tggagtctgg gggaggcttg       120
gtgcagcctg ggggttctct gaggctctcc tgtgaagcct ctggattcac tttggattat       180
tatgccatag gctggttccg ccaggcccca gggaaggagc gcgagggggt catatgtatt       240
agtagaagtg atggtagcac atactatgca gactccgtga aggccgatt caccatctcc       300 agagacaacg ccaagaaaac ggtgtatctg caaatgatca gcctgaaacc tgaggacacg       360

```
gccgcttatt actgtgcagc aggggccgat tgttcggggt acctacgaga ttatgagttc      420
cgggggcagg ggacccaggt caccgtctcc tcaactagta ccacgacgcc agcgccgcga      480
ccaccaacac cggcgcccac catcgcgtcg cagcccctgt ccctgcgccc agaggcgtgc      540
cggccagcgg cggggggcgc agtgcacacg aggggctgg  acttcgcctg tgattttttgg    600 gtgctggtgg tggttggtgg agtcctggct tgctatagct tgctagtaac agtggccttt      660
attattttct gggtgaggag taagaggagc aggctcctgc acagtgacta catgaacatg      720
actccccgcc gccccgggcc cacccgcaag cattaccagc cctatgcccc accacgcgac      780
ttcgcagcct atcgctccaa acggggcaga aagaaactcc tgtatatatt caaacaacca      840
tttatgagac cagtacaaac tactcaagag gaagatggct gtagctgccg atttccagaa      900
gaagaagaag gaggatgtga actgagagtg aagttcagca ggagcgcaga cgcccccgcg      960
tacaagcagg gccagaacca gctctataac gagctcaatc taggacgaag agaggagtac     1020
gatgttttgg acaagagacg tggccgggac cctgagatgg ggggaaagcc gagaaggaag     1080
aaccctcagg aaggcctgta caatgaactg cagaaagata gatggcggga ggcctacagt     1140
gagattggga tgaaaggcga gcgccggagg ggcaaggggc acgatggcct ttaccagggt     1200
ctcagtacag ccaccaagga cacctacgac gcccttcaca tgcaggccct gccccctcgc     1260
tga                                                                   1263
```

```
<210> SEQ ID NO 258
<211> LENGTH: 1281
<212> TYPE: DNA
<213> ORGANISM: Artificial Sequence
<220> FEATURE:
<223> OTHER INFORMATION: Synthetic Construct

<400> SEQUENCE: 258
atggccttac cagtgaccgc cttgctcctg ccgctggcct tgctgctcca cgccgccagg       60
ccggttaacc gcacgcgtcg catgcatcag gtaaagctgg aggagtctgg gggacgattg      120
gtgcagccaa ggggctctct gagactctcc tgtgcaggct ctggacgcac tttcagtacc      180
tatggtatgg cctggttccg ccaggctcca gggaaggagc gtgagttcgt agcgtctaaa      240
gcatcgatga attacagcgg tagaacatac tatgcagact ccgtgaaggg ccgattcacc      300
atcgccagac acaacgccaa gaacatggtg tttctgcaaa tgaacaacct gaagcctgag      360
gacacggccg tttattactg tgcagcgggc actggatgct caacatatgg tgttttgac     420 gcccagataa tagactactg gggcaaaggg accctggtca ccgtctcctc aactagtacc      480
acgacgccag cgccgcgacc accaacaccg gcgcccacca tcgcgtcgca gcccctgtcc      540
ctgcgcccag aggcgtgccg gccagcgcgg ggggcgcag tgcacacgag ggggctggac      600
ttcgcctgtg atttttgggt gctggtgtg gttggtggag tcctggcttg ctatagcttg      660
ctagtaacag tggcctttat tattttctgg gtgaggagta agaggagcag gctcctgcac      720
agtgactaca tgaacatgac tccccgccgc cccgggccca cccgcaagca ttaccagccc      780
tatgccccac cacgcgactt cgcagcctat cgctccaaac ggggcagaaa gaaactcctg      840
tatatattca acaaccatt tatgagacca gtacaaacta ctcaagagga gatggctgt      900 agctgccgat ttcagaaga agaagaagga ggatgtgaac tgagagtgaa gttcagcagg      960
agcgcagacg cccccgcgta caagcagggc cagaaccagc tctataacga gctcaatcta     1020
ggacgaagag aggagtacga tgttttggac aagagacgtg gccgggaccc tgagatgggg     1080
ggaaagccga aggaagaa ccctcaggaa ggcctgtaca atgaactgca gaaagataag     1140
```

| | |
|---|---|
| atggcggagg cctacagtga gattgggatg aaaggcgagc gccggagggg caaggggcac | 1200 |
| gatggccttt accagggtct cagtacagcc accaaggaca cctacgacgc ccttcacatg | 1260 |
| caggccctgc cccctcgctg a | 1281 |

<210> SEQ ID NO 259
<211> LENGTH: 1251
<212> TYPE: DNA
<213> ORGANISM: Artificial Sequence
<220> FEATURE:
<223> OTHER INFORMATION: Synthetic Construct

<400> SEQUENCE: 259

| | |
|---|---|
| atggccttac cagtgaccgc cttgctcctg ccgctggcct tgctgctcca cgccgccagg | 60 |
| ccggttaacc gcacgcgtcg catgcatgag gtgcagctgg tggagtctgg ggaggcttg | 120 |
| gtgcaggctg gggggtctct gagactctcc tgtgcagcct ctggacgcac cttcaccatg | 180 |
| gggtggttcc gtcaggctcc aggaaggag cgtgagtttg tagcagctat tagtttgagt | 240 |
| cctactttag catattatgc agagtccgtg aagggccgat tcaccatcag ccgagacaac | 300 |
| gccaagaaca cggtggtttt gcaaatgaac agcctgaaac ctgaggacac ggcccttat | 360 |
| tactgtgcag cagaccggaa atcagtaatg tctattcggc ccgactactg gggccagggg | 420 |
| acccaggtca ccgtctcctc aactagtacc acgacgccag cgccgcgacc accaacaccg | 480 |
| gcgcccacca tcgcgtcgca gccctgtcc ctgcgcccag aggcgtgccg gccagcggcg | 540 |
| gggggcgcag tgcacacgag ggggctggac ttcgcctgtg attttggt gctggtggtg | 600 |
| gttggtggag tcctggcttg ctatagcttg ctagtaacag tggcctttat tattttctgg | 660 |
| gtgaggagta agaggagcag gctcctgcac agtgactaca tgaacatgac tccccgccgc | 720 |
| cccgggccca ccgcaagca ttaccagccc tatgccccac cacgcgactt cgcagcctat | 780 |
| cgctccaaac ggggcagaaa gaaactcctg tatatattca acaaccatt tatgagacca | 840 |
| gtacaaacta ctcaagagga agatggctgt agctgccgat ttccagaaga agaagaagga | 900 |
| ggatgtgaac tgagagtgaa gttcagcagg agcgcagacg ccccgcgta caagcagggc | 960 |
| cagaaccagc tctataacga gctcaatcta ggacgaagag aggagtacga tgttttggac | 1020 |
| aagagacgtg gccgggaccc tgagatgggg ggaaagccga aaggaagaa ccctcaggaa | 1080 |
| ggcctgtaca tgaactgca gaaagataag atggcggagg cctacagtga gattgggatg | 1140 |
| aaaggcgagc gccggagggg caaggggcac gatggccttt accagggtct cagtacagcc | 1200 |
| accaaggaca cctacgacgc ccttcacatg caggccctgc cccctcgctg a | 1251 |

<210> SEQ ID NO 260
<211> LENGTH: 1257
<212> TYPE: DNA
<213> ORGANISM: Artificial Sequence
<220> FEATURE:
<223> OTHER INFORMATION: Synthetic Construct

<400> SEQUENCE: 260

| | |
|---|---|
| atggccttac cagtgaccgc cttgctcctg ccgctggcct tgctgctcca cgccgccagg | 60 |
| ccggttaacc gcacgcgtcg catgcatgcc gtgcagctgg tggattctgg gggaggcttg | 120 |
| gtgcagcctg gggggtctct gagactctcc tgtgtagcct ctggaggtat cttcgtcatc | 180 |
| aatgccatgg gctggtaccg ccaggctcca ggaaagcagc gcgagttggt cgcatctatt | 240 |
| cgtggactag gcagaacaaa ctatgacgac tccgtgaagg gccgattcac catctccaga | 300 |

| | |
|---|---|
| gacaacgcca acaacacggt gtatctgcag atgaacagcc tggaacctga ggacacggcc | 360 |
| gtctactact gtacagtcta cgttacacta cttggtgggg ttaataggga ctactggggc | 420 |
| caggggaccc aggtcaccgt ctcctcaact agtaccacga cgccagcgcc gcgaccacca | 480 |
| acaccggcgc ccaccatcgc gtcgcagccc ctgtccctgc gcccagaggc gtgccggcca | 540 |
| gcggcggggg gcgcagtgca cacgaggggg ctggacttcg cctgtgattt ttgggtgctg | 600 |
| gtggtggttg gtggagtcct ggcttgctat agcttgctag taacagtggc ctttattatt | 660 |
| ttctgggtga ggagtaagag gagcaggctc ctgcacagtg actacatgaa catgactccc | 720 |
| cgccgccccg gcccacccg caagcattac cagcccctatg ccccaccacg cgacttcgca | 780 |
| gcctatcgct ccaaacgggg cagaaagaaa ctcctgtata tattcaaaca accatttatg | 840 |
| agaccagtac aaactactca agaggaagat ggctgtagct gccgatttcc agaagaagaa | 900 |
| gaaggaggat gtgaactgag agtgaagttc agcaggagcg cagacgcccc cgcgtacaag | 960 |
| cagggccaga accagctcta taacgagctc aatctaggac gaagagagga gtacgatgtt | 1020 |
| ttggacaaga gacgtggccg ggaccctgag atgggggaaa gccgagaag gaagaaccct | 1080 |
| caggaaggcc tgtacaatga actgcagaaa gataagatgg cggaggccta cagtgagatt | 1140 |
| gggatgaaag cgagcgccg gaggggcaag gggcacgatg gcctttacca gggtctcagt | 1200 |
| acagccacca aggacaccta cgacgccctt cacatgcagg ccctgccccc tcgctga | 1257 |

<210> SEQ ID NO 261
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 261

| | |
|---|---|
| atggccttac cagtgaccgc cttgctcctg ccgctggcct tgctgctcca cgccgccagg | 60 |
| ccggttaacc gcacgcgtcg catgcatgag gtgcagctgg tggagtctgg gggaggattg | 120 |
| gtgcaggctg ggggctctct gagactctcc tgtgcagcct ctggacggac cttcagtagc | 180 |
| attgtcatgg gctggttccg ccaggctcca gggaaggagc gtgagtttgt aggagcgatt | 240 |
| atgtggaatg atggtattac atacttgcaa gactccgtga agggccgatt taccatcttc | 300 |
| agagacaatg ccaagaacac ggtgtatctg caaatgaaca gcctgaaact tgaggatacg | 360 |
| gccgtttatt actgtgcagc atccaagggt agatactcgg aatatgagta ctggggccag | 420 |
| gggacccagg tcaccgtctc ctcaactagt accacgacgc agcgccgcg accaccaaca | 480 |
| ccggcgccca ccatcgcgtc gcagccctg tcctgcgcc cagaggcgtg ccggccagcg | 540 |
| gcggggggcg cagtgcacac gagggggctg gacttcgcct gtgattttg ggtgctggtg | 600 |
| gtggttggtg gagtcctggc ttgctatagc ttgctagtaa cagtggcctt tattattttc | 660 |
| tgggtgagga gtaagaggag caggctcctg cacagtgact acatgaacat gactccccgc | 720 |
| cgccccgggc ccacccgcaa gcattaccag cccctatgccc caccacgcga cttcgcagcc | 780 |
| tatcgctcca aacggggcag aaagaaactc ctgtatatat tcaaacaacc atttatgaga | 840 |
| ccagtacaaa ctactcaaga ggaagatggc tgtagctgcc gatttccaga agaagaagaa | 900 |
| ggaggatgtg aactgagagt gaagttcagc aggagcgcag acgccccgc gtacaagcag | 960 |
| ggccagaacc agctctataa cgagctcaat ctaggacgaa gaggagta cgatgttttg | 1020 |
| gacaagagac gtggccggga ccctgagatg ggggaaagc cgagaaggaa gaaccctcag | 1080 |
| gaaggcctgt acaatgaact gcagaaagat aagatggcgg aggcctacag tgagattggg | 1140 |

| | |
|---|---|
| atgaaaggcg agcgccggag gggcaagggg cacgatggcc tttaccaggg tctcagtaca | 1200 |
| gccaccaagg acacctacga cgcccttcac atgcaggccc tgcccctcg ctga | 1254 |

<210> SEQ ID NO 262
<211> LENGTH: 1281
<212> TYPE: DNA
<213> ORGANISM: Artificial Sequence
<220> FEATURE:
<223> OTHER INFORMATION: Synthetic Construct

<400> SEQUENCE: 262

| | |
|---|---|
| atggccttac cagtgaccgc cttgctcctg ccgctggcct tgctgctcca cgccgccagg | 60 |
| ccggttaacc gcacgcgtcg catgcatgag gtgcagctgg tggagtctgg gggaggcgtg | 120 |
| gtgcaggctg gggggtctct gacagtctcc tgtacagcct ctggattcac tttcgaccgt | 180 |
| gctgtcatag tctggttccg ccaggccccc gggaagggcc gtgaggggt ctcatttatt | 240 |
| aaacctagtg atggcaccat atactacatt gactccctga aggccgatt cacgatctcc | 300 |
| agtgacatcg ccaagaatac ggtatatctg caaatgaaaa gtctggaatc ggaggactcg | 360 |
| gccgtttatt actgtgcggc ctcgcctgag gactggtaca cggattggat cgactggagt | 420 |
| atatatcggt ggcagcactg gggccagggg acccaggtca ctgtctcctc aactagtacc | 480 |
| acgacgccag cgccgcgacc accaacaccg gcgcccacca tcgcgtcgca gcccctgtcc | 540 |
| ctgcgcccag aggcgtgccg gccagcggcg ggggcgcag tgcacacgag ggggctggac | 600 |
| ttcgcctgtg atttttgggt gctggtggtg gttggtggag tcctggcttg ctatagcttg | 660 |
| ctagtaacag tggcctttat tattttctgg gtgaggagta agaggagcag gctcctgcac | 720 |
| agtgactaca tgaacatgac tccccgccgc cccgggccca cccgcaagca ttaccagccc | 780 |
| tatgccccac cacgcgactt cgcagcctat cgctccaaac ggggcagaaa gaaactcctg | 840 |
| tatatattca acaaccatt tatgagacca gtacaaacta ctcaagagga agatggctgt | 900 |
| agctgccgat ttccagaaga agaagaagga ggatgtgaac tgagagtgaa gttcagcagg | 960 |
| agcgcagacg cccccgcgta caagcagggc cagaaccagc tctataacga gctcaatcta | 1020 |
| ggacgaagag aggagtacga tgttttggac aagagacgtg gccgggaccc tgagatgggg | 1080 |
| ggaaagccga aggaagaa ccctcaggaa ggcctgtaca atgaactgca gaaagataag | 1140 |
| atggcggagg cctacagtga gattggatg aaaggcgagc gccggagggg caaggggcac | 1200 |
| gatggccttt accagggtct cagtacagcc accaaggaca cctacgacgc ccttcacatg | 1260 |
| caggccctgc cccctcgctg a | 1281 |

<210> SEQ ID NO 263
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 263

| | |
|---|---|
| atggccttac cagtgaccgc cttgctcctg ccgctggcct tgctgctcca cgccgccagg | 60 |
| ccggttaacc gcacgcgtcg catgcatgag gtgcagctgg tggagtctgg gggaggaatg | 120 |
| gtgcaggctg gggactctct gagactatcc tgtgtgcagt ctacttacac cgtcaatagc | 180 |
| gatgtcatgg gctggttccg ccaggctcca gggaaggagc gtgagtttgt aggagcgatt | 240 |
| atgtggaatg atggtattac atacttgcaa gactccgtga agggccgatt taccatcttc | 300 |

| | |
|---|---|
| agagacaacg ccaagaacac ggtgtatctg caaatgaaca gcctgaaact tgaggatacg | 360 |
| gccgtttatt actgtgcagc atccaagggt agatactcgg aatatgagta ctggggccag | 420 |
| gggacccagg tcaccgtctc ctcaactagt accacgacgc cagcgccgcg accaccaaca | 480 |
| ccggcgccca ccatcgcgtc gcagcccctg tccctgcgcc cagaggcgtg ccggccagcg | 540 |
| gcggggggcg cagtgcacac gagggggctg gacttcgcct gtgattttg ggtgctggtg | 600 |
| gtggttggtg gagtcctggc ttgctatagc ttgctagtaa cagtggcctt tattattttc | 660 |
| tgggtgagga gtaagaggag caggctcctg cacagtgact acatgaacat gactccccgc | 720 |
| cgccccgggc ccacccgcaa gcattaccag ccctatgccc caccacgcga cttcgcagcc | 780 |
| tatcgctcca acggggcag aaagaaactc ctgtatatat tcaaacaacc atttatgaga | 840 |
| ccagtacaaa ctactcaaga ggaagatggc tgtagctgcc gatttccaga agaagaagaa | 900 |
| ggaggatgtg aactgagagt gaagttcagc aggagcgcag acgccccgc gtacaagcag | 960 |
| ggccagaacc agctctataa cgagctcaat ctaggacgaa gagaggagta cgatgttttg | 1020 |
| gacaagagac gtggccggga ccctgagatg ggggaaagc cgagaaggaa gaaccctcag | 1080 |
| gaaggcctgt acaatgaact gcagaaagat aagatggcgg aggcctacag tgagattggg | 1140 |
| atgaaaggcg agcgccggag gggcaagggg cacgatggcc tttaccaggg tctcagtaca | 1200 |
| gccaccaagg acacctacga cgcccttcac atgcaggccc tgccccctcg ctga | 1254 |

<210> SEQ ID NO 264
<211> LENGTH: 1257
<212> TYPE: DNA
<213> ORGANISM: Artificial Sequence
<220> FEATURE:
<223> OTHER INFORMATION: Synthetic Construct

<400> SEQUENCE: 264

| | |
|---|---|
| atggccttac cagtgaccgc cttgctcctg ccgctggcct tgctgctcca cgccgccagg | 60 |
| ccggttaacc gcacgcgtcg catgcatgcg gtgcagctgg tggagtctgg ggaggattg | 120 |
| gtgcaggctg ggactctct gagactctcc tgtacagcct ctggtgcaac cttgactaac | 180 |
| gatcacatgg catggttccg ccaggctcca gggaaggggc gtgaatttgt agcagctatt | 240 |
| gactggagtg gtcgtaccac aaattacgca gaccccgtag agggccgatt caccatctcc | 300 |
| agaaacaacg ccaagaacac ggtgtatctg gaaatgaaca gcctgaaact tgaggacacg | 360 |
| gccgtttatt actgtgcggt cctccgcgct tggatctcat atgacaatga ctactggggc | 420 |
| caggggaccc aggtcaccgt ctcctcaact agtaccacga cgccagcgcc gcgaccacca | 480 |
| acaccggcgc ccaccatcgc gtcgcagccc ctgtccctgc gcccagaggc gtgccggcca | 540 |
| gcggcggggg gcgcagtgca cacgaggggg ctggacttcg cctgtgattt ttgggtgctg | 600 |
| gtggtggttg gtggagtcct ggcttgctat agcttgctag taacagtggc ctttattatt | 660 |
| ttctgggtga ggagtaagag gagcaggctc ctgcacagtg actacatgaa catgactccc | 720 |
| cgccgccccg ggcccacccg caagcattac cagccctatg ccccaccacg cgacttcgca | 780 |
| gcctatcgct ccaaacgggg cagaaagaaa ctcctgtata tattcaaaca accatttatg | 840 |
| agaccagtac aaactactca agaggaagat ggctgtagct gccgatttcc agaagaagaa | 900 |
| gaaggaggat gtgaactgag agtgaagttc agcaggagcg cagacgcccc cgcgtacaag | 960 |
| cagggccaga accagctcta taacgagctc aatctaggac gaagagagga gtacgatgtt | 1020 |
| ttggacaaga gacgtggccg ggaccctgag atgggggaa agccgagaag gaagaaccct | 1080 |
| caggaaggcc tgtacaatga actgcagaaa gataagatgg cggaggccta cagtgagatt | 1140 |

```
gggatgaaag gcgagcgccg gaggggcaag gggcacgatg gcctttacca gggtctcagt   1200
acagccacca aggacaccta cgacgccctt cacatgcagg ccctgccccc tcgctga      1257
```

<210> SEQ ID NO 265
<211> LENGTH: 1257
<212> TYPE: DNA
<213> ORGANISM: Artificial Sequence
<220> FEATURE:
<223> OTHER INFORMATION: Synthetic Construct

<400> SEQUENCE: 265

```
atggccttac cagtgaccgc cttgctcctg ccgctggcct tgctgctcca cgccgccagg    60
ccggttaacc gcacgcgtcg catgcatcag gtgcagctgg tggagtctgg gggaggattg   120
gtgcaggctg ggggctctct gagactctcc tgtgcagcct ctggaggcac cttaagtaaa   180
aataccgtgg cttggttccg ccaggctcca gggaaggagc gtgggtttgt agcgtctatt   240
acctgggatg tcgtacgac atactatgca gactccgtga agggccgatt caccatctcc    300
agagacaacg ccaagaacac agtgtatctg caaatgaaca gcctgaaacc tgaggatacg   360
gccgtttatt tctgtgcaga cttagggaaa tggcctgcgg gccggcgga ctactggggc    420 caggggaccc aggtcaccgt ctcctcaact agtaccacga cgccagcgcc gcgaccacca   480
acaccggcgc ccaccatcgc gtcgcagccc ctgtccctgc gcccagaggc gtgccggcca   540
gcggcggggg gcgcagtgca cacgagggggg ctggacttcg cctgtgattt ttgggtgctg   600
gtggtggttg gtggagtcct ggcttgctat agcttgctag taacagtggc ctttattatt   660
ttctgggtga ggagtaagag gagcaggctc ctgcacagtg actacatgaa catgactccc   720
cgccgccccg ggcccacccg caagcattac cagccctatg ccccaccacg cgacttcgca   780
gcctatcgct ccaaacgggg cagaaagaaa ctcctgtata tattcaaaca accatttatg   840
agaccagtac aaactactca agaggaagat ggctgtagct gccgatttcc agaagaagaa   900
gaaggaggat gtgaactgag agtgaagttc agcaggagcg cagacgcccc cgcgtacaag   960
cagggccaga accagctcta taacgagctc aatctaggac gaagagagga gtacgatgtt  1020
ttggacaaga gacgtggccg ggaccctgag atgggggaa agccgagaag gaagaaccct   1080
caggaaggcc tgtacaatga actgcagaaa gataagatgg cggaggccta cagtgagatt  1140
gggatgaaag gcgagcgccg gaggggcaag gggcacgatg gcctttacca gggtctcagt  1200
acagccacca aggacaccta cgacgccctt cacatgcagg ccctgccccc tcgctga     1257
```

<210> SEQ ID NO 266
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 266

```
atggccttac cagtgaccgc cttgctcctg ccgctggcct tgctgctcca cgccgccagg    60
ccggttaacc gcacgcgtcg catgcatcag gtaaagctgg aggagtctgg gggaggcttg   120
gtgcaggctg gcggtctctc gagactctcc tgtgcagcct ctgaacacac cttcagtagc   180
catgtcatgg gctggttccg ccaggctcca gggaaggagc gtgagtctgt tgcagttatt   240
ggctggagag atattagcac aagctatgca gactccgtga agggccgatt caccatctcc   300
agagacaacg ccaagaagac gctgtatctg caaatgaata gcctgaaacc tgaggacacg   360
```

```
gccgtttact actgtgcagc acgtcggatc gacgcagctg actttgattc ctgggggcag      420
gggacccagg tcaccgtctc ctcgactagt accacgacgc cagcgccgcg accaccaaca      480
ccggcgccca ccatcgcgtc gcagcccctg tccctgcgcc cagaggcgtg ccggccagcg      540 gcgggggggcg cagtgcacac gagggggctg gacttcgcct gtgattttg ggtgctggtg      600 gtggttggtg gagtcctggc ttgctatagc ttgctagtaa cagtggcctt tattattttc      660
tgggtgagga gtaagaggag caggctcctg cacagtgact acatgaacat gactccccgc      720
cgccccgggc ccacccgcaa gcattaccag ccctatgccc caccacgcga cttcgcagcc      780
tatcgctcca acggggcag aaagaaactc ctgtatatat tcaaacaacc atttatgaga      840
ccagtacaaa ctactcaaga ggaagatggc tgtagctgcc gatttccaga agaagaagaa      900
ggaggatgtg aactgagagt gaagttcagc aggagcgcag acgccccgc gtacaagcag      960 ggccagaacc agctctataa cgagctcaat ctaggacgaa gagaggagta cgatgttttg     1020
gacaagagac gtggccggga ccctgagatg gggggaaagc cgagaaggaa gaaccctcag     1080
gaaggcctgt acaatgaact gcagaaagat aagatggcgg aggcctacag tgagattggg     1140
atgaaaggcg agcgccggag gggcaagggg cacgatggcc tttaccaggg tctcagtaca     1200
gccaccaagg acacctacga cgcccttcac atgcaggccc tgccccctcg ctga           1254

<210> SEQ ID NO 267
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 267
atggccttac cagtgaccgc cttgctcctg ccgctggcct tgctgctcca cgccgccagg       60
ccggttaacc gcacgcgtcg catgcatgcg gtgcagctgg tggagtctgg gggaggattg      120
gtgcaggctg gggactctct gagactcacc tgtacagcct ctggacgcgc cttcagtacc      180
tatttcatgg cctggttccg ccaggctcca gggaaggagc gtgagtttgt agcaggaatt      240
gcatggagtg tggtagcac ggcgtatgca gactccgtga agggccgatt caccatctcc      300
agagacaacg ccaagaacac ggtgtatctg caaatgaaca gcctgaaatc tgaggacacg      360
gccgtttatt actgtgccag caggggggatt gaggtcgaag agtttggtgc ctggggccag      420
gggacccagg tcaccgtctc gtcgactagt accacgacgc cagcgccgcg accaccaaca      480
ccggcgccca ccatcgcgtc gcagcccctg tccctgcgcc cagaggcgtg ccggccagcg      540 gcgggggggcg cagtgcacac gagggggctg gacttcgcct gtgattttg ggtgctggtg      600 gtggttggtg gagtcctggc ttgctatagc ttgctagtaa cagtggcctt tattattttc      660
tgggtgagga gtaagaggag caggctcctg cacagtgact acatgaacat gactccccgc      720
cgccccgggc ccacccgcaa gcattaccag ccctatgccc caccacgcga cttcgcagcc      780
tatcgctcca acggggcag aaagaaactc ctgtatatat tcaaacaacc atttatgaga      840
ccagtacaaa ctactcaaga ggaagatggc tgtagctgcc gatttccaga agaagaagaa      900
ggaggatgtg aactgagagt gaagttcagc aggagcgcag acgccccgc gtacaagcag      960 ggccagaacc agctctataa cgagctcaat ctaggacgaa gagaggagta cgatgttttg     1020
gacaagagac gtggccggga ccctgagatg gggggaaagc cgagaaggaa gaaccctcag     1080
gaaggcctgt acaatgaact gcagaaagat aagatggcgg aggcctacag tgagattggg     1140
atgaaaggcg agcgccggag gggcaagggg cacgatggcc tttaccaggg tctcagtaca     1200
```

```
gccaccaagg acacctacga cgcccttcac atgcaggccc tgcccctcg ctga        1254
```

<210> SEQ ID NO 268
<211> LENGTH: 1131
<212> TYPE: DNA
<213> ORGANISM: Artificial Sequence
<220> FEATURE:
<223> OTHER INFORMATION: Synthetic Construct

<400> SEQUENCE: 268

```
atggccttac cagtgaccgc cttgctcctg ccgctggcct tgctgctcca cgccgccagg    60
ccggttaacc gcacgcgtcg catgcatcag gtgcagctgg tggagtctgg ggaggcttg    120
gtgcagcctg ggggttctct gaggctctcc tgtgaagcct ctggattcac tttggattat    180
tatgccatag gctggttccg ccaggcccca gggaaggagc gcgaggggt catatgtatt    240
agtagaagtg atggtagcac atactatgca gactccgtga agggccgatt caccatctcc    300
agagacaacg ccaagaaaac ggtgtatctg caaatgatca gcctgaaacc tgaggacacg    360
gccgcttatt actgtgcagc aggggccgat tgttcggggt acctacgaga ttatgagttc    420
cggggggcagg ggacccaggt caccgtctcc tcaactagta ccacgacgcc agcgccgcga    480
ccaccaacac cggcgcccac catcgcgtcg cagcccctgt ccctgcgccc agaggcgtgc    540
cggccagcgg cgggggggcgc agtgcacacg agggggctgg acttcgcctg tgatatctac    600
atctgggcgc ccttggccgg gacttgtggg gtccttctcc tgtcactggt tatcacccttt    660
tactgcaaac ggggcagaaa gaaactcctg tatatattca acaaccatt tatgagacca    720
gtacaaacta ctcaagagga gatggctgt agctgccgat tccagaaga agaagaagga    780
ggatgtgaac tgagagtgaa gttcagcagg agcgcagacg cccccgcgta ccagcagggc    840
cagaaccagc tctataacga gctcaatcta ggacgaagag aggagtacga tgttttggac    900
aagagacgtg gccgggaccc tgagatgggg ggaaagccga aaggaagaa ccctcaggaa    960
ggcctgtaca atgaactgca gaaagataag atggcggagg cctacagtga gattgggatg   1020
aaaggcgagc gccggagggg caaggggcac gatggccttt accagggtct cagtacagcc   1080
accaaggaca cctacgacgc ccttcacatg caggccctgc cctcgcta a              1131
```

<210> SEQ ID NO 269
<211> LENGTH: 1122
<212> TYPE: DNA
<213> ORGANISM: Artificial Sequence
<220> FEATURE:
<223> OTHER INFORMATION: Synthetic Construct

<400> SEQUENCE: 269

```
atggccttac cagtgaccgc cttgctcctg ccgctggcct tgctgctcca cgccgccagg    60
ccggttaacc gcacgcgtcg catgcatcag gtaaagctgg aggagtctgg ggaggcttg    120
gtgcaggctg gcggtctct gagactctcc tgtgcagcct ctgaacacac cttcagtagc    180
catgtcatgg gctggttccg ccaggctcca gggaaggagc gtgagtctgt tgcagttatt   240
ggctggagag atattagcac aagctatgca gactccgtga agggccgatt caccatctcc    300
agagacaacg ccaagaagac gctgtatctg caaatgaata gcctgaaacc tgaggacacg    360
gccgtttact actgtgcagc acgtcggatc gacgcagctg actttgattc ctggggcag    420
gggacccagg tcaccgtctc ctcgactagt accacgacgc cagcgccgcg accaccaaca    480
ccggcgccca ccatcgcgtc gcagcccctg tccctgcgcc cagaggcgtg ccggccagcg    540
```

```
gcggggggcg cagtgcacac gagggggctg gacttcgcct gtgatatcta catctgggcg    600
cccttggccg ggacttgtgg ggtccttctc ctgtcactgg ttatcaccct ttactgcaaa    660
cggggcagaa agaaactcct gtatatattc aacaaccat ttatgagacc agtacaaact     720
actcaagagg aagatggctg tagctgccga tttccagaag aagaagaagg aggatgtgaa    780
ctgagagtga agttcagcag gagcgcagac gcccccgcgt accagcaggg ccagaaccag    840
ctctataacg agctcaatct aggacgaaga gaggagtacg atgttttgga caagagacgt    900
ggccgggacc ctgagatggg gggaaagccg agaaggaaga accctcagga aggcctgtac    960
aatgaactgc agaaagataa gatggcggag gcctacagtg agattgggat gaaaggcgag   1020
cgccggaggg gcaaggggca cgatggcctt taccagggtc tcagtacagc caccaaggac   1080
acctacgacg cccttcacat gcaggccctg cccctcgct aa                       1122
```

<210> SEQ ID NO 270
<211> LENGTH: 1119
<212> TYPE: DNA
<213> ORGANISM: Artificial Sequence
<220> FEATURE:
<223> OTHER INFORMATION: Synthetic Construct

<400> SEQUENCE: 270

```
atggccttac cagtgaccgc cttgctcctg ccgctggcct tgctgctcca cgccgccagg     60
ccggttaacc gcacgcgtcg catgcatgag gtgcagctgg tggagtctgg gggaggcttg    120
gtgcaggctg gggggtctct gagactctcc tgtgcagcct ctggacgcac cttcaccatg    180
gggtggttcc gtcaggctcc agggaaggag cgtgagtttg tagcagctat tagttttgagt   240 cctactttag catattatgc agagtccgtg aagggccgat tcaccatcag ccgagacaac    300
gccaagaaca cggtggtttt gcaaatgaac agcctgaaac tgaggacac ggcccttat    360 tactgtgcag cagaccggaa atcagtaatg tctattcggc ccgactactg gggccagggg    420
acccaggtca ccgtctcctc aactagtacc acgacgccag cgccgcgacc accaacaccg    480
gcgcccacca tcgcgtcgca gccctgtcc ctgcgcccag aggcgtgccg gccagcggcg    540
gggggcgcag tgcacacgag ggggctggac ttcgcctgtg atatctacat ctgggcgccc    600
ttggccggga cttgtggggt ccttctcctg tcactggtta tcacccttta ctgcaaacgg    660
ggcagaaaga aactcctgta tatattcaaa caaccattta tgagaccagt acaaactact    720
caagaggaag atggctgtag ctgccgattt ccagaagaag aagaaggagg atgtgaactg    780
agagtgaagt tcagcaggag cgcagacgcc ccgcgtacc agcagggcca gaaccagctc    840
tataacgagc tcaatctagg acgaagagag gagtacgatg ttttggacaa gagacgtggc    900
cgggaccctg agatgggggg aaagccgaga aggaagaacc ctcaggaagg cctgtacaat    960
gaactgcaga aagataagat ggcggaggcc tacagtgaga ttgggatgaa aggcgagcgc   1020
cggaggggca aggggcacga tggcctttac cagggtctca gtacagccac caaggacacc   1080
tacgacgccc ttcacatgca ggccctgccc ctcgctaa                          1119
```

<210> SEQ ID NO 271
<211> LENGTH: 1113
<212> TYPE: DNA
<213> ORGANISM: Artificial Sequence
<220> FEATURE:
<223> OTHER INFORMATION: Synthetic Construct

<400> SEQUENCE: 271

```
atggctctgc ccgtcaccgc tctgctgctg cctctggctc tgctgctgca cgctgctcgc     60
```

```
cctgaggtgc agctggtgga gtctggggga ggcttggtgc cgcctggggg gtctctgaga    120
ctctcctgta cagcctctgg aagcacagtc agcatcaatg tcatggcctg gtaccgccag    180
gtttcaggga agcagcgcga gttggtcgcg gccgttacta gggatggtag gaaaagttgt    240
ggagactccg tgaagggccg attccacatt tccagacg gcgccaagaa tgcggtatat    300
ttgcaaatga acagtctgaa acctgaggac acagcggtct atttatgtgg agccgatggt    360
tggggtgcta ctaccttaga ttatacctac ggcatggact attggggcaa agggacccag    420
gtcaccgtct cctcaactag taccacgacg ccagcgccgc gaccaccaac accggcgccc    480
accatcgcgt cgcagcccct gtccctgcgc ccagaggcgt gccggccagc ggcgggggc    540 gcagtgcaca cgaggggggct ggacttcgcc tgtgatatct acatctgggc gcccttggcc    600
gggacttgtg gggtccttct cctgtcactg gttatcaccc tttactgcaa acggggcaga    660
aagaaactcc tgtatatatt caaacaacca tttatgagac cagtacaaac tactcaagag    720
gaagatggct gtagctgccg atttccagaa gaagaagaag aggatgtgaa actgagagtg    780
aagttcagca ggagcgcaga cgccccgcg taccagcagg gccagaacca gctctataac    840
gagctcaatc taggacgaag agaggagtac gatgttttgg acaagagacg tggccgggac    900
cctgagatgg ggggaaagcc gagaaggaag aaccctcagg aaggcctgta caatgaactg    960
cagaaagata gatggcgga ggcctacagt gagattggga tgaaaggcga cgcccggagg   1020 ggcaagggc acgatggcct ttaccagggt ctcagtacag ccaccaagga cacctacgac   1080
gcccttcaca tgcaggccct gcccctcgc taa                                 1113
```

<210> SEQ ID NO 272
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 272

```
atggctctgc ccgtcaccgc tctgctgctg cctctggctc tgctgctgca cgctgctcgc     60
cctgcggtgc agctggtgga gtctggggga ggattggtgc aggctggggg ctctctgaga    120
ctctcctgtg cagcctctgg acgcaccttc accatgggt ggttccgtca ggctccaggg    180
aaggagcgtg gtttgtagc gtctattacc tgggatggtc gttcggcata ctatgcagag    240
tccgtgaagg gccgattcac catcagccga gacaacgcca agaacacggt ggttttgcaa    300 atgaacagc tgaaacctga ggacacggcc ctttattact gtgcagcaga ccggaaatca    360
gtaatgtcta ttcggcccga ctactgggc caggggaccc aggtcaccgt ctcctcaact    420
agtaccacga cgccagcgcc gcgaccacca acaccggcgc caccatcgc gtcgcagccc    480 ctgtccctgc gcccagaggc gtgccggcca gcggcggggg gcgcagtgca cacgaggggg    540
ctggacttcg cctgtgatat ctacatctgg gcgcccttgg ccgggacttg tggggtcctt    600
ctcctgtcac tggttatcac cctttactgc aaacggggca gaaagaaact cctgtatata    660
ttcaaacaac catttatgag accagtacaa actactcaag aggaagatgg ctgtagctgc    720
cgatttccag aagaagaaga aggaggatgt gaactgagag tgaagttcag caggagcgca    780 gacgccccg cgtaccagca gggccagaac cagctctata acgagctcaa tctaggacga    840
agagaggagt acgatgtttt ggacaagaga cgtggccggg accctgagat ggggggaaag    900
ccgagaagga agaaccctca ggaaggcctg tacaatgaac tgcagaaaga taagatggcg    960
```

| | |
|---|---:|
| gaggcctaca gtgagattgg gatgaaaggc gagcgccgga ggggcaaggg gcacgatggc | 1020 |
| ctttaccagg gtctcagtac agccaccaag gacacctacg acgcccttca catgcaggcc | 1080 |
| ctgccccctc gctaa | 1095 |

<210> SEQ ID NO 273
<211> LENGTH: 1107
<212> TYPE: DNA
<213> ORGANISM: Artificial Sequence
<220> FEATURE:
<223> OTHER INFORMATION: Synthetic Construct

<400> SEQUENCE: 273

| | |
|---|---:|
| atggctctgc ccgtcaccgc tctgctgctg cctctggctc tgctgctgca cgctgctcgc | 60 |
| cctcaggtac agctggtgga gtctggggga ggattggtgc agcctggggg gtctctaaga | 120 |
| ctcgcatgtg aagcgcctgg aagcggcaat agtatcaatg ccatgggctg gtaccggcag | 180 |
| actccgggga gcggcgcga gttggtcgca actattactc ggggtggtag cacgaactat | 240 |
| ggaccctccg tgaagggccg attcacgatc accagagaca atgtcaagaa tacggtgcat | 300 |
| ctgcagatga acagcctgaa acctgacgac acggccgtct attattgcaa tgcggagagg | 360 |
| ctggacggct cggggtacgg atatgagtat gattactggg gccaggggac ccaggtcacc | 420 |
| gtctcctcaa ctagtaccac gacgccagcg ccgcgaccac caacaccggc gcccaccatc | 480 |
| gcgtcgcagc ccctgtccct gcgcccagag gcgtgccggc cagcggcggg gggcgcagtg | 540 |
| cacacgaggg ggctggactt cgcctgtgat atctacatct gggcgccctt ggccgggact | 600 |
| tgtgggtcc ttctcctgtc actggttatc acccttact gcaaacgggg cagaaagaaa | 660 |
| ctcctgtata tattcaaaca accatttatg agaccagtac aaactactca agaggaagat | 720 |
| ggctgtagct gccgatttcc agaagaagaa gaggaggat gtgaactgag agtgaagttc | 780 |
| agcaggagcg cagacgcccc cgcgtaccag cagggccaga accagctcta taacgagctc | 840 |
| aatctaggac gaagagagga gtacgatgtt ttggacaaga cgtggccg ggaccctgag | 900 |
| atgggggaa agccgagaag gaagaaccct caggaaggcc tgtacaatga actgcagaaa | 960 |
| gataagatgg cggaggccta cagtgagatt gggatgaaag cgagcgccg gaggggcaag | 1020 |
| ggcacgatg gcctttacca gggtctcagt acagccacca aggacaccta cgacgccctt | 1080 |
| cacatgcagg ccctgccccc tcgctaa | 1107 |

<210> SEQ ID NO 274
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 274

| | |
|---|---:|
| atggctctgc ccgtcaccgc tctgctgctg cctctggctc tgctgctgca cgctgctcgc | 60 |
| cctcaggtaa agctggagga gtctggggga ggattggtgc aggctggggg ctctctgaga | 120 |
| ctctcctgtg cagcctctgg aggcacctta agtaagaata ccgtggcttg ggtccgccag | 180 |
| gctccaggga aggagcgtgg gtttgtaacg tctattaccct gtgatggtcg tacgacatac | 240 |
| tatgcgaact ccgtaaacgg ccgattcccc atcaaccgaa caacgccga gaatttggtg | 300 |
| gttttgcaaa tgaacagcct gaaacctgac gacacggccc tttattactg tgcagcatac | 360 |
| cggaagtcaa taatgtctat tcagcccgac tactggggcc aggggaccca ggtcaccgtc | 420 |
| tcctcaacta gtaccacgac gccagcgccg cgaccaccaa caccggcgcc caccatcgcg | 480 |

```
tcgcagcccc tgtccctgcg cccagaggcg tgccggccag cggcggggg cgcagtgcac      540 acgaggggc tggacttcgc ctgtgatatc tacatctggg cgcccttggc cgggacttgt      600
ggggtccttc tcctgtcact ggttatcacc ctttactgca acggggcag aaagaaactc      660 ctgtatatat tcaaacaacc atttatgaga ccagtacaaa ctactcaaga ggaagatggc      720
tgtagctgcc gatttccaga agaagaagaa ggaggatgtg aactgagagt gaagttcagc      780
aggagcgcag acgccccgc gtaccagcag ggccagaacc agctctataa cgagctcaat      840
ctaggacgaa gagaggagta cgatgttttg acaagagac gtggccggga ccctgagatg      900
gggggaaagc cgagaaggaa gaaccctcag gaaggcctgt acaatgaact gcagaaagat      960
aagatggcgg aggcctacag tgagattggg atgaaaggcg agcgccggag gggcaagggg     1020
cacgatggcc tttaccaggg tctcagtaca gccaccaagg acacctacga cgcccttcac     1080
atgcaggccc tgccccctcg ctaa                                            1104

<210> SEQ ID NO 275
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 275
atggctctgc ccgtcaccgc tctgctgctg cctctggctc tgctgctgca cgctgctcgc      60
cctgatgtgc agctggtgga gtctggggga ggattggtgc aggctggggg ctctctgaga     120
ctctcctgtg cagcctctgg acggaccttc agtagcattg tcatgggctg gttccgccag     180
gctccaggga aggagcgtga gtttgtagga gcgattatgt ggaatgatgg tctgacatac     240
ttgcaagggt ccgtgaaggg ccgattcacc atttccagag acaacgccaa gaacacggtg     300
gttttgcaaa tgaacagcct gaaacctgag gacacggccc tttattactg tgcagcagac     360
cggaaatcag taatgtctat tcggcccgac tactggggcc aggggaccca ggtcaccgtc     420
tcctcaacta gtaccacgac gccagcgccg cgaccaccaa caccggcgcc caccatcgcg     480
tcgcagcccc tgtccctgcg cccagaggcg tgccggccag cggcggggg cgcagtgcac     540 acgaggggc tggacttcgc ctgtgatatc tacatctggg cgcccttggc cgggacttgt      600
ggggtccttc tcctgtcact ggttatcacc ctttactgca acggggcag aaagaaactc      660 ctgtatatat tcaaacaacc atttatgaga ccagtacaaa ctactcaaga ggaagatggc      720
tgtagctgcc gatttccaga agaagaagaa ggaggatgtg aactgagagt gaagttcagc      780
aggagcgcag acgccccgc gtaccagcag ggccagaacc agctctataa cgagctcaat      840
ctaggacgaa gagaggagta cgatgttttg acaagagac gtggccggga ccctgagatg      900
gggggaaagc cgagaaggaa gaaccctcag gaaggcctgt acaatgaact gcagaaagat      960
aagatggcgg aggcctacag tgagattggg atgaaaggcg agcgccggag gggcaagggg     1020
cacgatggcc tttaccaggg tctcagtaca gccaccaagg acacctacga cgcccttcac     1080
atgcaggccc tgccccctcg ctaa                                            1104

<210> SEQ ID NO 276
<211> LENGTH: 1089
<212> TYPE: DNA
<213> ORGANISM: Artificial Sequence
<220> FEATURE:
<223> OTHER INFORMATION: Synthetic Construct
```

<400> SEQUENCE: 276

```
atggctctgc cgtcaccgc tctgctgctg cctctggctc tgctgctgca cgctgctcgc      60
cctcaggtac agctggtgga gtctggggga ggattggtgc aggctggggg ctctctgaga     120
ctctcctgtg cagcctctgg acgcaccttc accatgggt ggttccgtca ggctccaggg      180
aaggagcgtg agtttgtagc agctattagt ttgagtccta ctttagcata ttatgcagag     240
tccgtgaagg gccgattcac catcagccga cacaacgcca gaacacggt ggttttgcaa      300
atgaacagcc tgaaacctga ggacacggcc gtttactact gtgcagcacg tcggatcgac     360
gcagctgact ttgattcctg ggggcagggg acccaggtca ccgtctcctc aactagtacc     420
acgacgccag cgccgcgacc accaacaccg gcgcccacca tcgcgtcgca gcccctgtcc     480
ctgcgcccag aggcgtgccg gccagcggcg ggggcgcag tgcacacgag ggggctggac      540
ttcgcctgtg atatctacat ctgggcgccc ttggccggga cttgtgggt ccttctcctg      600
tcactggtta tcacccttta ctgcaaacgg gcagaaaga aactcctgta tatattcaaa      660
caaccattta tgagaccagt acaaactact caagaggaag atgctgtag ctgccgattt       720
ccagaagaag aagaaggagg atgtgaactg agagtgaagt tcagcaggag cgcagacgcc     780
cccgcgtacc agcagggcca gaaccagctc tataacgagc tcaatctagg acgaagagag     840
gagtacgatg ttttggacaa gagacgtggc cgggaccctg agatggggg aaagccgaga     900
aggaagaacc ctcaggaagg cctgtacaat gaactgcaga agataagat ggcggaggcc      960
tacagtgaga ttgggatgaa aggcgagcgc ggagggggca aggggcacga tggcctttac     1020
cagggtctca gtacagccac caaggacacc tacgacgccc ttcacatgca ggccctgccc     1080
cctcgctaa                                                            1089
```

<210> SEQ ID NO 277
<211> LENGTH: 1101
<212> TYPE: DNA
<213> ORGANISM: Artificial Sequence
<220> FEATURE:
<223> OTHER INFORMATION: Synthetic Construct

<400> SEQUENCE: 277

```
atggctctgc cgtcaccgc tctgctgctg cctctggctc tgctgctgca cgctgctcgc      60
cctcaggtac agctggtgga gtctggggga ggattggtgc aggctggggg ctctctgaga     120
ctctcctgtg cagcctctgg aggcacctta agtaaaaata ccgtggcttg gttccgccag     180
gctccaggga aggagcgtgg gtttgtagcg tctattaccct gggatggtcg tacgacatac     240
tatgcagact ccgtgaaggg ccgattcacc atctccagag acaacgccaa gaacacagtg     300
tatctgcaaa tgaacagcct gaaacctgag gatacggccg tttatgtctg tgcagactta     360
gggaaatggc ctgcgggccc ggcggactac tggggccagg gacccaggt caccgtctcc      420
tcaactagta ccacgacgcc agcgccgcga ccaccaacac cggcgcccac catcgcgtcg     480
cagcccctgt ccctgcgccc agaggcgtgc cggccagcgg cgggggcgc agtgcacacg      540
aggggggctgg acttcgcctg tgatatctac atctgggcgc ccttggccgg gacttgtggg    600
gtccttctcc tgtcactggt tatcaccctt tactgcaaac ggggcagaaa gaaactcctg     660
tatatattca acaaccatt tatgagacca gtacaaacta ctcaagagga gatggctgt      720
agctgccgat ttccagaaga agaagaagga ggatgtgaac tgagagtgaa gttcagcagg    780
agcgcagacg ccccccgcgta ccagcagggc cagaaccagc tctataacga gctcaatcta    840
ggacgaagag aggagtacga tgttttggac aagagacgtg gccgggaccc tgagatgggg    900
```

| | |
|---|---|
| ggaaagccga gaaggaagaa ccctcaggaa ggcctgtaca atgaactgca gaaagataag | 960 |
| atggcggagg cctacagtga gattgggatg aaaggcgagc gccggagggg caaggggcac | 1020 |
| gatggccttt accagggtct cagtacagcc accaaggaca cctacgacgc ccttcacatg | 1080 |
| caggccctgc cccctcgcta a | 1101 |

<210> SEQ ID NO 278
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 278

| | |
|---|---|
| atggctctgc ccgtcaccgc tctgctgctg cctctggctc tgctgctgca cgctgctcgc | 60 |
| cctcaggtgc agctggtgga gtctggggga ggcttggtgc agcctggggg gtctctgaca | 120 |
| ctctcctgtg cagcctctgg aagcatcgac agtatcaata ccatggactg gttccgtcag | 180 |
| gctccaggga aggagcgtga gtttgtagca gctattagtt tgagtcccac tttagcatat | 240 |
| tatgcagagt ccgtgaaggg ccgattcacc atcagccgag acaacgccaa gaacacggtg | 300 |
| gttttgcaaa tgaacagcct gaaacctgag gacacggccc tttattactg tgcagcagac | 360 |
| cggaaatcag taatgtctat tcggcccgac tactggggcc aggggaccca ggtcaccgtc | 420 |
| tcctcaacta gtaccacgac gccagcgccg cgaccaccaa caccggcgcc caccatcgcg | 480 |
| tcgcagcccc tgtccctgcg cccagaggcg tgccggccag cggcgggggg cgcagtgcac | 540 |
| acgaggggc tggacttcgc ctgtgatatc tacatctggg cgcccttggc cgggacttgt | 600 |
| ggggtccttc tcctgtcact ggttatcacc ctttactgca acggggcag aaagaaactc | 660 |
| ctgtatatat tcaaacaacc atttatgaga ccagtacaaa ctactcaaga ggaagatggc | 720 |
| tgtagctgcc gatttccaga agaagaagaa ggaggatgtg aactgagagt gaagttcagc | 780 |
| aggagcgcag acgccccgc gtaccagcag ggccagaacc agctctataa cgagctcaat | 840 |
| ctaggacgaa gagaggagta cgatgttttg gacaagagac gtggccggga ccctgagatg | 900 |
| ggggaaagc cgagaaggaa gaaccctcag gaaggcctgt acaatgaact gcagaaagat | 960 |
| aagatggcgg aggcctacag tgagattggg atgaaaggcg agcgccggag gggcaagggg | 1020 |
| cacgatggcc tttaccaggg tctcagtaca gccaccaagg acacctacga cgcccttcac | 1080 |
| atgcaggccc tgcccctcg ctaa | 1104 |

<210> SEQ ID NO 279
<211> LENGTH: 1101
<212> TYPE: DNA
<213> ORGANISM: Artificial Sequence
<220> FEATURE:
<223> OTHER INFORMATION: Synthetic Construct

<400> SEQUENCE: 279

| | |
|---|---|
| atggctctgc ccgtcaccgc tctgctgctg cctctggctc tgctgctgca cgctgctcgc | 60 |
| cctgatgtgc agctggtgga gtctggggga ggattggtgc aggctggggg ctctctgaga | 120 |
| ctctcctgtg cagcctctgg aggcacctta agtaagaata ccgtggcttg gtccgccag | 180 |
| gctccaggga aggagcgtgg gtttgtaacg tctattacct gtgatggtcg tacgacatac | 240 |
| tatgcgaact ccgtgaaggg ccgattcccc atctccagag acaacgccga gaacacagtg | 300 |
| tatctgcaaa tgaacagcct gaaacctgag gatacggccg ttatgtctg tgcagactta | 360 |

| | |
|---|---|
| gggaagtggc ctgcgggttc ggcggactac tggggccagg ggacccacgt caccgtctcc | 420 |
| tccactagta ccacgacgcc agcgccgcga ccaccaacac cggcgcccac catcgcgtcg | 480 |
| cagcccctgt ccctgcgccc agaggcgtgc cggccagcgg cgggggggcgc agtgcacacg | 540 |
| aggggggctgg acttcgcctg tgatatctac atctgggcgc ccttggccgg gacttgtggg | 600 |
| gtccttctcc tgtcactggt tatcacccctt tactgcaaac ggggcagaaa gaaactcctg | 660 |
| tatatattca acaaccatt tatgagacca gtacaaacta ctcaagagga agatggctgt | 720 |
| agctgccgat ttccagaaga agaagaagga ggatgtgaac tgagagtgaa gttcagcagg | 780 |
| agcgcagacg ccccgcgta ccagcagggc cagaaccagc tctataacga gctcaatcta | 840 |
| ggacgaagag aggagtacga tgttttggac aagagacgtg gccgggaccc tgagatgggg | 900 |
| ggaaagccga aaggaagaa ccctcaggaa ggcctgtaca atgaactgca gaaagataag | 960 |
| atggcggagg cctacagtga gattgggatg aaaggcgagc gccggagggg caaggggcac | 1020 |
| gatggccttt accagggtct cagtacagcc accaaggaca cctacgacgc ccttcacatg | 1080 |
| caggccctgc ccctcgcta a | 1101 |

<210> SEQ ID NO 280
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 280

| | |
|---|---|
| atggctctgc ccgtcaccgc tctgctgctg cctctggctc tgctgctgca cgctgctcgc | 60 |
| cctcaggtaa agctggagga gtctgggggga ggcttggtgc agcctggggg gtctctgaga | 120 |
| ctctcctgta cagcctcgga attcacattc agtgactact ggatgcattg ggtccgtcag | 180 |
| gctccgggga aggggctcga gtgggtcgca tctatagata ctagtggaca gaccacatac | 240 |
| tatgcagact ccctgaaggg ccgattcacc atctccagag acaacgccaa gagcacgttg | 300 |
| tatctgcaaa tgaacagtct gaaatctgaa gacacgggcg tgtatttctg tgcaaaacga | 360 |
| tatagggggtg gtacctggta tggcatggcc aactggggca aagggaccca ggtcaccgtc | 420 |
| tcctcaacta gtaccacgac gccagcgccg cgaccaccaa caccggcgcc caccatcgcg | 480 |
| tcgcagcccc tgtccctgcg cccagaggcg tgccggccag cggcgggggg cgcagtgcac | 540 |
| acgagggggc tggacttcgc ctgtgatatc tacatctggg cgcccttggc cgggacttgt | 600 |
| ggggtccttc tcctgtcact ggttatcacc ctttactgca acggggcag aaagaaactc | 660 |
| ctgtatatat tcaaacaacc atttatgaga ccagtacaaa ctactcaaga ggaagatggc | 720 |
| tgtagctgcc gatttccaga agaagaagaa ggaggatgtg aactgagagt gaagttcagc | 780 |
| aggagcgcag acgcccccgc gtaccagcag ggccagaacc agctctataa cgagctcaat | 840 |
| ctaggacgaa gagaggagta cgatgttttg gacaagagac gtggccggga ccctgagatg | 900 |
| gggggaaagc cgagaaggaa gaaccctcag gaaggcctgt acaatgaact gcagaaagat | 960 |
| aagatggcgg aggcctacag tgagattggg atgaaaggcg agcgccggag gggcaagggg | 1020 |
| cacgatggcc tttaccaggg tctcagtaca gccaccaagg acacctacga cgcccttcac | 1080 |
| atgcaggccc tgcccctcg ctaa | 1104 |

<210> SEQ ID NO 281
<211> LENGTH: 1101
<212> TYPE: DNA
<213> ORGANISM: Artificial Sequence
<220> FEATURE:
<223> OTHER INFORMATION: Synthetic Construct

<400> SEQUENCE: 281

```
atggctctgc cgtcaccgc tctgctgctg cctctggctc tgctgctgca cgctgctcgc      60
cctcaggtgc agctggtgga gtctggggga ggattggtgc aggctggggg ctctctgaga     120
ctctcctgtg cagcctctgg acgcacctta agtagtaata ccatggcttg gttccgccag    180
gctccaggga aggagcgtga gtttgtagcg tctactacct ggaatggtcg tagcacatac    240
tatgcagact ccgtgaaggg ccgattcacc atctccagag acaacgccaa gaacacgatg    300
tatctgcaaa tgaacagcct gaaacctgag gatacggccg tttatgtctg tgcagactta    360
gggaaatggc ctgcgggccc ggcggactac tggggccagg gacccaggt caccgtctcc     420
tcaactagta ccacgacgcc agcgccgcga ccaccaacac cggcgccac catcgcgtcg     480
cagcccctgt ccctgcgccc agaggcgtgc cggccagcgg cgggggcgc agtgcacacg     540
agggggctgg acttcgcctg tgatatctac atctgggcgc ccttggccgg gacttgtggg    600
gtccttctcc tgtcactggt tatcaccctt tactgcaaac ggggcagaaa gaaactcctg    660
tatatattca acaaccatt tatgagacca gtacaaacta ctcaagagga gatggctgt     720
agctgccgat ttccagaaga agaagaagga ggatgtgaac tgagagtgaa gttcagcagg    780
agcgcagacg cccccgcgta ccagcagggc cagaaccagc tctataacga gctcaatcta    840
ggacgaagag aggagtacga tgttttggac aagagacgtg gccgggaccc tgagatgggg    900
ggaaagccga aaggaagaa ccctcaggaa ggcctgtaca tgaactgca gaaagataag     960
atggcggagg cctacagtga gattgggatg aaaggcgagc gccggagggg caaggggcac   1020
gatggccttt accagggtct cagtacagcc accaaggaca cctacgacgc ccttcacatg   1080
caggccctgc ccctcgcta a                                              1101
```

<210> SEQ ID NO 282
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 282

```
atggctctgc cgtcaccgc tctgctgctg cctctggctc tgctgctgca cgctgctcgc      60
cctcaggtgc agctggtgga gtctggggga ggattggtgc aggctggggg ctctctgaga    120
ctctcctgtg cagcctctgg acgcaccttc accatggggt ggttccgtca ggctccaggg    180
aagcagcgcg aattggtcgc agatattagt ggtggtcgca caaactatgc agattccgtg    240
aagggacgat tcaccatctc cagagacaac gccaagaaca cggtatatct gcaaatgaac    300
agcctgaaac ctgaggacac ggccgtttat tactgtgcag cagaccggaa atcagtaatg    360
tctattcggc ccgactactg gggccagggg acccaggtca ccgtctcctc aactagtacc    420
acgacgccag cgccgcgacc accaacaccg gcgccacca tcgcgtcgca gcccctgtcc     480
ctgcgcccag aggcgtgccg gccagcggcg ggggcgcag tgcacacgag gggctggac     540
ttcgcctgtg atatctacat ctgggcgccc ttggccggga cttgtgggt ccttctcctg    600
tcactggtta tcaccccttta ctgcaaacgg ggcagaaaga aactcctgta tatattcaaa   660
caaccattta tgagaccagt acaaactact caagaggaag atggctgtag ctgccgattt    720
ccagaagaag aagaaggagg atgtgaactg agagtgaagt tcagcaggag cgcagacgcc    780
```

```
cccgcgtacc agcagggcca gaaccagctc tataacgagc tcaatctagg acgaagagag        840
gagtacgatg ttttggacaa gagacgtggc cgggaccctg agatggggga aaagccgaga        900
aggaagaacc ctcaggaagg cctgtacaat gaactgcaga agataagat ggcggaggcc         960 tacagtgaga ttgggatgaa aggcgagcgc cggaggggca aggggcacga tggcctttac       1020
cagggtctca gtacagccac caaggacacc tacgacgccc ttcacatgca ggccctgccc       1080
cctcgctaa                                                                1089
```

```
<210> SEQ ID NO 283
<211> LENGTH: 1053
<212> TYPE: DNA
<213> ORGANISM: Artificial Sequence
<220> FEATURE:
<223> OTHER INFORMATION: Synthetic Construct

<400> SEQUENCE: 283
atggctctgc ccgtcaccgc tctgctgctg cctctggctc tgctgctgca cgctgctcgc         60
cctcaggtgc agctggtgga gtctggggga ggcttggtgc aggctgggc ctctctgaga        120 ctctcctgtg cagcctctgg acgcaccttc accgtggcag ctattagttt gagtcctact        180
ttagcatatt atgcagagtc cgtgaagggc cgattcacca tcagccgaga caacgccaag        240
aacacggtgg ttttgcaaat gaacagcctg aaacctgagg acacggccct ttattactgt        300
gcagcagacc ggaaatcagt aatgtctatt cggcccgact actggggcca ggggacccag        360
gtcaccgtct cctcaactag taccacgacg ccagcgccgc gaccaccaac accggcgccc        420
accatcgcgt cgcagcccct gtccctgcgc ccagaggcgt gccggccagc ggcgggggc         480 gcagtgcaca cgaggggct ggacttcgcc tgtgatatct acatctgggc gcccttggcc         540
gggacttgtg ggtccttct cctgtcactg gttatcaccc tttactgcaa cggggcaga         600 aagaaactcc tgtatatatt caaacaacca tttatgagac cagtacaaac tactcaagag        660
gaagatggct gtagctgccg atttccagaa gaagaagaag aggatgtga actgagagtg        720 aagttcagca ggagcgcaga cgccccgcg taccagcagg ccagaaacca gctctataac        780
gagctcaatc taggacgaag agaggagtac gatgttttgg acaagagacg tggccgggac        840
cctgagatgg ggaaagcc gagaaggaag aaccctcagg aaggcctgta caatgaactg        900
cagaaagata gatggcgga ggcctacagt gagattggga tgaaaggcga gcgccggagg        960
ggcaaggggc acgatggcct ttaccagggt ctcagtacag ccaccaagga cacctacgac       1020
gcccttcaca tgcaggccct gcccctcgc taa                                     1053
```

```
<210> SEQ ID NO 284
<211> LENGTH: 1116
<212> TYPE: DNA
<213> ORGANISM: Artificial Sequence
<220> FEATURE:
<223> OTHER INFORMATION: Synthetic Construct

<400> SEQUENCE: 284
atggctctgc ccgtcaccgc tctgctgctg cctctggctc tgctgctgca cgctgctcgc         60
cctgatgtgc agctggtgga gtctggggga ggattggagc aggctggggg ctctctgaga       120
ctctcctgtg cagcctctgg aggcacctta agtaaaaata ccgtggcttg gttccgccag       180
gctccaggga aggagcgtgg gtttgtagcg tctattacct gggatggtcg tacgacatac       240
tatgcagact ccgtgaaggg ccgattcacc atctccagag acaacgccaa gaacacagtg       300
tatctgcaaa tgaacagcct gaaacctgag gatacggccg tttattactg tgcgtcgacg       360
```

```
gcatcgtgcc acctcttcgg attggggtcc ggggcctttg tgtcctgggg ccggggggacc      420 caggtcaccg tctcctcaac tagtaccacg acgccagcgc cgcgaccacc aacaccggcg      480
cccaccatcg cgtcgcagcc cctgtccctg cgcccagagg cgtgccggcc agcggcgggg      540
ggcgcagtgc acacgagggg gctggacttc gcctgtgata tctacatctg ggcgcccttg      600
gccgggactt gtggggtcct tctcctgtca ctggttatca ccctttactg caaacggggc      660
agaaagaaac tcctgtatat attcaaacaa ccatttatga gaccagtaca aactactcaa      720
gaggaagatg gctgtagctg ccgatttcca gaagaagaag aaggaggatg tgaactgaga      780
gtgaagttca gcaggagcgc agacgccccc gcgtaccagc agggccagaa ccagctctat      840
aacgagctca atctaggacg aagagaggag tacgatgttt tggacaagag acgtggccgg      900
gaccctgaga tggggggaaa gccgagaagg aagaaccctc aggaaggcct gtacaatgaa      960
ctgcagaaag ataagatggc ggaggcctac agtgagattg ggatgaaagg cgagcgccgg     1020
aggggcaagg ggcacgatgg cctttaccag ggtctcagta cagccaccaa ggacacctac     1080
gacgcccttc acatgcaggc cctgcccct cgctaa                                1116

<210> SEQ ID NO 285
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 285
atggctctgc ccgtcaccgc tctgctgctg cctctggctc tgctgctgca cgctgctcgc       60
cctgcggtgc agctggtgga gtctggggga ggattggtgc aggctggggg ctctctgaga      120
ctctcctgtg cagcctctgg acgcaccttc accatggggt ggttccatca ggctccaggg      180
aaggagcgtg agtttgtagc agctattagt ttgagtccta ctttagcata ttatgcagag      240
tccgtgaagg gccgattcac catcagccga gacaacgcca agaacacggt ggttttgcaa      300
atgaacagcc tgaaacctga ggacacggcc ctttattact gtgcagcatc caaggataga      360
tattcggaat atgagtactg gggccagggg acccaggtca ccgtctcctc aactagtacc      420
acgacgccag cgccgcgacc accaacaccg gcgcccacca tcgcgtcgca gcccctgtcc      480
ctgcgcccag aggcgtgccg gccagcggcg ggggcgcag tgcacacgag ggggctggac      540
ttcgcctgtg atatctacat ctgggcgccc ttggccggga cttgtggggt ccttctcctg      600
tcactggtta tcacccttta ctgcaaacgg ggcagaaaga aactcctgta tatattcaaa      660
caaccattta tgagaccagt acaaactact caagaggaag atggctgtag ctgccgattt      720
ccagaagaag aagaaggagg atgtgaactg agagtgaagt tcagcaggag cgcagacgcc      780
cccgcgtacc agcagggcca gaaccagctc tataacgagc tcaatctagg acgaagagag      840
gagtacgatg ttttggacaa gagacgtggc cgggaccctg agatgggggg aaagccgaga      900
aggaagaacc tcaggaagg cctgtacaat gaactgcaga aagataagat ggcggaggcc      960
tacagtgaga ttgggatgaa aggcgagcgc cggaggggca aggggcacga tggcctttac     1020
cagggtctca gtacagccac caaggacacc tacgacgccc ttcacatgca ggcccctgccc    1080 cctcgctaa                                                             1089

<210> SEQ ID NO 286
<211> LENGTH: 1083
<212> TYPE: DNA
```

<213> ORGANISM: Artificial Sequence
<220> FEATURE:
<223> OTHER INFORMATION: Synthetic Construct

<400> SEQUENCE: 286

```
atggctctgc cgtcaccgc tctgctgctg cctctggctc tgctgctgca cgctgctcgc    60
cctcaggtaa agctggagga gtctggggga ggattggtgc aggctggggg ctctctgaga   120
ctctcctgtg cagcctctgg acgcaccttc accatggggt ggttccgtca ggctccaggg   180
aaggagcgtg agtttgtagc agctattagt ttgagtccta ctttagcata ttatgcagag   240
tccgtgaagg gccgattcac catcagccga gacaacgcca agaacacggt ggtttttgcaa   300
atgaacagcc tgaaacctga ggacacggcc ctttattact gtgcaaaaaa aaacgggggg   360
cctgtggact actggggcaa agggacccag gtcaccgtct cctcaactag taccacgacg   420
ccagcgccgc gaccaccaac accggcgccc accatcgcgt cgcagcccct gtccctgcgc   480
ccagaggcgt gccggccagc ggcggggggc gcagtgcaca cgaggggcct ggacttcgcc   540
tgtgatatct acatctgggc gcccttggcc gggacttgtg ggtccttct cctgtcactg   600
gttatcaccc tttactgcaa acggggcaga agaaactcc tgtatatatt caaacaacca   660
tttatgagac cagtacaaac tactcaagag gaagatggct gtagctgccg atttccagaa   720
gaagaagaag aggatgtgaa ctgagagtg aagttcagca ggagcgcaga cgcccccgcg   780
taccagcagg gccagaacca gctctataac gagctcaatc taggacgaag agaggagtac   840
gatgttttgg acaagagacg tggccgggac cctgagatgg ggggaaagcc gagaaggaag   900
aaccctcagg aaggcctgta caatgaactg cagaaagata gatggcggga ggcctacagt   960
gagattggga tgaaaggcga gcgccggagg ggcaaggggc acgatggcct ttaccagggt  1020
ctcagtacag ccaccaagga cacctacgac gcccttcaca tgcaggccct gccccctcgc  1080
taa                                                                1083
```

<210> SEQ ID NO 287
<211> LENGTH: 1098
<212> TYPE: DNA
<213> ORGANISM: Artificial Sequence
<220> FEATURE:
<223> OTHER INFORMATION: Synthetic Construct

<400> SEQUENCE: 287

```
atggctctgc cgtcaccgc tctgctgctg cctctggctc tgctgctgca cgctgctcgc    60
cctgatgtgc agctggtgga gtctggggga ggcttggtgc agcctggggg gtctctgaga   120
ctctcctgtg cagcctctgg acggaccttc agtagcattg tcatgggctg gttccgccag   180
gctccaggga aggagcgtga gtttgtagga gcgattatgt ggaatgatgg tattacatac   240
ttgcaagact ccgtgaaggg ccgatttacc atcttcagag acaacgccaa gaacacggtg   300
tatctgcaaa tgaacagcct gaaacttgag gatacggccg tttattactg tgcagcatcc   360
aagggtagat actcggaata tgagtactgg ggccagggga cccaggtcac cgtctcctca   420
actagtacca cgacgccagc gccgcgacca ccaacaccgg cgcccaccat cgcgtcgcag   480
cccctgtccc tgcgcccaga ggcgtgccgg ccagcggcgg gggcgcagt gcacacgagg   540
gggctggact cgcctgtga tatctacatc tgggcgccct tggccgggac ttgtggggtc   600
cttctcctgt cactggttat caccctttac tgcaaacggg gcagaaagaa actcctgtat  660
atattcaaac aaccatttat gagaccagta caaactactc aagaggaaga tggctgtagc   720
tgccgatttc cagaagaaga agaaggagga tgtgaactga gagtgaagtt cagcaggagc   780
```

```
gcagacgccc ccgcgtacca gcagggccag aaccagctct ataacgagct caatctagga      840
cgaagagagg agtacgatgt tttggacaag agacgtggcc gggaccctga gatgggggga      900
aagccgagaa ggaagaaccc tcaggaaggc ctgtacaatg aactgcagaa agataagatg      960
gcggaggcct acagtgagat tgggatgaaa ggcgagcgcc ggaggggcaa ggggcacgat     1020
ggcctttacc agggtctcag tacagccacc aaggacacct acgacgccct tcacatgcag     1080
gccctgcccc ctcgctaa                                                   1098
```

<210> SEQ ID NO 288
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 288

```
atggctctgc ccgtcaccgc tctgctgctg cctctggctc tgctgctgca cgctgctcgc       60
cctcaggtaa agctggagga atctggggga agattggtgc aggctggggg ctctctgaaa      120
ctctcctggg cagcctctgg acgcaccttc accatggggt ggttccgtca ggctccaggg      180
aaggaacgtg agtttgtaac agctattaat ttgagtccta ctttaacata ttatgcagaa      240
tccgtgaagg gccgattccc catcagccga acaacgccc agaacacggt ggttttgcaa      300
atgaacagcc tgaaacctga ggacacggcc ctttattact gtgcagcaga acggaaatca      360
gtaatggcta ttccgcccga ctactgggc caggggaccc aggtcaccgt ctcctcaact      420
agtaccacga cgccagcgcc gcgaccacca acaccggcgc ccaccatcgc gtcgcagccc      480
ctgtccctgc gcccagaggc gtgccggcca gcggcggggg gcgcagtgca cacgaggggg      540
ctggacttcg cctgtgatat ctacatctgg gcgcccttgg ccgggacttg tggggtcctt      600
ctcctgtcac tggttatcac cctttactgc aaacggggca gaaagaaact cctgtatata      660
ttcaaacaac catttatgag accagtacaa actactcaag aggaagatgg ctgtagctgc      720
cgatttccag aagaagaaga aggaggatgt gaactgagag tgaagttcag caggagcgca      780 gacgccccg cgtaccagca gggccagaac cagctctata cgagctcaa tctaggacga      840 agagaggagt acgatgtttt ggacaagaga cgtggccggg accctgagat ggggggaaag      900
ccgagaagga agaaccctca ggaaggcctg tacaatgaac tgcagaaaga taagatggcg     960
gaggcctaca gtgagattgg gatgaaaggc gagcgccgga ggggcaaggg gcacgatggc    1020
ctttaccagg gtctcagtac agccaccaag gacacctacg acgcccttca catgcaggcc    1080
ctgccccctc gctaa                                                      1095
```

<210> SEQ ID NO 289
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 289

```
atggctctgc ccgtcaccgc tctgctgctg cctctggctc tgctgctgca cgctgctcgc       60
cctgaggtgc agctggtgga gtctggggga ggattggtgc aggctggggg ctctctgaga      120
ctctcctgtg cagcctctgg acgcaccttc accatggggg ggttccgtcg ggttcctcgg      180
gatgagcggg agtttgtagc atctattact ttgattccta cttttcctta ttatgcatat      240
```

```
tccgtgaagg gccgattcgc cctcttccga gacaacccca acaacaccgt gattttgctg      300
atgatcagcc tgaaacctga ggacccggac ctttattact gtgcttcata ccggaaatac      360
ctaatgtcta ttctgcccga ctactggggc caggggaccc agggcaccgt ctcctccact      420
agtaccacga cgccagcgcc gcgaccacca acaccggcgc ccaccatcgc gtcgcagccc      480
ctgtccctgc gcccagaggc gtgccggcca gcggcggggg gcgcagtgca cacgaggggg      540
ctggacttcg cctgtgatat ctacatctgg gcgcccttgg ccgggacttg tggggtcctt      600
ctcctgtcac tggttatcac cctttactgc aaacggggca gaaagaaact cctgtatata      660
ttcaaacaac catttatgag accagtacaa actactcaag aggaagatgg ctgtagctgc      720
cgatttccag aagaagaaga aggaggatgt gaactgagag tgaagttcag caggagcgca      780
gacgccccg cgtaccagca gggccagaac cagctctata cgagctcaa tctaggacga      840
agagaggagt acgatgtttt ggacaagaga cgtggccggg accctgagat gggggaaag      900
ccgagaagga agaaccctca ggaaggcctg tacaatgaac tgcagaaaga taagatggcg      960
gaggcctaca gtgagattgg gatgaaaggc gagcgccgga ggggcaaggg gcacgatggc     1020
ctttaccagg gtctcagtac agccaccaag gacacctacg acgcccttca catgcaggcc     1080
ctgccccctc gctaa                                                      1095

<210> SEQ ID NO 290
<211> LENGTH: 1113
<212> TYPE: DNA
<213> ORGANISM: Artificial Sequence
<220> FEATURE:
<223> OTHER INFORMATION: Synthetic Construct

<400> SEQUENCE: 290
atggctctgc ccgtcaccgc tctgctgctg cctctggctc tgctgctgca cgctgctcgc       60
cctcaggtaa agctggagga gtctggggga ggattggtgc aggctggggg ctctctgaga      120
ctctcctgtg cagcctctgg acgcaccttc accatggggt ggttccgtca ggctccaggg      180
aaggagcgtg agtttgtagc agctattagt ttgagtccta ctttagcata ttatgcagag      240
tccgtgaagg gccgattcac catcagccga gacaacgcca agaacacggt ggatctgcaa      300
atgaacagcc tgaaacctga ggacacggcc gtctatttct gtgcagcaaa tcggaactcc      360
caacgggtaa ttgcggcact gtcctggatt ggcatgaact actggggcga atggacccag      420
gtcaccgtct cctccactag taccacgacg ccagcgccgc gaccaccaac accggcgccc      480
accatcgcgt cgcagcccct gtccctgcgc ccagaggcgt gccggccagc ggcgggggc      540
gcagtgcaca cgagggggct ggacttcgcc tgtgatatct acatctgggc gcccttggcc      600
gggacttgtg ggtccttct cctgtcactg gttatcaccc tttactgcaa acggggcaga      660
aagaaactcc tgtatatatt caaacaacca tttatgagac cagtacaaac tactcaagag      720
gaagatggct gtagctgccg atttccagaa gaagaagaag gaggatgtga actgagagtg      780
aagttcagca ggagcgcaga cgcccccgcg taccagcagg gccagaacca gctctataac      840
gagctcaatc taggacgaag agaggagtac gatgttttgg acaagagacg tggccgggac      900
cctgagatgg ggggaaagcc gagaaggaag aaccctcagg aaggcctgta caatgaactg      960
cagaaagata agatggcgga ggcctacagt gagattggga tgaaaggcga gcgccggagg     1020
ggcaagggc acgatggcct ttaccagggt ctcagtacag ccaccaagga cacctacgac     1080
gcccttcaca tgcaggccct gccccctcgc taa                                  1113
```

<210> SEQ ID NO 291
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 291

```
atggctctgc ccgtcaccgc tctgctgctg cctctggctc tgctgctgca cgctgctcgc      60
cctcaggtgc agctggtgga gtctggggga ggattggtgc aggctggggg ctctctgaga     120
ctctcctgtg cagcctctgg acgcaccttc accatggggt ggttccgtca ggctccaggg     180
aaggagcgtg agtttgtagc agctattagt ttgagtccta ctttagcata ttatgcagag     240
tccgtgaagg gccgattcac catctccaga gacaacgcca agaagacgct gtatctgcga     300
atgaatagcc tgaaacctga ggacacggcc gtttactact gtgcagcacg tcggatcgac     360
gcagctgact ttgattcctg ggggcagggg acccaggtca ccgtctcctc aactagtacc     420
acgacgccag cgccgcgacc accaacaccg gcgcccacca tcgcgtcgca gcccctgtcc     480
ctgcgcccag aggcgtgccg ccagcggcg ggggcgcag tgcacacgag ggggctggac     540
ttcgcctgtg atatctacat ctgggcgccc ttggccggga cttgtggggt ccttctcctg     600
tcactggtta tcacccttta ctgcaaacgg ggcagaaaga aactcctgta tatattcaaa     660
caaccattta tgagaccagt acaaactact caagaggaag atggctgtag ctgccgattt     720
ccagaagaag aagaaggagg atgtgaactg agagtgaagt tcagcaggag cgcagacgcc     780
cccgcgtacc agcagggcca gaaccagctc tataacgagc tcaatctagg acgaagagag     840
gagtacgatg ttttggacaa gagacgtggc cgggaccctg agatgggggg aaagccgaga     900
aggaagaacc ctcaggaagg cctgtacaat gaactgcaga agataagat ggcggaggcc     960
tacagtgaga ttgggatgaa aggcgagcgc cggagggca aggggcacga tggcctttac    1020
cagggtctca gtacagccac caaggacacc tacgacgccc ttcacatgca ggccctgccc    1080
cctcgctaa                                                             1089
```

<210> SEQ ID NO 292
<211> LENGTH: 1089
<212> TYPE: DNA
<213> ORGANISM: Artificial Sequence
<220> FEATURE:
<223> OTHER INFORMATION: Synthetic Construct

<400> SEQUENCE: 292

```
atggctctgc ccgtcaccgc tctgctgctg cctctggctc tgctgctgca cgctgctcgc      60
cctcaggtaa agctggagga gtctgggga ggattggtgc aggctggggg ctctctgaga     120
ctctcctgtg cagcctctgg acgcaccttc accatggggt ggttccgtcg gctccaggg     180
aaggagcgtg agtctgttgc agttattggc tggagagata ttaacgcaag ctatgcagac     240
tccgtgaagg gccgattcgc catctccaga gacaacgcca agaagacgct gtatctgcag     300
atgaatagcc tgaaacctga ggacacggcc gtttactact gtgcagcacg tcggatcgac     360
gcaactgact ttgattcctg ggggcagggg acccaggtca ccgtctcctc aactagtacc     420
acgacgccag cgccgcgacc accaacaccg gcgcccacca tcgcgtcgca gcccctgtcc     480
ctgcgcccag aggcgtgccg ccagcggcg ggggcgcag tgcacacgag ggggctggac     540
ttcgcctgtg atatctacat ctgggcgccc ttggccggga cttgtggggt ccttctcctg     600
tcactggtta tcacccttta ctgcaaacgg ggcagaaaga aactcctgta tatattcaaa     660
```

| | |
|---|---|
| caaccattta tgagaccagt acaaactact caagaggaag atggctgtag ctgccgattt | 720 |
| ccagaagaag aagaaggagg atgtgaactg agagtgaagt tcagcaggag cgcagacgcc | 780 |
| cccgcgtacc agcagggcca gaaccagctc tataacgagc tcaatctagg acgaagagag | 840 |
| gagtacgatg ttttggacaa gagacgtggc cgggaccctg agatgggggg aaagccgaga | 900 |
| aggaagaacc ctcaggaagg cctgtacaat gaactgcaga agataagat ggcggaggcc | 960 |
| tacagtgaga ttgggatgaa aggcgagcgc cggaggggca aggggcacga tggcctttac | 1020 |
| cagggtctca gtacagccac caaggacacc tacgacgccc ttcacatgca ggccctgccc | 1080 |
| cctcgctaa | 1089 |

<210> SEQ ID NO 293
<211> LENGTH: 1098
<212> TYPE: DNA
<213> ORGANISM: Artificial Sequence
<220> FEATURE:
<223> OTHER INFORMATION: Synthetic Construct

<400> SEQUENCE: 293

| | |
|---|---|
| atggctctgc ccgtcaccgc tctgctgctg cctctggctc tgctgctgca cgctgctcgc | 60 |
| cctcaggtaa agctggagga gtctggggga ggattggtgc agactggggg ctctctgaga | 120 |
| ctctcctgtg cagcctctga acacaccttc agtaaccatg tcatgggctg gttccgccag | 180 |
| gctccaggga aggagcgtga gtctgttgca gttattggct ggagagatat agcacaagc | 240 |
| tatgcagact ccgtgaaggg ccgattcacc atctccagag acaacgccaa gaagacgctg | 300 |
| tatctgcaaa tgaatagcct gaaacctgag gacacggccg tttactactg tgcagcacgt | 360 |
| cggatcgacg cagctgactt tgattcccgg gggcagggga cccaggtcac cgtctcctca | 420 |
| actagtacca cgacgccagc gccgcgacca ccaacaccgg cgccaccat cgcgtcgcag | 480 |
| cccctgtccc tgcgcccaga ggcgtgccgg ccagcggcgg ggggcgcagt gcacacgagg | 540 |
| gggctggact tcgcctgtga tatctacatc tgggcgccct tggccgggac ttgtggggtc | 600 |
| cttctcctgt cactggttat cacccttac tgcaaacggg gcagaaagaa actcctgtat | 660 |
| atattcaaac aaccatttat gagaccagta caaactactc aagaggaaga tggctgtagc | 720 |
| tgccgatttc cagaagaaga agaaggagga tgtgaactga gagtgaagtt cagcaggagc | 780 |
| gcagacgccc ccgcgtacca gcagggccag aaccagctct ataacgagct caatctagga | 840 |
| cgaagagagg agtacgatgt ttttggacaag agacgtggcc gggaccctga tgggggga | 900 |
| aagccgagaa ggaagaaccc tcaggaaggc ctgtacaatg aactgcagaa agataagatg | 960 |
| gcggaggcct acagtgagat tgggatgaaa ggcgagcgcc ggaggggcaa ggggcacgat | 1020 |
| ggcctttacc agggtctcag tacagccacc aaggacacct acgacgccct tcacatgcag | 1080 |
| gccctgcccc ctcgctaa | 1098 |

<210> SEQ ID NO 294
<211> LENGTH: 1110
<212> TYPE: DNA
<213> ORGANISM: Artificial Sequence
<220> FEATURE:
<223> OTHER INFORMATION: Synthetic Construct

<400> SEQUENCE: 294

| | |
|---|---|
| atggctctgc ccgtcaccgc tctgctgctg cctctggctc tgctgctgca cgctgctcgc | 60 |
| cctgccgtgc agctggtgga ttctggggga ggattggtgc aggctggggg ctctctgaga | 120 |
| atttcctgtg cagtctctgg acgcacctcc agtaactata tattggcctg gttccgtcag | 180 |

```
gctccaggaa aagagcgtga ctttgtagca catattagcc ggagtggtgg taagtccggc    240
tatggagact ccgtgaaggg ccgattcacc atctccagag acaacgccga gaacacggtc    300
agggtgtatc tgcaaatgaa cagtctgaaa cctggggaca cggccgtcta ttactgtaat    360
cgccccctct ggtacggaag tcccacgttg attgactact ggggccaggg gacccaggtc    420
accgtctcct caactagtac cacgacgcca gcgccgcgac caccaacacc ggcgcccacc    480
atcgcgtcgc agcccctgtc cctgcgccca gaggcgtgcc ggccagcggc gggggcgca    540 gtgcacacga gggggctgga cttcgcctgt gatatctaca tctgggcgcc cttggccggg    600
acttgtgggg tccttctcct gtcactggtt atcacccttt actgcaaacg ggcagaaag    660 aaactcctgt atatattcaa acaaccattt atgagaccag tacaaactac tcaagaggaa    720
gatggctgta gctgccgatt tccagaagaa gaagaaggag gatgtgaact gagagtgaag    780
ttcagcagga gcgcagacgc ccccgcgtac cagcagggcc agaaccagct ctataacgag    840
ctcaatctag gacgaagaga ggagtacgat gttttggaca agagacgtgg ccgggaccct    900
gagatggggg gaaagccgag aaggaagaac cctcaggaag gcctgtacaa tgaactgcag    960
aaagataaga tggcggaggc ctacagtgag attgggatga aggcgagcg ccggaggggc   1020 aagggcacg atggcccttta ccagggtctc agtacagcca ccaaggacac ctacgacgcc   1080
cttcacatgc aggccctgcc ccctcgctaa                                   1110

<210> SEQ ID NO 295
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 295
atggctctgc ccgtcaccgc tctgctgctg cctctggctc tgctgctgca cgctgctcgc     60
cctgcggtgc agctggtgga gtctggggga ggcttggtgc agcctggggg gtctctgaga    120
ctctcctgtg cagcctctgg acgcaccttc accatggggt ggttccgtca ggctccaggg    180
aaggagcgtg agtttgtagc agctattagt ttgagtccta ctttagcata ttatgcagag    240
tccgtgaagg gccgattcac catcagccga gacaacgcca agaacacggt ggttttgcaa    300
atgaacagcc tgaaacctga ggacacggcc ctttattact gtgcagcaga ccggaaatca    360
gtaatgtcta ttcggcccga ctactggggc caggggaccc aggtcaccgt ctcctcaact    420
agtaccacga cgccagcgcc gcgaccacca acaccggcgc ccaccatcgc gtcgcagccc    480
ctgtccctgc gcccagaggc gtgccggcca gcggcggggg cgcagtgca cacgagggg     540 ctggacttcg cctgtgatat ctacatctgg gcgcccttgg ccgggacttg tggggtcctt    600
ctcctgtcac tggttatcac cctttactgc aaacgggca gaaagaaact cctgtatata    660
ttcaaacaac catttatgag accagtacaa actactcaag aggaagatgg ctgtagctgc    720
cgatttccag aagaagaaga aggaggatgt gaactgagag tgaagttcag caggagcgca    780 gacgccccccg cgtaccagca gggccagaac cagctctata acgagctcaa tctaggacga    840
agagaggagt acgatgtttt ggacaagaga cgtggccggg accctgagat ggggggaaag    900
ccgagaagga gaacccctca ggaaggcctg tacaatgaac tgcagaaaga taagatggcg    960
gaggcctaca gtgagattgg gatgaaaggc gagcgccgga ggggcaaggg gcacgatggc   1020
ctttaccagg gtctcagtac agccaccaag gacacctacg acgcccttca catgcaggcc   1080
```

```
ctgccccctc gctaa                                                    1095

<210> SEQ ID NO 296
<211> LENGTH: 1095
<212> TYPE: DNA
<213> ORGANISM: Artificial Sequence
<220> FEATURE:
<223> OTHER INFORMATION: Synthetic Construct

<400> SEQUENCE: 296
atggctctgc ccgtcaccgc tctgctgctg cctctggctc tgctgctgca cgctgctcgc      60
cctgcggtgc agctggtgga gtctggggga ggattggtgc aggctggggg ctctctgaga     120
ctctcctgtg cagcctctgg acgcaccttc accatggggt ggttccgtca ggctccaggg     180
aaggagcgtg agtttgtagc agctattagt ttgagtccta ctttagcata ttatgcagag     240
tccgtgaagg gccgattcac catcagccga gacaacgcca gaacacggt ggttttgcaa      300 atgaacagcc tgaaacctga ggacacggcc ctttattact gtgcagcaga ccggaaatca     360
gtaatgtcta ttcggcccga ctactggggc caggggaccc aggtcaccgt ctcctcaact     420
agtaccacga cgccagcgcc gcgaccacca caccggcgc ccaccatcgc gtcgcagccc      480
ctgtccctgc gcccagaggc gtgccggcca cggcggggg gcgcagtgca cacgagggg      540 ctggacttcg cctgtgatat ctacatctgg gcgcccttgg ccgggacttg tggggtcctt     600
ctcctgtcac tggttatcac cctttactgc aaacggggca gaagaaact cctgtatata      660 ttcaaacaac catttatgag accagtacaa actactcaag aggaagatgg ctgtagctgc     720
cgatttccag aagaagaaga aggaggatgt gaactgagag tgaagttcag caggagcgca     780
gacgcccccg cgtaccagca gggccagaac cagctctata cgagctcaa tctaggacga     840 agagaggagt acgatgtttt ggacaagaga cgtggccggg accctgagat ggggggaaag     900
ccgagaagga agaaccctca ggaaggcctg tacaatgaac tgcagaaaga taagatggcg     960
gaggcctaca gtgagattgg gatgaaaggc gagcgccgga ggggcaaggg gcacgatggc    1020
ctttaccagg gtctcagtac agccaccaag gacacctacg acgcccttca catgcaggcc    1080
ctgccccctc gctaa                                                    1095

<210> SEQ ID NO 297
<211> LENGTH: 1104
<212> TYPE: DNA
<213> ORGANISM: Artificial Sequence
<220> FEATURE:
<223> OTHER INFORMATION: Synthetic Construct

<400> SEQUENCE: 297
atggctctgc ccgtcaccgc tctgctgctg cctctggctc tgctgctgca cgctgctcgc      60
cctgatgtgc agctggtgga gtctggggga ggatcggtgc agactggggg ctctctgaga     120
ctctcctgta cagcctctgg acgcaccctc aataactttg tcatgggctg gttccgtcag     180
gctccaggga aggagcgtga gtttgtagca gctattagtt tgagtcctac tttagcatat     240
tatgtagagt ccgtgaaggg ccgattcacc atcagccgag acaacgccaa gaacacggtg     300
gttttgcaaa tgaacagcct gaaacctgag gacacgccc tttattactg tgcagcagac     360
cggaaatcag taatgtctat tcggcccgac tactggggcc aggggaccca ggtcaccgtc    420
tcctcaacta gtaccacgac gccagcgccg cgaccaccaa caccggcgcc caccatcgcg    480
tcgcagcccc tgtccctgcg cccagaggcg tgccggccag ggcggggg cgcagtgcac      540 acgagggggc tggacttcgc ctgtgatatc tacatctggg cgcccttggc cgggacttgt    600
```

-continued

```
ggggtccttc tcctgtcact ggttatcacc ctttactgca aacgggcag aaagaaactc    660 ctgtatatat tcaaacaacc atttatgaga ccagtacaaa ctactcaaga ggaagatggc    720
tgtagctgcc gatttccaga agaagaagaa ggaggatgtg aactgagagt gaagttcagc    780
aggagcgcag acgccccgc gtaccagcag ggccagaacc agctctataa cgagctcaat    840
ctaggacgaa gagaggagta cgatgttttg gacaagagac gtggccggga ccctgagatg    900 ggggaaagc cgagaaggaa gaaccctcag gaaggcctgt acaatgaact gcagaaagat    960
aagatggcgg aggcctacag tgagattggg atgaaaggcg agcgccggag gggcaagggg   1020
cacgatggcc tttaccaggg tctcagtaca gccaccaagg acacctacga cgcccttcac   1080
atgcaggccc tgccccctcg ctaa                                          1104
```

<210> SEQ ID NO 298
<211> LENGTH: 495
<212> TYPE: PRT
<213> ORGANISM: Artificial Sequence
<220> FEATURE:
<223> OTHER INFORMATION: Synthetic Construct

<400> SEQUENCE: 298

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Glu Ala Ser Gly Phe
        35                  40                  45

Thr Leu Asp Tyr Tyr Ala Ile Gly Trp Phe Arg Gln Ala Pro Gly Lys
    50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125

Asp Tyr Glu Phe Arg Gly Gln Gly Thr Gln Val Thr Val Ser Ser Gly
    130                 135                 140

Gly Gly Gly Ser Gln Val Gln Leu Val Glu Ser Gly Gly Gly Leu Val
145                 150                 155                 160

Gln Pro Gly Gly Ser Leu Arg Leu Ser Cys Glu Ala Ser Gly Phe Thr
                165                 170                 175

Leu Asp Tyr Tyr Ala Ile Gly Trp Phe Arg Gln Ala Pro Gly Lys Glu
            180                 185                 190

Arg Glu Gly Val Ile Cys Ile Ser Arg Ser Asp Gly Ser Thr Tyr Tyr
        195                 200                 205

Ala Asp Ser Val Lys Gly Arg Phe Thr Ile Ser Arg Asp Asn Ala Lys
    210                 215                 220

Lys Thr Val Tyr Leu Gln Met Ile Ser Leu Lys Pro Glu Asp Thr Ala
225                 230                 235                 240

Ala Tyr Tyr Cys Ala Ala Gly Ala Asp Cys Ser Gly Tyr Leu Arg Asp
                245                 250                 255

Tyr Glu Phe Arg Gly Gln Gly Thr Gln Val Thr Val Ser Ser Thr Ser
            260                 265                 270
```

```
Thr Thr Thr Pro Ala Pro Arg Pro Thr Pro Ala Pro Thr Ile Ala
            275                 280                 285

Ser Gln Pro Leu Ser Leu Arg Pro Glu Ala Cys Arg Pro Ala Ala Gly
290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
                340                 345                 350

Lys Gln Pro Phe Met Arg Pro Val Gln Thr Thr Gln Glu Glu Asp Gly
            355                 360                 365

Cys Ser Cys Arg Phe Pro Glu Glu Glu Glu Gly Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
                420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 299
<211> LENGTH: 622
<212> TYPE: PRT
<213> ORGANISM: Artificial Sequence
<220> FEATURE:
<223> OTHER INFORMATION: Synthetic Construct

<400> SEQUENCE: 299

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
                20                  25                  30

Val Gln Pro Gly Gly Ser Leu Arg Leu Ser Cys Glu Ala Ser Gly Phe
            35                  40                  45

Thr Leu Asp Tyr Tyr Ala Ile Gly Trp Phe Arg Gln Ala Pro Gly Lys
        50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
                100                 105                 110

Ala Ala Tyr Tyr Cys Ala Ala Gly Ala Asp Cys Ser Gly Tyr Leu Arg
            115                 120                 125

Asp Tyr Glu Phe Arg Gly Gln Gly Thr Gln Val Thr Val Ser Ser Gly
        130                 135                 140
```

```
Gly Gly Gly Ser Gln Val Gln Leu Val Glu Ser Gly Gly Leu Val
145                 150                 155                 160
Gln Pro Gly Gly Ser Leu Arg Leu Ser Cys Glu Ala Ser Gly Phe Thr
                165                 170                 175
Leu Asp Tyr Tyr Ala Ile Gly Trp Phe Arg Gln Ala Pro Gly Lys Glu
            180                 185                 190
Arg Glu Gly Val Ile Cys Ile Ser Arg Ser Asp Gly Ser Thr Tyr Tyr
        195                 200                 205
Ala Asp Ser Val Lys Gly Arg Phe Thr Ile Ser Arg Asp Asn Ala Lys
    210                 215                 220
Lys Thr Val Tyr Leu Gln Met Ile Ser Leu Lys Pro Glu Asp Thr Ala
225                 230                 235                 240
Ala Tyr Tyr Cys Ala Ala Gly Ala Asp Cys Ser Gly Tyr Leu Arg Asp
                245                 250                 255
Tyr Glu Phe Arg Gly Gln Gly Thr Gln Val Thr Val Ser Ser Gly Gly
            260                 265                 270
Gly Gly Ser Gln Val Gln Leu Val Glu Ser Gly Gly Leu Val Gln
        275                 280                 285
Pro Gly Gly Ser Leu Arg Leu Ser Cys Glu Ala Ser Gly Phe Thr Leu
    290                 295                 300
Asp Tyr Tyr Ala Ile Gly Trp Phe Arg Gln Ala Pro Gly Lys Glu Arg
305                 310                 315                 320
Glu Gly Val Ile Cys Ile Ser Arg Ser Asp Gly Ser Thr Tyr Tyr Ala
                325                 330                 335
Asp Ser Val Lys Gly Arg Phe Thr Ile Ser Arg Asp Asn Ala Lys Lys
            340                 345                 350
Thr Val Tyr Leu Gln Met Ile Ser Leu Lys Pro Glu Asp Thr Ala Ala
        355                 360                 365
Tyr Tyr Cys Ala Ala Gly Ala Asp Cys Ser Gly Tyr Leu Arg Asp Tyr
    370                 375                 380
Glu Phe Arg Gly Gln Gly Thr Gln Val Thr Val Ser Ser Thr Ser Thr
385                 390                 395                 400
Thr Thr Pro Ala Pro Arg Pro Pro Thr Pro Ala Pro Thr Ile Ala Ser
                405                 410                 415
Gln Pro Leu Ser Leu Arg Pro Glu Ala Cys Arg Pro Ala Ala Gly Gly
            420                 425                 430
Ala Val His Thr Arg Gly Leu Asp Phe Ala Cys Asp Ile Tyr Ile Trp
        435                 440                 445
Ala Pro Leu Ala Gly Thr Cys Gly Val Leu Leu Leu Ser Leu Val Ile
    450                 455                 460
Thr Leu Tyr Cys Lys Arg Gly Arg Lys Lys Leu Leu Tyr Ile Phe Lys
465                 470                 475                 480
Gln Pro Phe Met Arg Pro Val Gln Thr Thr Gln Glu Glu Asp Gly Cys
                485                 490                 495
Ser Cys Arg Phe Pro Glu Glu Glu Gly Gly Cys Glu Leu Arg Val
            500                 505                 510
Lys Phe Ser Arg Ser Ala Asp Ala Pro Ala Tyr Gln Gln Gly Gln Asn
        515                 520                 525
Gln Leu Tyr Asn Glu Leu Asn Leu Gly Arg Arg Glu Glu Tyr Asp Val
    530                 535                 540
Leu Asp Lys Arg Arg Gly Arg Asp Pro Glu Met Gly Gly Lys Pro Arg
545                 550                 555                 560
```

Arg Lys Asn Pro Gln Glu Gly Leu Tyr Asn Glu Leu Gln Lys Asp Lys
                565                 570                 575

Met Ala Glu Ala Tyr Ser Glu Ile Gly Met Lys Gly Glu Arg Arg Arg
            580                 585                 590

Gly Lys Gly His Asp Gly Leu Tyr Gln Gly Leu Ser Thr Ala Thr Lys
        595                 600                 605

Asp Thr Tyr Asp Ala Leu His Met Gln Ala Leu Pro Pro Arg
    610                 615                 620

<210> SEQ ID NO 300
<211> LENGTH: 488
<212> TYPE: PRT
<213> ORGANISM: Artificial Sequence
<220> FEATURE:
<223> OTHER INFORMATION: Synthetic Construct

<400> SEQUENCE: 300

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Glu Val Gln Leu Val Glu Ser Gly Gly Gly Leu Val Gln Ala Gly
145                 150                 155                 160

Gly Ser Leu Arg Leu Ser Cys Ala Ala Ser Gly Arg Thr Phe Thr Met
                165                 170                 175

Gly Trp Phe Arg Gln Ala Pro Gly Lys Glu Arg Glu Phe Val Ala Ala
            180                 185                 190

Ile Ser Leu Ser Pro Thr Leu Ala Tyr Tyr Ala Glu Ser Val Lys Gly
        195                 200                 205

Arg Phe Thr Ile Ser Arg Asp Asn Ala Lys Asn Thr Val Val Leu Gln
    210                 215                 220

Met Asn Ser Leu Lys Pro Glu Asp Thr Ala Leu Tyr Tyr Cys Ala Ala
225                 230                 235                 240

Asp Arg Lys Ser Val Met Ser Ile Arg Pro Asp Tyr Trp Gly Gln Gly
                245                 250                 255

Thr Gln Val Thr Val Ser Ser Thr Ser Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Ser Leu Val Ile Thr Leu Tyr Cys Lys Arg
            325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 301
<211> LENGTH: 498
<212> TYPE: PRT
<213> ORGANISM: Artificial Sequence
<220> FEATURE:
<223> OTHER INFORMATION: Synthetic Construct

<400> SEQUENCE: 301

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Arg Ser Leu Arg Leu Ser Cys Ala Ala Ser Glu His
            35                  40                  45

Thr Phe Ser Ser His Val Met Gly Trp Phe Arg Gln Ala Pro Gly Lys
        50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Ile Asp Ala Ala Asp Phe Asp
        115                 120                 125

Ser Trp Gly Gln Gly Thr Gln Val Thr Val Ser Ser Gly Gly Gly Gly
130                 135                 140

Ser Gly Gly Gly Gly Ser Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

```
Cys Ala Ala Ser Gly Arg Thr Phe Thr Met Gly Trp Phe Arg Gln Ala
                180                 185                 190

Pro Gly Lys Glu Arg Glu Phe Val Ala Ala Ile Ser Leu Ser Pro Thr
            195                 200                 205

Leu Ala Tyr Tyr Ala Glu Ser Val Lys Gly Arg Phe Thr Ile Ser Arg
        210                 215                 220

Asp Asn Ala Lys Asn Thr Val Val Leu Gln Met Asn Ser Leu Lys Pro
225                 230                 235                 240

Glu Asp Thr Ala Leu Tyr Tyr Cys Ala Ala Asp Arg Lys Ser Val Met
                245                 250                 255

Ser Ile Arg Pro Asp Tyr Trp Gly Gln Gly Thr Gln Val Thr Val Ser
            260                 265                 270

Ser Thr Ser Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg

<210> SEQ ID NO 302
<211> LENGTH: 508
<212> TYPE: PRT
<213> ORGANISM: Artificial Sequence
<220> FEATURE:
<223> OTHER INFORMATION: Synthetic Construct

<400> SEQUENCE: 302

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
```

```
            35                  40                  45
Thr Phe Ser Ser His Val Met Gly Trp Phe Arg Gln Ala Pro Gly Lys
 50                  55                  60

Glu Arg Glu Ser Val Ala Val Ile Gly Trp Arg Asp Ile Ser Thr Ser
 65                  70                  75                  80

Tyr Ala Asp Ser Val Lys Gly Arg Phe Thr Ile Ser Arg Asp Asn Ala
                 85                  90                  95

Lys Lys Thr Leu Tyr Leu Gln Met Asn Ser Leu Lys Pro Glu Asp Thr
                100                 105                 110

Ala Val Tyr Tyr Cys Ala Ala Arg Arg Ile Asp Ala Ala Asp Phe Asp
            115                 120                 125

Ser Trp Gly Gln Gly Thr Gln Val Thr Val Ser Ser Gly Gly Gly Gly
    130                 135                 140

Ser Gly Gly Gly Gly Ser Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Ala Gly Gly Ser Leu Arg Leu Ser Cys Ala Ala Ser Gly Arg
            180                 185                 190

Thr Phe Thr Met Gly Trp Phe Arg Gln Ala Pro Gly Lys Glu Arg Glu
    195                 200                 205

Phe Val Ala Ala Ile Ser Leu Ser Pro Thr Leu Ala Tyr Tyr Ala Glu
210                 215                 220

Ser Val Lys Gly Arg Phe Thr Ile Ser Arg Asp Asn Ala Lys Asn Thr
225                 230                 235                 240

Val Val Leu Gln Met Asn Ser Leu Lys Pro Glu Asp Thr Ala Leu Tyr
                245                 250                 255

Tyr Cys Ala Ala Asp Arg Lys Ser Val Met Ser Ile Arg Pro Asp Tyr
            260                 265                 270

Trp Gly Gln Gly Thr Gln Val Thr Val Ser Ser Thr Ser Thr Thr Thr
    275                 280                 285

Pro Ala Pro Arg Pro Pro Thr Pro Ala Pro Thr Ile Ala Ser Gln Pro
290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
    355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
    435                 440                 445

Asn Pro Gln Glu Gly Leu Tyr Asn Glu Leu Gln Lys Asp Lys Met Ala
    450                 455                 460
```

```
Glu Ala Tyr Ser Glu Ile Gly Met Lys Gly Glu Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 303
<211> LENGTH: 493
<212> TYPE: PRT
<213> ORGANISM: Artificial Sequence
<220> FEATURE:
<223> OTHER INFORMATION: Synthetic Construct

<400> SEQUENCE: 303

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Gly Gly Gly Gly Ser
    130                 135                 140

Gly Gly Gly Gly Ser Gln Val Lys Leu Glu Glu Ser Gly Gly Gly Leu
145                 150                 155                 160

Val Gln Ala Gly Arg Ser Leu Arg Leu Ser Cys Ala Ala Ser Glu His
                165                 170                 175

Thr Phe Ser Ser His Val Met Gly Trp Phe Arg Gln Ala Pro Gly Lys
            180                 185                 190

Glu Arg Glu Ser Val Ala Val Ile Gly Trp Arg Asp Ile Ser Thr Ser
        195                 200                 205

Tyr Ala Asp Ser Val Lys Gly Arg Phe Thr Ile Ser Arg Asp Asn Ala
    210                 215                 220

Lys Lys Thr Leu Tyr Leu Gln Met Asn Ser Leu Lys Pro Glu Asp Thr
225                 230                 235                 240

Ala Val Tyr Tyr Cys Ala Ala Arg Arg Ile Asp Ala Ala Asp Phe Asp
                245                 250                 255

Ser Trp Gly Gln Gly Thr Gln Val Thr Val Ser Ser Thr Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320
```

```
Pro Leu Ala Gly Thr Cys Gly Val Leu Leu Ser Leu Val Ile Thr
                325                 330                 335

Leu Tyr Cys Lys Arg Gly Arg Lys Leu Leu Tyr Ile Phe Lys Gln
                340                 345                 350

Pro Phe Met Arg Pro Val Gln Thr Thr Gln Glu Glu Asp Gly Cys Ser
                355                 360                 365

Cys Arg Phe Pro Glu Glu Glu Gly Gly Cys Glu Leu Arg Val Lys
                370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
                420                 425                 430

Lys Asn Pro Gln Glu Gly Leu Tyr Asn Glu Leu Gln Lys Asp Lys Met
                435                 440                 445

Ala Glu Ala Tyr Ser Glu Ile Gly Met Lys Gly Glu Arg Arg Arg Gly
                450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 304
<211> LENGTH: 498
<212> TYPE: PRT
<213> ORGANISM: Artificial Sequence
<220> FEATURE:
<223> OTHER INFORMATION: Synthetic Construct

<400> SEQUENCE: 304

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ala Ala Ser Gly Arg
                35                  40                  45

Thr Phe Thr Met Gly Trp Phe Arg Gln Ala Pro Gly Lys Glu Arg Glu
                50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
                100                 105                 110

Tyr Cys Ala Ala Asp Arg Lys Ser Val Met Ser Ile Arg Pro Asp Tyr
                115                 120                 125

Trp Gly Gln Gly Thr Gln Val Thr Val Ser Ser Gly Gly Gly Gly Ser
                130                 135                 140

Gly Gly Gly Gly Ser Gly Gly Gly Ser Gln Val Lys Leu Glu Glu
145                 150                 155                 160

Ser Gly Gly Gly Leu Val Gln Ala Gly Arg Ser Leu Arg Leu Ser Cys
                165                 170                 175

Ala Ala Ser Glu His Thr Phe Ser Ser His Val Met Gly Trp Phe Arg
                180                 185                 190
```

```
Gln Ala Pro Gly Lys Glu Arg Glu Ser Val Ala Val Ile Gly Trp Arg
            195                 200                 205

Asp Ile Ser Thr Ser Tyr Ala Asp Ser Val Lys Gly Arg Phe Thr Ile
        210                 215                 220

Ser Arg Asp Asn Ala Lys Lys Thr Leu Tyr Leu Gln Met Asn Ser Leu
225                 230                 235                 240

Lys Pro Glu Asp Thr Ala Val Tyr Tyr Cys Ala Ala Arg Arg Ile Asp
                245                 250                 255

Ala Ala Asp Phe Asp Ser Trp Gly Gln Gly Thr Gln Val Thr Val Ser
            260                 265                 270

Ser Thr Ser Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg
```

<210> SEQ ID NO 305
<211> LENGTH: 503
<212> TYPE: PRT
<213> ORGANISM: Artificial Sequence
<220> FEATURE:
<223> OTHER INFORMATION: Synthetic Construct

<400> SEQUENCE: 305

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45
```

Thr Phe Thr Met Gly Trp Phe Arg Gln Ala Pro Gly Lys Glu Arg Glu
 50                  55                  60

Phe Val Ala Ala Ile Ser Leu Ser Pro Thr Leu Ala Tyr Tyr Ala Glu
 65                  70                  75                  80

Ser Val Lys Gly Arg Phe Thr Ile Ser Arg Asp Asn Ala Lys Asn Thr
                 85                  90                  95

Val Val Leu Gln Met Asn Ser Leu Lys Pro Glu Asp Thr Ala Leu Tyr
                100                 105                 110

Tyr Cys Ala Ala Asp Arg Lys Ser Val Met Ser Ile Arg Pro Asp Tyr
                115                 120                 125

Trp Gly Gln Gly Thr Gln Val Thr Val Ser Ser Gly Gly Gly Gly Ser
            130                 135                 140

Gly Gly Gly Gly Ser Gly Gly Gly Ser Gly Gly Gly Gly Ser Gln
145                 150                 155                 160

Val Lys Leu Glu Glu Ser Gly Gly Leu Val Gln Ala Gly Arg Ser
                165                 170                 175

Leu Arg Leu Ser Cys Ala Ala Ser Glu His Thr Phe Ser Ser His Val
                180                 185                 190

Met Gly Trp Phe Arg Gln Ala Pro Gly Lys Glu Arg Glu Ser Val Ala
            195                 200                 205

Val Ile Gly Trp Arg Asp Ile Ser Thr Ser Tyr Ala Asp Ser Val Lys
    210                 215                 220

Gly Arg Phe Thr Ile Ser Arg Asp Asn Ala Lys Thr Leu Tyr Leu
225                 230                 235                 240

Gln Met Asn Ser Leu Lys Pro Glu Asp Thr Ala Val Tyr Tyr Cys Ala
                245                 250                 255

Ala Arg Arg Ile Asp Ala Ala Asp Phe Asp Ser Trp Gly Gln Gly Thr
            260                 265                 270

Gln Val Thr Val Ser Ser Thr Ser Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Lys Arg Gly
            340                 345                 350

Arg Lys Lys Leu Leu Tyr Ile Phe Lys Gln Pro Phe Met Arg Pro Val
            355                 360                 365

Gln Thr Thr Gln Glu Glu Asp Gly Cys Ser Cys Arg Phe Pro Glu Glu
    370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
            435                 440                 445

Leu Tyr Asn Glu Leu Gln Lys Asp Lys Met Ala Glu Ala Tyr Ser Glu
450                 455                 460

Ile Gly Met Lys Gly Glu Arg Arg Arg Gly Lys Gly His Asp Gly Leu

| | | | |
|---|---|---|---|
|465|470|475|480|

Tyr Gln Gly Leu Ser Thr Ala Thr Lys Asp Thr Tyr Asp Ala Leu His
485 490 495

Met Gln Ala Leu Pro Pro Arg
500

<210> SEQ ID NO 306
<211> LENGTH: 489
<212> TYPE: PRT
<213> ORGANISM: Artificial Sequence
<220> FEATURE:
<223> OTHER INFORMATION: Synthetic Construct

<400> SEQUENCE: 306

Met Ala Leu Pro Val Thr Ala Leu Leu Leu Pro Leu Ala Leu Leu Leu
1               5                   10                  15

His Ala Ala Arg Pro Gln Val Lys Leu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Ala Val Gln Leu Val Glu Ser Gly Gly Gly Leu Val Gln Ala Gly
145                 150                 155                 160

Asp Ser Leu Arg Leu Thr Cys Thr Ala Ser Gly Arg Ala Phe Ser Thr
                165                 170                 175

Tyr Phe Met Ala Trp Phe Arg Gln Ala Pro Gly Lys Glu Arg Glu Phe
            180                 185                 190

Val Ala Gly Ile Ala Trp Ser Gly Gly Ser Thr Ala Tyr Ala Asp Ser
        195                 200                 205

Val Lys Gly Arg Phe Thr Ile Ser Arg Asp Asn Ala Lys Asn Thr Val
    210                 215                 220

Tyr Leu Gln Met Asn Ser Leu Lys Ser Glu Asp Thr Ala Val Tyr Tyr
225                 230                 235                 240

Cys Ala Ser Arg Gly Ile Glu Val Glu Glu Phe Gly Ala Trp Gly Gln
                245                 250                 255

Gly Thr Gln Val Thr Val Ser Ser Thr Thr Thr Pro Ala Pro
            260                 265                 270 Pro

Arg Pro Pro Thr Pro Ala Pro Thr Ile Ala Ser Gln Pro Leu Ser Leu
            275                 280                 285

Arg Pro Glu Ala Cys Arg Pro Ala Ala Gly Gly Ala Val His Thr Arg
            290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys

-continued

```
                325                 330                 335
Arg Gly Arg Lys Lys Leu Leu Tyr Ile Phe Lys Gln Pro Phe Met Arg
            340                 345                 350
Pro Val Gln Thr Thr Gln Glu Asp Gly Cys Ser Cys Arg Phe Pro
            355                 360             365
Glu Glu Glu Glu Gly Gly Cys Glu Leu Arg Val Lys Phe Ser Arg Ser
            370                 375                 380
Ala Asp Ala Pro Ala Tyr Gln Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Arg Arg Lys Asn Pro Gln
            420                 425                 430
Glu Gly Leu Tyr Asn Glu Leu Gln Lys Asp Lys Met Ala Glu Ala Tyr
                435                 440                 445
Ser Glu Ile Gly Met Lys Gly Glu Arg Arg Arg Gly Lys Gly His Asp
450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg
                485

<210> SEQ ID NO 307
<211> LENGTH: 499
<212> TYPE: PRT
<213> ORGANISM: Artificial Sequence
<220> FEATURE:
<223> OTHER INFORMATION: Synthetic Construct

<400> SEQUENCE: 307

Met Ala Leu Pro Val Thr Ala Leu Leu Leu Pro Leu Ala Leu Leu Leu
1               5                   10                  15
His Ala Ala Arg Pro Gln Val Lys Leu Glu Glu Ser Gly Gly Gly Leu
                20                  25                  30
Val Gln Ala Gly Arg Ser Leu Arg Leu Ser Cys Ala Ala Ser Glu His
            35                  40                  45
Thr Phe Ser Ser His Val Met Gly Trp Phe Arg Gln Ala Pro Gly Lys
        50                  55                  60
Glu Arg Glu Ser Val Ala Val Ile Gly Trp Arg Asp Ile Ser Thr Ser
65                  70                  75                  80
Tyr Ala Asp Ser Val Lys Gly Arg Phe Thr Ile Ser Arg Asp Asn Ala
                85                  90                  95
Lys Lys Thr Leu Tyr Leu Gln Met Asn Ser Leu Lys Pro Glu Asp Thr
            100                 105                 110
Ala Val Tyr Tyr Cys Ala Ala Arg Arg Ile Asp Ala Ala Asp Phe Asp
        115                 120                 125
Ser Trp Gly Gln Gly Thr Gln Val Thr Val Ser Ser Gly Gly Gly Gly
    130                 135                 140
Ser Gly Gly Gly Gly Ser Gly Gly Gly Ser Ala Val Gln Leu Val
145                 150                 155                 160
Glu Ser Gly Gly Gly Leu Val Gln Ala Gly Asp Ser Leu Arg Leu Thr
                165                 170                 175
Cys Thr Ala Ser Gly Arg Ala Phe Ser Thr Tyr Phe Met Ala Trp Phe
            180                 185                 190
Arg Gln Ala Pro Gly Lys Glu Arg Glu Phe Val Ala Gly Ile Ala Trp
```

```
            195                 200                 205
Ser Gly Gly Ser Thr Ala Tyr Ala Asp Ser Val Lys Gly Arg Phe Thr
210                 215                 220

Ile Ser Arg Asp Asn Ala Lys Asn Thr Val Tyr Leu Gln Met Asn Ser
225                 230                 235                 240

Leu Lys Ser Glu Asp Thr Ala Val Tyr Tyr Cys Ala Ser Arg Gly Ile
                245                 250                 255

Glu Val Glu Glu Phe Gly Ala Trp Gly Gln Gly Thr Gln Val Thr Val
                260                 265                 270

Ser Ser Thr Ser Thr Thr Thr Pro Ala Pro Arg Pro Pro Thr Pro Ala
                275                 280                 285

Pro Thr Ile Ala Ser Gln Pro Leu Ser Leu Arg Pro Glu Ala Cys Arg
                290                 295                 300

Pro Ala Ala Gly Gly Ala Val His Thr Arg Gly Leu Asp Phe Ala Cys
305                 310                 315                 320

Asp Ile Tyr Ile Trp Ala Pro Leu Ala Gly Thr Cys Gly Val Leu Leu
                325                 330                 335

Leu Ser Leu Val Ile Thr Leu Tyr Cys Lys Arg Gly Arg Lys Lys Leu
                340                 345                 350

Leu Tyr Ile Phe Lys Gln Pro Phe Met Arg Pro Val Gln Thr Thr Gln
                355                 360                 365

Glu Glu Asp Gly Cys Ser Cys Arg Phe Pro Glu Glu Glu Glu Gly Gly
370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
                420                 425                 430

Gly Gly Lys Pro Arg Arg Lys Asn Pro Gln Glu Gly Leu Tyr Asn Glu
                435                 440                 445

Leu Gln Lys Asp Lys Met Ala Glu Ala Tyr Ser Glu Ile Gly Met Lys
                450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg

<210> SEQ ID NO 308
<211> LENGTH: 509
<212> TYPE: PRT
<213> ORGANISM: Artificial Sequence
<220> FEATURE:
<223> OTHER INFORMATION: Synthetic Construct

<400> SEQUENCE: 308

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Arg Ser Leu Arg Leu Ser Cys Ala Ala Ser Glu His
            35                  40                  45

Thr Phe Ser Ser His Val Met Gly Trp Phe Arg Gln Ala Pro Gly Lys
        50                  55                  60
```

Glu Arg Glu Ser Val Ala Val Ile Gly Trp Arg Asp Ile Ser Thr Ser
 65                  70                  75                  80

Tyr Ala Asp Ser Val Lys Gly Arg Phe Thr Ile Ser Arg Asp Asn Ala
                 85                  90                  95

Lys Lys Thr Leu Tyr Leu Gln Met Asn Ser Leu Lys Pro Glu Asp Thr
             100                 105                 110

Ala Val Tyr Tyr Cys Ala Ala Arg Arg Ile Asp Ala Ala Asp Phe Asp
         115                 120                 125

Ser Trp Gly Gln Gly Thr Gln Val Thr Val Ser Ser Gly Gly Gly Gly
     130                 135                 140

Ser Gly Gly Gly Gly Ser Gly Gly Gly Ser Gly Gly Gly Gly Gly Ser
145                 150                 155                 160

Gly Gly Gly Gly Ser Ala Val Gln Leu Val Glu Ser Gly Gly Gly Leu
                 165                 170                 175

Val Gln Ala Gly Asp Ser Leu Arg Leu Thr Cys Thr Ala Ser Gly Arg
             180                 185                 190

Ala Phe Ser Thr Tyr Phe Met Ala Trp Phe Arg Gln Ala Pro Gly Lys
         195                 200                 205

Glu Arg Glu Phe Val Ala Gly Ile Ala Trp Ser Gly Gly Ser Thr Ala
     210                 215                 220

Tyr Ala Asp Ser Val Lys Gly Arg Phe Thr Ile Ser Arg Asp Asn Ala
225                 230                 235                 240

Lys Asn Thr Val Tyr Leu Gln Met Asn Ser Leu Lys Ser Glu Asp Thr
                 245                 250                 255

Ala Val Tyr Tyr Cys Ala Ser Arg Gly Ile Glu Val Glu Glu Phe Gly
             260                 265                 270

Ala Trp Gly Gln Gly Thr Gln Val Thr Val Ser Ser Thr Ser Thr Thr
         275                 280                 285

Thr Pro Ala Pro Arg Pro Pro Thr Pro Ala Pro Thr Ile Ala Ser Gln
     290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                 325                 330                 335

Pro Leu Ala Gly Thr Cys Gly Val Leu Leu Leu Ser Leu Val Ile Thr
             340                 345                 350

Leu Tyr Cys Lys Arg Gly Arg Lys Lys Leu Leu Tyr Ile Phe Lys Gln
         355                 360                 365

Pro Phe Met Arg Pro Val Gln Thr Thr Gln Glu Glu Asp Gly Cys Ser
     370                 375                 380

Cys Arg Phe Pro Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                 405                 410                 415

Leu Tyr Asn Glu Leu Asn Leu Gly Arg Arg Glu Glu Tyr Asp Val Leu
             420                 425                 430

Asp Lys Arg Arg Gly Arg Asp Pro Glu Met Gly Gly Lys Pro Arg Arg
         435                 440                 445

Lys Asn Pro Gln Glu Gly Leu Tyr Asn Glu Leu Gln Lys Asp Lys Met
     450                 455                 460

Ala Glu Ala Tyr Ser Glu Ile Gly Met Lys Gly Glu Arg Arg Arg Gly
465                 470                 475                 480

```
Lys Gly His Asp Gly Leu Tyr Gln Gly Leu Ser Ala Thr Lys Asp
                    485                 490                 495

Thr Tyr Asp Ala Leu His Met Gln Ala Leu Pro Pro Arg
                500                 505

<210> SEQ ID NO 309
<211> LENGTH: 494
<212> TYPE: PRT
<213> ORGANISM: Artificial Sequence
<220> FEATURE:
<223> OTHER INFORMATION: Synthetic Construct

<400> SEQUENCE: 309

Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
                20                  25                  30

Val Gln Ala Gly Asp Ser Leu Arg Leu Thr Cys Thr Ala Ser Gly Arg
            35                  40                  45

Ala Phe Ser Thr Tyr Phe Met Ala Trp Phe Arg Gln Ala Pro Gly Lys
        50                  55                  60

Glu Arg Glu Phe Val Ala Gly Ile Ala Trp Ser Gly Gly Ser Thr Ala
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Ser Glu Asp Thr
                100                 105                 110

Ala Val Tyr Tyr Cys Ala Ser Arg Gly Ile Glu Val Glu Glu Phe Gly
            115                 120                 125

Ala Trp Gly Gln Gly Thr Gln Val Thr Val Ser Ser Gly Gly Gly Gly
        130                 135                 140

Ser Gly Gly Gly Gly Ser Gln Val Lys Leu Glu Glu Ser Gly Gly Gly
145                 150                 155                 160

Leu Val Gln Ala Gly Arg Ser Leu Arg Leu Ser Cys Ala Ala Ser Glu
                165                 170                 175

His Thr Phe Ser Ser His Val Met Gly Trp Phe Arg Gln Ala Pro Gly
            180                 185                 190

Lys Glu Arg Glu Ser Val Ala Val Ile Gly Trp Arg Asp Ile Ser Thr
        195                 200                 205

Ser Tyr Ala Asp Ser Val Lys Gly Arg Phe Thr Ile Ser Arg Asp Asn
210                 215                 220

Ala Lys Lys Thr Leu Tyr Leu Gln Met Asn Ser Leu Lys Pro Glu Asp
225                 230                 235                 240

Thr Ala Val Tyr Tyr Cys Ala Arg Arg Ile Asp Ala Ala Asp Phe
                245                 250                 255

Asp Ser Trp Gly Gln Gly Thr Gln Val Thr Val Ser Ser Thr Ser Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
        290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335
```

```
Thr Leu Tyr Cys Lys Arg Gly Arg Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Gly Cys Glu Leu Arg Val
370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
        420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490
```

<210> SEQ ID NO 310
<211> LENGTH: 499
<212> TYPE: PRT
<213> ORGANISM: Artificial Sequence
<220> FEATURE:
<223> OTHER INFORMATION: Synthetic Construct

<400> SEQUENCE: 310

```
Met Ala Leu Pro Val Thr Ala Leu Leu Leu Pro Leu Ala Leu Leu Leu
1               5                   10                  15

His Ala Ala Arg Pro Ala Val Gln Leu Val Glu Ser Gly Gly Gly Leu
            20                  25                  30

Val Gln Ala Gly Asp Ser Leu Arg Leu Thr Cys Thr Ala Ser Gly Arg
        35                  40                  45

Ala Phe Ser Thr Tyr Phe Met Ala Trp Phe Arg Gln Ala Pro Gly Lys
    50                  55                  60

Glu Arg Glu Phe Val Ala Gly Ile Ala Trp Ser Gly Gly Ser Thr Ala
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Ser Glu Asp Thr
            100                 105                 110

Ala Val Tyr Tyr Cys Ala Ser Arg Gly Ile Glu Val Glu Glu Phe Gly
        115                 120                 125

Ala Trp Gly Gln Gly Thr Gln Val Thr Val Ser Ser Gly Gly Gly Gly
    130                 135                 140

Ser Gly Gly Gly Gly Ser Gly Gly Gly Ser Gln Val Lys Leu Glu
145                 150                 155                 160

Glu Ser Gly Gly Gly Leu Val Gln Ala Gly Arg Ser Leu Arg Leu Ser
                165                 170                 175

Cys Ala Ala Ser Glu His Thr Phe Ser Ser His Val Met Gly Trp Phe
            180                 185                 190

Arg Gln Ala Pro Gly Lys Glu Arg Glu Ser Val Ala Val Ile Gly Trp
        195                 200                 205
```

-continued

```
Arg Asp Ile Ser Thr Ser Tyr Ala Asp Ser Val Lys Gly Arg Phe Thr
    210                 215                 220
Ile Ser Arg Asp Asn Ala Lys Lys Thr Leu Tyr Leu Gln Met Asn Ser
225                 230                 235                 240
Leu Lys Pro Glu Asp Thr Ala Val Tyr Tyr Cys Ala Ala Arg Arg Ile
                245                 250                 255
Asp Ala Ala Asp Phe Asp Ser Trp Gly Gln Gly Thr Gln Val Thr Val
                260                 265                 270
Ser Ser Thr Ser Thr Thr Thr Pro Ala Pro Arg Pro Pro Thr Pro Ala
            275                 280                 285
Pro Thr Ile Ala Ser Gln Pro Leu Ser Leu Arg Pro Glu Ala Cys Arg
    290                 295                 300
Pro Ala Ala Gly Gly Ala Val His Thr Arg Gly Leu Asp Phe Ala Cys
305                 310                 315                 320
Asp Ile Tyr Ile Trp Ala Pro Leu Ala Gly Thr Cys Gly Val Leu Leu
                325                 330                 335
Leu Ser Leu Val Ile Thr Leu Tyr Cys Lys Arg Gly Arg Lys Lys Leu
                340                 345                 350
Leu Tyr Ile Phe Lys Gln Pro Phe Met Arg Pro Val Gln Thr Thr Gln
            355                 360                 365
Glu Glu Asp Gly Cys Ser Cys Arg Phe Pro Glu Glu Glu Glu Gly Gly
    370                 375                 380
Cys Glu Leu Arg Val Lys Phe Ser Arg Ser Ala Asp Ala Pro Ala Tyr
385                 390                 395                 400
Gln Gln Gly Gln Asn Gln Leu Tyr Asn Glu Leu Asn Leu Gly Arg Arg
                405                 410                 415
Glu Glu Tyr Asp Val Leu Asp Lys Arg Arg Gly Arg Asp Pro Glu Met
            420                 425                 430
Gly Gly Lys Pro Arg Arg Lys Asn Pro Gln Glu Gly Leu Tyr Asn Glu
        435                 440                 445
Leu Gln Lys Asp Lys Met Ala Glu Ala Tyr Ser Glu Ile Gly Met Lys
    450                 455                 460
Gly Glu Arg Arg Arg Gly Lys Gly His Asp Gly Leu Tyr Gln Gly Leu
465                 470                 475                 480
Ser Thr Ala Thr Lys Asp Thr Tyr Asp Ala Leu His Met Gln Ala Leu
                485                 490                 495
Pro Pro Arg

<210> SEQ ID NO 311
<211> LENGTH: 504
<212> TYPE: PRT
<213> ORGANISM: Artificial Sequence
<220> FEATURE:
<223> OTHER INFORMATION: Synthetic Construct

<400> SEQUENCE: 311

Met Ala Leu Pro Val Thr Ala Leu Leu Leu Pro Leu Ala Leu Leu Leu
1               5                   10                  15
His Ala Ala Arg Pro Ala Val Gln Leu Val Glu Ser Gly Gly Gly Leu
            20                  25                  30
Val Gln Ala Gly Asp Ser Leu Arg Leu Thr Cys Thr Ala Ser Gly Arg
        35                  40                  45
Ala Phe Ser Thr Tyr Phe Met Ala Trp Phe Arg Gln Ala Pro Gly Lys
    50                  55                  60
Glu Arg Glu Phe Val Ala Gly Ile Ala Trp Ser Gly Gly Ser Thr Ala
```

```
                65                  70                  75                  80
Tyr Ala Asp Ser Val Lys Gly Arg Phe Thr Ile Ser Arg Asp Asn Ala
                        85                  90                  95
Lys Asn Thr Val Tyr Leu Gln Met Asn Ser Leu Lys Ser Glu Asp Thr
                        100                 105                 110
Ala Val Tyr Tyr Cys Ala Ser Arg Gly Ile Glu Val Glu Glu Phe Gly
                        115                 120                 125
Ala Trp Gly Gln Gly Thr Gln Val Thr Val Ser Ser Gly Gly Gly Gly
    130                 135                 140
Ser Gly Gly Gly Gly Ser Gly Gly Gly Ser Gly Gly Gly Gly Ser
145                 150                 155                 160
Gln Val Lys Leu Glu Glu Ser Gly Gly Leu Val Gln Ala Gly Arg
                    165                 170                 175
Ser Leu Arg Leu Ser Cys Ala Ala Ser Glu His Thr Phe Ser Ser His
                180                 185                 190
Val Met Gly Trp Phe Arg Gln Ala Pro Gly Lys Glu Arg Glu Ser Val
            195                 200                 205
Ala Val Ile Gly Trp Arg Asp Ile Ser Thr Ser Tyr Ala Asp Ser Val
        210                 215                 220
Lys Gly Arg Phe Thr Ile Ser Arg Asp Asn Ala Lys Lys Thr Leu Tyr
225                 230                 235                 240
Leu Gln Met Asn Ser Leu Lys Pro Glu Asp Thr Ala Val Tyr Tyr Cys
                245                 250                 255
Ala Ala Arg Arg Ile Asp Ala Ala Asp Phe Asp Ser Trp Gly Gln Gly
                260                 265                 270
Thr Gln Val Thr Val Ser Ser Thr Ser Thr Thr Thr Pro Ala Pro Arg
            275                 280                 285
Pro Pro Thr Pro Ala Pro Thr Ile Ala Ser Gln Pro Leu Ser Leu Arg
        290                 295                 300
Pro Glu Ala Cys Arg Pro Ala Ala Gly Gly Ala Val His Thr Arg Gly
305                 310                 315                 320
Leu Asp Phe Ala Cys Asp Ile Tyr Ile Trp Ala Pro Leu Ala Gly Thr
                325                 330                 335
Cys Gly Val Leu Leu Leu Ser Leu Val Ile Thr Leu Tyr Cys Lys Arg
            340                 345                 350
Gly Arg Lys Lys Leu Leu Tyr Ile Phe Lys Gln Pro Phe Met Arg Pro
        355                 360                 365
Val Gln Thr Thr Gln Glu Glu Asp Gly Cys Ser Cys Arg Phe Pro Glu
    370                 375                 380
Glu Glu Glu Gly Gly Cys Glu Leu Arg Val Lys Phe Ser Arg Ser Ala
385                 390                 395                 400
Asp Ala Pro Ala Tyr Gln Gln Gly Gln Asn Gln Leu Tyr Asn Glu Leu
                405                 410                 415
Asn Leu Gly Arg Arg Glu Glu Tyr Asp Val Leu Asp Lys Arg Arg Gly
            420                 425                 430
Arg Asp Pro Glu Met Gly Gly Lys Pro Arg Arg Lys Asn Pro Gln Glu
        435                 440                 445
Gly Leu Tyr Asn Glu Leu Gln Lys Asp Lys Met Ala Glu Ala Tyr Ser
    450                 455                 460
Glu Ile Gly Met Lys Gly Glu Arg Arg Arg Gly Lys Gly His Asp Gly
465                 470                 475                 480
Leu Tyr Gln Gly Leu Ser Thr Ala Thr Lys Asp Thr Tyr Asp Ala Leu
                485                 490                 495
```

```
His Met Gln Ala Leu Pro Pro Arg
            500

<210> SEQ ID NO 312
<211> LENGTH: 498
<212> TYPE: PRT
<213> ORGANISM: Artificial Sequence
<220> FEATURE:
<223> OTHER INFORMATION: Synthetic Construct

<400> SEQUENCE: 312

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gln Val Lys Leu Glu Glu Ser Gly Gly Arg Leu Val Gln Pro Arg
145                 150                 155                 160

Gly Ser Leu Arg Leu Ser Cys Ala Gly Ser Gly Arg Thr Phe Ser Thr
                165                 170                 175

Tyr Gly Met Ala Trp Phe Arg Gln Ala Pro Gly Lys Glu Arg Glu Phe
            180                 185                 190

Val Ala Ser Lys Ala Ser Met Asn Tyr Ser Gly Arg Thr Tyr Tyr Ala
        195                 200                 205

Asp Ser Val Lys Gly Arg Phe Thr Ile Ala Arg Asp Asn Ala Lys Asn
    210                 215                 220

Met Val Phe Leu Gln Met Asn Asn Leu Lys Pro Glu Asp Thr Ala Val
225                 230                 235                 240

Tyr Tyr Cys Ala Ala Gly Thr Gly Cys Ser Thr Tyr Gly Cys Phe Asp
                245                 250                 255

Ala Gln Ile Ile Asp Tyr Trp Gly Lys Gly Thr Leu Val Thr Val Ser
            260                 265                 270

Ser Thr Ser Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350
```

Tyr Ile Phe Lys Gln Pro Phe Met Arg Pro Val Gln Thr Thr Gln Glu
            355                 360                 365

Glu Asp Gly Cys Ser Cys Arg Phe Pro Glu Glu Glu Gly Gly Cys
    370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
            405                 410                 415

Glu Tyr Asp Val Leu Asp Lys Arg Gly Arg Asp Pro Glu Met Gly
            420                 425                 430

Gly Lys Pro Arg Arg Lys Asn Pro Gln Glu Gly Leu Tyr Asn Glu Leu
            435                 440                 445

Gln Lys Asp Lys Met Ala Glu Ala Tyr Ser Glu Ile Gly Met Lys Gly
            450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
            485                 490                 495

Pro Arg

<210> SEQ ID NO 313
<211> LENGTH: 508
<212> TYPE: PRT
<213> ORGANISM: Artificial Sequence
<220> FEATURE:
<223> OTHER INFORMATION: Synthetic Construct

<400> SEQUENCE: 313

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gly Gly Gly Ser Gln Val Lys Leu Glu
145                 150                 155                 160

Glu Ser Gly Gly Arg Leu Val Gln Pro Arg Gly Ser Leu Arg Leu Ser
                165                 170                 175

Cys Ala Gly Ser Gly Arg Thr Phe Ser Thr Tyr Gly Met Ala Trp Phe
            180                 185                 190

Arg Gln Ala Pro Gly Lys Glu Arg Glu Phe Val Ala Ser Lys Ala Ser
        195                 200                 205

Met Asn Tyr Ser Gly Arg Thr Tyr Tyr Ala Asp Ser Val Lys Gly Arg
   210                 215                 220

Phe Thr Ile Ala Arg Asp Asn Ala Lys Asn Met Val Phe Leu Gln Met
225                 230                 235                 240

Asn Asn Leu Lys Pro Glu Asp Thr Ala Val Tyr Tyr Cys Ala Ala Gly
                245                 250                 255

Thr Gly Cys Ser Thr Tyr Gly Cys Phe Asp Ala Gln Ile Ile Asp Tyr
            260                 265                 270

Trp Gly Lys Gly Thr Leu Val Thr Val Ser Ser Thr Ser Thr Thr Thr
        275                 280                 285

Pro Ala Pro Arg Pro Pro Thr Pro Ala Pro Thr Ile Ala Ser Gln Pro
290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
        450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 314
<211> LENGTH: 518
<212> TYPE: PRT
<213> ORGANISM: Artificial Sequence
<220> FEATURE:
<223> OTHER INFORMATION: Synthetic Construct

<400> SEQUENCE: 314

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

-continued

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Gln Val Lys Leu Glu Glu Ser Gly Gly Arg Leu
                165                 170                 175

Val Gln Pro Arg Gly Ser Leu Arg Leu Ser Cys Ala Gly Ser Gly Arg
            180                 185                 190

Thr Phe Ser Thr Tyr Gly Met Ala Trp Phe Arg Gln Ala Pro Gly Lys
        195                 200                 205

Glu Arg Glu Phe Val Ala Ser Lys Ala Ser Met Asn Tyr Ser Gly Arg
    210                 215                 220

Thr Tyr Tyr Ala Asp Ser Val Lys Gly Arg Phe Thr Ile Ala Arg Asp
225                 230                 235                 240

Asn Ala Lys Asn Met Val Phe Leu Gln Met Asn Asn Leu Lys Pro Glu
                245                 250                 255

Asp Thr Ala Val Tyr Tyr Cys Ala Ala Gly Thr Gly Cys Ser Thr Tyr
            260                 265                 270

Gly Cys Phe Asp Ala Gln Ile Ile Asp Tyr Trp Gly Lys Gly Thr Leu
        275                 280                 285

Val Thr Val Ser Ser Thr Ser Thr Thr Thr Pro Ala Pro Arg Pro Pro
    290                 295                 300

Thr Pro Ala Pro Thr Ile Ala Ser Gln Pro Leu Ser Leu Arg Pro Glu
305                 310                 315                 320

Ala Cys Arg Pro Ala Ala Gly Gly Ala Val His Thr Arg Gly Leu Asp
                325                 330                 335

Phe Ala Cys Asp Ile Tyr Ile Trp Ala Pro Leu Ala Gly Thr Cys Gly
            340                 345                 350

Val Leu Leu Leu Ser Leu Val Ile Thr Leu Tyr Cys Lys Arg Gly Arg
        355                 360                 365

Lys Lys Leu Leu Tyr Ile Phe Lys Gln Pro Phe Met Arg Pro Val Gln
    370                 375                 380

Thr Thr Gln Glu Glu Asp Gly Cys Ser Cys Arg Phe Pro Glu Glu Glu
385                 390                 395                 400

Glu Gly Gly Cys Glu Leu Arg Val Lys Phe Ser Arg Ser Ala Asp Ala
                405                 410                 415

Pro Ala Tyr Gln Gln Gly Gln Asn Gln Leu Tyr Asn Glu Leu Asn Leu
            420                 425                 430

Gly Arg Arg Glu Glu Tyr Asp Val Leu Asp Lys Arg Gly Arg Asp
        435                 440                 445

Pro Glu Met Gly Gly Lys Pro Arg Arg Lys Asn Pro Gln Glu Gly Leu
    450                 455                 460

Tyr Asn Glu Leu Gln Lys Asp Lys Met Ala Glu Ala Tyr Ser Glu Ile
465                 470                 475                 480

Gly Met Lys Gly Glu Arg Arg Arg Gly Lys Gly His Asp Gly Leu Tyr 485                 490                 495
Gln Gly Leu Ser Thr Ala Thr Lys Asp Thr Tyr Asp Ala Leu His Met
            500                 505                 510

Gln Ala Leu Pro Pro Arg
        515

<210> SEQ ID NO 315
<211> LENGTH: 503
<212> TYPE: PRT
<213> ORGANISM: Artificial Sequence
<220> FEATURE:
<223> OTHER INFORMATION: Synthetic Construct

<400> SEQUENCE: 315

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
        35                  40                  45

Thr Val Asn Ser Asp Val Met Gly Trp Phe Arg Gln Ala Pro Gly Lys
    50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
                85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
        115                 120                 125

Tyr Trp Gly Gln Gly Thr Gln Val Thr Val Ser Ser Gly Gly Gly Gly
    130                 135                 140

Ser Gly Gly Gly Gly Ser Gln Val Lys Leu Glu Glu Ser Gly Gly Arg
145                 150                 155                 160

Leu Val Gln Pro Arg Gly Ser Leu Arg Leu Ser Cys Ala Gly Ser Gly
                165                 170                 175

Arg Thr Phe Ser Thr Tyr Gly Met Ala Trp Phe Arg Gln Ala Pro Gly
            180                 185                 190

Lys Glu Arg Glu Phe Val Ala Ser Lys Ala Ser Met Asn Tyr Ser Gly
        195                 200                 205

Arg Thr Tyr Tyr Ala Asp Ser Val Lys Gly Arg Phe Thr Ile Ala Arg
    210                 215                 220

Asp Asn Ala Lys Asn Met Val Phe Leu Gln Met Asn Asn Leu Lys Pro
225                 230                 235                 240

Glu Asp Thr Ala Val Tyr Tyr Cys Ala Ala Gly Thr Gly Cys Ser Thr
                245                 250                 255

Tyr Gly Cys Phe Asp Ala Gln Ile Ile Asp Tyr Trp Gly Lys Gly Thr
            260                 265                 270

Leu Val Thr Val Ser Ser Thr Ser Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys

```
            325                 330                 335
Gly Val Leu Leu Leu Ser Leu Val Ile Thr Leu Tyr Cys Lys Arg Gly
            340                 345                 350

Arg Lys Lys Leu Leu Tyr Ile Phe Lys Gln Pro Phe Met Arg Pro Val
            355                 360                 365

Gln Thr Thr Gln Glu Glu Asp Gly Cys Ser Cys Arg Phe Pro Glu Glu
            370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
            405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
            435                 440                 445

Leu Tyr Asn Glu Leu Gln Lys Asp Lys Met Ala Glu Ala Tyr Ser Glu
            450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
            485                 490                 495

Met Gln Ala Leu Pro Pro Arg
            500

<210> SEQ ID NO 316
<211> LENGTH: 508
<212> TYPE: PRT
<213> ORGANISM: Artificial Sequence
<220> FEATURE:
<223> OTHER INFORMATION: Synthetic Construct

<400> SEQUENCE: 316

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
            35                  40                  45

Thr Val Asn Ser Asp Val Met Gly Trp Phe Arg Gln Ala Pro Gly Lys
            50                  55                  60

Glu Arg Glu Phe Val Gly Ala Ile Met Trp Asn Asp Gly Ile Thr Tyr
65                  70                  75                  80

Leu Gln Asp Ser Val Lys Gly Arg Phe Thr Ile Phe Arg Asp Asn Ala
            85                  90                  95

Lys Asn Thr Val Tyr Leu Gln Met Asn Ser Leu Lys Leu Glu Asp Thr
            100                 105                 110

Ala Val Tyr Tyr Cys Ala Ala Ser Lys Gly Arg Tyr Ser Glu Tyr Glu
            115                 120                 125

Tyr Trp Gly Gln Gly Thr Gln Val Thr Val Ser Ser Gly Gly Gly Gly
            130                 135                 140

Ser Gly Gly Gly Gly Ser Gly Gly Gly Ser Gln Val Lys Leu Glu
145                 150                 155                 160

Glu Ser Gly Gly Arg Leu Val Gln Pro Arg Gly Ser Leu Arg Leu Ser
            165                 170                 175

Cys Ala Gly Ser Gly Arg Thr Phe Ser Thr Tyr Gly Met Ala Trp Phe
```

```
            180                 185                 190
Arg Gln Ala Pro Gly Lys Glu Arg Glu Phe Val Ala Ser Lys Ala Ser
            195                 200                 205

Met Asn Tyr Ser Gly Arg Thr Tyr Tyr Ala Asp Ser Val Lys Gly Arg
        210                 215                 220

Phe Thr Ile Ala Arg Asp Asn Ala Lys Asn Met Val Phe Leu Gln Met
225                 230                 235                 240

Asn Asn Leu Lys Pro Glu Asp Thr Ala Val Tyr Tyr Cys Ala Ala Gly
                245                 250                 255

Thr Gly Cys Ser Thr Tyr Gly Cys Phe Asp Ala Gln Ile Ile Asp Tyr
            260                 265                 270

Trp Gly Lys Gly Thr Leu Val Thr Val Ser Ser Thr Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
    370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
    450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
            500                 505

<210> SEQ ID NO 317
<211> LENGTH: 513
<212> TYPE: PRT
<213> ORGANISM: Artificial Sequence
<220> FEATURE:
<223> OTHER INFORMATION: Synthetic Construct

<400> SEQUENCE: 317

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Met
            20                  25                  30

Val Gln Ala Gly Asp Ser Leu Arg Leu Ser Cys Val Gln Ser Thr Tyr
```

-continued

```
              35                  40                  45
Thr Val Asn Ser Asp Val Met Gly Trp Phe Arg Gln Ala Pro Gly Lys
 50                  55                  60

Glu Arg Glu Phe Val Gly Ala Ile Met Trp Asn Asp Gly Ile Thr Tyr
 65                  70                  75                  80

Leu Gln Asp Ser Val Lys Gly Arg Phe Thr Ile Phe Arg Asp Asn Ala
                     85                  90                  95

Lys Asn Thr Val Tyr Leu Gln Met Asn Ser Leu Lys Leu Glu Asp Thr
                100                 105                 110

Ala Val Tyr Tyr Cys Ala Ala Ser Lys Gly Arg Tyr Ser Glu Tyr Glu
            115                 120                 125

Tyr Trp Gly Gln Gly Thr Gln Val Thr Val Ser Ser Gly Gly Gly Gly
        130                 135                 140

Ser Gly Gly Gly Gly Ser Gly Gly Gly Gly Ser Gly Gly Gly Gly Ser
145                 150                 155                 160

Gln Val Lys Leu Glu Glu Ser Gly Gly Arg Leu Val Gln Pro Arg Gly
                165                 170                 175

Ser Leu Arg Leu Ser Cys Ala Gly Ser Gly Arg Thr Phe Ser Thr Tyr
                180                 185                 190

Gly Met Ala Trp Phe Arg Gln Ala Pro Gly Lys Glu Arg Glu Phe Val
            195                 200                 205

Ala Ser Lys Ala Ser Met Asn Tyr Ser Gly Arg Thr Tyr Tyr Ala Asp
210                 215                 220

Ser Val Lys Gly Arg Phe Thr Ile Ala Arg Asp Asn Ala Lys Asn Met
225                 230                 235                 240

Val Phe Leu Gln Met Asn Asn Leu Lys Pro Glu Asp Thr Ala Val Tyr
                245                 250                 255

Tyr Cys Ala Ala Gly Thr Gly Cys Ser Thr Tyr Gly Cys Phe Asp Ala
            260                 265                 270

Gln Ile Ile Asp Tyr Trp Gly Lys Gly Thr Leu Val Thr Val Ser Ser
        275                 280                 285

Thr Ser Thr Thr Thr Pro Ala Pro Arg Pro Pro Thr Pro Ala Pro Thr
290                 295                 300

Ile Ala Ser Gln Pro Leu Ser Leu Arg Pro Glu Ala Cys Arg Pro Ala
305                 310                 315                 320

Ala Gly Gly Ala Val His Thr Arg Gly Leu Asp Phe Ala Cys Asp Ile
                325                 330                 335

Tyr Ile Trp Ala Pro Leu Ala Gly Thr Cys Gly Val Leu Leu Leu Ser
            340                 345                 350

Leu Val Ile Thr Leu Tyr Cys Lys Arg Gly Arg Lys Lys Leu Leu Tyr
        355                 360                 365

Ile Phe Lys Gln Pro Phe Met Arg Pro Val Gln Thr Thr Gln Glu Glu
    370                 375                 380

Asp Gly Cys Ser Cys Arg Phe Pro Glu Glu Glu Glu Gly Gly Cys Glu
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
            420                 425                 430

Tyr Asp Val Leu Asp Lys Arg Arg Gly Arg Asp Pro Glu Met Gly Gly
        435                 440                 445

Lys Pro Arg Arg Lys Asn Pro Gln Glu Gly Leu Tyr Asn Glu Leu Gln
450                 455                 460
```

```
Lys Asp Lys Met Ala Glu Ala Tyr Ser Glu Ile Gly Met Lys Gly Glu
465                 470                 475                 480

Arg Arg Arg Gly Lys Gly His Asp Gly Leu Tyr Gln Gly Leu Ser Thr
            485                 490                 495

Ala Thr Lys Asp Thr Tyr Asp Ala Leu His Met Gln Ala Leu Pro Pro
        500                 505                 510

Arg

<210> SEQ ID NO 318
<211> LENGTH: 500
<212> TYPE: PRT
<213> ORGANISM: Artificial Sequence
<220> FEATURE:
<223> OTHER INFORMATION: Synthetic Construct

<400> SEQUENCE: 318

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Gly Ser Gln Val Lys Leu Glu Glu
145                 150                 155                 160

Ser Gly Gly Gly Leu Val Gln Ala Gly Gly Ser Leu Arg Leu Ser Cys
                165                 170                 175

Ala Ala Ser Gly Gly Thr Leu Ser Lys Asn Thr Val Ala Trp Val Arg
            180                 185                 190

Gln Ala Pro Gly Lys Glu Arg Gly Phe Val Thr Ser Ile Thr Cys Asp
        195                 200                 205

Gly Arg Thr Thr Tyr Tyr Ala Asn Ser Val Asn Gly Arg Phe Pro Ile
    210                 215                 220

Asn Arg Asn Asn Ala Glu Asn Leu Val Val Leu Gln Met Asn Ser Leu
225                 230                 235                 240

Lys Pro Asp Asp Thr Ala Leu Tyr Tyr Cys Ala Ala Tyr Arg Lys Ser
                245                 250                 255

Ile Met Ser Ile Gln Pro Asp Tyr Trp Gly Gln Gly Thr Gln Val Thr
            260                 265                 270

Val Ser Ser Thr Ser Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300
```

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
            325                 330                 335

Leu Leu Ser Leu Val Ile Thr Leu Tyr Cys Lys Arg Gly Arg Lys Lys
            340                 345                 350

Leu Leu Tyr Ile Phe Lys Gln Pro Phe Met Arg Pro Val Gln Thr Thr
            355                 360                 365

Gln Glu Glu Asp Gly Cys Ser Cys Arg Phe Pro Glu Glu Glu Glu Gly
        370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
            435                 440                 445

Glu Leu Gln Lys Asp Lys Met Ala Glu Ala Tyr Ser Glu Ile Gly Met
450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
            485                 490                 495

Leu Pro Pro Arg
            500

<210> SEQ ID NO 319
<211> LENGTH: 510
<212> TYPE: PRT
<213> ORGANISM: Artificial Sequence
<220> FEATURE:
<223> OTHER INFORMATION: Synthetic Construct

<400> SEQUENCE: 319

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
            35                  40                  45

Thr Phe Ser Thr Tyr Gly Met Ala Trp Phe Arg Gln Ala Pro Gly Lys
        50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
            115                 120                 125

Gly Cys Phe Asp Ala Gln Ile Ile Asp Tyr Trp Gly Lys Gly Thr Leu
        130                 135                 140

Val Thr Val Ser Ser Gly Gly Gly Gly Ser Gly Gly Gly Gly Ser Gly
145                 150                 155                 160

Gly Gly Gly Ser Gln Val Lys Leu Glu Glu Ser Gly Gly Gly Leu Val
                165                 170                 175

Gln Ala Gly Gly Ser Leu Arg Leu Ser Cys Ala Ala Ser Gly Gly Thr
            180                 185                 190

Leu Ser Lys Asn Thr Val Ala Trp Val Arg Gln Ala Pro Gly Lys Glu
        195                 200                 205

Arg Gly Phe Val Thr Ser Ile Thr Cys Asp Gly Arg Thr Thr Tyr Tyr
    210                 215                 220

Ala Asn Ser Val Asn Gly Arg Phe Pro Ile Asn Arg Asn Asn Ala Glu
225                 230                 235                 240

Asn Leu Val Val Leu Gln Met Asn Ser Leu Lys Pro Asp Asp Thr Ala
                245                 250                 255

Leu Tyr Tyr Cys Ala Ala Tyr Arg Lys Ser Ile Met Ser Ile Gln Pro
            260                 265                 270

Asp Tyr Trp Gly Gln Gly Thr Gln Val Thr Val Ser Ser Thr Ser Thr
        275                 280                 285

Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 320
<211> LENGTH: 520
<212> TYPE: PRT
<213> ORGANISM: Artificial Sequence
<220> FEATURE:
<223> OTHER INFORMATION: Synthetic Construct

<400> SEQUENCE: 320

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Ser Gly Gly Gly Ser Gly
145                 150                 155                 160

Gly Gly Gly Ser Gly Gly Gly Ser Gly Gly Gly Ser Gln Val
                165                 170                 175

Lys Leu Glu Glu Ser Gly Gly Leu Val Gln Ala Gly Gly Ser Leu
            180                 185                 190

Arg Leu Ser Cys Ala Ala Ser Gly Gly Thr Leu Ser Lys Asn Thr Val
        195                 200                 205

Ala Trp Val Arg Gln Ala Pro Gly Lys Glu Arg Gly Phe Val Thr Ser
    210                 215                 220

Ile Thr Cys Asp Gly Arg Thr Thr Tyr Ala Asn Ser Val Asn Gly
225                 230                 235                 240

Arg Phe Pro Ile Asn Arg Asn Asn Ala Glu Asn Leu Val Val Leu Gln
                245                 250                 255

Met Asn Ser Leu Lys Pro Asp Asp Thr Ala Leu Tyr Tyr Cys Ala Ala
            260                 265                 270

Tyr Arg Lys Ser Ile Met Ser Ile Gln Pro Asp Tyr Trp Gly Gln Gly
        275                 280                 285

Thr Gln Val Thr Val Ser Ser Thr Thr Thr Pro Ala Pro Arg
    290                 295                 300

Pro Pro Thr Pro Ala Pro Thr Ile Ala Ser Gln Pro Leu Ser Leu Arg
305                 310                 315                 320

Pro Glu Ala Cys Arg Pro Ala Ala Gly Gly Ala Val His Thr Arg Gly
                325                 330                 335

Leu Asp Phe Ala Cys Asp Ile Tyr Ile Trp Ala Pro Leu Ala Gly Thr
            340                 345                 350

Cys Gly Val Leu Leu Leu Ser Leu Val Ile Thr Leu Tyr Cys Lys Arg
        355                 360                 365

Gly Arg Lys Lys Leu Leu Tyr Ile Phe Lys Gln Pro Phe Met Arg Pro
    370                 375                 380

Val Gln Thr Thr Gln Glu Glu Asp Gly Cys Ser Cys Arg Phe Pro Glu
385                 390                 395                 400

Glu Glu Glu Gly Gly Cys Glu Leu Arg Val Lys Phe Ser Arg Ser Ala
                405                 410                 415

Asp Ala Pro Ala Tyr Gln Gln Gly Gln Asn Gln Leu Tyr Asn Glu Leu
            420                 425                 430

Asn Leu Gly Arg Arg Glu Glu Tyr Asp Val Leu Asp Lys Arg Arg Gly

```
                435                 440                 445
Arg Asp Pro Glu Met Gly Gly Lys Pro Arg Arg Lys Asn Pro Gln Glu
450                 455                 460

Gly Leu Tyr Asn Glu Leu Gln Lys Asp Lys Met Ala Glu Ala Tyr Ser
465                 470                 475                 480

Glu Ile Gly Met Lys Gly Glu Arg Arg Arg Gly Lys Gly His Asp Gly
                485                 490                 495

Leu Tyr Gln Gly Leu Ser Thr Ala Thr Lys Asp Thr Tyr Asp Ala Leu
                500                 505                 510

His Met Gln Ala Leu Pro Pro Arg
                515                 520

<210> SEQ ID NO 321
<211> LENGTH: 505
<212> TYPE: PRT
<213> ORGANISM: Artificial Sequence
<220> FEATURE:
<223> OTHER INFORMATION: Synthetic Construct

<400> SEQUENCE: 321

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
                20                  25                  30

Val Gln Pro Arg Gly Ser Leu Arg Leu Ser Cys Ala Gly Ser Gly Arg
                35                  40                  45

Thr Phe Ser Thr Tyr Gly Met Ala Trp Phe Arg Gln Ala Pro Gly Lys
50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
                100                 105                 110

Asp Thr Ala Val Tyr Tyr Cys Ala Ala Gly Thr Gly Cys Ser Thr Tyr
                115                 120                 125

Gly Cys Phe Asp Ala Gln Ile Ile Asp Tyr Trp Gly Lys Gly Thr Leu
130                 135                 140

Val Thr Val Ser Ser Gly Gly Gly Ser Gly Gly Gly Gly Ser Gln
145                 150                 155                 160

Val Lys Leu Glu Glu Ser Gly Gly Gly Leu Val Gln Ala Gly Gly Ser
                165                 170                 175

Leu Arg Leu Ser Cys Ala Ala Ser Gly Gly Thr Leu Ser Lys Asn Thr
                180                 185                 190

Val Ala Trp Val Arg Gln Ala Pro Gly Lys Glu Arg Gly Phe Val Thr
                195                 200                 205

Ser Ile Thr Cys Asp Gly Arg Thr Thr Tyr Ala Asn Ser Val Asn
                210                 215                 220

Gly Arg Phe Pro Ile Asn Arg Asn Asn Ala Glu Asn Leu Val Val Leu
225                 230                 235                 240

Gln Met Asn Ser Leu Lys Pro Asp Asp Thr Ala Leu Tyr Tyr Cys Ala
                245                 250                 255

Ala Tyr Arg Lys Ser Ile Met Ser Ile Gln Pro Asp Tyr Trp Gly Gln
                260                 265                 270

Gly Thr Gln Val Thr Val Ser Ser Thr Ser Thr Thr Thr Pro Ala Pro
```

```
                275                 280                 285
Arg Pro Pro Thr Pro Ala Pro Thr Ile Ala Ser Gln Pro Leu Ser Leu
            290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Lys
            340                 345                 350

Arg Gly Arg Lys Lys Leu Leu Tyr Ile Phe Lys Gln Pro Phe Met Arg
                355                 360                 365

Pro Val Gln Thr Thr Gln Glu Glu Asp Gly Cys Ser Cys Arg Phe Pro
            370                 375                 380

Glu Glu Glu Glu Gly Gly Cys Glu Leu Arg Val Lys Phe Ser Arg Ser
385                 390                 395                 400

Ala Asp Ala Pro Ala Tyr Gln Gln Gly Gln Asn Gln Leu Tyr Asn Glu
                405                 410                 415

Leu Asn Leu Gly Arg Arg Glu Glu Tyr Asp Val Leu Asp Lys Arg Arg
            420                 425                 430

Gly Arg Asp Pro Glu Met Gly Gly Lys Pro Arg Arg Lys Asn Pro Gln
                435                 440                 445

Glu Gly Leu Tyr Asn Glu Leu Gln Lys Asp Lys Met Ala Glu Ala Tyr
            450                 455                 460

Ser Glu Ile Gly Met Lys Gly Glu Arg Arg Gly Lys Gly His Asp
465                 470                 475                 480

Gly Leu Tyr Gln Gly Leu Ser Thr Ala Thr Lys Asp Thr Tyr Asp Ala
                485                 490                 495

Leu His Met Gln Ala Leu Pro Pro Arg
            500                 505

<210> SEQ ID NO 322
<211> LENGTH: 510
<212> TYPE: PRT
<213> ORGANISM: Artificial Sequence
<220> FEATURE:
<223> OTHER INFORMATION: Synthetic Construct

<400> SEQUENCE: 322

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
                35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
                115                 120                 125

Gly Cys Phe Asp Ala Gln Ile Ile Asp Tyr Trp Gly Lys Gly Thr Leu
```

```
            130                 135                 140
Val Thr Val Ser Ser Gly Gly Gly Ser Gly Gly Gly Ser Gly
145                 150                 155                 160
Gly Gly Gly Ser Gln Val Lys Leu Glu Glu Ser Gly Gly Gly Leu Val
                165                 170                 175
Gln Ala Gly Gly Ser Leu Arg Leu Ser Cys Ala Ala Ser Gly Gly Thr
            180                 185                 190
Leu Ser Lys Asn Thr Val Ala Trp Val Arg Gln Ala Pro Gly Lys Glu
        195                 200                 205
Arg Gly Phe Val Thr Ser Ile Thr Cys Asp Gly Arg Thr Thr Tyr Tyr
    210                 215                 220
Ala Asn Ser Val Asn Gly Arg Phe Pro Ile Asn Arg Asn Asn Ala Glu
225                 230                 235                 240
Asn Leu Val Val Leu Gln Met Asn Ser Leu Lys Pro Asp Asp Thr Ala
                245                 250                 255
Leu Tyr Tyr Cys Ala Ala Tyr Arg Lys Ser Ile Met Ser Ile Gln Pro
            260                 265                 270
Asp Tyr Trp Gly Gln Gly Thr Gln Val Thr Val Ser Ser Thr Ser Thr
        275                 280                 285
Thr Thr Pro Ala Pro Arg Pro Pro Thr Pro Ala Pro Thr Ile Ala Ser
    290                 295                 300
Gln Pro Leu Ser Leu Arg Pro Glu Ala Cys Arg Pro Ala Ala Gly Gly
305                 310                 315                 320
Ala Val His Thr Arg Gly Leu Asp Phe Ala Cys Asp Ile Tyr Ile Trp
                325                 330                 335
Ala Pro Leu Ala Gly Thr Cys Gly Val Leu Leu Leu Ser Leu Val Ile
            340                 345                 350
Thr Leu Tyr Cys Lys Arg Gly Arg Lys Lys Leu Leu Tyr Ile Phe Lys
        355                 360                 365
Gln Pro Phe Met Arg Pro Val Gln Thr Thr Gln Glu Glu Asp Gly Cys
    370                 375                 380
Ser Cys Arg Phe Pro Glu Glu Glu Gly Gly Cys Glu Leu Arg Val
385                 390                 395                 400
Lys Phe Ser Arg Ser Ala Asp Ala Pro Ala Tyr Gln Gln Gly Gln Asn
                405                 410                 415
Gln Leu Tyr Asn Glu Leu Asn Leu Gly Arg Arg Glu Glu Tyr Asp Val
            420                 425                 430
Leu Asp Lys Arg Arg Gly Arg Asp Pro Glu Met Gly Gly Lys Pro Arg
        435                 440                 445
Arg Lys Asn Pro Gln Glu Gly Leu Tyr Asn Glu Leu Gln Lys Asp Lys
    450                 455                 460
Met Ala Glu Ala Tyr Ser Glu Ile Gly Met Lys Gly Glu Arg Arg Arg
465                 470                 475                 480
Gly Lys Gly His Asp Gly Leu Tyr Gln Gly Leu Ser Thr Ala Thr Lys
                485                 490                 495
Asp Thr Tyr Asp Ala Leu His Met Gln Ala Leu Pro Pro Arg
            500                 505                 510

<210> SEQ ID NO 323
<211> LENGTH: 515
<212> TYPE: PRT
<213> ORGANISM: Artificial Sequence
<220> FEATURE:
<223> OTHER INFORMATION: Synthetic Construct
```

<400> SEQUENCE: 323

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Arg Leu
            20                  25                  30

Val Gln Pro Arg Gly Ser Leu Arg Leu Ser Cys Ala Gly Ser Gly Arg
        35                  40                  45

Thr Phe Ser Thr Tyr Gly Met Ala Trp Phe Arg Gln Ala Pro Gly Lys
    50                  55                  60

Glu Arg Glu Phe Val Ala Ser Lys Ala Ser Met Asn Tyr Ser Gly Arg
65                  70                  75                  80

Thr Tyr Tyr Ala Asp Ser Val Lys Gly Arg Phe Thr Ile Ala Arg Asp
                85                  90                  95

Asn Ala Lys Asn Met Val Phe Leu Gln Met Asn Asn Leu Lys Pro Glu
            100                 105                 110

Asp Thr Ala Val Tyr Tyr Cys Ala Ala Gly Thr Gly Cys Ser Thr Tyr
        115                 120                 125

Gly Cys Phe Asp Ala Gln Ile Ile Asp Tyr Trp Gly Lys Gly Thr Leu
    130                 135                 140

Val Thr Val Ser Ser Gly Gly Gly Ser Gly Gly Gly Ser Gly
145                 150                 155                 160

Gly Gly Gly Ser Gly Gly Gly Ser Gln Val Lys Leu Glu Glu Ser
                165                 170                 175

Gly Gly Gly Leu Val Gln Ala Gly Gly Ser Leu Arg Leu Ser Cys Ala
                180                 185                 190

Ala Ser Gly Gly Thr Leu Ser Lys Asn Thr Val Ala Trp Val Arg Gln
        195                 200                 205

Ala Pro Gly Lys Glu Arg Gly Phe Val Thr Ser Ile Thr Cys Asp Gly
    210                 215                 220

Arg Thr Thr Tyr Tyr Ala Asn Ser Val Asn Gly Arg Phe Pro Ile Asn
225                 230                 235                 240

Arg Asn Asn Ala Glu Asn Leu Val Val Leu Gln Met Asn Ser Leu Lys
                245                 250                 255

Pro Asp Asp Thr Ala Leu Tyr Tyr Cys Ala Ala Tyr Arg Lys Ser Ile
            260                 265                 270

Met Ser Ile Gln Pro Asp Tyr Trp Gly Gln Gly Thr Gln Val Thr Val
        275                 280                 285

Ser Ser Thr Ser Thr Thr Pro Ala Pro Arg Pro Pro Thr Pro Ala
    290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Asp Ile Tyr Ile Trp Ala Pro Leu Ala Gly Thr Cys Gly Val Leu Leu
            340                 345                 350

Leu Ser Leu Val Ile Thr Leu Tyr Cys Lys Arg Gly Arg Lys Lys Leu
        355                 360                 365

Leu Tyr Ile Phe Lys Gln Pro Phe Met Arg Pro Val Gln Thr Thr Gln
    370                 375                 380

Glu Glu Asp Gly Cys Ser Cys Arg Phe Pro Glu Glu Glu Glu Gly Gly
385                 390                 395                 400

Cys Glu Leu Arg Val Lys Phe Ser Arg Ser Ala Asp Ala Pro Ala Tyr
                405                 410                 415
```

-continued

```
Gln Gln Gly Gln Asn Gln Leu Tyr Asn Glu Leu Asn Leu Gly Arg Arg
                420                 425                 430

Glu Glu Tyr Asp Val Leu Asp Lys Arg Arg Gly Arg Asp Pro Glu Met
            435                 440                 445

Gly Gly Lys Pro Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515

<210> SEQ ID NO 324
<211> LENGTH: 492
<212> TYPE: PRT
<213> ORGANISM: Artificial Sequence
<220> FEATURE:
<223> OTHER INFORMATION: Synthetic Construct

<400> SEQUENCE: 324

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gln Val Gln Leu Val Glu Ser Gly Gly Gly Leu Val Gln
145                 150                 155                 160

Ala Gly Gly Ser Leu Arg Leu Ser Cys Ala Ala Ser Gly Gly Thr Leu
                165                 170                 175

Ser Lys Asn Thr Val Ala Trp Phe Arg Gln Ala Pro Gly Lys Glu Arg
            180                 185                 190

Gly Phe Val Ala Ser Ile Thr Trp Asp Gly Arg Thr Thr Tyr Tyr Ala
        195                 200                 205

Asp Ser Val Lys Gly Arg Phe Thr Ile Ser Arg Asp Asn Ala Lys Asn
    210                 215                 220

Thr Val Tyr Leu Gln Met Asn Ser Leu Lys Pro Glu Asp Thr Ala Val
225                 230                 235                 240

Tyr Val Cys Ala Asp Leu Gly Lys Trp Pro Ala Gly Pro Ala Asp Tyr
                245                 250                 255
```

Trp Gly Gln Gly Thr Gln Val Thr Val Ser Ser Thr Thr Thr
            260                 265                 270

Pro Ala Pro Arg Pro Pro Thr Pro Ala Pro Thr Ile Ala Ser Gln Pro
                275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Glu Gly Gly Cys Glu Leu Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
                450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 325
<211> LENGTH: 502
<212> TYPE: PRT
<213> ORGANISM: Artificial Sequence
<220> FEATURE:
<223> OTHER INFORMATION: Synthetic Construct

<400> SEQUENCE: 325

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Val Arg Gln Ala Pro Gly Lys
        50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

-continued

Pro Asp Tyr Trp Gly Gln Gly Thr Gln Val Thr Val Ser Gly Gly
    130                 135                 140

Gly Gly Ser Gly Gly Gly Ser Gly Gly Gly Ser Gln Val Gln
145                 150                 155                 160

Leu Val Glu Ser Gly Gly Leu Val Gln Ala Gly Gly Ser Leu Arg
                165                 170                 175

Leu Ser Cys Ala Ala Ser Gly Gly Thr Leu Ser Lys Asn Thr Val Ala
                180                 185                 190

Trp Phe Arg Gln Ala Pro Gly Lys Glu Arg Gly Phe Val Ala Ser Ile
                195                 200                 205

Thr Trp Asp Gly Arg Thr Thr Tyr Tyr Ala Asp Ser Val Lys Gly Arg
                210                 215                 220

Phe Thr Ile Ser Arg Asp Asn Ala Lys Asn Thr Val Tyr Leu Gln Met
225                 230                 235                 240

Asn Ser Leu Lys Pro Glu Asp Thr Ala Val Tyr Val Cys Ala Asp Leu
                245                 250                 255

Gly Lys Trp Pro Ala Gly Pro Ala Asp Tyr Trp Gly Gln Gly Thr Gln
                260                 265                 270

Val Thr Val Ser Ser Thr Ser Thr Thr Pro Ala Pro Arg Pro Pro
                275                 280                 285

Thr Pro Ala Pro Thr Ile Ala Ser Gln Pro Leu Ser Leu Arg Pro Glu
290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
                340                 345                 350

Lys Lys Leu Leu Tyr Ile Phe Lys Gln Pro Phe Met Arg Pro Val Gln
                355                 360                 365

Thr Thr Gln Glu Glu Asp Gly Cys Ser Cys Arg Phe Pro Glu Glu Glu
                370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Gly Arg Asp
                420                 425                 430

Pro Glu Met Gly Gly Lys Pro Arg Arg Lys Asn Pro Gln Glu Gly Leu
                435                 440                 445

Tyr Asn Glu Leu Gln Lys Asp Lys Met Ala Glu Ala Tyr Ser Glu Ile
450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
                500

<210> SEQ ID NO 326
<211> LENGTH: 512
<212> TYPE: PRT
<213> ORGANISM: Artificial Sequence
<220> FEATURE:

<223> OTHER INFORMATION: Synthetic Construct

<400> SEQUENCE: 326

```
Met Ala Leu Pro Val Thr Ala Leu Leu Leu Pro Leu Ala Leu Leu Leu
1               5                   10                  15
His Ala Ala Arg Pro Gln Val Lys Leu Glu Glu Ser Gly Gly Gly Leu
            20                  25                  30
Val Gln Ala Gly Gly Ser Leu Arg Leu Ser Cys Ala Ala Ser Gly Gly
        35                  40                  45
Thr Leu Ser Lys Asn Thr Val Ala Trp Val Arg Gln Ala Pro Gly Lys
    50                  55                  60
Glu Arg Gly Phe Val Thr Ser Ile Thr Cys Asp Gly Arg Thr Thr Tyr
65                  70                  75                  80
Tyr Ala Asn Ser Val Asn Gly Arg Phe Pro Ile Asn Arg Asn Asn Ala
                85                  90                  95
Glu Asn Leu Val Val Leu Gln Met Asn Ser Leu Lys Pro Asp Asp Thr
            100                 105                 110
Ala Leu Tyr Tyr Cys Ala Ala Tyr Arg Lys Ser Ile Met Ser Ile Gln
        115                 120                 125
Pro Asp Tyr Trp Gly Gln Gly Thr Gln Val Thr Val Ser Ser Gly Gly
    130                 135                 140
Gly Gly Ser Gly Gly Gly Ser Gly Gly Gly Ser Gly Gly Gly Gly Gly
145                 150                 155                 160
Gly Ser Gly Gly Gly Ser Gln Val Gln Leu Val Glu Ser Gly Gly
                165                 170                 175
Gly Leu Val Gln Ala Gly Gly Ser Leu Arg Leu Ser Cys Ala Ala Ser
            180                 185                 190
Gly Gly Thr Leu Ser Lys Asn Thr Val Ala Trp Phe Arg Gln Ala Pro
        195                 200                 205
Gly Lys Glu Arg Gly Phe Val Ala Ser Ile Thr Trp Asp Gly Arg Thr
    210                 215                 220
Thr Tyr Tyr Ala Asp Ser Val Lys Gly Arg Phe Thr Ile Ser Arg Asp
225                 230                 235                 240
Asn Ala Lys Asn Thr Val Tyr Leu Gln Met Asn Ser Leu Lys Pro Glu
                245                 250                 255
Asp Thr Ala Val Tyr Val Cys Ala Asp Leu Gly Lys Trp Pro Ala Gly
            260                 265                 270
Pro Ala Asp Tyr Trp Gly Gln Gly Thr Gln Val Thr Val Ser Ser Thr
        275                 280                 285
Ser Thr Thr Thr Pro Ala Pro Arg Pro Pro Thr Pro Ala Pro Thr Ile
    290                 295                 300
Ala Ser Gln Pro Leu Ser Leu Arg Pro Glu Ala Cys Arg Pro Ala Ala
305                 310                 315                 320
Gly Gly Ala Val His Thr Arg Gly Leu Asp Phe Ala Cys Asp Ile Tyr
                325                 330                 335
Ile Trp Ala Pro Leu Ala Gly Thr Cys Gly Val Leu Leu Leu Ser Leu
            340                 345                 350
Val Ile Thr Leu Tyr Cys Lys Arg Gly Arg Lys Lys Leu Leu Tyr Ile
        355                 360                 365
Phe Lys Gln Pro Phe Met Arg Pro Val Gln Thr Thr Gln Glu Glu Asp
    370                 375                 380
Gly Cys Ser Cys Arg Phe Pro Glu Glu Glu Gly Gly Cys Glu Leu
385                 390                 395                 400
```

```
Arg Val Lys Phe Ser Arg Ser Ala Asp Ala Pro Ala Tyr Gln Gln Gly
            405                 410                 415

Gln Asn Gln Leu Tyr Asn Glu Leu Asn Leu Gly Arg Arg Glu Glu Tyr
            420                 425                 430

Asp Val Leu Asp Lys Arg Arg Gly Arg Asp Pro Glu Met Gly Gly Lys
            435                 440                 445

Pro Arg Arg Lys Asn Pro Gln Glu Gly Leu Tyr Asn Glu Leu Gln Lys
450                 455                 460

Asp Lys Met Ala Glu Ala Tyr Ser Glu Ile Gly Met Lys Gly Glu Arg
465                 470                 475                 480

Arg Arg Gly Lys Gly His Asp Gly Leu Tyr Gln Gly Leu Ser Thr Ala
            485                 490                 495

Thr Lys Asp Thr Tyr Asp Ala Leu His Met Gln Ala Leu Pro Pro Arg
            500                 505                 510

<210> SEQ ID NO 327
<211> LENGTH: 497
<212> TYPE: PRT
<213> ORGANISM: Artificial Sequence
<220> FEATURE:
<223> OTHER INFORMATION: Synthetic Construct

<400> SEQUENCE: 327

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gly Gly Gly Gly Ser Gln Val Gln Leu Val Glu Ser Gly
145                 150                 155                 160

Gly Gly Leu Val Gln Ala Gly Gly Ser Leu Arg Leu Ser Cys Ala Ala
                165                 170                 175

Ser Gly Gly Thr Leu Ser Lys Asn Thr Val Ala Trp Phe Arg Gln Ala
            180                 185                 190

Pro Gly Lys Glu Arg Gly Phe Val Ala Ser Ile Thr Trp Asp Gly Arg
        195                 200                 205

Thr Thr Tyr Tyr Ala Asp Ser Val Lys Gly Arg Phe Thr Ile Ser Arg
    210                 215                 220

Asp Asn Ala Lys Asn Thr Val Tyr Leu Gln Met Asn Ser Leu Lys Pro
225                 230                 235                 240

Glu Asp Thr Ala Val Tyr Val Cys Ala Asp Leu Gly Lys Trp Pro Ala
                245                 250                 255
```

Gly Pro Ala Asp Tyr Trp Gly Gln Gly Thr Gln Val Thr Val Ser Ser
                260                 265                 270

Thr Ser Thr Thr Thr Pro Ala Pro Arg Pro Thr Pro Ala Pro Thr
    275                 280                 285

Ile Ala Ser Gln Pro Leu Ser Leu Arg Pro Glu Ala Cys Arg Pro Ala
290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
                340                 345                 350

Ile Phe Lys Gln Pro Phe Met Arg Pro Val Gln Thr Thr Gln Glu Glu
                355                 360                 365

Asp Gly Cys Ser Cys Arg Phe Pro Glu Glu Glu Glu Gly Gly Cys Glu
                370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
                420                 425                 430

Lys Pro Arg Arg Lys Asn Pro Gln Glu Gly Leu Tyr Asn Glu Leu Gln
                435                 440                 445

Lys Asp Lys Met Ala Glu Ala Tyr Ser Glu Ile Gly Met Lys Gly Glu
450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 328
<211> LENGTH: 502
<212> TYPE: PRT
<213> ORGANISM: Artificial Sequence
<220> FEATURE:
<223> OTHER INFORMATION: Synthetic Construct

<400> SEQUENCE: 328

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65                  70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
                100                 105                 110

Ala Leu Tyr Tyr Cys Ala Ala Tyr Arg Lys Ser Ile Met Ser Ile Gln

```
            115                 120                 125
Pro Asp Tyr Trp Gly Gln Gly Thr Gln Val Thr Val Ser Ser Gly Gly
    130                 135                 140

Gly Gly Ser Gly Gly Gly Ser Gly Gly Gly Ser Gln Val Gln
145                 150                 155                 160

Leu Val Glu Ser Gly Gly Leu Val Gln Ala Gly Ser Leu Arg
                165                 170                 175

Leu Ser Cys Ala Ala Ser Gly Gly Thr Leu Ser Lys Asn Thr Val Ala
                180                 185                 190

Trp Phe Arg Gln Ala Pro Gly Lys Glu Arg Gly Phe Val Ala Ser Ile
        195                 200                 205

Thr Trp Asp Gly Arg Thr Thr Tyr Tyr Ala Asp Ser Val Lys Gly Arg
    210                 215                 220

Phe Thr Ile Ser Arg Asp Asn Ala Lys Asn Thr Val Tyr Leu Gln Met
225                 230                 235                 240

Asn Ser Leu Lys Pro Glu Asp Thr Ala Val Tyr Val Cys Ala Asp Leu
                245                 250                 255

Gly Lys Trp Pro Ala Gly Pro Ala Asp Tyr Trp Gly Gln Gly Thr Gln
            260                 265                 270

Val Thr Val Ser Ser Thr Ser Thr Thr Thr Pro Ala Pro Arg Pro Pro
            275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
            355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
            435                 440                 445

Tyr Asn Glu Leu Gln Lys Asp Lys Met Ala Glu Ala Tyr Ser Glu Ile
            450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500

<210> SEQ ID NO 329
<211> LENGTH: 507
<212> TYPE: PRT
<213> ORGANISM: Artificial Sequence
```

<220> FEATURE:
<223> OTHER INFORMATION: Synthetic Construct

<400> SEQUENCE: 329

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Val Arg Gln Ala Pro Gly Lys
    50                  55                  60

Glu Arg Gly Phe Val Thr Ser Ile Thr Cys Asp Gly Arg Thr Thr Tyr
65              70                  75                  80

Tyr Ala Asn Ser Val Asn Gly Arg Phe Pro Ile Asn Arg Asn Asn Ala
                85                  90                  95

Glu Asn Leu Val Val Leu Gln Met Asn Ser Leu Lys Pro Asp Asp Thr
            100                 105                 110

Ala Leu Tyr Tyr Cys Ala Ala Tyr Arg Lys Ser Ile Met Ser Ile Gln
        115                 120                 125

Pro Asp Tyr Trp Gly Gln Gly Thr Gln Val Thr Val Ser Ser Gly Gly
    130                 135                 140

Gly Gly Ser Gly Gly Gly Ser Gly Gly Gly Ser Gly Gly Gly Gly Gly
145                 150                 155                 160

Gly Ser Gln Val Gln Leu Val Glu Ser Gly Gly Gly Leu Val Gln Ala
                165                 170                 175

Gly Gly Ser Leu Arg Leu Ser Cys Ala Ala Ser Gly Gly Thr Leu Ser
            180                 185                 190

Lys Asn Thr Val Ala Trp Phe Arg Gln Ala Pro Gly Lys Glu Arg Gly
        195                 200                 205

Phe Val Ala Ser Ile Thr Trp Asp Gly Arg Thr Thr Tyr Tyr Ala Asp
    210                 215                 220

Ser Val Lys Gly Arg Phe Thr Ile Ser Arg Asp Asn Ala Lys Asn Thr
225                 230                 235                 240

Val Tyr Leu Gln Met Asn Ser Leu Lys Pro Glu Asp Thr Ala Val Tyr
                245                 250                 255

Val Cys Ala Asp Leu Gly Lys Trp Pro Ala Gly Pro Ala Asp Tyr Trp
            260                 265                 270

Gly Gln Gly Thr Gln Val Thr Val Ser Ser Thr Ser Thr Thr Thr Pro
        275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

Cys Lys Arg Gly Arg Lys Lys Leu Leu Tyr Ile Phe Lys Gln Pro Phe
        355                 360                 365

Met Arg Pro Val Gln Thr Thr Gln Glu Glu Asp Gly Cys Ser Cys Arg
    370                 375                 380

Phe Pro Glu Glu Glu Glu Gly Gly Cys Glu Leu Arg Val Lys Phe Ser
385                 390                 395                 400
```

```
Arg Ser Ala Asp Ala Pro Ala Tyr Gln Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg
                500                 505

<210> SEQ ID NO 330
<211> LENGTH: 491
<212> TYPE: PRT
<213> ORGANISM: Artificial Sequence
<220> FEATURE:
<223> OTHER INFORMATION: Synthetic Construct

<400> SEQUENCE: 330

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
    130                 135                 140

Gly Ser Asp Val Gln Leu Val Glu Ser Gly Gly Gly Leu Val Gln Ala
145                 150                 155                 160

Gly Gly Ser Leu Arg Leu Ser Cys Ala Ala Ser Gly Gly Thr Leu Ser
                165                 170                 175

Lys Asn Thr Val Ala Trp Val Arg Gln Ala Pro Gly Lys Glu Arg Gly
            180                 185                 190

Phe Val Thr Ser Ile Thr Cys Asp Gly Arg Thr Thr Tyr Tyr Ala Asn
        195                 200                 205

Ser Val Lys Gly Arg Phe Pro Ile Ser Arg Asp Asn Ala Glu Asn Thr
    210                 215                 220

Val Tyr Leu Gln Met Asn Ser Leu Lys Pro Glu Asp Thr Ala Gly Tyr
225                 230                 235                 240

Val Cys Ala Asp Leu Gly Lys Trp Pro Ala Gly Ser Ala Asp Tyr Trp
                245                 250                 255
```

```
Gly Gln Gly Thr His Val Thr Val Ser Ser Thr Ser Thr Thr Thr Pro
                260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
            355                 360                 365

Phe Pro Glu Glu Glu Glu Gly Gly Cys Glu Leu Arg Val Lys Phe Ser
        370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
                450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 331
<211> LENGTH: 501
<212> TYPE: PRT
<213> ORGANISM: Artificial Sequence
<220> FEATURE:
<223> OTHER INFORMATION: Synthetic Construct

<400> SEQUENCE: 331

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Phe Arg Gln Ala Pro Gly Lys
        50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
                100                 105                 110

Ala Val Tyr Val Cys Ala Asp Leu Gly Lys Trp Pro Ala Gly Pro Ala
            115                 120                 125
```

Asp Tyr Trp Gly Gln Gly Thr Gln Val Thr Val Ser Ser Gly Gly Gly
            130                 135                 140

Gly Ser Gly Gly Gly Ser Gly Gly Gly Ser Asp Val Gln Leu
145                 150                 155                 160

Val Glu Ser Gly Gly Gly Leu Val Gln Ala Gly Gly Ser Leu Arg Leu
                165                 170                 175

Ser Cys Ala Ala Ser Gly Gly Thr Leu Ser Lys Asn Thr Val Ala Trp
            180                 185                 190

Val Arg Gln Ala Pro Gly Lys Glu Arg Gly Phe Val Thr Ser Ile Thr
        195                 200                 205

Cys Asp Gly Arg Thr Thr Tyr Tyr Ala Asn Ser Val Lys Gly Arg Phe
210                 215                 220

Pro Ile Ser Arg Asp Asn Ala Glu Asn Thr Val Tyr Leu Gln Met Asn
225                 230                 235                 240

Ser Leu Lys Pro Glu Asp Thr Ala Gly Tyr Val Cys Ala Asp Leu Gly
                245                 250                 255

Lys Trp Pro Ala Gly Ser Ala Asp Tyr Trp Gly Gln Gly Thr His Val
            260                 265                 270

Thr Val Ser Ser Thr Ser Thr Thr Pro Ala Pro Arg Pro Pro Thr
        275                 280                 285

Pro Ala Pro Thr Ile Ala Ser Gln Pro Leu Ser Leu Arg Pro Glu Ala
290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
        355                 360                 365

Thr Gln Glu Glu Asp Gly Cys Ser Cys Arg Phe Pro Glu Glu Glu Glu
370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500

<210> SEQ ID NO 332
<211> LENGTH: 511
<212> TYPE: PRT
<213> ORGANISM: Artificial Sequence
<220> FEATURE:

<223> OTHER INFORMATION: Synthetic Construct

<400> SEQUENCE: 332

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
130                 135                 140

Gly Ser Gly Gly Gly Ser Gly Gly Gly Ser Gly Gly Gly Gly
145                 150                 155                 160

Ser Gly Gly Gly Gly Ser Asp Val Gln Leu Val Glu Ser Gly Gly Gly
                165                 170                 175

Leu Val Gln Ala Gly Gly Ser Leu Arg Leu Ser Cys Ala Ala Ser Gly
            180                 185                 190

Gly Thr Leu Ser Lys Asn Thr Val Ala Trp Val Arg Gln Ala Pro Gly
        195                 200                 205

Lys Glu Arg Gly Phe Val Thr Ser Ile Thr Cys Asp Gly Arg Thr Thr
    210                 215                 220

Tyr Tyr Ala Asn Ser Val Lys Gly Arg Phe Pro Ile Ser Arg Asp Asn
225                 230                 235                 240

Ala Glu Asn Thr Val Tyr Leu Gln Met Asn Ser Leu Lys Pro Glu Asp
                245                 250                 255

Thr Ala Gly Tyr Val Cys Ala Asp Leu Gly Lys Trp Pro Ala Gly Ser
            260                 265                 270

Ala Asp Tyr Trp Gly Gln Gly Thr His Val Thr Val Ser Ser Thr Ser
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Ile Tyr Ile
                325                 330                 335

Trp Ala Pro Leu Ala Gly Thr Cys Gly Val Leu Leu Leu Ser Leu Val
            340                 345                 350

Ile Thr Leu Tyr Cys Lys Arg Gly Arg Lys Lys Leu Leu Tyr Ile Phe
        355                 360                 365

Lys Gln Pro Phe Met Arg Pro Val Gln Thr Thr Gln Glu Glu Asp Gly
    370                 375                 380

Cys Ser Cys Arg Phe Pro Glu Glu Glu Glu Gly Gly Cys Glu Leu Arg
385                 390                 395                 400
```

```
Val Lys Phe Ser Arg Ser Ala Asp Ala Pro Ala Tyr Gln Gln Gly Gln
                405                 410                 415

Asn Gln Leu Tyr Asn Glu Leu Asn Leu Gly Arg Arg Glu Glu Tyr Asp
            420                 425                 430

Val Leu Asp Lys Arg Arg Gly Arg Asp Pro Glu Met Gly Gly Lys Pro
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510

<210> SEQ ID NO 333
<211> LENGTH: 496
<212> TYPE: PRT
<213> ORGANISM: Artificial Sequence
<220> FEATURE:
<223> OTHER INFORMATION: Synthetic Construct

<400> SEQUENCE: 333

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
    130                 135                 140

Gly Ser Gly Gly Gly Gly Ser Asp Val Gln Leu Val Glu Ser Gly Gly
145                 150                 155                 160

Gly Leu Val Gln Ala Gly Gly Ser Leu Arg Leu Ser Cys Ala Ala Ser
                165                 170                 175

Gly Gly Thr Leu Ser Lys Asn Thr Val Ala Trp Val Arg Gln Ala Pro
            180                 185                 190

Gly Lys Glu Arg Gly Phe Val Thr Ser Ile Thr Cys Asp Gly Arg Thr
        195                 200                 205

Thr Tyr Tyr Ala Asn Ser Val Lys Gly Arg Phe Pro Ile Ser Arg Asp
    210                 215                 220

Asn Ala Glu Asn Thr Val Tyr Leu Gln Met Asn Ser Leu Lys Pro Glu
225                 230                 235                 240

Asp Thr Ala Gly Tyr Val Cys Ala Asp Leu Gly Lys Trp Pro Ala Gly
                245                 250                 255
```

Ser Ala Asp Tyr Trp Gly Gln Gly Thr His Val Thr Val Ser Ser Thr
                260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 334
<211> LENGTH: 501
<212> TYPE: PRT
<213> ORGANISM: Artificial Sequence
<220> FEATURE:
<223> OTHER INFORMATION: Synthetic Construct

<400> SEQUENCE: 334

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
                20                  25                  30

Val Gln Ala Gly Gly Ser Leu Arg Leu Ser Cys Ala Ala Ser Gly Gly
            35                  40                  45

Thr Leu Ser Lys Asn Thr Val Ala Trp Phe Arg Gln Ala Pro Gly Lys
        50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
                100                 105                 110

Ala Val Tyr Val Cys Ala Asp Leu Gly Lys Trp Pro Ala Gly Pro Ala
            115                 120                 125

-continued

```
Asp Tyr Trp Gly Gln Gly Thr Gln Val Thr Val Ser Gly Gly Gly
    130                 135                 140

Gly Ser Gly Gly Gly Ser Gly Gly Gly Ser Asp Val Gln Leu
145                 150                 155                 160

Val Glu Ser Gly Gly Gly Leu Val Gln Ala Gly Gly Ser Leu Arg Leu
                165                 170                 175

Ser Cys Ala Ala Ser Gly Gly Thr Leu Ser Lys Asn Thr Val Ala Trp
                180                 185                 190

Val Arg Gln Ala Pro Gly Lys Glu Arg Gly Phe Val Thr Ser Ile Thr
            195                 200                 205

Cys Asp Gly Arg Thr Thr Tyr Tyr Ala Asn Ser Val Lys Gly Arg Phe
210                 215                 220

Pro Ile Ser Arg Asp Asn Ala Glu Asn Thr Val Tyr Leu Gln Met Asn
225                 230                 235                 240

Ser Leu Lys Pro Glu Asp Thr Ala Gly Tyr Val Cys Ala Asp Leu Gly
                245                 250                 255

Lys Trp Pro Ala Gly Ser Ala Asp Tyr Trp Gly Gln Gly Thr His Val
                260                 265                 270

Thr Val Ser Ser Thr Ser Thr Thr Thr Pro Ala Pro Arg Pro Pro Thr
            275                 280                 285

Pro Ala Pro Thr Ile Ala Ser Gln Pro Leu Ser Leu Arg Pro Glu Ala
290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Lys Arg Gly Arg Lys
                340                 345                 350

Lys Leu Leu Tyr Ile Phe Lys Gln Pro Phe Met Arg Pro Val Gln Thr
            355                 360                 365

Thr Gln Glu Glu Asp Gly Cys Ser Cys Arg Phe Pro Glu Glu Glu Glu
        370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
                420                 425                 430

Glu Met Gly Gly Lys Pro Arg Arg Lys Asn Pro Gln Glu Gly Leu Tyr
            435                 440                 445

Asn Glu Leu Gln Lys Asp Lys Met Ala Glu Ala Tyr Ser Glu Ile Gly
450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
                500
```

<210> SEQ ID NO 335
<211> LENGTH: 506
<212> TYPE: PRT
<213> ORGANISM: Artificial Sequence
<220> FEATURE:
<223> OTHER INFORMATION: Synthetic Construct

<400> SEQUENCE: 335

Met Ala Leu Pro Val Thr Ala Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Ala Gly Gly Ser Leu Arg Leu Ser Cys Ala Ala Ser Gly Gly
        35                  40                  45

Thr Leu Ser Lys Asn Thr Val Ala Trp Phe Arg Gln Ala Pro Gly Lys
    50                  55                  60

Glu Arg Gly Phe Val Ala Ser Ile Thr Trp Asp Gly Arg Thr Thr Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Val Cys Ala Asp Leu Gly Lys Trp Pro Ala Gly Pro Ala
        115                 120                 125

Asp Tyr Trp Gly Gln Gly Thr Gln Val Thr Val Ser Ser Gly Gly Gly
    130                 135                 140

Gly Ser Gly Gly Gly Gly Ser Gly Gly Gly Ser Gly Gly Gly Gly
145                 150                 155                 160

Ser Asp Val Gln Leu Val Glu Ser Gly Gly Gly Leu Val Gln Ala Gly
                165                 170                 175

Gly Ser Leu Arg Leu Ser Cys Ala Ala Ser Gly Gly Thr Leu Ser Lys
            180                 185                 190

Asn Thr Val Ala Trp Val Arg Gln Ala Pro Gly Lys Glu Arg Gly Phe
        195                 200                 205

Val Thr Ser Ile Thr Cys Asp Gly Arg Thr Thr Tyr Tyr Ala Asn Ser
210                 215                 220

Val Lys Gly Arg Phe Pro Ile Ser Arg Asp Asn Ala Glu Asn Thr Val
225                 230                 235                 240

Tyr Leu Gln Met Asn Ser Leu Lys Pro Glu Asp Thr Ala Gly Tyr Val
                245                 250                 255

Cys Ala Asp Leu Gly Lys Trp Pro Ala Gly Ser Ala Asp Tyr Trp Gly
            260                 265                 270

Gln Gly Thr His Val Thr Val Ser Ser Thr Ser Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
        340                 345                 350

Lys Arg Gly Arg Lys Lys Leu Leu Tyr Ile Phe Lys Gln Pro Phe Met
    355                 360                 365

Arg Pro Val Gln Thr Thr Gln Glu Glu Asp Gly Cys Ser Cys Arg Phe
370                 375                 380

Pro Glu Glu Glu Glu Gly Gly Cys Glu Leu Arg Val Lys Phe Ser Arg
385                 390                 395                 400

Ser Ala Asp Ala Pro Ala Tyr Gln Gln Gly Gln Asn Gln Leu Tyr Asn

```
              405                 410                 415
Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
        435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg
                500                 505

<210> SEQ ID NO 336
<211> LENGTH: 1488
<212> TYPE: DNA
<213> ORGANISM: Artificial Sequence
<220> FEATURE:
<223> OTHER INFORMATION: Synthetic Construct

<400> SEQUENCE: 336
atggctctgc cgtcactgc tctgctgctg ccctggctc tgctgctgca cgctgctcgc     60
cctcaggtcc agctggtgga agcggagga ggcctggtgc agccaggag cagcctgagg    120
ctgtcctgcg aggcctctgg cttcaccctg gactactatg ccatcggctg gtttaggcag    180
gcacctggaa aggagaggga gggagtgatc tgtatctctc gcagcgacgg cagcacatac    240
tatgccgatt ccgtgaaggg ccggttcacc atcagcagag acaacgccaa gaagacagtg    300
tacctgcaga tgatctccct gaagcctgag gataccgcag catactattg cgcagcagga    360
gcagactgta gcggatacct gagggattat gagtttaggg gacagggaac ccaggtgaca    420
gtgagctccg gaggaggagg ctcccaggtg cagctggtgg agtctggagg cggcctggtg    480
cagcctggag gcagcctgag actgagctgt gaagcttccg gatttaccct ggactactat    540
gcaatcggat ggtttaggca ggcaccagga aaggagagag aaggcgtgat ctgtatctcc    600
agatctgacg gctctacata ctatgccgat agtgtcaaag gacggttcac catctctaga    660
gataatgcca agaagacagt ctatctgcag atgattagcc tgaagcccga ggacacagcc    720
gcctattact gcgcagcagg agcagattgt agtgggtatc tgagggacta tgagtttcgg    780
gggcagggga cacaggtgac agtgagttct actagtacca cgacgccagc gccgcgacca    840
ccaacaccgg cgcccaccat cgcgtcgcag cccctgtccc tgcgcccaga ggcgtgccgg    900
ccagcggcgg ggggcgcagt gcacacgagg gggctggact cgcctgtga tatctacatc    960
tgggcgccct tggccgggac ttgtgggtc cttctcctgt cactggttat caccctttac   1020
tgcaaacggg gcagaaagaa actcctgtat atattcaaac aaccatttat gagaccagta   1080
caaactactc aagaggaaga tggctgtagc tgccgatttc agaagaaga agaaggagga   1140
tgtgaactga gagtgaagtt cagcaggagc gcagacgccc ccgcgtacca gcagggccag   1200
aaccagctct ataacgagct caatctagga cgaagagagg agtacgatgt tttggacaag   1260
agacgtggcc gggaccctga tgggggga aagccgagaa ggaagaaccc tcaggaaggc   1320
ctgtacaatg aactgcagaa agataagatg gcggaggcct acagtgagat tgggatgaaa   1380
ggcgagcgcc ggaggggcaa ggggcacgat ggcctttacc agggtctcag tacagccacc   1440
aaggacaccct acgacgccct tcacatgcag gccctgcccc ctcgctaa              1488
```

<210> SEQ ID NO 337
<211> LENGTH: 1869
<212> TYPE: DNA
<213> ORGANISM: Artificial Sequence
<220> FEATURE:
<223> OTHER INFORMATION: Synthetic Construct

<400> SEQUENCE: 337

| | | | | | |
|---|---|---|---|---|---|
| atggctctgc | ccgtcactgc | tctgctgctg | cctctggccc | tgctgctgca | cgccgcacgc | 60 |
| cctcaggtcc | agctggtcga | gtcaggagga | ggcctggtgc | agccaggagg | ctccctgcgg | 120 |
| ctgtcttgcg | aggccagcgg | cttcaccctg | gactactatg | ccatcggctg | gtttaggcag | 180 |
| gcacctggaa | aggagaggga | gggagtgatc | tgtatctcca | gatctgacgg | ctccacatac | 240 |
| tatgccgatt | ctgtgaaggg | ccggttcacc | atctctagag | acaacgccaa | gaagacagtg | 300 |
| tacctgcaga | tgatcagcct | gaagcccgag | gataccgcag | catactattg | cgcagcagga | 360 |
| gcagactgtt | ccggataccct | gagggattat | gagtttaggg | gacagggaac | ccaggtgaca | 420 |
| gtgagctccg | gaggaggagg | ctcccaggtg | cagctggtgg | agtctggagg | cggcctggtg | 480 |
| cagcctggag | gctccctgag | gctgtcttgc | gaggcaagcg | gcttcaccct | ggattactat | 540 |
| gcaatcggat | ggtttaggca | ggcaccagga | aaggagagag | aaggcgtgat | ctgtatcagc | 600 |
| cgctccgacg | gcagtaccta | ctatgccgat | tccgtcaaag | gccggttcac | catctccaga | 660 |
| gacaatgcca | agaagacagt | ctatctgcag | atgatctctc | tgaagcctga | ggatacagcc | 720 |
| gcctattact | gtgccgcagg | agcagactgt | agtggctatc | tgagagatta | tgagtttcgc | 780 |
| ggccagggca | cccaggtgac | agtgtctagc | ggaggaggag | gcagccaggt | ccagctggtg | 840 |
| gaatccggcg | gaggcctggt | gcagcccggc | ggctccctga | gactgtcctg | tgaagcctcc | 900 |
| ggatttactc | tggattatta | cgctattgga | tggttcagac | aggcccctgg | caaagaaaga | 960 |
| gaagggtga | tctgtatctc | tcggagcgac | ggctctacat | actatgccga | tagcgtcaag | 1020 |
| ggaagattta | ccatctccag | agataatgcc | aagaagacag | tgtatctgca | gatgatttcc | 1080 |
| ctgaagcccg | aggacactgc | cgcctattac | tgtgcagcag | gagcagattg | tagcgggtat | 1140 |
| ctgcgggatt | atgaatttag | gacagggc | actcaggtga | cagtctcaag | cactagtacc | 1200 |
| acgacgccag | cgccgcgacc | accaacaccg | gcgcccacca | tcgcgtcgca | gcccctgtcc | 1260 |
| ctgcgcccag | aggcgtgccg | gccagcggcg | ggggcgcag | tgcacacgag | ggggctggac | 1320 |
| ttcgcctgtg | atatctacat | ctgggcgccc | ttggccggga | cttgtggggt | ccttctcctg | 1380 |
| tcactggtta | tcacccttta | ctgcaaacgg | ggcagaaaga | aactcctgta | tatattcaaa | 1440 |
| caaccatttta | tgagaccagt | acaaactact | caagaggaag | atggctgtag | ctgccgattt | 1500 |
| ccagaagaag | aagaaggagg | atgtgaactg | agagtgaagt | tcagcaggag | cgcagacgcc | 1560 |
| cccgcgtacc | agcagggcca | gaaccagctc | tataacgagc | tcaatctagg | acgaagagag | 1620 |
| gagtacgatg | ttttggacaa | gagacgtggc | cgggaccctg | agatgggggg | aaagccgaga | 1680 |
| aggaagaacc | ctcaggaagg | cctgtacaat | gaactgcaga | agataagat | ggcggaggcc | 1740 |
| tacagtgaga | ttgggatgaa | aggcgagcgc | cggaggggca | aggggcacga | tggcctttac | 1800 |
| cagggtctca | gtacagccac | caaggacacc | tacgacgccc | ttcacatgca | ggccctgccc | 1860 |
| cctcgctaa | | | | | 1869 |

<210> SEQ ID NO 338
<211> LENGTH: 1467
<212> TYPE: DNA

<213> ORGANISM: Artificial Sequence
<220> FEATURE:
<223> OTHER INFORMATION: Synthetic Construct

<400> SEQUENCE: 338

```
atggctctgc cgtcaccgc tctgctgctg cctctggctc tgctgctgca cgctgctcgc      60
cctcaggtca aactggaaga atctggcgga ggcctggtgc aggcaggacg gagcctgcgc    120
ctgagctgcg cagcatccga gcacaccttc agctcccacg tgatgggctg gtttcggcag    180
gccccaggca aggagagaga gagcgtggcc gtgatcggct ggagggacat ctccacatct    240
tacgccgatt ccgtgaaggg ccggttcacc atcagccggg acaacgccaa gaagacactg    300
tatctgcaga tgaacagcct gaagcccgag gacaccgccg tgtactattg cgcagcaagg    360
agaatcgacg cagcagactt tgattcctgg ggccagggca cccaggtgac agtgtctagc    420
ggaggaggag gatctgaggt gcagctggtg gagagcggag cggcctggt gcaggccgga    480
ggctctctga ggctgagctg tgcagcatcc ggaagaacct tcacaatggg ctggtttagg    540
caggcaccag gaaaggagag ggagttcgtg gcagcaatca gcctgtcccc tacccctggcc    600
tactatgccg agagcgtgaa gggcaggttt accatctccc gcgataacgc caagaataca    660
gtggtgctgc agatgaactc cctgaaacct gaggacacag ccctgtacta ttgtgccgcc    720
gatcggaaga gcgtgatgag cattagacca gactattggg ggcagggaac acaggtgacc    780
gtgagcagca ctagtaccac gacgccagcg ccgcgaccac caacaccggc gcccaccatc    840
gcgtcgcagc ccctgtccct gcgcccagag gcgtgccggc cagcggcggg gggcgcagtg    900
cacacgaggg ggctggactt cgcctgtgat atctacatct gggcgccctt ggccgggact    960
tgtggggtcc ttctcctgtc actggttatc acccttact gcaaacgggg cagaaagaaa   1020
ctcctgtata tattcaaaca accatttatg agaccagtac aaactactca agaggaagat   1080
ggctgtagct gccgatttcc agaagaagaa gaaggaggat gtgaactgag agtgaagttc   1140
agcaggagcg cagacgcccc cgcgtaccag cagggccaga accagctcta taacgagctc   1200
aatctaggac gaagagagga gtacgatgtt ttggacaaga cgtggccg ggaccctgag   1260
atgggggga agccgagaag gaagaaccct caggaaggcc tgtacaatga actgcagaaa   1320
gataagatgg cggaggccta cagtgagatt gggatgaaag gcgagcgccg gaggggcaag   1380
gggcacgatg gcctttacca gggtctcagt acagccacca aggacaccta cgacgccctt   1440
cacatgcagg ccctgccccc tcgctaa                                        1467
```

<210> SEQ ID NO 339
<211> LENGTH: 1497
<212> TYPE: DNA
<213> ORGANISM: Artificial Sequence
<220> FEATURE:
<223> OTHER INFORMATION: Synthetic Construct

<400> SEQUENCE: 339

```
atggctctgc ctgtcaccgc tctgctgctg cctctggctc tgctgctgca cgctgctcgc      60
cctcaggtca aactggaaga aagtggggga ggcctggtgc aggcaggacg gagcctgcgc    120
ctgagctgcg cagcatccga gcacaccttc agctcccacg tgatgggctg gtttcggcag    180
gccccaggca aggagagaga gtccgtggcc gtgatcggct ggagggacat ctccacatct    240
tacgccgatt ctgtgaaggg ccggttcacc atcagcagag acaacgccaa gaagacactg    300
tatctgcaga tgaatagcct gaagcccgag gacaccgccg tgtactattg cgcagcaagg    360
agaatcgacg cagcagactt tgattcctgg ggccagggca cccaggtgac agtgtctagc    420
```

```
ggaggaggag gatctggagg aggaggaagc ggaggaggag gatccgaggt gcagctggtg      480
gagtctggag gcggcctggt gcaggccgga ggctctctga ggctgagctg tgcagcatcc      540
ggaagaacct tcacaatggg ctggtttagg caggcaccag aaaggagag ggagttcgtg       600 gcagcaatca gcctgtcccc taccctggcc tactatgccg agtccgtgaa gggcaggttt      660
accatctctc gcgataacgc caagaataca gtggtgctgc agatgaacag cctgaaacct     720
gaggacacag ccctgtacta ttgtgccgcc gatcggaaga gcgtgatgag cattagaccc     780
gattattggg gacagggcac acaggtgaca gtgagtagca ctagtaccac gacgccagcg     840
ccgcgaccac caacaccggc gcccaccatc gcgtcgcagc ccctgtccct gcgcccagag     900
gcgtgccggc cagcggcggg gggcgcagtg cacacgaggg ggctggactt cgcctgtgat     960
atctacatct gggcgccctt ggccgggact tgtggggtcc ttctcctgtc actggttatc    1020
accctttact gcaaacgggg cagaaagaaa ctcctgtata tattcaaaca accatttatg    1080
agaccagtac aaactactca agaggaagat ggctgtagct gccgatttcc agaagaagaa    1140
gaaggaggat gtgaactgag agtgaagttc agcaggagcg cagacgcccc cgcgtaccag    1200
cagggccaga accagctcta taacgagctc aatctaggac gaagagagga gtacgatgtt    1260
ttggacaaga gacgtggccg ggaccctgag atgggggaa agccgagaag gaagaaccct    1320
caggaaggcc tgtacaatga actgcagaaa gataagatgg cggaggccta cagtgagatt    1380
gggatgaaag gcgagcgccg gaggggcaag gggcacgatg gcctttacca gggtctcagt    1440
acagccacca aggacaccta cgacgcccctt cacatgcagg ccctgccccc tcgctaa      1497

<210> SEQ ID NO 340
<211> LENGTH: 1527
<212> TYPE: DNA
<213> ORGANISM: Artificial Sequence
<220> FEATURE:
<223> OTHER INFORMATION: Synthetic Construct

<400> SEQUENCE: 340
atggctctgc ccgtcaccgc actgctgctg cctctggctc tgctgctgca cgccgcaaga      60
ccacaggtca aactggaaga atcaggagga ggcctggtgc aggcaggacg gagcctgcgc     120
ctgagctgcg cagcatccga gcacaccttc agctcccacg tgatgggctg gtttcggcag     180
gccccaggca aggagagaga gtccgtggcc gtgatcggct ggagggacat ctccacatct     240
tacgccgatt ccgtgaaggg ccggttcacc atcagccggg acaacgccaa gaagacactg     300
tatctgcaga tgaacagcct gaagcccgag gacaccgccg tgtactattg cgcagcaagg     360
agaatcgacg cagcagactt tgatagctgg ggccagggca cccaggtgac agtgtctagc     420
ggaggaggag gatctggagg aggaggaagc ggaggaggag gaagcggcgg cggcggctct     480
ggcggcggcg gcagcgaggt gcagctggtg gagagcggcg gcggcctggt gcaggccggc     540
ggctctctga ggctgagctg tgcagcatcc ggaagaacct tcacaatggg ctggtttagg     600
caggcaccag aaaggagag ggagttcgtg gcagcaatca gcctgtcccc taccctggcc     660
tactatgccg agagcgtgaa gggcaggttt accatctccc gcgataacgc caagaataca     720
gtggtgttac aaatgaacag cctgaaacct gaggacacag ccctgtacta ttgtgccgcc     780
gatcggaaga gcgtgatgag cattagaccc gattattggg gcagggac acaggtgacc      840 gtgagcagca ctagtaccac gacgccagcg ccgcgaccac caacaccggc gcccaccatc     900
gcgtcgcagc ccctgtccct gcgcccagag gcgtgccggc cagcggcggg gggcgcagtg     960
```

| | |
|---|---|
| cacacgaggg ggctggactt cgcctgtgat atctacatct gggcgccctt ggccgggact | 1020 |
| tgtggggtcc ttctcctgtc actggttatc acccttact gcaaacgggg cagaaagaaa | 1080 |
| ctcctgtata tattcaaaca accatttatg agaccagtac aaactactca agaggaagat | 1140 |
| ggctgtagct gccgatttcc agaagaagaa gaaggaggat gtgaactgag agtgaagttc | 1200 |
| agcaggagcg cagacgcccc cgcgtaccag cagggccaga accagctcta taacgagctc | 1260 |
| aatctaggac gaagagagga gtacgatgtt ttggacaaga cgtggccg ggaccctgag | 1320 |
| atgggggaa agccgagaag gaagaaccct caggaaggcc tgtacaatga actgcagaaa | 1380 |
| gataagatgg cggaggccta cagtgagatt gggatgaaag cgagcgccg gaggggcaag | 1440 |
| gggcacgatg gcctttacca gggtctcagt acagccacca aggacaccta cgacgccctt | 1500 |
| cacatgcagg ccctgccccc tcgctaa | 1527 |

<210> SEQ ID NO 341
<211> LENGTH: 1482
<212> TYPE: DNA
<213> ORGANISM: Artificial Sequence
<220> FEATURE:
<223> OTHER INFORMATION: Synthetic Construct

<400> SEQUENCE: 341

| | |
|---|---|
| atggctctgc ctgtgaccgc actgctgctg cctctggctc tgctgctgca cgccgcacga | 60 |
| cctgaagtcc agctggtgga atccggggga ggcctggtgc aggcaggagg ctccctgagg | 120 |
| ctgtcttgcg cagcaagcgg aagaaccttc acaatgggct ggtttaggca ggcaccagga | 180 |
| aaggagaggg agttcgtggc cgccatctcc ctgtctccta ccctggccta ctatgccgag | 240 |
| agcgtgaagg gcaggtttac catctcccgc gacaacgcca agaatacagt ggtgctgcag | 300 |
| atgaacagcc tgaagccaga ggacacagcc ctgtactatt gcgccgccga tcggaagtct | 360 |
| gtgatgagca tcagacccga ttactggggc cagggcaccc aggtgacagt gagctccgga | 420 |
| ggaggaggat ccggcggagg aggctctcag gtgaagctgg aggagtccgg aggcggcctg | 480 |
| gtgcaggccg acggtccct gagactgtct tgtgccgcca gcgagcacac cttctctagc | 540 |
| cacgtgatgg gatggttcag gcaggcacct ggaaaggaga gggagtccgt ggcagtgatc | 600 |
| ggatggaggg acatcagcac atcctacgcc gattctgtga agggccggtt caccatcagc | 660 |
| agagacaacg ccaagaagac actgtattta caaatgaaca gcctgaagcc cgaggatacc | 720 |
| gccgtgtact attgtgccgc ccggcggatt gacgccgcag actttgactc atgggggcag | 780 |
| ggaactcagg tgaccgtgtc ctcaactagt accacgacgc cagcgccgcg accaccaaca | 840 |
| ccggcgccca ccatcgcgtc gcagccctg tccctgcgcc cagaggcgtg ccggccagcg | 900 |
| gcggggggcg cagtgcacac gagggggctg gacttcgcct gtgatatcta catctgggcg | 960 |
| cccttggccg ggacttgtgg ggtccttctc ctgtcactgg ttatcaccct ttactgcaaa | 1020 |
| cggggcagaa agaaactcct gtatatattc aacaaccat ttatgagacc agtacaaact | 1080 |
| actcaagagg aagatggctg tagctgccga tttccagaag aagaagaagg aggatgtgaa | 1140 |
| ctgagagtga agttcagcag gagcgcagac gccccgcgt accagcaggg ccagaaccag | 1200 |
| ctctataacg agctcaatct aggacgaaga gaggagtacg atgttttgga caagagacgt | 1260 |
| ggccgggacc ctgagatggg gggaaagccg agaaggaaga accctcagga aggcctgtac | 1320 |
| aatgaactgc agaaagataa gatggcggag gcctacagtg agattgggat gaaaggcgag | 1380 |
| cgccggaggg gcaaggggca cgatggcctt taccagggtc tcagtacagc caccaaggac | 1440 |
| acctacgacg cccttcacat gcaggccctg ccccctcgct aa | 1482 |

<210> SEQ ID NO 342
<211> LENGTH: 1497
<212> TYPE: DNA
<213> ORGANISM: Artificial Sequence
<220> FEATURE:
<223> OTHER INFORMATION: Synthetic Construct

<400> SEQUENCE: 342

| | |
|---|---|
| atggccctgc ctgtcaccgc tctgctgctg cccctggccc tgctgctgca cgccgcacgc | 60 |
| cctgaggtcc agctggtcga gtccggggga ggcctggtgc aggcaggagg ctccctgagg | 120 |
| ctgtcttgcg cagcaagcgg aagaaccttc acaatgggct ggtttaggca ggcaccagga | 180 |
| aaggagaggg agttcgtggc cgccatctcc ctgtctccta ccctggccta ctatgccgag | 240 |
| tccgtgaagg gcaggtttac catctctcgc gacaacgcca agaatacagt ggtgctgcag | 300 |
| atgaactccc tgaagccaga ggacacagcc ctgtactatt gcgccgccga tcggaagtct | 360 |
| gtgatgagca tcagacccga ttactggggc cagggcaccc aggtgacagt gagctccgga | 420 |
| ggaggaggat ccggcggagg aggctctggc ggcggcggca gccaggtgaa gctggaggag | 480 |
| agcggaggcg gcctggtgca ggccggacgg tccctgagac tgtcttgtgc cgccagcgag | 540 |
| cacaccttct ctagccacgt gatgggatgg ttcaggcagg cacctggaaa ggagagggag | 600 |
| tctgtggccg tgatcggctg gagggacatc agcacatcct acgccgatag cgtgaagggc | 660 |
| cggttcacca tctccagaga caacgccaag aagacactgt atctgcagat gaatagcctg | 720 |
| aagcccgagg ataccgccgt gtactattgt gccgcccggc ggattgacgc cgcagatttt | 780 |
| gattcttggg ggcagggaac tcaggtgacc gtgtcctcaa ctagtaccac gacgccagcg | 840 |
| ccgcgaccac caacaccggc gcccaccatc gcgtcgcagc cctgtccct gcgcccagag | 900 |
| gcgtgccggc cagcggcggg gggcgcagtg cacacgaggg ggctggactt cgcctgtgat | 960 |
| atctacatct gggcgccctt ggccgggact tgtggggtcc ttctcctgtc actggttatc | 1020 |
| acccttact gcaaacgggg cagaaagaaa ctcctgtata tattcaaaca accatttatg | 1080 |
| agaccagtac aaactactca agaggaagat ggctgtagct gccgatttcc agaagaagaa | 1140 |
| gaaggaggat gtgaactgag agtgaagttc agcaggagcg cagacgcccc cgcgtaccag | 1200 |
| cagggccaga accagctcta taacgagctc aatctaggac gaagagagga gtacgatgtt | 1260 |
| ttggacaaga cgtggccg ggaccctgag atgggggaa agccgagaag gaagaaccct | 1320 |
| caggaaggcc tgtacaatga actgcagaaa gataagatgg cggaggccta cagtgagatt | 1380 |
| gggatgaaag cgagcgccg gaggggcaag ggcacgatg cctttaccca gggtctcagt | 1440 |
| acagccacca aggacaccta cgacgccctt cacatgcagg ccctgccccc tcgctaa | 1497 |

<210> SEQ ID NO 343
<211> LENGTH: 1512
<212> TYPE: DNA
<213> ORGANISM: Artificial Sequence
<220> FEATURE:
<223> OTHER INFORMATION: Synthetic Construct

<400> SEQUENCE: 343

| | |
|---|---|
| atggctctgc ctgtgaccgc cctgctgctg cccctggccc tgctgctgca cgccgcacga | 60 |
| cctgaagtcc agctggtgga atctggcgga ggcctggtgc aggcaggagg ctccctgagg | 120 |
| ctgtcttgcg cagcaagcgg aagaaccttc acaatgggct ggtttaggca ggcaccagga | 180 |
| aaggagaggg agttcgtggc cgccatctcc ctgtctccta ccctggccta ctatgccgag | 240 |

```
tctgtgaagg gcaggtttac catcagccgc gacaacgcca agaatacagt ggtgctgcag    300
atgaacagcc tgaagccaga ggacacagcc ctgtactatt gcgccgccga tcggaagtct    360
gtgatgagca tcagacccga ttactggggc cagggcaccc aggtgacagt gagctccgga    420
ggaggaggat ccggcggagg aggctctggc ggcggcggct ccggcggcgg cggctcccag    480
gtgaagctgg aggagtccgg aggcggcctg gtgcaggccg gacggtccct gagactgtct    540
tgtgccgcca gcagcacac cttctctagc cacgtgatgg gatggttcag gcaggcacct    600
ggaaaggaga gggagagcgt ggcagtgatc ggatggaggg acatcagcac atcctacgcc    660
gattccgtga agggccggtt caccatcagc cgggacaacg ccaagaagac actgtattta    720
caaatgaaca gcctgaagcc cgaggatacc gccgtgtact attgtgccgc ccggcggatt    780
gatgccgcag actttgatag ttggggacag gggactcagg tcaccgtcag cagcactagt    840
accacgacgc cagcgccgcg accaccaaca ccggcgccca ccatcgcgtc gcagccctg    900
tccctgcgcc cagaggcgtg ccggccagcg cgggggggcg cagtgcacac gagggggctg    960
gacttcgcct gtgatatcta catctgggcg cccttggccg ggacttgtgg ggtccttctc    1020
ctgtcactgg ttatcaccct ttactgcaaa cggggcagaa agaaactcct gtatatattc    1080
aaacaaccat ttatgagacc agtacaaact actcaagagg aagatggctg tagctgccga    1140
tttccagaag aagaagaagg aggatgtgaa ctgagagtga agttcagcag gagcgcagac    1200
gccccccgcg accagcaggg ccagaaccag ctctataacg agctcaatct aggacgaaga    1260
gaggagtacg atgttttgga caagagacgt ggccgggacc ctgagatggg gggaaagccg    1320
agaaggaaga accctcagga aggcctgtac aatgaactgc agaaagataa gatggcggag    1380
gcctacagtg agattgggat gaaaggcgag cgccggaggg caaggggca cgatggcctt    1440
taccagggtc tcagtacagc caccaaggac acctacgacg cccttcacat gcaggccctg    1500
ccccctcgct aa                                                        1512

<210> SEQ ID NO 344
<211> LENGTH: 1470
<212> TYPE: DNA
<213> ORGANISM: Artificial Sequence
<220> FEATURE:
<223> OTHER INFORMATION: Synthetic Construct

<400> SEQUENCE: 344
atggctctgc ccgtcaccgc actgctgctg cctctggctc tgctgctgca cgctgctcgc     60
cctcaggtca aactggaaga atctggcgga ggcctggtgc aggcaggcag gtccctgagg    120
ctgtcttgcg cagcaagcga gcacaccttt agctcccacg tgatgggatg gttcaggcag    180
gcaccaggca aggagagaga gtccgtggcc gtgatcggct ggagggacat ctccacatct    240
tacgccgatt ctgtgaaggg ccggtttacc atcagcagag acaacgccaa gaagacactg    300
tatctgcaga tgaatagcct gaagcctgag gacaccgccg tgtactattg cgcagcaagg    360
agaatcgatg cagcagactt cgattcctgg ggacagggaa cccaggtgac agtgtctagc    420
ggaggaggag gaagcgccgt gcagctggtg gagtccggcg gcggcctggt gcaggccggc    480
gattctctgc ggctgacctg tacagcctcc ggcagagcct ctctacccta ctttatggcc    540
tggtttagac aggcccctgg caaggagagg gagtttgtgg caggaatcgc atggagcgga    600
ggatccacac atacgccga ctccgtgaag gcaggttca ccatctctcg cgataacgcc    660
aagaatacag tgtatctgca gatgaactct ctgaagagcg aggacacagc cgtgtactat    720
tgtgccagcc ggggaatcga ggtggaggaa tttgggggctt gggggcaggg aactcaggtg    780
```

```
accgtctcat caactagtac cacgacgcca gcgccgcgac caccaacacc ggcgcccacc    840
atcgcgtcgc agcccctgtc cctgcgccca gaggcgtgcc ggccagcggc gggggggcgca   900 gtgcacacga gggggctgga cttcgcctgt gatatctaca tctgggcgcc cttggccggg    960
acttgtgggg tccttctcct gtcactggtt atcacccttt actgcaaacg gggcagaaag   1020
aaactcctgt atatattcaa acaaccattt atgagaccag tacaaactac tcaagaggaa   1080
gatggctgta gctgccgatt ccagaagaa gaagaaggag gatgtgaact gagagtgaag    1140
ttcagcagga gcgcagacgc ccccgcgtac cagcagggcc agaaccagct ctataacgag   1200
ctcaatctag gacgaagaga ggagtacgat gttttggaca agagacgtgg ccgggaccct   1260
gagatggggg gaaagccgag aaggaagaac cctcaggaag gcctgtacaa tgaactgcag   1320
aaagataaga tggcggaggc ctacagtgag attgggatga aggcgagcg ccggaggggc    1380 aagggggcacg atggccttta ccagggtctc agtacagcca ccaaggacac ctacgacgcc   1440
cttcacatgc aggccctgcc ccctcgctaa                                    1470
```

<210> SEQ ID NO 345
<211> LENGTH: 1500
<212> TYPE: DNA
<213> ORGANISM: Artificial Sequence
<220> FEATURE:
<223> OTHER INFORMATION: Synthetic Construct

<400> SEQUENCE: 345

```
atggctctgc ccgtcaccgc tctgctgctg cctctggctc tgctgctgca cgctgctcgc     60
cctcaggtca aactggaaga atctggcgga ggcctggtgc aggcaggcag gtccctgagg    120
ctgtcttgcg cagcaagcga gcacaccttt agctcccacg tgatgggatg gttcaggcag    180
gcaccaggca aggagagaga gagcgtggcc gtgatcggct ggagggacat ctccacatct    240
tacgccgata gcgtgaaggg ccggtttacc atctccagag acaacgccaa gaagacactg    300
tatctgcaga tgaatagcct gaagcctgag gacaccgccg tgtactattg cgcagcaagg    360
agaatcgatg cagcagactt cgattcctgg ggacagggaa cccaggtgac agtgtctagc    420
ggaggaggag gatccggagg aggaggatct ggcggcggcg gcagcgccgt gcagctggtg    480
gagtccggcg gcggcctggt gcaggccggc gactctctga ggctgacctg tacagcctcc    540
ggcagagcct tctctaccta ctttatggcc tggtttagac aggcccctgg caaggagagg    600
gagtttgtgg caggaatcgc atggagcgga ggatccacag catacgcaga ctctgtgaag    660
ggcaggttca ccatcagccg cgataacgcc aagaatacag tgtatctgca gatgaactct    720
ctgaagagcg aggatacagc cgtgtactat tgtgcctccc gggggattga agtcgaggaa    780 tttgggctt gggggcaggg cactcaggtc accgtctcat ctactagtac cacgacgcca    840
gcgccgcgac caccaacacc ggcgcccacc atcgcgtcgc agcccctgtc cctgcgccca    900
gaggcgtgcc ggccagcggc gggggggcgca gtgcacacga gggggctgga cttcgcctgt    960
gatatctaca tctgggcgcc cttggccggg acttgtgggg tccttctcct gtcactggtt   1020
atcacccttt actgcaaacg gggcagaaag aaactcctgt atatattcaa acaaccattt   1080
atgagaccag tacaaactac tcaagaggaa gatggctgta gctgccgatt ccagaagaa    1140 gaagaaggag gatgtgaact gagagtgaag ttcagcagga gcgcagacgc ccccgcgtac   1200
cagcagggcc agaaccagct ctataacgag ctcaatctag gacgaagaga ggagtacgat   1260
gttttggaca agagacgtgg ccgggaccct gagatggggg gaaagccgag aaggaagaac   1320
```

```
cctcaggaag gcctgtacaa tgaactgcag aaagataaga tggcggaggc ctacagtgag       1380
attgggatga aaggcgagcg ccggaggggc aaggggcacg atggccttta ccagggtctc       1440
agtacagcca ccaaggacac ctacgacgcc cttcacatgc aggccctgcc ccctcgctaa       1500
```

<210> SEQ ID NO 346
<211> LENGTH: 1530
<212> TYPE: DNA
<213> ORGANISM: Artificial Sequence
<220> FEATURE:
<223> OTHER INFORMATION: Synthetic Construct

<400> SEQUENCE: 346

```
atggctctgc ccgtcactgc tctgctgctg cctctggctc tgctgctgca cgctgctaga        60
ccacaggtca aactggagga gtcagggggga ggcctggtgc aggcaggcag gtccctgagg      120
ctgtcttgcg cagcaagcga gcacaccttt agctcccacg tgatgggatg gttcaggcag      180
gcaccaggca aggagagaga gagcgtggcc gtgatcggct ggaggacat ctccacatct        240 tacgccgatt ctgtgaaggg ccggtttacc atcagcagag acaacgccaa gaagacactg      300
tatctgcaga tgaacagcct gaagcctgag gacaccgccg tgtactattg cgcagcaagg      360
agaatcgatg cagcagactt cgattcctgg ggacaggaa cccaggtgac agtgtctagc        420
ggaggaggag gatccggagg aggaggatct ggcggcggcg gcagtggcgg cggcggctcc      480
ggcggcggcg gctctgccgt gcagctggtg gagtccggcg gcggcctggt gcaggccggc      540
gactccctga ggctgacctg tacagccagc ggcagagcct ctccaccta ctttatggcc        600 tggtttagac aggcccctgg caaggagagg gagtttgtgg caggaatcgc atggagcgga      660
ggatccacag catacgccga ctccgtgaag ggcaggttca ccatctctcg cgataacgcc      720
aagaatacag tgtatctgca gatgaactct ctgaagagcg aggatacagc cgtgtactat      780
tgtgcctccc ggggcattga agtggaagaa tttggggctt ggggacaggg gactcaggtc      840
accgtcagca gcactagtac cacgacgcca gcgccgcgac caccaacacc ggcgcccacc      900
atcgcgtcgc agccctgtc cctgcgccca gaggcgtgcc ggccagcggc ggggggcgca      960
gtgcacacga ggggctgga cttcgcctgt gatatctaca tctgggcgcc cttggccggg     1020
acttgtgggg tccttctcct gtcactggtt atcacccttt actgcaaacg gggcagaaag     1080
aaactcctgt atatattcaa acaaccattt atgagaccag tacaaactac tcaagaggaa     1140
gatggctgta gctgccgatt tccagaagaa gaagaaggag gatgtgaact gagagtgaag     1200
ttcagcagga gcgcagacgc ccccgcgtac cagcagggcc agaaccagct ctataacgag     1260
ctcaatctag gacgaagaga ggagtacgat gtttttggaca agagacgtgg ccgggaccct     1320
gagatggggg gaaagccgag aaggaagaac cctcaggaag gcctgtacaa tgaactgcag     1380
aaagataaga tggcggaggc ctacagtgag attgggatga aaggcgagcg ccggaggggc     1440
aaggggcacg atggccttta ccagggtctc agtacagcca ccaaggacac ctacgacgcc     1500
cttcacatgc aggccctgcc ccctcgctaa                                     1530
```

<210> SEQ ID NO 347
<211> LENGTH: 1485
<212> TYPE: DNA
<213> ORGANISM: Artificial Sequence
<220> FEATURE:
<223> OTHER INFORMATION: Synthetic Construct

<400> SEQUENCE: 347

```
atggctctgc ccgtgaccgc tctgctgctg cctctggctc tgctgctgca tgctgctcgc        60
```

```
cctcaggtga aactggaaga atctggcgga ggcctggtgc aggcaggcag gtccctgagg      120
ctgtcttgcg cagcaagcga gcacaccttt agctcccacg tgatgggatg gttcaggcag      180
gcaccaggca aggagagaga gtccgtggcc gtgatcggct ggagggacat ctccacatct      240
tacgccgatt ctgtgaaggg ccggtttacc atcagcagag acaacgccaa gaagacactg      300
tatctgcaga tgaacagcct gaagcctgag gacaccgccg tgtactattg cgcagcaagg      360
agaatcgatg cagcagactt cgatagctgg ggacagggaa cccaggtgac agtgtctagc      420
ggaggaggag gatccggagg aggaggatct gccgtgcagc tggtggagag cggcggcggc      480
ctggtgcagg ccggcgattc cctgaggctg acctgtacag ccagcggcag agccttctcc      540
acctacttta tggcctggtt tagacaggcc cctggcaagg agagggagtt tgtggcagga      600
atcgcatgga gcgaggatc acagcatac gccgactccg tgaagggcag gttcaccatc      660
tctcgcgata cgccaagaa tacagtgtat ctgcagatga actctctgaa gagcgaggac      720
acagccgtgt actattgtgc cagccggggg attgaagtgg aagaatttgg ggcttggggg      780
caggggactc aggtcacagt gtcatctact agtaccacga cgccagcgcc gcgaccacca      840
acaccggcgc ccaccatcgc gtcgcagccc tgtccctgc cccagaggc gtgccggcca      900 gcggcggggg gcgcagtgca cacgaggggg ctggacttcg cctgtgatat ctacatctgg      960
gcgcccttgg ccgggacttg tggggtcctt ctcctgtcac tggttatcac cctttactgc     1020
aaacggggca gaaagaaact cctgtatata ttcaaacaac catttatgag accagtacaa     1080
actactcaag aggaagatgg ctgtagctgc cgatttccag aagaagaaga aggaggatgt     1140
gaactgagag tgaagttcag caggagcgca gacgcccccg cgtaccagca gggccagaac     1200
cagctctata cgagctcaa tctaggacga agagaggagt acgatgtttt ggacaagaga     1260
cgtggccggg accctgagat gggggaaag ccgagaagga agaaccctca ggaaggcctg     1320
tacaatgaac tgcagaaaga taagatggcg gaggcctaca gtgagattgg gatgaaaggc     1380
gagcgccgga ggggcaaggg gcacgatggc ctttaccagg gtctcagtac agccaccaag     1440
gacacctacg acgcccttca catgcaggcc ctgccccctc gctaa                     1485
```

<210> SEQ ID NO 348
<211> LENGTH: 1500
<212> TYPE: DNA
<213> ORGANISM: Artificial Sequence
<220> FEATURE:
<223> OTHER INFORMATION: Synthetic Construct

<400> SEQUENCE: 348

```
atggctctgc ccgtcaccgc actgctgctg ccccctggctc tgctgctgca cgctgctcgc       60
cctcaggtca aactggaaga atctggagga ggcctggtgc aggcaggcag gtccctgagg      120
ctgtcttgcg cagcaagcga gcacaccttt agctcccacg tgatgggatg gttcaggcag      180
gcaccaggca aggagagaga gagcgtggcc gtgatcggct ggagggacat ctccacatct      240
tacgccgata gcgtgaaggg ccggtttacc atctccagag acaacgccaa gaagacactg      300
tatctgcaga tgaatagcct gaagcctgag gacaccgccg tgtactattg cgcagcaagg      360
agaatcgatg cagcagactt cgattcctgg ggacagggaa cccaggtgac agtgtctagc      420
ggaggaggag gatccggagg aggaggatct ggcggcggcg cagcgccgt gcagctggtg      480 gagtccggcg gcgcctggt gcaggccggc gactctctga ggctgacctg tacagcctcc      540
ggcagagcct tctctaccta cttatggcc tggtttagac aggcccctgg caaggagagg      600
```

```
gagtttgtgg caggaatcgc atggagcgga ggatccacag catacgcaga ctctgtgaag      660
ggcaggttca ccatcagccg cgataacgcc aagaatacag tgtatctgca gatgaactct      720
ctgaagagcg aggatacagc cgtgtactat tgtgcctccc gggggattga agtggaagaa      780
tttgggcttt gggggcaggg gactcaggtc accgtcagca gcactagtac cacgacgcca      840
gcgccgcgac caccaacacc ggcgcccacc atcgcgtcgc agcccctgtc cctgcgccca      900
gaggcgtgcc ggccagcggc gggggcgca gtgcacacga ggggctgga cttcgcctgt       960 gatatctaca tctgggcgcc cttggccggg acttgtgggg tccttctcct gtcactggtt     1020 atcaccctt actgcaaacg gggcagaaag aaactcctgt atatattcaa acaaccattt     1080
atgagaccag tacaaactac tcaagaggaa gatggctgta gctgccgatt ccagaagaa     1140 gaagaaggag gatgtgaact gagagtgaag ttcagcagga gcgcagacgc ccccgcgtac     1200
cagcagggcc agaaccagct ctataacgag ctcaatctag gacgaagaga ggagtacgat     1260
gttttggaca gagacgtgg ccgggaccct gagatggggg gaaagccgag aaggaagaac      1320
cctcaggaag gcctgtacaa tgaactgcag aaagataaga tggcggaggc ctacagtgag     1380
attgggatga aggcgagcg ccggagggg caaggggcacg atggcctta ccagggtctc       1440 agtacagcca ccaaggacac ctacgacgcc cttcacatgc aggccctgcc ccctcgctaa     1500

<210> SEQ ID NO 349
<211> LENGTH: 1515
<212> TYPE: DNA
<213> ORGANISM: Artificial Sequence
<220> FEATURE:
<223> OTHER INFORMATION: Synthetic Construct

<400> SEQUENCE: 349
atggctctgc ctgtgaccgc tctgctgctg cctctggctc tgctgctgca cgccgctcgc       60
cctcaggtga aactggaaga atctggagga ggcctggtgc aggcaggcag gtccctgagg      120
ctgtcttgcg cagcaagcga gcacaccttt agctcccacg tgatgggatg gttcaggcag      180
gcaccaggca aggagagaga gtccgtggcc gtgatcggct ggagggacat ctccacatct      240
tacgccgatt ccgtgaaggg ccggtttacc atcagccggg acaacgccaa gaagacactg      300
tatctgcaga tgaacagcct gaagcctgag gacaccgccg tgtactattg cgcagcaagg      360
agaatcgatg cagcagactt cgattcttgg ggccagggca cccaggtgac agtgtctagc      420
ggaggaggag gatccggagg aggaggatct ggcggcggcg gctccggcgg cggcggctcc      480
gccgtgcagc tggtggagtc tggcggcggc ctggtcagg ccggcgacag cctgaggctg      540
acctgtacag cctctggcag agccttcagc acctacttta tggcctggtt tagacaggcc      600
cctggcaagg agagggagtt tgtggcagga atcgcatgga gcggaggatc cacagcatac      660
gccgacagcg tgaagggcag gttcaccatc tcccgcgata cgccaagaa tacagtgtat      720 ctgcagatga actctctgaa gagcgaggat acagccgtgt actattgtgc agccggggg      780 attgaagtgg aagaatttgg ggcatggggg caggggactc aggtcaccgt cagtagcact      840
agtaccacga cgccagcgcc gcgaccacca acaccggcgc ccaccatcgc gtcgcagccc      900
ctgtccctgc gcccagaggc gtgccggcca gggcgggggg cgcagtgca cgcgagggggg     960 ctggacttcg cctgtgatat ctacatctgg gcgcccttgg ccgggacttg tggggtcctt     1020
ctcctgtcac tggttatcac cctttactgc aaacggggca gaaagaaact cctgtatata     1080
ttcaaacaac catttatgag accagtacaa actactcaag aggaagatgg ctgtagctgc     1140
cgatttccag aagaagaaga aggaggatgt gaactgagag tgaagttcag caggagcgca     1200
```

```
gacgccccg cgtaccagca gggccagaac cagctctata acgagctcaa tctaggacga    1260
agagaggagt acgatgtttt ggacaagaga cgtggccggg accctgagat ggggggaaag    1320
ccgagaagga agaaccctca ggaaggcctg tacaatgaac tgcagaaaga taagatggcg    1380
gaggcctaca gtgagattgg gatgaaaggc gagcgccgga ggggcaaggg gcacgatggc    1440
ctttaccagg gtctcagtac agccaccaag acacctacg acgcccttca catgcaggcc    1500
ctgccccctc gctaa                                                    1515
```

<210> SEQ ID NO 350
<211> LENGTH: 1470
<212> TYPE: DNA
<213> ORGANISM: Artificial Sequence
<220> FEATURE:
<223> OTHER INFORMATION: Synthetic Construct

<400> SEQUENCE: 350

```
atggctctgc ccgtcaccgc tctgctgctg cctctggctc tgctgctgca cgctgctcgc     60
cctgaggtgc agctggtgga gtctggggga ggaatggtgc aggctgggga ctctctgaga    120
ctatcctgtg tgcagtctac ttacaccgtc aatagcgatg tcatgggctg gttccgccag    180
gctccaggga aggagcgtga gtttgtagga gcgattatgt ggaatgatgg tattacatac    240
ttgcaagact ccgtgaaggg ccgatttacc atcttcagag acaacgccaa gaacacggtg    300
tatctgcaaa tgaacagcct gaaacttgag gatacggccg tttattactg tgcagcatcc    360
aagggtagat actcggaata tgagtactgg ggccagggga cccaggtcac cgtctcctca    420
ggaggaggag gatctgcggt gcagctggtg gagtctgggg gaggattggt gcaggctggg    480
gactctctga gactcacctg tacagcctct ggacgcgcct tcagtaccta tttcatggcc    540
tggttccgcc aggctccagg gaaggagcgt gagtttgtag caggaattgc atggagtggt    600
ggtagcacgg cgtatgcaga ctccgtgaag ggccgattca ccatctccag agacaacgcc    660
aagaacacgg tgtatctgca aatgaacagc ctgaaatctg aggacacggc cgtttattac    720
tgtgccagca gggggattga ggtcgaagag tttggtgcct ggggccaggg gacccaggtc    780
accgtctcgt cgactagtac cacgacgcca gcgccgcgac caccaacacc ggcgcccacc    840
atcgcgtcgc agcccctgtc cctgcgccca gaggcgtgcc ggccagcggc gggggggcgca    900 gtgcacacga gggggctgga cttcgcctgt gatatctaca tctgggcgcc cttggccggg    960
acttgtgggg tccttctcct gtcactggtt atcaccctttt actgcaaacg gggcagaaag   1020
aaactcctgt atatattcaa acaaccattt atgagaccag tacaaactac tcaagaggaa   1080
gatggctgta gctgccgatt ccagaagaa gaagaaggag gatgtgaact gagagtgaag   1140
ttcagcagga gcgcagacgc ccccgcgtac cagcagggcc agaaccagct ctataacgag   1200
ctcaatctag gacgaagaga ggagtacgat gttttggaca gagacgtgg ccgggaccct   1260 gagatggggg gaaagccgag aaggaagaac cctcaggaag gcctgtacaa tgaactgcag   1320
aaagataaga tggcggaggc ctacagtgag attgggatga aggcgagcg ccggaggggc   1380 aaggggcacg atggccttta ccagggtctc agtacagcca ccaaggacac ctacgacgcc   1440
cttcacatgc aggccctgcc ccctcgctaa                                    1470
```

<210> SEQ ID NO 351
<211> LENGTH: 1500
<212> TYPE: DNA
<213> ORGANISM: Artificial Sequence
<220> FEATURE:

<223> OTHER INFORMATION: Synthetic Construct

<400> SEQUENCE: 351

| | | | | | |
|---|---|---|---|---|---|
| atggctctgc | ccgtcaccgc | tctgctgctg | cctctggctc | tgctgctgca | cgctgctcgc | 60 |
| cctgaggtgc | agctggtgga | gtctggggga | ggaatggtgc | aggctggga | ctctctgaga | 120 |
| ctatcctgtg | tgcagtctac | ttacaccgtc | aatagcgatg | tcatgggctg | gttccgccag | 180 |
| gctccaggga | aggagcgtga | gtttgtagga | gcgattatgt | ggaatgatgg | tattacatac | 240 |
| ttgcaagact | ccgtgaaggg | ccgatttacc | atcttcagag | acaacgccaa | gaacacggtg | 300 |
| tatctgcaaa | tgaacagcct | gaaacttgag | gatacggccg | tttattactg | tgcagcatcc | 360 |
| aagggtagat | actcggaata | tgagtactgg | ggccagggga | cccaggtcac | cgtctcctca | 420 |
| ggaggaggag | gatctggagg | aggaggaagc | ggaggaggag | gatccgcggt | gcagctggtg | 480 |
| gagtctgggg | gaggattggt | gcaggctggg | gactctctga | gactcacctg | tacagcctct | 540 |
| ggacgcgcct | tcagtaccta | tttcatggcc | tggttccgcc | aggctccagg | gaaggagcgt | 600 |
| gagtttgtag | caggaattgc | atggagtggt | ggtagcacgc | gtatgcaga | ctccgtgaag | 660 |
| ggccgattca | ccatctccag | agacaacgcc | aagaacacgg | tgtatctgca | aatgaacagc | 720 |
| ctgaaatctg | aggacacggc | cgtttattac | tgtgccagca | gggggattga | ggtcgaagag | 780 |
| tttggtgcct | ggggccaggg | gacccaggtc | accgtctcgt | cgactagtac | cacgacgcca | 840 |
| gcgccgcgac | caccaacacc | ggcgcccacc | atcgcgtcgc | agcccctgtc | cctgcgccca | 900 |
| gaggcgtgcc | ggccagcggc | ggggggcgca | gtgcacacga | ggggctgga | cttcgcctgt | 960 |
| gatatctaca | tctgggcgcc | cttggccggg | acttgtgggg | tccttctcct | gtcactggtt | 1020 |
| atcacccttt | actgcaaacg | gggcagaaag | aaactcctgt | atatattcaa | acaaccattt | 1080 |
| atgagaccag | tacaaactac | tcaagaggaa | gatggctgta | gctgccgatt | tccagaagaa | 1140 |
| gaagaaggag | gatgtgaact | gagagtgaag | ttcagcagga | gcgcagacgc | ccccgcgtac | 1200 |
| cagcagggcc | agaaccagct | ctataacgag | ctcaatctag | gacgaagaga | ggagtacgat | 1260 |
| gttttggaca | agagacgtgg | ccgggaccct | gagatggggg | gaaagccgag | aaggaagaac | 1320 |
| cctcaggaag | gcctgtacaa | tgaactgcag | aaagataaga | tggcggaggc | ctacagtgag | 1380 |
| attgggatga | aaggcgagcg | ccggagggc | aaggggcacg | atggccttta | ccagggtctc | 1440 |
| agtacagcca | ccaaggacac | ctacgacgcc | cttcacatgc | aggccctgcc | ccctcgctaa | 1500 |

<210> SEQ ID NO 352
<211> LENGTH: 1530
<212> TYPE: DNA
<213> ORGANISM: Artificial Sequence
<220> FEATURE:
<223> OTHER INFORMATION: Synthetic Construct

<400> SEQUENCE: 352

| | | | | | |
|---|---|---|---|---|---|
| atggctctgc | ccgtcaccgc | tctgctgctg | cctctggctc | tgctgctgca | cgctgctcgc | 60 |
| cctgaggtgc | agctggtgga | gtctggggga | ggaatggtgc | aggctggga | ctctctgaga | 120 |
| ctatcctgtg | tgcagtctac | ttacaccgtc | aatagcgatg | tcatgggctg | gttccgccag | 180 |
| gctccaggga | aggagcgtga | gtttgtagga | gcgattatgt | ggaatgatgg | tattacatac | 240 |
| ttgcaagact | ccgtgaaggg | ccgatttacc | atcttcagag | acaacgccaa | gaacacggtg | 300 |
| tatctgcaaa | tgaacagcct | gaaacttgag | gatacggccg | tttattactg | tgcagcatcc | 360 |
| aagggtagat | actcggaata | tgagtactgg | ggccagggga | cccaggtcac | cgtctcctca | 420 |
| ggaggaggag | gatctggagg | aggaggaagc | ggaggaggag | gaagcggcgg | cggcggctct | 480 |

```
ggcggcggcg gcagcgcggt gcagctggtg gagtctgggg gaggattggt gcaggctggg      540
gactctctga gactcacctg tacagcctct ggacgcgcct tcagtaccta tttcatggcc      600
tggttccgcc aggctccagg gaaggagcgt gagtttgtag caggaattgc atggagtggt      660
ggtagcacgg cgtatgcaga ctccgtgaag ggccgattca ccatctccag agacaacgcc      720
aagaacacgg tgtatctgca aatgaacagc ctgaaatctg aggacacggc cgtttattac      780
tgtgccagca gggggattga ggtcgaagag tttggtgcct ggggccaggg gacccaggtc      840
accgtctcgt cgactagtac cacgacgcca gcgccgcgac caccaacacc ggcgcccacc      900
atcgcgtcgc agcccctgtc cctgcgccca gaggcgtgcc ggccagcggc gggggggcgca     960 gtgcacacga gggggctgga cttcgcctgt gatatctaca tctgggcgcc cttggccggg     1020
acttgtgggg tccttctcct gtcactggtt atcaccctt actgcaaacg gggcagaaag      1080
aaactcctgt atatattcaa acaaccattt atgagaccag tacaaactac tcaagaggaa     1140
gatggctgta gctgccgatt ccagaagaa gaagaaggag gatgtgaact gagagtgaag      1200
ttcagcagga gcgcagacgc ccccgcgtac cagcagggcc agaaccagct ctataacgag     1260
ctcaatctag gacgaagaga ggagtacgat gttttggaca gagacgtgg ccgggacccct      1320 gagatggggg gaaagccgag aaggaagaac cctcaggaag gcctgtacaa tgaactgcag     1380
aaagataaga tggcggaggc ctacagtgag attgggatga aggcgagcg ccggagggggc      1440 aagggggcacg atggccttta ccagggtctc agtacagcca ccaaggacac ctacgacgcc     1500
cttcacatgc aggccctgcc ccctcgctaa                                      1530
```

<210> SEQ ID NO 353
<211> LENGTH: 1485
<212> TYPE: DNA
<213> ORGANISM: Artificial Sequence
<220> FEATURE:
<223> OTHER INFORMATION: Synthetic Construct

<400> SEQUENCE: 353

```
atggctctgc ccgtcaccgc tctgctgctg cctctggctc tgctgctgca cgctgctcgc       60
cctgaggtgc agctggtgga gtctggggga ggaatggtgc aggctgggga ctctctgaga      120
ctatcctgtg tgcagtctac ttacaccgtc aatagcgatg tcatgggctg gttccgccag      180
gctccaggga aggagcgtga gtttgtagga gcgattatgt ggaatgatgg tattacatac      240
ttgcaagact ccgtgaaggg ccgatttacc atcttcagag acaacgccaa gaacacggtg      300
tatctgcaaa tgaacagcct gaaacttgag gatacggccg tttattactg tgcagcatcc      360
aagggtagat actcggaata tgagtactgg ggccagggga cccaggtcac cgtctcctca      420
ggaggaggag gatccggcgg aggaggctct gcggtgcagc tggtggagtc tgggggagga      480
ttggtgcagg ctgggggactc tctgagactc acctgtacag cctctggacg cgccttcagt      540
acctatttca tggcctggtt ccgccaggct ccagggaagg agcgtgagtt tgtagcagga      600
attgcatgga gtggtggtag cacggcgtat gcagactccg tgaagggccg attcaccatc      660
tccagagaca cgccaagaa cacggtgtat ctgcaaatga acagcctgaa atctgaggac      720
acggccgttt attactgtgc cagcaggggg attgaggtcg aagagtttgg tgcctggggc      780
caggggaccc aggtcaccgt ctcgtcgact agtaccacga cgccagcgcc gcgaccacca     840
acaccggcgc ccaccatcgc gtcgcagccc ctgtccctgc gcccagaggc gtgcggccca    900
gcggcggggg gcgcagtgca cacgaggggg ctggacttcg cctgtgatat ctacatctgg    960
```

```
gcgcccttgg ccgggacttg tggggtcctt ctcctgtcac tggttatcac cctttactgc    1020
aaacggggca gaaagaaact cctgtatata ttcaaacaac catttatgag accagtacaa    1080
actactcaag aggaagatgg ctgtagctgc cgatttccag aagaagaaga aggaggatgt    1140
gaactgagag tgaagttcag caggagcgca gacgcccccg cgtaccagca gggccagaac    1200
cagctctata cgagctcaa tctaggacga agagaggagt acgatgtttt ggacaagaga    1260
cgtggccggg accctgagat ggggggaaag ccgagaagga gaaccctca ggaaggcctg    1320 tacaatgaac tgcagaaaga taagatggcg gaggcctaca gtgagattgg gatgaaaggc    1380
gagcgccgga ggggcaaggg gcacgatggc ctttaccagg gtctcagtac agccaccaag    1440
gacacctacg acgcccttca catgcaggcc ctgccccctc gctaa                   1485

<210> SEQ ID NO 354
<211> LENGTH: 1500
<212> TYPE: DNA
<213> ORGANISM: Artificial Sequence
<220> FEATURE:
<223> OTHER INFORMATION: Synthetic Construct

<400> SEQUENCE: 354
atggctctgc ccgtcaccgc tctgctgctg cctctggctc tgctgctgca cgctgctcgc      60
cctgaggtgc agctggtgga gtctggggga ggattggtgc aggctgggga ctctctgaga     120
ctatcctgtg tgcagtctac ttacaccgtc aatagcgatg tcatgggctg gttccgccag     180
gctccaggga aggagcgtga gtttgtagga gcgattatgt ggaatgatgg tattacatac     240
ttgcaagact ccgtgaaggg ccgatttacc atcttcagag acaacgccaa gaacacggtg     300
tatctgcaaa tgaacagcct gaaacttgag gatacggccg tttattactg tgcagcatcc     360
aagggtagat actcggaata tgagtactgg ggccagggga cccaggtcac cgtctcctca     420
ggaggaggag gatccggcgg aggaggctct ggcggcggcg gcagcgcggt gcagctggtg     480
gagtctgggg gaggattggt gcaggctggg gactctctga gactcacctg tacagcctct     540
ggacgcgcct tcagtaccta tttcatggcc tggttccgcc aggctccagg gaaggagcgt     600
gagtttgtag caggaattgc atggagtggt ggtagcacgg cgtatgcaga ctccgtgaag     660
ggccgattca ccatctccag agacaacgcc aagaacacgg tgtatctgca aatgaacagc     720
ctgaaatctg aggacacggc cgtttattac tgtgccagca gggggattga ggtcgaagag     780
tttggtgcct ggggccaggg gacccaggtc accgtctcgt cgactagtac cacgacgcca     840
gcgccgcgac caccaacacc ggcgcccacc atcgcgtcgc agcccctgtc cctgcgccca     900
gaggcgtgcc ggccagcggc ggggggcgca gtgcacacga ggggctgga cttcgcctgt     960 gatatctaca cctgggcgcc cttggccggg acttgtgggg tccttctcct gtcactggtt    1020
atcacccttt actgcaaacg gggcagaaag aaactcctgt atatattcaa acaaccattt    1080
atgagaccag tacaaactac tcaagaggaa gatggctgta gctgccgatt tccagaagaa    1140
gaagaaggag gatgtgaact gagagtgaag ttcagcagga gcgcagacgc ccccgcgtac    1200
cagcagggcc agaaccagct ctataacgag ctcaatctag gacgaagaga ggagtacgat    1260
gttttggaca gagacgtgg ccgggaccct gagatggggg gaaagccgag aaggaagaac    1320
cctcaggaag gcctgtacaa tgaactgcag aaagataaga tggcggaggc ctacagtgag    1380
attgggatga aggcgagcg ccggagggc aaggggcacg atggccttta ccagggtctc    1440
agtacagcca ccaaggacac ctacgacgcc cttcacatgc aggccctgcc ccctcgctaa    1500
```

<210> SEQ ID NO 355
<211> LENGTH: 1515
<212> TYPE: DNA
<213> ORGANISM: Artificial Sequence
<220> FEATURE:
<223> OTHER INFORMATION: Synthetic Construct

<400> SEQUENCE: 355

| | |
|---|---|
| atggctctgc ccgtcaccgc tctgctgctg cctctggctc tgctgctgca cgctgctcgc | 60 |
| cctgaggtgc agctggtgga gtctggggga ggaatggtgc aggctgggga ctctctgaga | 120 |
| ctatcctgtg tgcagtctac ttacaccgtc aatagcgatg tcatgggctg gttccgccag | 180 |
| gctccaggga aggagcgtga gtttgtagga gcgattatgt ggaatgatgg tattacatac | 240 |
| ttgcaagact ccgtgaaggg ccgatttacc atcttcagag acaacgccaa gaacacggtg | 300 |
| tatctgcaaa tgaacagcct gaaacttgag gatacggccg tttattactg tgcagcatcc | 360 |
| aagggtagat actcggaata tgagtactgg ggccagggga cccaggtcac cgtctcctca | 420 |
| ggaggaggag gatccggcgg aggaggctct ggcggcggcg gctccggcgg cggcggctcc | 480 |
| gcggtgcagc tggtggagtc tgggggagga ttggtgcagg ctggggactc tctgagactc | 540 |
| acctgtacag cctctggacg cgccttcagt acctatttca tggcctggtt ccgccaggct | 600 |
| ccagggaagg agcgtgagtt tgtagcagga attgcatgga gtggtggtag cacggcgtat | 660 |
| gcagactccg tgaagggccg attcaccatc tccagagaca cgccaagaa cacggtgtat | 720 |
| ctgcaaatga acagcctgaa atctgaggac acggccgttt attactgtgc cagcaggggg | 780 |
| attgaggtcg aagagtttgg tgcctggggc caggggaccc aggtcaccgt ctcgtcgact | 840 |
| agtaccacga cgccagcgcc gcgaccacca acaccggcgc ccaccatcgc gtcgcagccc | 900 |
| ctgtccctgc gcccagaggc gtgccggcca cggcgggggg cgcagtgca cacgaggggg | 960 |
| ctggacttcg cctgtgatat ctacatctgg gcgcccttgg ccgggacttg tggggtcctt | 1020 |
| ctcctgtcac tggttatcac cctttactgc aaacggggca gaaagaaact cctgtatata | 1080 |
| ttcaaacaac catttatgag accagtacaa actactcaag aggaagatgg ctgtagctgc | 1140 |
| cgatttccag aagaagaaga aggaggatgt gaactgagag tgaagttcag caggagcgca | 1200 |
| gacgcccccg cgtaccagca gggccagaac cagctctata cgagctcaa tctaggacga | 1260 |
| agagaggagt acgatgtttt ggacaagaga cgtggccggg accctgagat gggggggaaag | 1320 |
| ccgagaagga agaaccctca ggaaggcctg tacaatgaac tgcagaaaga taagatggcg | 1380 |
| gaggcctaca gtgagattgg atgaaaggc gagcgccgga ggggcaaggg gcacgatggc | 1440 |
| ctttaccagg gtctcagtac agccaccaag gacacctacg acgcccttca catgcaggcc | 1500 |
| ctgccccctc gctaa | 1515 |

<210> SEQ ID NO 356
<211> LENGTH: 1479
<212> TYPE: DNA
<213> ORGANISM: Artificial Sequence
<220> FEATURE:
<223> OTHER INFORMATION: Synthetic Construct

<400> SEQUENCE: 356

| | |
|---|---|
| atggctctgc ccgtcaccgc tctgctgctg cctctggctc tgctgctgca cgctgctcgc | 60 |
| cctcaggtaa agctggagga gtctggggga ggattggtgc aggctggggg ctctctgaga | 120 |
| ctctcctgtg cagcctctgg aggcacctta agtaagaata ccgtggcttg ggtccgccag | 180 |
| gctccaggga aggagcgtgg gtttgtaacg tctattacct gtgatggtcg tacgacatac | 240 |

```
tatgcgaact ccgtaaacgg ccgattcccc atcaaccgaa acaacgccga gaatttggtg    300
gttttgcaaa tgaacagcct gaaacctgac gacacggccc tttattactg tgcagcatac    360
cggaagtcaa taatgtctat tcagcccgac tactggggcc aggggaccca ggtcaccgtc    420
tcctcaggag gaggaggatc tcaggtacag ctggtggagt ctgggggagg attggtgcag    480
gctgggggct ctctgagact ctcctgtgca gcctctggag gcaccttaag taaaaatacc    540
gtggcttggt ccgccaggc tccagggaag gagcgtgggt ttgtagcgtc tattacctgg     600
gatggtcgta cgacatacta tgcagactcc gtgaagggcc gattcaccat ctccagagac    660
aacgccaaga acacagtgta tctgcaaatg aacagcctga acctgagga tacgccgtt     720 tatgtctgtg cagacttagg gaaatggcct gcgggcccgg cggactactg gggccagggg    780
acccaggtca ccgtctcctc aactagtacc acgacgccag cgccgcgacc accaacaccg    840
gcgcccacca tcgcgtcgca gccctgtcc ctgcgcccag aggcgtgccg gccagcggcg      900
gggggcgcag tgcacacgag ggggctggac ttcgcctgtg atatctacat ctgggcgccc    960
ttggccggga cttgtggggt ccttctcctg tcactggtta tccccttta ctgcaaacgg    1020 ggcagaaaga aactcctgta tatattcaaa caaccattta tgagaccagt acaaactact    1080
caagaggaag atggctgtag ctgccgattt ccagaagaag aagaaggagg atgtgaactg    1140
agagtgaagt tcagcaggag cgcagacgcc ccgcgtacc agcagggcca gaaccagctc     1200
tataacgagc tcaatctagg acgaagagag gagtacgatg ttttggacaa gagacgtggc    1260
cgggaccctg agatgggggg aaagccgaga aggaagaacc ctcaggaagg cctgtacaat    1320
gaactgcaga aagataagat ggcggaggcc tacagtgaga ttgggatgaa aggcgagcgc    1380
cggaggggca aggggcacga tggcctttac cagggtctca gtacagccac caaggacacc    1440
tacgacgccc ttcacatgca ggccctgccc cctcgctaa                           1479
```

<210> SEQ ID NO 357  
<211> LENGTH: 1509  
<212> TYPE: DNA  
<213> ORGANISM: Artificial Sequence  
<220> FEATURE:  
<223> OTHER INFORMATION: Synthetic Construct

<400> SEQUENCE: 357

```
atggctctgc ccgtcaccgc tctgctgctg cctctggctc tgctgctgca cgctgctcgc     60
cctcaggtaa agctggagga gtctggggga ggattggtgc aggctggggg ctctctgaga    120
ctctcctgtg cagcctctgg aggcacctta agtaagaata ccgtggcttg gtccgccag    180 gctccaggga aggagcgtgg gtttgtaacg tctattacct gtgatggtcg tacgacatac    240
tatgcgaact ccgtaaacgg ccgattcccc atcaaccgaa acaacgccga gaatttggtg    300
gttttgcaaa tgaacagcct gaaacctgac gacacggccc tttattactg tgcagcatac    360
cggaagtcaa taatgtctat tcagcccgac tactggggcc aggggaccca ggtcaccgtc    420
tcctcaggag gaggaggatc tggaggagga ggaagcggag gaggaggatc ccaggtacag    480
ctggtggagt ctgggggagg attggtgcag gctgggggct ctctgagact ctcctgtgca    540
gcctctggag gcaccttaag taaaaatacc gtggcttggt ccgccaggc tccagggaag    600 gagcgtgggt ttgtagcgtc tattacctgg gatggtcgta cgacatacta tgcagactcc    660
gtgaagggcc gattcaccat ctccagagac aacgccaaga acacagtgta tctgcaaatg    720
aacagcctga acctgagga tacgccgtt tatgtctgtg cagacttagg gaaatggcct      780
gcgggcccgg cggactactg gggccagggg acccaggtca ccgtctcctc aactagtacc    840
```

| | | |
|---|---|---|
| acgacgccag cgccgcgacc accaacaccg gcgcccacca tcgcgtcgca gcccctgtcc | 900 | |
| ctgcgcccag aggcgtgccg gccagcggcg ggggcgcag tgcacacgag ggggctggac | 960 | |
| ttcgcctgtg atatctacat ctgggcgccc ttggccggga cttgtggggt ccttctcctg | 1020 | |
| tcactggtta tcacccttta ctgcaaacgg ggcagaaaga aactcctgta tatattcaaa | 1080 | |
| caaccattta tgagaccagt acaaactact caagaggaag atggctgtag ctgccgattt | 1140 | |
| ccagaagaag aagaaggagg atgtgaactg agagtgaagt tcagcaggag cgcagacgcc | 1200 | |
| cccgcgtacc agcagggcca gaaccagctc tataacgagc tcaatctagg acgaagagag | 1260 | |
| gagtacgatg ttttggacaa gagacgtggc cgggaccctg agatgggggg aaagccgaga | 1320 | |
| aggaagaacc ctcaggaagg cctgtacaat gaactgcaga agataagat ggcggaggcc | 1380 | |
| tacagtgaga ttgggatgaa aggcgagcgc cggaggggca aggggcacga tggcctttac | 1440 | |
| cagggtctca gtacagccac caaggacacc tacgacgccc ttcacatgca ggccctgccc | 1500 | |
| cctcgctaa | 1509 | |

<210> SEQ ID NO 358
<211> LENGTH: 1539
<212> TYPE: DNA
<213> ORGANISM: Artificial Sequence
<220> FEATURE:
<223> OTHER INFORMATION: Synthetic Construct

<400> SEQUENCE: 358

| | | |
|---|---|---|
| atggctctgc ccgtcaccgc tctgctgctg cctctggctc tgctgctgca cgctgctcgc | 60 | |
| cctcaggtaa agctggagga gtctggggga ggattggtgc aggctggggg ctctctgaga | 120 | |
| ctctcctgtg cagcctctgg aggcacctta agtaagaata ccgtggcttg ggtccgccag | 180 | |
| gctccaggga aggagcgtgg gtttgtaacg tctattacct gtgatggtcg tacgacatac | 240 | |
| tatgcgaact ccgtaaacgg ccgattcccc atcaaccgaa acaacgccga gaatttggtg | 300 | |
| gttttgcaaa tgaacagcct gaaacctgac gacacggccc tttattactg tgcagcatac | 360 | |
| cggaagtcaa taatgtctat tcagcccgac tactgggggcc aggggaccca ggtcaccgtc | 420 | |
| tcctcaggag gaggaggatc tggaggagga ggaagcggag gaggaggaag cggcggcggc | 480 | |
| ggctctggcg gcggcggcag ccaggtacag ctggtggagt ctgggggagg attggtgcag | 540 | |
| gctgggggct ctctgagact ctcctgtgca gcctctggag gcaccttaag taaaaatacc | 600 | |
| gtggcttggt tccgccaggc tccagggaag gagcgtgggt ttgtagcgtc tattacctgg | 660 | |
| gatggtcgta cgacatacta tgcagactcc gtgaagggcc gattcaccat ctccagagac | 720 | |
| aacgccaaga cacagtgta tctgcaaatg aacagcctga acctgagga tacggccgtt | 780 | |
| tatgtctgtg cagacttagg gaaatggcct gcgggcccgg cggactactg gggccagggg | 840 | |
| acccaggtca ccgtctcctc aactagtacc acgacgccag cgccgcgacc accaacaccg | 900 | |
| gcgcccacca tcgcgtcgca gcccctgtcc ctgcgcccag aggcgtgccg gccagcggcg | 960 | |
| ggggcgcag tgcacacgag ggggctggac ttcgcctgtg atatctacat ctgggcgccc | 1020 | |
| ttggccggga cttgtggggt ccttctcctg tcactggtta tcacccttta ctgcaaacgg | 1080 | |
| ggcagaaaga aactcctgta tatattcaaa caaccattta tgagaccagt acaaactact | 1140 | |
| caagaggaag atggctgtag ctgccgattt ccagaagaag aagaaggagg atgtgaactg | 1200 | |
| agagtgaagt tcagcaggag cgcagacgcc cccgcgtacc agcagggcca gaaccagctc | 1260 | |
| tataacgagc tcaatctagg acgaagagag gagtacgatg ttttggacaa gagacgtggc | 1320 | |

| | | |
|---|---|---|
| cgggaccctg agatggggg aaagccgaga aggaagaacc ctcaggaagg cctgtacaat | 1380 | |
| gaactgcaga aagataagat ggcggaggcc tacagtgaga ttgggatgaa aggcgagcgc | 1440 | |
| cggaggggca aggggcacga tggcctttac cagggtctca gtacagccac caaggacacc | 1500 | |
| tacgacgccc ttcacatgca ggccctgccc cctcgctaa | 1539 | |

<210> SEQ ID NO 359
<211> LENGTH: 1494
<212> TYPE: DNA
<213> ORGANISM: Artificial Sequence
<220> FEATURE:
<223> OTHER INFORMATION: Synthetic Construct

<400> SEQUENCE: 359

| | | |
|---|---|---|
| atggctctgc ccgtcaccgc tctgctgctg cctctggctc tgctgctgca cgctgctcgc | 60 | |
| cctcaggtaa agctggagga gtctggggga ggattggtgc aggctggggg ctctctgaga | 120 | |
| ctctcctgtg cagcctctgg aggcacctta agtaagaata ccgtggcttg ggtccgccag | 180 | |
| gctccaggga aggagcgtgg gtttgtaacg tctattacct gtgatggtcg tacgacatac | 240 | |
| tatgcgaact ccgtaaacgg ccgattcccc atcaaccgaa caacgccga gaatttggtg | 300 | |
| gttttgcaaa tgaacagcct gaaacctgac gacacgcccc tttattactg tgcagcatac | 360 | |
| cggaagtcaa taatgtctat tcagcccgac tactggggcc aggggaccca ggtcaccgtc | 420 | |
| tcctcaggag gaggaggatc cggcggagga ggctctcagg tacagctggt ggagtctggg | 480 | |
| ggaggattgg tgcaggctgg gggctctctg agactctcct gtgcagcctc tggaggcacc | 540 | |
| ttaagtaaaa ataccgtggc ttggttccgc caggctccag ggaaggagcg tgggtttgta | 600 | |
| gcgtctatta cctgggatgg tcgtacgaca tactatgcag actccgtgaa gggccgattc | 660 | |
| accatctcca gagacaacgc caagaacaca gtgtatctgc aaatgaacag cctgaaacct | 720 | |
| gaggatacgg ccgtttatgt ctgtgcagac ttagggaaat ggcctgcggg cccggcggac | 780 | |
| tactggggcc aggggaccca ggtcaccgtc tcctcaacta gtaccacgac gccagcgccg | 840 | |
| cgaccaccaa caccggcgcc caccatcgcg tcgcagcccc tgtcctgcg cccagaggcg | 900 | |
| tgccggccag cggcggggg cgcagtgcac acgagggggc tggacttcgc ctgtgatatc | 960 | |
| tacatctggg cgcccttggc cgggacttgt ggggtccttc tcctgtcact ggttatcacc | 1020 | |
| ctttactgca acggggcag aagaaactc ctgtatatat tcaaacaacc atttatgaga | 1080 | |
| ccagtacaaa ctactcaaga ggaagatggc tgtagctgcc gatttccaga agaagaagaa | 1140 | |
| ggaggatgtg aactgagagt gaagttcagc aggagcgcag acgcccccgc gtaccagcag | 1200 | |
| ggccagaacc agctctataa cgagctcaat ctaggacgaa gagaggagta cgatgttttg | 1260 | |
| gacaagagac gtggccggga ccctgagatg ggggaaagc cgagaaggaa gaaccctcag | 1320 | |
| gaaggcctgt acaatgaact gcagaaagat aagatggcgg aggcctacag tgagattggg | 1380 | |
| atgaaaggcg agcgccggag gggcaagggg cacgatggcc tttaccaggg tctcagtaca | 1440 | |
| gccaccaagg acacctacga cgcccttcac atgcaggccc tgccccctcg ctaa | 1494 | |

<210> SEQ ID NO 360
<211> LENGTH: 1509
<212> TYPE: DNA
<213> ORGANISM: Artificial Sequence
<220> FEATURE:
<223> OTHER INFORMATION: Synthetic Construct

<400> SEQUENCE: 360

| | | |
|---|---|---|
| atggctctgc ccgtcaccgc tctgctgctg cctctggctc tgctgctgca cgctgctcgc | 60 | |

```
cctcaggtaa agctggagga gtctggggga ggattggtgc aggctggggg ctctctgaga    120
ctctcctgtg cagcctctgg aggcacctta agtaagaata ccgtggcttg ggtccgccag    180
gctccaggga aggagcgtgg gtttgtaacg tctattacct gtgatggtcg tacgacatac    240
tatgcgaact ccgtaaacgg ccgattcccc atcaaccgaa acaacgccga gaatttggtg    300
gttttgcaaa tgaacagcct gaaacctgac gacacggccc tttattactg tgcagcatac    360
cggaagtcaa taatgtctat tcagcccgac tactggggcc aggggaccca ggtcaccgtc    420
tcctcaggag gaggaggatc cggcggagga ggctctggcg gcggcggcag ccaggtacag    480
ctggtggagt ctgggggagg attggtgcag gctgggggct ctctgagact ctcctgtgca    540
gcctctggag gcaccttaag taaaaatacc gtggcttggt tccgccaggc tccagggaag    600
gagcgtgggt tgtagcgtc tattacctgg gatggtcgta cgacatacta tgcagactcc    660
gtgaagggcc gattcaccat ctccagagac aacgccaaga cacagtgta tctgcaaatg    720 aacagcctga acctgagga tacgccgtt tatgtctgtg cagacttagg gaaatggcct    780
gcgggcccgg cggactactg gggccagggg acccaggtca ccgtctcctc aactagtacc    840
acgacgccag cgccgcgacc accaacaccg gcgcccacca tcgcgtcgca gcccctgtcc    900
ctgcgcccag aggcgtgccg gccagcggcg gggggcgcag tgcacacgag ggggctggac    960
ttcgcctgtg atatctacat ctgggcgccc ttggccggga cttgtggggt ccttctcctg   1020
tcactggtta tcacccttta ctgcaaacgg ggcagaaaga aactcctgta tatattcaaa   1080
caaccattta tgagaccagt acaaactact caagaggaag atggctgtag ctgccgattt   1140
ccagaagaag aagaaggagg atgtgaactg agagtgaagt tcagcaggag cgcagacgcc   1200
cccgcgtacc agcagggcca gaaccagctc tataacgagc tcaatctagg acgaagagag   1260
gagtacgatg ttttggacaa gagacgtggc cgggaccctg atgggggg aaagccgaga   1320 aggaagaacc tcaggaagg cctgtacaat gaactgcaga agataagat ggcggaggcc   1380 tacagtgaga ttgggatgaa aggcgagcgc cggaggggca aggggcacga tggcctttac   1440
cagggtctca gtacagccac caaggacacc tacgacgccc ttcacatgca ggccctgccc   1500
cctcgctaa                                                          1509
```

<210> SEQ ID NO 361
<211> LENGTH: 1524
<212> TYPE: DNA
<213> ORGANISM: Artificial Sequence
<220> FEATURE:
<223> OTHER INFORMATION: Synthetic Construct

<400> SEQUENCE: 361

```
atggctctgc ccgtcaccgc tctgctgctg cctctggctc tgctgctgca cgctgctcgc     60
cctcaggtaa agctggagga gtctggggga ggattggtgc aggctggggg ctctctgaga    120
ctctcctgtg cagcctctgg aggcacctta agtaagaata ccgtggcttg ggtccgccag    180
gctccaggga aggagcgtgg gtttgtaacg tctattacct gtgatggtcg tacgacatac    240
tatgcgaact ccgtaaacgg ccgattcccc atcaaccgaa acaacgccga gaatttggtg    300
gttttgcaaa tgaacagcct gaaacctgac gacacggccc tttattactg tgcagcatac    360
cggaagtcaa taatgtctat tcagcccgac tactggggcc aggggaccca ggtcaccgtc    420
tcctcaggag gaggaggatc cggcggagga ggctctggcg gcggcggctc cggcggcggc    480
ggctcccagg tacagctggt ggagtctggg ggaggattgg tgcaggctgg ggctctctg    540
```

| | |
|---|---:|
| agactctcct gtgcagcctc tggaggcacc ttaagtaaaa ataccgtggc ttggttccgc | 600 |
| caggctccag ggaaggagcg tgggtttgta gcgtctatta cctgggatgg tcgtacgaca | 660 |
| tactatgcag actccgtgaa gggccgattc accatctcca gagacaacgc caagaacaca | 720 |
| gtgtatctgc aaatgaacag cctgaaacct gaggatacgg ccgtttatgt ctgtgcagac | 780 |
| ttagggaaat ggcctgcggg cccggcggac tactggggcc aggggaccca ggtcaccgtc | 840 |
| tcctcaacta gtaccacgac gccagcgccg cgaccaccaa caccggcgcc caccatcgcg | 900 |
| tcgcagcccc tgtccctgcg cccagaggcg tgccggccag cggcgggggg cgcagtgcac | 960 |
| acgaggggc tggacttcgc ctgtgatatc tacatctggg cgcccttggc cgggacttgt | 1020 |
| ggggtccttc tcctgtcact ggttatcacc ctttactgca acggggcag aaagaaactc | 1080 |
| ctgtatatat tcaaacaacc atttatgaga ccagtacaaa ctactcaaga ggaagatggc | 1140 |
| tgtagctgcc gatttccaga agaagaagaa ggaggatgtg aactgagagt gaagttcagc | 1200 |
| aggagcgcag acgccccgc gtaccagcag ggccagaacc agctctataa cgagctcaat | 1260 |
| ctaggacgaa gagaggagta cgatgttttg acaagagac gtggccggga ccctgagatg | 1320 |
| ggggaaagc cgagaaggaa gaaccctcag gaaggcctgt acaatgaact gcagaaagat | 1380 |
| aagatggcgg aggcctacag tgagattggg atgaaaggcg agcgccggag gggcaagggg | 1440 |
| cacgatggcc tttaccaggg tctcagtaca gccaccaagg acacctacga cgcccttcac | 1500 |
| atgcaggccc tgccccctcg ctaa | 1524 |

<210> SEQ ID NO 362
<211> LENGTH: 1476
<212> TYPE: DNA
<213> ORGANISM: Artificial Sequence
<220> FEATURE:
<223> OTHER INFORMATION: Synthetic Construct

<400> SEQUENCE: 362

| | |
|---|---:|
| atggctctgc ccgtcaccgc tctgctgctg cctctggctc tgctgctgca cgctgctcgc | 60 |
| cctcaggtac agctggtgga gtctggggga ggattggtgc aggctggggg ctctctgaga | 120 |
| ctctcctgtg cagcctctgg aggcacctta agtaaaaata ccgtggcttg gttccgccag | 180 |
| gctccaggga aggagcgtgg gtttgtagcg tctattacct gggatggtcg tacgacatac | 240 |
| tatgcagact ccgtgaaggg ccgattcacc atctccagag acaacgccaa gaacacagtg | 300 |
| tatctgcaaa tgaacagcct gaaacctgag gatacggccg tttatgtctg tgcagactta | 360 |
| gggaaatggc ctgcgggccc ggcggactac tggggccagg gacccaggt caccgtctcc | 420 |
| tcaggaggag gaggatctga tgtgcagctg gtggagtctg ggggaggatt ggtgcaggct | 480 |
| gggggctctc tgagactctc ctgtgcagcc tctggaggca ccttaagtaa aataccgtg | 540 |
| gcttgggtcc gccaggctcc agggaaggag cgtgggtttg taacgtctat tacctgtgat | 600 |
| ggtcgtacga catactatgc gaactccgtg aagggccgat tccccatctc cagagacaac | 660 |
| gccgagaaca cagtgtatct gcaaatgaac agcctgaaac ctgaggatac ggccggttat | 720 |
| gtctgtgcag acttagggaa gtggcctgcg ggttcggcgg actactgggg ccaggggacc | 780 |
| cacgtcaccg tctcctccac tagtaccacg acgccagcgc cgcgaccacc aacaccggcg | 840 |
| cccaccatcg cgtcgcagcc cctgtccctg cgcccagagg cgtgccggcc agcggcgggg | 900 |
| ggcgcagtgc acacgagggg gctggacttc gcctgtgata tctacatctg ggcgcccttg | 960 |
| gccgggactt gtggggtcct tctcctgtca ctggttatca cccttactg caacgggc | 1020 |
| agaaagaaac tcctgtatat attcaaacaa ccatttatga ccagtacaa aactactcaa | 1080 |

```
gaggaagatg gctgtagctg ccgatttcca gaagaagaag aaggaggatg tgaactgaga    1140
gtgaagttca gcaggagcgc agacgccccc gcgtaccagc agggccagaa ccagctctat    1200
aacgagctca atctaggacg aagagaggag tacgatgttt tggacaagag acgtggccgg    1260
gaccctgaga tgggggggaaa gccgagaagg aagaaccctc aggaaggcct gtacaatgaa    1320
ctgcagaaag ataagatggc ggaggcctac agtgagattg ggatgaaagg cgagcgccgg    1380
aggggcaagg ggcacgatgg cctttaccag ggtctcagta cagccaccaa ggacacctac    1440
gacgcccttc acatgcaggc cctgcccccct cgctaa                             1476
```

<210> SEQ ID NO 363
<211> LENGTH: 1506
<212> TYPE: DNA
<213> ORGANISM: Artificial Sequence
<220> FEATURE:
<223> OTHER INFORMATION: Synthetic Construct

<400> SEQUENCE: 363

```
atggctctgc ccgtcaccgc tctgctgctg cctctggctc tgctgctgca cgctgctcgc      60
cctcaggtac agctggtgga gtctggggga ggattggtgc aggctggggg ctctctgaga     120
ctctcctgtg cagcctctgg aggcacctta agtaaaaata ccgtggcttg gttccgccag     180
gctccaggga aggagcgtgg gtttgtagcg tctattacct gggatggtcg tacgacatac     240
tatgcagact ccgtgaaggg ccgattcacc atctccagag acaacgccaa gaacacagtg     300
tatctgcaaa tgaacagcct gaaacctgag gatacggccg tttatgtctg tgcagactta     360
gggaaatggc ctgcgggccc ggcggactac tggggccagg ggacccaggt caccgtctcc     420
tcaggaggag gaggatctgg aggaggagga agcggaggag gaggatccga tgtgcagctg     480
gtggagtctg ggggaggatt ggtgcaggct gggggctctc tgagactctc ctgtgcagcc     540
tctggaggca ccttaagtaa gaataccgtg gcttgggtcc gccaggctcc agggaaggag     600
cgtgggtttg taacgtctat tacctgtgat ggtcgtacga catactatgc gaactccgtg     660
aagggccgat tccccatctc cagagacaac gccgagaaca cagtgtatct gcaaatgaac     720
agcctgaaac tgaggatac ggccggttat gtctgtgcag acttagggaa gtggcctgcg     780
ggttcggcgg actactgggg ccaggggacc cacgtcaccg tctcctccac tagtaccacg     840
acgccagcgc cgcgaccacc aacaccggcg cccaccatcg cgtcgcagcc cctgtccctg     900
cgcccagagg cgtgccggcc agcggcgggg ggcgcagtgc acacgagggg gctggacttc     960
gcctgtgata tctacatctg gcgcccctttg ccgggactt gtggggtcct tctcctgtca    1020
ctggttatca ccctttactg caaacggggc agaagaaaac tcctgtatat attcaaacaa    1080
ccatttatga gaccagtaca aactactcaa gaggaagatg gctgtagctg ccgatttcca    1140
gaagaagaag aaggaggatg tgaactgaga gtgaagttca gcaggagcgc agacgccccc    1200
gcgtaccagc agggccagaa ccagctctat aacgagctca atctaggacg aagagaggag    1260
tacgatgttt tggacaagag acgtggccgg gaccctgaga tgggggggaaa gccgagaagg    1320 aagaaccctc aggaaggcct gtacaatgaa ctgcagaaag ataagatggc ggaggcctac    1380
agtgagattg ggatgaaagg cgagcgccgg aggggcaagg ggcacgatgg cctttaccag    1440
ggtctcagta cagccaccaa ggacacctac gacgcccttc acatgcaggc cctgcccccct    1500 cgctaa                                                                1506
```

<210> SEQ ID NO 364

<211> LENGTH: 1536
<212> TYPE: DNA
<213> ORGANISM: Artificial Sequence
<220> FEATURE:
<223> OTHER INFORMATION: Synthetic Construct

<400> SEQUENCE: 364

```
atggctctgc cgtcaccgc tctgctgctg cctctggctc tgctgctgca cgctgctcgc    60
cctcaggtac agctggtgga gtctggggga ggattggtgc aggctggggg ctctctgaga   120
ctctcctgtg cagcctctgg aggcacctta agtaaaaata ccgtggcttg gttccgccag   180
gctccaggga aggagcgtgg gtttgtagcg tctattacct gggatggtcg tacgacatac   240
tatgcagact ccgtgaaggg ccgattcacc atctccagag acaacgccaa gaacacagtg   300
tatctgcaaa tgaacagcct gaaacctgag gatacggccg tttatgtctg tgcagactta   360
gggaaatggc ctgcgggccc ggcggactac tggggccagg gacccaggt caccgtctcc   420
tcaggaggag gaggatctgg aggaggagga agcggaggag gaggaagcgg cggcggcggc   480
tctggcggcg gcggcagcga tgtgcagctg gtggagtctg ggggaggatt ggtgcaggct   540
gggggctctc tgagactctc ctgtgcagcc tctgaggca ccttaagtaa aataccgtg   600
gcttgggtcc gccaggctcc agggaaggag cgtgggtttg taacgtctat tacctgtgat   660
ggtcgtacga catactatgc gaactccgtg aagggccgat tccccatctc cagagacaac   720
gccgagaaca cagtgtatct gcaaatgaac agcctgaaac tgaggatac ggccggttat   780
gtctgtgcag acttagggaa gtggcctgcg ggttcggcgg actactgggg ccaggggacc   840
cacgtcaccg tctcctccac tagtaccacg acgccagcgc cgcgaccacc aacaccggcg   900
cccaccatcg cgtcgcagcc cctgtccctg cgcccagagg cgtgccggcc agcggcgggg   960
ggcgcagtgc acacgagggg gctggacttc gcctgtgata tctacatctg ggcgcccttg  1020
gccgggactt gtggggtcct tctcctgtca ctggttatca ccctttactg caaacggggc  1080
agaaagaaac tcctgtatat attcaaacaa ccatttatga ccagtacaa actactcaa  1140
gaggaagatg gctgtagctg ccgatttcca gaagaagaag aaggaggatg tgaactgaga  1200
gtgaagttca gcaggagcgc agacgccccc cgcgtaccag cagggccagaa ccagctctat  1260
aacgagctca atctaggacg aagagaggag tacgatgttt tggacaagag acgtggccgg  1320
gacccctgaga tggggggaaa gccgagaagg aagaaccctc aggaaggcct gtacaatgaa  1380
ctgcagaaag ataagatggc ggaggcctac agtgagattg ggatgaaagg cgagcgccgg  1440
aggggcaagg gcacgatgg cctttaccag ggtctcagta cagccaccaa ggacacctac  1500
gacgcccttc acatgcaggc cctgcccct cgctaa                             1536
```

<210> SEQ ID NO 365
<211> LENGTH: 1491
<212> TYPE: DNA
<213> ORGANISM: Artificial Sequence
<220> FEATURE:
<223> OTHER INFORMATION: Synthetic Construct

<400> SEQUENCE: 365

```
atggctctgc cgtcaccgc tctgctgctg cctctggctc tgctgctgca cgctgctcgc    60
cctcaggtac agctggtgga gtctggggga ggattggtgc aggctggggg ctctctgaga   120
ctctcctgtg cagcctctgg aggcacctta agtaaaaata ccgtggcttg gttccgccag   180
gctccaggga aggagcgtgg gtttgtagcg tctattacct gggatggtcg tacgacatac   240
tatgcagact ccgtgaaggg ccgattcacc atctccagag acaacgccaa gaacacagtg   300
```

```
tatctgcaaa tgaacagcct gaaacctgag gatacggccg tttatgtctg tgcagactta        360
gggaaatggc ctgcgggccc ggcggactac tggggccagg ggacccaggt caccgtctcc        420
tcaggaggag gaggatccgg cggaggaggc tctgatgtgc agctggtgga gtctggggga        480
ggattggtgc aggctggggg ctctctgaga ctctcctgtg cagcctctgg aggcacctta        540
agtaagaata ccgtggcttg ggtccgccag gctccaggga aggagcgtgg gtttgtaacg        600
tctattacct gtgatggtcg tacgacatac tatgcgaact ccgtgaaggg ccgattcccc        660
atctccagag acaacgccga gaacacagtg tatctgcaaa tgaacagcct gaaacctgag        720
gatacggccg tttatgtctg tgcagactta gggaagtggc ctgcgggttc ggcggactac        780
tggggccagg ggacccacgt caccgtctcc tccactagta ccacgacgcc agcgccgcga        840
ccaccaacac cggcgcccac catcgcgtcg cagcccctgt ccctgcgccc agaggcgtgc        900
cggccagcgg cggggggcgc agtgcacacg agggggctgg acttcgcctg tgatatctac        960
atctgggcgc ccttggccgg gacttgtggg gtccttctcc tgtcactggt tatcacccct        1020
tactgcaaac ggggcagaaa gaaactcctg tatatattca acaaccatt tatgagacca         1080 gtacaaacta ctcaagagga agatggctgt agctgccgat tccagaaga agaagaagga        1140 ggatgtgaac tgagagtgaa gttcagcagg agcgcagacg ccccccgcgta ccagcagggc        1200 cagaaccagc tctataacga gctcaatcta ggacgaagag aggagtacga tgttttggac        1260
aagagacgtg gccgggaccc tgagatgggg ggaaagccga aaggaagaa ccctcaggaa         1320 ggcctgtaca atgaactgca gaaagataag atggcggagg cctacagtga gattgggatg        1380
aaaggcgagc gccggagggg caaggggcac gatggccttt accagggtct cagtacagcc        1440
accaaggaca cctacgacgc ccttcacatg caggccctgc cccctcgcta a                1491

<210> SEQ ID NO 366
<211> LENGTH: 1506
<212> TYPE: DNA
<213> ORGANISM: Artificial Sequence
<220> FEATURE:
<223> OTHER INFORMATION: Synthetic Construct

<400> SEQUENCE: 366
atggctctgc ccgtcaccgc tctgctgctg cctctggctc tgctgctgca cgctgctcgc         60
cctcaggtac agctggtgga gtctggggga ggattggtgc aggctggggg ctctctgaga        120
ctctcctgtg cagcctctgg aggcacctta agtaaaaata ccgtggcttg gttccgccag        180
gctccaggga aggagcgtgg gtttgtagcg tctattacct gggatggtcg tacgacatac        240
tatgcagact ccgtgaaggg ccgattcacc atctccagag acaacgccaa gaacacagtg        300
tatctgcaaa tgaacagcct gaaacctgag gatacggccg tttatgtctg tgcagactta        360
gggaaatggc ctgcgggccc ggcggactac tggggccagg gacccaggt caccgtctcc         420 tcaggaggag gaggatccgg cggaggaggc tctgcggcg cggcagcga tgtgcagctg        480 gtggagtctg ggggaggatt ggtgcaggct gggggctctc tgagactctc ctgtgcagcc        540
tctggaggca ccttaagtaa gaataccgtg gcttgggtcc gccaggctcc agggaaggag        600
cgtgggtttg taacgtctat tacctgtgat ggtcgtacga catactatgc gaactccgtg        660
aagggccgat tccccatctc cagagacaac gccgagaaca cagtgtatct gcaaatgaac        720
agcctgaaac ctgaggatac ggccggttat gtctgtgcag acttagggaa gtggcctgcg        780
ggttcggcgg actactgggg ccaggggacc cacgtcaccg tctcctccac tagtaccacg        840
```

```
acgccagcgc cgcgaccacc aacaccggcg cccaccatcg cgtcgcagcc cctgtccctg      900
cgcccagagg cgtgccggcc agcggcgggg ggcgcagtgc acacgagggg gctggacttc      960
gcctgtgata tctacatctg ggcgcccttg gccgggactt gtggggtcct tctcctgtca     1020
ctggttatca ccctttactg caaacggggc agaaagaaac tcctgtatat attcaaacaa     1080
ccatttatga gaccagtaca aactactcaa gaggaagatg gctgtagctg ccgatttcca     1140
gaagaagaag aaggaggatg tgaactgaga gtgaagttca gcaggagcgc agacgccccc     1200
gcgtaccagc agggccagaa ccagctctat aacgagctca atctaggacg aagagaggag     1260
tacgatgttt tggacaagag acgtggccgg gaccctgaga tgggggaaa gccgagaagg     1320 aagaaccctc aggaaggcct gtacaatgaa ctgcagaaag ataagatggc ggaggcctac     1380
agtgagattg ggatgaaagg cgagcgccgg aggggcaagg gcacgatgg cctttaccag     1440 ggtctcagta cagccaccaa ggacacctac gacgcccttc acatgcaggc cctgccccct     1500
cgctaa                                                                1506

<210> SEQ ID NO 367
<211> LENGTH: 1521
<212> TYPE: DNA
<213> ORGANISM: Artificial Sequence
<220> FEATURE:
<223> OTHER INFORMATION: Synthetic Construct

<400> SEQUENCE: 367
atggctctgc ccgtcaccgc tctgctgctg cctctggctc tgctgctgca cgctgctcgc       60
cctcaggtac agctggtgga gtctggggga ggattggtgc aggctggggg ctctctgaga      120
ctctcctgtg cagcctctgg aggcacctta agtaaaaata ccgtggcttg gttccgccag      180
gctccaggga aggagcgtgg gtttgtagcg tctattacct gggatggtcg tacgacatac      240
tatgcagact ccgtgaaggg ccgattcacc atctccagag acaacgccaa gaacacagtg      300
tatctgcaaa tgaacagcct gaaacctgag gatacggccg tttatgtctg tgcagactta      360
gggaaatggc ctgcgggccc ggcggactac tggggccagg ggacccaggt caccgtctcc      420
tcaggaggag gaggatccgg cggagggagc tctggcggcg gcggctccgg cggcggcggc      480
tccgatgtgc agctggtgga gtctggggga ggattggtgc aggctggggg ctctctgaga      540
ctctcctgtg cagcctctgg aggcacctta agtaagaata ccgtggcttg ggtccgccag      600
gctccaggga aggagcgtgg gtttgtaacg tctattacct gtgatggtcg tacgacatac      660
tatgcgaact ccgtgaaggg ccgattcccc atctccagag acaacgccga gaacacagtg      720
tatctgcaaa tgaacagcct gaaacctgag gatacggccg ttatgtctg tgcagactta      780 gggaagtggc ctgcgggttc ggcggactac tggggccagg ggacccacgt caccgtctcc      840
tccactagta ccacgacgcc agcgccgcga ccaccaacac cggcgcccac catcgcgtcg      900
cagcccctgt ccctgcgccc agaggcgtgc cggccagcgg cggggggcgc agtgcacacg      960
agggggctgg acttcgcctg tgatatctac atctgggcgc ccttggccgg gacttgtggg     1020
gtccttctcc tgtcactggt tatcacccct tactgcaaac ggggcagaaa gaaactcctg     1080
tatatattca acaaccatt tatgagacca gtacaaacta ctcaagagga gatggctgt     1140 agctgccgat tccagaaga agaagaagga ggatgtgaac tgagagtgaa gttcagcagg     1200
agcgcagacg ccccgcgta ccagcagggc cagaaccagc tctataacga gctcaatcta     1260
ggacgaagag aggagtacga tgttttggac aagagacgtg gccgggaccc tgagatgggg     1320
ggaaagccga gaaggaagaa ccctcaggaa ggcctgtaca atgaactgca gaaagataag     1380
```

```
atggcggagg cctacagtga gattgggatg aaaggcgagc gccggagggg caaggggcac    1440
gatggccttt accagggtct cagtacagcc accaaggaca cctacgacgc ccttcacatg    1500
caggccctgc cccctcgcta a                                              1521
```

<210> SEQ ID NO 368
<211> LENGTH: 1473
<212> TYPE: DNA
<213> ORGANISM: Artificial Sequence
<220> FEATURE:
<223> OTHER INFORMATION: Synthetic Construct

<400> SEQUENCE: 368

```
atggctctgc ccgtcaccgc tctgctgctg cctctggctc tgctgctgca cgctgctcgc      60
cctgatgtgc agctggtgga gtctggggga ggattggtgc aggctggggg ctctctgaga     120
ctctcctgtg cagcctctgg aggcacctta agtaagaata ccgtggcttg ggtccgccag     180
gctccaggga aggagcgtgg gtttgtaacg tctattacct gtgatggtcg tacgacatac     240
tatgcgaact ccgtgaaggg ccgattcccc atctccagag acaacgccga aacacagtg      300 tatctgcaaa tgaacagcct gaaacctgag gatacggccg ttatgtctg tgcagactta     360 gggaagtggc ctgcgggttc ggcggactac tggggccagg ggacccacgt caccgtctcc    420
tccggaggag gaggatctga tgtgcagctg gtggagtctg ggggaggctt ggtgcagcct    480
ggggggtctc tgagactctc ctgtgcagcc tctggacgga ccttcagtag cattgtcatg    540
ggctggttcc gccaggctcc agggaaggag cgtgagtttg taggagcgat tatgtggaat    600
gatggtatta catacttgca agactccgtg aagggccgat ttaccatctt cagagacaac    660
gccaagaaca cggtgtatct gcaaatgaac agcctgaaac ttgaggatac ggccgtttat    720
tactgtgcag catccaaggg tagatactcg gaatatgagt actggggcca ggggacccag    780
gtcaccgtct cctcaactag taccacgacg ccagcgccgc gaccaccaac accggcgccc    840
accatcgcgt cgcagcccct gtccctgcgc ccagaggcgt gccggccagc ggcgggggc    900 gcagtgcaca cgaggggct ggacttcgcc tgtgatatct acatctgggc gcccttggcc     960
gggacttgtg ggtccttct cctgtcactg gttatcaccc tttactgcaa acggggcaga   1020
aagaaactcc tgtatatatt caaacaacca tttatgagac cagtacaaac tactcaagag   1080
gaagatggct gtagctgccg atttccagaa gaagaagaag aggatgtgaa actgagagtg   1140
aagttcagca ggagcgcaga cgcccccgcg taccagcagg gccagaacca gctctataac   1200
gagctcaatc taggacgaag agaggagtac gatgttttgg acaagagacg tggccggac   1260 cctgagatgg ggggaaagcc gagaaggaag aaccctcagg aaggcctgta caatgaactg   1320
cagaaagata gatggcggag gcctacagt gagattggga tgaaaggcga gccgccggagg   1380 ggcaaggggc acgatggcct ttaccagggt ctcagtacag ccaccaagga cacctacgac   1440
gcccttcaca tgcaggccct gccccctcgc taa                                1473
```

<210> SEQ ID NO 369
<211> LENGTH: 1503
<212> TYPE: DNA
<213> ORGANISM: Artificial Sequence
<220> FEATURE:
<223> OTHER INFORMATION: Synthetic Construct

<400> SEQUENCE: 369

```
atggctctgc ccgtcaccgc tctgctgctg cctctggctc tgctgctgca cgctgctcgc      60
```

-continued

```
cctgatgtgc agctggtgga gtctggggga ggattggtgc aggctggggg ctctctgaga      120
ctctcctgtg cagcctctgg aggcaccta agtaagaata ccgtggcttg ggtccgccag      180
gctccaggga aggagcgtgg gtttgtaacg tctattacct gtgatggtcg tacgacatac      240
tatgcgaact ccgtgaaggg ccgattcccc atctccagag acaacgccga gaacacagtg      300
tatctgcaaa tgaacagcct gaaacctgag gatacggccg ttatgtctg tgcagactta      360 gggaagtggc ctgcgggttc ggcggactac tggggccagg gacccacgt caccgtctcc      420 tccggaggag gaggatctgg aggaggagga agcggaggag gaggatccga tgtgcagctg      480
gtggagtctg ggggaggctt ggtgcagcct ggggggtctc tgagactctc ctgtgcagcc      540
tctggacgga ccttcagtag cattgtcatg ggctggttcc gccaggctcc agggaaggag      600
cgtgagtttg taggagcgat tatgtggaat gatggtatta catacttgca agactccgtg      660
aagggccgat ttaccatctt cagagacaac gccaagaaca cggtgtatct gcaaatgaac      720
agcctgaaac ttgaggatac ggccgtttat tactgtgcag catccaaggg tagatactcg      780
gaatatgagt actggggcca ggggaccag gtcaccgtct cctcaactag taccacgacg      840
ccagcgccgc gaccaccaac accggcgccc accatcgcgt cgcagcccct gtccctgcgc      900
ccagaggcgt gccggccagc ggcggggggc gcagtgcaca cgagggggct ggacttcgcc      960
tgtgatatct acatctgggc gcccttggcc gggacttgtg gggtccttct cctgtcactg     1020
gttatcaccc tttactgcaa acggggcaga aagaaactcc tgtatatatt caaacaacca     1080
tttatgagac cagtacaaac tactcaagag gaagatggct gtagctgccg atttccagaa     1140
gaagaagaag aggatgtga actgagagtg aagttcagca ggagcgcaga cgccccgcg     1200 taccagcagg gccagaacca gctctataac gagctcaatc taggacgaag agaggagtac     1260 gatgtttgg acaagagacg tggccggac cctgagatgg ggggaaagcc gagaaggaag     1320
aaccctcagg aaggcctgta caatgaactg cagaaagata gatggcgga ggcctacagt     1380 gagattggga tgaaaggcga gcgccggagg ggcaaggggc acgatggcct ttaccagggt     1440
ctcagtacag ccaccaagga cacctacgac gcccttcaca tgcaggccct gccccctcgc     1500
taa                                                                  1503
```

```
<210> SEQ ID NO 370
<211> LENGTH: 1533
<212> TYPE: DNA
<213> ORGANISM: Artificial Sequence
<220> FEATURE:
<223> OTHER INFORMATION: Synthetic Construct

<400> SEQUENCE: 370
```

```
atggctctgc ccgtcaccgc tctgctgctg cctctggctc tgctgctgca cgctgctcgc       60
cctgatgtgc agctggtgga gtctggggga ggattggtgc aggctggggg ctctctgaga      120
ctctcctgtg cagcctctgg aggcaccta agtaagaata ccgtggcttg ggtccgccag      180
gctccaggga aggagcgtgg gtttgtaacg tctattacct gtgatggtcg tacgacatac      240
tatgcgaact ccgtgaaggg ccgattcccc atctccagag acaacgccga gaacacagtg      300
tatctgcaaa tgaacagcct gaaacctgag gatacggccg ttatgtctg tgcagactta      360 gggaagtggc ctgcgggttc ggcggactac tggggccagg gacccacgt caccgtctcc      420 tccggaggag gaggatctgg aggaggagga agcggaggag gaggaagcgg cggcggcggc      480
tctggcggcg cgcagcga tgtgcagctg gtggagtctg ggggaggctt ggtgcagcct      540
ggggggtctc tgagactctc ctgtgcagcc tctggacgga ccttcagtag cattgtcatg      600
```

```
ggctggttcc gccaggctcc agggaaggag cgtgagtttg taggagcgat tatgtggaat    660
gatggtatta catacttgca agactccgtg aagggccgat ttaccatctt cagagacaac    720
gccaagaaca cggtgtatct gcaaatgaac agcctgaaac ttgaggatac ggccgtttat    780
tactgtgcag catccaaggg tagatactcg gaatatgagt actggggcca ggggacccag    840
gtcaccgtct cctcaactag taccacgacg ccagcgccgc gaccaccaac accggcgccc    900
accatcgcgt cgcagcccct gtccctgcgc ccagaggcgt gccggccagc ggcgggggc     960
gcagtgcaca cgagggggct ggacttcgcc tgtgatatct acatctgggc gcccttggcc   1020
gggacttgtg ggtccttct cctgtcactg gttatcaccc tttactgcaa acggggcaga   1080
aagaaactcc tgtatatatt caaacaacca tttatgagac cagtacaaac tactcaagag   1140
gaagatggct gtagctgccg atttccagaa gaagaagaag gaggatgtga actgagagtg   1200
aagttcagca ggagcgcaga cgccccgcg taccagcagg gccagaacca gctctataac   1260
gagctcaatc taggacgaag agaggagtac gatgttttgg acaagagacg tggccgggac   1320
cctgagatgg ggggaaagcc gagaaggaag aaccctcagg aaggcctgta caatgaactg   1380
cagaaagata gatggcgga ggcctacagt gagattggga tgaaaggcga cgcgcggagg   1440
ggcaagggc acgatggcct ttaccagggt ctcagtacag ccaccaagga cacctacgac   1500
gcccttcaca tgcaggccct gccccctcgc taa                                1533
```

<210> SEQ ID NO 371
<211> LENGTH: 1488
<212> TYPE: DNA
<213> ORGANISM: Artificial Sequence
<220> FEATURE:
<223> OTHER INFORMATION: Synthetic Construct

<400> SEQUENCE: 371

```
atggctctgc ccgtcaccgc tctgctgctg cctctggctc tgctgctgca cgctgctcgc     60
cctgatgtgc agctggtgga gtctggggga ggattggtgc aggctggggg ctctctgaga    120
ctctcctgtg cagcctctgg aggcacctta agtaagaata ccgtggcttg ggtccgccag    180
gctccaggga aggagcgtgg gtttgtaacg tctattacct gtgatggtcg tacgacatac    240
tatgcgaact ccgtgaaggg ccgattcccc atctccagag acaacgccga gaacacagtg    300
tatctgcaaa tgaacagcct gaaacctgag gatacggccg ttatgtctg tcagacttta    360
gggaagtggc ctgcgggttc ggcggactac tggggccagg ggacccacgt caccgtctcc    420
tccggaggag gaggatccgg cggaggaggc tctgatgtgc agctggtgga gtctggggga    480
ggcttggtgc agcctggggg gtctctgaga ctctcctgtg cagcctctgg acggaccttc    540
agtagcattg tcatgggctg gttccgccag gctccaggga aggagcgtga gtttgtagga    600
gcgattatgt ggaatgatgg tattacatac ttgcaagact ccgtgaaggg ccgatttacc    660
atcttcagag acaacgccaa gaacacggtg tatctgcaaa tgaacagcct gaaacttgag    720
gatacggccg tttattactg tgcagcatcc aagggtagat actcggaata tgagtactgg    780
ggccagggga cccaggtcac cgtctcctca actagtacca cgacgccagc gccgcgacca    840
ccaacaccgg cgcccaccat cgcgtcgcag cccctgtccc tgcgcccaga ggcgtgccgg    900
ccagcggcgg ggggcgcagt gcacacgagg gggctggact cgcctgtga tatctacatc    960
tgggcgccct tggccgggac ttgtggggtc cttctcctgt cactggttat cacccttac   1020
tgcaaacggg gcagaaagaa actcctgtat atattcaaac aaccatttat gagaccagta   1080
```

```
caaactactc aagaggaaga tggctgtagc tgccgatttc cagaagaaga agaaggagga    1140
tgtgaactga gagtgaagtt cagcaggagc gcagacgccc ccgcgtacca gcagggccag    1200
aaccagctct ataacgagct caatctagga cgaagagagg agtacgatgt tttggacaag    1260
agacgtggcc gggaccctga gatgggggga aagccgagaa ggaagaaccc tcaggaaggc    1320
ctgtacaatg aactgcagaa agataagatg gcggaggcct acagtgagat tgggatgaaa    1380
ggcgagcgcc ggaggggcaa ggggcacgat ggcctttacc agggtctcag tacagccacc    1440 aaggacaccct acgacgccct tcacatgcag gccctgcccc tcgctaa               1488

<210> SEQ ID NO 372
<211> LENGTH: 1503
<212> TYPE: DNA
<213> ORGANISM: Artificial Sequence
<220> FEATURE:
<223> OTHER INFORMATION: Synthetic Construct

<400> SEQUENCE: 372
atggctctgc ccgtcaccgc tctgctgctg cctctggctc tgctgctgca cgctgctcgc      60
cctgatgtgc agctggtgga gtctggggga ggattggtgc aggctggggg ctctctgaga     120
ctctcctgtg cagcctctgg aggcacctta agtaagaata ccgtggcttg ggtccgccag     180
gctccaggga aggagcgtgg gtttgtaacg tctattacct gtgatggtcg tacgacatac     240
tatgcgaact ccgtgaaggg ccgattcccc atctccagag acaacgccga gaacacagtg     300
tatctgcaaa tgaacagcct gaaacctgag gatacggccg ttatgtctg cagactta       360 gggaagtggc ctgcgggttc ggcggactac tggggccagg gaccacgt caccgtctcc      420 tccggaggag gaggatccgg cggaggaggc tctggcggcg gcggcagcga tgtgcagctg     480
gtggagtctg ggggaggctt ggtgcagcct gggggggtctc tgagactctc ctgtgcagcc    540
tctggacgga ccttcagtag cattgtcatg ggctggttcc gccaggctcc agggaaggag    600
cgtgagtttg taggagcgat tatgtggaat gatggtatta catacttgca agactccgtg    660
aagggccgat ttaccatctt cagagacaac gccaagaaca cggtgtatct gcaaatgaac    720
agcctgaaac ttgaggatac ggccgtttat tactgtgcag catccaaggg tagatactcg    780
gaatatgagt actggggcca ggggacccag gtcaccgtct cctcaactag taccacgacg    840
ccagcgccgc gaccaccaac accggcgccc accatcgcgt cgcagcccct gtccctgcgc    900
ccagaggcgt gccggccagc ggcggggggc gcagtgcaca cgagggggct ggacttcgcc    960
tgtgatatct acatctgggc gcccttggcc gggacttgtg ggtccttct cctgtcactg   1020 gttatcaccc tttactgcaa acggggcaga aagaaactcc tgtatatatt caaacaacca   1080
tttatgagac cagtacaaac tactcaagag gaagatggct gtagctgccg atttccagaa   1140
gaagaagaag gaggatgtga actgagagtg aagttcagca ggagcgcaga cgcccccgcg   1200
taccagcagg gccagaacca gctctataac gagctcaatc taggacgaag agaggagtac   1260
gatgttttgg acaagagacg tggccgggac cctgagatgg ggggaaagcc gagaaggaag   1320
aaccctcagg aaggcctgta caatgaactg cagaaagata agatggcgga ggcctacagt   1380
gagattggga tgaaaggcga gcgcggagg ggcaaggggc acgatggcct ttaccagggt   1440
ctcagtacag ccaccaagga cacctacgac gcccttcaca tgcaggccct gcccctcgc   1500 taa                                                              1503

<210> SEQ ID NO 373
<211> LENGTH: 1518
```

```
<212> TYPE: DNA
<213> ORGANISM: Artificial Sequence
<220> FEATURE:
<223> OTHER INFORMATION: Synthetic Construct

<400> SEQUENCE: 373
atggctctgc cgtcaccgc tctgctgctg cctctggctc tgctgctgca cgctgctcgc    60
cctgatgtgc agctggtgga gtctggggga ggattggtgc aggctggggg ctctctgaga   120
ctctcctgtg cagcctctgg aggcacctta agtaagaata ccgtggcttg ggtccgccag   180
gctccaggga aggagcgtgg gtttgtaacg tctattacct gtgatggtcg tacgacatac   240
tatgcgaact ccgtgaaggg ccgattcccc atctccagag acaacgccga gaacacagtg   300
tatctgcaaa tgaacagcct gaaacctgag gatacggccg ttatgtctg tgcagactta    360 gggaagtggc ctgcgggttc ggcggactac tggggccagg gaacccacgt caccgtctcc   420
tccggaggag gaggatccgg cggaggaggc tctggcggcg gcggctccgg cggcggcggc   480
tccgatgtgc agctggtgga gtctggggga ggcttggtgc agcctggggg gtctctgaga   540
ctctcctgtg cagcctctgg acggaccttc agtagcattg tcatgggctg gttccgccag   600
gctccaggga aggagcgtga gtttgtagga gcgattatgt ggaatgatgg tattacatac   660
ttgcaagact ccgtgaaggg ccgatttacc atcttcagag acaacgccaa gaacacggtg   720
tatctgcaaa tgaacagcct gaaacttgag gatacggccg tttattactg tgcagcatcc   780
aagggtagat actcggaata tgagtactgg ggccagggga cccaggtcac cgtctcctca   840
actagtacca cgacgccagc gccgcgacca ccaacaccgg cgcccaccat cgcgtcgcag   900
cccctgtccc tgcgcccaga ggcgtgccgg ccagcggcgg ggggcgcagt gcacacgagg   960
gggctggact cgcctgtga tatctacatc tgggcgccct tggccgggac ttgtgggtc  1020 cttctcctgt cactggttat caccctttac tgcaaacggg gcagaaagaa actcctgtat  1080
atattcaaac aaccatttat gagaccagta caaactactc aagaggaaga tggctgtagc  1140
tgccgatttc cagaagaaga agaaggagga tgtgaactga gagtgaagtt cagcaggagc  1200
gcagacgccc ccgcgtacca gcagggccag aaccagctct ataacgagct caatctagga  1260
cgaagagagg agtacgatgt tttggacaag agacgtggcc gggaccctga gatggggga   1320 aagccgagaa ggaagaaccc tcaggaaggc ctgtacaatg aactgcagaa agataagatg  1380
gcggaggcct acagtgagat tgggatgaaa ggcgagcgcc ggaggggcaa ggggcacgat  1440
ggcctttacc agggtctcag tacagccacc aaggacacct cgacgccct tcacatgcag  1500 gccctgcccc ctcgctaa                                                1518

<210> SEQ ID NO 374
<211> LENGTH: 23
<212> TYPE: DNA
<213> ORGANISM: Artificial Sequence
<220> FEATURE:
<223> OTHER INFORMATION: Synthetic Construct

<400> SEQUENCE: 374
gtcctggctg ctcttctaca agg                                            23

<210> SEQ ID NO 375
<211> LENGTH: 23
<212> TYPE: DNA
<213> ORGANISM: Artificial Sequence
<220> FEATURE:
<223> OTHER INFORMATION: Synthetic Construct
```

-continued

```
<400> SEQUENCE: 375
ggtacgtgct gttgaactgt tcc                                              23

<210> SEQ ID NO 376
<211> LENGTH: 29
<212> TYPE: DNA
<213> ORGANISM: Artificial Sequence
<220> FEATURE:
<223> OTHER INFORMATION: Synthetic Construct

<400> SEQUENCE: 376
gatgtgcagc tgcaggagtc tggaggagg                                        29

<210> SEQ ID NO 377
<211> LENGTH: 29
<212> TYPE: DNA
<213> ORGANISM: Artificial Sequence
<220> FEATURE:
<223> OTHER INFORMATION: Synthetic Construct

<400> SEQUENCE: 377
gatgtgcagc tgcaggagtc tgggggagg                                        29

<210> SEQ ID NO 378
<211> LENGTH: 34
<212> TYPE: DNA
<213> ORGANISM: Artificial Sequence
<220> FEATURE:
<223> OTHER INFORMATION: Synthetic Construct

<400> SEQUENCE: 378
ctagtgcggc cgctgaggag acggtgacct gggt                                  34

<210> SEQ ID NO 379
<211> LENGTH: 9
<212> TYPE: DNA
<213> ORGANISM: Artificial Sequence
<220> FEATURE:
<223> OTHER INFORMATION: Synthetic Construct

<400> SEQUENCE: 379 gccgccacc                                                               9

<210> SEQ ID NO 380
<211> LENGTH: 6
<212> TYPE: DNA
<213> ORGANISM: Artificial Sequence
<220> FEATURE:
<223> OTHER INFORMATION: Synthetic Construct

<400> SEQUENCE: 380 gaattc                                                                  6

<210> SEQ ID NO 381
<211> LENGTH: 6
<212> TYPE: DNA
<213> ORGANISM: Artificial Sequence
<220> FEATURE:
<223> OTHER INFORMATION: Synthetic Construct

<400> SEQUENCE: 381 actagt                                                                  6

<210> SEQ ID NO 382
<211> LENGTH: 6
```

<212> TYPE: DNA
<213> ORGANISM: Artificial Sequence
<220> FEATURE:
<223> OTHER INFORMATION: Synthetic Construct

<400> SEQUENCE: 382 gttaac                                                                    6

<210> SEQ ID NO 383
<211> LENGTH: 6
<212> TYPE: DNA
<213> ORGANISM: Artificial Sequence
<220> FEATURE:
<223> OTHER INFORMATION: Synthetic Construct

<400> SEQUENCE: 383 acgcgt                                                                    6

<210> SEQ ID NO 384
<211> LENGTH: 6
<212> TYPE: DNA
<213> ORGANISM: Artificial Sequence
<220> FEATURE:
<223> OTHER INFORMATION: Synthetic Construct

<400> SEQUENCE: 384 atgcat                                                                    6

<210> SEQ ID NO 385
<211> LENGTH: 21
<212> TYPE: PRT
<213> ORGANISM: Artificial Sequence
<220> FEATURE:
<223> OTHER INFORMATION: Synthetic Construct

<400> SEQUENCE: 385

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 386
<211> LENGTH: 18
<212> TYPE: PRT
<213> ORGANISM: Homo sapiens

<400> SEQUENCE: 386

Met Lys Trp Val Thr Phe Ile Ser Leu Leu Phe Leu Phe Ser Ser Ala
1               5                   10                  15

Tyr Ser

<210> SEQ ID NO 387
<211> LENGTH: 9
<212> TYPE: PRT
<213> ORGANISM: Artificial Sequence
<220> FEATURE:
<223> OTHER INFORMATION: Synthetic Construct

<400> SEQUENCE: 387

Gly Ser Gly His His His His His His
1               5

<210> SEQ ID NO 388
<211> LENGTH: 10
<212> TYPE: PRT

```
<213> ORGANISM: Artificial Sequence
<220> FEATURE:
<223> OTHER INFORMATION: Synthetic Construct

<400> SEQUENCE: 388

Met Leu Gln Met Ala Gly Gln Cys Ser Gln
1               5                   10

<210> SEQ ID NO 389
<211> LENGTH: 14
<212> TYPE: PRT
<213> ORGANISM: Artificial Sequence
<220> FEATURE:
<223> OTHER INFORMATION: Synthetic Construct

<400> SEQUENCE: 389

Cys Ser Gln Asn Glu Tyr Phe Asp Ser Leu Leu His Ala Cys
1               5                   10

<210> SEQ ID NO 390
<211> LENGTH: 13
<212> TYPE: PRT
<213> ORGANISM: Artificial Sequence
<220> FEATURE:
<223> OTHER INFORMATION: Synthetic Construct

<400> SEQUENCE: 390

Asn Glu Tyr Phe Asp Ser Leu Leu His Ala Cys Ile Pro
1               5                   10

<210> SEQ ID NO 391
<211> LENGTH: 11
<212> TYPE: PRT
<213> ORGANISM: Artificial Sequence
<220> FEATURE:
<223> OTHER INFORMATION: Synthetic Construct

<400> SEQUENCE: 391

Ala Cys Ile Pro Cys Gln Leu Arg Cys Ser Ser
1               5                   10

<210> SEQ ID NO 392
<211> LENGTH: 19
<212> TYPE: PRT
<213> ORGANISM: Artificial Sequence
<220> FEATURE:
<223> OTHER INFORMATION: Synthetic Construct

<400> SEQUENCE: 392

Cys Gln Leu Arg Cys Ser Ser Asn Thr Pro Pro Leu Thr Cys Gln Arg
1               5                   10                  15

Tyr Cys Asn

<210> SEQ ID NO 393
<211> LENGTH: 10
<212> TYPE: PRT
<213> ORGANISM: Artificial Sequence
<220> FEATURE:
<223> OTHER INFORMATION: Synthetic Construct

<400> SEQUENCE: 393

Leu Thr Cys Gln Arg Tyr Cys Asn Ala Ser
1               5                   10

<210> SEQ ID NO 394
<211> LENGTH: 12
```

<212> TYPE: PRT
<213> ORGANISM: Artificial Sequence
<220> FEATURE:
<223> OTHER INFORMATION: Synthetic Construct

<400> SEQUENCE: 394

Ala Ser Val Thr Asn Ser Val Lys Gly Thr Asn Ala
1               5                   10

<210> SEQ ID NO 395
<211> LENGTH: 54
<212> TYPE: PRT
<213> ORGANISM: Artificial Sequence
<220> FEATURE:
<223> OTHER INFORMATION: Synthetic Construct

<400> SEQUENCE: 395

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50

<210> SEQ ID NO 396
<211> LENGTH: 23
<212> TYPE: PRT
<213> ORGANISM: Artificial Sequence
<220> FEATURE:
<223> OTHER INFORMATION: Synthetic Construct

<400> SEQUENCE: 396

Ile Leu Trp Thr Cys Leu Gly Leu Ser Leu Ile Ile Ser Leu Ala Val
1               5                   10                  15

Phe Val Leu Met Phe Leu Leu
            20

<210> SEQ ID NO 397
<211> LENGTH: 107
<212> TYPE: PRT
<213> ORGANISM: Artificial Sequence
<220> FEATURE:
<223> OTHER INFORMATION: Synthetic Construct

<400> SEQUENCE: 397

Arg Lys Ile Asn Ser Glu Pro Leu Lys Asp Glu Phe Lys Asn Thr Gly
1               5                   10                  15

Ser Gly Leu Leu Gly Met Ala Asn Ile Asp Leu Glu Lys Ser Arg Thr
            20                  25                  30

Gly Asp Glu Ile Ile Leu Pro Arg Gly Leu Glu Tyr Thr Val Glu Glu
        35                  40                  45

Cys Thr Cys Glu Asp Cys Ile Lys Ser Lys Pro Lys Val Asp Ser Asp
    50                  55                  60

His Cys Phe Pro Leu Pro Ala Met Glu Glu Gly Ala Thr Ile Leu Val
65                  70                  75                  80

Thr Thr Lys Thr Asn Asp Tyr Cys Lys Ser Leu Pro Ala Ala Leu Ser
                85                  90                  95

Ala Thr Glu Ile Glu Lys Ser Ile Ser Ala Arg
            100                 105

```
<210> SEQ ID NO 398
<211> LENGTH: 23
<212> TYPE: DNA
<213> ORGANISM: Artificial Sequence
<220> FEATURE:
<223> OTHER INFORMATION: Synthetic Construct

<400> SEQUENCE: 398
gtccttctcc tgtcactggt tat                                              23

<210> SEQ ID NO 399
<211> LENGTH: 23
<212> TYPE: DNA
<213> ORGANISM: Artificial Sequence
<220> FEATURE:
<223> OTHER INFORMATION: Synthetic Construct

<400> SEQUENCE: 399
tcttcttctt ctggaaatcg gca                                              23
```

CHIMERIC ANTIGEN RECEPTORS TARGETING BCMA AND METHODS OF USE THEREOF

CROSS-REFERENCE TO RELATED APPLICATIONS

This application is a Section 371 of International Application No. PCT/CN2017/096938, filed Aug. 10, 2017, which was published in the English language on Feb. 15, 2018 under International Publication No. WO 2018/028647 A1, and claims priority under 35 U.S.C. § 119(b) to International Application No. PCT/CN2016/094408, filed Aug. 10, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "689296_1U1 Sequence Listing," a creation date of Sep. 26, 2018, and having a size of about 520 kb. The sequence listing submitted via EFS-Web is part of the specification and is herein incorporated by reference in its entirety.

FIELD OF THE PRESENT APPLICATION

The present invention relates to single-domain antibodies, chimeric antigen receptors and engineered immune effector cells that target BCMA, and methods of use thereof.

BACKGROUND OF THE PRESENT APPLICATION

With the development of tumor immunotherapy and clinical technology, chimeric antigen receptor T cell (CAR-T) immunotherapy is now one of the most promising tumor immunotherapy approaches. Generally, a chimeric antigen receptor (CAR) comprises an extracellular antigen binding domain, a transmembrane domain and an intracellular signaling domain. The extracellular antigen binding domain may comprise a single chain variable fragment (scFv) targeting an identified tumor antigen. CARs can be expressed on the surface of T cells using gene transfection techniques. Upon binding to the target tumor antigen, the CARs can activate the T cells to launch specific anti-tumor response in an antigen-dependent manner without being limited by the availability of major histocompatibility complexes (MHC) specific to the target tumor antigen.

Single-domain antibodies (sdAbs) are different from conventional 4-chain antibodies by having a single monomeric antibody variable domain. For example, camelids and sharks produce sdAbs named heavy chain-only antibodies (HcAbs), which naturally lack light chains. The antigen-binding fragment in each arm of the camelid heavy-chain only antibodies has a single heavy chain variable domain ($V_HH$), which can have high affinity to an antigen without the aid of a light chain. Camelid $V_HH$ is known as the smallest functional antigen-binding fragment with a molecular weight of approximately 15 kD.

Multiple myeloma (MM) is an incurable aggressive plasma malignancy, which is categorized as a B-cell neoplasia and proliferates in uncontrollably method in the bone marrow, interfering with the normal metabolic production of blood cells and causing painful bone lesions (Garfall, A. L. et al., Discovery Med. 2014, 17, 37). Multiple myeloma can present clinically with hypercalcemia, renal insufficiency, anemia, bony lesions, bacterial infections, hyperviscosity, and amyloidosis (Robert Z. Orlowski, Cancer Cell. 2013, 24(3)). According to investigation and statistics, nearly 86,000 patients will be diagnosed each year with myeloma, and while about 63,000 patients die every year from the disease-related complications (Becker, 2011). Because of an aging populace, it is predicted that the number of cases of myeloma will increase year by year. Like many cancers, there is no known cause of multiple myeloma, and no cure. Some treatments for multiple myeloma are similar to treatments for other cancers, such as chemotherapy or radiation therapy, stem cell transplant or bone marrow transplant, targeted therapy or biological therapy (George, 2014). Antibody-based cell immunotherapies have demonstrated substantial clinical benefit for patients with hematological malignancies, particular in B cell Non-Hodgkin's lymphoma. Although current therapies for multiple myeloma often lead to remissions, nearly all patients eventually relapse. There is a need for effective immunotherapeutic agent for treating multiple myeloma.

The LCAR-B38M disclosed in the current invention is a bivalent BCMA targeting CAR-T which have already shown clinical advantages in terms of both safety and efficacy in treating refractory or relapsed multiple myeloma patients in a clinical trial. In an early clinical trial, 33 out of 35 (94%) patients had clinical remission of multiple myeloma upon receiving LCAR-B38M CAR-T cells. Most patients had only mild side effects. The study was presented by the major inventor at both the 2017 ASCO Annual Meeting (Abstract LBA3001) and the press briefing which recruited extensive media coverage (http://www.ascopost.com/News/55713).

Overall, the objective response rate was 100%, and 33 patients (94%) had an evident clinical remission of myeloma (complete response, very good partial response, or partial response) within 2 months of receiving CAR T cells. After following the group for a period of more than 4 months, of the 19 patients, 14 have reached stringent complete response criteria, 1 patient has reached partial response, and 4 patients have achieved very good partial remission criteria in efficacy.

Since the outstanding efficacy and safety profile obtained from LCAR-B38M clinical trial are significantly superior than a few other BCMA CAR-T trials reported at the same time in the ASCO, the works had been widely recognized as an "revolutionized breakthrough" in the immunotherapy field. It is notable that all these BCMA CAR design are conventional CAR in which BCMA antigen binding domain is composed of a monovalent ScFv antibody.

The disclosures of all publications, patents, patent applications and published patent applications referred to herein are hereby incorporated herein by reference in their entirety.

BRIEF SUMMARY OF THE PRESENT APPLICATION

The present application provides anti-BCMA single-domain antibodies (sdAb), chimeric antigen receptors (CARs) comprising one or more anti-BCMA sdAbs (such as $V_HH$ fragments), engineered immune effector cells, and methods of use thereof in cancer immunotherapy.

One aspect of the present application provides an anti-BCMA sdAb comprising the CDR regions of any one of SEQ ID NOs: 115-152. In some embodiments, the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the anti-BCMA sdAb comprises a $V_HH$ domain comprising an amino acid sequence selected from the group consisting of SEQ ID NO: 115-152.

In some embodiments, there is provided an anti-BCMA heavy-chain only antibody (HCAB) or an antigen binding protein comprising any one of the anti-BCMA sdAbs described above. Also provided are BCMA epitopes that any one of the anti-BCMA sdAbs described above specifically bind to, and anti-BCMA antibodies (such as anti-BCMA sdAbs) that compete with any one of the anti-BCMA sdAbs described above.

In some embodiments according to any one of the anti-BCMA sdAbs described above, the anti-BCMA sdAb is a camelid antibody. In some embodiments, the anti-BCMA sdAb is a chimeric antibody. In some embodiments, the anti-BCMA sdAb is humanized. In some embodiments, the anti-BCMA sdAb is a $V_HH$ fragment.

One aspect of the present application provides a BCMA chimeric antigen receptor comprising a polypeptide comprising: (a) an extracellular antigen binding domain comprising an anti-BCMA sdAb (such as any one of the anti-BCMA sdAbs described above); (b) a transmembrane domain; and (c) an intracellular signaling domain. In some embodiments, the CAR is monospecific. In some embodiments, the CAR is monovalent. In some embodiments, the CAR is multivalent (such as bivalent or trivalent). In some embodiments, the CAR is multispecific (such as bispecific). In some embodiments, the extracellular antigen binding domain comprises at least two anti-BCMA sdAbs (such as any one or more of the anti-BCMA sdAbs described above).

One aspect of the present application provides a multivalent chimeric antigen receptor (CAR) comprising a polypeptide comprising: (a) an extracellular antigen binding domain comprising a first BCMA binding moiety and a second BCMA binding moiety; (b) a transmembrane domain; and (c) an intracellular signaling domain. In some embodiments, one or more of the first BCMA binding moiety and the second BCMA binding moiety is an anti-BCMA sdAb. In some embodiments, the first BCMA binding moiety is a first anti-BCMA sdAb and the second BCMA binding moiety is a second anti-BCMA sdAb. In some embodiments, the first BCMA binding moiety is an anti-BCMA sdAb and the second BCMA binding moiety is derived from a human antibody. In some embodiments, the first BCMA binding moiety is an anti-BCMA sdAb and the second BCMA binding moiety is a polypeptide ligand of BCMA. In some embodiments, the first BCMA binding moiety and the second BCMA binding moiety specifically bind to the same epitope on BCMA. In some embodiments, the first BCMA binding moiety and the second BCMA binding moiety specifically bind to the different epitopes on BCMA. In some embodiments, the first BCMA binding moiety and/or the second BCMA binding moiety specifically binds to an epitope on BCMA derived from an amino acid sequence selected from SEQ ID NOs: 388-394. In some embodiments, the first BCMA binding moiety specifically binds to an epitope derived from SEQ ID NO: 389 and/or 390. In some embodiments, the second BCMA binding moiety specifically binds to an epitope derived from SEQ ID NO: 391 and/or 392.

One aspect of the present application provides a multivalent (such as bivalent or trivalent) chimeric antigen receptor comprising a polypeptide comprising: (a) an extracellular antigen binding domain comprising a first anti-BCMA sdAb (such as any one of the anti-BCMA sdAbs described above) and a second anti-BCMA sdAb (such as any one of the anti-BCMA sdAbs described above); (b) a transmembrane domain; and (c) an intracellular signaling domain. In some embodiments, the first anti-BCMA sdAb and the second anti-BCMA sdAb specifically bind to the same epitope on BCMA. In some embodiments, the first anti-BCMA sdAb and the second anti-BCMA sdAb specifically bind to different epitopes on BCMA. In some embodiments, the first anti-BCMA sdAb and/or the second anti-BCMA sdAb specifically binds to an epitope on BCMA derived from an amino acid sequence selected from SEQ ID NOs: 388-394. In some embodiments, the first anti-BCMA sdAb specifically binds to an epitope derived from SEQ ID NO: 389 and/or 390. In some embodiments, the second anti-BCMA sdAb specifically binds to an epitope derived from SEQ ID NO: 391 and/or 392.

In some embodiments according to any one of the multivalent CARs provided above, the first BCMA binding moiety (e.g., the first anti-BCMA sdAb) is located at the N-terminus of the second BCMA binding moiety (e.g., the second anti-BCMA sdAb). In some embodiments, the first BCMA binding moiety (e.g., the first anti-BCMA sdAb) is located at the C-terminus of the second BCMA binding moiety (e.g., the second anti-BCMA sdAb). In some embodiments, the first BCMA binding moiety (e.g., the first anti-BCMA sdAb) and the second BCMA binding moiety (e.g., the second anti-BCMA sdAb) are directly fused to each other via a peptide bond. In some embodiments, the first BCMA binding moiety (e.g., the first anti-BCMA sdAb) and the second BCMA binding moiety (e.g., the second anti-BCMA sdAb) are fused to each other via a peptide linker. In some embodiments, the peptide linker is no more than about 50 (such as no more than about any one 35, 25, 20, 15, 10, or 5) amino acids long. In some embodiments, the peptide linker comprises an amino acid sequence selected from SEQ ID NOs: 208-215.

In some embodiments according to any one of the CARs (including multivalent CARs) described above, the transmembrane domain is derived from a molecule selected from the group consisting of CD8α, CD4, CD28, CD137, CD80, CD86, CD152 and PD1. In some embodiments, the transmembrane domain is derived from CD8α or CD28. In some embodiments, the transmembrane domain comprises the amino acid sequence of SEQ ID NO: 193 or 194.

In some embodiments according to any one of the CARs (including multivalent CARs) described above, the intracellular signaling domain comprises a primary intracellular signaling domain of an immune effector cell (such as a T cell). In some embodiments, the primary intracellular signaling domain is derived from CD3ζ. In some embodiments, the primary intracellular signaling domain comprises the amino acid sequence of SEQ ID NO: 197 or 198.

In some embodiments according to any one of the CARs (including multivalent CARs) described above, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the co-stimulatory signaling domain comprises a cytoplasmic domain of CD28 and/or a cytoplasmic domain of CD137. In some embodiments, the co-stimulatory signaling domain comprises the amino acid sequence of SEQ ID NO: 195 and/or SEQ ID NO: 196.

In some embodiments according to any one of the CARs (including multivalent CARs) described above, the CAR further comprises a hinge domain located between the C-terminus of the extracellular antigen binding domain and the N-terminus of the transmembrane domain. In some embodiments, the hinge domain is derived from CD8α. In some embodiments, the hinge domain comprises the amino acid sequence of SEQ ID NO: 192.

In some embodiments according to any one of the CARs (including multivalent CARs) described above, the CAR further comprises a signal peptide located at the N-terminus of the polypeptide. In some embodiments, the signal peptide is derived from a molecule selected from the group consisting of CD8α, GM-CSF receptor α, and IgG1 heavy chain. In some embodiments, the signal peptide is derived from CD8α. In some embodiments, the signal peptide comprises the amino acid sequence of SEQ ID NO: 191.

One aspect of the present application provides a CAR as listed in Tables 4 and 5. In some embodiments, the CAR comprises an amino acid sequence selected from the group consisting of SEQ ID NOs: 216-256 and 298-335.

One aspect of the present application provides a polypeptide comprising an amino acid sequence selected from the group consisting of SEQ ID NOs: 115-152, 216-256 and 298-335.

One aspect of the present application provides an isolated nucleic acid comprising a nucleic acid sequence encoding any one of the anti-BCMA sdAbs or CARs (including multivalent CARs) described above. In some embodiments, the nucleic acid sequence is selected from the group consisting of SEQ ID NOs: 153-190, 257-297 and 336-373. In some embodiments, the isolated nucleic acid further comprises a first nucleic acid sequence encoding a first CAR, wherein the second nucleic acid sequence encoding second CAR is operably linked to the first nucleic acid sequence via a third nucleic acid sequence encoding a self-cleaving peptide, such as a T2A, P2A, or F2A peptide. Wherein the third nucleic acid sequence is SEQ ID NO: 385. In some embodiments, the isolated nucleic acid is a DNA molecule. In some embodiments, the isolated nucleic acid is an RNA molecule.

One aspect of the present application provides a vector comprising any one of the isolated nucleic acids described above. In some embodiments, the vector is an expression vector. In some embodiments, the vector is a viral vector. In some embodiments, the vector is a lentiviral vector. In some embodiments, the vector is a non-viral vector.

One aspect of the present application provides an engineered immune effector cell, comprising any one of the CARs (including multivalent CARs) provided above, or any one of the isolated nucleic acids described above, or any one of the vectors described above. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

One aspect of the present application provides a pharmaceutical composition comprising any one of the engineered immune effector cells described above and a pharmaceutically acceptable carrier. Further provided is a method of treating cancer in an individual, comprising administering to the individual an effective amount of any one of the pharmaceutical compositions described above. In some embodiments, the engineered immune effector cell is autologous. In some embodiments, the engineered immune effector cell is allogenic. In some embodiments, the cancer is a liquid cancer. In some embodiments, the cancer is multiple myeloma, acute lymphoblastic leukemia, or chronic lymphocytic leukemia. In some embodiments, the cancer is a solid cancer, such as glioblastoma. In some embodiments, the cancer is refractory or relapsed multiple myeloma.

One aspect of the present application provides a pharmaceutical composition comprising any one of the anti-BCMA sdAbs described above and a pharmaceutically acceptable carrier. In some embodiments, there is provided a method of treating a disease (such as cancer) in an individual, comprising administering to the individual an effective amount of the pharmaceutical composition.

Also provided are methods of use, kits, and articles of manufacture comprising any one of the anti-BCMA sdAbs, CARs (including multivalent CARs), engineered immune effector cells, isolated nucleic acids, or vectors described above.

BRIEF DESCRIPTION OF THE DRAWINGS

FIG. 8B shows BCMA epitope peptides.

FIG. 12B shows bioluminescence imaging data in LCAR-B38M CAR-T treated mice and untransduced T cell (UnT) treated mice.

FIG. 12C shows the study design and bioluminescence images of mice in CAR-T group and UnT group. FIG. 12D shows images of livers from UnT-treated mice. FIG. 12E shows an ex vivo luciferase assay validating tumors in the livers of UnT-treated mice.

FIG. 14A shows the in vitro cytotoxicity results of LCAR-B38M CAR-T cells and LCAR-B27S CAR-T cells prepared from multiple myeloma patient A. FIG. 14B shows the in vitro cytotoxicity results of LCAR-B38M CAR-T cells and LCAR-B27S CAR-T cells prepared from multiple myeloma patient B. FIG. 14C shows the in vitro cytotoxicity results of LCAR-B38M CAR-T cells and LCAR-B27S CAR-T cells prepared from multiple myeloma patient C.

DETAILED DESCRIPTION OF THE PRESENT APPLICATION

Figure 1A:
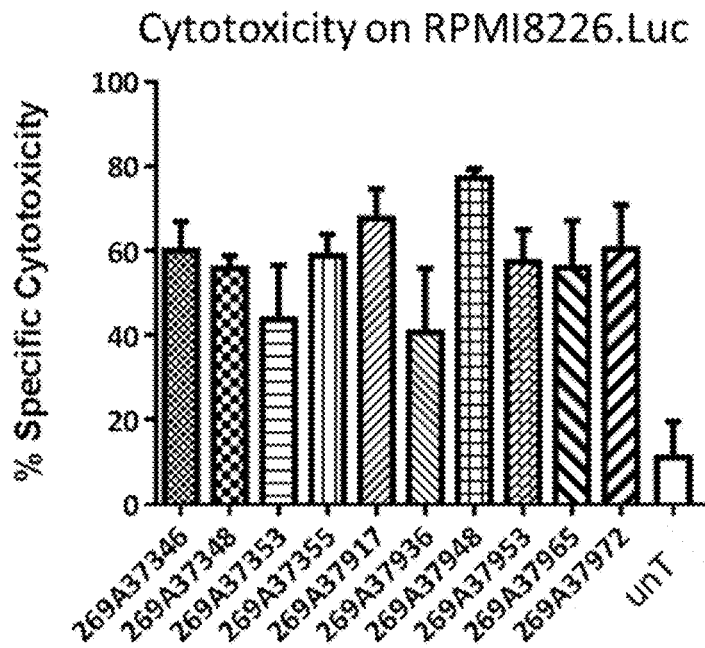
FIGS. 1A-1B show results of an in vitro cytotoxicity assay of T cells expressing exemplary monospecific CARs comprising various anti-BCMA sdAbs against RPMI8226.Luc cells (FIG. 1A), or U87MG.Luc cells (FIG. 1B).

The present application provides anti-BCMA single-domain antibodies (sdAb) and chimeric antigen receptors (CARs) comprising an extracellular antigen binding domain comprising one or more BCMA binding moieties (such as anti-BCMA sdAbs). Multivalent CARs comprising at least two binding moieties (such as sdAbs) that specifically bind to a single antigen are also provided. In some embodiments, the present application provides multivalent (such as bivalent or trivalent) CARs comprising at least two anti-BCMA sdAbs. In some embodiments, the at least two anti-BCMA sdAbs are different anti-BCMA sdAbs that specifically bind to different epitopes on BCMA. The anti-BCMA sdAbs, CARs and engineered immune cells expressing CARs described in the present application are useful agents for cancer treatment.

Notably, the present application has demonstrated superior efficacy of bivalent bi-epitope CARs comprising two anti-BCMA sdAbs targeting different BCMA epitopes (e.g., LCAR-B38M), in treating multiple myeloma among human patients. At an interim analysis of a Phase I/II clinical trial, 100% of patients with relapsed or refractory multiple myeloma responded to the LCAR-B38M CAR-T treatment. 94% of the patients had evident clinical remission of myeloma within two months of receiving the CAR-T treatment. Patients who reached Stringent Complete Response (sCR) criteria remained free of minimal residual disease after more than a year of receiving the CAR-T treatment. Additionally, the LCAR-B38M CAR-T treatment was well tolerated by the patients as most patients only experienced mild and manageable cytokine release syndrome, a common side effect of CAR-T cell-based therapy. No patients experienced neurological side effects. In comparison, a pilot clinical study of a monovalent CAR comprising a single anti-BCMA sdAb showed lower objective response rate and complete remission rate, and higher relapse rate among treated patients. Prior to this application, all BCMA CARs under clinical studies had only one BCMA binding moiety in the extracellular antigen binding domain. The improved clinical efficacy and safety of the multivalent BCMA CARs of the present application are unexpected.

Accordingly, one aspect of the present application provides a multivalent CAR comprising a polypeptide comprising: (a) an extracellular antigen binding domain comprising a plurality of a single-domain antibody (sdAb) specifically binding to BCMA; (b) a transmembrane domain; and (c) an intracellular signaling domain.

In another aspect, there is provided a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope is different from the second epitope.

Further provided are novel anti-BCMA sdAbs and CARs comprising any one or more of the anti-BCMA sdAbs described herein.

Engineered immune effector cells (such as T cells) comprising the CARs, pharmaceutical compositions, kits, articles of manufacture and methods of treating cancer using the engineered immune effectors cells or the sdAbs are also described herein.

I. Definitions

The term "antibody" includes monoclonal antibodies (including full length 4-chain antibodies or full length heavy-chain only antibodies which have an immunoglobulin Fc region), antibody compositions with polyepitopic specificity, multispecific antibodies (e.g., bispecific antibodies, diabodies, and single-chain molecules), as well as antibody fragments (e.g., Fab, F(ab')$_2$, and Fv). The term "immunoglobulin" (Ig) is used interchangeably with "antibody" herein. Antibodies contemplated herein include single-domain antibodies, such as heavy chain only antibodies.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for 11 and c isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H$Hs". Some $V_H$Hs may also be known as Nanobodies. Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_H$H". $V_H$H is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture or recombinantly, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present application may be made by a variety of techniques, including, for example, the hybridoma method (e.g., Kohler and Milstein, Nature, 256: 495-97 (1975); Hongo et al., Hybridoma, 14 (3): 253-260 (1995), Harlow et al., Antibodies: A Laboratory Manual, (Cold Spring Harbor Laboratory Press, 2$^{nd}$ ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_HH$) and an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10): 1057-1062 [1995]); single-chain antibody molecules; single-domain antibodies (such as $V_HH$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Natl. Acad. Sci. USA 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include PRIMATTZFD® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., camelid) antibodies are chimeric antibodies that contain minimal sequence derived from non-human immunoglobulin. In some embodiments, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227: 381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, sdAbs comprise three HVRs (or CDRs): HVR1 (or CDR1), HVR2 (or CDR2), and HVR3 (or CDR3). HVR3 displays the most diversity of the three HVRs, and is believed to play a unique role in conferring fine specificity to antibodies. See, e.g., Hamers-Casterman et al., Nature 363:446-448 (1993); Sheriff et al., Nature Struct. Biol. 3:733-736 (1996).

The term "Complementarity Determining Region" or "CDR" are used to refer to hypervariable regions as defined by the Kabat system. See Kabat et al., Sequences of Proteins of Immunological Interest, 5th Ed. Public Health Service, National Institutes of Health, Bethesda, Md. (1991)

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

| HVR delineations. | | | | |
|---|---|---|---|---|
| Loop | Kabat | AbM | Chothia | Contact |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |

TABLE 1-continued

HVR delineations.

| Loop | Kabat | AbM | Chothia | Contact |
|---|---|---|---|---|
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a sdAb (such as $V_HH$) are numbered according to the general numbering for $V_H$ domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans, J. Immunol. Methods 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5$^{th}$ Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the VH, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds," "specifically recognizes," or is "specific for" refers to measurable and reproducible interactions such as binding between a target and an antigen binding protein (such as a CAR or an sdAb), which is determinative of the presence of the target in the presence of a heterogeneous population of molecules including biological molecules. For example, an antigen binding protein (such as a CAR or an sdAb) that specifically binds a target (which can be an epitope) is an antigen binding protein (such as a CAR or an sdAb) that binds this target with greater affinity, avidity, more readily, and/or with greater duration than it binds other targets. In some embodiments, the extent of binding of an antigen binding protein (such as a CAR or an sdAb) to an unrelated target is less than about 10% of the binding of the antigen binding protein (such as a CAR or an sdAb) to the target as measured, e.g., by a radioimmunoassay (RIA). In some embodiments, an antigen binding protein (such as a CAR or an sdAb) that specifically binds a target has a dissociation constant (Kd) of ≤1 μM, ≤100 nM, ≤10 nM, ≤1 nM, or ≤0.1 nM. In some embodiments, an antigen binding protein (such as a CAR or an sdAb) specifically binds an epitope on a protein that is conserved among the protein from different species. In some embodiments, specific binding can include, but does not require exclusive binding.

The term "specificity" refers to selective recognition of an antigen binding protein (such as a CAR or an sdAb) for a particular epitope of an antigen. Natural antibodies, for example, are monospecific. The term "multispecific" as used herein denotes that an antigen binding protein (such as a CAR or an sdAb) has two or more antigen-binding sites of which at least two bind different antigens. "Bispecific" as used herein denotes that an antigen binding protein (such as a CAR or an sdAb) has two different antigen-binding specificities. The term "monospecific" CAR as used herein denotes an antigen binding protein (such as a CAR or an sdAb) that has one or more binding sites each of which bind the same antigen.

The term "valent" as used herein denotes the presence of a specified number of binding sites in an antigen binding protein (such as a CAR or an sdAb). A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein (such as a CAR or an sdAb).

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody—dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effector-less mutation." In one aspect, the effector-less mutation is an N297A or DANA mutation (D265A+N297A) in the $C_H2$ region. Shields et al., J. Biol. Chem. 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., E. coli.) or in which result in an altered glycosylation pattern that is ineffective or less effective at promoting effector function (e.g., Shinkawa et al., J. Biol. Chem. 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRT, FcγRII and FcγRIII Fc expression on hematopoietic cells is summarized in Table 3 on page 464 of Ravetch and Kinet, Annu. Rev. Immunol. 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS USA 95:652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Binding affinity" generally refers to the strength of the sum total of non-covalent interactions between a single binding site of a molecule (e.g., an antibody or a CAR) and its binding partner (e.g., an antigen). Unless indicated otherwise, as used herein, "binding affinity" refers to intrinsic binding affinity that reflects a 1:1 interaction between members of a binding pair (e.g., antibody and antigen, or CAR and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present application. Specific illustrative and exemplary embodiments for measuring binding affinity are described in the following.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

"Chimeric antigen receptor" or "CAR" as used herein refers to genetically engineered receptors, which can be used to graft one or more antigen specificity onto immune effector cells, such as T cells. Some CARs are also known as "artificial T-cell receptors," "chimeric T cell receptors," or "chimeric immune receptors." In some embodiments, the CAR comprises an extracellular antigen binding domain specific for one or more antigens (such as tumor antigens), a transmembrane domain, and an intracellular signaling domain of a T cell and/or other receptors. "CAR-T" refers to a T cell that expresses a CAR. "BCMA CAR" refers to a CAR having an extracellular binding domain specific for BCMA. "Bi-epitope CAR" refers to a CAR having an extracellular binding domain specific for two different epitopes on BCMA.

An "isolated" nucleic acid molecule encoding a CAR or an sdAb described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the term "autologous" is meant to refer to any material derived from the same individual to whom it is later to be re-introduced into the individual.

"Allogeneic" refers to a graft derived from a different individual of the same species.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the present application contemplate any one or more of these aspects of treatment.

As used herein, an "individual" or a "subject" refers to a mammal, including, but not limited to, human, bovine, horse, feline, canine, rodent, or primate. In some embodiments, the individual is a human.

The term "effective amount" used herein refers to an amount of an agent, such as a sdAb, an engineered immune effector cell, or a pharmaceutical composition thereof, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

A "stable" formulation is one in which the protein therein essentially retains its physical and chemical stability and integrity upon storage. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein is dispersed throughout. The reconstituted formulation is suitable for administration (e.g. subcutaneous administration) to a patient to be treated with the protein of interest and, In some embodiments of the present application, may be one which is suitable for parenteral or intravenous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

It is understood that embodiments of the present application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Anti-BCMA Single-Domain Antibodies

One aspect of the present application provides isolated single-domain antibodies (referred herein as "anti-BCMA sdAbs") that specifically bind to BCMA, such as human BCMA. In some embodiments, the anti-BCMA sdAb modulates BCMA activity. In some embodiments, the anti-BCMA sdAb is an antagonist antibody. Further provided are antigen-binding fragments derived from any one of the anti-BCMA sdAbs described herein, and antigen binding proteins comprising any one of the anti-BCMA sdAbs described herein. Exemplary anti-BCMA sdAbs are listed in Table 2 below.

TABLE 2

Exemplary anti-BCMA sdAbs.

| SdAb | Ex. AA SEQ ID | Ex. NA SEQ ID | CDR1 | CDR2 | CDR3 |
| --- | --- | --- | --- | --- | --- |
| 269A37346 | 115 | 153 | DYYAIG (SEQ ID NO: 1) | CISRSDGSTYYADSVK G (SEQ ID NO: 39) | AGADCSGYLRDYEF (SEQ ID NO: 77) |
| 269A37348 | 116 | 154 | TYGMA (SEQ ID NO: 2) | SKASMNYSGRTYYAD SVKG (SEQ ID NO: 40) | AGTGCSTYGCFDAQI IDY (SEQ ID NO: 78) |
| 269A37917 | 117 | 155 | TFTMG (SEQ ID NO: 3) | AISLSPTLAYYAESVK G (SEQ ID NO: 41) | ADRKSVMSIRPDY (SEQ ID NO: 79) |
| 269A37355 | 118 | 156 | INAMG (SEQ ID NO: 4) | SIRGLGRTNYDDSVK G (SEQ ID NO: 42) | VYVTLLGGVNRDY (SEQ ID NO: 80) |
| 269A37915 | 119 | 157 | SIVMG (SEQ ID NO: 5) | AIMWNDGITYLQDSV KG (SEQ ID NO: 43) | ASKGRYSEYEY (SEQ ID NO: 81) |
| 269A37936 | 120 | 158 | RAVIV (SEQ ID NO: 6) | FIKPSDGTIYYIDSLKG (SEQ ID NO: 44) | ASPEDWYTDWIDWS IYR (SEQ ID NO: 82) |
| 269A37953 | 121 | 159 | SDVMG (SEQ ID NO: 7) | AIMWNDGITYLQDSV KG (SEQ ID NO: 45) | ASKGRYSEYEY (SEQ ID NO: 83) |
| 269A37965 | 122 | 160 | NDHMA (SEQ ID NO: 8) | AIDWSGRTTNYADPV EG (SEQ ID NO: 46) | VLRAWISYDNDY (SEQ ID NO: 84) |
| 269A37972 | 123 | 161 | KNTVA (SEQ ID NO: 9) | SITWDGRTTYYADSV KG (SEQ ID NO: 47) | DLGKWPAGPADY (SEQ ID NO: 85) |
| 269A37353 | 124 | 162 | SHVMG (SEQ ID NO: 10) | VIGWRDISTSYADSVK G (SEQ ID NO: 48) | ARRIDAADFDS (SEQ ID NO: 86) |
| 269A37948 | 125 | 163 | TYFMA (SEQ ID NO: 11) | GIAWSGGSTAYADSV KG (SEQ ID NO: 49) | SRGIEVEEFGA (SEQ ID NO: 87) |
| 269B005 | 126 | 164 | INVMA (SEQ ID NO: 12) | AVTRDGRKSCGDSVKG (SEQ ID NO: 50) | DGWGATTLDYTYGMD Y (SEQ ID NO: 88) |
| 269B023 | 127 | 165 | TFTMG (SEQ ID NO: 13) | SITWDGRSAYYAESVK G (SEQ ID NO: 51) | DRKSVMSIRPDY (SEQ ID NO: 89) |
| 269B024 | 128 | 166 | INAMG (SEQ ID NO: 14) | TITRGGSTNYGPSVKG (SEQ ID NO: 52) | ERLDGSGYGYEYDY (SEQ ID NO: 90) |
| 269B028 | 129 | 167 | KNTVA (SEQ ID NO: 15) | SITCDGRTTYYANSVNG (SEQ ID NO: 53) | YRKSIMSIQPDY (SEQ ID NO: 91) |

TABLE 2-continued

Exemplary anti-BCMA sdAbs.

| SdAb | Ex. AA SEQ ID | Ex. NA SEQ ID | CDR1 | CDR2 | CDR3 |
|---|---|---|---|---|---|
| 269B030 | 130 | 168 | SIVMG (SEQ ID NO: 16) | AIMWNDGLTYLQGSVKG (SEQ ID NO: 54) | DRKSVMSIRPDY (SEQ ID NO: 92) |
| 269B038 | 131 | 169 | TFTMG (SEQ ID NO: 17) | AISLSPTLAYYAESVKG (SEQ ID NO: 55) | RRIDAADFDS (SEQ ID NO: 93) |
| 269B054 | 132 | 170 | KNTVA (SEQ ID NO: 18) | SITWDGRTTYYADSVKG (SEQ ID NO: 56) | LGKWPAGPADY (SEQ ID NO: 94) |
| 269B059 | 133 | 171 | INTMD (SEQ ID NO: 19) | AISLSPTLAYYAESVKG (SEQ ID NO: 57) | DRKSVMSIRPDY (SEQ ID NO: 95) |
| 269B060 | 134 | 172 | KNTVA (SEQ ID NO: 20) | SITCDGRTTYYANSVKG (SEQ ID NO: 58) | LGKWPAGSADY (SEQ ID NO: 96) |
| 269B069 | 135 | 173 | DYWMH (SEQ ID NO: 21) | SIDTSGQTTYYADSLKG (SEQ ID NO: 59) | RYRGGTWYGMAN (SEQ ID NO: 97) |
| 269B074 | 136 | 174 | SNTMA (SEQ ID NO: 22) | STTWNGRSTYYADSVKG (SEQ ID NO: 60) | LGKWPAGPADY (SEQ ID NO: 98) |
| 269B076 | 137 | 175 | TFTMG (SEQ ID NO: 23) | DISGGRTNYADSVKG (SEQ ID NO: 61) | DRKSVMSIRPDY (SEQ ID NO: 99) |
| 269B079 | 138 | 176 | VAAISL (SEQ ID NO: 24) | FTISRDNAKNTVVLQMNSLKP (SEQ ID NO: 62) | DRKSVMSIRPDY (SEQ ID NO: 100) |
| 269B083 | 139 | 177 | KNTVA (SEQ ID NO: 25) | SITWDGRTTYYADSVKG (SEQ ID NO: 63) | TASCHLFGLGSGAFVS (SEQ ID NO: 101) |
| 269B085 | 140 | 178 | TFTMG (SEQ ID NO: 26) | AISLSPTLAYYAESVKG (SEQ ID NO: 64) | SKDRYSEYEY (SEQ ID NO: 102) |
| 269B093 | 141 | 179 | TFTMG (SEQ ID NO: 27) | AISLSPTLAYYAESVKG (SEQ ID NO: 65) | KNGGPVDY (SEQ ID NO: 103) |
| 269B094 | 142 | 180 | SIVMG (SEQ ID NO: 28) | AIMWNDGITYLQDSVKG (SEQ ID NO: 66) | SKGRYSEYEY (SEQ ID NO: 104) |
| 269B104 | 143 | 181 | TFTMG (SEQ ID NO: 29) | AINLSPTLTYYAESVKG (SEQ ID NO: 67) | ERKSVMAIPPDY (SEQ ID NO: 105) |
| 269B109 | 144 | 182 | TFTMG (SEQ ID NO: 30) | SITLIPTFPYYAYSVKG (SEQ ID NO: 68) | YRKYLMSILPDY (SEQ ID NO: 106) |
| 269B110 | 145 | 183 | TFTMG (SEQ ID NO: 31) | AISLSPTLAYYAESVKG (SEQ ID NO: 69) | NRNSQRVIAALSWIGMNY (SEQ ID NO: 107) |
| 269B113 | 146 | 184 | TFTMG (SEQ ID NO: 32) | AISLSPTLAYYAESVKG (SEQ ID NO: 70) | RRIDAADFDS (SEQ ID NO: 108) |
| 269B126 | 147 | 185 | TFTMG (SEQ ID NO: 33) | VIGWRDINASYADSVKG (SEQ ID NO: 71) | RRIDATDFDS (SEQ ID NO: 109) |
| 269B129 | 148 | 186 | NHVMG (SEQ ID NO: 34) | VIGWRDISTSYADSVKG (SEQ ID NO: 72) | RRIDAADFDS (SEQ ID NO: 110) |
| 269B131 | 149 | 187 | NYILA (SEQ ID NO: 35) | HISRSGGKSGYGDSVKG (SEQ ID NO: 73) | PLWYGSPTLIDY (SEQ ID NO: 111) |
| 269B135 | 150 | 188 | TFTMG (SEQ ID NO: 36) | AISLSPTLAYYAESVKG (SEQ ID NO: 74) | DRKSVMSIRPDY (SEQ ID NO: 112) |
| 269B136 | 151 | 189 | TFTMG (SEQ ID NO: 37) | AISLSPTLAYYAEPVKG (SEQ ID NO: 75) | DRKSVMSIRPDY (SEQ ID NO: 113) |
| 269B139 | 152 | 190 | NNFVMG (SEQ ID NO: 38) | AISLSPTLAYYVESVKG (SEQ ID NO: 76) | DRKSVMSIRPDY (SEQ ID NO: 114) |

B cell mature antigen (BCMA), also known as CD269, is a member of the tumor necrosis factor receptor superfamily, namely TNFRSF17 (Thompson et al., J. Exp. Medicine, 192 (1):129-135, 2000). Human BCMA is almost exclusively expressed in plasma cells and multiple myeloma cells (see e.g. Novak et al., Blood, 103(2): 689-694, 2004; Neri et al., Clinical Cancer Research, 73(19):5903-5909; Felix et al., Mol. Oncology, 9(7):1348-58, 2015). BCMA can bind B-cell activating factor (BAFF) and a proliferation including ligand (APRIL) (e.g. Mackay et al., 2003 and Kalled et al., Immunological Review, 204: 43-54, 2005). BCMA can be a suitable tumor antigen target for immunotherapeutic agents against multiple myeloma. Antibodies of high affinity can block the binding between BCMA and its native ligands BAFF and APRIL. The anti-BCMA sdAbs can be used in combination with cell immunotherapy using CAR-T cells, for example, to enhance cytotoxic effects against tumor cells.

In some embodiments, there is provided an anti-BCMA sdAb comprising one, two, or all three CDRs of the amino acid sequence of SEQ ID NO: 115. In some embodiments, there is provided an anti-BCMA sdAb comprising one, two, or all three CDRs of the amino acid sequence of SEQ ID NO: 116. In some embodiments, there is provided an anti-BCMA sdAb comprising one, two, or all three CDRs of the amino acid sequence of SEQ ID NO: 117. In some embodiments, there is provided an anti-BCMA sdAb comprising one, two, or all three CDRs of the amino acid sequence of SEQ ID NO: 118. In some embodiments, there is provided an anti-BCMA sdAb comprising one, two, or all three CDRs of the amino acid sequence of SEQ ID NO: 119. In some embodiments, there is provided an anti-BCMA sdAb comprising one, two, or all three CDRs of the amino acid sequence of SEQ ID NO: 120. In some embodiments, there is provided an anti-BCMA sdAb comprising one, two, or all three CDRs of the amino acid sequence of SEQ ID NO: 121. In some embodiments, there is provided an anti-BCMA sdAb comprising one, two, or all three CDRs of the amino acid sequence of SEQ ID NO: 122. In some embodiments, there is provided an anti-BCMA sdAb comprising one, two, or all three CDRs of the amino acid sequence of SEQ ID NO: 123. In some embodiments, there is provided an anti-BCMA sdAb comprising one, two, or all three CDRs of the amino acid sequence of SEQ ID NO: 124. In some embodiments, there is provided an anti-BCMA sdAb comprising one, two, or all three CDRs of the amino acid sequence of SEQ ID NO: 125. In some embodiments, there is provided an anti-BCMA sdAb comprising one, two, or all three CDRs of the amino acid sequence of SEQ ID NO: 126. In some embodiments, there is provided an anti-BCMA sdAb comprising one, two, or all three CDRs of the amino acid sequence of SEQ ID NO: 127. In some embodiments, there is provided an anti-BCMA sdAb comprising one, two, or all three CDRs of the amino acid sequence of SEQ ID NO: 128. In some embodiments, there is provided an anti-BCMA sdAb comprising one, two, or all three CDRs of the amino acid sequence of SEQ ID NO: 129. In some embodiments, there is provided an anti-BCMA sdAb comprising one, two, or all three CDRs of the amino acid sequence of SEQ ID NO: 130. In some embodiments, there is provided an anti-BCMA sdAb comprising one, two, or all three CDRs of the amino acid sequence of SEQ ID NO: 131. In some embodiments, there is provided an anti-BCMA sdAb comprising one, two, or all three CDRs of the amino acid sequence of SEQ ID NO: 132. In some embodiments, there is provided an anti-BCMA sdAb comprising one, two, or all three CDRs of the amino acid sequence of SEQ ID NO: 133. In some embodiments, there is provided an anti-BCMA sdAb comprising one, two, or all three CDRs of the amino acid sequence of SEQ ID NO: 134. In some embodiments, there is provided an anti-BCMA sdAb comprising one, two, or all three CDRs of the amino acid sequence of SEQ ID NO: 135. In some embodiments, there is provided an anti-BCMA sdAb comprising one, two, or all three CDRs of the amino acid sequence of SEQ ID NO: 136. In some embodiments, there is provided an anti-BCMA sdAb comprising one, two, or all three CDRs of the amino acid sequence of SEQ ID NO: 137. In some embodiments, there is provided an anti-BCMA sdAb comprising one, two, or all three CDRs of the amino acid sequence of SEQ ID NO: 138. In some embodiments, there is provided an anti-BCMA sdAb comprising one, two, or all three CDRs of the amino acid sequence of SEQ ID NO: 139. In some embodiments, there is provided an anti-BCMA sdAb comprising one, two, or all three CDRs of the amino acid sequence of SEQ ID NO: 140. In some embodiments, there is provided an anti-BCMA sdAb comprising one, two, or all three CDRs of the amino acid sequence of SEQ ID NO: 141. In some embodiments, there is provided an anti-BCMA sdAb comprising one, two, or all three CDRs of the amino acid sequence of SEQ ID NO: 142. In some embodiments, there is provided an anti-BCMA sdAb comprising one, two, or all three CDRs of the amino acid sequence of SEQ ID NO: 143. In some embodiments, there is provided an anti-BCMA sdAb comprising one, two, or all three CDRs of the amino acid sequence of SEQ ID NO: 144. In some embodiments, there is provided an anti-BCMA sdAb comprising one, two, or all three CDRs of the amino acid sequence of SEQ ID NO: 145. In some embodiments, there is provided an anti-BCMA sdAb comprising one, two, or all three CDRs of the amino acid sequence of SEQ ID NO: 146. In some embodiments, there is provided an anti-BCMA sdAb comprising one, two, or all three CDRs of the amino acid sequence of SEQ ID NO: 147. In some embodiments, there is provided an anti-BCMA sdAb comprising one, two, or all three CDRs of the amino acid sequence of SEQ ID NO: 148. In some embodiments, there is provided an anti-BCMA sdAb comprising one, two, or all three CDRs of the amino acid sequence of SEQ ID NO: 149. In some embodiments, there is provided an anti-BCMA sdAb comprising one, two, or all three CDRs of the amino acid sequence of SEQ ID NO: 150. In some embodiments, there is provided an anti-BCMA sdAb comprising one, two, or all three CDRs of the amino acid sequence of SEQ ID NO: 151. In some embodiments, there is provided an anti-BCMA sdAb comprising one, two, or all three CDRs of the amino acid sequence of SEQ ID NO: 152. In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework.

In some embodiments, there is provided an anti-BCMA sdAb comprising at least one, at least two, or all three CDRs selected from (a) a CDR1 comprising an amino acid sequence selected from SEQ ID NO: 1-38; (b) a CDR2 comprising an amino acid sequence selected from SEQ ID NO: 39-76; and (c) a CDR3 comprising an amino acid sequence selected from SEQ ID NO: 77-114. In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework.

In some embodiments, there is provided an anti-BCMA sdAb comprising three CDRs comprising: (a) a CDR1 having at least about any one of 85%, 86%, 87%, 88%, 89%, 90%, 91%, 92%, 93%, 94%, 95%, 96%, 97%, 98%, 99%, or 100%0/sequence identity to an amino acid sequence selected from SEQ ID NO:1-38; (b) a CDR2 having at least about any one of 85%, 86%, 87%, 88%, 89%, 90%, 91%, 92%, 93%, 94%, 95%, 96%, 97%, 98%, 99%, or 100%0/sequence identity to an amino acid sequence selected from SEQ ID NO:39-76; and (c) a CDR3 having at least about any one of 85%, 86%, 87%, 88%, 89%, 90%, 91%, 92%, 93%, 94%, 95%, 96%, 97%, 98%, 99%, or 100%0/sequence identity to an amino acid sequence selected from SEQ ID NO: 77-114. In some embodiments, a CDR having at least about any one of 85%, 86%, 87%, 88%, 89%/o, 90%, 91%, 92%, 93%, 94%, 95%, 96%, 97%, 98%, or 99% identity contains substitutions (e.g., conservative substitutions), insertions, or deletions relative to the reference sequence, but the anti-BCMA sdAb comprising that sequence retains the ability to bind to BCMA. In some embodiments, there is provided an anti-BCMA sdAb comprising three CDRs comprising: (a) a CDR1 having about any one of 1, 2, 3, or 4 amino acid substitutions (e.g., conservative substitutions), insertions, or deletions to an amino acid sequence selected from SEQ ID NO:1-38. (b) a CDR2 having about any one of 1, 2, 3, or 4 amino acid substitutions (e.g., conservative substitutions), insertions, or deletions to an amino acid sequence selected from SEQ ID NO:39-76; and (c) a CDR3 having about any one of 1, 2, 3, or 4 amino acid substitutions (e.g., conservative substitutions), insertions, or deletions to an amino acid sequence selected from SEQ ID NO: 77-114. In some embodiments, the anti-BCMA sdAb is affinity matured. In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework.

In some embodiments, there is provided an anti-BCMA sdAb comprising three CDRs comprising: (a) a CDR1 comprising the amino acid sequence of SEQ ID NO: 1; (b) a CDR2 comprising the amino acid sequence of SEQ ID NO: 39; and (c) a CDR3 comprising the amino acid sequence of SEQ ID NO: 77. In some embodiments, there is provided an anti-BCMA sdAb comprising three CDRs comprising: (a) a CDR1 comprising the amino acid sequence of SEQ ID NO: 2; (b) a CDR2 comprising the amino acid sequence of SEQ ID NO: 40; and (c) a CDR3 comprising the amino acid sequence of SEQ ID NO: 78. In some embodiments, there is provided an anti-BCMA sdAb comprising three CDRs comprising: (a) a CDR1 comprising the amino acid sequence of SEQ ID NO: 3; (b) a CDR2 comprising the amino acid sequence of SEQ ID NO: 41; and (c) a CDR3 comprising the amino acid sequence of SEQ ID NO: 79. In some embodiments, there is provided an anti-BCMA sdAb comprising three CDRs comprising: (a) a CDR1 comprising the amino acid sequence of SEQ ID NO: 4; (b) a CDR2 comprising the amino acid sequence of SEQ ID NO: 42; and (c) a CDR3 comprising the amino acid sequence of SEQ ID NO: 80. In some embodiments, there is provided an anti-BCMA sdAb comprising three CDRs comprising: (a) a CDR1 comprising the amino acid sequence of SEQ ID NO: 5; (b) a CDR2 comprising the amino acid sequence of SEQ ID NO: 43; and (c) a CDR3 comprising the amino acid sequence of SEQ ID NO: 81. In some embodiments, there is provided an anti-BCMA sdAb comprising three CDRs comprising: (a) a CDR1 comprising the amino acid sequence of SEQ ID NO: 6; (b) a CDR2 comprising the amino acid sequence of SEQ ID NO: 44; and (c) a CDR3 comprising the amino acid sequence of SEQ ID NO: 82. In some embodiments, there is provided an anti-BCMA sdAb comprising three CDRs comprising: (a) a CDR1 comprising the amino acid sequence of SEQ ID NO: 7; (b) a CDR2 comprising the amino acid sequence of SEQ ID NO: 45; and (c) a CDR3 comprising the amino acid sequence of SEQ ID NO: 83. In some embodiments, there is provided an anti-BCMA sdAb comprising three CDRs comprising: (a) a CDR1 comprising the amino acid sequence of SEQ ID NO: 8; (b) a CDR2 comprising the amino acid sequence of SEQ ID NO: 46; and (c) a CDR3 comprising the amino acid sequence of SEQ ID NO: 84. In some embodiments, there is provided an anti-BCMA sdAb comprising three CDRs comprising: (a) a CDR1 comprising the amino acid sequence of SEQ ID NO: 9; (b) a CDR2 comprising the amino acid sequence of SEQ ID NO: 47; and (c) a CDR3 comprising the amino acid sequence of SEQ ID NO: 85. In some embodiments, there is provided an anti-BCMA sdAb comprising three CDRs comprising: (a) a CDR1 comprising the amino acid sequence of SEQ ID NO: 10; (b) a CDR2 comprising the amino acid sequence of SEQ ID NO: 48; and (c) a CDR3 comprising the amino acid sequence of SEQ ID NO: 86. In some embodiments, there is provided an anti-BCMA sdAb comprising three CDRs comprising: (a) a CDR1 comprising the amino acid sequence of SEQ ID NO: 11; (b) a CDR2 comprising the amino acid sequence of SEQ ID NO: 49; and (c) a CDR3 comprising the amino acid sequence of SEQ ID NO: 87. In some embodiments, there is provided an anti-BCMA sdAb comprising three CDRs comprising: (a) a CDR1 comprising the amino acid sequence of SEQ ID NO: 12; (b) a CDR2 comprising the amino acid sequence of SEQ ID NO: 50; and (c) a CDR3 comprising the amino acid sequence of SEQ ID NO: 88. In some embodiments, there is provided an anti-BCMA sdAb comprising three CDRs comprising: (a) a CDR1 comprising the amino acid sequence of SEQ ID NO: 13; (b) a CDR2 comprising the amino acid sequence of SEQ ID NO: 51; and (c) a CDR3 comprising the amino acid sequence of SEQ ID NO: 89. In some embodiments, there is provided an anti-BCMA sdAb comprising three CDRs comprising: (a) a CDR1 comprising the amino acid sequence of SEQ ID NO: 14; (b) a CDR2 comprising the amino acid sequence of SEQ ID NO: 52; and (c) a CDR3 comprising the amino acid sequence of SEQ ID NO: 90. In some embodiments, there is provided an anti-BCMA sdAb comprising three CDRs comprising: (a) a CDR1 comprising the amino acid sequence of SEQ ID NO: 15; (b) a CDR2 comprising the amino acid sequence of SEQ ID NO: 53; and (c) a CDR3 comprising the amino acid sequence of SEQ ID NO: 91. In some embodiments, there is provided an anti-BCMA sdAb comprising three CDRs comprising: (a) a CDR1 comprising the amino acid sequence of SEQ ID NO: 16; (b) a CDR2 comprising the amino acid sequence of SEQ ID NO: 54; and (c) a CDR3 comprising the amino acid sequence of SEQ ID NO: 92. In some embodiments, there is provided an anti-BCMA sdAb comprising three CDRs comprising: (a) a CDR1 comprising the amino acid sequence of SEQ ID NO: 17; (b) a CDR2 comprising the amino acid sequence of SEQ ID NO: 55; and (c) a CDR3 comprising the amino acid sequence of SEQ ID NO: 93. In some embodiments, there is provided an anti-BCMA sdAb comprising three CDRs comprising: (a) a CDR1 comprising the amino acid sequence of SEQ ID NO: 18; (b) a CDR2 comprising the amino acid sequence of SEQ ID NO: 56; and (c) a CDR3 comprising the amino acid sequence of SEQ ID NO: 94. In some embodiments, there is provided an anti-BCMA sdAb comprising three CDRs comprising: (a) a CDR1 comprising the amino acid sequence of SEQ ID NO: 19; (b) a CDR2 comprising the amino acid sequence of SEQ ID NO: 57; and (c) a CDR3 comprising the amino acid sequence of SEQ ID NO: 95. In some embodiments, there is provided an anti-BCMA sdAb comprising three CDRs comprising: (a) a CDR1 comprising the amino acid sequence of SEQ ID NO: 20; (b) a CDR2 comprising the amino acid sequence of SEQ ID NO: 58; and (c) a CDR3 comprising the amino acid sequence of SEQ ID NO: 96. In some embodiments, there is provided an anti-BCMA sdAb comprising three CDRs comprising: (a) a CDR1 comprising the amino acid sequence of SEQ ID NO: 21; (b) a CDR2 comprising the amino acid sequence of SEQ ID NO: 59; and (c) a CDR3 comprising the amino acid sequence of SEQ ID NO: 97. In some embodiments, there is provided an anti-BCMA sdAb comprising three CDRs comprising: (a) a CDR1 comprising the amino acid sequence of SEQ ID NO: 22; (b) a CDR2 comprising the amino acid sequence of SEQ ID NO: 60; and (c) a CDR3 comprising the amino acid sequence of SEQ ID NO: 98. In some embodiments, there is provided an anti-BCMA sdAb comprising three CDRs comprising: (a) a CDR1 comprising the amino acid sequence of SEQ ID NO: 23; (b) a CDR2 comprising the amino acid sequence of SEQ ID NO: 61; and (c) a CDR3 comprising the amino acid sequence of SEQ ID NO: 99. In some embodiments, there is provided an anti-BCMA sdAb comprising three CDRs comprising: (a) a CDR1 comprising the amino acid sequence of SEQ ID NO: 24; (b) a CDR2 comprising the amino acid sequence of SEQ ID NO: 62; and (c) a CDR3 comprising the amino acid sequence of SEQ ID NO: 100. In some embodiments, there is provided an anti-BCMA sdAb comprising three CDRs comprising: (a) a CDR1 comprising the amino acid sequence of SEQ ID NO: 25; (b) a CDR2 comprising the amino acid sequence of SEQ ID NO: 63; and (c) a CDR3 comprising the amino acid sequence of SEQ ID NO: 101. In some embodiments, there is provided an anti-BCMA sdAb comprising three CDRs comprising: (a) a CDR1 comprising the amino acid sequence of SEQ ID NO: 26; (b) a CDR2 comprising the amino acid sequence of SEQ ID NO: 64; and (c) a CDR3 comprising the amino acid sequence of SEQ ID NO: 102. In some embodiments, there is provided an anti-BCMA sdAb comprising three CDRs comprising: (a) a CDR1 comprising the amino acid sequence of SEQ ID NO: 27; (b) a CDR2 comprising the amino acid sequence of SEQ ID NO: 65; and (c) a CDR3 comprising the amino acid sequence of SEQ ID NO: 103. In some embodiments, there is provided an anti-BCMA sdAb comprising three CDRs comprising: (a) a CDR1 comprising the amino acid sequence of SEQ ID NO: 28; (b) a CDR2 comprising the amino acid sequence of SEQ ID NO: 66; and (c) a CDR3 comprising the amino acid sequence of SEQ ID NO: 104. In some embodiments, there is provided an anti-BCMA sdAb comprising three CDRs comprising: (a) a CDR1 comprising the amino acid sequence of SEQ ID NO: 29, (b) a CDR2 comprising the amino acid sequence of SEQ ID NO: 67; and (c) a CDR3 comprising the amino acid sequence of SEQ ID NO: 105. In some embodiments, there is provided an anti-BCMA sdAb comprising three CDRs comprising: (a) a CDR1 comprising the amino acid sequence of SEQ ID NO: 30; (b) a CDR2 comprising the amino acid sequence of SEQ ID NO: 68; and (c) a CDR3 comprising the amino acid sequence of SEQ ID NO: 106. In some embodiments, there is provided an anti-BCMA sdAb comprising three CDRs comprising: (a) a CDR1 comprising the amino acid sequence of SEQ ID NO: 31, (b) a CDR2 comprising the amino acid sequence of SEQ ID NO: 69; and (c) a CDR3 comprising the amino acid sequence of SEQ ID NO: 107. In some embodiments, there is provided an anti-BCMA sdAb comprising three CDRs comprising: (a) a CDR1 comprising the amino acid sequence of SEQ ID NO: 32; (b) a CDR2 comprising the amino acid sequence of SEQ ID NO: 70; and (c) a CDR3 comprising the amino acid sequence of SEQ ID NO: 108. In some embodiments, there is provided an anti-BCMA sdAb comprising three CDRs comprising: (a) a CDR1 comprising the amino acid sequence of SEQ ID NO: 33; (b) a CDR2 comprising the amino acid sequence of SEQ ID NO: 71; and (c) a CDR3 comprising the amino acid sequence of SEQ ID NO: 109. In some embodiments, there is provided an anti-BCMA sdAb comprising three CDRs comprising: (a) a CDR1 comprising the amino acid sequence of SEQ ID NO: 34; (b) a CDR2 comprising the amino acid sequence of SEQ ID NO: 72; and (c) a CDR3 comprising the amino acid sequence of SEQ ID NO: 110. In some embodiments, there is provided an anti-BCMA sdAb comprising three CDRs comprising: (a) a CDR1 comprising the amino acid sequence of SEQ ID NO: 35; (b) a CDR2 comprising the amino acid sequence of SEQ ID NO: 73; and (c) a CDR3 comprising the amino acid sequence of SEQ ID NO: 111. In some embodiments, there is provided an anti-BCMA sdAb comprising three CDRs comprising: (a) a CDR1 comprising the amino acid sequence of SEQ ID NO: 36; (b) a CDR2 comprising the amino acid sequence of SEQ ID NO: 74; and (c) a CDR3 comprising the amino acid sequence of SEQ ID NO: 112. In some embodiments, there is provided an anti-BCMA sdAb comprising three CDRs comprising: (a) a CDR1 comprising the amino acid sequence of SEQ ID NO: 37; (b) a CDR2 comprising the amino acid sequence of SEQ ID NO: 75; and (c) a CDR3 comprising the amino acid sequence of SEQ ID NO: 113. In some embodiments, there is provided an anti-BCMA sdAb comprising three CDRs comprising: (a) a CDR1 comprising the amino acid sequence of SEQ ID NO: 38; (b) a CDR2 comprising the amino acid sequence of SEQ ID NO: 76; and (c) a CDR3 comprising the amino acid sequence of SEQ ID NO: 114. In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework.

In some embodiments, the anti-BCMA sdAb, including any of the embodiments described above (i.e., anti-BCMA sdAb comprising specific CDR1, CDR2, and/or CDR3) comprises a $V_HH$ domain having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO: 115-152. In some embodiments, a $V_HH$ sequence having at least about any one of 85%, 86%, 87%, 88%, 89%, 90%, 91%, 92%, 93%, 94%, 95%, 960%, 97%, 98%, or 99% identity contains substitutions (e.g., conservative substitutions), insertions, or deletions relative to the reference sequence, but the anti-BCMA sdAb comprising that sequence retains the ability to bind to BCMA. In some embodiments, a total of 1 to 10 amino acids have been substituted, inserted and/or deleted in an amino acid sequence selected from SEQ ID NO: 115-152. In some embodiments, substitutions, insertions, or deletions occur in regions outside the CDRs (i.e., in the FRs). Optionally, the anti-BCMA sdAb comprises an amino acid sequence selected from SEQ ID NO: 115-152, including post-translational modifications of that sequence.

In some embodiments, there is provided an isolated anti-BCMA sdAb comprising a $V_HH$ domain having an amino acid sequence selected from the group consisting of SEQ ID NOs: 115-152. In some embodiments, there is provided a polypeptide comprising an amino acid sequence selected from the group consisting of SEQ ID NOs: 115-152.

In some embodiments, functional epitopes can be mapped by combinatorial alanine scanning. In this process, a combinatorial alanine-scanning strategy can be used to identify amino acids in the BCMA protein that are necessary for interaction with anti-BCMA sdAbs. In some embodiments, the epitope is conformational and crystal structure of anti-BCMA sdAb bound to BCMA may be employed to identify the epitopes. In some embodiments, the present application provides an epitope of BCMA derived from an amino acid sequence selected from the group consisting of SEQ ID NOs: 388-394. In some embodiments, the present application provides an epitope of BCMA comprising an amino acid sequence selected from the group consisting of SEQ ID NOs: 388-394.

In some embodiments, the present application provides antibodies which compete with any one of the anti-BCMA sdAbs described herein for binding to BCMA. In some embodiments, the invention provides antibodies which compete with the anti-BCMA sdAbs provided herein for binding to an epitope on the BCMA. In some embodiments, an antibody is provided that binds to the same epitope as an anti-BCMA sdAb comprising an amino acid sequence selected from the group consisting of SEQ ID NOs: 115-152. In some embodiments, an antibody is provided that specifically binds to BCMA competitively with an anti-BCMA sdAb comprising an amino acid sequence selected from the group consisting of SEQ ID NOs: 115-152.

In some embodiments, competition assays may be used to identify a monoclonal antibody that competes with an anti-BCMA sdAb described herein for binding to BCMA.

Competition assays can be used to determine whether two antibodies bind the same epitope by recognizing identical or sterically overlapping epitopes or one antibody competitively inhibits binding of another antibody to the antigen. In certain embodiments, such a competing antibody binds to the same epitope (e.g., a BCMA epitope derived from an amino acid sequence selected from the group consisting of SEQ ID NOs: 388-394) that is bound by an antibody described herein. Exemplary competition assays include, but are not limited to, routine assays such as those provided in Harlow and Lane (1988) Antibodies: A Laboratory Manual ch.14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-BCMA sdAb described herein is a camelid, chimeric, humanized or human antibody. In some embodiments, the present application provides an antibody that competes with a camelid, chimeric, humanized, or human anti-BCMA sdAb as described herein.

In some embodiments, there is provided an anti-BCMA antibody or antigen binding protein comprising any one of the anti-BCMA sdAbs described above. In some embodiments, the anti-BCMA antibody is a monoclonal antibody, including a camelid, chimeric, humanized or human antibody. In some embodiments, the anti-BCMA antibody is an antibody fragment, e.g., a $V_HH$ fragment. In some embodiments, the anti-BCMA antibody is a full-length heavy-chain only antibody comprising an Fc region of any antibody class or isotype, such as IgG1 or IgG4. In some embodiments, the Fc region has reduced or minimized effector function.

In some embodiments, the anti-BCMA antibody (such as anti-BCMA sdAb) or antigen binding protein according to any of the above embodiments may incorporate any of the features, singly or in combination, as described in Sections 1-7 of "Features of antibodies" below.

In some embodiments, there is provided an isolated nucleic acid encoding any one of the anti-BCMA antibodies (such as anti-BCMA sdAbs) described above. In some embodiments, an isolated nucleic acid encoding an anti-BCMA sdAb is provided wherein the nucleic acid comprises a sequence having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NO: 153-190. In some embodiments, there is provided an isolated nucleic acid comprising a nucleic acid sequence selected from the group consisting of SEQ ID NO: 153-190. In some embodiments, a vector (e.g., expression vector) comprising such nucleic acid are provided. In some embodiments, a host cell comprising such nucleic acid is provided. In some embodiments, a method of making an anti-BCMA antibody is provided, wherein the method comprises culturing a host cell comprising a nucleic acid encoding the anti-BCMA antibody, as provided above, under conditions suitable for expression of the anti-BCMA antibody, and optionally recovering the anti-BCMA antibody from the host cell (or host cell culture medium).

Features of Antibodies
1. Antibody Affinity

In some embodiments, an anti-BCMA antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$M).

In some embodiments, Kd is measured by a radiolabeled antigen binding assay (RIA) performed with the Fab version or $V_HH$ fragment of an antibody of interest and its antigen as described by the following assay. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)).

In some embodiments, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab or $V_HH$ of the antibody of interest (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In some embodiments, an antibody provided herein is an antibody fragment. Antibody fragments include, but are not limited to, Fab, Fab', Fab'-SH, F(ab')$_2$, Fv, and scFv fragments, V$_H$H, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Antibody fragments can be made by various techniques, including but not limited to proteolytic digestion of an intact antibody as well as production by recombinant host cells (e.g. E. coli or phage), as described herein.

3. Chimeric and Humanized Antibodies

In some embodiments, the antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In some embodiments, the sdAbs are modified, such as humanized, without diminishing the native affinity of the domain for antigen and while reducing its immunogenicity with respect to a heterologous species. For example, the amino acid residues of the antibody variable domain (V$_H$H) of an llama antibody can be determined, and one or more of the Camelid amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelid sdAbs requires the introduction and mutagenesis of a limited amount of amino acids in a single polypeptide chain. This is in contrast to humanization of scFv, Fab', (Fab')2 and IgG, which requires the introduction of amino acid changes in two chains, the light and the heavy chain and the preservation of the assembly of both chains.

Single-domain antibodies comprising a V$_H$H domain can be humanized to have human-like sequences. In some embodiments, the FR regions of the V$_H$H domain used herein comprise at least about any one of 50%, 60%, 70%, 80%, 90%, 95% or more of amino acid sequence homology to human V$_H$ framework regions. One exemplary class of humanized V$_H$H domains is characterized in that the V$_H$Hs carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human V$_H$ framework regions and said polypeptides might be administered to a human directly without expectation of an unwanted immune response therefrom, and without the burden of further humanization.

Another exemplary class of humanized Camelid sdAbs has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in V$_H$ from double-chain antibodies. As such, peptides belonging to these two classes show a high amino acid sequence homology to human V$_H$ framework regions and said peptides might be administered to a human directly without expectation of an unwanted immune response therefrom, and without the burden of further humanization.

4. Human Antibodies

In some embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Transgenic mice or rats capable of producing fully human sdAbs are known in the art. See, e.g., US20090307787A1, U.S. Pat. No. 8,754,287, US20150289489A1, US20100122358A1, and WO2004049794.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl Acad. Sci. USA*, 1033557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining $V_HH$ sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said $V_HH$ sequences (such as a blood sample, serum sample or sample of B-cells), and then generating $V_HH$ sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

5. Library-Derived Antibodies

Antibodies of the present application may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004). Methods for constructing sdAb libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In some embodiments, an antibody provided herein is a multispecific antibody, e.g. a bispecific antibody. Multispecific antibodies are antibodies that have binding specificities for at least two different sites. In some embodiments, one of the binding specificities is for an antigen selected from the group consisting of CD19, CD20, BCMA, and CD38, and the other is for any other antigen. In some embodiments, bispecific antibodies may bind to two different epitopes of an antigen selected from the group consisting of CD19, CD20, BCMA, and CD38. Bispecific antibodies may also be used to localize cytotoxic agents to cells which express an antigen selected from the group consisting of CD19, CD20, BCMA, and CD38.

Bispecific antibodies can be prepared as full length antibodies or antibody fragments. Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g., Gruber et al., *J. Immunol.*, 152:5368 (1994)); and preparing trispecific antibodies as described, e.g., in Tutt et al. *J. Immunol.* 147: 60 (1991); and creating polypeptides comprising tandem single-domain antibodies (see, e.g, U.S. Patent Application No. 20110028695; and Conrath et al. J. Biol. Chem., 2001; 276(10):7346-50). Engineered antibodies with three or more functional antigen binding sites, including "Octopus antibodies," are also included herein (see, e.g., US 2006/0025576A1).

7. Antibody Variants

In some embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In some embodiments, antibody variants having one or more amino acid substitutions are provided. Sites of interest for substitutional mutagenesis include the HVRs and FRs. Conservative substitutions are shown in Table 3 under the heading of "Preferred substitutions." More substantial changes are provided in Table 3 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 3

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the present application may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4): 680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In some embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In some embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Methods of Preparation

The antibodies (such as sdAbs) described herein may be prepared using any methods known in the art or as described herein.

Methods of preparing sdAbs have been described. See, for example, Els Pardon et al, *Nature Protocol,* 2014; 9(3): 674. Single-domain antibodies (such as $V_H$Hs) may be obtained using methods known in the art such as by immunizing a Camelid species (such as camel or llama) and obtaining hybridomas therefrom, or by cloning a library of sdAbs using molecular biology techniques known in the art and subsequent selection by ELISA with individual clones of unselected libraries or by using phage display.

For recombinant production of the sdAbs, the nucleic acids encoding the sdAbs are isolated and inserted into a replicable vector for further cloning (amplification of the DNA) or for expression. DNA encoding the sdAb is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

1. Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 µg or 5 µg or the protein or conjugate (for rabbits or mice, respectively) with 3 volumes of Freund's complete adjuvant and injecting the solution intradermally at multiple sites. One month later, the animals are boosted with ⅕ to ¹/₁₀ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

2. Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, Monoclonal Antibodies: Principles and Practice, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applicalions, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., Curr. Opinion in Immunol., 5:256-262 (1993) and Pluckthun, Immunol. Revs. 130:151-188 (1992).

In a further embodiment, antibodies can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nucl. Acids Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl Acad. Sci. USA, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3. Recombinant Production in Prokaryotic Cells a) Vector Construction

Polynucleotide sequences encoding the antibodies of the present application can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RB S), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as E. coli LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments of the present application, the signal sequences used in both cistrons of the expression system are STII signal sequences or variants thereof.

In some embodiments, the production of the antibodies according to the present application can occur in the cytoplasm of the host cell, and therefore does not require the presence of secretion signal sequences within each cistron. In some embodiments, polypeptide components, such as the polypeptide encoding the $V_H$ domain of the first antigen binding portion optionally fused to the second antigen binding portion, and the polypeptide encoding the $V_L$ domain of the first antigen binding portion optionally fused to the second antigen binding portion, are expressed, folded and assembled to form functional antibodies within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun Gene, 159:203 (1995).

The present invention provides an expression system in which the quantitative ratio of expressed polypeptide components can be modulated in order to maximize the yield of secreted and properly assembled the antibodies of the present application. Such modulation is accomplished at least in part by simultaneously modulating translational strengths for the polypeptide components. One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleic acid sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired protein products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the present application.

b) Prokaryotic Host Cells

Prokaryotic host cells suitable for expressing the antibodies of the present application include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In some embodiments, gram-negative cells are used. In some embodiments, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 AfhuA (AtonA) ptr3 lac Iq lacL8 AompT A(nmpc-fepE) degP41 kan$^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

c) Protein Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

The expressed antibodies of the present application are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

During the fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the antibodies of the present application, various fermentation conditions can be modified. For example, to improve the proper assembly and folding of the secreted polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275: 17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

*E. coli* strains deficient for proteolytic enzymes and transformed with plasmids overexpressing one or more chaperone proteins may be used as host cells in the expression system encoding the antibodies of the present application.

d) Protein Purification

The antibodies produced herein are further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibodies comprising an Fc region of the present application. Protein A is a 41 kD cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants non-specifically bound to the solid phase. Finally the antibodies of interest is recovered from the solid phase by elution.

4. Recombinant Production in Eukaryotic Cells

For Eukaryotic expression, the vector components generally include, but are not limited to, one or more of the following, a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibodies of the present application.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

d) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. A the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter,—lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibodies.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the antibodies of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/−DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibodies production and cultured in conventional nutrient media modified as appropriate for inducing promoters, selecting transformants, or amplifying the genes encoding the desired sequences.

h) Culturing the Host Cells

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Protein Purification

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify the antibodies that are based on human immunoglobulins containing 1, 2, or 4 heavy chains (Lindmark et al., *J. Immunol. Meth.* 62:1-13 (1983)). Protein G is recommended for all mouse isotypes and for human 3 (Guss et al., *EMBO J* 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_H3$ domain, the Bakerbond ABXTMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

In some embodiments, the present application also provides immunoconjugates comprising any of the antibodies (such as sdAbs) described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Methods and Compositions for Diagnostics and Detection

In some embodiments, any of the antibodies (such as sdAbs) provided herein is useful for detecting the presence of BCMA in a biological sample. The term "detecting" as used herein encompasses quantitative or qualitative detection. In certain embodiments, a biological sample is blood, serum or other liquid samples of biological origin. In some embodiments, a biological sample comprises a cell or tissue.

In some embodiments, an anti-BCMA antibody (such as any one of the anti-BCMA sdAbs described herein) for use in a method of diagnosis or detection is provided. In a further aspect, a method of detecting the presence of BCMA in a biological sample is provided. In certain embodiments, the method comprises detecting the presence of BCMA protein in a biological sample. In certain embodiments, BCMA is human BCMA. In certain embodiments, the method comprises contacting the biological sample with an anti-BCMA antibody as described herein under conditions permissive for binding of the anti-BCMA antibody to BCMA, and detecting whether a complex is formed between the anti-BCMA antibody and BCMA. Such method may be an in vitro or in vivo method. In some embodiments, an anti-BCMA antibody is used to select subjects eligible for therapy with an anti-BCMA antibody, e.g. where BCMA is a biomarker for selection of patients.

In certain embodiments, labeled anti-BCMA sdAbs are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

III. Chimeric Antigen Receptors

One aspect of the present application provides a chimeric antigen receptor (CAR) comprising an extracellular antigen binding domain comprising one or more single-domain antibodies (such as $V_HHs$). Any one of the anti-BCMA sdAbs described in Section II can be used in the CARs described herein. Exemplary structures of CARs are shown in FIGS. 15A-15D.

In some embodiments, there is provided a CAR targeting BCMA (also referred herein as "BCMA CAR") comprising a polypeptide comprising: (a) an extracellular antigen binding domain comprising an anti-BCMA sdAb; (b) a transmembrane domain; and (c) an intracellular signaling domain. In some embodiments, the anti-BCMA sdAb is camelid, chimeric, human, or humanized. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the BCMA CAR is monospecific. In some embodiments, the BCMA CAR is monovalent.

In some embodiments, there is provided a BCMA CAR comprising a polypeptide comprising: (a) an extracellular antigen binding domain comprising an anti-BCMA sdAb; (b) a transmembrane domain; and (c) an intracellular signaling domain, wherein the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the anti-BCMA sdAb is camelid, chimeric, human, or humanized. In some embodiments, the anti-BCMA sdAb comprises a $V_HH$ domain comprising an amino acid sequence selected from the group consisting of SEQ ID NO: 115-152. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the BCMA CAR is monospecific. In some embodiments, the BCMA CAR is monovalent.

In some embodiments, there is provided a BCMA CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NO: 216-256 and 298-335. In some embodiments, there is provided a BCMA CAR comprising an amino acid sequence selected from the group consisting of SEQ ID NO: 216-256 and 298-335. Also provided is a polypeptide comprising an amino acid sequence selected from the group consisting of SEQ ID NO: 216-256 and 298-335.

In some embodiments, there is provided an isolated nucleic acid encoding any of the BCMA CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NOs: 257-297 and 336-373. In some embodiments, there is provided an isolated nucleic acid comprising a nucleic acid sequence selected from the group consisting of SEQ ID NO: 257-297 and 336-373. In some embodiments, the isolated nucleic acid is a DNA. In some embodiments, the isolated nucleic acid is an RNA. In some embodiments, there is provided a vector comprising any one of the nucleic acids encoding the BCMA CARs described above. In some embodiments, the vector is an expression vector. In some embodiments, the vector is a viral vector, such as a lentiviral vector. In some embodiments, the vector is a non-viral vector. Exemplary monovalent BCMA CARs are shown in Table 4 below.

TABLE 4

Exemplary monovalent BCMA CARs.

| Ex. Vector or CAR name | Ex. AA SEQ ID | Ex. NA SEQ ID | SP | Extra-cellular. sdAb | Hinge | TM | Intracellular signaling | | |
|---|---|---|---|---|---|---|---|---|---|
| | | | | | | | CO1 | CO2 | Prim. |
| PLLV-hEF1a-269A37346 | 216 | 257 | CD8α | 269A37346 | CD8α | CD28 | CD28 | CD137 | CD3ζ |
| PLLV-hEF1a-269A37348 | 217 | 258 | CD8α | 269A37348 | CD8α | CD28 | CD28 | CD137 | CD3ζ |

TABLE 4-continued

Exemplary monovalent BCMA CARs.

| Ex. Vector or CAR name | Ex. AA SEQ ID | Ex. NA SEQ ID | SP | Extra-cellular. sdAb | Hinge | TM | Intracellular signaling CO1 | CO2 | Prim. |
|---|---|---|---|---|---|---|---|---|---|
| PLLV-hEF1a-269A37917 | 218 | 259 | CD8α | 269A37917 | CD8α | CD28 | CD28 | CD137 | CD3ζ |
| PLLV-hEF1a-269A37355 | 219 | 260 | CD8α | 269A37355 | CD8α | CD28 | CD28 | CD137 | CD3ζ |
| PLLV-hEF1a-269A37915 | 220 | 261 | CD8α | 269A37915 | CD8α | CD28 | CD28 | CD137 | CD3ζ |
| PLLV-hEF1a-269A37936 | 221 | 262 | CD8α | 269A37936 | CD8α | CD28 | CD28 | CD137 | CD3ζ |
| PLLV-hEF1a-269A37953 | 222 | 263 | CD8α | 269A37953 | CD8α | CD28 | CD28 | CD137 | CD3ζ |
| PLLV-hEF1a-269A37965 | 223 | 264 | CD8α | 269A37965 | CD8α | CD28 | CD28 | CD137 | CD3ζ |
| PLLV-hEF1a-269A37972 | 224 | 265 | CD8α | 269A37972 | CD8α | CD28 | CD28 | CD137 | CD3ζ |
| PLLV-hEF1a-269A37353 | 225 | 266 | CD8α | 269A37353 | CD8α | CD28 | CD28 | CD137 | CD3ζ |
| PLLV-hEF1a-269A37948 | 226 | 267 | CD8α | 269A37948 | CD8α | CD28 | CD28 | CD137 | CD3ζ |
| GSI5011 CAR | 227 | 268 | CD8α | 269A37346 | CD8α | CD8α | CD137 | NA | CD3ζ |
| GSI5019 CAR | 228 | 269 | CD8α | 269A37353 | CD8α | CD8α | CD137 | NA | CD3ζ |
| GSI5020 CAR | 229 | 270 | CD8α | 269A37917 | CD8α | CD8α | CD137 | NA | CD3ζ |
| 269B005S | 230 | 271 | CD8α | 269B005 | CD8α | CD8α | CD137 | NA | CD3ζ |
| 269B023S | 231 | 272 | CD8α | 269B023 | CD8α | CD8α | CD137 | NA | CD3ζ |
| 269B024S | 232 | 273 | CD8α | 269B024 | CD8α | CD8α | CD137 | NA | CD3ζ |
| 269B028S | 233 | 274 | CD8α | 269B028 | CD8α | CD8α | CD137 | NA | CD3ζ |
| 269B030S | 234 | 275 | CD8α | 269B030 | CD8α | CD8α | CD137 | NA | CD3ζ |
| 269B038S | 235 | 276 | CD8α | 269B038 | CD8α | CD8α | CD137 | NA | CD3ζ |
| 269B054S | 236 | 277 | CD8α | 269B054 | CD8α | CD8α | CD137 | NA | CD3ζ |
| 269B059S | 237 | 278 | CD8α | 269B059 | CD8α | CD8α | CD137 | NA | CD3ζ |
| 269B060S | 238 | 279 | CD8α | 269B060 | CD8α | CD8α | CD137 | NA | CD3ζ |
| 269B069S | 239 | 280 | CD8α | 269B069 | CD8α | CD8α | CD137 | NA | CD3ζ |
| 269B074S | 240 | 281 | CD8α | 269B074 | CD8α | CD8α | CD137 | NA | CD3ζ |
| 269B076S | 241 | 282 | CD8α | 269B076 | CD8α | CD8α | CD137 | NA | CD3ζ |
| 269B079S | 242 | 283 | CD8α | 269B083 | CD8α | CD8α | CD137 | NA | CD3ζ |
| 269B083S | 243 | 284 | CD8α | 269B085 | CD8α | CD8α | CD137 | NA | CD3ζ |
| 269B085S | 244 | 285 | CD8α | 269B093 | CD8α | CD8α | CD137 | NA | CD3ζ |
| 269B093S | 245 | 286 | CD8α | 269B094 | CD8α | CD8α | CD137 | NA | CD3ζ |
| 269B094S | 246 | 287 | CD8α | 269B104 | CD8α | CD8α | CD137 | NA | CD3ζ |
| 269B104S | 247 | 288 | CD8α | 269B109 | CD8α | CD8α | CD137 | NA | CD3ζ |
| 269B109S | 248 | 289 | CD8α | 269B110 | CD8α | CD8α | CD137 | NA | CD3ζ |
| 269B110S | 249 | 290 | CD8α | 269B113 | CD8α | CD8α | CD137 | NA | CD3ζ |
| 269B113S | 250 | 291 | CD8α | 269B126 | CD8α | CD8α | CD137 | NA | CD3ζ |
| 269B126S | 251 | 292 | CD8α | 269B129 | CD8α | CD8α | CD137 | NA | CD3ζ |
| 269B129S | 252 | 293 | CD8α | 269B131 | CD8α | CD8α | CD137 | NA | CD3ζ |
| 269B131S | 253 | 294 | CD8α | 269B135 | CD8α | CD8α | CD137 | NA | CD3ζ |
| 269B135S | 254 | 295 | CD8α | 269B136 | CD8α | CD8α | CD137 | NA | CD3ζ |
| 269B136S | 255 | 296 | CD8α | 269B139 | CD8α | CD8α | CD137 | NA | CD3ζ |
| 269B139S | 256 | 297 | CD8α | 269B024 | CD8α | CD8α | CD137 | NA | CD3ζ |

Multivalent Chimeric Antigen Receptors

The present application also provides multivalent CARs that have two or more (such as about any one of 2, 3, 4, 5, 6, or more) binding moieties that specifically bind to an antigen, such as BCMA. In some embodiments, one or more of the binding moieties are antigen binding fragments. In some embodiments, one or more of the binding moieties comprise single-domain antibodies. In some embodiments, one or more of the binding moieties are derived from camelid antibodies. In some embodiments, one or more of the binding moieties are derived from a four-chain antibody. In some embodiments, one or more of the binding moieties are scFvs. In some embodiments, one or more of the binding moieties are derived from human antibodies. In some embodiments, one or more of the binding moieties are polypeptide ligands or other non-antibody polypeptides that specifically bind to the antigen. In some embodiments, the multivalent CAR is monospecific, i.e., the multivalent CAR targets a single antigen, and comprises two or more binding sites for the single antigen. In some embodiments, the multivalent CAR is multispecific, i.e., the multivalent CAR targets more than one antigen, and the multivalent CAR comprises two or more binding sites for at least one antigen. The binding moieties specific for the same antigen may bind to the same epitope of the antigen (i.e., "mono-epitope CAR") or bind to different epitopes (i.e., "multi-epitope CAR" such as bi-epitope CAR or tri-epitope CAR) of the antigen. The binding sites specific for the same antigen may comprise the same or different sdAbs.

In some embodiments, the present application provides a multivalent (such as bivalent, trivalent, or of higher number of valencies) chimeric antigen receptor comprising a polypeptide comprising: (a) an extracellular antigen binding domain comprising a plurality (such as at least about any one of 2, 3, 4, 5, 6, or more) of binding moieties specifically binding to an antigen (such as a tumor antigen); (b) a transmembrane domain; and (c) an intracellular signaling domain. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In some embodiments, the present application provides a multivalent (such as bivalent, trivalent, or of higher number of valencies) chimeric antigen receptor comprising a polypeptide comprising: (a) an extracellular antigen binding domain comprising a plurality (such as at least about any one of 2, 3, 4, 5, 6, or more) of single-domain antibodies (sdAbs) specifically binding to an antigen (such as a tumor antigen); (b) a transmembrane domain; and (c) an intracellular signaling domain. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In some embodiments, the present application provides a multivalent (such as bivalent, trivalent, or of higher number of valencies) chimeric antigen receptor comprising a polypeptide comprising: (a) an extracellular antigen binding domain comprising a first binding moiety specifically binding to a first epitope of an antigen (such as a tumor antigen), and a second binding moiety specifically binding to a second epitope of the antigen; (b) a transmembrane domain; and (c) an intracellular signaling domain, wherein the first epitope and the second epitope are different. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first binding moiety is an sdAb and the second binding moiety is derived from a human antibody (e.g., an scFv). In some embodiments, the first binding moiety is an sdAb and the second binding moiety is a polypeptide ligand. In some embodiments, the first epitope is the same as the second epitope. In some embodiments, the first epitope is different from the second epitope. In some embodiments, the multivalent CAR specifically binds to two different epitopes on an antigen. In some embodiments, the multivalent CAR specifically binds to three or more different epitopes on an antigen.

In some embodiments, the present application provides a multivalent (such as bivalent, trivalent, or of higher number of valencies) chimeric antigen receptor comprising a polypeptide comprising: (a) an extracellular antigen binding domain comprising a first sdAb specifically binding to a first epitope of an antigen (such as a tumor antigen), and a second sdAb specifically binding to a second epitope of the antigen; (b) a transmembrane domain; and (c) an intracellular signaling domain, wherein the first epitope and the second epitope are different. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In some embodiments, the binding moieties, such as sdAbs (including the plurality of sdAbs, or the first sdAb and/or the second sdAb) are camelid, chimeric, human, or humanized. In some embodiments, the binding moieties or sdAbs are fused to each other via peptide bonds or peptide linkers. In some embodiments, each peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CAR is monospecific. In some embodiments, the multivalent CAR is multispecific, such as bispecific.

The multivalent CARs describe herein may be specially suitable for targeting multimeric antigens via synergistic binding by the different antigen binding sites, or for enhancing binding affinity or avidity to the antigen. Any of the anti-BCMA sdAbs described herein may be used in the extracellular antigen binding domain of the multivalent CARs described herein. A list of exemplary multivalent BCMA CARs, exemplary sequences, constructs and vectors thereof are shown in Table 5.

In some embodiments, there is provided a multivalent CAR targeting BCMA comprising: (a) an extracellular antigen binding domain comprising a plurality (such as at least about any one of 2, 3, 4 or more) of a BCMA binding moiety (e.g., an anti-BCMA sdAb); (b) a transmembrane domain; and (c) an intracellular signaling domain. Any of the anti-BCMA sdAbs can be used to construct the multivalent BCMA CAR. In some embodiments, the extracellular antigen binding domain specifically binds to a single epitope of BCMA, and these CARs are referred herein as mono-epitope multivalent BCMA CARs.

In some embodiments, there is provided a multivalent BCMA CAR comprising: (a) an extracellular antigen binding domain comprising a plurality (such as at least about any one of 2, 3, 4 or more) of an anti-BCMA sdAb; (b) a transmembrane domain; and (c) an intracellular signaling domain, wherein the anti-BCMA sdAb comprises a CDR1 comprising the amino acid sequence of SEQ ID NO:1, a CDR2 comprising the amino acid sequence of SEQ ID NO:39, and a CDR3 comprising the amino acid sequence of SEQ ID NO:77.

In some embodiments, there is provided a multivalent BCMA CAR (also referred herein as "multi-epitope multivalent CAR") comprising: (a) an extracellular antigen binding domain comprising at least two (such as any one of 2, 3, 4, or more) BCMA binding moieties; (b) a transmembrane domain; and (c) an intracellular signaling domain, wherein the at least two BCMA binding moieties specifically bind to at least two different epitopes on BCMA. In some embodiments, the extracellular antigen binding domain comprises a first BCMA binding moiety and a second BCMA binding moiety. In some embodiments, the first BCMA binding moiety is an anti-BCMA sdAb and the second BCMA binding moiety is derived from a human antibody (e.g., an scFv). In some embodiments, the first BCMA binding moiety is an sdAb and the second BCMA binding moiety is a BCMA polypeptide ligand. In some embodiments, the first anti-BCMA binding moiety and/or the second BCMA binding moiety specifically binds to an epitope on BCMA derived from an amino acid sequence selected from SEQ ID NOs: 388-394. In some embodiments, the first BCMA binding moiety specifically binds to an epitope derived from SEQ ID NO: 389 and/or 390. In some embodiments, the second BCMA binding moiety specifically binds to an epitope derived from SEQ ID NO: 391 and/or 392.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb and the second anti-BCMA sdAb specifically binds to different epitopes on BCMA. Any of the anti-BCMA sdAbs can be used to construct the multivalent BCMA CAR. In some embodiments, the first anti-BCMA sdAb and/or the second anti-BCMA sdAb specifically binds to an epitope on BCMA derived from an amino acid sequence selected from SEQ ID NOs: 388-394. In some embodiments, the first anti-BCMA sdAb specifically binds to an epitope derived from SEQ ID NO: 389 and/or 390. In some embodiments, the second anti-BCMA sdAb specifically binds to an epitope derived from SEQ ID NO: 391 and/or 392.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:3, a CDR2 comprising the amino acid sequence of SEQ ID NO:41, and a CDR3 comprising the amino acid sequence of SEQ ID NO:79; and wherein the second anti-BCMA sdAb comprises a CDR1 comprising the amino acid sequence of SEQ ID NO:10, a CDR2 comprising the amino acid sequence of SEQ ID NO:48, and a CDR3 comprising the amino acid sequence of SEQ ID NO:86. In some embodiments, the first anti-BCMA sdAb comprises a $V_HH$ domain comprising the amino acid sequence of SEQ ID NO: 117. In some embodiments, the second anti-BCMA sdAb comprises a $V_HH$ domain comprising the amino acid sequence of SEQ ID NO: 124. In some embodiments, the first anti-BCMA sdAb comprises a $V_HH$ domain comprising the amino acid sequence of SEQ ID NO: 124. In some embodiments, the second anti-BCMA sdAb comprises a $V_HH$ domain comprising the amino acid sequence of SEQ ID NO: 117.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:10, a CDR2 comprising the amino acid sequence of SEQ ID NO:48, and a CDR3 comprising the amino acid sequence of SEQ ID NO:86; and wherein anti-BCMA sdAb comprises a CDR1 comprising the amino acid sequence of SEQ ID NO:11, a CDR2 comprising the amino acid sequence of SEQ ID NO:49, and a CDR3 comprising the amino acid sequence of SEQ ID NO:87. In some embodiments, the first anti-BCMA sdAb comprises a $V_HH$ domain comprising the amino acid sequence of SEQ ID NO: 124. In some embodiments, the second anti-BCMA sdAb comprises a $V_HH$ domain comprising the amino acid sequence of SEQ ID NO: 125.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:7, a CDR2 comprising the amino acid sequence of SEQ ID NO:45, and a CDR3 comprising the amino acid sequence of SEQ ID NO:83; and wherein anti-BCMA sdAb comprises a CDR1 comprising the amino acid sequence of SEQ ID NO:11, a CDR2 comprising the amino acid sequence of SEQ ID NO:49, and a CDR3 comprising the amino acid sequence of SEQ ID NO:87. In some embodiments, the first anti-BCMA sdAb comprises a $V_HH$ domain comprising the amino acid sequence of SEQ ID NO: 121. In some embodiments, the second anti-BCMA sdAb comprises a $V_HH$ domain comprising the amino acid sequence of SEQ ID NO: 125.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:15, a CDR2 comprising the amino acid sequence of SEQ ID NO:53, and a CDR3 comprising the amino acid sequence of SEQ ID NO:91; and wherein anti-BCMA sdAb comprises a CDR1 comprising the amino acid sequence of SEQ ID NO:18, a CDR2 comprising the amino acid sequence of SEQ ID NO:56, and a CDR3 comprising the amino acid sequence of SEQ ID NO:94. In some embodiments, the first anti-BCMA sdAb comprises a $V_HH$ domain comprising the amino acid sequence of SEQ ID NO: 129. In some embodiments, the second anti-BCMA sdAb comprises a $V_HH$ domain comprising the amino acid sequence of SEQ ID NO: 132.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:18, a CDR2 comprising the amino acid sequence of SEQ ID NO:56, and a CDR3 comprising the amino acid sequence of SEQ ID NO:94; and wherein anti-BCMA sdAb comprises a CDR1 comprising the amino acid sequence of SEQ ID NO:20, a CDR2 comprising the amino acid sequence of SEQ ID NO:58, and a CDR3 comprising the amino acid sequence of SEQ ID NO:96. In some embodiments, the first anti-BCMA sdAb comprises a $V_HH$ domain comprising the amino acid sequence of SEQ ID NO: 132. In some embodiments, the second anti-BCMA sdAb comprises a $V_HH$ domain comprising the amino acid sequence of SEQ ID NO: 134.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO:20, a CDR2 comprising the amino acid sequence of SEQ ID NO:58, and a CDR3 comprising the amino acid sequence of SEQ ID NO:96; and wherein anti-BCMA sdAb comprises a CDR1 comprising the amino acid sequence of SEQ ID NO:28, a CDR2 comprising the amino acid sequence of SEQ ID NO:66, and a CDR3 comprising the amino acid sequence of SEQ ID NO:104. In some embodiments, the first anti-BCMA sdAb comprises a V$_H$H domain comprising the amino acid sequence of SEQ ID NO: 134. In some embodiments, the second anti-BCMA sdAb comprises a V$_H$H domain comprising the amino acid sequence of SEQ ID NO: 142.

In some embodiments, the first BCMA binding moiety (e.g., the first anti-BCMA sdAb) is located at the N-terminus of the second BCMA binding moiety (e.g., the second anti-BCMA sdAb). In some embodiments, the first BCMA binding moiety (e.g., the first anti-BCMA sdAb) is located at the C-terminus of the second BCMA binding moiety (e.g., the second anti-BCMA sdAb). In some embodiments, the first BCMA binding moiety (e.g., the first anti-BCMA sdAb) and the second BCMA binding moiety (e.g., the second anti-BCMA sdAb) are fused to each other via a peptide bond or a peptide linker. In some embodiments, the peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the multivalent BCMA CAR further comprises a hinge domain (such as a CD8α hinge domain) located between the C-terminus of the extracellular antigen binding domain and the N-terminus of the transmembrane domain. In some embodiments, the multivalent BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent BCMA CAR is bivalent. In some embodiments, the multivalent BCMA CAR is trivalent. In some embodiments, the multivalent BCMA CAR specifically binds to two different epitopes on BCMA. In some embodiments, the multivalent BCMA CAR specifically binds to three or more different epitopes on BCMA.

In some embodiments, there is provided a multivalent BCMA CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NOs: 298-335. In some embodiments, there is provided a multivalent BCMA CAR comprising an amino acid sequence selected from the group consisting of SEQ ID NOs: 298-335. Also provided is a polypeptide comprising an amino acid sequence selected from the group consisting of SEQ ID NOs: 298-335.

In some embodiments, there is provided an isolated nucleic acid encoding any of the multivalent BCMA CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NOs: 336-373. In some embodiments, there is provided an isolated nucleic acid comprising a nucleic acid sequence selected from the group consisting of SEQ ID NOs: 336-373. In some embodiments, the isolated nucleic acid is a DNA. In some embodiments, the isolated nucleic acid is an RNA. In some embodiments, there is provided a vector comprising any one of the nucleic acids encoding the multivalent BCMA CARs described above. In some embodiments, the vector is an expression vector. In some embodiments, the vector is a viral vector, such as a lentiviral vector. In some embodiments, the vector is a non-viral vector. Exemplary multivalent BCMA CARs are shown in Table 5 below.

TABLE 5

Exemplary multivalent BCMA CARs.

| | | | | Extracellular Antigen binding domain | | | | | | | Intracellular signaling | |
|---|---|---|---|---|---|---|---|---|---|---|---|---|
| CAR | Ex. AA SEQ ID | Ex. NA SEQ ID | SP | sdAb #1 | Lnk. #1 SEQ ID | sdAb #2 | Lnk. #2 SEQ ID | sdAb #3 | Hinge | TM | CO1 | Prim. |
| GSI5014 | 298 | 336 | CD8α | 269A37346 | 208 | 269A37346 | NA | NA | CD8α | CD8α | CD137 | CD3ζ |
| GSI5015 | 299 | 337 | CD8α | 269A37346 | 208 | 269A37346 | 208 | 269A37346 | CD8α | CD8α | CD137 | CD3ζ |
| GSI5021 | 300 | 338 | CD8α | 269A37353 | 208 | 269A37917 | NA | NA | CD8α | CD8α | CD137 | CD3ζ |
| GSI5022 | 301 | 339 | CD8α | 269A37353 | 213 | 269A37917 | NA | NA | CD8α | CD8α | CD137 | CD3ζ |
| GSI5023 | 302 | 340 | CD8α | 269A37353 | 215 | 269A37917 | NA | NA | CD8α | CD8α | CD137 | CD3ζ |
| GSI5024 | 303 | 341 | CD8α | 269A37917 | 209 | 269A37353 | NA | NA | CD8α | CD8α | CD137 | CD3ζ |
| GSI5025 | 304 | 342 | CD8α | 269A37917 | 213 | 269A37353 | NA | NA | CD8α | CD8α | CD137 | CD3ζ |
| GSI5026 | 305 | 343 | CD8α | 269A37917 | 214 | 269A37353 | NA | NA | CD8α | CD8α | CD137 | CD3ζ |
| BCAR001 | 306 | 344 | CD8α | 269A37353 | 208 | 269A37948 | NA | NA | CD8α | CD8α | CD137 | CD3ζ |
| BCAR002 | 307 | 345 | CD8α | 269A37353 | 213 | 269A37948 | NA | NA | CD8α | CD8α | CD137 | CD3ζ |
| BCAR003 | 308 | 346 | CD8α | 269A37353 | 215 | 269A37948 | NA | NA | CD8α | CD8α | CD137 | CD3ζ |
| BCAR004 | 309 | 347 | CD8α | 269A37948 | 209 | 269A37353 | NA | NA | CD8α | CD8α | CD137 | CD3ζ |
| BCAR005 | 310 | 348 | CD8α | 269A37948 | 213 | 269A37353 | NA | NA | CD8α | CD8α | CD137 | CD3ζ |
| BCAR006 | 311 | 349 | CD8α | 269A37948 | 214 | 269A37353 | NA | NA | CD8α | CD8α | CD137 | CD3ζ |
| BCAR007 | 312 | 350 | CD8α | 269A37953 | 208 | 269A37948 | NA | NA | CD8α | CD8α | CD137 | CD3ζ |

TABLE 5-continued

Exemplary multivalent BCMA CARs.

| CAR | Ex. AA SEQ ID | Ex. NA SEQ ID | SP | sdAb #1 | Lnk. #1 SEQ ID | sdAb #2 | Lnk. #2 SEQ ID | sdAb #3 | Hinge | TM | Intracellular signaling CO1 | Prim. |
|---|---|---|---|---|---|---|---|---|---|---|---|---|
| BCAR008 | 313 | 351 | CD8α | 269A37953 | 213 | 269A37948 | NA | NA | CD8α | CD8α | CD137 | CD3ζ |
| BCAR009 | 314 | 352 | CD8α | 269A37953 | 215 | 269A37948 | NA | NA | CD8α | CD8α | CD137 | CD3ζ |
| BCAR010 | 315 | 353 | CD8α | 269A37953 | 209 | 269A37948 | NA | NA | CD8α | CD8α | CD137 | CD3ζ |
| BCAR011 | 316 | 354 | CD8α | 269A37953 | 213 | 269A37948 | NA | NA | CD8α | CD8α | CD137 | CD3ζ |
| BCAR012 | 317 | 355 | CD8α | 269A37953 | 214 | 269A37948 | NA | NA | CD8α | CD8α | CD137 | CD3ζ |
| BCAR013 | 318 | 356 | CD8α | 269B028 | 208 | 269B054 | NA | NA | CD8α | CD8α | CD137 | CD3ζ |
| BCAR014 | 319 | 357 | CD8α | 269B028 | 213 | 269B054 | NA | NA | CD8α | CD8α | CD137 | CD3ζ |
| BCAR015 | 320 | 358 | CD8α | 269B028 | 215 | 269B054 | NA | NA | CD8α | CD8α | CD137 | CD3ζ |
| BCAR016 | 321 | 359 | CD8α | 269B028 | 209 | 269B054 | NA | NA | CD8α | CD8α | CD137 | CD3ζ |
| BCAR017 | 322 | 360 | CD8α | 269B028 | 213 | 269B054 | NA | NA | CD8α | CD8α | CD137 | CD3ζ |
| BCAR018 | 323 | 361 | CD8α | 269B028 | 214 | 269B054 | NA | NA | CD8α | CD8α | CD137 | CD3ζ |
| BCAR019 | 324 | 362 | CD8α | 269B054 | 208 | 269B060 | NA | NA | CD8α | CD8α | CD137 | CD3ζ |
| BCAR020 | 325 | 363 | CD8α | 269B054 | 213 | 269B060 | NA | NA | CD8α | CD8α | CD137 | CD3ζ |
| BCAR021 | 326 | 364 | CD8α | 269B054 | 215 | 269B060 | NA | NA | CD8α | CD8α | CD137 | CD3ζ |
| BCAR022 | 327 | 365 | CD8α | 269B054 | 209 | 269B060 | NA | NA | CD8α | CD8α | CD137 | CD3ζ |
| BCAR023 | 328 | 366 | CD8α | 269B054 | 213 | 269B060 | NA | NA | CD8α | CD8α | CD137 | CD3ζ |
| BCAR024 | 329 | 367 | CD8α | 269B054 | 214 | 269B060 | NA | NA | CD8α | CD8α | CD137 | CD3ζ |
| BCAR025 | 330 | 368 | CD8α | 269B060 | 208 | 269B094 | NA | NA | CD8α | CD8α | CD137 | CD3ζ |
| BCAR026 | 331 | 369 | CD8α | 269B060 | 213 | 269B094 | NA | NA | CD8α | CD8α | CD137 | CD3ζ |
| BCAR027 | 332 | 370 | CD8α | 269B060S | 215 | 269B094 | NA | NA | CD8α | CD8α | CD137 | CD3ζ |
| BCAR028 | 333 | 371 | CD8α | 269B060 | 209 | 269B094 | NA | NA | CD8α | CD8α | CD137 | CD3ζ |
| BCAR029 | 334 | 372 | CD8α | 269B060 | 213 | 269B094 | NA | NA | CD8α | CD8α | CD137 | CD3ζ |
| BCAR030 | 335 | 373 | CD8α | 269B060 | 214 | 269B094 | NA | NA | CD8α | CD8α | CD137 | CD3ζ |

Multispecific Chimeric Antigen Receptor

The present application further provides multispecific chimeric antigen receptors targeting two or more (such as about any one of 2, 3, 4, 5, 6, or more) different antigens. In some embodiments, the multispecific CAR has one antigen binding site for each antigen. In some embodiments, the multispecific CAR has more than two binding sites for at least one antigen. Each antigen binding site may comprise a sdAb. For example, in some embodiments, the multispecific CAR is a bispecific CAR comprising an extracellular antigen binding domain comprising two different sdAbs each specifically binding to an antigen. In some embodiments, the multispecific CAR is a trispecific CAR comprising an extracellular antigen binding domain comprising three different sdAbs each specifically binding to an antigen.

In some embodiments, there is provided a multispecific (such as bispecific) chimeric antigen receptor (CAR) comprising a polypeptide comprising: (a) an extracellular antigen binding domain comprising a first single-domain antibody (sdAb) specifically binding to BCMA and a second single-domain antibody (sdAb) specifically binding to a second antigen (such as a tumor antigen); (b) a transmembrane domain; and (c) an intracellular signaling domain, wherein the first antigen is different from the second antigen. In some embodiments, the second antigen is selected from the group consisting of CD19, CD20, CD22, CD33, CD38, CS1, ROR1, GPC3, CD123, IL-13R, CD138, c-Met, EGFRvIII, GD-2, NY-ESO-1, MAGE A3, and glycolipid F77. In some embodiments, the first sdAb and/or the second sdAb is camelid, chimeric, human, or humanized. In some embodiments, the first sdAb and the second sdAb are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the multispecific CAR further comprises a hinge domain (such as a CD8α hinge domain) located between the C-terminus of the extracellular antigen binding domain and the N-terminus of the transmembrane domain. In some embodiments, the multispecific CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ.

Extracellular Antigen Binding Domain

The extracellular antigen binding domain of the CARs described herein comprises one or more (such as any one of 1, 2, 3, 4, 5, 6 or more) binding moieties, such as sdAbs. In some embodiments, the one or more binding moieties are antibodies or antigen-binding fragments thereof. In some embodiments, the one or more binding moieties are derived from four-chain antibodies. In some embodiments, the one or more binding moieties are derived from camelid antibodies. In some embodiments, the one or more binding moieties are derived from human antibodies. In some embodiments, the one or more binding moieties are non-antibody binding proteins, such as polypeptide ligands or engineered proteins that bind to an antigen. The binding moieties can be fused to each other directly via peptide bonds, or via peptide linkers.

1. Single-Domain Antibodies

In some embodiments, the CAR comprises an extracellular antigen binding domain comprising one or more sdAbs. The sdAbs may be of the same of different origins, and of the same or different sizes. Exemplary sdAbs include, but are not limited to, heavy chain variable domains from heavy-chain only antibodies (e.g., $V_HH$ or $V_{NAR}$), binding molecules naturally devoid of light chains, single domains (such as $V_H$ or $V_L$) derived from conventional 4-chain antibodies, humanized heavy-chain only antibodies, human sdAbs produced by transgenic mice or rats expressing human heavy chain segments, and engineered domains and single domain scaffolds other than those derived from antibodies. Any sdAbs known in the art or developed by the inventors, including the sdAbs described in Section II of the present application, may be used to construct the CARs described herein. The sdAbs may be derived from any species including, but not limited to mouse, rat, human, camel, llama, lamprey, fish, shark, goat, rabbit, and bovine. Single-domain antibodies contemplated herein also include naturally occurring sdAb molecules from species other than Camelidae and sharks.

In some embodiments, the sdAb is derived from a naturally occurring single-domain antigen binding molecule known as heavy chain antibody devoid of light chains (also referred herein as "heavy chain only antibodies"). Such single domain molecules are disclosed in WO 94/04678 and Hamers-Casterman, C. et al. (1993) Nature 363:446-448, for example. For clarity reasons, the variable domain derived from a heavy chain molecule naturally devoid of light chain is known herein as a $V_HH$ to distinguish it from the conventional $V_H$ of four chain immunoglobulins. Such a $V_HH$ molecule can be derived from antibodies raised in Camelidae species, for example, camel, llama, vicuna, dromedary, alpaca and guanaco. Other species besides Camelidae may produce heavy chain molecules naturally devoid of light chain, and such $V_HH$s are within the scope of the present application.

$V_HH$ molecules from Camelids are about 10 times smaller than IgG molecules. They are single polypeptides and can be very stable, resisting extreme pH and temperature conditions. Moreover, they can be resistant to the action of proteases which is not the case for conventional 4-chain antibodies. Furthermore, in vitro expression of $V_HH$ s produces high yield, properly folded functional $V_HH$s. In addition, antibodies generated in Camelids can recognize epitopes other than those recognized by antibodies generated in vitro through the use of antibody libraries or via immunization of mammals other than Camelids (see, for example, WO9749805). As such, multispecific or multivalent CARs comprising one or more $V_HH$ domains may interact more efficiently with targets than multispecific or multivalent CARs comprising antigen binding fragments derived from conventional 4-chain antibodies. Since $V_HH$s are known to bind into 'unusual' epitopes such as cavities or grooves, the affinity of CARs comprising such $V_HH$s may be more suitable for therapeutic treatment than conventional multispecific polypeptides.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) $V_H$ domain from a conventional 4-chain antibody by one or more of the amino acid residues that occur at the corresponding position(s) in a $V_HH$ domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$—$V_L$ interface, and/or at the so-called Camelidae hallmark residues, as defined herein (see for example WO 94/04678, Davies and Riechmann FEBS Letters 339: 285-290, 1994; Davies and Riechmann Protein Engineering 9 (6): 531-537, 1996; Riechmann J. Mol. Biol. 259: 957-969, 1996; and Riechmann and Muyldermans J. Immunol. Meth. 231: 25-38, 1999).

In some embodiments, the sdAb is a human sdAb produced by transgenic mice or rats expressing human heavy chain segments. See, e.g., US20090307787A1, U.S. Pat. No. 8,754,287, US20150289489A1, US20100122358A1, and WO2004049794. In some embodiments, the sdAb is affinity matured.

In some embodiments, naturally occurring $V_HH$ domains against a particular antigen or target, can be obtained from (naïve or immune) libraries of Camelid $V_HH$ sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naïve or immune) $V_HH$ libraries may be used, such as $V_HH$ libraries obtained from (naïve or immune) $V_HH$ libraries by techniques such as random mutagenesis and/or CDR shuffling, as for example described in WO 00/43507.

In some embodiments, the sdAbs are generated from conventional four-chain antibodies. See, for example, EP 0 368 684, Ward et al. (Nature 1989 Oct. 12; 341 (6242): 544-6), Holt et al., Trends Biotechnol., 2003, 21(11):484-490; WO 06/030220; and WO 06/003388.

2. Antigens

The antigen(s) targeted by the CARs of the present application are cell surface molecules. The binding moieties (such as sdAbs) may be chosen to recognize an antigen that acts as a cell surface marker on target cells associated with a special disease state. In some embodiments, the antigen (such as the first antigen and/or the second antigen) is a tumor antigen. In some embodiments, the multispecific CARs target two or more tumor antigens. In some embodiments, the tumor antigen is associated with a B cell malignancy. Tumors express a number of proteins that can serve as a target antigen for an immune response, particularly T cell mediated immune responses. The antigens targeted by the CAR may be antigens on a single diseased cell or antigens that are expressed on different cells that each contribute to the disease. The antigens targeted by the CAR may be directly or indirectly involved in the diseases.

Tumor antigens are proteins that are produced by tumor cells that can elicit an immune response, particularly T-cell mediated immune responses. The selection of the targeted antigen of the invention will depend on the particular type of cancer to be treated. Exemplary tumor antigens include, for example, a glioma-associated antigen, carcinoembryonic antigen (CEA), β human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and gp100 in melanoma and prostatic acid phosphatase (PAP) and prostate-specific antigen (PSA) in prostate cancer. Other target molecules belong to the group of transformation-related molecules such as the oncogene HER2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma.

In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include the following: Differentiation antigens such as MART-1/MelanA (MART-I), gp 100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23HI, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS 1, SDCCAG16, TA-90\Mac-2 binding protein\cyclophilin C-associated protein, TAAL6, TAG72, TLP, and TPS.

In some embodiments, the antigen (such as the first antigen and/or the second antigen) are selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

3. Peptide Linkers

The various binding moieties (such as sdAbs) in the multispecific or multivalent CARs described herein may be fused to each other via peptide linkers. In some embodiments, the binding moieties (such as sdAbs) are directly fused to each other without any peptide linkers. The peptide linkers connecting different binding moieties (such as sdAbs) may be the same or different. Different domains of the CARs may also be fused to each other via peptide linkers.

Each peptide linker in a CAR may have the same or different length and/or sequence depending on the structural and/or functional features of the sdAbs and/or the various domains. Each peptide linker may be selected and optimized independently. The length, the degree of flexibility and/or other properties of the peptide linker(s) used in the CARs may have some influence on properties, including but not limited to the affinity, specificity or avidity for one or more particular antigens or epitopes. For example, longer peptide linkers may be selected to ensure that two adjacent domains do not sterically interfere with one another. For example, in a multivalent or multispecific CAR of the present application that comprise sdAbs directed against a multimeric antigen, the length and flexibility of the peptide linkers are preferably such that it allows each sdAb in the multivalent CAR to bind to the antigenic determinant on each of the subunits of the multimer. In some embodiments, a short peptide linker may be disposed between the transmembrane domain and the intracellular signaling domain of a CAR. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include glycine polymers $(G)_n$, glycine-serine polymers (including, for example, $(GS)_n$, $(GSGGS)_n$, $(GGGS)_n$, and $(GGGGS)_n$, where n is an integer of at least one), glycine-alanine polymers, alanine-serine polymers, and other flexible linkers known in the art. In some embodiments, the peptide linker comprises the amino acid sequence GGGGS (SEQ ID NO: 208), $(GGGGS)_2$ (SEQ ID NO: 209), $(GGGS)_4$ (SEQ ID NO: 210), GGGGSGGGGSGGGGGSGSGGGS (SEQ ID NO: 211), GGGGSGGGGSGGGGGSGSGGGGSGGGGS-GGGGS (SEQ ID NO: 212), $(GGGGS)_3$ (SEQ ID NO: 213), $(GGGGS)_4$ (SEQ ID NO: 214), or $(GGGGS)_3$ (SEQ ID NO: 215).

Transmembrane Domain

The CARs of the present application comprise a transmembrane domain that can be directly or indirectly fused to the extracellular antigen binding domain. The transmembrane domain may be derived either from a natural or from a synthetic source. As used herein, a "transmembrane domain" refers to any protein structure that is thermodynamically stable in a cell membrane, preferably a eukaryotic cell membrane. Transmembrane domains compatible for use in the CARs described herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the CAR described herein is derived from a Type I single-pass membrane protein. In some embodiments, transmembrane domains from multi-pass membrane proteins may also be compatible for use in the CARs described herein. Multi-pass membrane proteins may comprise a complex (at least 2, 3, 4, 5, 6, 7 or more) alpha helices or a beta sheet structure. Preferably, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side.

In some embodiments, the transmembrane domain of the CAR comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL-2R beta, IL-2R gamma, IL-7R a, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain is derived from a molecule selected from the group consisting of CD8α, CD4, CD28, CD137, CD80, CD86, CD152 and PD1.

In some embodiments, the transmembrane domain is derived from CD28. In some embodiments, the transmembrane domain is a transmembrane domain of CD28 comprising the amino acid sequence of SEQ ID NO: 194. In some embodiments, the transmembrane domain of CD28 is encoded by the nucleic acid sequence of SEQ ID NO: 203.

In some embodiments, the transmembrane domain is derived from CD8α. In some embodiments, the transmembrane domain is a transmembrane domain of CD8α comprising the amino acid sequence of SEQ ID NO: 193. In some embodiments, the transmembrane domain of CD8☐ is encoded by the nucleic acid sequence of SEQ ID NO: 202.

Transmembrane domains for use in the CARs described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 B1 and PCT Publication No. WO 2000/032776 A2, the relevant disclosures of which are incorporated by reference herein.

The transmembrane domain may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane domain of the CAR comprises an artificial hydrophobic sequence. For example, a triplet of phenylalanine, tryptophan and valine may be present at the C terminus of the transmembrane domain. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence. The hydropathy, or hydrophobic or hydrophilic characteristics of a protein or protein segment, can be assessed by any method known in the art, for example the Kyte and Doolittle hydropathy analysis.

Intracellular Signaling Domain

The CARs of the present application comprise an intracellular signaling domain. The intracellular signaling domain is responsible for activation of at least one of the normal effector functions of the immune effector cell expressing the CARs. The term "effector function" refers to a specialized function of a cell. Effector function of a T cell, for example, may be cytolytic activity or helper activity including the secretion of cytokines. Thus the term "cytoplasmic signaling domain" refers to the portion of a protein which transduces the effector function signal and directs the cell to perform a specialized function. While usually the entire cytoplasmic signaling domain can be employed, in many cases it is not necessary to use the entire chain. To the extent that a truncated portion of the cytoplasmic signaling domain is used, such truncated portion may be used in place of the intact chain as long as it transduces the effector function signal. The term cytoplasmic signaling domain is thus meant to include any truncated portion of the cytoplasmic signaling domain sufficient to transduce the effector function signal.

In some embodiments, the intracellular signaling domain comprises a primary intracellular signaling domain of an immune effector cell. In some embodiments, the CAR comprises an intracellular signaling domain consisting essentially of a primary intracellular signaling domain of an immune effector cell. "Primary intracellular signaling domain" refers to cytoplasmic signaling sequence that acts in a stimulatory manner to induce immune effector functions. In some embodiments, the primary intracellular signaling domain contains a signaling motif known as immunoreceptor tyrosine-based activation motif, or ITAM. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif YxxL/Ix(6-8)YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. Exemplary ITAM-containing primary cytoplasmic signaling sequences include those derived from CD3ζ, FcR gamma(FCER1G), FcR beta (Fc Epsilon Rib), CD3 gamma, CD3 delta, CD3 epsilon, CD5, CD22, CD79a, CD79b, and CD66d.

In some embodiments, the primary intracellular signaling domain is derived from CD3ζ. In some embodiments, the intracellular signaling domain consists of the cytoplasmic signaling domain of CD3ζ. In some embodiments, the primary intracellular signaling domain is a cytoplasmic signaling domain of wildtype CD3ζ. In some embodiments, the primary intracellular signaling domain of wildtype CD3ζ comprises the amino acid sequence of SEQ ID NO: 197. In some embodiments, the primary intracellular signaling domain is a functional mutant of the cytoplasmic signaling domain of CD3ζ containing one or more mutations, such as Q65K. In some embodiments, the primary intracellular signaling domain of mutant CD3ζ comprises the amino acid sequence of SEQ ID NO: 198. In some embodiments, the primary intracellular signaling domain is encoded by the nucleic acid sequence of SEQ ID NO: 206 or 207.

Co-Stimulatory Signaling Domain

Many immune effector cells require co-stimulation, in addition to stimulation of an antigen-specific signal, to promote cell proliferation, differentiation and survival, as well as to activate effector functions of the cell. In some embodiments, the CAR comprises at least one co-stimulatory signaling domain. The term "co-stimulatory signaling domain," as used herein, refers to at least a portion of a protein that mediates signal transduction within a cell to induce an immune response such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils. "Co-stimulatory signaling domain" can be the cytoplasmic portion of a co-stimulatory molecule. The term "co-stimulatory molecule" refers to a cognate binding partner on an immune cell (such as T cell) that specifically binds with a co-stimulatory ligand, thereby mediating a co-stimulatory response by the immune cell, such as, but not limited to, proliferation and survival.

In some embodiments, the intracellular signaling domain comprises a single co-stimulatory signaling domain. In some embodiments, the intracellular signaling domain comprises two or more (such as about any of 2, 3, 4, or more) co-stimulatory signaling domains. In some embodiments, the intracellular signaling domain comprises two or more of the same co-stimulatory signaling domains, for example, two copies of the co-stimulatory signaling domain of CD28. In some embodiments, the intracellular signaling domain comprises two or more co-stimulatory signaling domains from different co-stimulatory proteins, such as any two or more co-stimulatory proteins described herein. In some embodiments, the intracellular signaling domain comprises a primary intracellular signaling domain (such as cytoplasmic signaling domain of CD3ζ) and one or more co-stimulatory signaling domains. In some embodiments, the one or more co-stimulatory signaling domains and the primary intracellular signaling domain (such as cytoplasmic signaling domain of CD3ζ) are fused to each other via optional peptide linkers. The primary intracellular signaling domain, and the one or more co-stimulatory signaling domains may be arranged in any suitable order. In some embodiments, the one or more co-stimulatory signaling domains are located between the transmembrane domain and the primary intracellular signaling domain (such as cytoplasmic signaling domain of CD3ζ). Multiple co-stimulatory signaling domains may provide additive or synergistic stimulatory effects.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the CARs described herein. The type(s) of co-stimulatory signaling domain is selected based on factors such as the type of the immune effector cells in which the effector molecules would be expressed (e.g., T cells, NK cells, macrophages, neutrophils, or eosinophils) and the desired immune effector function (e.g., ADCC effect). Examples of co-stimulatory signaling domains for use in the CARs can be the cytoplasmic signaling domain of co-stimulatory proteins, including, without limitation, members of the B7/CD28 family (e.g., B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (e.g., 4-1BB/TNFSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TNFRSF4, OX40 Ligand/TNFSF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C.

In some embodiments, the one or more co-stimulatory signaling domains are selected from the group consisting of CD27, CD28, 4-1BB, OX40, CD30, CD40, CD3, lymphocyte function-associated antigen-1(LFA-1), CD2, CD7, LIGHT, NKG2C, B7-H3 and ligands that specially bind to CD83.

In some embodiments, the intracellular signaling domain in the CAR of the present application comprises a co-stimulatory signaling domain derived from CD28. In some embodiments, the intracellular signaling domain comprises a cytoplasmic signaling domain of CD3ζ and a co-stimulatory signaling domain of CD28. In some embodiments, the intracellular signaling domain comprises a co-stimulatory signaling domain of CD28 comprising the amino acid sequence of SEQ ID NO: 195. In some embodiments, the co-stimulatory signaling domain of CD28 is encoded by the nucleic acid sequence of SEQ ID NO: 204.

In some embodiments, the intracellular signaling domain in the CAR of the present application comprises a co-stimulatory signaling domain derived from CD137 (i.e., 4-1BB). In some embodiments, the intracellular signaling domain comprises a cytoplasmic signaling domain of CD3ζ and a co-stimulatory signaling domain of CD137. In some embodiments, the intracellular signaling domain comprises a co-stimulatory signaling domain of CD137 comprising the amino acid sequence of SEQ ID NO: 196. In some embodiments, the co-stimulatory signaling domain of CD137 is encoded by the nucleic acid sequence of SEQ ID NO: 205.

In some embodiments, the intracellular signaling domain in the CAR of the present application comprises a co-stimulatory signaling domain of CD28 and a co-stimulatory signaling domain of CD137. In some embodiments, the intracellular signaling domain comprises a cytoplasmic signaling domain of CD3ζ, a co-stimulatory signaling domain of CD28, and a co-stimulatory signaling domain of CD137. In some embodiments, the intracellular signaling domain comprises a polypeptide comprising from the N-terminus to the C-terminus: a co-stimulatory signaling domain of CD28, a co-stimulatory signaling domain of CD137, and a cytoplasmic signaling domain of CD3ζ. In some embodiments, the co-stimulatory signaling domain of CD28 comprising the amino acid sequence of SEQ ID NO: 195. In some embodiments, the co-stimulatory signaling domain of CD137 comprising the amino acid sequence of SEQ ID NO: 196.

Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue variations (e.g., 1, 2, 3, 4, 5, or 8) as compared to a wild-type counterpart. Such co-stimulatory signaling domains comprising one or more amino acid variations may be referred to as variants. Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation.

Hinge Region

The CARs of the present application may comprise a hinge domain that is located between the extracellular antigen binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular antigen binding domain relative to the transmembrane domain of the effector molecule can be used.

The hinge domain may contain about 10-100 amino acids, e.g., about any one of 15-75 amino acids, 20-50 amino acids, or 30-60 amino acids. In some embodiments, the hinge domain may be at least about any one of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is derived from CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α. In some embodiments, the hinge domain of CD8α comprises the amino acid sequence of SEQ ID NO: 192. In some embodiments, the hinge domain of CD8α is encoded by the nucleic acid sequence of SEQ ID NO: 201.

Hinge domains of antibodies, such as an IgG, IgA, IgM, IgE, or IgD antibodies, are also compatible for use in the pH-dependent chimeric receptor systems described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N-terminus of the transmembrane domain is a peptide linker, such as a (GxS)n linker, wherein x and n, independently can be an integer between 3 and 12, including 3, 4, 5, 6, 7, 8, 9, 10, 11, 12, or more.

Signal Peptide

The CARs of the present application may comprise a signal peptide (also known as a signal sequence) at the N-terminus of the polypeptide. In general, signal peptides are peptide sequences that target a polypeptide to the desired site in a cell. In some embodiments, the signal peptide targets the effector molecule to the secretory pathway of the cell and will allow for integration and anchoring of the effector molecule into the lipid bilayer. Signal peptides including signal sequences of naturally occurring proteins or synthetic, non-naturally occurring signal sequences, which are compatible for use in the CARs described herein will be evident to one of skill in the art. In some embodiments, the signal peptide is derived from a molecule selected from the group consisting of CD8α, GM-CSF receptor α, and IgG1 heavy chain. In some embodiments, the signal peptide is derived from CD8α. In some embodiments, the signal peptide of CD8α comprises the amino acid sequence of SEQ ID NO: 191. In some embodiments, the signal peptide of CD8α is encoded by the nucleic acid sequence of SEQ ID NO: 199 or 200.

IV. Engineered Immune Effector Cells

Further provided in the present application are host cells (such as immune effector cells) comprising any one of the CARs described herein.

Thus, in some embodiments, there is provided an engineered immune effector cell (such as T cell) comprising a multivalent CAR comprising a polypeptide comprising: (a) an extracellular antigen binding domain comprising a first BCMA binding moiety specifically binding to a first epitope of BCMA, and a second BCMA binding moiety specifically binding to a second epitope of BCMA; (b) a transmembrane domain; and (c) an intracellular signaling domain, wherein the first epitope and the second epitope are different.

In some embodiments, there is provided an engineered immune effector cell (such as T cell) comprising a multivalent CAR comprising a polypeptide comprising: (a) an extracellular antigen binding domain comprising a first anti-BCMA sdAb specifically binding to a first epitope of BCMA, and a second anti-BCMA sdAb specifically binding to a second epitope of BCMA; (b) a transmembrane domain; and (c) an intracellular signaling domain, wherein the first epitope and the second epitope are different. In some embodiments, the first anti-BCMA sdAb and/or the second anti-BCMA sdAb is camelid, chimeric, human, or humanized. In some embodiments, the first anti-BCMA and the second anti-BCMA are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a BCMA CAR comprising a polypeptide comprising: (a) an extracellular antigen binding domain comprising an anti-BCMA sdAb; (b) a transmembrane domain; and (c) an intracellular signaling domain, wherein the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the extracellular antigen binding domain comprises at least two anti-BCMA sdAbs. In some embodiments, the anti-BCMA sdAb is camelid, chimeric, human, or humanized. In some embodiments, the anti-BCMA sdAb comprises a $V_HH$ domain comprising an amino acid sequence selected from the group consisting of SEQ ID NO: 115-152. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the BCMA CAR comprises an amino acid sequence selected from the group consisting of SEQ ID NO: 216-256, 298-335. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

Figure 15A:
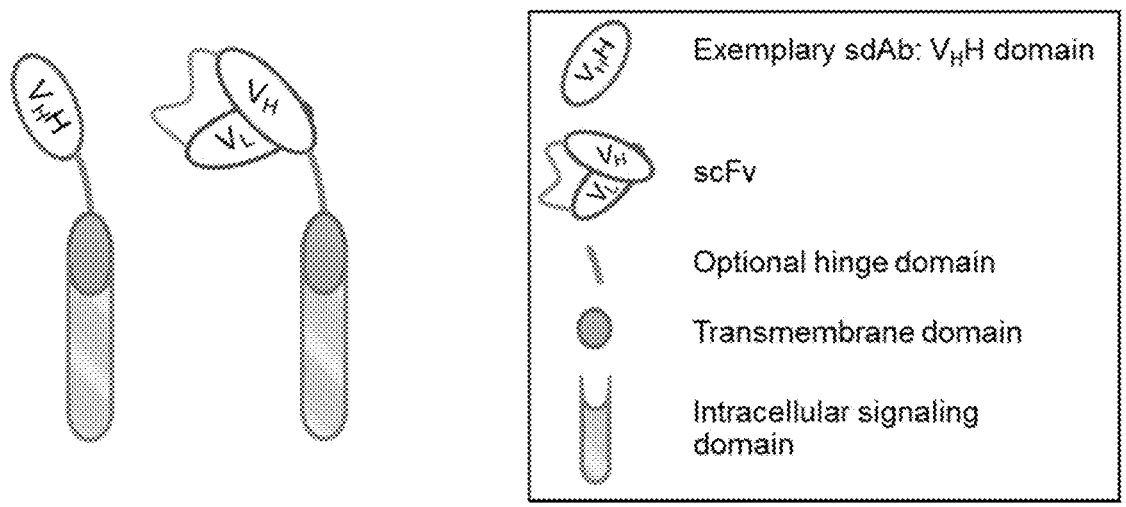
FIG. 15A compares the structures of a $V_HH$-based CAR and a conventional scFv-based CAR. The schematic structure on the left shows an exemplary monospecific monovalent CAR having an extracellular antigen binding domain comprising a VHH domain. The schematic structure on the right shows an exemplary monospecific monovalent CAR having an extracellular antigen binding domain comprising a scFv domain.
Figure 15B:
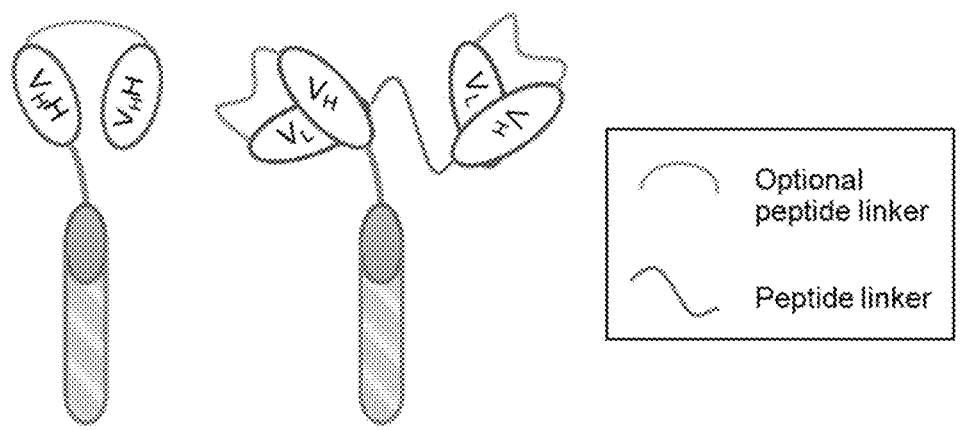
FIG. 15B compares the structures of a $V_HH$-based CAR having two antigen binding sites and a conventional scFv-based CAR having two antigen binding sites. The schematic structure on the left is an exemplary CAR having an extracellular antigen binding domain comprising two $V_HH$ domains. The two $V_HH$ domains may be the same or different. The schematic structure on the right shows an exemplary CAR having an extracellular antigen binding domain comprising two scFv domains. The two scFv domains may be the same or different.
Figure 15C:
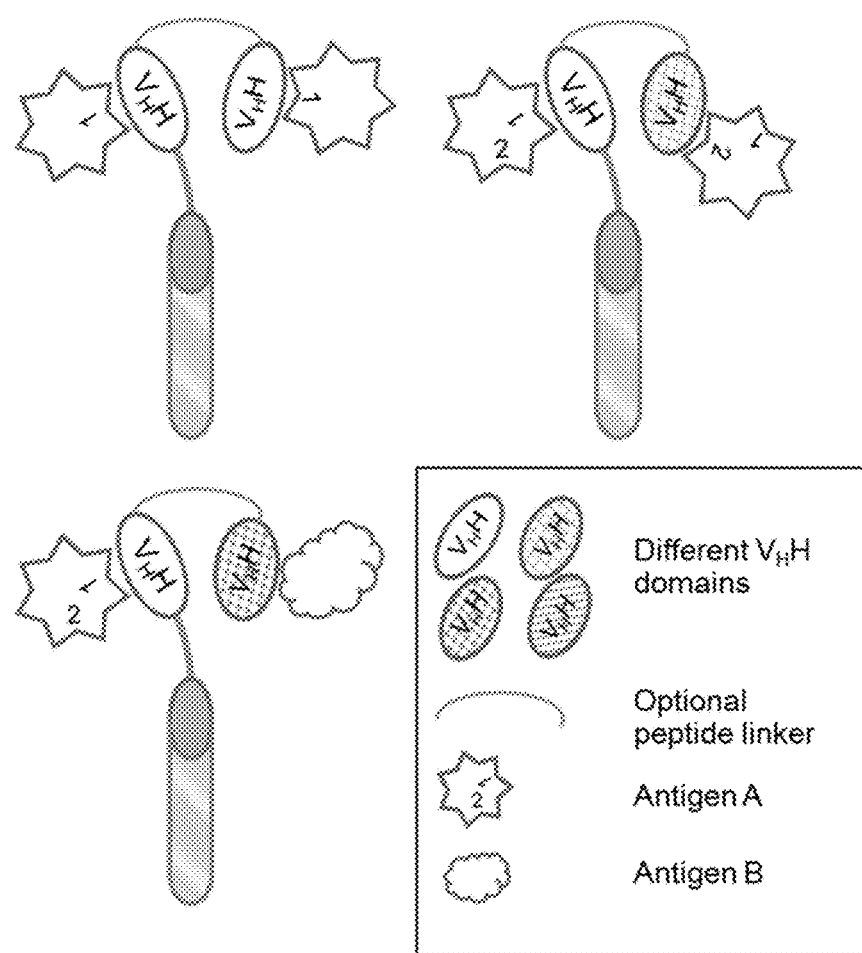
FIG. 15C shows schematic structures of exemplary bivalent and bispecific $V_HH$-based CARs. The schematic structure in the top left panel shows an exemplary mono-epitope, bivalent CAR having an extracellular antigen binding domain comprising two identical $V_HH$ domains, each of which specifically binds to epitope 1 of antigen A. The schematic structure in the top right panel shows an exemplary bi-epitope, bivalent CAR having an extracellular antigen binding domain comprising a first $V_HH$ domain specifically binding to epitope 1 of antigen A, and a second $V_HH$ domain specifically binding to epitope 2 of antigen A. Epitope 1 and epitope 2 of antigen A may be different in their structures and/or sequences. The schematic structure in the bottom left panel shows an exemplary bispecific CAR having an extracellular antigen binding domain comprising a first $V_HH$ domain specifically binding to antigen A, and a second $V_HH$ domain specifically binding to antigen B. Antigen A and antigen B are different antigens.
Figure 15D:
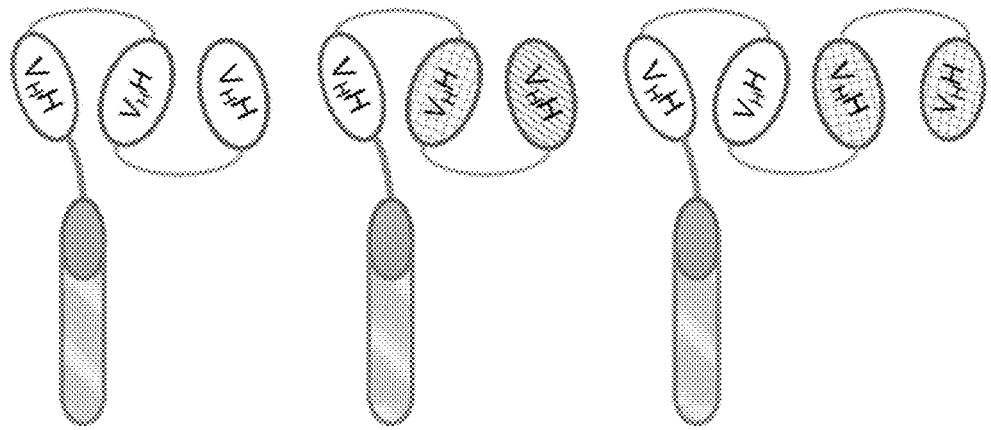
FIG. 15D shows schematic structures of exemplary $V_HH$-based CARs having three or more $V_HH$ domains. The CARs may have a plurality of $V_HH$ domains fused to each other directly or via peptide linkers. The $V_HH$ domains may be the same or different. Different $V_HH$ domains may specifically bind to different epitopes on the same antigen or different antigens.
Figure 15E:
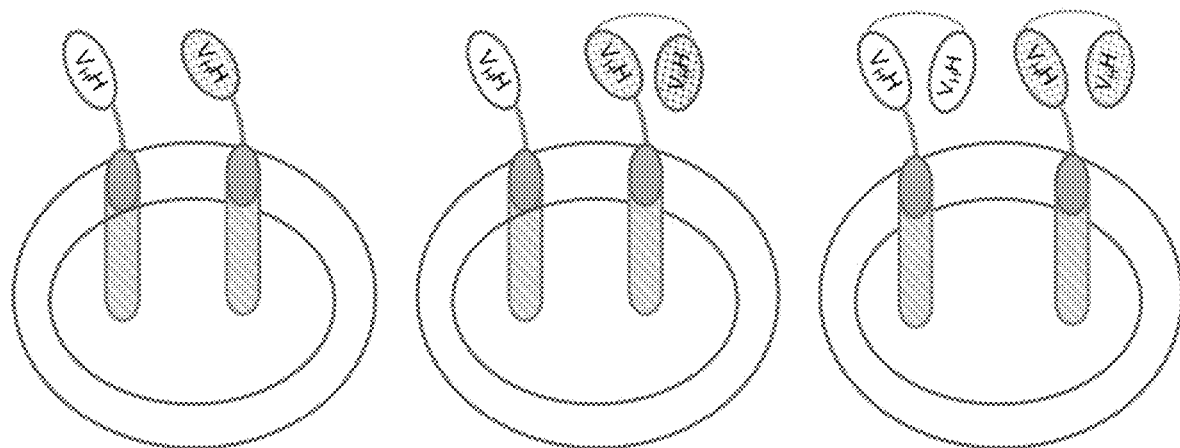
FIG. 15E shows exemplary engineered immune effector cells co-expressing two different $V_HH$-based CARs. The exemplary engineered immune effector cell in the left panel co-expresses two different monospecific, monovalent CARs. The exemplary engineered immune effector cell in the middle panel co-expresses a monospecific, monovalent CAR and a bispecific or bivalent CAR. The exemplary engineered immune effector cell in the right panel co-expresses two different bispecific or bivalent CARs. The CARs may recognize different antigens.

Also provided are engineered immune effector cells comprising (or expressing) two or more different CARs. Any two or more of the CARs described herein may be expressed in combination. The CARs may target different antigens, thereby providing synergistic or additive effects. As the single-domain antibodies in the extracellular antigen binding domains of the CARs have only single antigen variable chains (such as heavy chains), such CAR-expressing cells do not have variable chain mispairing problems, as seen in engineered immune effector cells co-expressing two or more scFv-based CARs. Exemplary engineered immune effector cells co-expressing two VHH-based CARs are illustrated in FIG. 15E. One of skill in the art would recognize that CARs based on other sdAbs or having other structures as described herein may be co-expressed in the engineered immune effector cells as well. The two or more CARs may be encoded on the same vector or different vectors.

The engineered immune effector cell may further express one or more therapeutic proteins and/or immunomodulators, such as immune checkpoint inhibitors. See, for example, International Patent Application NOs. PCT/CN2016/073489 and PCT/CN2016/087855, which are incorporated herein by reference in their entirety.

Vectors

The present application provides vectors for cloning and expressing any one of the CARs described herein. In some embodiments, the vector is suitable for replication and integration in eukaryotic cells, such as mammalian cells. In some embodiments, the vector is a viral vector. Examples of viral vectors include, but are not limited to, adenoviral vectors, adeno-associated virus vectors, lentiviral vector, retroviral vectors, vaccinia vector, herpes simplex viral vector, and derivatives thereof. Viral vector technology is well known in the art and is described, for example, in Sambrook et al. (2001, Molecular Cloning: A Laboratory Manual, Cold Spring Harbor Laboratory, New York), and in other virology and molecular biology manuals.

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the immunomodulator (such as immune checkpoint inhibitor) coding sequence and/or self-inactivating lentiviral vectors carrying CARs can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector is a non-viral vector. In some embodiments, the vector is a transposon, such as a Sleeping Beauty (SB) transposon system, or a PiggyBac transposon system. In some embodiments, the vector is a polymer-based non-viral vector, including for example, poly (lactic-co-glycolic acid) (PLGA) and poly lactic acid (PLA), poly(ethylene imine) (PEI), and dendrimers. In some embodiments, the vector is a cationic-lipid based non-viral vector, such as cationic liposome, lipid nanoemulsion, and solid lipid nanoparticle (SLN). In some embodiments, the vector is a peptide-based gene non-viral vector, such as poly-L-lysine. Any of the known non-viral vectors suitable for genome editing can be used for introducing the CAR-encoding nucleic acids to the engineered immune effector cells. See, for example, Yin H. et al. *Nature Rev. Genetics* (2014) 15:521-555; Aronovich E L et al. "The Sleeping Beauty transposon system: a non-viral vector for gene therapy." *Hum. Mol. Genet.* (2011) R1: R14-20; and Zhao S. et al. "PiggyBac transposon vectors: the tools of the human gene editing." *Transl. Lung Cancer Res.* (2016) 5(1): 120-125, which are incorporated herein by reference. In some embodiments, any one or more of the nucleic acids encoding a CAR is introduced to the engineered immune effector cells by a physical method, including, but not limited to electroporation, sonoporation, photoporation, magnetofection, hydroporation.

In some embodiments, the vector comprises any one of the nucleic acids encoding a CAR described herein. The nucleic acid can be cloned into the vector using any known molecular cloning methods in the art, including, for example, using restriction endonuclease sites and one or more selectable markers. In some embodiments, the nucleic acid is operably linked to a promoter. Varieties of promoters have been explored for gene expression in mammalian cells, and any of the promoters known in the art may be used in the present invention. Promoters may be roughly categorized as constitutive promoters or regulated promoters, such as inducible promoters.

In some embodiments, the nucleic acid encoding the CAR is operably linked to a constitutive promoter. Constitutive promoters allow heterologous genes (also referred to as transgenes) to be expressed constitutively in the host cells. Exemplary constitutive promoters contemplated herein include, but are not limited to, Cytomegalovirus (CMV) promoters, human elongation factors-1alpha (hEF1a), ubiquitin C promoter (UbiC), phosphoglycerokinase promoter (PGK), simian virus 40 early promoter (SV40), and chicken β-Actin promoter coupled with CMV early enhancer (CAGG). The efficiencies of such constitutive promoters on driving transgene expression have been widely compared in a huge number of studies. For example, Michael C. Milone et al compared the efficiencies of CMV, hEF1α, UbiC and PGK to drive CAR expression in primary human T cells, and concluded that hEF1α promoter not only induced the highest level of transgene expression, but was also optimally maintained in the CD4 and CD8 human T cells (Molecular Therapy, 17(8): 1453-1464 (2009)). In some embodiments, the nucleic acid encoding the CAR is operably linked to a hEF1α promoter.

In some embodiments, the nucleic acid encoding the CAR is operably linked to an inducible promoter. Inducible promoters belong to the category of regulated promoters. The inducible promoter can be induced by one or more conditions, such as a physical condition, microenvironment of the engineered immune effector cell, or the physiological state of the engineered immune effector cell, an inducer (i.e., an inducing agent), or a combination thereof. In some embodiments, the inducing condition does not induce the expression of endogenous genes in the engineered mammalian cell, and/or in the subject that receives the pharmaceutical composition. In some embodiments, the inducing condition is selected from the group consisting of: inducer, irradiation (such as ionizing radiation, light), temperature (such as heat), redox state, tumor environment, and the activation state of the engineered mammalian cell.

In some embodiments, the vector also contains a selectable marker gene or a reporter gene to select cells expressing the CAR from the population of host cells transfected through lentiviral vectors. Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

In some embodiments, the vector comprises more than one nucleic acid encoding CARs. In some embodiments, the vector comprises a nucleic acid comprising a first nucleic acid sequence encoding a first CAR and a second nucleic acid sequence encoding a second CAR, wherein the first nucleic acid is operably linked to the second nucleic acid via a third nucleic acid sequence encoding a self-cleaving peptide. In some embodiments, the self-cleaving peptide is selected from the group consisting of T2A, P2A and F2A. In some embodiments, the T2A peptide has an amino acid sequence of SEQ ID NO: 385.

Immune Effector Cells

"Immune effector cells" are immune cells that can perform immune effector functions. In some embodiments, the immune effector cells express at least FcγRIII and perform ADCC effector function. Examples of immune effector cells which mediate ADCC include peripheral blood mononuclear cells (PBMC), natural killer (NK) cells, monocytes, cytotoxic T cells, neutrophils, and eosinophils.

In some embodiments, the immune effector cells are T cells. In some embodiments, the T cells are CD4+/CD8−, CD4−/CD8+, CD4+/CD8+, CD4−/CD8−, or combinations thereof. In some embodiments, the T cells produce IL-2, TFN, and/or TNF upon expressing the CAR and binding to the target cells, such as CD20+ or CD19+ tumor cells. In some embodiments, the CD8+ T cells lyse antigen-specific target cells upon expressing the CAR and binding to the target cells.

In some embodiments, the immune effector cells are NK cells. In other embodiments, the immune effector cells can be established cell lines, for example, NK-92 cells.

In some embodiments, the immune effector cells are differentiated from a stem cell, such as a hematopoietic stem cell, a pluripotent stem cell, an iPS, or an embryonic stem cell.

The engineered immune effector cells are prepared by introducing the CARs into the immune effector cells, such as T cells. In some embodiments, the CAR is introduced to the immune effector cells by transfecting any one of the isolated nucleic acids or any one of the vectors described in Section III. In some embodiments, the CAR is introduced to the immune effector cells by inserting proteins into the cell membrane while passing cells through a microfluidic system, such as CELL SQUEEZE (see, for example, U.S. Patent Application Publication No. 20140287509).

Methods of introducing vectors or isolated nucleic acids into a mammalian cell are known in the art. The vectors described can be transferred into an immune effector cell by physical, chemical, or biological methods.

Physical methods for introducing the vector into an immune effector cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001) Molecular Cloning: A Laboratory Manual, Cold Spring Harbor Laboratory, New York. In some embodiments, the vector is introduced into the cell by electroporation.

Biological methods for introducing the vector into an immune effector cell include the use of DNA and RNA vectors. Viral vectors have become the most widely used method for inserting genes into mammalian, e.g., human cells.

Chemical means for introducing the vector into an immune effector cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro is a liposome (e.g., an artificial membrane vesicle).

In some embodiments, RNA molecules encoding any of the CARs described herein may be prepared by a conventional method (e.g., in vitro transcription) and then introduced into the immune effector cells via known methods such as mRNA electroporation. See, e.g., Rabinovich et al., Human Gene Therapy 17:1027-1035.

In some embodiments, the transduced or transfected immune effector cell is propagated ex vivo after introduction of the vector or isolated nucleic acid. In some embodiments, the transduced or transfected immune effector cell is cultured to propagate for at least about any of 1 day, 2 days, 3 days, 4 days, 5 days, 6 days, 7 days, 10 days, 12 days, or 14 days. In some embodiments, the transduced or transfected immune effector cell is further evaluated or screened to select the engineered mammalian cell.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479: 79-82 (2000)). Suitable expression systems are well known and may be prepared using known techniques or obtained commercially.

Other methods to confirm the presence of the nucleic acid encoding the CARs in the engineered immune effector cell, include, for example, molecular biological assays well known to those of skill in the art, such as Southern and Northern blotting, RT-PCR and PCR; biochemical assays, such as detecting the presence or absence of a particular peptide, e.g., by immunological methods (such as ELISAs and Western blots).

1. Sources of T Cells

Prior to expansion and genetic modification of the T cells, a source of T cells is obtained from an individual. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as FICOLL™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In some embodiments, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5 \times 10^6$/ml. In some embodiments, the concentration used can be from about $1 \times 10^5$/ml to $1 \times 10^6$/ml, and any integer value in between.

In some embodiments, the cells may be incubated on a rotator for varying lengths of time at varying speeds at either 2-10° C., or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation.

Also contemplated in the present application is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

2. Activation and Expansion of T Cells

Whether prior to or after genetic modification of the T cells with the CARs described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, T cells can be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

V. Pharmaceutical Compositions

Further provided by the present application are pharmaceutical compositions comprising any one of the anti-BCMA single-domain antibodies, or any one of the engineered immune effector cells comprising any one of the CARs (such as BCMA CARs) as described herein, and a pharmaceutically acceptable carrier. Pharmaceutical compositions can be prepared by mixing a sdAb, or a plurality of engineered immune effector cells having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions described herein may also contain more than one active compound or agent as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules)

or in macroemulsions. Such techniques are disclosed in *Remington's Pharmaceutical Sciences* 18th edition.

VI. Methods of Treatment

The present application further relates to methods and compositions for use in cell immunotherapy. In some embodiments, the cell immunotherapy is for treating cancer, including but not limited to hematological malignancies and solid tumors. Any of the anti-BCMA sdAbs, CARs, and engineered immune effector cells (such as CAR-T cells) described herein may be used in the method of treating cancer. The CARs described herein may be useful for treating tumors having antigen loss escape mutations, and for reducing resistance to existing therapies. In some embodiments, the methods and compositions described herein may be used for treating other diseases that are associated with the antigens specifically recognized by the single-domain antibodies or CARs, including, for example, autoimmune diseases.

In some embodiments, there is provided a method of treating a cancer (such as multiple myeloma, e.g., relapsed or refractory multiple myeloma) in an individual (such as a human individual), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety specifically binding to a first epitope of BCMA, and a second BCMA binding moiety specifically binding to a second epitope of BCMA; (b) a transmembrane domain; and (c) an intracellular signaling domain, wherein the first epitope and the second epitope are different; and (2) a pharmaceutically acceptable carrier. In some embodiments, there is provided a method of treating a cancer (such as multiple myeloma, e.g., relapsed or refractory multiple myeloma) in an individual (such as a human individual), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first anti-BCMA sdAb specifically binding to a first epitope of BCMA, and a second anti-BCMA sdAb specifically binding to a second epitope of BCMA; (b) a transmembrane domain; and (c) an intracellular signaling domain, wherein the first epitope and the second epitope are different; and (2) a pharmaceutically acceptable carrier. In some embodiments, the engineered immune effector cell is autologous. In some embodiments, the engineered immune effector cell is allogenic. In some embodiments, the engineered immune effector cells are CAR-T cells. In some embodiments, the cancer is a liquid cancer, such as multiple myeloma, acute lymphoblastic leukemia, or chronic lymphocytic leukemia. In some embodiments, the cancer is refractory or relapsed multiple myeloma. In some embodiments, the engineered immune effector cell is administered at a dose of about $10^5$ to about $10^7$ cells/kg, such as about $3\times10^5$ to about $7\times10^6$ cells/kg, or about $3\times10^6$ cells/kg. In some embodiments, the engineered immune effector cell is administered by intravenous injection. In some embodiments, the engineered immune effector cell is administered in three split doses over about a week.

In some embodiments, there is provided a method of treating a cancer (such as multiple myeloma, e.g., relapsed or refractory multiple myeloma) in an individual (such as a human individual), comprising administering to the individual an effective amount of a pharmaceutical composition comprising: (1) an engineered immune effector cell (such as T cell) comprising a BCMA CAR comprising a polypeptide comprising: (a) an extracellular antigen binding domain comprising an anti-BCMA sdAb; (b) a transmembrane domain; and (c) an intracellular signaling domain; and (2) a pharmaceutically acceptable carrier, wherein the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the extracellular antigen binding domain comprises at least two anti-BCMA sdAbs. In some embodiments, the anti-BCMA sdAb is camelid, chimeric, human, or humanized. In some embodiments, the anti-BCMA sdAb comprises a $V_HH$ domain comprising an amino acid sequence selected from the group consisting of SEQ ID NO: 115-152. In some embodiments, the BCMA CAR comprises an amino acid sequence selected from the group consisting of SEQ ID NOs: 216-256 and 298-335. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is refractory or relapsed multiple myeloma. In some embodiments, the engineered immune effector cell is administered at a dose of about $10^5$ to about $10^7$ cells/kg, such as about $3\times10^5$ to about $7\times10^6$ cells/kg, or about $3\times10^6$ cells/kg. In some embodiments, the engineered immune effector cell is administered by intravenous injection. In some embodiments, the engineered immune effector cell is administered in three split doses over about a week.

In some embodiments, there is provided a method of obtaining partial or complete clinical remission in an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some embodiments, the engineered immune effector cell is autologous. In some embodiments, the engineered immune effector cell is allogenic. In some embodiments, the engineered immune effector cells are CAR-T cells. In some embodiments, the cancer is a liquid cancer, such as multiple myeloma, acute lymphoblastic leukemia, or chronic lymphocytic leukemia. In some embodiments, the cancer is refractory or relapsed multiple myeloma. In some embodiments, the engineered immune effector cell is administered at a dose of about $10^5$ to about $10^7$ cells/kg, such as about $3\times10^5$ to about $7\times10^6$ cells/kg, or about $3\times10^6$ cells/kg. In some embodiments, the engineered immune effector cell is administered by intravenous injection. In some embodiments, the engineered immune effector cell is administered in three split doses over about a week.

In some embodiments, there is provided a method of treating a cancer (such as multiple myeloma, e.g., relapsed or refractory multiple myeloma) in an individual (such as a human individual), comprising administering to the individual an effective amount of a pharmaceutical composition comprising an anti-BCMA sdAb and a pharmaceutically acceptable carrier, wherein the anti-BCMA sdAb comprises any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114. In some embodiments, the anti-BCMA sdAb is camelid, chimeric, human, or humanized. In some embodiments, the anti-BCMA sdAb comprises an amino acid sequence selected from the group consisting of SEQ ID NO: 115-152. In some embodiments, the cancer is a liquid cancer, such as multiple myeloma, acute lymphoblastic leukemia, or chronic lymphocytic leukemia. In some embodiments, the cancer is refractory or relapsed multiple myeloma.

The methods described herein are suitable for treating various cancers, including both solid cancer and liquid cancer. The methods are applicable to cancers of all stages, including early stage, advanced stage and metastatic cancer. The methods described herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting.

In some embodiments, the cancer is multiple myeloma. In some embodiments, the cancer is stage I, stage II or stage III, and/or stage A or stage B multiple myeloma based on the Durie-Salmon staging system. In some embodiments, the cancer is stage I, stage II or stage III multiple myeloma based on the International staging system published by the International Myeloma Working Group (IMWG). In some embodiments, the cancer is monoclonal gammopathy of undetermined significance (MGUS). In some embodiments, the cancer is asymptomatic (smoldering/indolent) myeloma. In some embodiments, the cancer is symptomatic or active myeloma. In some embodiments, the cancer is refractory multiple myeloma. In some embodiments, the cancer is metastatic multiple myeloma. In some embodiments, the individual did not respond to a previous treatment for multiple myeloma. In some embodiments, the individual has progressive disease after a previous treatment of multiple myeloma. In some embodiments, the individual has previously received at least about any one of 2, 3, 4, or more treatment for multiple myeloma. In some embodiments, the cancer is relapsed multiple myeloma.

In some embodiments, the individual has active multiple myeloma. In some embodiments, the individual has clonal bone marrow plasma cells of at least 10%. In some embodiments, the individual has a biopsy-proven bony or extramedullary plasmacytoma. In some embodiments, the individual has evidence of end organ damage that can be attributed to the underlying plasma cell proliferative disorder. In some embodiments, the individual has hypercalcemia, e.g., serum calcium >0.25 mmol/L (>1 mg/dL) higher than the upper limit of normal or >2.75 mmol/L (>11 mg/dL). In some embodiments, the individual has renal insufficiency, e.g., creatinine clearance <40 mL per minute or serum creatinine >177 μmol/L (>2 mg/dL). In some embodiments, the individual has anemia, e.g., hemoglobin value of >20 g/L below the lowest limit of normal, or a hemoglobin value <100 g/L. In some embodiments, the individual has one or more bone lesions, e.g., one or more osteolytic lesion on skeletal radiography, CT, or PET/CT. In some embodiments, the individual has one or more of the following biomarkers of malignancy (MDEs): (1) 60% or greater clonal plasma cells on bone marrow examination; (2) serum involved/uninvolved free light chain ratio of 100 or greater, provided the absolute level of the involved light chain is at least 100 mg/L; and (3) more than one focal lesion on MRI that is at least 5 mm or greater in size.

Administration of the pharmaceutical compositions may be carried out in any convenient manner, including by injection, ingestion, transfusion, implantation or transplantation. The compositions may be administered to a patient transarterially, subcutaneously, intradermally, intratumorally, intranodally, intramedullary, intramuscularly, intravenously, or intraperitoneally. In some embodiments, the pharmaceutical composition is administered systemically. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)). In some embodiments, the pharmaceutical composition is administered to an individual by intradermal or subcutaneous injection. In some embodiments, the compositions are administered by intravenous injection. In some embodiments, the compositions are injected directly into a tumor, or a lymph node. In some embodiments, the pharmaceutical composition is administered locally to a site of tumor, such as directly into tumor cells, or to a tissue having tumor cells.

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46. It is within the scope of the present application that different formulations will be effective for different treatments and different disorders, and that administration intended to treat a specific organ or tissue may necessitate delivery in a manner different from that to another organ or tissue.

In some embodiments, wherein the pharmaceutical composition comprises any one of the sdAbs described herein, the pharmaceutical composition is administered at to dosage of about 10 ng/kg up to about 100 mg/kg of body weight of the individual or more per day, for example, at about 1 mg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212.

In some embodiments, wherein the pharmaceutical composition comprises any one of the engineered immune cells described herein, the pharmaceutical composition is administered at a dosage of at least about any of $10^4$, $10^5$, $10^6$, $10^7$, $10^8$, or $10^9$ cells/kg of body weight of the individual. In some embodiments, the pharmaceutical composition is administered at a dosage of any of about $10^4$ to about $10^5$, about $10^5$ to about $10^6$, about $10^6$ to about $10^7$, about $10^7$ to about $10^8$, about $10^8$ to about $10^9$, about $10^4$ to about $10^9$, about $10^4$ to about $10^6$, about $10^6$ to about $10^8$, or about $10^5$ to about $10^7$ cells/kg of body weight of the individual. In some embodiments, the pharmaceutical composition is administered at a dose of at least about any $1\times10^5$ $2\times10^5$ $3\times10^5$ $4\times10^5$ $5\times10^5$ $6\times10^5$ $7\times10^5$ $8\times10^5$ $9\times10^5$ $1\times10^6$ $2\times10^6$ $3\times10^6$ $4\times10^6$ $5\times10^6$, $6\times10^6$, $7\times10^6$, $8\times10^6$, $9\times10^6$, $1\times10^7$ cells/kg or more. In some embodiments, the pharmaceutical composition is administered at a dose of about $3\times10^5$ to about $7\times10^6$ cells/kg, or about $3\times10^6$ cells/kg.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once per week, once 2 weeks, once 3 weeks, once 4 weeks, once per month, once per 2 months, once per 3 months, once per 4 months, once per 5 months, once per 6 months, once per 7 months, once per 8 months, once per 9 months, or once per year. In some embodiments, the interval between administrations is about any one of 1 week to 2 weeks, 2 weeks to 1 month, 2 weeks to 2 months, 1 month to 2 months, 1 month to 3 months, 3 months to 6 months, or 6 months to a year. The optimal dosage and treatment regime for a particular patient can readily be determined by one skilled in the art of medicine by monitoring the patient for signs of disease and adjusting the treatment accordingly.

Moreover, dosages may be administered by one or more separate administrations, or by continuous infusion. In some embodiments, the pharmaceutical composition is administered in split doses, such as about any one of 2, 3, 4, 5, or more doses. In some embodiments, the split doses are administered over about a week. In some embodiments, the dose is equally split. In some embodiments, the split doses are about 20%, about 30% and about 50% of the total dose. In some embodiments, the interval between consecutive split doses is about 1 day, 2 days, 3 days or longer. For repeated administrations over several days or longer, depending on the condition, the treatment is sustained until a desired suppression of disease symptoms occurs. However, other dosage regimens may be useful. The progress of this therapy is easily monitored by conventional techniques and assays.

In some embodiments, the amount of the pharmaceutical composition is effective to cause an objective clinical response in the individual. In some embodiments, there is provided a method of obtaining an objective clinical response in an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some embodiments, Stringent Clinical Response (sCR) is obtained in the individual.

In some embodiments, the amount of the pharmaceutical composition is effective to cause disease remission (partial or complete) in the individual. In some embodiments, there is provided a method of causing disease remission (partial or complete) in an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some the clinical remission is obtained after no more than about any one of 6 months, 5 months, 4 months, 3 months, 2 months, 1 months or less after the individual receives the pharmaceutical composition.

In some embodiments, the amount of the pharmaceutical composition is effective to prevent relapse or disease progression of the cancer in the individual. In some embodiments, there is provided a method of preventing relapse or disease progression in an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some embodiments, the relapse or disease progression is prevented for at least about 6 months, 1 year, 2 years, 3 years, 4 years, 5 years or more.

In some embodiments, the amount of the pharmaceutical composition is effective to prolong survival (such as disease free survival) in the individual. In some embodiments, the survival is prolonged for at least about 2, 3, 4, 5, 6, 12, or 24 months. In some embodiments, there is provided a method of prolonging survival of an individual having multiple myeloma (e.g., relapsed or refractory multiple myeloma), comprising: administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier.

In some embodiments, the pharmaceutical composition is effective to improve quality of life in the individual. In some embodiments, there is provided a method of improving quality of life of an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier.

In some embodiments, the amount of the pharmaceutical composition is effective to inhibit growth or reducing the size of a solid or lymphatic tumor. In some embodiments, the size of the solid or lymphatic tumor is reduced for at least about 10% (including for example at least about any of 20%, 30%, 40%, 60%, 70%, 80%, 90%, or 100%). In some embodiments, a method of inhibiting growth or reducing the size of a solid or lymphatic tumor in an individual is provided.

In some embodiments, the amount of the pharmaceutical composition is effective to inhibit tumor metastasis in the individual. In some embodiments, at least about 10% (including for example at least about any of 20%, 30%, 40%, 60%, 70%, 80%, 90%, or 100%) metastasis is inhibited. In some embodiments, there is provided a method of inhibiting tumor metastasis of an individual having multiple myeloma (e.g., relapsed or refractory multiple myeloma), comprising administering to the individual an effective amount of a pharmaceutical composition comprising: (1) an engineered immune effector cell (such as T cell) comprising a multivalent CAR comprising a polypeptide comprising: (a) an extracellular antigen binding domain comprising a first BCMA binding moiety (such as a first anti-BCMA sdAb) specifically binding to a first epitope of BCMA, and a second BCMA binding moiety (such as a second anti-BCMA sdAb) specifically binding to a second epitope of BCMA; (b) a transmembrane domain; and (c) an intracellular signaling domain, wherein the first epitope and the second epitope are different; and (2) a pharmaceutically acceptable carrier. In some embodiments, a method of inhibiting metastasis to lymph node is provided. In some embodiments, a method of inhibiting metastasis to the lung is provided. In some embodiments, a method of inhibiting metastasis to the liver is provided. Metastasis can be assessed by any known methods in the art, such as by blood tests, bone scans, x-ray scans, CT scans, PET scans, and biopsy.

VII. Kits and Articles of Manufacture

Further provided are kits, unit dosages, and articles of manufacture comprising any of the single-domain antibodies, the chimeric antigen receptors, or the engineered immune effector cells described herein. In some embodiments, a kit is provided which contains any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

The examples and exemplary embodiments below are intended to be purely exemplary of the invention and should therefore not be considered to limit the invention in any way. The following examples and exemplary embodiments are offered by way of illustration and not by way of limitation.

VIII. Exemplary Embodiments

The invention provides the following embodiments:

Embodiment 1

An anti-BCMA single-domain antibody (sdAb) comprising any one of the following: (1) a CDR1 comprising the amino acid sequence of SEQ ID NO:1; a CDR2 comprising the amino acid sequence of SEQ ID NO:39; and a CDR3 comprising the amino acid sequence of SEQ ID NO:77; (2) a CDR1 comprising the amino acid sequence of SEQ ID NO:2; a CDR2 comprising the amino acid sequence of SEQ ID NO:40; and a CDR3 comprising the amino acid sequence of SEQ ID NO:78; (3) a CDR1 comprising the amino acid sequence of SEQ ID NO:3; a CDR2 comprising the amino acid sequence of SEQ ID NO:41; and a CDR3 comprising the amino acid sequence of SEQ ID NO:79; (4) a CDR1 comprising the amino acid sequence of SEQ ID NO:4; a CDR2 comprising the amino acid sequence of SEQ ID NO:42; and a CDR3 comprising the amino acid sequence of SEQ ID NO:80; (5) a CDR1 comprising the amino acid sequence of SEQ ID NO:5; a CDR2 comprising the amino acid sequence of SEQ ID NO:43; and a CDR3 comprising the amino acid sequence of SEQ ID NO:81; (6) a CDR1 comprising the amino acid sequence of SEQ ID NO:6; a CDR2 comprising the amino acid sequence of SEQ ID NO:44; and a CDR3 comprising the amino acid sequence of SEQ ID NO:82; (7) a CDR1 comprising the amino acid sequence of SEQ ID NO:7; a CDR2 comprising the amino acid sequence of SEQ ID NO:45; and a CDR3 comprising the amino acid sequence of SEQ ID NO:83; (8) a CDR1 comprising the amino acid sequence of SEQ ID NO:8; a CDR2 comprising the amino acid sequence of SEQ ID NO:46; and a CDR3 comprising the amino acid sequence of SEQ ID NO:84; (9) a CDR1 comprising the amino acid sequence of SEQ ID NO:9; a CDR2 comprising the amino acid sequence of SEQ ID NO:47; and a CDR3 comprising the amino acid sequence of SEQ ID NO:85; (10) a CDR1 comprising the amino acid sequence of SEQ ID NO:10; a CDR2 comprising the amino acid sequence of SEQ ID NO:48; and a CDR3 comprising the amino acid sequence of SEQ ID NO:86; (11) a CDR1 comprising the amino acid sequence of SEQ ID NO:11; a CDR2 comprising the amino acid sequence of SEQ ID NO:49; and a CDR3 comprising the amino acid sequence of SEQ ID NO:87; (12) a CDR1 comprising the amino acid sequence of SEQ ID NO:12; a CDR2 comprising the amino acid sequence of SEQ ID NO:50; and a CDR3 comprising the amino acid sequence of SEQ ID NO:88; (13) a CDR1 comprising the amino acid sequence of SEQ ID NO:13; a CDR2 comprising the amino acid sequence of SEQ ID NO:51; and a CDR3 comprising the amino acid sequence of SEQ ID NO:89; (14) a CDR1 comprising the amino acid sequence of SEQ ID NO:14; a CDR2 comprising the amino acid sequence of SEQ ID NO:52; and a CDR3 comprising the amino acid sequence of SEQ ID NO:90; (15) a CDR1 comprising the amino acid sequence of SEQ ID NO:15; a CDR2 comprising the amino acid sequence of SEQ ID NO:53; and a CDR3 comprising the amino acid sequence of SEQ ID NO:91; (16) a CDR1 comprising the amino acid sequence of SEQ ID NO:16; a CDR2 comprising the amino acid sequence of SEQ ID NO:54; and a CDR3 comprising the amino acid sequence of SEQ ID NO:92; (17) a CDR1 comprising the amino acid sequence of SEQ ID NO:17; a CDR2 comprising the amino acid sequence of SEQ ID NO:55; and a CDR3 comprising the amino acid sequence of SEQ ID NO:93; (18) a CDR1 comprising the amino acid sequence of SEQ ID NO:18; a CDR2 comprising the amino acid sequence of SEQ ID NO:56; and a CDR3 comprising the amino acid sequence of SEQ ID NO:94; (19) a CDR1 comprising the amino acid sequence of SEQ ID NO:19; a CDR2 comprising the amino acid sequence of SEQ ID NO:57; and a CDR3 comprising the amino acid sequence of SEQ ID NO:95; (20) a CDR1 comprising the amino acid sequence of SEQ ID NO:20; a CDR2 comprising the amino acid sequence of SEQ ID NO:58; and a CDR3 comprising the amino acid sequence of SEQ ID NO:96; (21) a CDR1 comprising the amino acid sequence of SEQ ID NO:21; a CDR2 comprising the amino acid sequence of SEQ ID NO:59; and a CDR3 comprising the amino acid sequence of SEQ ID NO:97; (22) a CDR1 comprising the amino acid sequence of SEQ ID NO:22; a CDR2 comprising the amino acid sequence of SEQ ID NO:60; and a CDR3 comprising the amino acid sequence of SEQ ID NO:98; (23) a CDR1 comprising the amino acid sequence of SEQ ID NO:23; a CDR2 comprising the amino acid sequence of SEQ ID NO:61; and a CDR3 comprising the amino acid sequence of SEQ ID NO:99; (24) a CDR1 comprising the amino acid sequence of SEQ ID NO:24; a CDR2 comprising the amino acid sequence of SEQ ID NO:62; and a CDR3 comprising the amino acid sequence of SEQ ID NO:100; (25) a CDR1 comprising the amino acid sequence of SEQ ID NO:25; a CDR2 comprising the amino acid sequence of SEQ ID NO:63; and a CDR3 comprising the amino acid sequence of SEQ ID NO:101; (26) a CDR1 comprising the amino acid sequence of SEQ ID NO:26; a CDR2 comprising the amino acid sequence of SEQ ID NO:64; and a CDR3 comprising the amino acid sequence of SEQ ID NO:102; (27) a CDR1 comprising the amino acid sequence of SEQ ID NO:27; a CDR2 comprising the amino acid sequence of SEQ ID NO:65; and a CDR3 comprising the amino acid sequence of SEQ ID NO:103; (28) a CDR1 comprising the amino acid sequence of SEQ ID NO:28; a CDR2 comprising the amino acid sequence of SEQ ID NO:66; and a CDR3 comprising the amino acid sequence of SEQ ID NO:104; (29) a CDR1 comprising the amino acid sequence of SEQ ID NO:29; a CDR2 comprising the amino acid sequence of SEQ ID NO:67; and a CDR3 comprising the amino acid sequence of SEQ ID NO:105; (30) a CDR1 comprising the amino acid sequence of SEQ ID NO:30; a CDR2 comprising the amino acid sequence of SEQ ID NO:68; and a CDR3 comprising the amino acid sequence of SEQ ID NO:106; (31) a CDR1 comprising the amino acid sequence of SEQ ID NO:31; a CDR2 comprising the amino acid sequence of SEQ ID NO:69; and a CDR3 comprising the amino acid sequence of SEQ ID NO:107; (32) a CDR1 comprising the amino acid sequence of SEQ ID NO:32; a CDR2 comprising the amino acid sequence of SEQ ID NO:70; and a CDR3 comprising the amino acid sequence of SEQ ID NO:108; (33) a CDR1 comprising the amino acid sequence of SEQ ID NO:33; a CDR2 comprising the amino acid sequence of SEQ ID NO:71; and a CDR3 comprising the amino acid sequence of SEQ ID NO:109; (34) a CDR1 comprising the amino acid sequence of SEQ ID NO:34; a CDR2 comprising the amino acid sequence of SEQ ID NO:72; and a CDR3 comprising the amino acid sequence of SEQ ID NO:110; (35) a CDR1 comprising the amino acid sequence of SEQ ID NO:35; a CDR2 comprising the amino acid sequence of SEQ ID NO:73; and a CDR3 comprising the amino acid sequence of SEQ ID NO:111; (36) a CDR1 comprising the amino acid sequence of SEQ ID NO:36; a CDR2 comprising the amino acid sequence of SEQ ID NO:74; and a CDR3 comprising the amino acid sequence of SEQ ID NO:112; (37) a CDR1 comprising the amino acid sequence of SEQ ID NO:37; a CDR2 comprising the amino acid sequence of SEQ ID NO:75; and a CDR3 comprising the amino acid sequence of SEQ ID NO:113; or (38) a CDR1 comprising the amino acid sequence of SEQ ID NO:38; a CDR2 comprising the amino acid sequence of SEQ ID NO:76; and a CDR3 comprising the amino acid sequence of SEQ ID NO:114.

Embodiment 2

The anti-BCMA sdAb of embodiment 1, wherein the anti-BCMA sdAb comprises an amino acid sequence selected from the group consisting of SEQ ID NOs: 115-152.

Embodiment 3

An anti-BCMA antibody that competes with the anti-BCMA sdAb of embodiment 1 or 2.

Embodiment 4

The anti-BCMA antibody of embodiment 3, wherein the anti-BCMA antibody is an sdAb.

Embodiment 5

The anti-BCMA sdAb of any one of embodiments 1, 2 and 4, wherein the anti-BCMA sdAb is a camelid antibody.

Embodiment 6

The anti-BCMA sdAb of any one of embodiments 1, 2 and 4, wherein the anti-BCMA sdAb is a chimeric antibody.

Embodiment 7

The anti-BCMA sdAb of any one of embodiments 1, 2 and 4, wherein the anti-BCMA sdAb is humanized.

Embodiment 8

The anti-BCMA sdAb of any one of embodiments 1-2 and 4-7, wherein the anti-BCMA sdAb is a $V_HH$ fragment.

Embodiment 9

A chimeric antigen receptor (CAR) comprising a polypeptide comprising: (a) an extracellular antigen binding domain comprising the anti-BCMA sdAb of any one of embodiments 1-2 and 4-7; (b) a transmembrane domain; and (c) an intracellular signaling domain.

Embodiment 10

The CAR of embodiment 9, wherein the extracellular antigen binding domain comprises at least two anti-BCMA sdAbs.

Embodiment 11

A multivalent chimeric antigen receptor (CAR) comprising a polypeptide comprising: (a) an extracellular antigen binding domain comprising at least two BCMA binding moieties; (b) a transmembrane domain; and (c) an intracellular signaling domain.

Embodiment 12

The multivalent CAR of embodiment 11, wherein the extracellular antigen binding domain comprises a first BCMA binding moiety and a second BCMA binding moiety.

Embodiment 13

The multivalent CAR of embodiment 12, wherein one or more of the first BCMA binding moiety and the second BCMA binding moiety is a sdAb.

Embodiment 14

The multivalent CAR of embodiment 12 or 13, wherein the first BCMA binding moiety is a first anti-BCMA sdAb and the second BCMA binding moiety is a second anti-BCMA sdAb.

Embodiment 15

The multivalent CAR of embodiment 12 or 13, wherein the first BCMA binding moiety is an anti-BCMA sdAb and the second BCMA binding moiety is derived from a human antibody.

Embodiment 16

The multivalent CAR of embodiment 12 or 13, wherein the first BCMA binding moiety is an anti-BCMA sdAb and the second BCMA binding moiety is a polypeptide ligand of BCMA.

Embodiment 17

The multivalent CAR of any one of embodiments 12-16, wherein the first BCMA binding moiety and the second BCMA binding moiety specifically bind to the same epitope on BCMA.

Embodiment 18

The multivalent CAR of any one of embodiments 12-16, wherein the first BCMA binding moiety and the second BCMA binding moiety specifically bind to different epitopes on BCMA.

Embodiment 19

The multivalent CAR of any one of embodiments 12-18, wherein the first BCMA binding moiety and/or the second BCMA binding moiety specifically binds to an epitope on BCMA derived from an amino acid sequence selected from SEQ ID NOs: 388-394.

Embodiment 20

The multivalent CAR of any one of embodiments 12-19, wherein one or more of the first BCMA binding moiety and the second BCMA binding moiety is the anti-BCMA sdAb of embodiment 1.

Embodiment 21

The multivalent CAR of any one of embodiments 12-20, wherein the first BCMA binding moiety is located at the N-terminus of the second BCMA binding moiety.

Embodiment 22

The multivalent CAR of any one of embodiments 12-20, wherein the first BCMA binding moiety is located at the C-terminus of the second BCMA binding moiety.

Embodiment 23

The multivalent CAR of any one of embodiments 12-22, wherein the first BCMA binding moiety and the second BCMA binding moiety are fused to each other via a peptide linker.

Embodiment 24

The multivalent CAR of embodiment 23, wherein the peptide linker is no more than about 50 amino acids long.

Embodiment 25

The multivalent CAR of embodiment 24, wherein the peptide linker comprises an amino acid sequence selected from the group consisting of SEQ ID NOs: 208-215.

Embodiment 26

The CAR or multivalent CAR of any one of embodiments 9-25, wherein the transmembrane domain is derived from a molecule selected from the group consisting of CD8α, CD4, CD28, CD137, CD80, CD86, CD152 and PD1.

Embodiment 27

The CAR or multivalent CAR of embodiment 26, wherein the transmembrane domain is derived from CD8α or CD28.

Embodiment 28

The CAR or multivalent CAR of embodiment 27, wherein the transmembrane domain comprises the amino acid sequence of SEQ ID NO: 193 or 194.

Embodiment 29

The CAR or multivalent CAR of any one of embodiments 9-28, wherein the intracellular signaling domain comprises a primary intracellular signaling domain of an immune effector cell.

Embodiment 30

The CAR or multivalent CAR of embodiment 29, wherein the primary intracellular signaling domain is derived from CD3ζ.

Embodiment 31

The CAR or multivalent CAR of embodiment 30, wherein the primary intracellular signaling domain comprises the amino acid sequence of SEQ ID NO: 197 or 198.

Embodiment 32

The CAR or multivalent CAR of any one of embodiments 9-31, wherein the intracellular signaling domain comprises a co-stimulatory signaling domain.

Embodiment 33

The CAR or multivalent CAR of embodiment 32, wherein the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, Ligands of CD83 and combinations thereof.

Embodiment 34

The CAR or multivalent CAR of embodiment 33, the co-stimulatory signaling domain comprises a cytoplasmic domain of CD28 and/or a cytoplasmic domain of CD137.

Embodiment 35

The CAR or multivalent CAR of embodiment 34, wherein the co-stimulatory signaling domain comprises the amino acid sequence of SEQ ID NO: 195 and/or SEQ ID NO: 196.

Embodiment 36

The CAR or multivalent CAR of any one of embodiments 32-35, wherein the intracellular signaling domain comprises at least two co-stimulatory signaling domains.

Embodiment 37

The CAR or multivalent CAR of any one of embodiments 9-36, further comprising a hinge domain located between the C-terminus of the extracellular antigen binding domain and the N-terminus of the transmembrane domain.

Embodiment 38

The CAR or multivalent CAR of embodiment 37, wherein the hinge domain is derived from CD8α.

Embodiment 39

The CAR or multivalent CAR of embodiment 38, wherein the hinge domain comprises the amino acid sequence of SEQ ID NO: 192.

Embodiment 40

The CAR or multivalent CAR of any one of embodiments 9-39, further comprising a signal peptide located at the N-terminus of the polypeptide.

Embodiment 41

The CAR or multivalent CAR of embodiment 40, wherein the signal peptide is derived from CD8α.

Embodiment 42

The CAR or multivalent CAR of embodiment 41, wherein the signal peptide comprises the amino acid sequence of SEQ ID NO: 191.

Embodiment 43

A chimeric antigen receptor comprising an amino acid sequence selected from the group consisting of SEQ ID NOs: 216-256 and 298-335.

Embodiment 44

An isolated nucleic acid comprising a nucleic acid sequence encoding the CAR or multivalent CAR of any one of embodiments 11-43.

Embodiment 45

The isolated nucleic acid of claim 44, comprising a nucleic acid sequence selected from the group consisting of SEQ ID NOs: 257-297 and 336-373.

Embodiment 46

The isolated nucleic acid of embodiment 45, further comprising a second nucleic acid sequence encoding a second CAR, wherein the nucleic acid sequence encoding the CAR is operably linked to the second nucleic acid sequence via a third nucleic acid sequence encoding a self-cleaving peptide.

Embodiment 47

The isolated nucleic acid of embodiment 46, the self-cleaving peptide is selected from the group consisting of T2A, P2A, and F2A.

Embodiment 48

The isolated nucleic acid of embodiment 47, the third nucleic acid sequence is SEQ ID NO: 385.

Embodiment 49

The isolated nucleic acid of any one of embodiments 44-48, the isolated nucleic acid is an RNA molecule.

Embodiment 50

A vector comprising the isolated nucleic acid of any one of embodiments 44-49.

Embodiment 51

The vector of embodiment 50, wherein the vector is an expression vector.

Embodiment 52

The vector of embodiment 50 or 51, wherein the vector is a viral vector.

Embodiment 53

The vector of embodiment 52, wherein the vector is a lentiviral vector.

Embodiment 54

The vector of embodiment 50 or 51, wherein the vector is a non-viral vector.

Embodiment 55

An engineered immune effector cell, comprising the CAR or multivalent CAR of any one of embodiments 9-43, the isolated nucleic acid of any one of embodiments 44-49, or the vector of any one of embodiments 50-54.

Embodiment 56

The engineered immune effector cell of embodiment 55, wherein the immune effector cell is a T cell, an NK cell, a peripheral blood mononuclear cell (PBMC), a hematopoietic stem cell, a pluripotent stem cell, or an embryonic stem cell.

Embodiment 57

The engineered immune effector cell of embodiment 56, wherein the immune effector cell is a T cell.

Embodiment 58

A pharmaceutical composition, comprising the engineered immune effector cell of any one of embodiments 55-57, and a pharmaceutically acceptable carrier.

Embodiment 59

A method of treating cancer in an individual, comprising administering to the individual an effective amount of the pharmaceutical composition of embodiment 58.

Embodiment 60

The method of embodiment 59, wherein the cancer is multiple myeloma.

Embodiment 61

The method of embodiment 60, wherein the cancer is refractory or relapsed multiple myeloma.

Embodiment 62

The method of any one of embodiments 59-61, wherein the engineered immune effector cell is autologous.

Embodiment 63

The method of any one of embodiments 59-61, wherein the engineered immune effector cell is allogenic.

Embodiment 64

The method of any one of embodiments 59-63, wherein the individual is human.

Embodiment 65

The method of any one of embodiments 59-64, wherein the pharmaceutical composition is administered intravenously.

Embodiment 66

The method of any one of embodiments 59-65, wherein the pharmaceutical composition is administered at a dose of about $1\times10^5$ to about $1\times10^7$ cells/kg.

Embodiment 67

The method of any one of embodiments, 59-66, wherein the pharmaceutical composition is administered in 3 split doses over about one week.

Embodiment 68

Use of the pharmaceutical composition of embodiment 58 for treating cancer in an individual.

Embodiment 69

Use of the pharmaceutical composition of embodiment 58 in the preparation of a medicament for treating cancer in an individual.

Embodiment 70

A pharmaceutical composition, comprising the anti-BCMA sdAb of any one of embodiments 1-8.

Embodiment 71

A method of treating a disease in an individual, comprising administering to the individual an effective amount of the pharmaceutical composition of embodiment 70.

Embodiment 72

The method of embodiment 71, wherein the disease is cancer.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Preparation of Anti-BCMA sdAbs

To develop sdAbs with high binding affinity to BCMA, llamas were immunized with a recombinant BCMA antigen. A phage-display library was then constructed to identify $V_HH$ leads. Distinct clones were picked at random and were classified according to the heavy chain complementarity determining region 3 (CDR3), a region that can play a major role in antigen binding. An exemplary protocol is described below. Other protocols for preparing sdAbs have been described. See, for example, Els Pardon et al, *Nature Protocol,* 2014; 9(3): 674.

1. Animal Immunization and Immune Response Assay
1.1 Animal Immunization

An immunogen comprising a recombinant human BCMA protein having a C-terminal Fc tag (ACRO Biosystems, Cat No.: BC7-H5254) was mixed with adjuvant or PBS and injected to llamas. The animals were immunized by service vendor (Cedarline) for seven times, typically with 200 μg immunogen and CFA (Complete Freund's Adjuvant) each time at about 1-week to 2-week intervals. Peripheral blood samples were collected at the pre-immunization stage and after the 5th and 7th immunization. After multiple rounds of immunization, immune reactions of the llamas against the target antigen were evaluated to confirm the titer of antigen-specific sdAbs. Lymphocytes were isolated by gradient centrifugation from about 100 ml of peripheral blood. The cells were supplemented with RNALATER' and stored at −80° C. Sera were obtained by centrifugation of anti-coagulated blood samples and stored at −80° C.

1.2 IgG Fractionation

IgG-subclass fractionation was carried out according to GenScript's Standard Operating Procedure. The IgG subclasses were fractionated from terminal bleed serum using Protein G and Protein A resins. The 1 ml serum sample was loaded onto a 1 ml HITRAP® Protein G HP column, and the column was washed with 10 ml phosphate buffer (20 mM, pH 7.0). The IgG3 (MW 100,000 Da) fraction was eluted with 0.15 M NaCl, 0.58% acetic acid (pH 3.5), and the eluate was neutralized with 1 M Tris-HCl (pH 9.0) to pH 7.4. Subsequently, the IgG1 (MW 170,000 Da) fraction was eluted with 0.1 M glycine-HCl (pH 2.7), and the eluate was neutralized with 1 M Tris-HCl (pH 8.5) to pH 7.4. The flow-through of HITRAP® Protein G HP column was then loaded onto a 1 ml HITRAP® Protein A HP column, and the column was washed with 20 ml phosphate buffer (20 mM, pH 7.0). The IgG2 (MW 100,000 Da) fraction was eluted with 0.15 M NaCl, 0.58% acetic acid (pH 4.5), and the eluate was neutralized with 1M Tris-HCl (pH 9.0) to pH 7.4. The concentrations of the purified IgG1, IgG2 and IgG3 antibodies were determined by OD280, and the purity of each was assessed by both reducing and non-reducing SDS-PAGE analysis.

1.3 Immune Response Assay

Immune response of the llamas was evaluated by ELISA, in which the serum samples and purified IgGs were assayed for binding to immobilized immunogens. Sera collected pre-immunization, after 5th immunization and at terminal bleed were evaluated. The antigen (i.e., recombinant human antigen protein) was diluted in coating buffer at 4 μg/ml. The microtiter plate was coated with diluted antigen at 4° C. overnight. The plate was then washed 3 times with washing buffer followed by blocking at room temperature for 2 hours. The plate was subsequently washed 4 times with washing buffer. A series of diluted sera or IgGs were added to the plate and incubated at room temperature for 1.5 hours. The plate was then washed 4 times with washing buffer. HRP-conjugated anti-llama IgG secondary antibody was added to the plate and incubated at room temperature for 1 hour. After washing, the TMB substrate was added to each well and incubated for 10 minutes before stopping with 1 M HCl. To quantify binding, absorbance at 450 nm was measured for each well using a MK3 spectrometer.

2. $V_HH$ Phage Display Library Construction
2.1 RNA Extraction

Total RNA was extracted from the isolated lymphocytes (from 1.1.1) using TRIZOL® Reagent according to the manufacturer's protocol. Quantity and quality of the total RNA were assessed by gel electrophoresis and quantified by measuring absorbance at OD260/280.

2.2 RT-PCR and $V_HH$ Amplification

Total RNA was reverse transcribed into cDNA with an oligo(dT)$_{20}$ primer using PRIMESCRIPT™ 1st Strand cDNA Synthesis Kit according to the manufacturer's protocol. Six forward and two reverse specific degenerate primers were designed to amplify the $V_HH$ fragments, which had two BglI restriction sites introduced. The $V_HH$ fragments were amplified according to GenScript's standard operating procedure as described below.

The variable regions of the heavy-chain immunoglobulins (i.e., $V_H$Hs) were amplified using a two-step polymerase chain reaction (PCR). In the first PCR, 100 ng of cDNA template was mixed with primers CALL001 (SEQ ID NO: 374) and CALL002 (SEQ ID NO: 375). The DNA products from the first PCR reaction were analyzed by agarose gel electrophoresis. After gel purification, the DNA products of the first PCR were used as templates in the second PCR. The second PCR was performed with the primers BACK-1 (SEQ ID NO: 376), BACK-2 (SEQ ID NO: 377) and PMCF (SEQ ID NO: 378). The amplified second PCR products containing $V_HH$ PCR fragments were gel purified and enzyme digested, and then inserted into phagemid plasmids. The recombinant plasmids with $V_HH$ gene fragments were electro-transferred into *E. coli* cells in order to generate the phage display $V_HH$ immune library.

The procedure of the PCR reaction has an initial denaturation step at 94° C. for 7 min, followed by 30 cycles of 94° C. for 1 min, 55° C. for 1 min, and 72° C. for 1 min; and followed by a final extension step at 72° C. for 7 min.

2.3 Phage Library Construction

The $V_HH$ PCR products were obtained by amplification using different primer pairs. The PCR products were then digested with BglI and gel purified. The gel purified fragments were inserted into GenScript's in-house phagemid vector. A pilot library was constructed to optimize the ligation and transformation conditions. The optimized ligation and transformation conditions were employed to develop the phagemid library. A small portion of the transformed cells was diluted and streaked on 2×YT plates supplemented with 100 μg/ml ampicillin. The colonies were counted to calculate the library size. Positive clones were randomly picked and sequenced to assess the quality of the library. The rest of the transformed cells were streaked onto YT plates supplemented with 100 μg/ml ampicillin and 2% glucose. Lawns of colonies were scraped off the plates. A small aliquot of the cells was used for library plasmid isolation. The rest was supplemented with glycerol and stored at −80° C. as stock.

3. Phage Display Panning 3.1 Bio-Panning

The constructed $V_HH$ phage library was panned against recombinant human BCMA protein and CHO cells expressing human BCMA (i.e., CHO-BCMA cells, prepared in house by Legend Biotec) respectively using a standard procedure developed by GenScript. The library stock was grown to log phase, and then the library was rescued with M13K07 helper phage and was amplified overnight at 25° C. in a shaker. The phage was then precipitated with PEG/NaCl, re-suspended in PBS and stored at −80° C. For solid phase panning, microplate wells were coated with recombinant human BCMA protein in PBS at 4° C. overnight. For liquid phase panning, CHO-BCMA cells were blocked with blocking buffer at room temperature for 1 hour. During the coating or blocking step, phage particles were pre-incubated with the blocking buffer and Fc control protein in microplate wells. After pre-incubation, phage particles were added to the wells coated with BCMA proteins or CHO-BCMA solution respectively and incubated for 1 hour. After incubation, unbound and nonspecifically bound phages were washed away by rinsing the wells or the CHO-BCMA cells with PBST for six times supplemented with two additional PBS washes. The bound phage particles were eluted by 100 mM triethylamine(TEA), and the eluate was neutralized by 1 M Tris-HCl (pH 7.4). Half of the eluate was then used to infect exponentially growing *E. coli* TG1 cells ($OD_{600}$=0.4~0.6) for output titration.

3.2 Phage ELISA

Phage ELISA was performed to identify clones specific to the target antigens. Individual output phage clones were grown in 96-deep-well plate and rescued by M13K07 helper phage overnight. To identify clones that bind to antigen proteins, 96-well ELISA microtiter plates were coated with recombinant human BCMA protein and Fc control protein respectively in coating buffer overnight at 4° C., and the plates were then blocked with blocking buffer. After blocking, approximately 50 µl per well of phage supernatant from the overnight cell culture was added to the plates for 1.5-hour incubation at 4° C. The plates were washed four times, and the HRP-conjugated anti-M13 monoclonal antibody was added to the plates for 45-minute incubation at 4° C. The plates were again washed five times and substrate solution was added to the wells for developing. Absorption at 450 nm was measured for each well.

To identify clones that bind CHO-BCMA cells, the CHO-BCMA cells were blocked with blocking buffer at room temperature for 1 hour. After blocking, approximately 20 µl per well of phage supernatant from the overnight cell culture was added to the cell solutions for 1-hour incubation at room temperature. After the cells were washed 4 times, the HRP-conjugated anti-M13 monoclonal antibody was added for 30-minute incubation at room temperature. The cells were washed five times and substrate solution was then added for developing. The absorption was measured at 450 nm. After panning, ELISA positive phage clones were randomly selected and DNA was prepared from output phage using a plasmid extraction kit. The anti-BCMA $V_HHs$ in the plasmids were sequenced.

Example 2. Preparation of Exemplary Monovalent BCMA Chimeric Antigen Receptors

A nucleic acid sequence encoding a CAR backbone polypeptide comprising from the N-terminus to the C-terminus: a CD8α hinge domain, a CD28 transmembrane domain, a CD28 cytoplasmic domain, a CD137 cytoplasmic domain, and a CD3ζ cytoplasmic domain was chemically synthesized and cloned into a pre-modified lentiviral vector downstream and operably linked to a constitutive hEF1α promoter. The resulting CAR backbone vector was named "PLLV-hEF1α-8281373." Multi-cloning sites (MCS) in the vector allowed insertion of a nucleic acid sequence comprising a Kozak sequence (SEQ ID NO:379) operably linked to a nucleic acid sequence encoding a CD8α signal peptide fused to the N-terminus of a $V_HH$ fragment into the PLLV-hEF1α-8281373 vector, upstream and operably linked to the CAR backbone sequence.

To construct a monospecific CAR having a single $V_HH$ domain using the PLLV-hEF1α-8281373 backbone, the nucleic acid sequence encoding the $V_HH$ domain was operably linked to the 3' of the nucleic acid sequence encoding the CD8α signal peptide. The fusion nucleic acid sequence was chemically synthesized and cloned into the PLLV-hEF1α-8281373 CAR backbone via the EcoRI (SEQ ID NO: 380: 5'-GAATTC-3') and SpeI (SEQ ID NO: 381: 5'-ACTAGT-3') restriction sites by molecular cloning techniques known in the art. Table 4 lists the vectors that were constructed to express the exemplary monospecific, monovalent anti-BCMA CARs.

For ease of further inserting additional sequences, such as a nucleotide encoding a second $V_HH$, when designing a monospecific CAR construct, restriction sites including HpaI (SEQ ID NO: 382: 5'-GTTAAC-3'), MluI (SEQ ID NO: 383: 5'-ACGCGT-3'), NsiI (SEQ ID NO: 384: 5'-ATGCAT-3') sites were included between the CD8α signal peptide nucleic acid sequence and the $V_HH$ nucleic acid sequence.

The lentivirus packaging plasmid mixture including pCMV-ΔR-8.74 and pMD2.G (Addgene #12259) was pre-mixed with the vectors PLLV-hEF1α-8281373 having $V_HH$ fragments at a pre-optimized ratio with polyetherimide (PEI), then mixed properly and incubated at room temperature for 5 minutes. The transfection mix was then added dropwise to the HEK293 cells and mixed gently. Afterwards, cells were incubated overnight in a 37° C. and 5% $CO_2$ cell incubator. The supernatants were collected after centrifugation at 4° C., 500 g for 10 min.

The virus-containing supernatants were filtered through a 0.45 µm PES filter, followed by ultra-centrifugation for lentivirus concentration. After ultra-centrifugation, the supernatants were carefully discarded and the virus pellets were rinsed cautiously with pre-chilled DPBS. The virus was aliquoted properly, then stored at −80° C. immediately. The virus titer was determined by p24 based on HTRF kit developed by GenScript.

PBMC Preparation

Leukocytes were collected from healthy donors by apheresis, and cell concentration was adjusted to 5×10⁶ cells/ml in R10 medium. Leukocytes were then mixed with 0.9% NaCl solution at 1:1 (v/v) ratio. 3 ml lymphoprep medium was added to a 15 ml centrifuge tube, and 6 ml of diluted lymphocyte mix was slowly layered on top of the lymphoprep medium. The lymphocyte mix was centrifuged at 800 g for 30 minutes without brakes at 20° C. Lymphocyte buffy coat was then collected with a 200 µl pipette. The harvested fraction was diluted at least 6 folds with 0.9% NaCl or R10 to reduce density of the solution. The harvested fraction was then centrifuged at 250 g for 10 minutes at 20° C. The supernatant was aspirated completely, and 10 ml of R10 was added to the cell pellet to resuspend the cell pellet. The mixture was further centrifuged at 250 g for 10 minutes at 20° C. The supernatant was again aspirated. 2 ml of 37° C. pre-warmed R10 with 100 IU/ml IL-2 was added to the cell pellet, and the cell pellet was re-suspended softly. The cell number was determined following Trypan Blue staining, and this PBMC sample was ready for later experiments.

T Cell Purification

Human T cells were purified from PBMCs using Miltenyi Pan T cell isolation kit (Cat #130-096-535), following manufacturer's protocol as described below. Cell number was first determined and the cell suspension was centrifuged at 300 g for 10 minutes. The supernatant was then aspirated completely, and the cell pellets were re-suspended in 40 µl buffer per $10^7$ total cells. 10 µl of Pan T Cell Biotin-Antibody Cocktail was added per $10^7$ total cells, mixed thoroughly and incubated for about 5 minutes in the refrigerator (2~8° C.). 30 µl of buffer was then added per $10^7$ cells. 20 µl of Pan T Cell MicroBead Cocktail was added per $10^7$ cells. The cell suspension mixture was mixed well and incubated for an additional 10 minutes in the refrigerator (2~8° C.). A minimum of 500 µl is required for magnetic separation. For magnetic separation, an LS column was placed in the magnetic field of a suitable MACS Separator. The column was prepared by rinsing with 3 ml of buffer. The cell suspension was then applied onto the column, and flow-through containing the unlabeled cells was collected, which represented the enriched T cell fractions. Additional T cells were collected by washing the column with 3 ml of buffer and collecting unlabeled cells that pass through. These unlabeled cells again represented the enriched T cells, and were combined with the flow-through from previous step. The pooled enriched T cells were then centrifuged and re-suspended in R10+100 IU/ml IL-2.

The prepared T cells were subsequently pre-activated for 48-96 hours with human T cell activation/expansion kit (Miltenyi #130-091-441) according to manufacturer's protocol in which anti-CD3/CD28 MACSiBead particles were added at a bead-to-cell ratio of 1:2.

In Vitro Cytotoxicity Assay

The pre-activated T cells were transduced with lentivirus stock in the presence of 7 µg/ml polybrene with centrifugation at 1200 g, 32° C. for 1.5 h. The transduced cells were then transferred to the cell culture incubator for transgene expression under suitable conditions.

On day 3 or day 7 post-transduction, transduced T cells were harvested and co-incubated with tumor cells at an effector (CAR-T) to target cell ratio of 20:1 for 20 hours. Target cells were human multiple myeloma cell line RPMI8226.Luc, human cell line K562.BCMA.Luc cells which recombinantly expressed BCMA, K562.CD19. Luc cell line which recombinantly expressed CD19, or human glioblastoma cell line U87MG.Luc cells. All of the cell lines were engineered in house to express firefly luciferase. To assay the cytotoxicity of CAR-T on tumor cells, ONE-GLO™ luminescent luciferase assay reagents (Promega #E6110) were prepared according to manufacturer's protocol and added to the co-cultured cells to detect the remaining luciferase activity in the well. Since luciferase is expressed only in the target cells, the remaining luciferase activity in the well correlates directly to the number of viable target cells in the well. The maximum luciferase activity was obtained by adding culture media to target cells in the absence of effector cells. The minimum luciferase activity was determined by adding Triton X-100 at a final concentration of 1% at the time when the cytotoxicity assays were initiated. The specific cytotoxicity was calculated by the formula: Specific Cytotoxicity %=100%*(1−(RLUsample−RLUmin)/(RLUmax−RLUmin)).

Figure 1B:
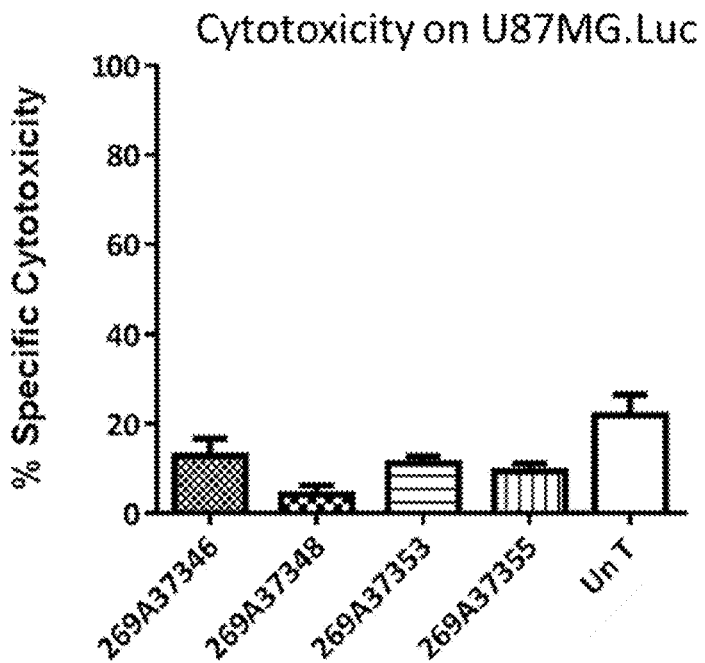

Exemplary monovalent CAR targeting BCMA (CD269) were selected and tested in the cytotoxicity assay. As shown in FIG. 1A, among a first group of monovalent BCMA CARs tested, the selected clones exhibited different levels of cytotoxicity against multiple myeloma cell line RPMI8226.Luc cells, with over 60% monovalent $V_HH$-based CAR-Ts showing >50% cytotoxicity against RPMI8226.Luc cells. Clones 269A37346, 269A37348, 269A37353, and 269A37355 based CAR-T were selected for further testing. In particular, clones 269A37346, 269A37348, 267A37353 and 269A37355 based CAR-T exhibited potent cytotoxicity against multiple myeloma cell line RPMI8226.Luc cells with more than 20%-30% increase in RPMI8226.Luc cell killing by CAR-T treatment as compared with untransduced control T cells (UnT). Nevertheless, such cytotoxicity increase did not occur against human glioblastoma cell line U87MG.Luc cells (see FIG. 1B). No significant cytotoxicity effects were detected against U87MG.Luc by these monovalent $V_HH$-based CAR-T cells as compared to UnT controls. The observation above indicated that some of these clones might be target specific and potent against BCMA positive cells.

Figure 2A:
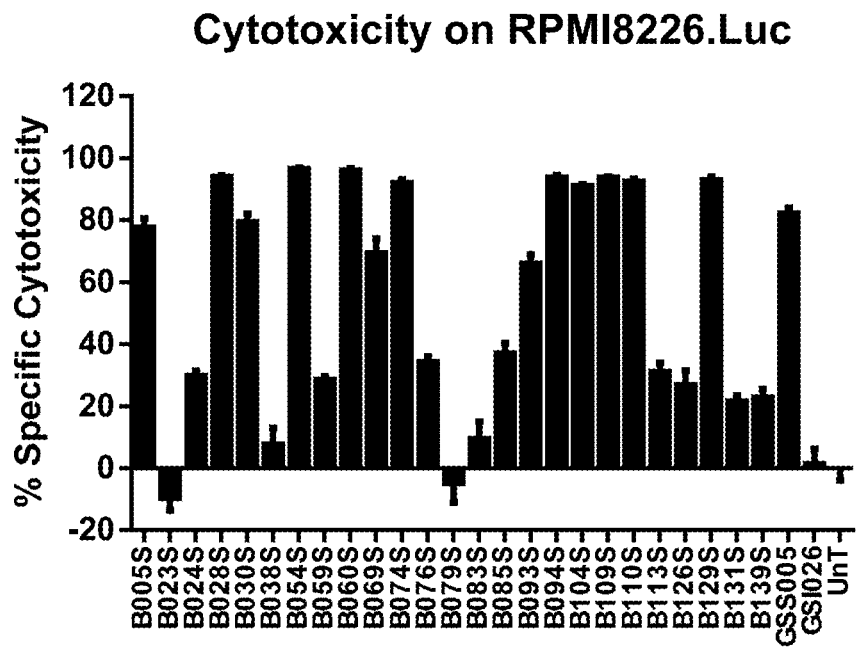
FIGS. 2A-2C show results of an in vitro cytotoxicity assay of T cells expressing exemplary monospecific CARs comprising various anti-BCMA sdAbs against RPMI8226.Luc cells (FIG. 2A), K562.BCMA.Luc cells (FIG. 2B), or K562.CD19.Luc cells (FIG. 2C).
Figure 2B:
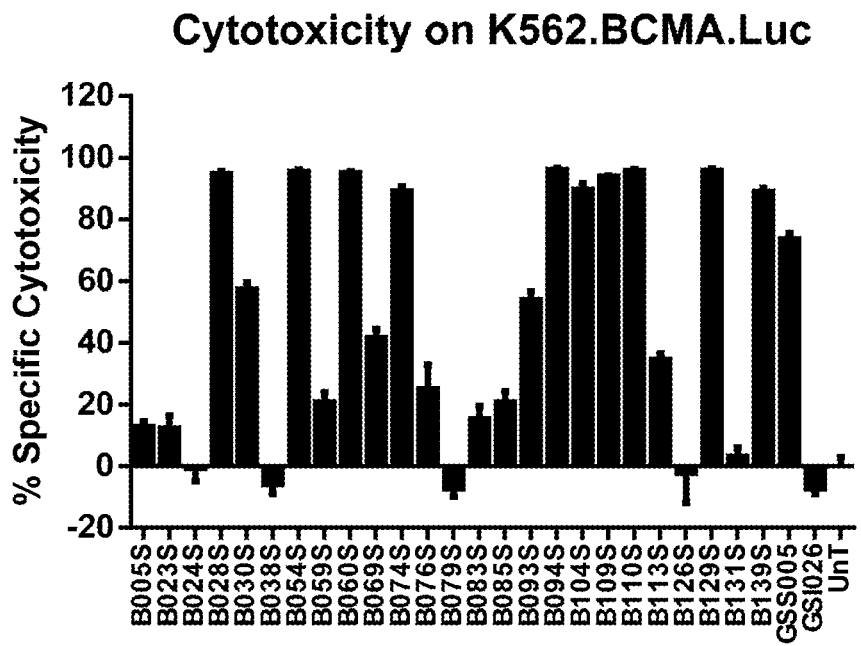
Figure 2C:
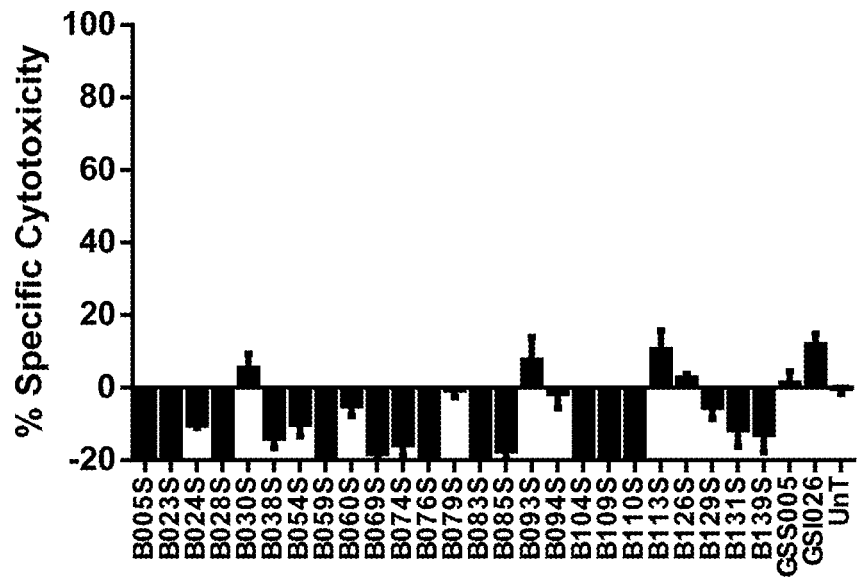

A second group of exemplary monovalent BCMA CARs were assessed for in vitro cytotoxicity. GSS005, a CAR comprising an anti-BMCA scFv, served as a positive control. GSI026, a CAR comprising an anti-EGFRvIII scFv, served as a negative control. As shown in FIGS. 2A-2B, the selected clones exhibited different levels of cytotoxicity against the multiple myeloma cells RPMI8226.Luc, and BCMA over-expressing stable cell line K562.BCMA.Luc. No clones showed potent cytotoxicity against BCMA negative cell line K562.CD19.Luc (FIG. 2C). Among these clones, 269B005S, 269B028S, 269B030S, 269B054S, 269B060S, 269B069S, 269B093S, 269B094S, 269B104S, 269B109S, 269B110S and 269B129S based CAR-T were most potent according to the cytotoxicity data.

IFNgamma Release

Figure 3:
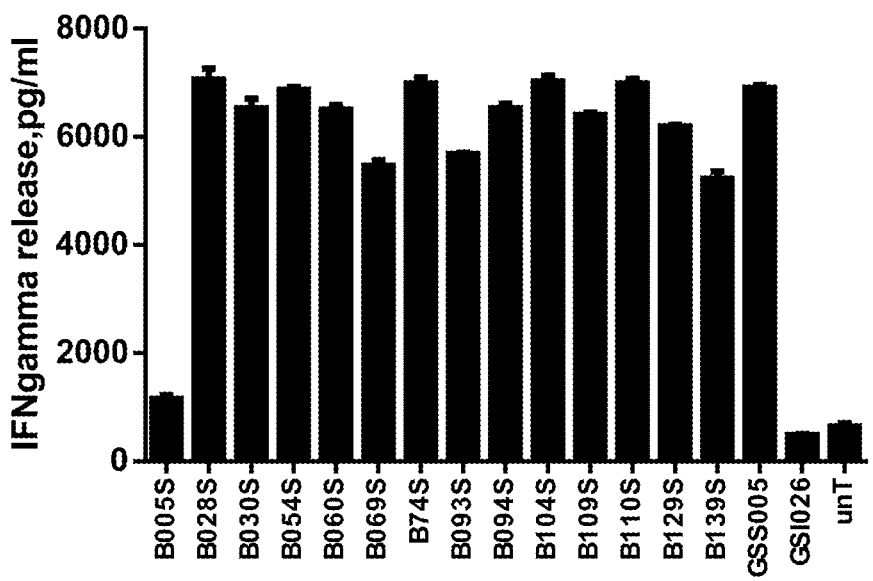
FIG. 3 shows results of an in vitro IFNγ release assay of T cells expressing exemplary monospecific CARs comprising various anti-BCMA sdAbs against K562.BCMA.Luc cells.

Additionally, supernatants from the in vitro co-culture assays were collected to assess CAR-induced cytokine release, e.g., interferon gamma (i.e IFNγ) release. As shown in FIG. 3, T cells expressing selected monovalent BCMA CARs released high levels of IFNγ upon co-culturing with BCMA-expressing target cells K562.BCMA.Luc. Nonspecific CAR-Ts, such as GSI026, or untransduced T cells (UnT) did not induce release of IFNγ in the co-culture. The cytokine release data is consistent with the in vitro cytotoxicity data.

Example 3. Preparation of Exemplary Multivalent BCMA Chimeric Antigen Receptors

Multivalent $V_HH$-based CARs can be constructed by cloning a nucleic acid sequence encoding multiple copies of a $V_HH$, or multiple different $V_HH$s fused to each other via peptide linkers into a CAR signal domain backbone vector. Exemplary multivalent BCMA CAR constructs are shown in Table 5. These constructs were prepared by fusing 2-3 anti-BCMA $V_HH$s by Glycine-serine peptide linkers followed by directly synthesizing this fusion sequence in combination with a Kozak-CD8α signal peptide nucleic acid sequence, and cloning into the PLLV-hEF1α-81373 CAR backbone via EcoRI and SpeI restriction sites. Monovalent BCMA CAR constructs were also cloned into the same PLLV-hEF1α-81373 CAR backbone to serve as controls (e.g., GSI5011, GSI5019, and GSI5020, Table 4).

Lentiviral vectors carrying CAR genes were packaged and titrated with protocols as described in Example 2. Using protocols described in Example 2, human PBMCs were prepared from peripheral bloods of volunteers for further isolation of primary human T cells using Miltenyi human PanT cell isolation kits. The purified T cells were pre-activated and expanded using Miltenyi anti-CD3/CD28 micro-beads as described in Example 2. The pre-activated T cells were then transduced with lentivirus stock in the presence of 7 μg/ml polybrene by centrifugation at 1200 g, 32° C. for 1.5 h. The transduced cells were then transferred to the cell culture incubator for transgene expression under suitable conditions.

In Vitro Cytotoxicity Assay

On day 3 post transduction, transduced T cells were harvested and co-incubated with tumor cells. To assay the cytotoxicity of CAR-T on tumor cells, ONE-GLO™ luminescent luciferase assay reagents were added to the co-cultured cells and the specific cytotoxicity for each CAR-T was measured as described in Example 2.

Figure 4A:
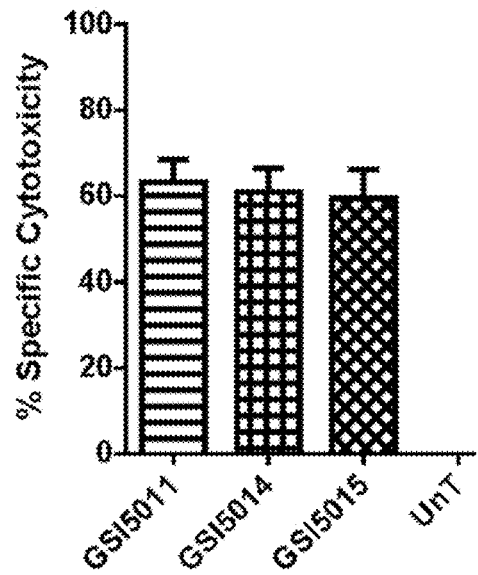
FIGS. 4A-4C show results of an in vitro cytotoxicity assay of T cells expressing exemplary multivalent BCMA CARs against RPMI8226.Luc cells (FIGS. 4A-4B) or U87MG.Luc cells (FIG. 4C).

In a first experiment, monovalent BCMA CAR (GSI5011), bivalent BCMA CAR (GSI5014), and trivalent BCMA CAR (GSI5015) expressing T cells were co-cultured with RPMI8226.Luc cells at an effector to target ratio of 20:1 for 20 hours. All three CAR constructs comprise anti-BCMA VHH domains of clone 269A37346. As shown in FIG. 4A, the specific percentage lysis of RPMI8226.Luc cells were 63.25±2.64% by GSI5011-expressing CAR-T cells, 61.04±2.75% by GSI5014-expressing CAR-T cells, and 59.57±2.64% by GSI5015-expressing CAR-T cells, as compared to 0.05%±2.33% by untransduced control T cells (UnT). The BCMA CARs tested having different antigen binding modalities had potent antitumor activity against BCMA positive cells.

Figure 4B:
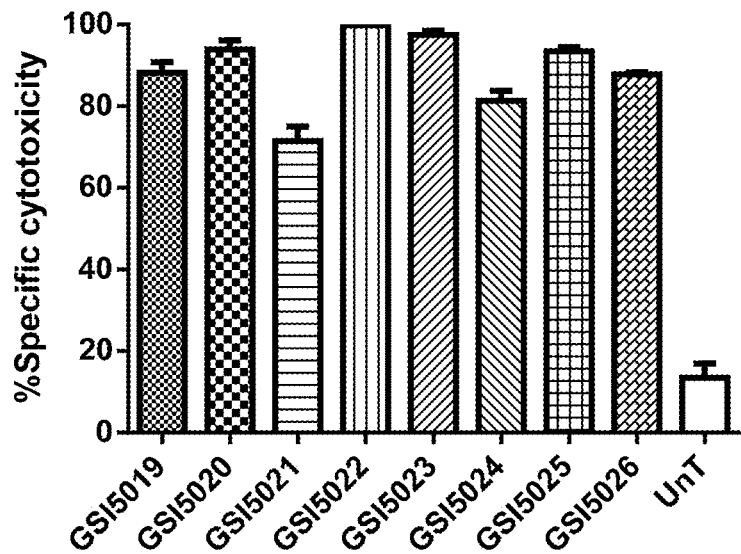
Figure 4C:
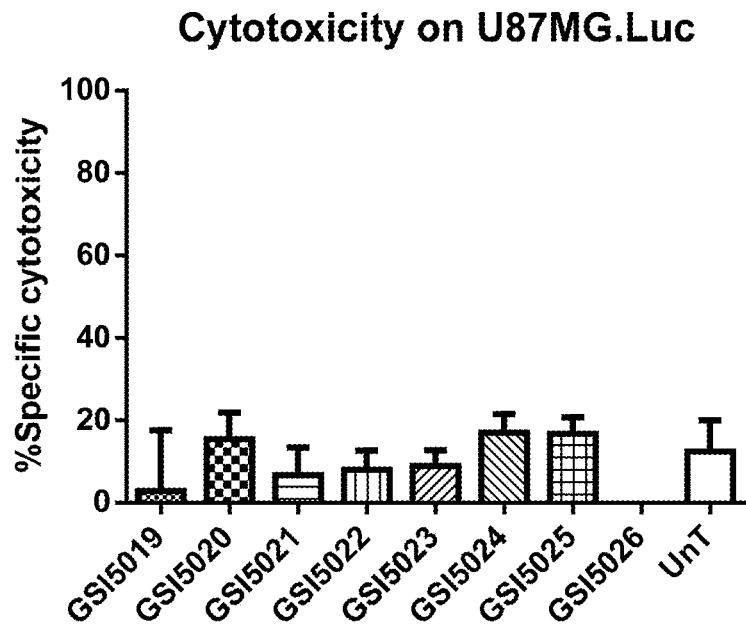

In a second experiment, exemplary bivalent BCMA CARs (GSI5021-GSI5026) having two different BCMA binding moieties 269A37353 and 269A37917 were tested. Engineered T cells expressing each bivalent BCMA CAR was co-cultured with RPMI8226.Luc cells at an effector to target ratio of 20:1 for 20 hours. Monovalent BCMA CARs, GSI5019 and GSI5020 were also tested for comparison. As shown in FIG. 4B, the specific percentage of lysis of RPMI8226.Luc cells were 88.21±1.29% by GSI5019-expressing CAR-T cells, 93.84±1.13% by GSI5020-expressing CAR-T cells, 71.45±1.79% by GSI5021-expressing CAR-T cells, 99.80±0.45% by GSI5022-expressing CAR-T cells, 97.46±0.50% by GSI5023-expressing CAR-T cells, 81.29±1.27% by GSI5024-expressing CAR-T cells, 93.50±0.47% by GSI5025-expressing CAR-T cells, 87.83±0.23% by GSI5026-expressing CAR-T cells, respectively, as compared to 13.49%±1.75% by untransduced control T cells (UnT). Also, as depicted in FIG. 4C, the specific percentage of lysis of BCMA-negative cell line U87MG.Luc was 2.84±7.41% by GSI5019-expressing CAR-T cells, 15.50±2.24% by GSI5020-expressing CAR-T cells, 6.74±3.37% by GSI5021-expressing CAR-T cells, 8.03±2.36% by GSI5022-expressing CAR-T cells, 9.00±1.88% by GSI5023-expressing CAR-T cells, 17.03±2.27% by GSI5024-expressing CAR-T cells, 16.81±1.98% by GSI5025-expressing CAR-T cells, −11.55±5.43% by GSI5026-expressing CAR-T cells, as compared to 12.49%±3.79% by untransduced control T cells (UnT). The data suggests that the bivalent CARs with different antigen-binding modalities had potent antitumor activity against BCMA positive cells, but not against BCMA negative cells.

Figure 5A:
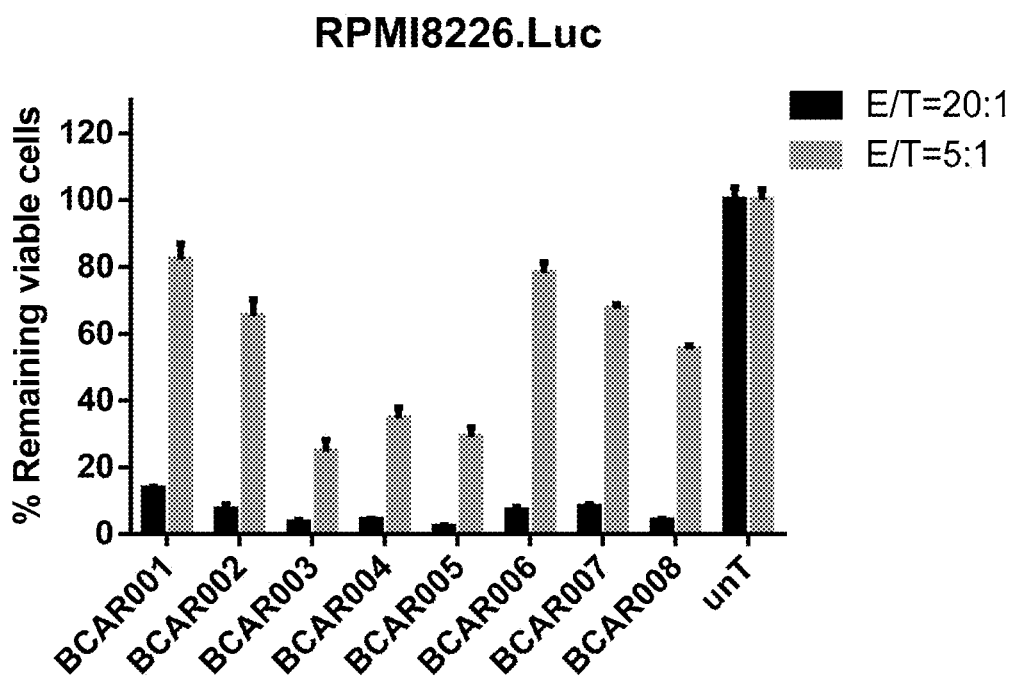
FIGS. 5A-5E show results of an in vitro cytotoxicity assay of T cells expressing exemplary bivalent BCMA CARs against RPMI8226.Luc cells (FIG. 5A), K562.CD19.Luc cells (FIG. 5B), A549.Luc cells (FIG. 5C), U87MG.Luc cells (FIG. 5D), or Raji.Luc cells (FIG. 5E).
Figure 5B:
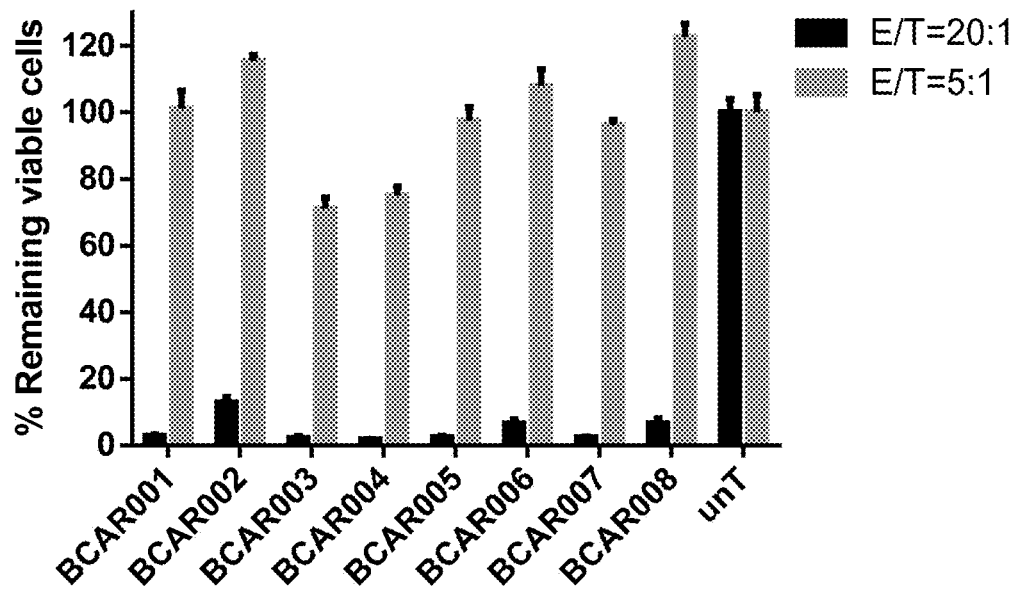
Figure 5C:
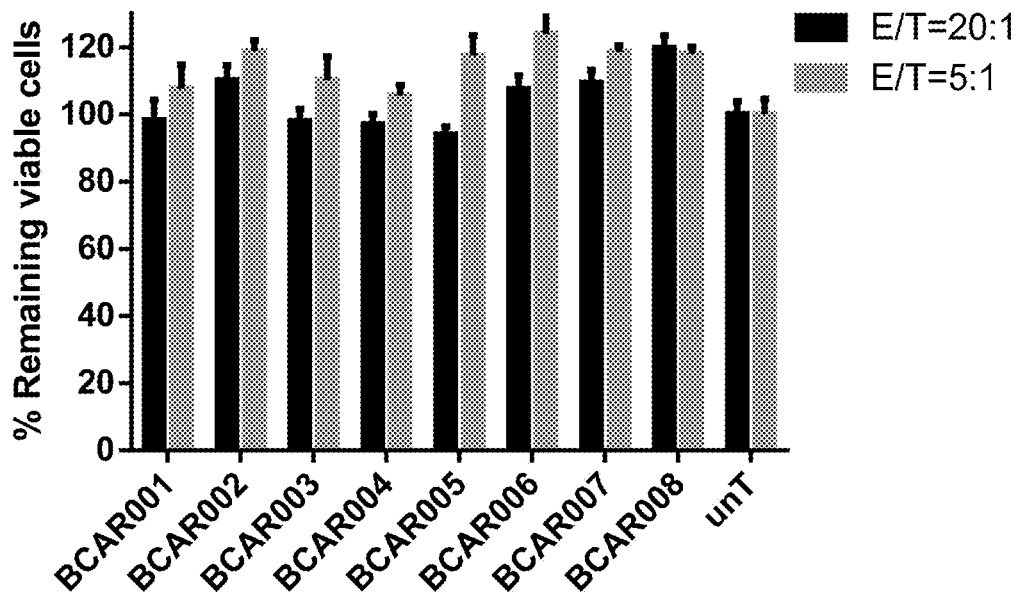
Figure 5D:
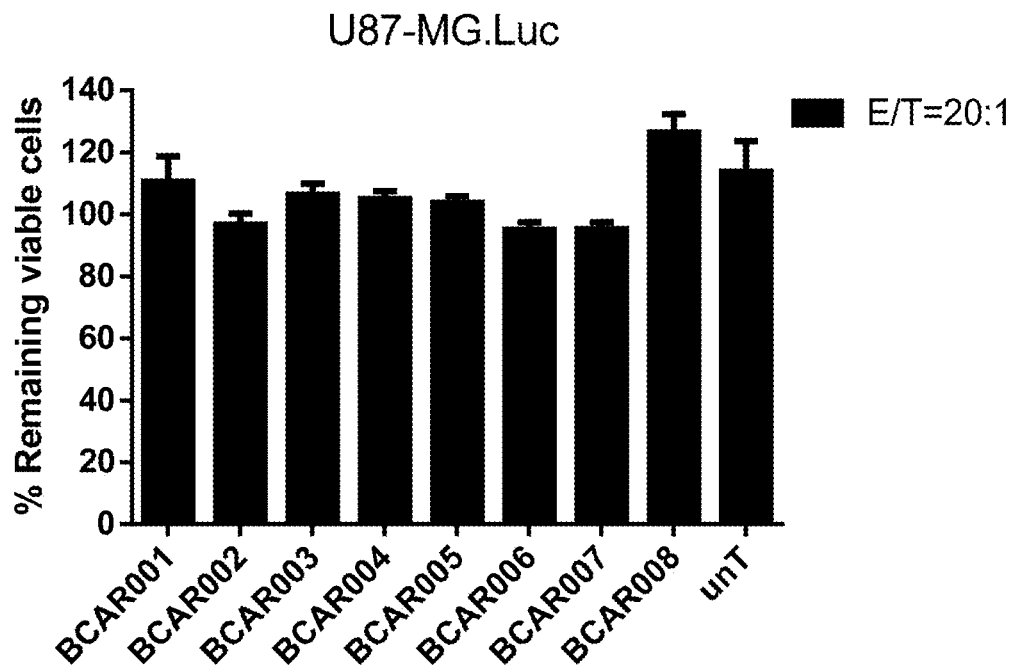
Figure 5E:
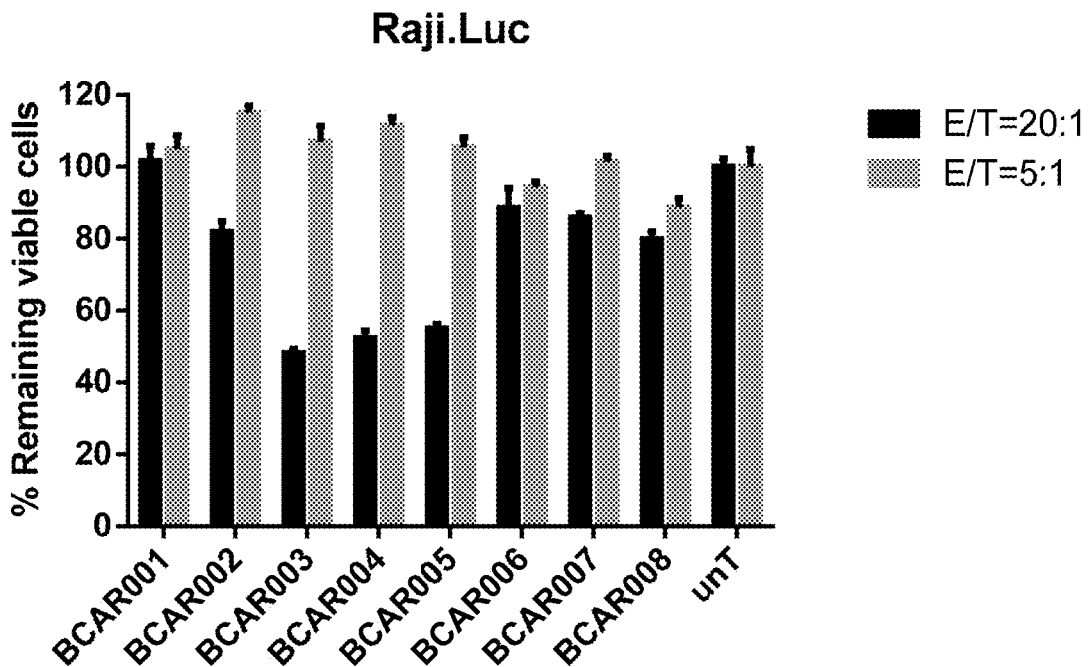
Figure 5F:
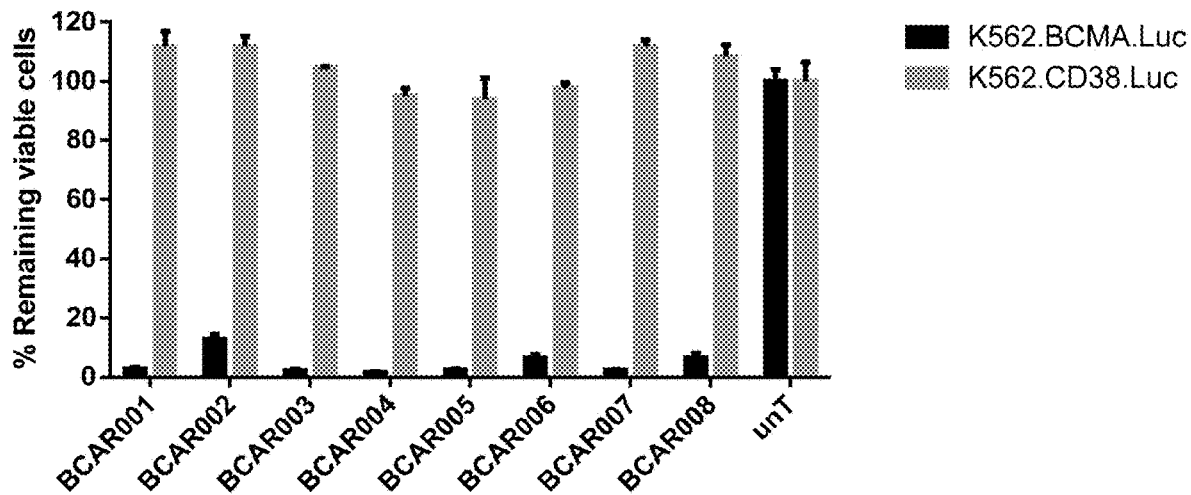
FIG. 5F shows results of an in vitro cytotoxicity assay of T cells expressing exemplary bivalent BCMA CARs against K562.BCMA.Luc cells and K562.CD38.Luc cells.

In a third experiment, exemplary bivalent BCMA CARs (i.e., BCAR001-BCAR008) having two different BCMA binding moieties were constructed, and engineered CAR-T cells expressing the bivalent BCMA CARs were prepared from primary T cells obtained from R/R MINI patient donor #13. In-house developed firefly luciferase expressing cell lines including RPMI8226 (human multiple myeloma cell line), A549 (human lung cancer cell line), U87-MG (human glioblastoma cell line) and Raji (human Burkitt's lymphoma cell line) were used as target cells and co-cultured with each group of transduced T cells side by side (with Effector:target cell ratio of 20:1 or 5:1) for 20 hours in a 37° C./5% $CO_2$ cell incubator. Upon completion of co-culture, the remaining luciferase activities (relative light unit, RLU) were assayed with ONE-GLO™ luminescent luciferase assay kit (Promega) to assess the cytotoxicity of each CAR-T. As shown in FIGS. 5A-5E, the bivalent BCMA CAR-Ts had dose-dependent cytotoxicity against RPMI8226.Luc, K562.BCMA.Luc and Raji.Luc cells, but little cytotoxicity against BCMA negative A549.Luc and U87-MG.Luc cells. Data in FIG. 5F demonstrate that the cytotoxicity of the bivalent BCMA CAR-T cells against tumor cells are BCMA-specific as the CAR-T cells were not cytotoxic against K562.C38.Luc cells that were $CD38^+/BCMA^-$. K562.BCMA.Luc treated with BCAR001-BCAR008 CAR-T cells only showed limited residual Luciferase activities (i.e., viable cells) as compared to UnT treated target cells (2.88±0.45%, 12.84±1.67%, 2.22±0.56%, 1.77±0.14%, 2.59±0.28%, 6.58±1.19%, 2.47±0.20%, 6.61±1.47% for BCAR001-BCAR008 respectively, as compared to UnT of 100±3.95%, mean±standard error). These results demonstrate potent cytotoxicity of the bivalent BCMA CAR-T cells against K562.BCMA.Luc cells. BCAR001-BCAR008 CAR-T cells did not have significant cytotoxicity against K562.CD38.Luc cells as no significant decrease in Luciferase activity was detected as compared to UnT-treated target cells (111.82±5.11%, 111.72±3.43%, 104.74±0.24%, 95.04±2.70%, 93.93±7.23%, 97.72±1.86%, 111.90±2.01%, 108.33±4.05%, for BCAR001-BCAR008 respectively, as compared to UnT of 100±6.58%, mean±standard error). These data suggested the cytotoxicity of the bivalent BCMA CAR-T is BCMA dependent.

IFNgamma Release

Figure 6A:
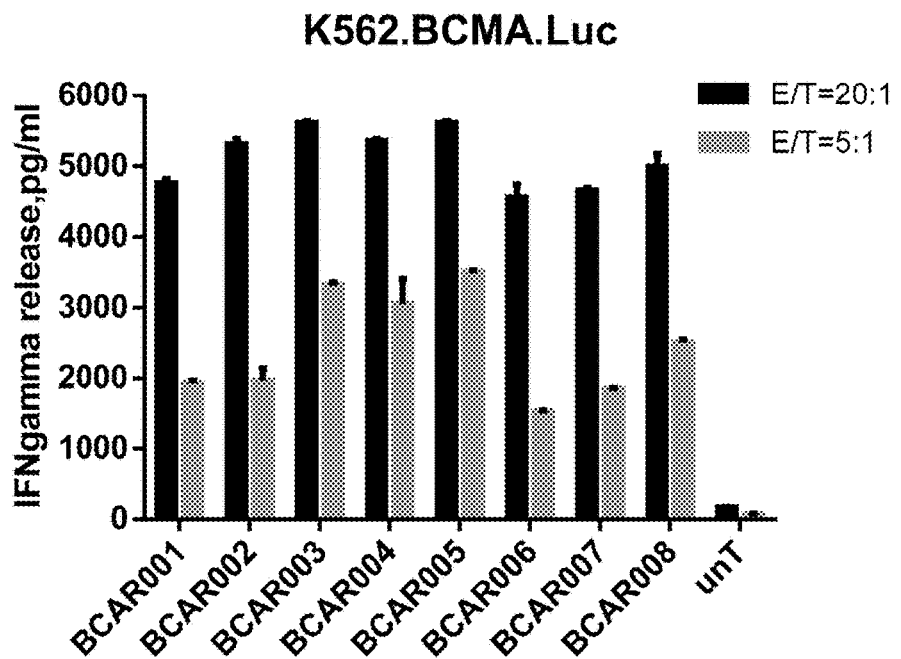
FIG. 6A shows results of an in vitro IFNγ release assay of T cells expressing exemplary bivalent BCMA CARs against K562.BCMA.Luc cells at two different effector cell to target cell ratios.
Figure 6B:
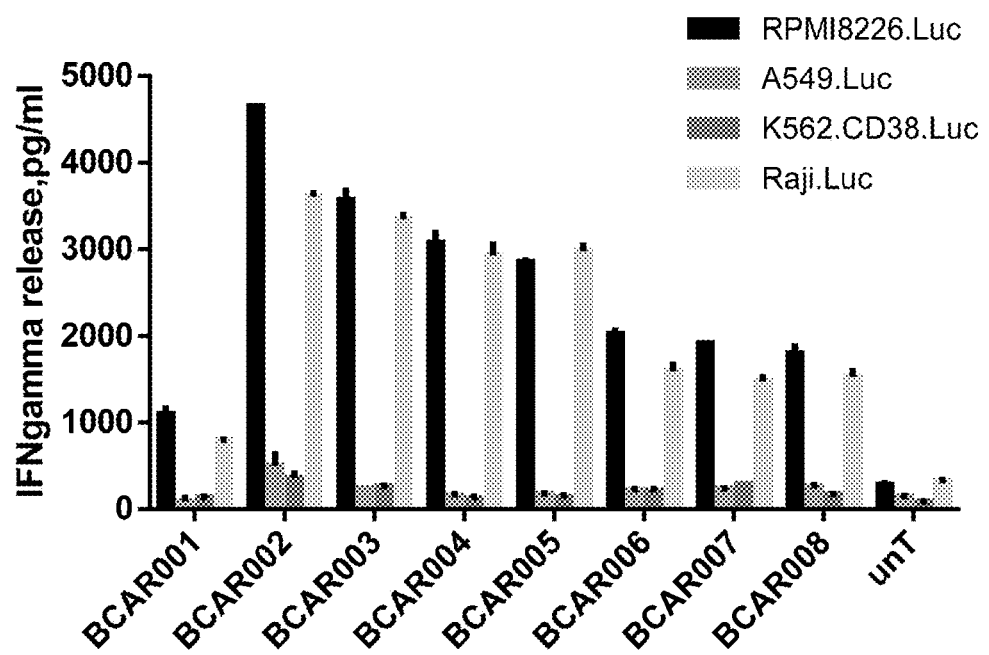
FIG. 6B shows results of an in vitro IFNγ release assay of T cells expressing exemplary bivalent BCMA CARs against RPMI8226.Luc, A549.Luc, K562.CD38.Luc and Raji.Luc cells.

Additionally, supernatants from in vitro co-culture assays were collected to assess CAR-induced cytokine release (e.g., interferon gamma, IFNγ release). As shown in FIGS. 6A-6B, IFNγ release in the co-culture assays was CAR-dependent and BCMA-specific, which is consistent with the in vitro cytotoxicity data (Table 6).

TABLE 6

| | IFN gamma release in co-culture assays by bivalent BCMA CAR-T | | | | | | | |
|---|---|---|---|---|---|---|---|---|
| | RPMI8226.Luc | | A549.Luc | | K562.CD38.Luc | | Raji.Luc | |
| | Mean, pg/ml | s.e. | Mean, pg/ml | s.e. | Mean, pg/ml | s.e. | Mean, pg/ml | s.e. |
| BCAR001 | 1097.23 | 61.87 | 89.18 | 42.19 | 135.81 | 5.87 | 795.87 | 7.29 |
| BCAR002 | 4651.22 | 1.13 | 503.63 | 130.73 | 361.87 | 49.68 | 3613.30 | 34.04 |

TABLE 6-continued

IFN gamma release in co-culture assays by bivalent BCMA CAR-T

| | RPMI8226.Luc | | A549.Luc | | K562.CD38.Luc | | Raji.Luc | |
|---|---|---|---|---|---|---|---|---|
| | Mean, pg/ml | s.e. | Mean, pg/ml | s.e. | Mean, pg/ml | s.e. | Mean, pg/ml | s.e. |
| BCAR003 | 3569.84 | 108.19 | 243.82 | 1.31 | 265.08 | 3.24 | 3348.66 | 49.80 |
| BCAR004 | 3077.41 | 110.82 | 161.70 | 12.97 | 128.50 | 17.08 | 2931.11 | 120.31 |
| BCAR005 | 2850.34 | 20.16 | 170.90 | 8.27 | 141.20 | 17.54 | 2976.27 | 67.22 |
| BCAR006 | 2023.71 | 37.61 | 223.96 | 6.21 | 215.00 | 17.87 | 1588.54 | 77.96 |
| BCAR007 | 1912.98 | 2.28 | 239.43 | 1.93 | 289.72 | 1.94 | 1472.87 | 49.76 |
| BCAR008 | 1798.90 | 76.85 | 258.71 | 19.39 | 171.89 | 6.51 | 1526.93 | 66.70 |
| UnT | 281.75 | 20.55 | 143.70 | 10.46 | 85.65 | 1.98 | 328.61 | 6.69 |

Copy Numbers of Integrated CAR Genes

The copy numbers of integrated CAR genes for each transduced T cell group was determined by a semi-quantitative PCR (q-PCR) assay. Briefly, genomic DNA from each group of CAR-T was prepared with Gentra Puregene Cell Kit (Qiagen). The concentration of genomic DNA was determined by Nanodrop, and 10 ng genomic DNA sample was processed for a standardized q-PCR assay with SYBR Green Realtime PCR Master mix plus (Toyobo) on ABI #7300 q-PCR instrument using CAR specific primers (forward primer 137P2F, SEQ ID NO: 398: 5'-GTCCTTCTCCTGTCACTGGTTAT-3'; and reverse primer 137P2R, SEQ ID NO: 399: 5'-TCTTCTTCTTCTG-GAAATCGGCA-3'). The relative copy number of each integrated CAR gene was calculated based on a standard curve established using plasmid containing target sequences.

As shown in Table 7, a high copy number of CAR vector was integrated into the genome of the T cells in each CAR-T preparation.

TABLE 7

Genome integration copy numbers.

| CAR-T cells with constructs | Copies/ng gDNA |
|---|---|
| GSI5019 | 35091.6 |
| GSI5020 | 27627.2 |
| GSI5021 | 24926.8 |
| GSI5022 | 26393.6 |
| GSI5023 | 32376.3 |
| GSI5024 | 39319.8 |
| GSI5025 | 22269.3 |
| GSI5026 | 34790.4 |
| UnT | 26.6 |

Example 4. Epitope Mapping and Differential Epitope Binding of Two $V_HH$ Domains in LCAR-B38M The epitopes of the four anti-BCMA $V_HH$ domains were mapped. An exemplary bivalent BCMA CAR having two different anti-BCMA $V_HH$ domains that specifically bind to different epitopes of BCMA was constructed. Bivalent/biepitope CAR comprising $V_HH1$ and $V_HH2$, named LCAR-B38M CAR, is one multivalent BCMA CAR listed in Table 5.

Surface Plasmon Resonance (SPR) Assay

Each of four exemplary anti-BCMA $V_HH$ sequences was cloned into a vector containing a human IgG1 Fc fragment (hIgG1Fc) sequence to facilitate recombinant expression of BCMA $V_HH$-hIgG1Fc. Recombinant proteins were obtained and purified for SPR assays.

The affinity of each $V_HH$-hIgG1Fc for BCMA was determined by SPR using a BIACORE® 2000 analytical system (GE Healthcare). Briefly, each $V_HH$-hIgG1Fc protein was covalently coupled to a CM5(s) sensor chip using 4 μg/ml $V_HH$-hIgG1Fc. Recombinant BCMA-His protein (ACRO Biosystems, Cat #BCA-H522y) was serially diluted in running buffer (10 mM HEPES, 150 mM NaCl, 3 mM EDTA, 0.05% Tween-20, pH 7.4) and injected at a flowrate of 10 μl/min followed by dissociation. The association and dissociation rate constants were determined using the BIACORE® 2000 evaluation software version 3.0 (Langmuir binding, local fit, 1:1 binding model). The binding affinities of the four $V_HH$-hIgG1Fcs are shown in Table 8.

TABLE 8

Binding affinities of $V_HH$-hIgG1Fcs to human BCMA-His protein.

| Ligand | $k_a$ (1/Ms) | $k_d$ (1/s) | $K_D$ (M) |
|---|---|---|---|
| $V_HH1$-hIgG1Fc | 5.5E+04 | <1.0E−05* | <1.8E−10* |
| $V_HH2$-hIgG1Fc | 1.9E+06 | 1.5E−02 | 7.8E−09 |
| $V_HH3$-hIgG1Fc | 3.4E+04 | 1.7E−04 | 5.1E−09 |
| $V_HH4$-hIgG1Fc | 2.1E+06 | 9.4E−04 | 4.6E−10 |

Binding of Recombinant $V_HH$-his Proteins to Target Cells

Recombinant anti-BCMA $V_HH$-His proteins were constructed by fusing the anti-BCMA $V_HH$ sequence to a human albumin signal peptide sequence (N'-MKWVTFISLLFLF-SSAYS-C'; SEQ ID NO: 386) at the N terminus, and a 6×His-tag (N'-GSGHHHHHH-C'; SEQ ID NO: 387) at the C terminus. The codons were further optimized for optimal expression in mammalian host cells. The obtained nucleotide sequences were then cloned into a mammalian expression vector pTT5 via 5'-XbaI and 3'-HindIII restriction sites to provide plasmids, pTT5-LAB001 (for $V_HH1$), pTT5-LAB002 (for $V_HH2$) and pTT5-LAB003 (for $V_HH1 \times V_HH2$).

In order to obtain recombinant BCMA $V_HH$ proteins, HEK293T cells were transiently transfected with the plasmids. Briefly, 5×10⁶ HEK293T cells were seeded in 10 cm cell culture dishes one day prior to the transfection. On the next day, the cells were transfected with each plasmid using LIPOFECTAMINE™ 2000 Reagent (Thermofisher Scientific, Cat. No.: 11668-019) following the manufacturer's manual. Four days after transfection, supernatant was harvested and the expression levels of the antibodies were detected by ELSIA using HRP anti-His Tag (Biolegend, Cat.No.: 652504). The expression levels of LAB001, LAB002 and LAB003 were 109.31 ng/ml, 152.48 ng/ml and 396.62 ng/ml respectively.

Binding affinities of LAB001, LAB002 and LAB003 anti-BCMA $V_HH$-His proteins were determined using cell-based assays. Briefly, serially diluted anti-BCMA $V_HH$-His proteins were incubated with 1×10⁵ target cells (either K562.BCMA.Luc or K562.CD38.Luc cells, which were in-house developed cell lines stably expressing BCMA or CD39 respectively) at 4° C. for 2 hours. Afterwards, cells were centrifuged at 300 g for 10 min, and the supernatant was discarded. The cell pellets were re-suspended with DPBS. The cell pellets were washed, centrifuged, and the supernatant was discarded for 2 more times. Then cell pellets were subsequently re-suspended with detection antibody (THE™ His tag Antibody [FITC], GenScript Cat: A01620) containing buffers for 45 min at 4° C. for 2 hours. Afterwards, cells were centrifuged at 300 g for 10 min, and the supernatant was discarded. The cell pellets were washed, centrifuged, and the supernatant was discarded for 2 more times. Binding affinities of LAB001, LAB002 and LAB003 to either K562.BCMA.Luc or K562.CD38.Luc cells were determined using an ATTUNE® Nxt flow cytometer. Data was fitted by GraphPad PRISM™ version 6.0 using a "One site—Specific binding with Hill slope".

Figure 7A:
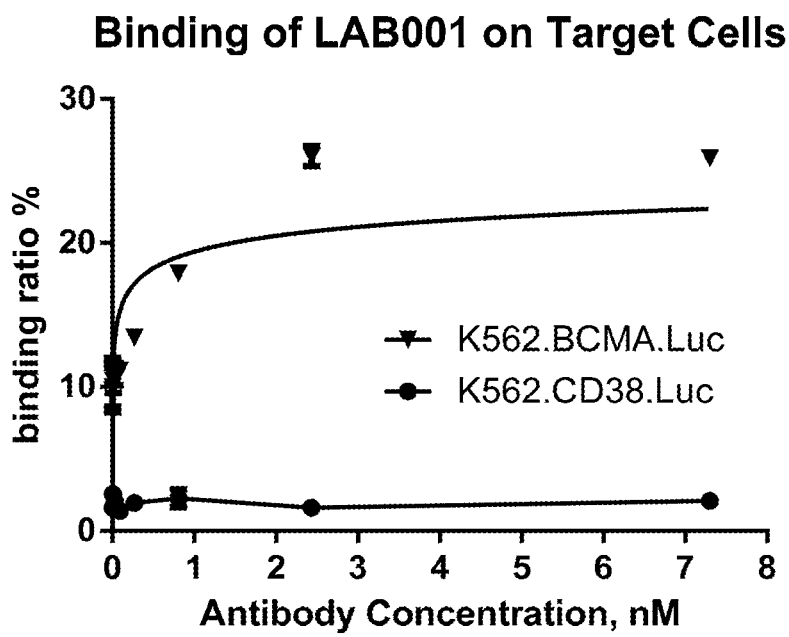
FIGS. 7A-7C show binding of three exemplary VHH fragments to K562.BCMA.Luc cells and K562.CD38.Luc cells (negative control).
Figure 7B:
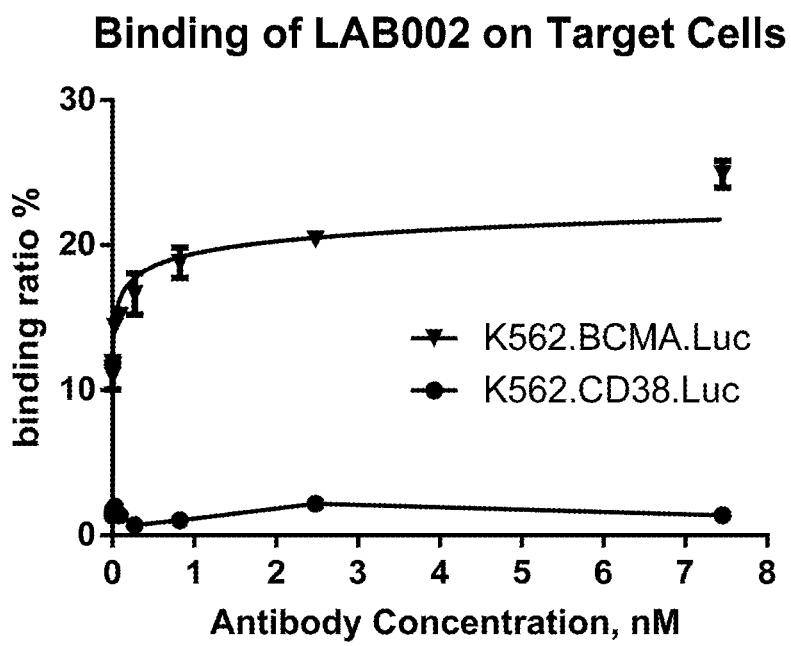
Figure 7C:
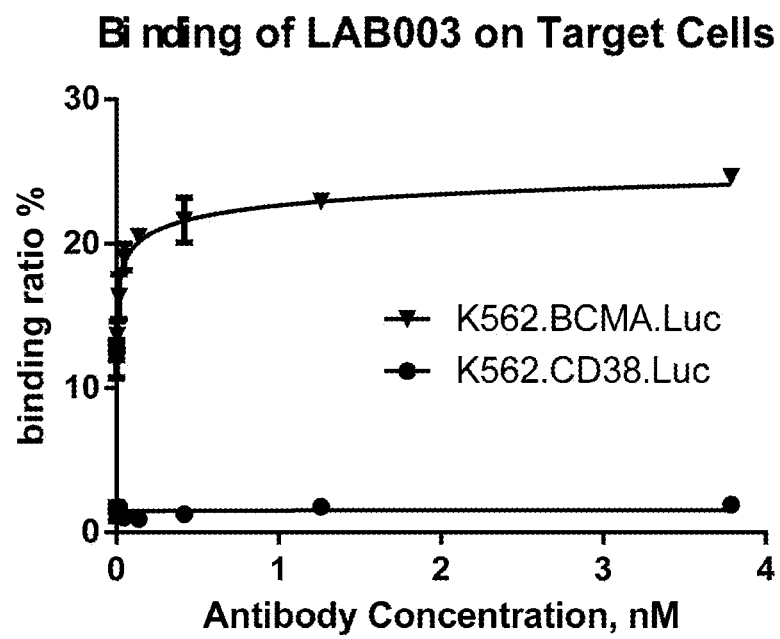

As shown in FIG. 7A-7C, LAB001, LAB002 and LAB003 specifically bind to K562.BCMA.Luc cells in a dose-dependent manner. The binding affinities are 0.079 nM, 0.035 nM and 0.0047 nM respectively. None of the antibodies showed significant binding to BCMA negative cell line K562.CD38.Luc. Moreover, LAB003 ($V_HH1 \times V_HH2$) showed significantly higher binding affinity (0.0047 nM) than either LAB001 ($V_HH1$) or LAB002 ($V_HH2$).

Epitope Binding

BCMA (NP_001183, UniProt #Q02223) is a transmembrane protein of 184 amino acids long. Human BCMA consists of an extracellular domain (ECD, amino residue number 1-54), a transmembrane domain (TM, amino residue number 55-77) and a cytoplasmic domain (CD, amino residue number 78-184). In addition, sequence analysis suggests that BCMA has no recognizable signal peptide at its N terminus (Laabi Y et al. (1992) EMBO J 11:3897-3904; Laabi Y et al. (1994) Nucleic Acids Res 22:1147-1154; Gras M P (1995) Int Immunol 7:1093-1106; Hong-Bing Shu and Holly Johnson (2000): Proc. Natl. Acad. Sci. USA, 10.1073).

Figure 8A:
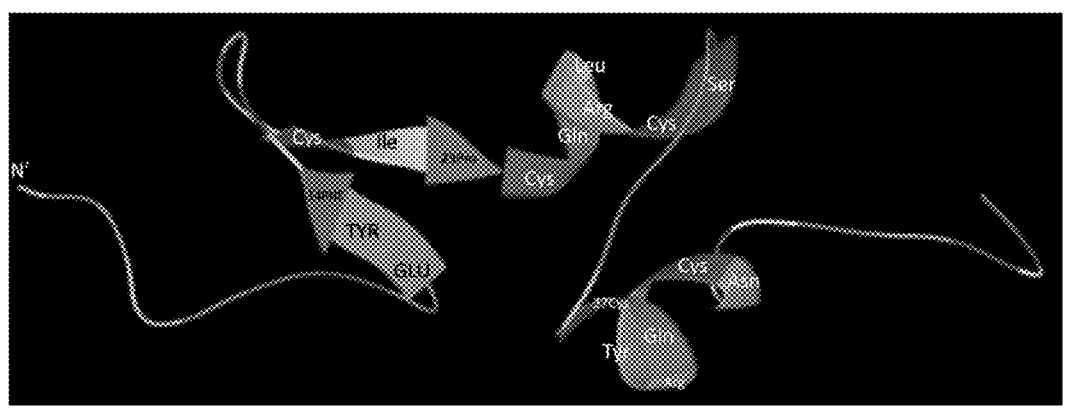
FIG. 8A shows a crystal structure of the extracellular domain of BCMA.

As also illustrated by the online database UniProt (worldwide web.uniprot.org/uniprot/Q02223), 3 disulfide bonds (Cys-Cys) are located in the ECD of BCMA, which are at positions 8↔21, 24↔37 and 28↔41 (Table 9). The secondary structure of the BCMA ECD from the N-terminus to the C-terminus consists of a beta strand (aa12-15), a turn (aa16-19), a beta strand (aa20-23), a helix (aa 24-27), a beta strand (aa30-32), a helix (aa35-37), a turn (aa38-40), and a turn (aa42-44). A structure of the BCMA ECD is shown in FIG. 8A, which is replicated from the structure from the PDB database worldwide web.ebi.ac.uk/pdbe/entry/pdb/2kn1/.

TABLE 9

Protein sequences of human BCMA.

| Position(s) | Description | Length | AA sequence |
|---|---|---|---|
| 1-54 | Extra-cellular domain | 54 | MLQMAGQCSQNEYFDSLLHAC IPCQLRCSSNTPPLTCQRYCN ASVTNSVKGTNA (SEQ ID NO: 395) |
| 55-77 | Trans-membrane domain | 23 | ILWTCLGLSLIISLAVFVLMF LL (SEQ ID NO: 396) |

TABLE 9-continued

Protein sequences of human BCMA.

| Position(s) | Description | Length | AA sequence |
|---|---|---|---|
| 78-184 | Cyto-plasmic domain | 107 | RKINSEPLKDEFKNTGSGLLG MANIDLEKSRTGDEIILPRGL EYTVEECTCEDCIKSKPKVDS DHCFPLPAMEEGATILVTTKT NDYCKSLPAALSATEIEKSIS AR (SEQ ID NO: 397) |

BCMA epitope peptides (269EP001-269EP007) were designed as shown in FIG. 8B and TABLE 10, and chemically synthesized and biotinylated at the N-terminus. Binding affinities of $V_HH1$-hIgG1Fc or $V_HH2$-hIgG1Fc were determined using ELISA. Briefly, peptides described above were coated on MAXISORP™ ELISA plate at 1 μM overnight at 4° C. The next day, the plates were washed with PBST (add 0.5% TWEEN-20) twice, followed by plate blocking with 0.5% BSA at room temperature for 1 h. The plates were then washed with PBST twice, followed by addition of serially diluted $V_HH1$-hIgG1Fc or $V_HH2$-hIgG1Fc at 10 nM in triplicates, then incubated at 4° C. for 2 h. The plates were then washed for 3 times with cold PBST, after which goat anti-Llama-HRP (1:1500, Bethyl Lab #A160) was added to each well and further incubated at room temperature for 1 h. The plates were then washed for 4 times with PBST, and TMB substrates were added to each well and incubated at room temperature for 10-30 min. The plates were then read on TECAN® 10M microplate reader with absorbance at 450 nm.

TABLE 10

BCMA epitope peptide sequences.

| Epitope | Positions | Amino acid residue sequence | Length |
|---|---|---|---|
| 269EP001 | 1-10 | MLQMAGQCSQ (SEQ ID NO: 388) | 10 |
| 269EP002 | 8-21 | CSQNEYFDSLLHAC (SEQ ID NO: 389) | 14 |
| 269EP003 | 11-23 | NEYFDSLLHACIP (SEQ ID NO: 390) | 13 |
| 269EP004 | 20-30 | ACIPCQLRCSS (SEQ ID NO: 391) | 11 |
| 269EP005 | 24-42 | CQLRCSSNTPPLTCQRYCN (SEQ ID NO: 392) | 19 |
| 269EP006 | 36-43 | LTCQRYCNAS (SEQ ID NO: 393) | 10 |
| 269EP007 | 43-54 | ASVTNSVKGTNA (SEQ ID NO: 394) | 12 |

Figure 9A:
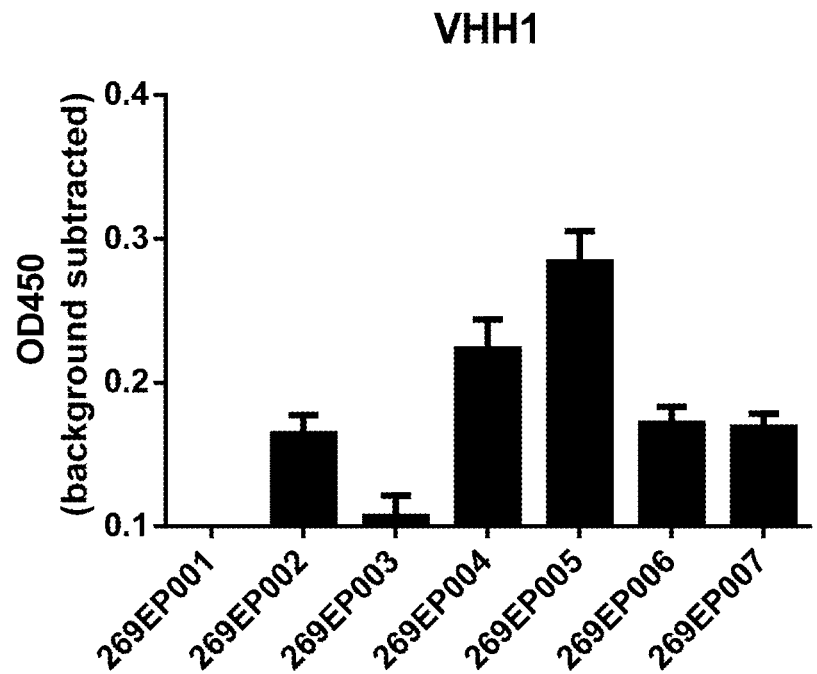
FIGS. 9A-9B show results of epitope mapping assays of VHH1 and VHH2.

As shown in FIG. 9A, $V_HH1$ showed strongest binding to the 269EP005 peptide followed by the 269EP004 peptide. However, binding of $V_HH1$ to 269EP003 and 269EP006 was relatively weak compared to 269EP005 and 269EP004. $V_HH1$ tends to bind an epitope located in the 269EP005 peptide (i.e., amino acid 24-36 of BCMA ECD), which contains the secondary structures of a helix (aa24-27), a beta strand (aa30-32), and a helix (aa35-37).

Figure 9B:
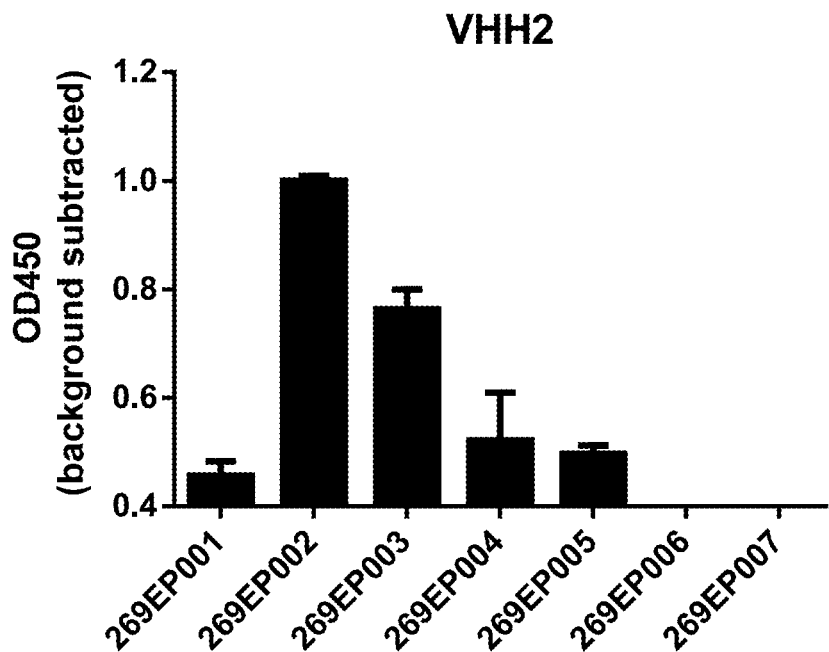

As shown in FIG. 9B, $V_HH2$ showed strongest binding to the 269EP002 peptide followed by the 269EP003 peptide.

However, binding of $V_HH1$ to 269EP001 and 269EP004 was relatively weak compared to 269EP002 and 269EP003. While the first beta strand (aa12-15) and the beta strand (aa20-23) of the BCMA ECD are mainly located in the sequence covered by 269EP002 (aa8-21) and 269EP003 (aa11-23), $V_HH2$ tends to bind to an epitope located in the first two beta strands.

Competitive Binding Assay

Differential epitope binding of $V_HH1$ and $V_HH2$ was further validated by a cell-based competitive binding assay. A stable CHO cell line overexpressing human BCMA ("CHO-BCMA") was used in the assay.

Figure 10:
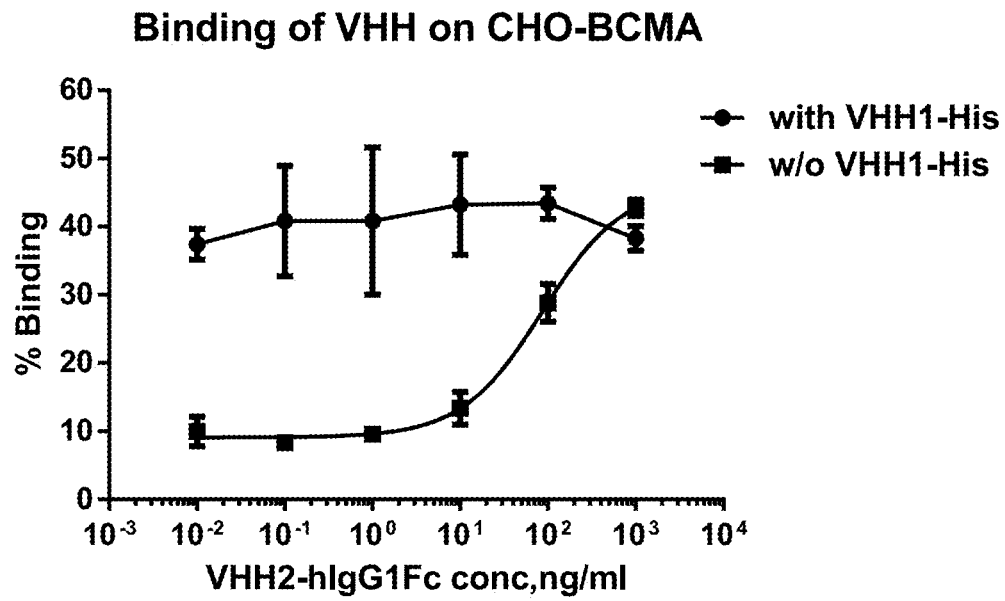
FIG. 10 shows results of a competitive binding assay using CHO-BCMA cells.

Briefly, $0.5 \times 10^6$ CHO-BCMA cells were pre-incubated with 12.5 ng/ml LAB001 (which contains 6×His tag at the C terminus) at 4° C. for 0.5 h in duplicates. Then serially diluted $V_HH2$-hIgG1Fc recombinant antibody was added to each well of the plate and further incubated at 4° C. for another 1 h. After incubation, cells were washed with 500p1 DPBS and centrifuged at 300 g for 10 min. The cell pellets were re-suspended with DPBS containing anti-His tag-FITC (1:200, GenScript Cat: A16020), then cells were washed with 500 μl DPBS and centrifuged at 300 g for 10 min. The cell pellets were re-suspended with DPBS, and were then subject to FACS analysis on an ATTUNE™ Nxt flow cytometer. As an assay control, serially diluted $V_HH2$-hIgG1Fc was directly incubated with CHO-BCMA cells without the presence of LAB001 following identical procedures as above side-by-side. Goat anti-Human IgG (Fc specific)-FITC antibody (Sigma Aldrich Cat:F9512) was used to detect binding of $V_HH2$-hIgG1Fc to the CHO-BCMA cells. As shown in FIG. 10, $V_HH2$-hIgG1Fc alone binds to CHO-BCMA in a dose-dependent manner. However, $V_HH2$-hIgG1Fc was not able to compete with $V_HH1$-His binding to CHO-BCMA cells, which indicates different binding sites of $V_HH1$ and $V_HH2$ on BCMA.

Example 5. In Vivo Efficacy of LCAR-B38M CAR-T in Tumor Xenograft Mice

In vivo anti-tumor efficacy of LCAR-B38M CAR-T cells was evaluated in a NCG mouse model (NOD-Prkdc$^{em26Cd52}$Il$^{em26Cd22}$/NjuCrl) having a multiple myeloma tumor xenograft. LCAR-B38M CAR is a bivalent BCMA CAR having two anti-BCMA $V_HH$ domains that target different BCMA epitopes.

The NCG mouse model was created by sequential CRISPR/Cas9 editing of the Prkdc and Il2rg loci in the NOD/Nju mouse, providing a mouse coisogenic to the NOD/Nju. The NOD/Nju mouse carries a mutation in the Sirpa (SIRP α) gene that allows for engrafting of foreign hematopoietic stem cells. The Prkdc knockout generates a SCID-like phenotype lacking proper T-cell and B-cell formation. The knockout of the Il2rg gene further exacerbates the SCID-like phenotype while additionally resulting in a decrease of NK cell production. Thus, the NCG mouse is a "triple-immunodeficient" mouse strain that is more immunocompromised than commonly used immunodeficient mouse strains including SCID and nude mice.

Prkdc and Il2rg are part of the SCID (severe combined immunodeficiency) family of genes affecting maturation and formation of T cells, B cells, NK cells and, to a lesser degree, dendritic cells. Prkdc encodes the catalytic subunit of the DNA-dependent protein kinase enzyme, which is required for V(D)J recombination, a necessary process to propagate antibody diversity in maturing T and B cells. Il2rg encodes the common gamma subunit found in IL-2 and multiple IL receptors (IL-4, IL-7, IL-9, IL-15 and IL-21), which are required to induce cytokine-mediated signaling for maturation of immature lymphocytes (e.g., T, B and NK cells) and other leukocytes.

Figure 11:
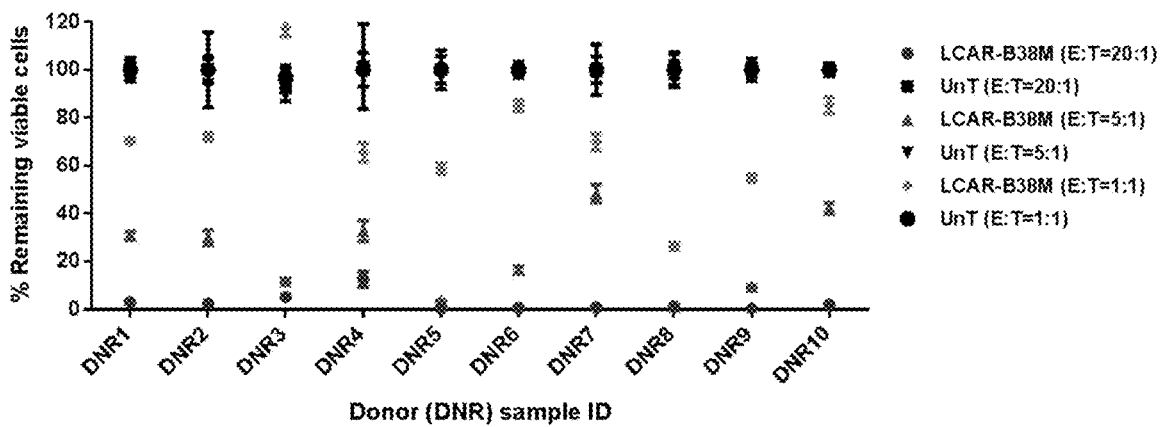
FIG. 11 shows in vitro cytotoxicity of donor-derived T cells expressing LCAR-B38M against RPMI8226.Luc cells.
Figure 12A:
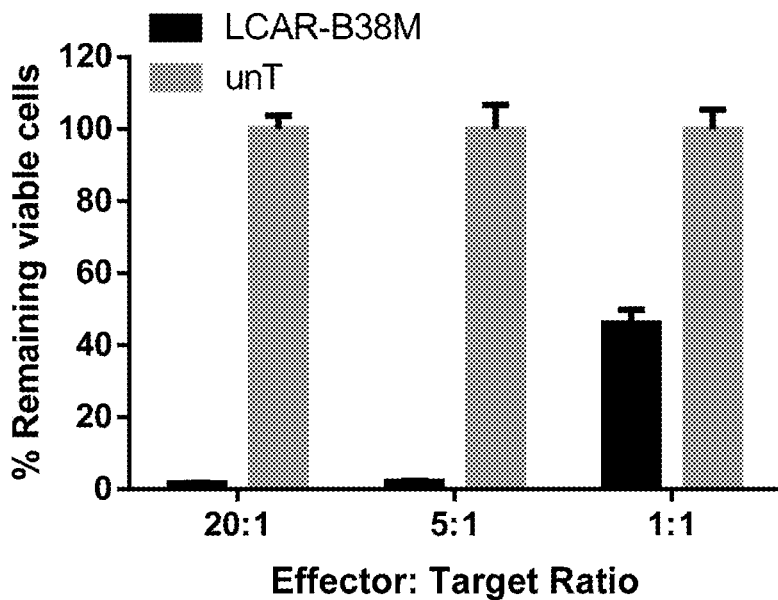
FIG. 12A shows in vitro cytotoxicity of LCAR-B38M CAR-T cells prepared from a selected donor against RPMI8226.Luc cells.

LCAR-B38M CAR-T cells were prepared using T cells from various donors to screen for T cell source yielding CAR-T with the highest efficacy of killing RPMI8226.Luc cells in vitro (FIG. 11). Based on the results of FIG. 11, LCAR-B38M CAR-T cells were prepared using T cells of the selected donor for in vivo animal assays. FIG. 12A shows dose-dependent in vitro cytotoxicity of this batch of LCAR-B38M CAR-T cells. To create the tumor xenograft, NCG mice were injected intravenously with RPMI8226.Luc cells. 14 days later, tumor engrafted mice were treated with the LCAR-B38M CAR-T cells or un-transduced T cells, followed by in vivo bioluminescence imaging (BLI).

Figure 12B:
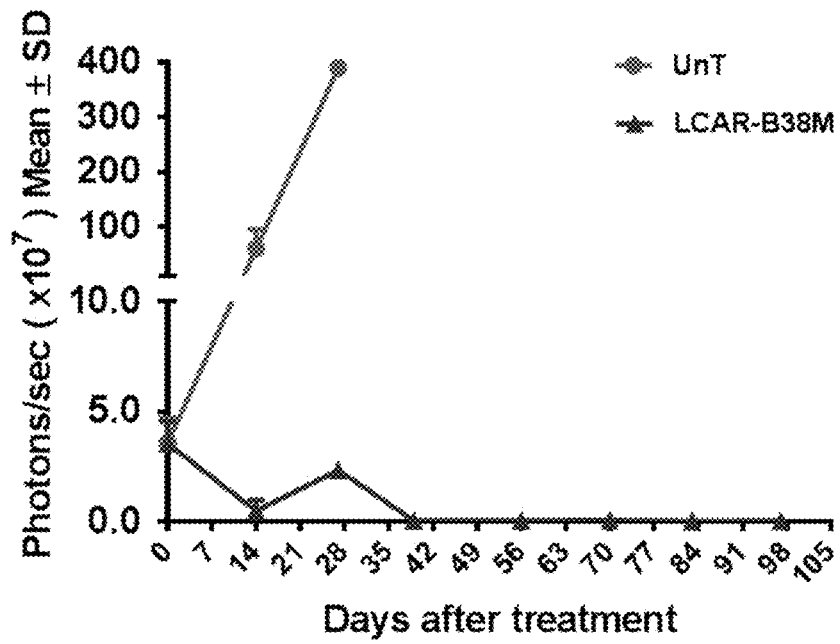
FIGS. 12B-12E show in vivo anti-tumor activity of LCAR-B38M CAR-T cells in tumor xenograft mice model.
Figure 12C:
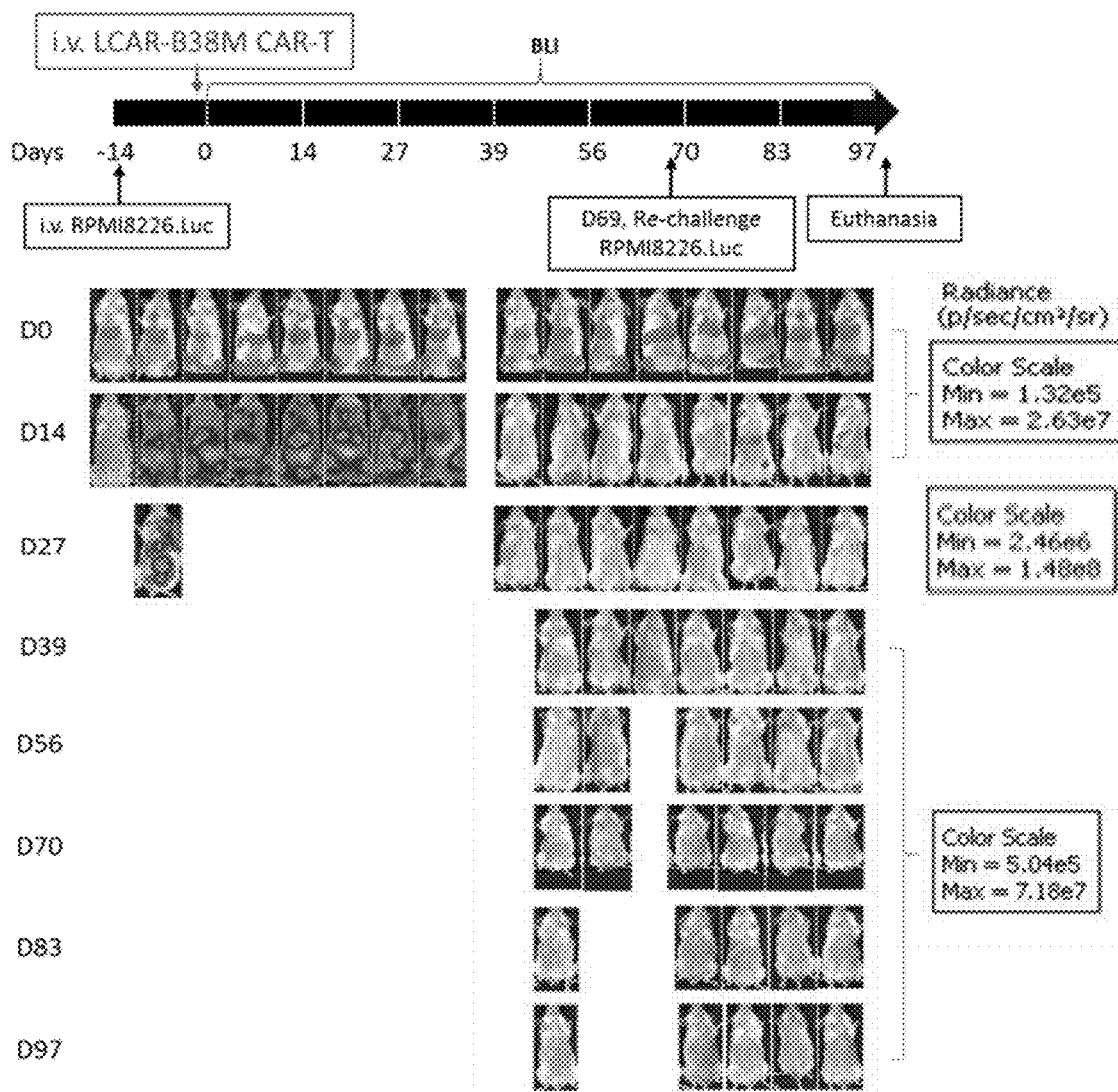
Figure 12D:
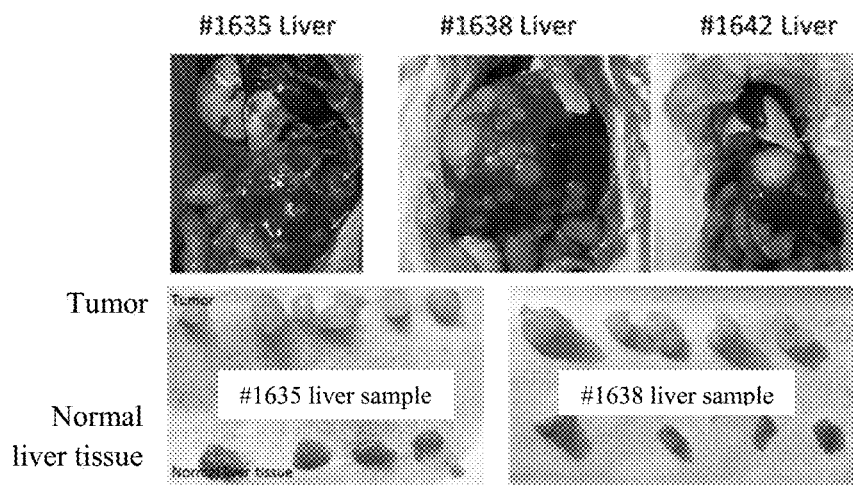
Figure 12E:
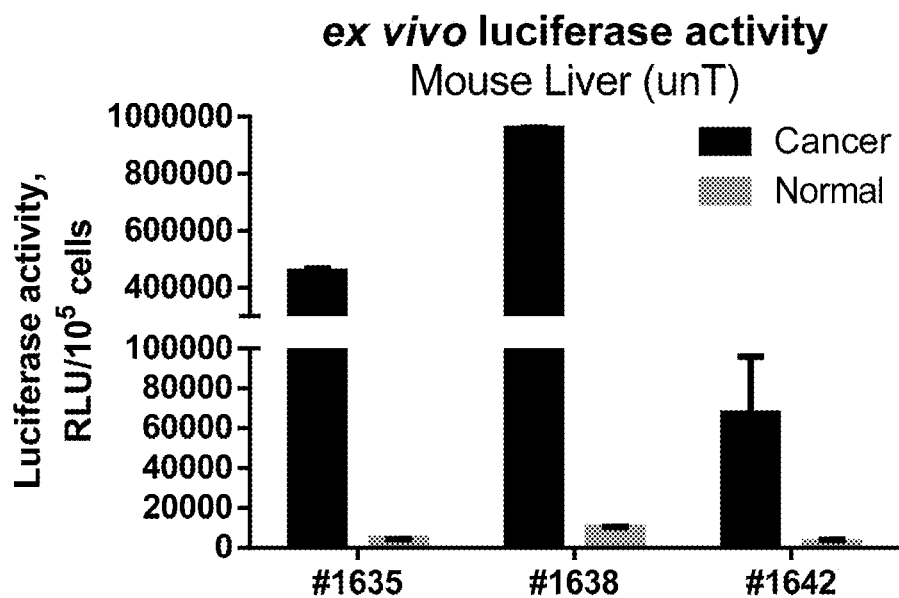
Figure 13A:
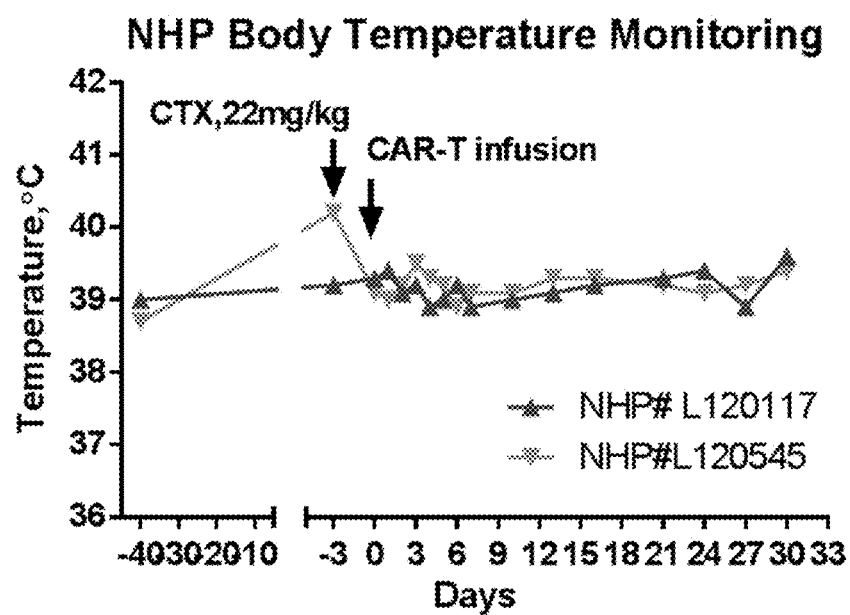
FIGS. 13A-13F show clinical parameters of two monkeys treated with LCAR-B38M CAR-T cells. The clinical parameters monitored in the study include body temperature (FIG. 13A), body weight (FIG. 13B), Complete Blood Count (CBC, FIGS. 13C and 13D), as well as serum chemistry and cytokine levels (FIGS. 13E and 13F).
Figure 13B:
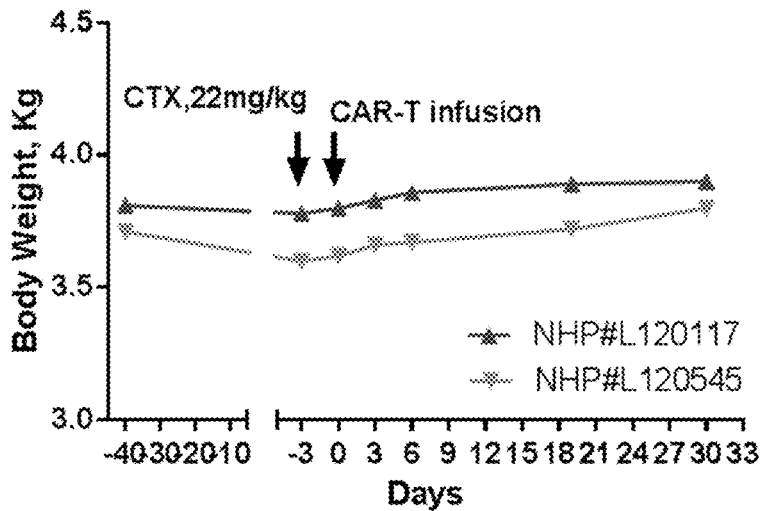
Figure 13C:
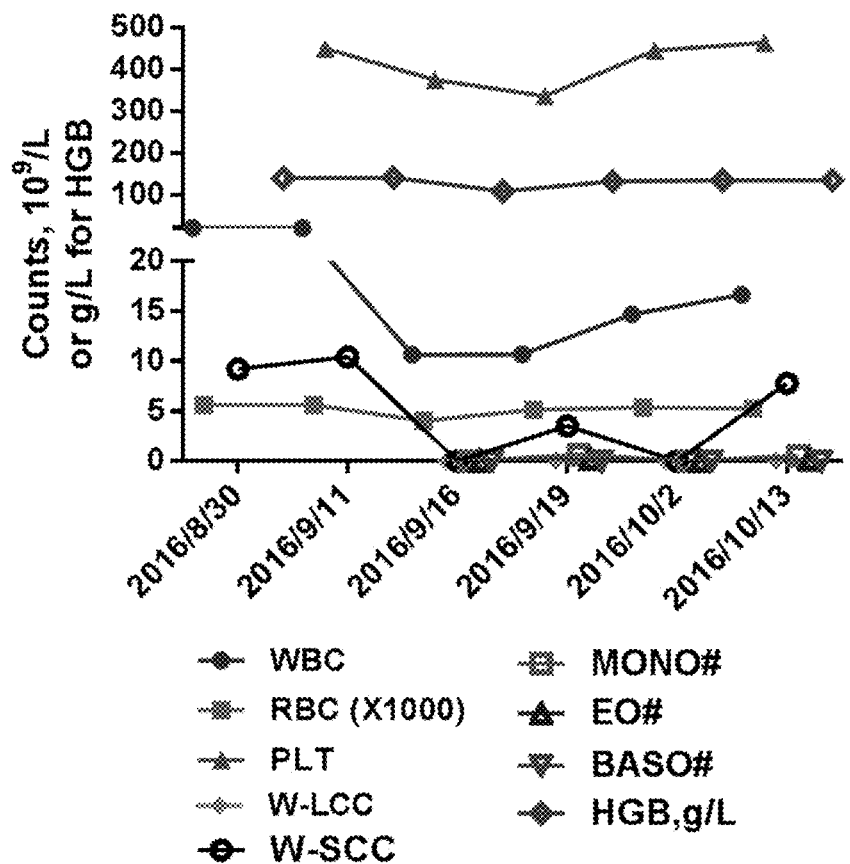
Figure 13D:
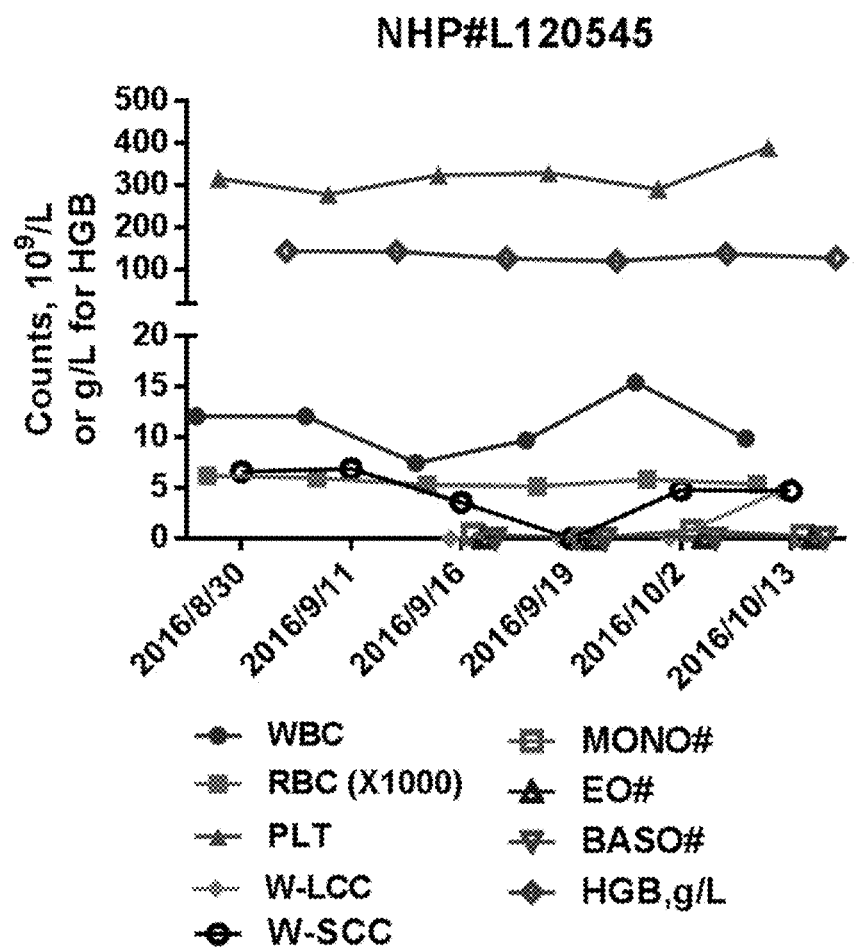
Figure 13E:
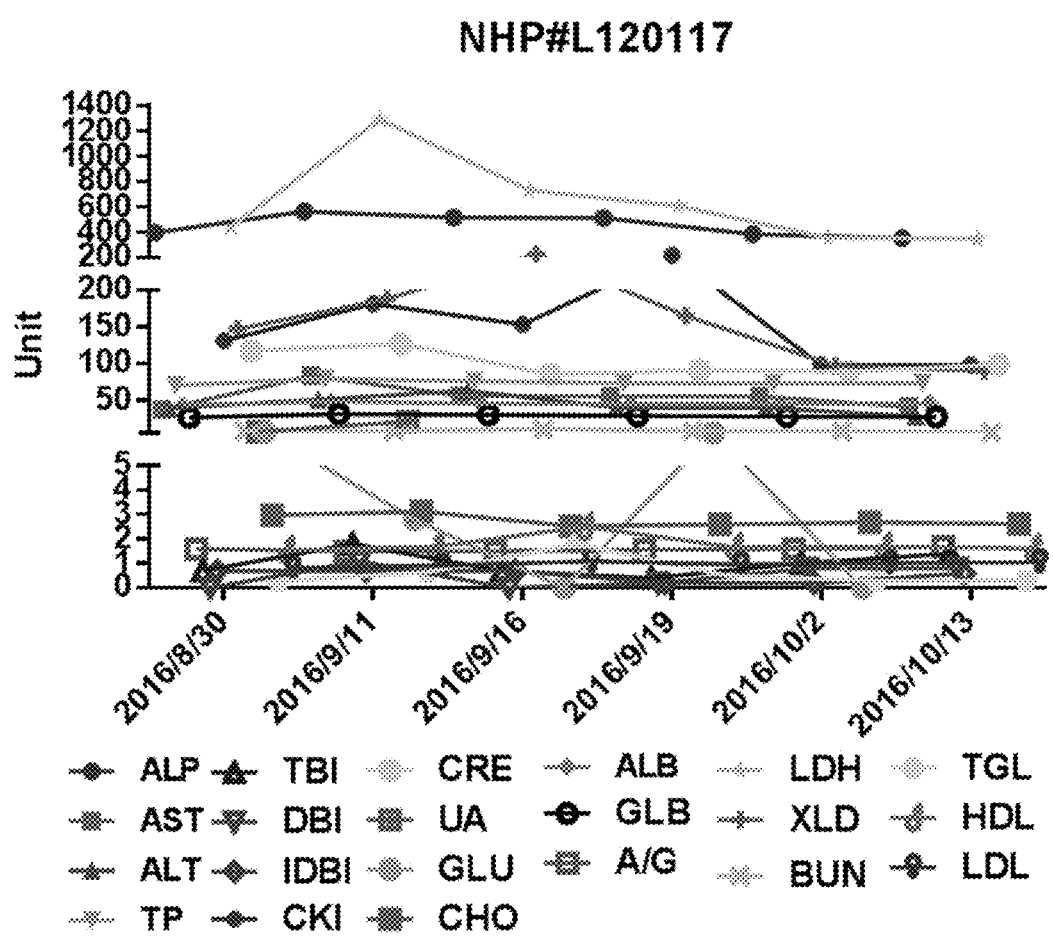
Figure 13F:
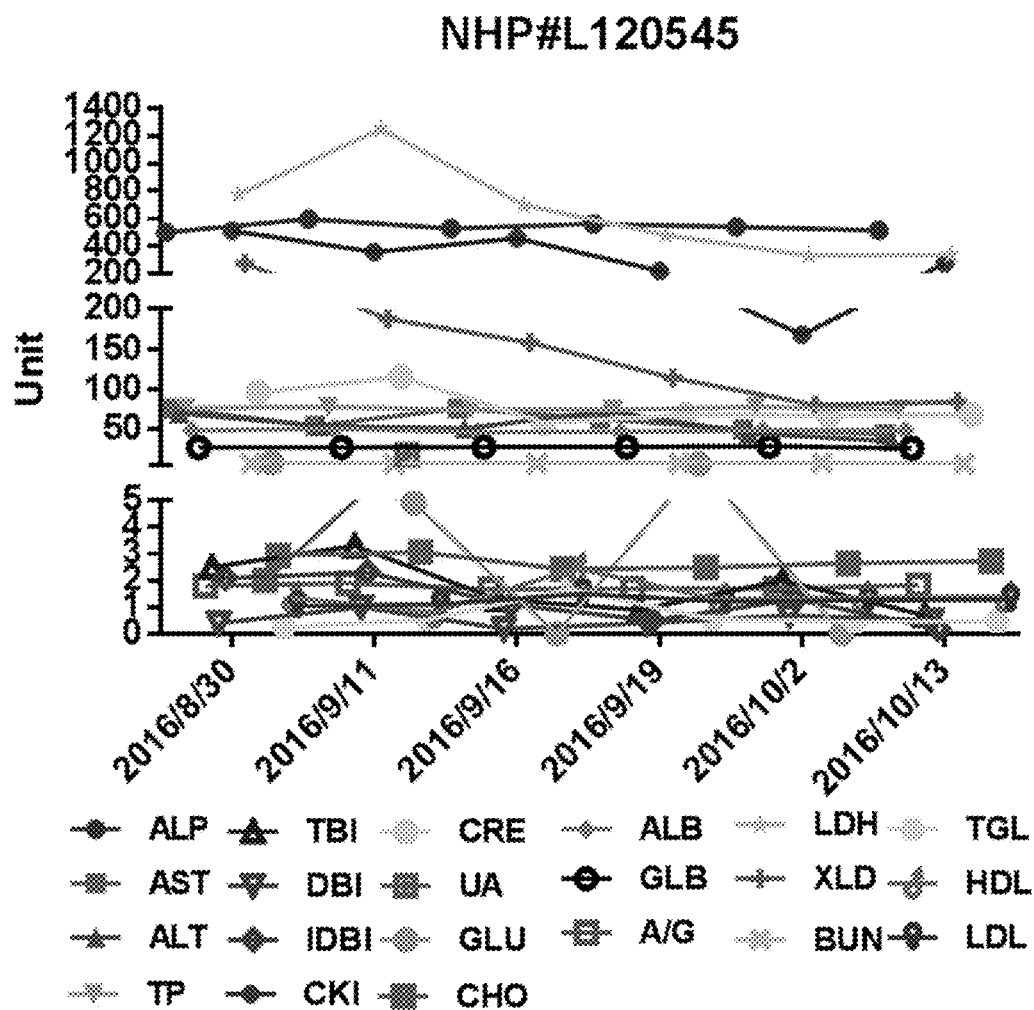

As shown in FIGS. 12B-12C, LCAR-B38M CAR-T cells were efficient to eradicate the engrafted RPMI8226.Luc tumor cells in NCG mice and rescue the mice, while most mice in the control (UnT) group died within 4 weeks. Interestingly, during autopsy, numerous metastatic tumors were observed in the liver of all mice in the UnT group. This observation was further validated by assessing ex vivo luciferase activities from the tumor samples (FIGS. 12D-12E). In contrast, the LCAR-B38M CAR-T treated mice did not have metastatic tumors in the livers. In summary, the in vivo study demonstrates the potency of LCAR-B38M CAR-T cells in eradication of multiple myeloma cells (e.g., RPMI8226.Luc) from NCG mice.

Example 6. Safety Study of LCAR-B38M CAR-T Treatment on Non-Human Primates

The in vivo safety of the LCAR-B38M CAR-T cells was evaluated in a cynomolgus monkey model. PBMC was obtained from peripheral blood samples of two monkeys (NHP #120117 and NHP #120545, both male, around 4 kg), and prepared by density gradient centrifugation. Cynomolgus monkey T cells were isolated from PBMC using non-human primate Pan T Cell Isolation Kit (Miltenyi #130-091-993) according to the manufacturer's manual. The prepared monkey T cells were pre-activated with non-human primate T Cell Activation/Expansion Kit (Miltenyi #130-092-919), human IL-2, and autologous monkey serum for 3 days. Afterwards, the pre-activated T cells were transduced with the LCAR-B38M lentivirus, followed by expansion for 10 additional days.

3 days prior to the infusion of autologous CAR-T cells, the monkeys were pre-treated with Cyclophosphamide at a dose of 22 mg/kg body weight by intravenous infusion. On the day of autologous infusion, cells were thawed in a 37° C. water bath by gentle swirling and immediately infused to the animals intravenously within 5 minutes. Monkey NHP #120117 was infused with $5 \times 10^6$/kg CAR-T cells, and monkey NHP #120545 was infused with $4 \times 10^7$/kg CAR-T cells.

The monkeys were monitored after the T-cell administration for fever, respiratory distress, change in appetite, diarrhea, and weight loss. Pre- and post-administration blood samples were obtained and examined for CBC, serum chemistry, and cytokine levels. As shown in FIGS. 13A-13F, the CAR-T cells had no significant toxicity in the monkeys.

Example 7. A Clinical Study of LCAR-B38M CAR-T in Human Patients with Refractory/Relapsed Multiple Myeloma A single-arm, open-label, multi-center, phase 1/2 clinical study was conducted to determine the safety and efficacy of LCAR-B38M CAR-T cells in treating human patients diagnosed with refractory or relapsed multiple myeloma ("r/r MM"). Information of the clinical trial can be found on worldwide web.clinicaltrials.gov, with identifier NCT03090659.

In the study, refractory/relapsed multiple myeloma patients were treated with LCAR-B38M CAR-T cells derived from autologous T cells of the patients. A total dose of $0.5 \times 10^6$-$5 \times 10^6$ cells/kg body weight was administered to each patient by intravenous injection in three split doses (20%, 30%, and 50% respectively) over the duration of a week (e.g., on Days 0, 2, and 6). During Days 1-30 of the study, patients were monitored for adverse events, and patient samples were obtained for laboratory assessment. All patients are followed up for at least 36 months after the CAR-T administration.

The primary outcome of the study measures occurrence of treatment related adverse events as assessed by Common Terminology Criteria for Adverse Events (CTCAE) v4.0 within 1-30 days after injection of the LCAR-B38M CAR-T cells. Secondary outcome assesses CAR-T induced anti-myeloma responses, e.g., by determining aberrant immunoglobulin levels in the serum, and number of multiple myeloma cells in the bone marrow of the patients before and after administration of the LCAR-B38M CAR-T cells. Efficacy objectives of the study include pathological Complete Response proportion, 3-year Disease Free Survival, 3-year Progression Free Survival.

Patients 18-75 years old are eligible for the study if: (1) the patient has a confirmed prior diagnosis of active multiple myeloma as defined by the updated IMWG criteria; (2) Clear BCMA expression is detected on malignant plasma cells from either bone marrow or a plasmacytoma by flow cytometry or immunohistochemistry; and (3) the patient has refractory multiple myeloma as defined by having received at least 3 prior treatment regimens including bortezomib, or otherwise identified by clinical doctors; or the patient has relapsed multiple myeloma as defined by in the NCCN clinical practice guidelines in Oncology: Multiple Myeloma (2016 V2).

The following patients are excluded from the study: (1) women of child-bearing potential or who are pregnant or breastfeeding; (2) patients who have any active and uncontrolled infection: hepatitis B, hepatitis C, HIV, or other fatal viral and bacterial infection; (3) patients who have received systemic corticosteroid steroid therapy of greater than 5 mg/day of prednisone or equivalent dose of another corticosteroid are not allowed within 2 weeks prior to either the required leukapheresis or the initiation of the conditioning chemotherapy regimen; (4) patients with any uncontrolled intercurrent illness or serious uncontrolled medical disorder; (5) patients with CNS metastases or symptomatic CNS involvement (including cranial neuropathies or mass lesions and spinal cord compression); (6) patients with a history of allogeneic stem cell transplantation, who have active acute or chronic graft-versus-host-disease (GVHD), or require immunosuppressant medications for GVHD, within 6 months of enrollment; or (7) patients with active autoimmune skin diseases such as psoriasis or other active autoimmune diseases such as rheumatoid arthritis.

At an interim analysis in May 2017, 35 patients with relapsed or treatment resistant (refractory) multiple myeloma received LCAR-B38M CAR-T treatment. First signs of treatment efficacy appeared as early as 10 days after initial injection of the CAR-T cells. Overall, the objective response rate was 100% and 33 out of 35 (94%) patients had an evident clinical remission of myeloma (complete response or very good partial response) within two months of receiving the CAR-T cells.

By the time of the analysis, 19 patients were followed for more than four months, a pre-set time for full efficacy assessment by the International Myeloma Working Group (IMWG) consensus criteria. One patient reached partial response and four patients achieved very good partial remission criteria (VgPR) in efficacy. No patients who reached the Stringent Complete Response ("sCR") criteria relapsed. Five patients who had been followed for over a year (12-14 months) remained at the sCR status and were free of minimal residual disease (i.e., no detectable cancer cells in the bone marrow).

Cytokine release syndrome ("CRS") is a common and potentially dangerous side effect of CAR T-cell therapy. Only transient CRS was experience by 85% of the 35 patients. CRS symptoms include fever, low blood pressure, difficulty of breathing, and problems with multiple organs. In a majority of the patients, CRS symptoms were mild and manageable. Only two patients experienced severe CRS (grade 3), but recovered upon receiving tocilizumab (an inflammation-reducing treatment commonly used to manage CRS in clinical trials of CAR-T cell therapy). No patients experienced neurologic side effects, another common and serious complication from CAR T-cell therapy.

The interim clinical trial data demonstrate potent efficacy and safety of the LCAR-B38M CAR-T treatment on patients with refractory/relapsed multiple myeloma.

In a pilot clinical study, 3 patients were treated with autologous T cells expressing a monovalent BCMA CAR, i.e., LCAR-B27S CAR-T cells. The LCAR-B27S CAR (one monovalent BCMA CAR listed in Table 4) has an antigen binding domain containing a single $V_HH$ fragment that recognizes a single epitope of the BCMA molecule. This $V_HH$ domain is identical to the second $V_HH$ domain of the bi-epitope/bivalent LCAR-B38M CAR.

Figure 14A:
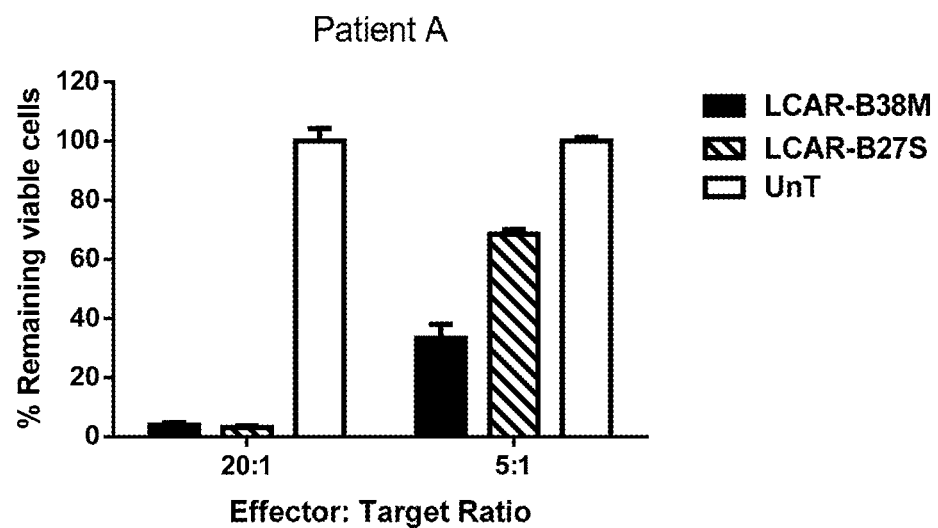
FIG. 14A-C show the in vitro cytotoxicity assays about LCAR-B38M CAR-T cells and LCAR-B27S CAR-T cells prepared from the same three multiple myeloma patients respectively.
Figure 14B:
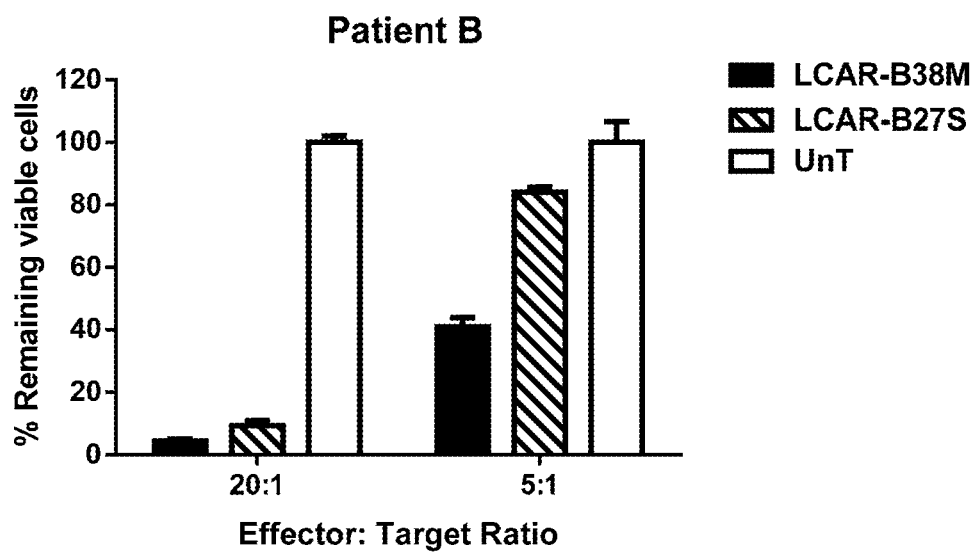
Figure 14C:
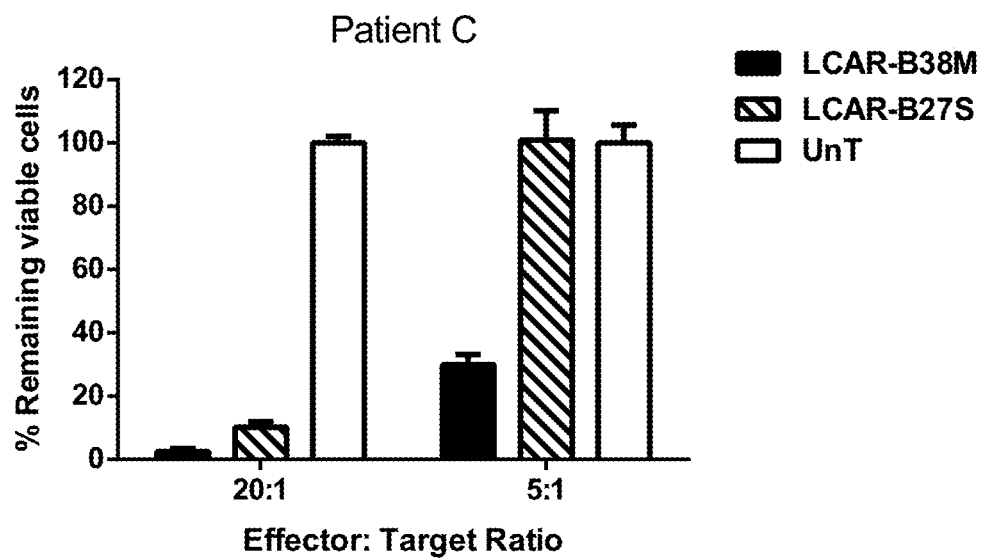

In an in vitro cytotoxicity assay, LCAR-B27S CAR-T cells were prepared from three multiple myeloma patients respectively, and LCAR-B38M CAR-T cells were also prepared respectively from the same three multiple myeloma patients as a control. Both CAR-T cells were co-cultured with RPMI8226.Luc cells at an effector to target ratio (E/T ratio) of 20:1 and 5:1 for 20 hours. As shown in FIG. 14A, CAR-T cells were prepared using T cells from patient A. The percentage of remaining viable cells, as assessed by remaining luciferase activity in RPMI8226.Luc cells, were 3.97±0.75% for LCAR-B38M and 3.17±0.57% for LCAR-B27S, when E/T ratio was 20:1. However, when E/T ratio was 5:1, LCAR-B38M showed higher potencies of killing RPMI8226.Luc cells as compared with LCAR-B27S (33.37±0.75% remaining viable cells for LCAR-B38M, 68.60±1.60% for LCAR-B27S). As shown in FIG. 14B, CAR-T cells were prepared using T cells from patient B. The percentage of remaining viable cells, as assessed by remaining luciferase activity in RPMI8226.Luc cells, were 4.45±0.57% for LCAR-B38M and 9.32±1.16% for LCAR-B27S, when E/T ratio was 20:1. However, when E/T ratio was 5:1, LCAR-B38M again showed higher potencies of killing RPMI8226.Luc cells as compared with LCAR-B27S (40.92±3.00% remaining viable cells for LCAR-B38M, 84.05±1.56% for LCAR-B27S). As shown in FIG. 14C, CAR-T cells were prepared using T cells from patient C. The percentage of remaining viable cells, as assessed by remaining luciferase activity in RPMI8226.Luc cells, were 2.56±0.88% for LCAR-B38M and 10.12±1.83% for LCAR-B27S, when E/T ratio was 20:1. However, when E/T ratio was 5:1, LCAR-B38M again showed higher potencies of killing RPMI8226.Luc cells as compared with LCAR-B27S (29.99±3.13% remaining viable cells for LCAR-B38M, 100.93±9.25% for LCAR-B27S).

In the pilot clinical study, 3 patients were treated with the LCAR-B27S CAR-T cells, in which all the preconditioning, injection and follow-up protocols were identical to those of the clinical study with the bivalent LCAR-B38M CAR. A total dose of $3×10^6$ cells/kg (patient A), $5×10^6$ cells/kg (patient B) and $7×10^6$ cells/kg (patient C) body weight of autologous LCAR-B27S modified CAR-T cells were administered to each patient respectively by intravenous injection in three split doses (20%, 30%, and 50% respectively) over the duration of a week (e.g., on Days 0, 2, and 6). During Days 1-30 of the study, patients were monitored for adverse events, and patient samples were obtained for laboratory assessment. All patients were followed up for at least 36 months after the CAR-T administration.

2 patients among the three patients reached very good partial response (VgPR), but both patients relapsed within 6 months after the CAR-T infusion. The third patient did not show any clinical response. The pilot study with LCAR-B27S was consequently terminated by the IRB with no further patient enrollment.

Objective response rate, complete remission rate and relapse rate from this pilot monovalent BCMA CAR study (LCAR-B27S) and the bivalent BCMA CAR study (LCAR-B38M CAR-T) are shown in Table 11 below. The bivalent BCMA CAR-T had superior clinical efficacy in comparison to the monovalent BCMA CAR-T.

TABLE 11

Comparable clinical data of monovalent and bivalent/bi-epitope BCMA CAR-T therapies

| Agent | N | Dose (cells/kg) | Clinical trial | Objective Response Rate (ORR) | Complete Remission (CR) rate | Relapse Rate (>6 mon) |
|---|---|---|---|---|---|---|
| Monovalent BCMA CAR-T (LCAR-B27S) | 3 | 3, 5, 7 × $10^6$ respectively | Pilot study | 67% | 0% | 67% |
| Bivalent/Bi-epitope BCMA CAR-T (LCAR-B38M) | 35 | 0.3 × $10^6$-5.6 × $10^6$ (median = 2.9 × $10^6$) | NCT03090659 | 100% | 57.1% | 7.5% |

What is claimed is:

1. An isolated nucleic acid comprising a nucleic acid sequence encoding a multivalent chimeric antigen receptor (CAR) comprising a polypeptide comprising:
   (a) an extracellular antigen binding domain comprising a first anti-BCMA binding moiety and a second BCMA binding moiety, wherein each of the first and the second anti-BCMA binding moieties is a VHH domain;
   (b) a transmembrane domain; and
   (c) an intracellular signaling domain,
   wherein the first BCMA binding moiety comprises
   a CDR1 comprising the amino acid sequence of SEQ ID NO:15; a CDR2 comprising the amino acid sequence of SEQ ID NO:53; and a CDR3 comprising the amino acid sequence of SEQ ID NO:91, and the second BCMA binding moiety comprises
   a CDR1 comprising the amino acid sequence of SEQ ID NO:18; a CDR2 comprising the amino acid sequence of SEQ ID NO:56; and a CDR3 comprising the amino acid sequence of SEQ ID NO:94.

2. The isolated nucleic acid of claim 1, wherein the first BCMA binding moiety comprises the amino acid sequence of SEQ ID NO: 129 and the second BCMA binding moiety comprises the amino acid sequence of SEQ ID NO: 132.

3. A vector comprising the isolated nucleic acid of claim 1.

4. The isolated nucleic acid of claim 1, wherein the first BCMA binding moiety is located at the N-terminus of the second BCMA binding moiety.

5. The isolated nucleic acid of claim 1, wherein the first BCMA binding moiety is located at the C-terminus of the second BCMA binding moiety.

6. The isolated nucleic acid of claim 1, wherein the first BCMA binding moiety and the second BCMA binding moiety are fused to each other via a peptide linker.

7. The isolated nucleic acid of claim 6, wherein the peptide linker is no more than about 50 amino acids long.

8. The isolated nucleic acid of claim 1, wherein the transmembrane domain is derived from a molecule selected from the group consisting of CD8α, CD4, CD28, CD137, CD80, CD86, CD152 and PD1.

9. The isolated nucleic acid of claim 8, wherein the transmembrane domain is derived from CD8α or CD28.

10. The isolated nucleic acid of claim 1, wherein the intracellular signaling domain comprises a primary intracellular signaling domain of an immune effector cell.

11. The isolated nucleic acid of claim 10, wherein the primary intracellular signaling domain is derived from CD3ζ.

12. The isolated nucleic acid of claim 1, wherein the intracellular signaling domain comprises a co-stimulatory signaling domain.

13. The isolated nucleic acid of claim 12, wherein the co-stimulatory signaling domain is derived from a co-stimulatory molecule selected from the group consisting of CD27, CD28, CD137, OX40, CD30, CD40, CD3, LFA-1, ICOS, CD2, CD7, LIGHT, NKG2C, B7-H3, ligands of CD83 and combinations thereof.

14. The isolated nucleic acid of claim 13, wherein the co-stimulatory signaling domain comprises a cytoplasmic domain of CD28 and/or a cytoplasmic domain of CD137.

15. The isolated nucleic acid of claim 1, wherein the multivalent CAR further comprises a hinge domain located between the C-terminus of the extracellular antigen binding domain and the N-terminus of the transmembrane domain.

16. The isolated nucleic acid of claim 15, wherein the hinge domain is derived from CD8α.

17. The isolated nucleic acid of claim 16, wherein the multivalent CAR further comprises a signal peptide located at the N-terminus of the polypeptide.

18. The isolated nucleic acid of claim 17, wherein the signal peptide is derived from CD8α.

19. The isolated nucleic acid of claim 1, comprising the nucleic acid sequence of SEQ ID NO: 356.

20. A multivalent CAR encoded by the isolated nucleic acid of claim 1.

21. The multivalent CAR of claim 20, comprising the amino acid sequence of SEQ ID NO: 318.

22. An engineered immune effector cell, comprising the multivalent CAR of claim 20.

23. A pharmaceutical composition, comprising the engineered immune effector cell of claim 22.

24. A method of treating cancer that expresses BCMA in an individual, comprising administering to the individual an effective amount of the pharmaceutical composition of claim 23.

25. The method of claim 24, wherein the cancer is multiple myeloma.

26. The method of claim 25, wherein the cancer is refractory or relapsed multiple myeloma.

* * * * *